(12) United States Patent
Ehrhardt et al.

(10) Patent No.: US 7,807,709 B2
(45) Date of Patent: Oct. 5, 2010

(54) ORGANIC COMPOUNDS

(75) Inventors: Claus Ehrhardt, Lörrach (DE); Osamu Irie, Tsukuba (JP); Edwige Liliane Lorthiois, Niffer (FR); Juergen Klaus Maibaum, Weil-Haltingen (DE); Nils Ostermann, Binzen (DE); Holger Sellner, Therwil (CH)

(73) Assignee: Novartis AG, Basel (CH)

( * ) Notice: Subject to any disclaimer, the term of this patent is extended or adjusted under 35 U.S.C. 154(b) by 137 days.

(21) Appl. No.: 11/909,402

(22) PCT Filed: Mar. 21, 2006

(86) PCT No.: PCT/EP2006/002578

§ 371 (c)(1),
(2), (4) Date: Sep. 21, 2007

(87) PCT Pub. No.: WO2006/100036

PCT Pub. Date: Sep. 28, 2006

(65) Prior Publication Data

US 2008/0194549 A1 Aug. 14, 2008

(30) Foreign Application Priority Data

Mar. 23, 2005 (GB) ................... 0505969.6

(51) Int. Cl.
 A61K 31/40 (2006.01)
 C07D 207/00 (2006.01)
(52) U.S. Cl. .................... 514/428; 548/566
(58) Field of Classification Search ........... 548/566; 514/428
 See application file for complete search history.

(56) References Cited

U.S. PATENT DOCUMENTS

| 7,582,782 | B2 | 9/2009 | Baeschlin et al. |
|---|---|---|---|
| 2004/0019137 | A1 | 1/2004 | Hebrault |
| 2004/0077551 | A1 | 4/2004 | Campbell et al. |
| 2009/0312304 | A1 | 12/2009 | Breitenstein et al. |
| 2010/0029647 | A1 | 2/2010 | Masuya et al. |

FOREIGN PATENT DOCUMENTS

| CN | 1583724 A | 2/2005 |
|---|---|---|
| EP | 0242789 A | 10/1987 |
| WO | WO 93/12108 A1 | 6/1993 |
| WO | WO 95/09858 A1 | 4/1995 |
| WO | WO 99/09984 A1 | 3/1999 |
| WO | WO 99/65867 A1 | 12/1999 |
| WO | WO 00/26211 A1 | 5/2000 |
| WO | 0051609 A | 9/2000 |
| WO | WO 00/51607 A1 | 9/2000 |
| WO | WO 00/51608 A1 | 9/2000 |
| WO | WO 00/51610 A1 | 9/2000 |
| WO | WO 01/70673 A2 | 9/2001 |
| WO | WO 02/34716 A2 | 5/2002 |
| WO | WO 03/024899 A2 | 3/2003 |
| WO | WO 03/031443 A1 | 4/2003 |
| WO | WO 03/032962 A2 | 4/2003 |
| WO | 03/099767 | 12/2003 |
| WO | WO 04/004665 A2 | 1/2004 |
| WO | 2005/070870 | 8/2005 |
| WO | 2005/070871 | 8/2005 |
| WO | 2005/070877 | 8/2005 |
| WO | 2005/090304 | 9/2005 |
| WO | 2005/090305 | 9/2005 |
| WO | 2006/061426 | 6/2006 |
| WO | 2006/095020 | 9/2006 |

OTHER PUBLICATIONS

Specker et al., 2006, CAS: 145: 210822.*
Taylor G M et al: "On the Ritter Reaction of Cyclic Hydroxyamines: Synthesis of Conformationally-Restricted Reduced Amide Dipeptide Isoteres" Tetrahedron Letters, vol. 37, No. 8, Feb. 19, 1996, pp. 1297-1300. The whole document.
N.D.L. Fischer and N.K. Hollenberg: "Is there a future for renin inhibitors?" Expert Opinion on Investigational Drugs, vol. 10, No. 3, 2001, pp. 417-426. The whole document.
Wood J M et al: "Inhibitors of renin as potential therapeutic agents" Journal of Enzyme Inhibition, vol. 1, No. 3, 1987, pp. 169-185. The whole document.
Wood Jeanette M et al: "Structure-based design of aliskiren, a novel orally effective renin inhibitor." Biochemical and Biophysical Research Communications, vol. 308, No. 4, Sep. 5, 2003, pp. 698-705. The whole document.
Specker et al.; Angew Chem Int Ed (2005); 44; 3140.
Fevig et al.; Bioorg & Med Chem Letters (1996); 6(3); 295.
Thomas et al.; Bioorg & Med Chem Letters (1998); 8; 2885.
Bucsh et al.; J Med Chem (1993); 36(26); 4139.
Co-pending U.S. Appl. No. 11/721,457 filed Oct. 13, 2009 owned by Novartis AG.
Co-pending U.S. Appl. No. 11/908,182 filed Sep. 10, 2007 owned by Novartis AG.
Maibaum, et al., "Renin inhibitors as novel treatment for cardiovascular diseases" Expert opinion on therapeutic patents, vol. 13, No. 5, 2003, 589-603.

* cited by examiner

Primary Examiner—Rei-tsang Shiao
(74) Attorney, Agent, or Firm—Sophie Binet Cross

(57) ABSTRACT

The invention relates to the use of (3,4-di-, 3,3,4-tri, 3,4,4-tri- or 3,3,4,4-tetra-)substituted pyrrolidine compounds for the preparation of a pharmaceutical formulation for the treatment of a disease that depends on activity of renin; the use of a compound of that class in the treatment of a disease that depends on activity of renin; compounds that are part of a subclass of these substituted pyrrolidine compounds for use in the diagnostic and therapeutic treatment of a warm-blooded animal, especially for the treatment of a disease (=disorder) that depends on activity of renin; new compounds that are part of a subclass of these substituted pyrrolidine compounds; pharmaceutical formulations comprising said substituted pyrrolidine compounds, and/or a method of treatment comprising administering said substituted pyrrolidine compounds, a method for the manufacture especially of said new substituted pyrrolidine compounds, as well as novel intermediates, starting materials and/or partial steps for their synthesis.

7 Claims, No Drawings

ORGANIC COMPOUNDS

This application is the National Stage of Application No. PCT/EP2006/002578, filed on Mar. 21, 2006, which claims benefit under 35 U.S.C. §119(e) of Great Britain Application No. 0505969.6, filed Mar. 23, 2005. The contents of both are incorporated herein by reference in their entirety.

The invention relates to the use of (3,4-di-, 3,3,4,- tri, 3,4,4-tri- or 3,3,4,4-tetra-)substituted pyrrolidine compounds for the preparation of a pharmaceutical formulation for the treatment of a disease that depends on activity of renin; the use of a compound of that class in the treatment of a disease that depends on activity of renin; compounds that are part of a subclass of these substituted pyrrolidine compounds for use in the diagnostic and therapeutic treatment of a warm-blooded animal, especially for the treatment of a disease (=disorder) that depends on activity of renin; new compounds that are part of a subclass of these substituted pyrrolidine compounds; pharmaceutical formulations or products comprising said substituted pyrrolidine compounds, and/or a method of treatment comprising administering said substituted pyrrolidine compounds, a method for the manufacture especially of said new substituted pyrrolidine compounds, as well as novel intermediates, starting materials and/or partial steps for their synthesis.

Especially, the invention relates to the use of a compound of the formula I,

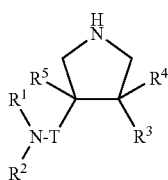
(I)

as described in the claims or wherein $R^1$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl, substituted or unsubstituted alkynyl or acyl;

$R^2$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl, substituted or unsubstituted alkynyl or acyl;

$R^3$ is a moiety selected from the group of moieties of the formulae

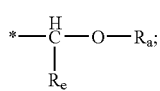
(a)

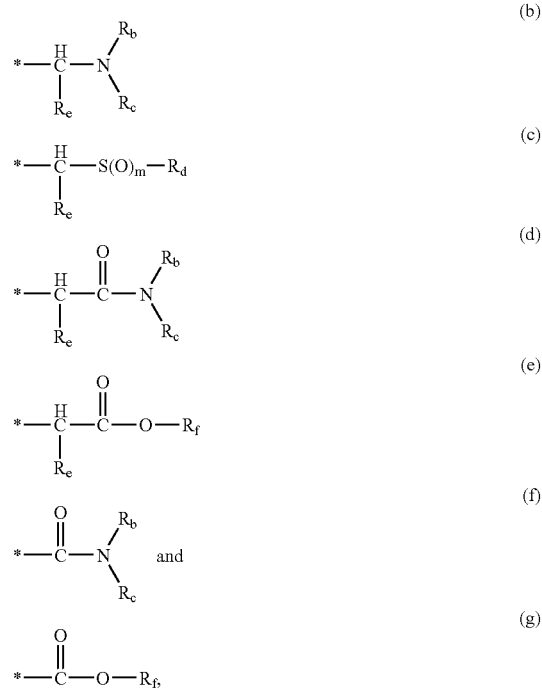

where in any of the moieties of the formulae given above under (a), (b), (c), (d), (e), (f) and (g) the asterisk (*) shows the bond binding the respective moiety $R^3$ to the rest of the molecule in formula I, $R_a$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, acyl or hydrogen;

$R_b$ and $R_c$ are independently selected from the moieties given under $R_a$, with the proviso that preferably not more than one of $R_b$ and $R_c$ is acyl, Rd is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (preferably if m is 0) acyl, or can have one of these meanings or can be —N($R_b$)($R_c$) if m is 1 or preferably 2;

$R_e$ is hydrogen, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (especially) substituted or preferably unsubstituted $C_1$-$C_7$-alkyl; and $R_f$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl;

m is 0, 1 or 2;

each of $R^4$ and $R^5$ is selected, independently from the other, from hydrogen, unsubstituted or substituted alkyl, hydroxy or esterified or etherified hydroxy;

and T is methylene (—$CH_2$—), methylene mono-substituted by alkyl (—[C(H)(alkyl)]-), carbonyl (—C(=O)—) or thiocarbonyl (—C(=S)—);

or a pharmaceutically acceptable salt thereof, in the preparation of a pharmaceutical formulation for the treatment of a disease that depends on activity of renin, especially hypertension.

The compounds of the present invention exhibit inhibitory activity on the natural enzyme renin. Thus, compounds of formula I may be employed for the treatment (this term also including prophylaxis) of one or more disorders or diseases selected from, inter alia, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, cognitive impairment, alzheimers, dementia, anxiety states and cognitive disorders, especially as far as these diseases can be modulated (more especially beneficially influenced) by renin inhibition.

Listed in the claims and below are definitions of various terms used to describe the compounds of the present invention as well as their use and synthesis, starting materials and intermediates and the like. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Halo or halogen is preferably fluoro, chloro, bromo or iodo, most preferably fluoro, chloro or bromo. If not explicitly or implicitly stated otherwise, halo can also stand for more than one halogen substituent in moieties such as alkyl, alkanoyl and the like (e.g. in trifluoromethyl, trifluoroacetyl).

Unsubstituted or substituted mono- or bicyclic aryl preferably is a mono- or bicyclic aryl with 6 to 22 carbon atoms, especially phenyl, indenyl or naphthyl, and is unsubstituted or substituted by one or more, especially one to three, moieties, preferably independently selected from the group consisting of a substituent of the formula —($C_0$-$C_7$-alkylene)-(X)$_r$—($C_1$-$C_7$-alkylene)-(Y)$_s$—($C_0$-$C_7$-alkylene)-H (especially in substituted aryl or substituted aryl-alkyl as $R^1$) where $C_0$-alkylene means that a bond is present instead of bound alkylene, alkylene in each case may be straight-chained or branched and unsubstituted or (with lower preference) substituted e.g. by one or more moieties as defined for substituted alkyl, especially by halo, especially fluoro, hydroxy, $C_1$-$C_7$-alkoxy, phenyloxy, naphthyloxy, $C_1$-$C_7$-alkanoyloxy, benzoyloxy, naphthoyloxy, amino, mono- or di-($C_1$-$C_7$-alkyl, $C_1$-$C_7$-alkanoyl, phenyl-$C_1$-$C_7$-alkanoyl, naphthyl-$C_1$-$C_7$-alkanoyl, phenyl, naphthyl, phenyl-$C_1$-$C_7$-alkyl and/or naphthyl-$C_1$-$C_7$-alkyl)-amino, carboxy, $C_1$-$C_7$-alkoxycarbonyl or cyano, r and s, each independently of the other, are 0 or 1 and each of X and Y, if present and independently of the others, is —O—, —NV—, —S—, —O—CO—, —CO—O—, —NV—CO—; —CO—NV—; —NV—$SO_2$—, —$SO_2$—NV; —NV—CO—NV—, —NV—CO—O—, —O—CO—NV—, —NV—$SO_2$—NV— wherein V is hydrogen or unsubstituted or substituted alkyl as defined below, especially $C_1$-$C_7$-alkyl, or is phenyl, naphthyl, phenyl- or naphthyl-$C_1$-$C_7$-alkyl or halo-$C_1$-$C_7$-alkyl; e.g. $C_1$-$C_7$-alkyl, such as methyl, ethyl, n-propyl, isopropyl, n-butyl, isobutyl, sec-butyl or tert-butyl, halo-$C_1$-$C_7$-alkyl, such as trifluoromethyl, hydroxy-$C_1$-$C_7$-alkyl, $C_1$-$C_7$-alkoxy-$C_1$-$C_7$-alkyl, such as 3-methoxypropyl or 2-methoxyethyl, $C_1$-$C_7$-alkoxy-$C_1$-$C_7$-alkoxy-$C_1$-$C_7$-alkyl, phenyloxy- or naphthyloxy-$C_1$-$C_7$-alkyl, $C_1$-$C_7$-alkanoyloxy-$C_1$-$C_7$-alkyl, amino-$C_1$-$C_7$-alkyl, such as aminomethyl, $C_1$-$C_7$-alkoxy-$C_1$-$C_7$-alkylamino-$C_1$-$C_7$-alkyl, mono- or di-($C_1$-$C_7$-alkyl-, naphthyl-, phenyl, naphthyl-$C_1$-$C_7$-alkyl and/or phenyl-$C_1$-$C_7$-alkyl)-amino-$C_1$-$C_7$-alkyl, $C_1$-$C_7$-alkanoylamino-$C_1$-$C_7$-alkyl, $C_1$-$C_7$-alkyl-O—CO—NH—$C_1$-$C_7$-alkyl, $C_1$-$C_7$-alkylsulfonylamino-$C_1$-$C_7$-alkyl, $C_1$-$C_7$-alkyl-NH—CO—NH—$C_1$-$C_7$-alkyl, $C_1$-$C_7$-alkyl-NH—$SO_2$—NH—$C_1$-$C_7$-alkyl, $C_1$-$C_7$-alkoxy, hydroxy-$C_1$-$C_7$-alkoxy, $C_1$-$C_7$-alkoxy-$C_1$-$C_7$alkoxy, $C_1$-$C_7$-alkanoyloxy, halo-$C_1$-$C_7$-alkoxy, such as trifluoromethoxy, phenyl- or naphthyl-$C_1$-$C_7$-alkanoyloxy, phenyl- or naphthyl-$C_1$-$C_7$-alkylaminocarbonyloxy, halo-$C_1$-$C_7$-alkylthio, such as trifluoromethylthio, phenyl- or naphthyl-$C_1$-$C_7$-alkylthio, mono- or di-($C_1$-$C_7$-alkyl-, naphthyl-$C_1$-$C_7$-alkyl-, phenyl-$C_1$-$C_7$-alkyl- and/or $C_1$-$C_7$-alkoxy-$C_1$-$C_7$-alkyl-)amino, $C_1$-$C_7$-alkanoylamino, $C_1$-$C_7$-alkylsulfonylamino, phenyl- or naphthyl-$C_1$-$C_7$-alkanoylamino, phenyl- or naphthyl-$C_1$-$C_7$-alkylaminocarbonylamino, carboxy-$C_1$-$C_7$-alkyl, $C_1$-$C_7$-alkoxy-carbonyl, hydroxy-$C_1$-$C_7$-alkoxycarbonyl, $C_1$-$C_7$-alkoxy-$C_1$-$C_7$-alkoxycarbonyl, amino-$C_1$-$C_7$-alkoxycarbonyl, (N-) mono- ($C_1$-$C_7$-alkyl)-amino-$C_1$-$C_7$-alkoxycarbonyl, $C_1$-$C_7$-alkanoylamino-$C_1$-$C_7$-alkoxycarbonyl, N-mono- or N,N-di-($C_1$-$C_7$-alkyl, naphthyl-$C_1$-$C_7$alkyl and/ or phenyl-$C_1$-$C_7$-alkyl)-aminocarbonyl, $C_1$-$C_7$-alkylsulfonyl, halo-$C_1$-$C_7$-alkylsulfonyl, hydroxy-$C_1$-$C_7$-alkylsulfonyl, $C_1$-$C_7$-alkoxy-$C_1$-$C_7$-alkylsulfonyl, amino-$C_1$-$C_7$-alkylsulfonyl, N-mono- or di-($C_1$-$C_7$-alkyl)-amino-$C_1$-$C_7$-alkylsulfonyl, $C_1$-$C_7$-alkanoylamino-$C_1$-$C_7$-alkylsulfonyl, N—$C_1$-$C_7$-alkoxy-$C_1$-$C_7$-alkylcarbamoyl or N-mono- or N,N-di-($C_1$l-$C_7$-alkyl)-aminosulfonyl;

from $C_2$-$C_7$-alkenyl, $C_2$-$C_7$-alkynyl, phenyl, naphthyl, mono- or bicyclic heterocyclyl, especially as defined below for mono- or bicyclic heterocyclyl, preferably selected from pyrrolyl, furanyl, thienyl, pyrimidine-2,4-dione-1-, -3- or -5-yl and tetrahydrofuranyl, phenyl- or naphthyl- or (mono- or bicyclic heterocyclyl)-$C_1$-$C_7$-alkyl or $C_1$-$C_7$-alkyloxy wherein mono- or bicyclic heterocyclyl is as defined below, preferably selected from pyrrolyl, furanyl, tetrahydrofuranyl, tetrahydropyranyl and thienyl; such as benzyl or naphthylmethyl, tetrahydrofuranyl- or tetrahydropyranyl-$C_1$-$C_7$-alkyloxycarbonyl, benzoyl- or naphthoylamino-$C_1$-$C_7$-alkyl, (phenyl- or naphthyl- or mono- or bicyclic heterocyclyl)-sulfonylamino-$C_1$-$C_7$-alkyl wherein phenyl or naphthyl or mono- or bicyclic heterocyclyl is unsubstituted or substituted, preferably by one or more, especially one to three, $C_1$-$C_7$-alkyl moieties, (phenyl or naphthyl or mono- or bicyclic heterocyclyl)-$C_1$-$C_7$-alkylsulfonylamino-$C_1$-$C_7$-alkyl, halo, hydroxy, phenyl-$C_1$-$C_7$-alkoxy wherein phenyl is preferably unsubstituted or substituted, preferably by $C_1$-$C_7$-alkoxy and/or halo, mono- or bicyclic heterocyclyl-$C_1$-$C_7$-alkoxy, (mono- or bicyclic heterocyclyl or phenyl or naphthyl)-oxy, naphthyl-$C_1$-$C_7$-alkyloxy, benzoyl or naphthoyl or mono- or bicyclic heterocyclylcarbonyl)-oxy, (phenyl or naphthyl or mono- or bicyclic heterocyclyl)-aminocarbonyloxy, (phenyl or naphthyl or mono- or bicyclic heterocyclyl)-thio, (benzoyl or naphthoyl or mono- or bicyclic heterocyclyl)-thio, nitro, amino, di-((naphthyl or phenyl or mono- or bicyclic heterocyclyl)-$C_1$-$C_7$-alkyl)-amino, (benzoyl or naphthoyl or mono- or bicyclic heterocyclyl)-amino, (phenyl or naphthyl or mono- or bicyclic heterocyclyl)-sulfonylamino wherein phenyl or naphthyl is unsubstituted or substituted preferably by one or more, especially one to three, $C_1$-$C_7$-alkyl moieties, (phenyl or naphthyl or mono- or bicyclic heterocyclyl)-$C_1$-$C_7$-alkylsulfonylamino, (phenyl or naphthyl or mono- or bicyclic heterocyclyl)-aminocarbonylamino, (phenyl or naphthyl or mono- or bicyclic heterocyclyl)-oxycarbonylamino, (phenyl or naphthyl or mono- or bicyclic heterocyclyl)-$C_1$-$C_7$-alkyloxycarbonylamino, carboxyl, $C_1$-$C_7$-alkylcarbonyl, halo-$C_1$-$C_7$-alkylcarbonyl, hydroxy-$C_1$-$C_7$-alkylcarbonyl, $C_1$-$C_7$-alkoxy-$C_1$-$C_7$-alkylcarbonyl, amino-$C_1$-$C_7$-alkylcarbonyl, (N-) mono- or (N,N-) di-($C_1$-$C_7$-alkyl)-amino-$C_1$-$C_7$-alkylcarbonyl, $C_1$-$C_7$-alkanoylamino-$C_1$-$C_7$-alkylcarbonyl, halo-$C_1$-$C_7$-alkoxycarbonyl, (phenyl or naphthyl or mono- or bicyclic heterocyclyl)-oxycarbonyl, (phenyl or naphthyl or mono- or bicyclic heterocyclyl )-$C_1$-$C_7$alkoxycarbonyl, (N,N-) di-($C_1$-$C_7$-alkyl)-amino-$C_1$-$C_7$-alkoxycarbonyl, carbamoyl, N-mono or N,N-di-(naphthyl or phenyl or mono- or bicyclic heterocyclyl)-aminocarbonyl, cyano, $C_1$-$C_7$-alkylene which is unsubstituted or substituted by up to four $C_1$-$C_7$-alkyl substituents and bound to two adjacent ring atoms of the aryl moiety, sulfenyl, sulfinyl, $C_1$-$C_7$-alkylsulfinyl, (phenyl or naphthyl or mono- or bicyclic heterocyclyl)-sulfinyl wherein phenyl or naphthyl is unsubstituted or substituted preferably by one or more, especially one to three, $C_1$-$C_7$-alkyl moieties, phenyl- or naphthyl-$C_1$-$C_7$-alkylsulfinyl, sulfonyl, (phenyl or naphthyl or mono- or bicyclic heterocyclyl)-sulfonyl wherein phenyl or naphthyl is unsubstituted or substituted preferably by one or more, especially one to three, $C_1$-$C_7$-alkyl moieties, (phenyl or naphthyl or mono- or bicyclic heterocyclyl)-$C_1$-$C_7$-alkylsulfonyl, sulfamoyl and N-mono or N,N-di-($C_1$-$C_7$-alkyl, phenyl-, naphthyl, mono- or bicyclic heterocyclyl, phenyl-$C_1$-$C_7$-alkyl, naphthyl-$C_1$-$C_7$-alkyl and/or mono- or bicyclic heterocyclyl-$C_1$-$C_7$-alkyl)-aminosulfonyl;

where any phenyl or naphthyl or mono- or bicyclic heterocyclyl (which mono- or bicyclic heterocyclyl is preferably as defined for mono- or bicyclic heterocyclyl, more preferably is selected from pyrrolyl, furanyl, tetrahydrofuranyl, tetrahydropyranyl and thienyl) mentioned as substituent of or as part of a substituent of substituted aryl is unsubstituted or substituted by one or more, preferably up to three, moieties independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycabonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-C7-alkyl)-aminocarbonyl, cyano, sulfo, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro, or preferably, where preferred substituents are mentioned, by one or more of these mentioned substituents. Unsubstituted or substituted mono- or bicyclic heterocyclyl is a mono- or bicyclic heterocyclic moiety with an unsaturated, partially saturated or saturated ring system with preferably 3 to 22 (more preferably 3 to 14) ring atoms and with one or more, preferably one to four, heteroatoms independently selected from nitrogen (=N—, —NH— or substituted —NH—), oxygen and sulfur (—S—, S(=O)— or S—(=O)$_2$—) which is unsubstituted or substituted by one or more, e.g. up to three, substitutents preferably independently selected from the substitutents mentioned above for aryl and from oxo (=O) and thioxo (=S). Preferably, unsubstituted or substituted mono- or bicyclic heterocyclyl is selected from the following moieties:

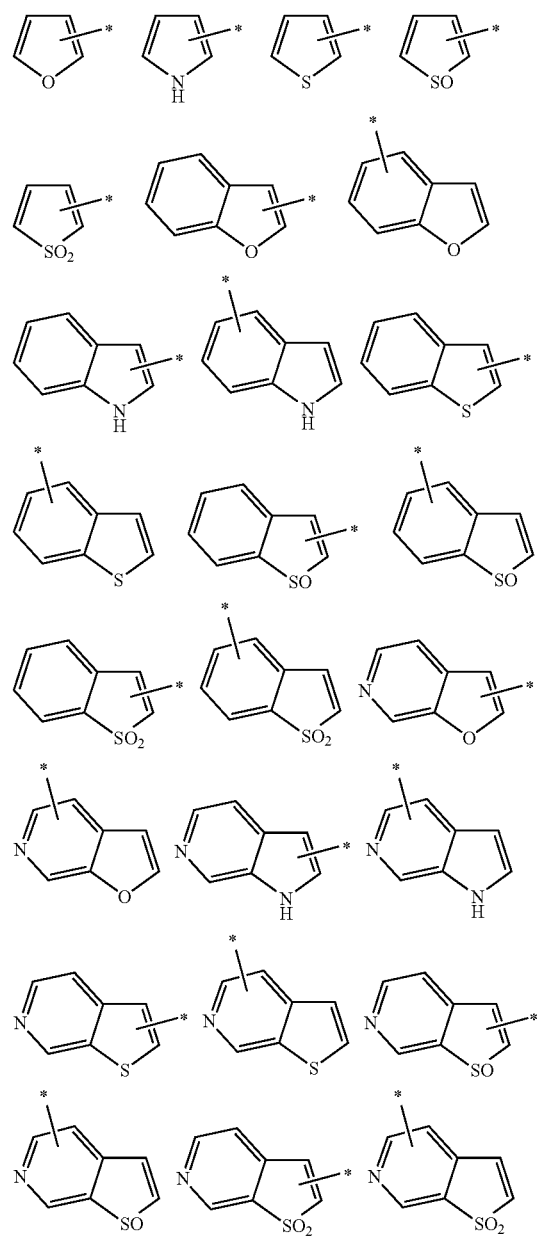

-continued
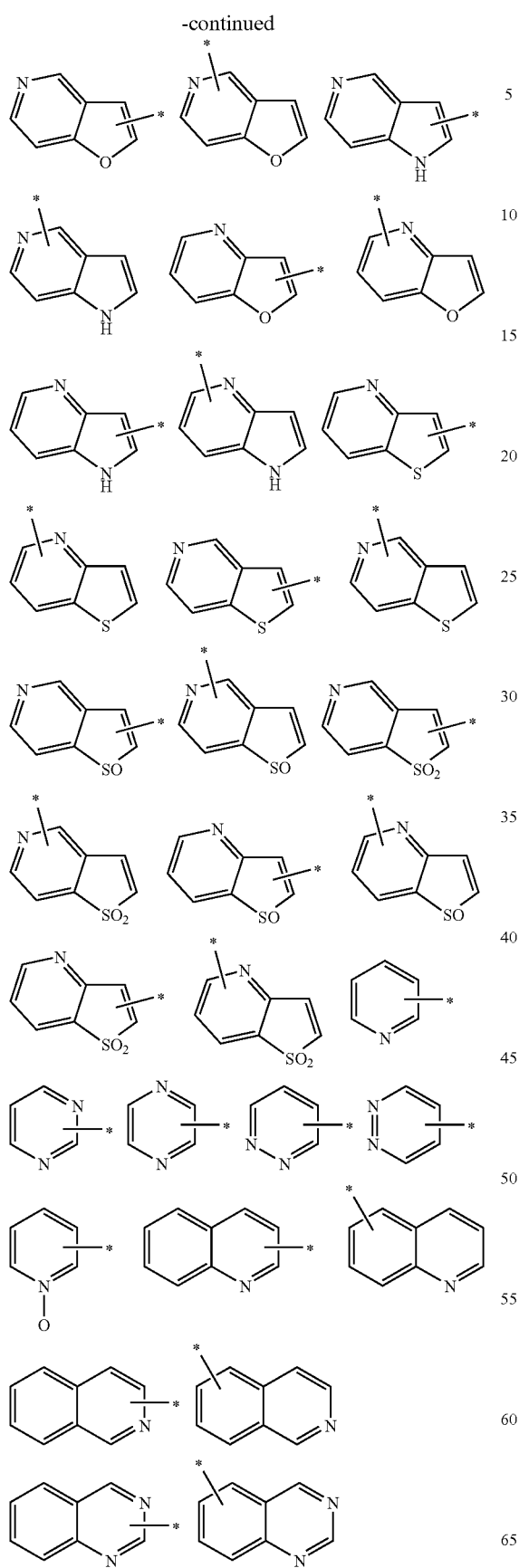
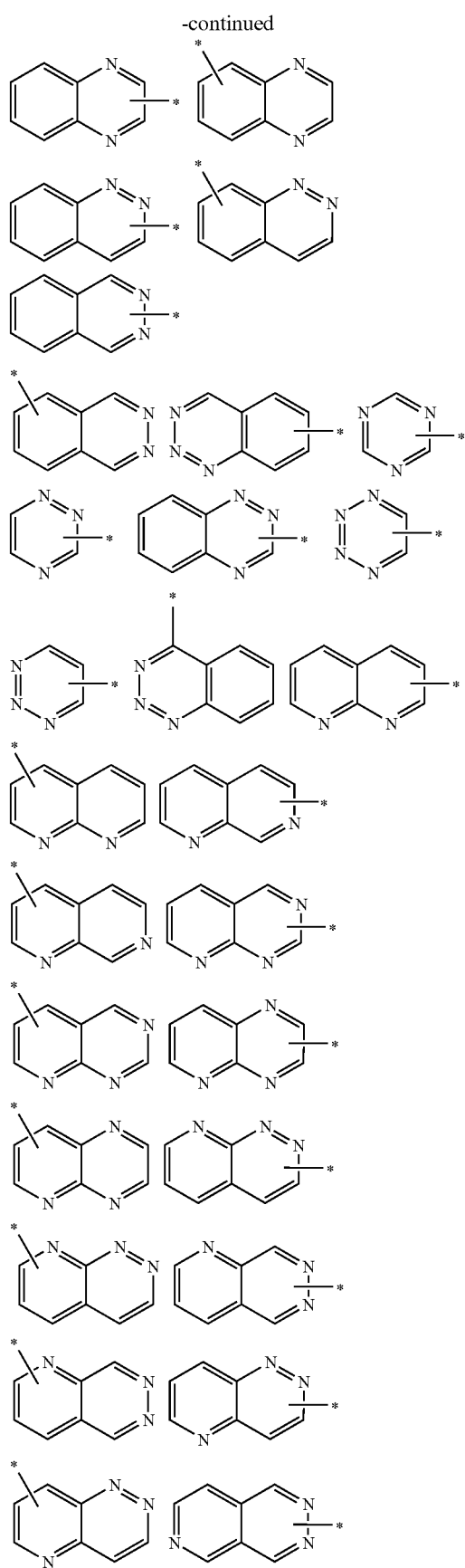

-continued
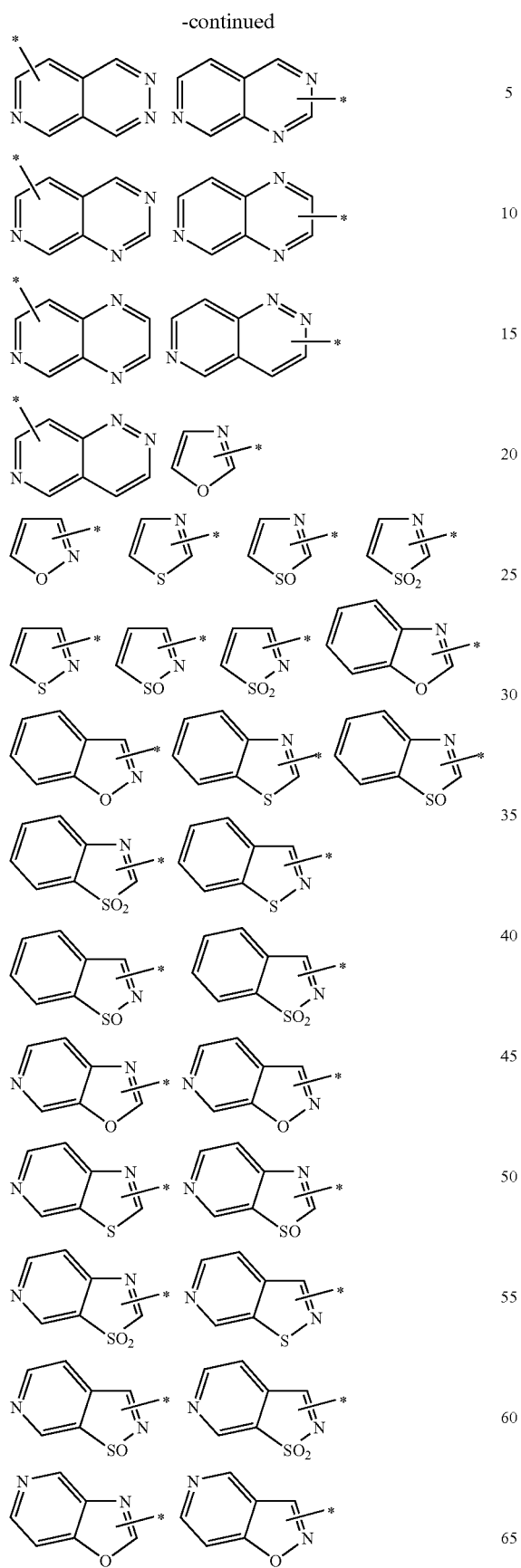
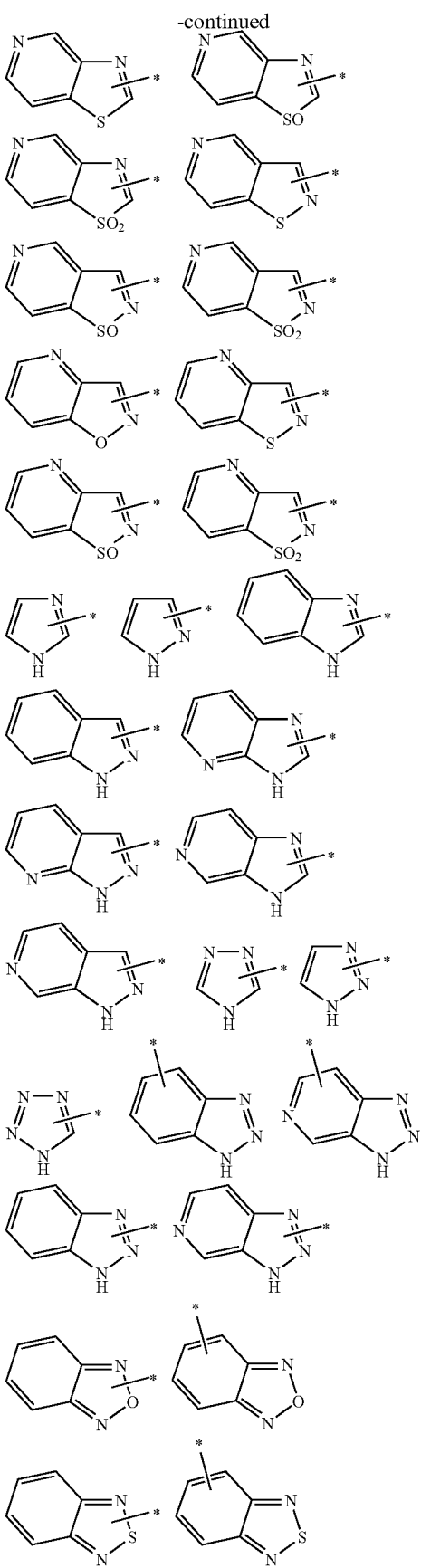

-continued
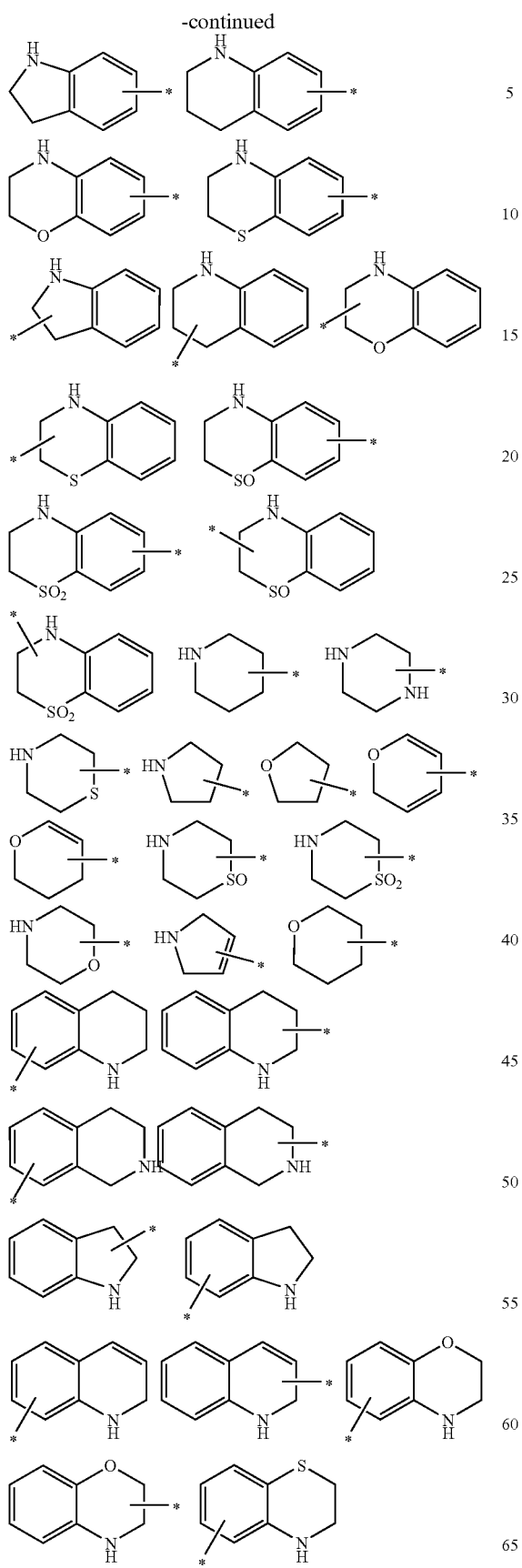
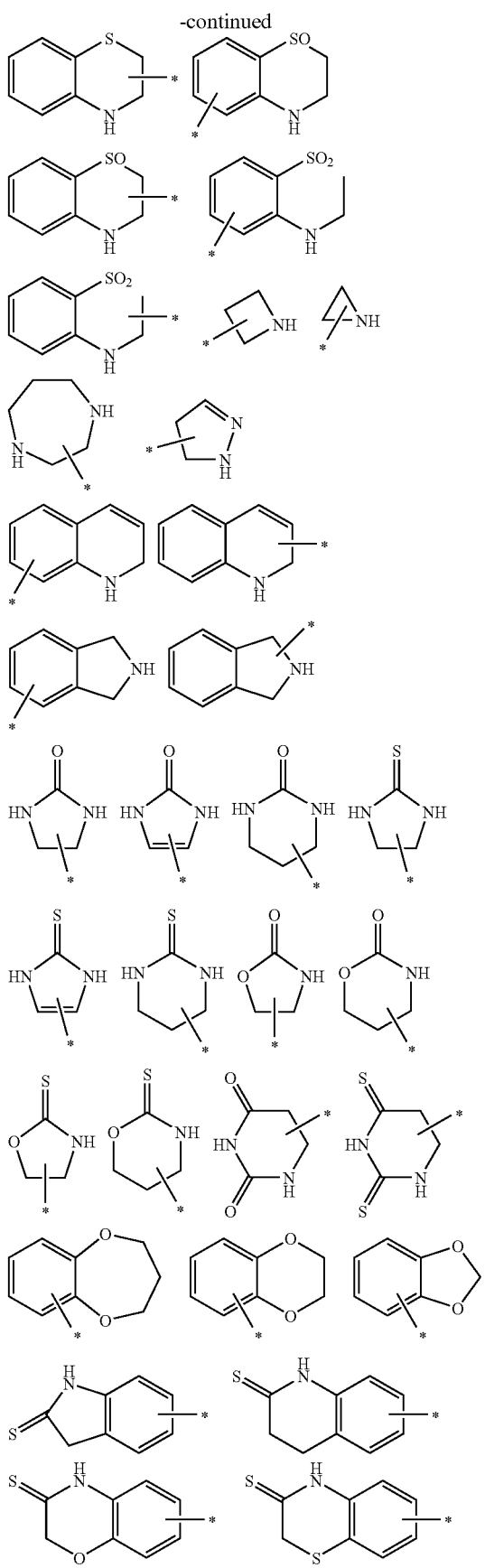

-continued
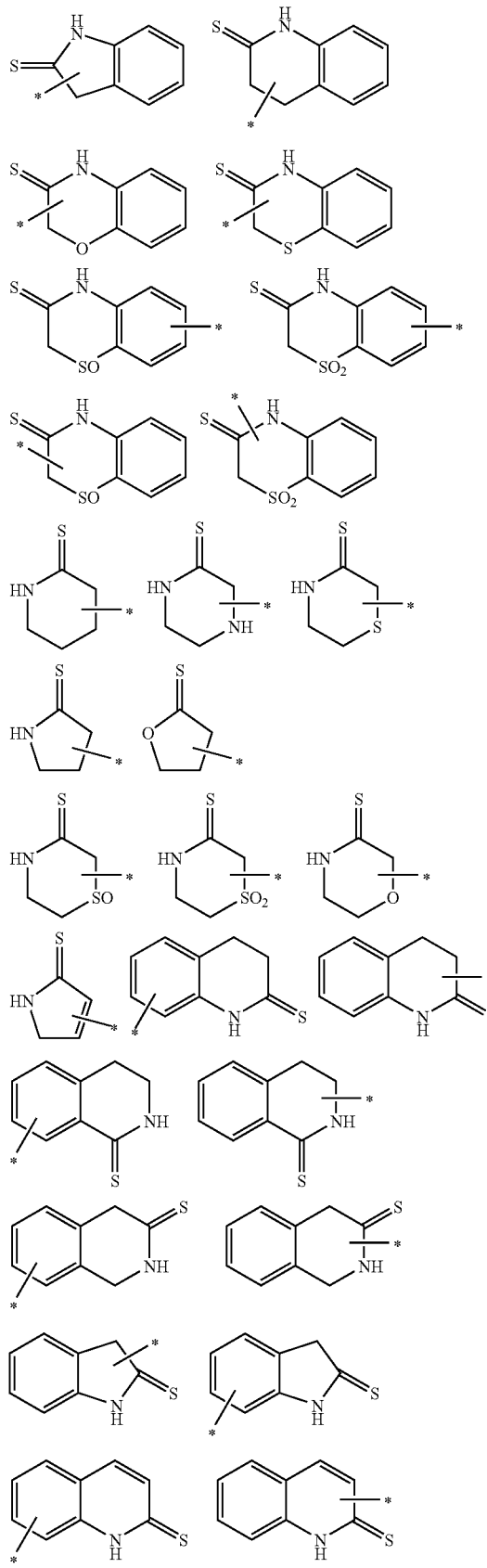
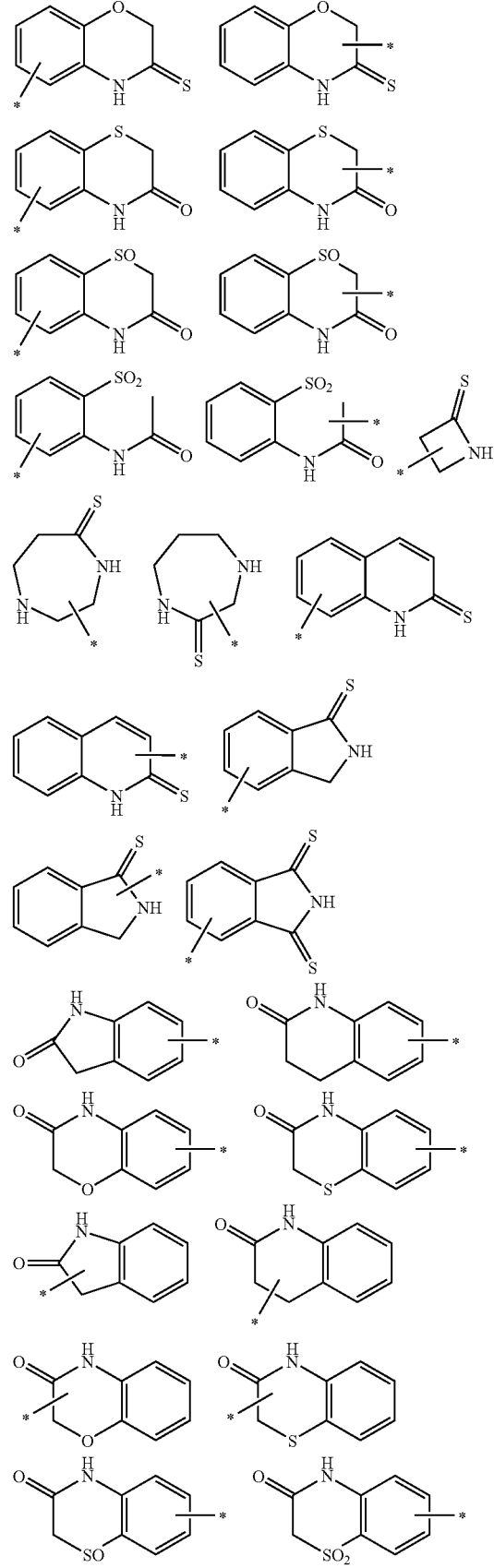

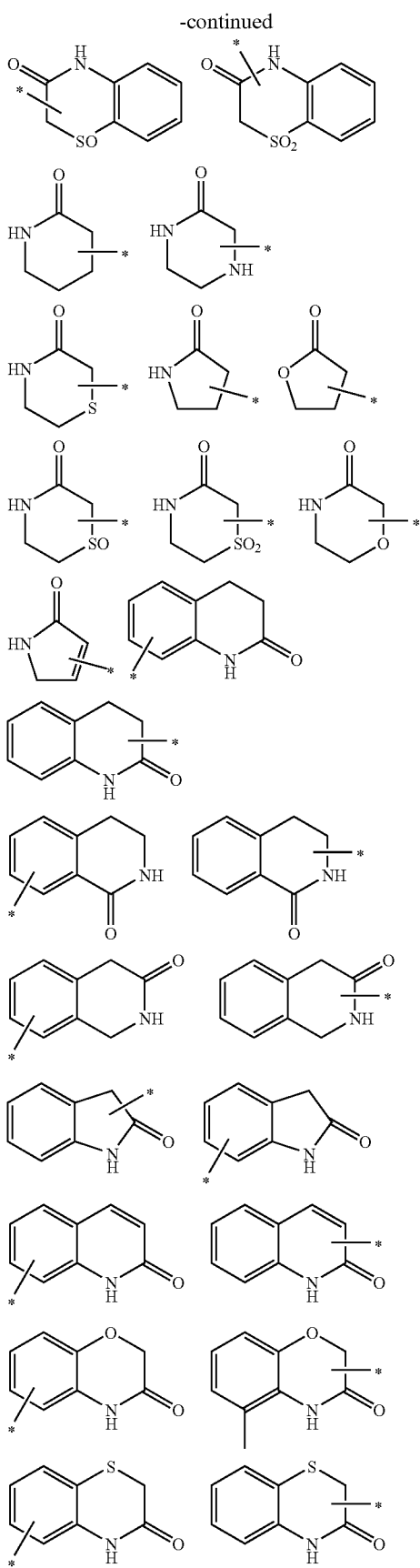
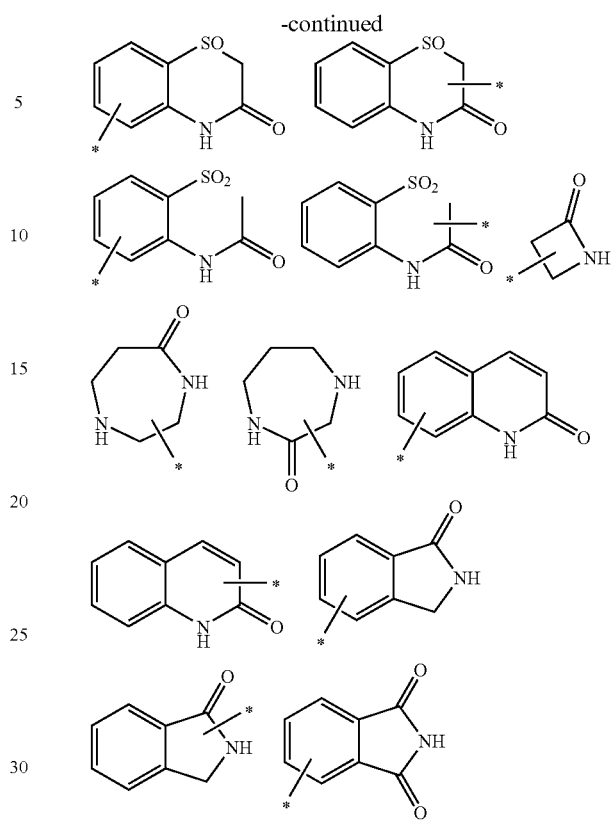

where in each case where an NH is present the bond with the asterisk connecting the respective heterocyclyl moiety to the rest of the molecule the H may be replaced with said bond and/or the H may be replaced by a substituent (thus forming substituted imino), and one or more substituents may be present as just described.

Unsubstituted or substituted mono- or bicyclic cycloalkyl is preferably mono- or bicyclic, more preferably monocyclic, $C_3$-$C_{16}$, more preferably $C_3$-$C_{10}$-cycloalkyl, which may include one or more double (e.g. in cycloalkenyl) and/or triple bonds (e.g. in cycloalkinyl) with less double and/or triple bonds than required to form a fully unsaturated ring (e.g. aryl) system. Preferably, mono- or bicyclic cycloalkyl is saturated. The mono- or bicyclic cycloalkyl is unsubstituted or substituted by one or more, e.g. one to three substitutents preferably independently selected from those mentioned above as substituents for aryl.

In unsubstituted or substituted mono- or bicyclic aryl-alkyl or —$C_1$-$C_7$-alkyl, mono- or bicyclic aryl (which is preferably unsubstituted or substituted by one or more substituents, e.g. one to three substituents independently selected from those mentioned above as substituents for aryl) is preferably as described above for aryl and is bound to alkyl, preferably $C_1$-$C_7$-alkyl, either terminally or at any other carbon in the alkyl chain, e.g. at the 1-carbon; where the $C_1$-$C_7$-alkyl is otherwise unsubstituted or substituted as described below for unsubstituted or substituted alkyl and/or with unsubstituted or substituted mono- or bicyclic aryl as described above.

In unsubstituted or substituted mono- or bicyclic heterocyclyl-alkyl or —$C_1$-$C_7$-alkyl, mono- or bicyclic heterocyclyl is preferably as described above and is unsubstituted or substituted by one or more, e.g. up to three, substitutents independently selected from those mentioned above for substituted aryl, and heterocyclyl is bound to alkyl, preferably $C_1$-$C_7$-alkyl, either terminally or at any other carbon in the alkyl chain, e.g. at the 1-carbon; where the $C_1$-$C_7$-alkyl is otherwise unsubstituted or substituted as described below for unsubstituted or substituted alkyl and/or with unsubstituted or substituted mono- or bicyclic aryl as described above.

In unsubstituted or substituted mono- or bicyclic cycloalkyl-alkyl or —$C_1$-$C_7$-alkyl, mono- or bicyclic cycloalkyl is preferably as described above and is unsubstituted or substituted by one or more, e.g. up to three, substitutents independently selected from those mentioned above for substituted aryl, and cycloalkyl is bound to alkyl, preferably $C_1$-$C_7$-alkyl, either terminally or at any other carbon in the alkyl chain, e.g. at the 1-carbon; where the $C_1$-$C_7$-alkyl is otherwise unsubstituted or substituted as described below for unsubstituted or substituted alkyl and/or with unsubstituted or substituted mono- or bicyclic aryl as described above.

Acyl is preferably unsubstituted or substituted mono- or bicyclic aryl-carbonyl or -sulfonyl, unsubstituted or substituted mono- or bicyclic heterocyclylcarbonyl or -sulfonyl, unsubstituted or substituted mono- or bicyclic cycloalkylcarbonyl or -sulfonyl, formyl or (unsubstituted or substituted alkyl, unsubstituted or substituted mono- or bicyclic aryl-$C_1$-$C_7$-alkyl, unsubstituted or substituted mono- or bicyclic heterocyclyl-$C_1$-$C_7$-alkyl or unsubstituted or substituted mono- or bicyclic cycloalkyl-$C_1$-$C_7$-alkyl)-carbonyl or -sulfonyl, or (especially if bound to N, S or O) unsubstituted or substituted alkyloxycarbonyl unsubstituted or substituted mono- or bicyclic aryl-oxycarbonyl, unsubstituted or substituted mono- or bicyclic heterocyclyloxycarbonyl, unsubstituted or substituted mono- or bicyclic cycloalkyloxycarbonyl, unsubstituted or substituted mono- or bicyclic aryl-$C_1$-$C_7$-oxycarbonyl, unsubstituted or substituted mono- or bicyclic heterocyclyl-$C_1$-$C_7$-oxycarbonyl, unsubstituted or substituted mono- or bicyclic cycloalkyl-$C_1$-$C_7$-oxycarbonyl or N-mono- or N,N-di-(unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-$C_1$-$C_7$-alkyl, unsubstituted or substituted mono- or bicyclic heterocyclyl-$C_1$-$C_7$-alkyl, unsubstituted or substituted mono- or bicyclic cycloalkyl-$C_1$-$C_7$-alkyl and/or unsubstituted or substituted alkyl)-aminocarbonyl or -aminosulfonyl, with the proviso that-oxycarbonyl bound moieties are preferably bound to a nitrogen in the rest of the molecule. Examples of preferred acyl moieties other than $R^1$ and/or $R^2$ (e.g. $R_a$, $R_b$, $R_c$ and/or $R_d$) are $C_1$-$C_7$-alkanoyl, (such as acetyl, 3,3-dimethyl-butyryl, 2,2-dimethyl-propionyl or 3,3-dimethyl-butyryl, unsubstituted (or mono-, di- or tri-(halo, $C_1$-$C_7$alkoxy, $C_1$-$C_7$-alkyloxy-$C_1$-$C_7$-alkyoxy, $C_1$-$C_7$-alkyloxy-$C_1$-$C_7$-alkyl and/or $C_1$-$C_7$-alkyl)-substituted)-phenyl-$C_1$-$C_7$-alkanoyl (e.g. the corresponding unsubstituted or substituted benzoyl or phenylacetyl) such as benzoyl or phenylacetyl, $C_3$-$C_8$-cycloalkyl-carbonyl or $C_3$-$C_8$-cycloalkyl-$C_1$-$C_7$-alkyl-carbonyll, such as cyclopropylcarbonyl, cyclobutylcarbonyl, cyclohexylacetyl or cyclohexylcarbonyl, (tetrahydrofuranyl or tetrahydropyranyl)-carbonyl or (tetrahydrofuranyl or tetrahydropyranyl)-$C_1$-$C_7$-alkyl-carbonyl, such as tetrahydrofuranyl-carbonyl, tetrahydropyranylcarbonyl, tetrahydrofuranylacetyl or tetrahydropyranylacetyl, unsubstituted or mono-, di- or tri-(halo and/or $C_1$-$C_7$-alkyl)-substituted) (phenyl- or phenyl-$C_1$-$C_7$-alkyl)-sulfonyl, such as phenylsulfonyl (=benzenesulfonyl) or phenylmethanesulfonyl, $C_1$-$C_7$-alkylsulfonyl, such as methylsulfonyl (=methanesulfonyl), ((N-mono- or N,N-di-($C_1$-$C_7$-alkyl)-aminocarbonyl, N-[phenyl or phenyl-$C_1$-$C_7$-alkyl (e.g. benzyl)]-aminocarbonyl, N-[$C_3$-$C_8$-cycloalkyl (e.g. cyclohexyl-), $C_3$-$C_8$-cycloalkyl-$C_1$-$C_7$-alkyl]aminocarbonyl, $C_1$-$C_7$-alkylaminocarbonyl or ($C_1$-$C_7$-alkyl, phenyl, naphthyl, phenyl-$C_1$-$C_7$-alkyl, napthyl-$C_1$-$C_7$-alkyl, $C_3$-$C_8$-cycloalkyl, $C_3$-$C_8$-cycloalkyl-$C_1$-$C_7$-alkyl and/or mono- or bicyclic heterocyclyl selected preferably from pyrrolyl, furanyl, thienyl (=thiophenyl), thiazolyl, pyrazolyl, triazolyl, tetrazolyl, oxetidinyl, 3-($C_1$-$C_7$-alkyl)-oxetidinyl, pyridyl, pyrimidinyl, morpholino, thiomorpholino, piperidinyl, piperazinyl, pyrrolidinyl, tetrahydrofuran-onyl, tetrahydro-pyranyl, 1H-indazanyl, benzofuranyl, benzothiophenyl, (more preferably) isoquinolinyl, quinolinyl and indolyl)-oxycarbonyl, e.g. $C_1$-$C_7$-alkoxycarbonyl, such as tert-butyloxycarbonyl, isobutyloxycarbonyl or phenyl-$C_1$-$C_7$-alkyloxycarbonyl. As acyl $R^1$ or $R^2$, indolyl-$C_1$-$C_7$-alkanoyl, e.g. indolylcarbonyl, quinolyl-$C_1$-$C_7$alkanoyl, e.g. quinolinylcarbonyl, or phenyl-$C_1$-$C_7$-alkanoyl, e.g. phenylacetyl, wherein indolyl, quinolyl and phenyl are unsubstituted or substituted by a substituent of the formula —($C_0$-$C_7$-alkylene)-(X)$_r$—($C_1$-$C_7$-alkylene)-(Y)$_s$—($C_0$-$C_7$-alkylene)-H where $C_0$-alkylene means that a bond is present instead of bound alkylene, alkylene in each case may be straight-chained or branched and unsubstituted or (with lower preference) substituted e.g. by one or more moieties as defined for substituted alkyl, especially by halo, especially fluoro, hydroxy, $C_1$-$C_7$-alkoxy, phenyloxy, naphthyloxy, $C_1$-$C_7$-alkanoyloxy, benzoyloxy, naphthoyloxy, amino, mono- or di-($C_1$-$C_7$alkyl, $C_1$-$C_7$-alkanoyl, phenyl, naphthyl, phenyl-$C_1$-$C_7$-alkyl and/or naphthyl-$C_1$-$C_7$-alkyl)-amino, carboxy, $C_1$-$C_7$-alkoxycarbonyl or cyano, r and s, each independently of the other, are 0 or 1 and each of X and Y, if present and independently of the others, is —O—, —NV—, —S—, —O—CO—, —CO—O—, —NV—CO—; —CO—NV—; —NV—SO$_2$—, —SO$_2$—NV; —NV—CO—NV—, —NV—CO—O—, —O—CO—NV—, —NV—SO$_2$—NV— wherein V is hydrogen or unsubstituted or substituted alkyl as defined below, especially $C_1$-$C_7$-alkyl, or is phenyl, naphthyl, phenyl- or naphthyl-$C_1$-$C_7$-alkyl or halo-$C_1$-$C_7$-alkyl; and optionally one or more, e.g. up to two, further substituents selected from the other substituents mentioned for substituted aryl. Unsubstituted or substituted mono- or bicyclic aryl, unsubstituted or substituted mono- or bicyclic heterocyclyl and unsubstituted or substituted mono- or bicyclic cycloalkyl are preferably as defined above whereever they are mentioned as part of acyl, unsubstituted or substituted alkyl is preferably as defined below.

Unsubstituted or substituted alkyl is preferably $C_1$-$C_{20}$-alkyl, more preferably $C_1$-$C_7$-alkyl, that is straight-chained or branched (one or, where appropriate, more times), which is unsubstituted or substituted by one or more, e.g. up to three moieties selected from unsubstituted or substituted mono- or bicyclic heterocyclyl as described below, especially pyrrolyl, furanyl, thienyl (=thiophenyl), thiazolyl, pyrazolyl, triazolyl, tetrazolyl, oxetidinyl, 3-($C_1$-$C_7$-alkyl)-oxetidinyl, pyridyl, pyrimidinyl, morpholino, thiomorpholino, piperidinyl, piperazinyl, pyrrolidinyl, tetrahydrofuran-onyl, tetrahydro-pyranyl, 1H-indazanyl, benzofuranyl, benzothiophenyl, (more preferably) isoquinolinyl, quinolinyl or especially indolyl, each of which is unsubstituted or substituted as described above for unsubstituted or substituted heterocyclyl, e.g. by one to three substitutents independently selected from halo, hydroxy, such as chloro, $C_1$-$C_7$-alkyl, such as methyl, cyano and $C_1$-$C_7$-alkanoyl, such as acetyl; from unsubstituted or substituted mono- or bicyclic cycloalkyl as described above, especially cyclopropyl, cyclobutyl, cyclopentyl or cyclohexyl each of which is unsubstituted or substituted as described below for unsubstituted or substituted cycloalkyl; or especially from the group consisting of $C_2$-$C_7$-alkenyl, $C_2$-$C_7$-alkinyl, halo, hydroxy, $C_1$-$C_7$-alkoxy, halo-$C_1$-$C_7$- alkoxy, such as trifluoromethoxy, hydroxy-$C_1$-$C_7$-alkoxy, $C_1$-$C_7$-alkoxy-$C_1$-$C_7$-alkoxy, phenyl- or naphthyloxy, phenyl- or naphthyl-$C_1$-$C_7$-alkyloxy, $C_1$-$C_7$-alkanoyloxy, ($C_1$-$C_7$-alkyl, hydroxy-$C_1$-$C_7$-alkyl, $C_1$-$C_7$-alkoxy-$C_1$-$C_7$-alkyl, phenyl and/or phenyl-$C_1$-$C_7$-alkyl)-aminocarbonyloxy, benzoyl- or naphthoyloxy, $C_1$-$C_7$-alkylthio, halo-$C_1$-$C_7$-alkthio, such as trifluoromethylthio, hydroxy-$C_1$-$C_7$-alkylthio, $C_1$-$C_7$-alkoxy-$C_1$-$C_7$-alkylthio, phenyl- or naphthylthio, phenyl- or naphthyl-$C_1$-$C_7$-alkylthio, nitro, amino, mono- or di-($C_1$-$C_7$-alkyl, phenyl, naphthyl, phenyl-$C_1$-$C_7$-alkyl, naphthyl-$C_1$-$C_7$-alkyl, hydroxy-$C_1$-$C_7$-alkyl and/or $C_1$-$C_7$-alkoxy-$C_1$-$C_7$-alkyl)-amino, $C_1$-$C_7$-alkanoylamino **, benzoyl- or naphthoylamino—**, $C_1$-$C_7$-alkylsulfonylamino, phenyl- or naphthylsulfonylamino), phenyl- or naphthyl-$C_1$-$C_7$-alkylsulfonylamino, phenyl- or naphthyl-$C_1$-$C_7$-alkylcarbonylamino, carboxyl, $C_1$-$C_7$-alkyl-carbonyl, $C_1$-$C_7$-alkoxy-carbonyl, phenyl- or naphthyloxycarbonyl, phenyl- or naphthyl-$C_1$-$C_7$-alkoxycarbonyl, carbamoyl, N-mono- or N,N-di-($C_1$-$C_7$-alkyl)-aminocarbonyl, N-mono- or N,N-di-(naphthyl- or phenyl-$C_1$-$C_7$-alkyl)-aminocarbonyl, cyano, sulfenyl (—S—OH), sulfonyl (—S(═O)—OH), $C_1$-$C_7$-alkylsulfinyl ($C_1$-$C_7$-alkyl-S(═O)—), phenyl- or naphthylsulfinyl, phenyl- or naphthyl-$C_1$-$C_7$-alkylsulfinyl, sulfonyl, $C_1$-$C_7$-alkylsulfonyl, phenyl- or naphthylsulfonyl, phenyl- or naphthyl-$C_1$-$C_7$-alkylsulfonyl, sulfamoyl, N-mono or N,N-di-($C_1$-$C_7$-alkyl, phenyl-, naphthyl, phenyl-$C_1$-$C_7$-alkyl or naphthyl-$C_1$-$C_7$-alkyl)-aminosulfonyl, N-mono-, N'-mono-, N,N-di- or N,N,N'-tri-($C_1$-$C_7$-alkyl, hydroxy-$C_1$-$C_7$-alkyl, $C_1$-$C_7$-alkoxy-$C_1$-$C_7$-alkyl, phenyl and/or phenyl-$C_1$-$C_7$-alkyl)-aminocarbonylamino or -aminocarbonyloxy and N-mono-, N'-mono-, N,N-di- or N,N,N'-tri-($C_1$-$C_7$alkyl, hydroxy-$C_1$-$C_7$-alkyl and/or $C_1$-$C_7$-alkoxy-$C_1$-$C_7$-alkyl)aminosulfonylamino;

where any phenyl or naphthyl mentioned as substituent of or as part of a substituent of substituted alkyl is unsubstituted or substituted by one or more, preferably up to three, moieties independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycabonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfo, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro, or preferably, where preferred substituents are mentioned, by one or more of these mentioned substituents.

Unsubstituted or substituted alkenyl is preferably $C_2$-$C_{20}$-alkenyl, more preferably $C_2$-$C_7$-alkenyl with one or, if possible, more double bonds, that is straight-chained or branched (one or, where appropriate, more times), which is unsubstituted or substituted by one or more, e.g. up to three moieties selected from those mentioned as substituents for substituted alkyl and from unsubstituted or substituted mono- or bicyclic aryl, each preferably as described above. Substituents with an active hydrogen (e.g. hydroxy or amino) are preferably present in the form of tautomers in equilibrium if bound directly to a carbon with a double bond, preferably at such positions substituents with active hydrogen are avoided.

Unsubstituted or substituted alkynyl is preferably $C_2$-$C_{20}$-alkynyl, more preferably $C_2$-$C_7$-alkynyl with one or, if possible, more triple bonds, that is straight-chained or branched (one or, where appropriate, more times), which is unsubstituted or substituted by one or more, e.g. up to three moieties selected from those mentioned as substituents for subsituted alkyl and from unsubstituted or substituted mono- or bicyclic aryl, each preferably as described above. Substituents with an active hydrogen (e.g. hydroxy or amino) are preferably present in the form of tautomers in equilibrium if bound directly to a carbon with a triple bond, preferably at such positions substituents with active hydrogen are avoided.

Esterified hydroxy is preferably acyloxy with acyl as defined above, more preferably $C_1$-$C_7$-alkanoyloxy or benzoyloxy.

Etherified hydroxy is preferably substituted $C_1$-$C_7$-alkyloxy wherein substituted alkyl is preferably as defined above, unsubstituted or substituted mono- or bicyclic aryloxy, unsubstituted or substituted mono- or bicyclic aryl-$C_1$-$C_7$-alkyloxy, unsubstituted or substituted mono- or bicyclic heterocyclyloxy, unsubstituted or substituted mono- or bicyclic heterocyclyloxy-$C_1$-$C_7$-alkyloxy, unsubstituted or substituted mono- or bicyclic cycloalkyloxy or unsubstituted or substituted mono- or bicyclic cycloalkyl-$C_1$-$C_7$-alkyloxy (where in each case the moieties are preferably defined as above) or more preferably unsubstituted alkyloxy, especially $C_1$-$C_7$-alkyloxy.

Where an asterisk (*) marks a the bond binding a moiety, the corresponding bond is that shown in the corresponding formula of the respective compound of the formula I (or a precursor thereof) binding the respective moiety.

The preceding and especially the following preferred embodiments of the moieties and symbols in formula I can be employed independently of each other to replace more general definitions and thus to define specially preferred embodiments of the invention, where the remaining definitions can be kept broad as defined in embodiments of the inventions defined above of below.

Preferably, not more than one of $R_1$ and $R_2$ is acyl, the other has one of the meanings given hereinabove or hereinbelow for these moieties other than acyl.

As $R^3$, moieties of the formulae (a), (b), (c), (f) and slightly less (g), more preferably of the formulae (a), (b) or (f), are especially preferred.

The symbol m preferably stands for 0 or 2.

$R_d$ preferably is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, or (if m=2) is —N($R_b$)($R_c$) wherein $R_b$ and $R_c$ are as defined above or below.

$R_e$ is preferably hydrogen.

Preferably, at least one of $R^4$ and $R^5$ is hydrogen (i.e. the preferred compounds of the invention are (3,4-di-, 3,3,- tri, 3,4,4-tri-)substituted pyrrolidines), more preferably both are hydrogen.

In all definitions above and below the person having skill in the art will, without undue experimentation or considerations, be able to recognize which are relevant (e.g. those that if present provide compounds that are sufficiently stable for the manufacture of pharmaceuticals, e.g. having a half-life of more than 30 seconds) and thus are preferably encompassed by the present claims and that only chemically feasible bonds and substitutions (e.g. in the case of double or triple bonds, hydrogen carrying amino or hydroxy groups and the like) are encompassed, as well as tautomeric forms where present, especially in equilibrium. For example, preferably, for reasons of stability or chemical feasibility, directly vicinal atoms in chains preferably are not selected from oxy plus oxy, thio plus oxy, oxy plus thio or thio plus thio, except where ring systems or the like are present that are sufficiently stable. Substitutents binding via an O (e.g. in $C_1$-$C_7$-alkoxy) or S that is part of them are preferably not bound to nitrogen e.g. in rings.

Salts are especially the pharmaceutically acceptable salts of compounds of formula I. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula I with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between the compounds in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula I or their precursors, is to be understood as referring also to one or more salts thereof or a mixture of a corresponding free compound and one or more salts thereof, each of which is intended to include also any solvate, metabolic precursor such as ester or amide of the compound of formula I, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is intended to include the plural (for example also different configuration isomers of the same compound, e.g. enantiomers in racemates or the like) or preferably the singular ("one").

The compounds of the present invention can possess two or more asymmetric centers depending on the choice of the substituents. The preferred absolute configurations are as indicated herein specifically. However, any possible isolated or pure diastereoisomers, enantiomers or geometric enantiomers, and mixtures thereof, e.g., mixtures of enantiomers, such as racemates, are encompassed by the present invention.

As described above, the present invention provides in some of its important embodiments the use of (3,4-di-, 3,4,4-tri- or 3,3,4,4-tetra-)substituted pyrrolidine compounds for the preparation of a pharmaceutical formulation for the treatment of a disease that depends on activity of renin; the use of a compound of that class in the treatment of a disease that depends on activity of renin; compounds that are part of a subclass of these substituted pyrrolidine compounds for use in the diagnostic and therapeutic treatment of a warm-blooded animal, especially for the treatment of a disease (=disorder) that depends on activity of renin; new compounds that are part of a subclass of these substituted pyrrolidine compounds; pharmaceutical formulations comprising said substituted pyrrolidine compounds, and/or a method of treatment comprising administering said substituted pyrrolidine compounds, a method for the manufacture especially of said new substituted pyrrolidine compounds, as well as novel intermediates, starting materials and/or partial steps for their synthesis.

"Inappropriate" renin activity preferably relates to a state of a warm-blooded animal, especially a human, where renin shows a renin activity that is too high in the given situation (e.g. due to one or more of misregulation, overexpression e.g. due to gene amplification or chromosome rearrangement or infection by microorganisms such as virus that express an aberrant gene, abnormal activity e.g. leading to an erroneous substrate specificity or a hyperactive renin e.g. produced in normal amounts, too low activity of renin activity product removing pathways, high substrate concentration and/or the like) and/or leads to or supports a renin dependent disease or disorder as mentioned above and below, e.g. by too high renin activity. Such inappropriate renin activity may, for example, comprise a higher than normal activity, or further an activity in the normal or even below the normal range which, however, due to preceding, parallel and or subsequent processes, e.g. signaling, regulatory effect on other processes, higher substrate or product concentration and the like, leads to direct or indirect support or maintenance of a disease or disorder, and/or an activity that supports the outbreak and/ or presence of a disease or disorder in any other way. The inappropriate activity of renin may or may not be dependent on parallel other mechanisms supporting the disorder or disease, and/or the prophylactic or therapeutic effect may or may include other mechanisms in addition to inhibition of renin. Therefore "dependent" has to be read as "dependent inter alia", (especially in cases where a disease or disorder is really exclusively dependent only on renin) preferably as "dependent mainly", more preferably as "dependent essentially only". A disease dependent on (especially inappropriate) activity of renin may also be one that simply responds to modulation of renin activity, especially responding in a beneficial way (e.g. lowering the blood pressure) in case of renin inhibition.

Where a disease or disorder dependent on inappropriate activity of a renin is mentioned (such in the definition of "use" in the following paragraph and also especially where a compound of the formula I is mentioned for use in the diagnostic or therapeutic treatment which is preferably the treatment of a disease or disorder dependent on inappropriate renin activity, this refers preferably to any one or more diseases or disorders that depend on inappropriate activity of natural renin and/or one or more altered or mutated forms thereof.

Where subsequently or above the term "use" is mentioned (as verb or noun) (relating to the use of a compound of the formula I or of a pharmaceutically acceptable salt thereof, or a method of use thereof), this (if not indicated differently or to be read differently in the context) includes any one or more of the following embodiments of the invention, respectively (if not stated otherwise): the use in the treatment of a disease or disorder that depends on (especially inappropriate) activity of renin, the use for the manufacture of pharmaceutical compositions for use in the treatment of a disease or disorder that depends on (especially inappropriate) activity of renin; a method of use of one or more compounds of the formula I in the treatment of a disease or disorder that depends on (especially inappropriate) activity of renin; a pharmaceutical preparation comprising one or more compounds of the formula I for the treatment of a disease or disorder that depends on (especially inappropriate) activity of renin; and one or more compounds of the formula I for use in the treatment of a disease or disorder in a warm-blooded animal, especially a human, preferably a disease that depends on (especially inappropriate) activity of renin; as appropriate and expedient, if not stated otherwise.

The terms "treat", "treatment" or "therapy" refer to the prophylactic (e.g. delaying or preventing the onset of a disease or disorder) or preferably therapeutic (including but not limited to preventive, delay of onset and/or progression, palliative, curing, symptom-alleviating, symptom-reducing, patient condition ameliorating, renin-modulating and/or renin-inhibiting) treatment of said disease(s) or disorder(s), especially of the one or more diseases or disorders mentioned above or below.

PREFERRED EMBODIMENTS ACCORDING TO THE INVENTION

The groups of preferred embodiments of the invention mentioned in the claims and below are not to be regarded as exclusive, rather, e.g., in order to replace general expressions or symbols with more specific definitions, parts of those groups of compounds can be interchanged or exchanged using the definitions given above, or omitted, as appropriate, and each of the more specific definitions, independent of any others, may be introduced independently of or together with one or more other more specific definitions for other more general expressions or symbols.

In a first preferred embodiment, the invention relates to a compound of the formula I wherein $R^1$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl, substituted or unsubstituted alkynyl or acyl;

$R^2$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, substituted monocyclic or (preferably) unsubstituted or substituted bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl or substituted or unsubstituted alkynyl; with the proviso that if $R^1$ is one of the moieties mentioned in the definition of $R^1$ other than acyl then $R^2$ can also be unsubstituted (or substituted) monocyclic aryl-alkyl (meaning that in addition to the group of other moieties mentioned in the definition of $R^2$, the substituent $R^2$ can also be selected from unsubstituted monocyclic aryl-alkyl);

$R^3$ is a moiety selected from the group of moieties of the formulae

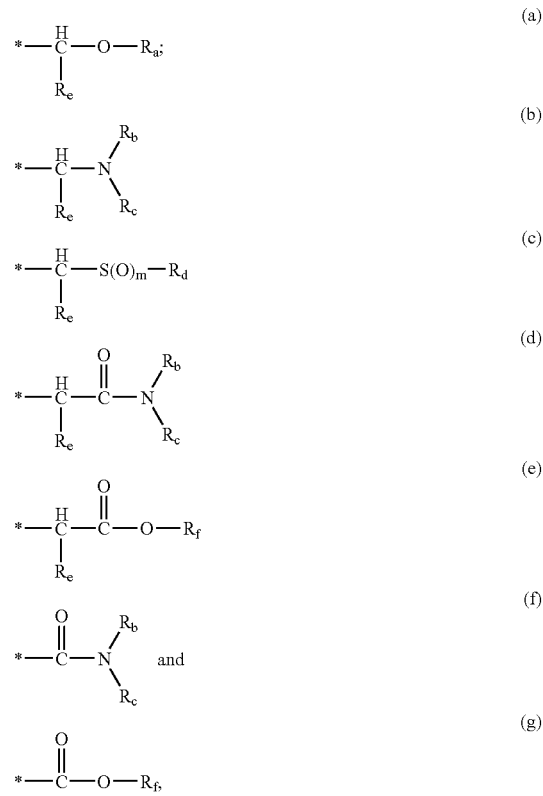

where in any of the moieties of the formulae given above under (a), (b), (c), (d), (e), (f) and (g) the asterisk (*) shows the bond binding the respective moiety $R^3$ to the rest of the molecule in formula I, $R_a$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, acyl or hydrogen;

$R_b$ and $R_c$ are independently selected from the group consisting of unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted bicyclic aryl-alkyl, unsubstituted or substituted mono- or bicyclic heterocyclyl-alkyl, unsubstituted or substituted mono- or bicyclic cycloalkyl-alkyl, acyl or hydrogen, with the proviso that preferably not more than one of $R_b$ and $R_c$ is acyl, and with the proviso that if $R_c$ is one of the mentioned moieties other than acyl (meaning here and hereinafter that $R_c$ is one of the moieties mentioned for $R_b$ and $R_c$ except for acyl, especially $R_c$=hydrogen or $C_1$-$C_7$-alkyl) then $R_b$ can (as additional alternative to the other mentioned moieties) also be unsubstituted or substituted monocyclic aryl-alkyl;

Rd is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (preferably if m is 0) acyl, or can have one of these meanings or can be —N($R_b$)($R_c$) if m is 1 or preferably 2;

$R_e$ is hydrogen, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or substituted or preferably unsubstituted $C_1$-$C_7$-alkyl; and $R_f$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl;

m is 0, 1 or 2;

each of $R^4$ and $R^5$ is selected, independently from the other, from hydrogen, unsubstituted or substituted alkyl, hydroxy or esterified or etherified hydroxy;

and T is methylene (—$CH_2$—) (preferred), methylene monosubstituted by alkyl (—[C(H)(alkyl)]-), carbonyl (—C(=O)—) (preferred) or thiocarbonyl (—C(=S)—);

or a pharmaceutically acceptable salt thereof, for use in the (therapeutic or prophylactic) treatment of a mammal, especially a human, preferably of a disease that depends on the activity of renin, especially a disease that responds to inhibition of renin in a beneficial way, most preferably hypertension.

Regarding new compounds, the invention especially, in a still more preferred embodiment, relates to a compound of the formula I wherein $R^1$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl, substituted or unsubstituted alkynyl or acyl;

$R^2$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl or substituted or unsubstituted alkynyl, with the proviso that if $R^1$ is one of the moieties mentioned in the definition of $R^1$ other than acyl then $R^2$ can also be unsubstituted or substituted monocyclic aryl-alkyl (meaning that in addition to the group of other moieties mentioned in the definition of $R^2$, the substituent $R^2$ can also be selected from unsubstituted monocyclic aryl-alkyl);

$R^3$ is a moiety selected from the group of moieties of the formulae

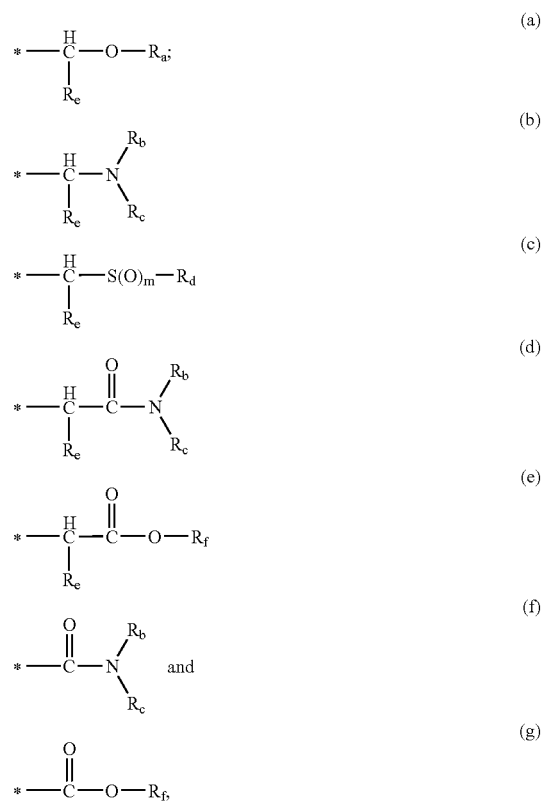

where in any of the moieties of the formulae given above under (a), (b), (c), (d), (e), (f) and (g) the asterisk (*) shows the bond binding the respective moiety $R^3$ to the rest of the molecule in formula I, $R_a$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, acyl or hydrogen;

$R_b$ and $R_c$ are independently selected from the group consisting of unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted bicyclic aryl-alkyl, unsubstituted or substituted mono- or bicyclic heterocyclyl-alkyl, unsubstituted or substituted mono- or bicyclic cycloalkyl-alkyl, acyl or hydrogen, with the proviso that preferably not more than one of $R_b$ and $R_c$ is acyl, and with the proviso that if $R_c$ is one of the mentioned (in the definition of $R_c$ in this paragraph) moieties other than acyl then $R_b$ can also be unsubstituted or substituted monocyclic aryl-alkyl;

Rd in a moiety of the formulae (c) or (e) is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (preferably if m is 0) acyl, or can have one of these meanings or can be —N($R_b$)($R_c$) if m is 1 or preferably 2;

$R_e$ is hydrogen (preferred), unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or substituted or preferably unsubstituted $C_1$-$C_7$-alkyl; and $R_f$ is substituted alkyl or preferably unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl;

m is 0, 1 or 2;

each of $R^4$ and $R^5$ is selected, independently from the other, from hydrogen, unsubstituted or substituted alkyl, hydroxy or esterified or etherified hydroxy;

and T is methylene (—$CH_2$—) (preferred), methylene monosubstituted by alkyl (—[C(H)(alkyl)]-), carbonyl (—C(=O)—) (preferred) or thiocarbonyl (—C(=S)—);

or a (preferably pharmaceutically acceptable) salt thereof.

A compound of the formula I as such

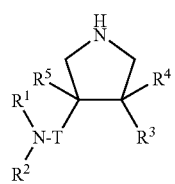

wherein $R^1$ is acyl;

$R^2$ is unsubstituted or substituted alkyl, $R^3$ is a moiety selected from the group of moieties of the formulae

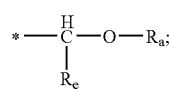

(a)

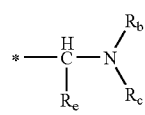

(b)

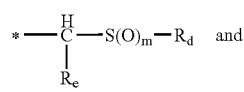

(c) and

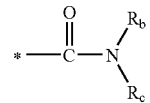

(f)

where in any of the moieties of the formulae given above under (a), (b), (c) and (f) the asterisk (*) shows the bond binding the respective moiety $R^3$ to the rest of the molecule in formula I, more preferably selected from the moieties of the formula (a), (b) or (f);

$R_a$ is acyl or hydrogen;

$R_b$ is unsubstituted or substituted alkyl, unsubstituted or substituted mono- or bicyclic aryl, unsubstituted or substituted mono- or bicyclic aryl-$C_1$-$C_7$-alkyl or acyl;

$R_c$ is hydrogen, hydroxy-$C_1$-$C_7$-alkyl, $C_1$-$C_7$-alkyloxy-$C_1$-$C_7$-alkyl or preferably $C_3$-$C_8$-cycloalkyl or $C_1$-$C_7$-alkyl;

$R_d$ is unsubstituted or substituted mono- or bicyclic aryl-$C_1$-$C_7$-alkyl or —N($R_b$)($R_c$);

$R_e$ is hydrogen or $C_1$-$C_7$-alkyl; and m is 2;

each of $R^4$ and $R^5$ is selected, independently from the other, from hydrogen, unsubstituted or substituted alkyl, hydroxy or esterified or etherified hydroxy; where preferably at least one, more preferably both of $R^4$ and $R^5$ are hydrogen;

and T is methylene (—$CH_2$—) (preferred), methylene monosubstituted by alkyl (—[C(H)(alkyl)]-), carbonyl (—C(=O)—) (preferred) or thiocarbonyl (—C(=S)—);

or an (especially pharmaceutically acceptable) salt thereof, is one further preferred embodiment of the invention.

Highly preferably, a compound of the formula I in the preceding and subsequent embodiments (be it use, compound for use or new compound) is of the formula IA with the following configuration:

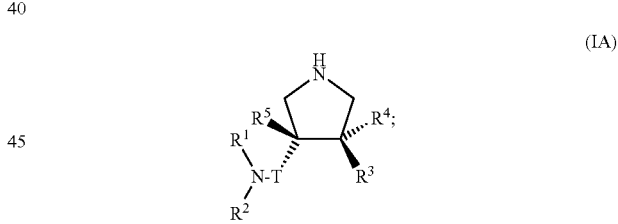

Alternatively and defining a still preferred embodiment of the invention; a compound of the formula I in the preceding and subsequent embodiments (be it use, compound for use or new compound) can be of the formula IB with the following configuration:

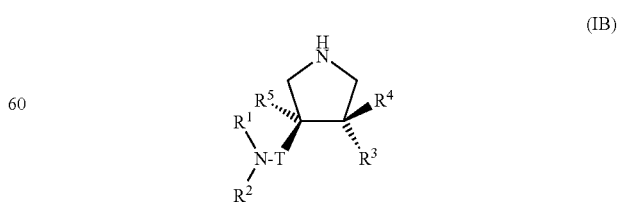

Alternatively and defining a still preferred embodiment of the invention, a compound of the formula I in the preceding and subsequent embodiments (be it use, compound for use or new compound) can be of the formula IC with the following configuration:

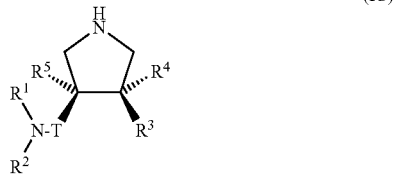
(IC)

Alternatively and defining a still preferred embodiment of the invention; a compound of the formula I in the preceding and subsequent embodiments (be it use, compound for use or new compound) can be of the formula ID with the following configuration:

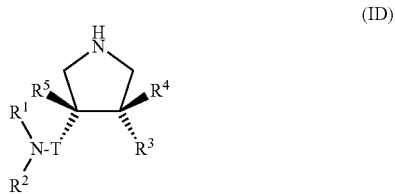
(ID)

In each of the formulae IA, IB, IC and ID, the moieties $R^1$, $R^2$, $R^3$, $R^4$, $R^5$ and L are as defined hereinbefore or preferably hereinafter for the respective more general or especially more preferred embodiments of the invention.

The formula IA, IB, IC or ID can replace formula I wherever a compound of the formula I (including a salt thereof) is mentioned hereinbefore or hereinafter; also, the corresponding intermediates are preferred.

A further preferred embodiment of the invention relates to the use of a compound of the formula I wherein $R^1$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl, substituted or unsubstituted alkynyl or acyl;

$R^2$ is unsubstituted or substituted mono- or bicyclic aryl-alkyl;

$R^3$ is a moiety selected from the group of moieties of the formulae (a), (b), (c), (d), (e), (f) or (g), more preferably of the formulae (a), (b), (c) and (f), still more preferably of the formulae (a), (b) or (f), given in the first description of a compound of the formula I in this disclosure; where in any of the moieties of these moiety formulae the asterisk (*) shows the bond binding the respective moiety $R^3$ to the rest of the molecule in formula I, $R_a$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, acyl or hydrogen;

$R_b$ and $R_c$ are independently selected from the moieties given under $R_a$, with the proviso that preferably not more than one of $R_b$ and $R_c$ is acyl, $R_d$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (preferably if m is 0) acyl, or can have one of these meanings or can be —$N(R_b)(R_c)$ if m is 1 or preferably 2;

$R_e$ is unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or substituted or preferably unsubstituted $C_1$-$C_7$-alkyl or hydrogen; and $R_f$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl;

m is 0, 1 or 2, preferably 0 or more preferably 2;

each of $R^4$ and $R^5$ is selected, independently from the other, from hydrogen, unsubstituted or substituted alkyl, hydroxy or esterified or etherified hydroxy;

and T is methylene (—$CH_2$—), methylene mono-substituted by alkyl (—[C(H)(alkyl)]-) , carbonyl (—C(=O)—) or thiocarbonyl (—C(=S)—);

or a pharmaceutically acceptable salt thereof, in the preparation of a pharmaceutical formulation for the treatment of a disease that depends on activity of renin, especially hypertension; or in the treatment of a disease that depends on activity of renin, especially hypertension.

Another preferred embodiment of the invention relates to the use of a compound of the formula I, wherein $R^1$ is phenyl, naphthyl, mono- or bicyclic heterocyclyl, phenylcarbonyl, phenylacetyl, naphthylcarbonyl, naphthylacetyl, mono- or bicyclic heterocyclylcarbonyl or -acetyl, phenylsulfonyl, naphthylsulfonyl or mono- or bicyclic heterocyclylsulfonyl; wherein mono- or bicyclic heterocyclyl is pyrrolyl, furanyl, thienyl (=thiophenyl), thiazolyl, pyrazolyl, triazolyl, tetrazolyl, oxetidinyl, 3-($C_1$-$C_7$-alkyl)-oxetidinyl, pyridyl, pyrimidinyl, morpholino, thiomorpholino, piperidinyl, piperazinyl, pyrrolidinyl, tetrahydrofuranyl, tetrahydrofuran-onyl, tetrahydro-pyranyl, 1H-indazolyl, benzofuranyl, benzothiophenyl, or more preferably isoquinolyl, quinolyl or especially indolyl, and each such mono- or bicyclic heterocyclyl, phenyl or naphthyl mentioned under $R^1$ is unsubstituted or preferably substituted by one or more, especially one to three, moieties, preferably independently selected from the group consisting of (i) a substituent of the formula —($C_0$-$C_7$-alkylene)-(X)$_r$—($C_1$-$C_7$-alkylene)-(Y)$_s$—($C_0$-$C_7$-alkylene)-H (especially in substituted aryl or substituted aryl-alkyl as $R^1$) where $C_0$-alkylene means that a bond is present instead of bound alkylene, alkylene in each case may be straight-chained or branched and unsubstituted or (with lower preference) substituted e.g. by one or more moieties as defined for substituted alkyl, especially by halo, especially fluoro, hydroxy, $C_1$-$C_7$-alkoxy, phenyloxy, naphthyloxy, $C_1$-$C_7$-alkanoyloxy, benzoyloxy, naphthoyloxy, amino, mono- or di-($C_1$-$C_7$-alkyl, $C_1$-$C_7$-alkanoyl, phenyl-$C_1$-$C_7$-alkanoyl, naphthyl-$C_1$-$C_7$-alkanoyl, phenyl, naphthyl, phenyl-$C_1$-$C_7$-alkyl and/or naphthyl-$C_1$-$C_7$-alkyl)-amino, carboxy, $C_1$-$C_7$-alkoxycarbonyl or cyano, r and s, each independently of the other, are 0 or 1 and each of X and Y, if present and independently of the others, is —O—, —NV—, —S—, —O—CO—, —CO—O—, —NV—CO—; —CO—NV—; —NV—SO$_2$—, —SO$_2$—NV; —NV—CO—NV—, —NV—CO—O—, —O—CO—NV—, —NV—SO$_2$—NV— wherein V is hydrogen or unsubstituted or substituted alkyl as defined below, especially $C_1$-$C_7$-alkyl, or is phenyl, naphthyl, phenyl- or naphthyl-$C_1$-$C_7$-alkyl or halo-$C_1$-$C_7$-alkyl; e.g. $C_1$-$C_7$-alkyl, such as methyl, ethyl, n-propyl, isopropyl, n-butyl, isobutyl, sec-butyl or tert-butyl, halo-$C_1$-$C_7$-alkyl, such as trifluoromethyl, hydroxy-$C_1$-$C_7$-alkyl, $C_1$-$C_7$-alkoxy-$C_1$-$C_7$-alkyl, such as 3-methoxypropyl or 2-methoxyethyl, $C_1$-$C_7$-alkoxy-$C_1$-$C_7$-alkoxy-$C_1$-$C_7$-alkyl, phenyloxy- or naphthyloxy-$C_1$-$C_7$-alkyl, $C_1$-$C_7$-alkanoyloxy-$C_1$-$C_7$-alkyl, amino-$C_1$-$C_7$-alkyl, such as aminomethyl, $C_1$-$C_7$-alkoxy-$C_1$-$C_7$-alkylamino-$C_1$-$C_7$-alkyl, mono- or di- ($C_1$-$C_7$-alkyl-, naphthyl-, phenyl, naphthyl-$C_1$-$C_7$-alkyl and/or phenyl-$C_1$-$C_7$-alkyl)-amino-$C_1$-$C_7$-alkyl, $C_1$-$C_7$-alkanoylamino-$C_1$-$C_7$-alkyl, $C_1$-$C_7$-alkyl-O—CO—NH—$C_1$-$C_7$-alkyl, $C_1$-$C_7$-alkylsulfonylamino-$C_1$-$C_7$-alkyl, $C_1$-$C_7$-alkyl-NH—CO—NH—$C_1$-$C_7$-alkyl, $C_1$-$C_7$-alkyl-NH—SO$_2$—NH—$C_1$-$C_7$-alkyl, $C_1$-$C_7$-alkoxy, hydroxy-$C_1$-$C_7$-alkoxy, $C_1$-$C_7$-alkoxy-$C_1$-$C_7$-alkoxy, $C_1$-$C_7$-alkanoyloxy, halo-$C_1$-$C_7$-alkoxy, such as trifluoromethoxy, phenyl- or naphthyl-$C_1$-$C_7$-alkanoyloxy, phenyl- or naphthyl-$C_1$-$C_7$-alkylaminocarbonyloxy, halo-$C_1$-$C_7$-alkylthio, such as trifluoromethylthio, phenyl- or naphthyl-$C_1$-$C_7$-alkylthio, mono- or di-($C_1$-$C_7$-alkyl-, naphthyl-$C_1$-$C_7$-alkyl-, phenyl-$C_1$-$C_7$-alkyl- and/or $C_1$-$C_7$-alkoxy-$C_1$-$C_7$-alkyl-) amino, $C_1$-$C_7$-alkanoylamino, $C_1$-$C_7$-alkylsulfonylamino, phenyl- or naphthyl-$C_1$-$C_7$-alkanoylamino, phenyl- or naphthyl-$C_1$-$C_7$-alkylaminocarbonylamino, carboxy-$C_1$-$C_7$-alkyl, $C_1$-$C_7$-alkoxy-carbonyl, hydroxy-$C_1$-$C_7$-alkoxy-carbonyl, $C_1$-$C_7$-alkoxy-$C_1$-$C_7$-alkoxycarbonyl, amino-$C_1$-$C_7$-alkoxycarbonyl, (N-) mono-($C_1$-$C_7$-alkyl)-amino-$C_1$-$C_7$-alkoxycarbonyl, $C_1$-$C_7$-alkanoylamino-$C_1$-$C_7$-alkoxycarbonyl, N- mono- or N,N-di-($C_1$-$C_7$-alkyl, naphthyl-$C_1$-$C_7$alkyl and/ or phenyl-$C_1$-$C_7$-alkyl)-aminocarbonyl, $C_1$-$C_7$-alkylsulfonyl, halo-$C_1$-$C_7$-alkylsulfonyl, hydroxy-$C_1$-$C_7$-alkylsulfonyl, $C_1$-$C7$-alkoxy-$C_1$-$C_7$-alkylsulfonyl, amino-$C_1$-$C_7$-alkylsulfonyl, N-mono- or di-($C_1$-$C_7$-alkyl)-amino-$C_1$-$C_7$-alkylsulfonyl, $C_1$-$C_7$-alkanoylamino-$C_1$-$C_7$-alkylsulfonyl, N—$C_1$-$C_7$-alkoxy-$C_1$-$C_7$-alkylcarbamoyl or N-mono- or N,N-di-($C_1$-$C_7$-alkyl)-aminosulfonyl, (ii) from $C_2$-$C_7$-alkenyl, $C_2$-$C_7$-alkynyl, phenyl, naptyl, mono- or bicyclic heterocyclyl, especially as defined below for mono- or bicyclic heterocyclyl, preferably selected from pyrrolyl, furanyl, thienyl, pyrimidine-2,4-dione-1-, -3- or -5-yl, tetrahydropyranyl and tetrahydrofuranyl, phenyl- or naphthyl- or (mono- or bicyclic heterocyclyl)-$C_1$-$C_7$-alkyl or $C_1$-$C_7$-alkyloxy wherein mono- or bicyclic heterocyclyl is as defined below, preferably selected from pyrrolyl, furanyl, tetrahydrofuranyl, tetrahydropyranyl and thienyl; such as benzyl or naphthylmethyl, tetrahydrofuranyl- or tetrahydropyranyl-$C_1$-$C_7$-alkyloxycarbonyl, benzoyl- or naphthoylamino-$C_1$-$C_7$-alkyl, (phenyl- or naphthyl- or mono- or bicyclic heterocyclyl)-sulfonylamino-$C_1$-$C_7$-alkyl wherein phenyl or naphthyl or mono- or bicyclic heterocyclyl is unsubstituted or substituted, preferably by one or more, especially one to three, $C_1$-$C_7$-alkyl moieties, (phenyl or naphthyl or mono- or bicyclic heterocyclyl)-$C_1$-$C_7$-alkylsulfonylamino-$C_1$-$C_7$-alkyl, halo, hydroxy, phenyl-$C_1$-$C_7$-alkoxy wherein phenyl is preferably unsubstituted or substituted, preferably by $C_1$-$C_7$-alkoxy and/or halo, mono- or bicyclic heterocyclyl-$C_1$-$C_7$-alkoxy, (mono- or bicyclic heterocyclyl or phenyl or naphthyl)-oxy, naphthyl-$C_1$-$C_7$-alkyloxy, benzoyl or naphthoyl or mono- or bicyclic heterocyclylcarbonyl)-oxy, (phenyl or naphthyl or mono- or bicyclic heterocyclyl)-aminocarbonyloxy, (phenyl or naphthyl or mono- or bicyclic heterocyclyl)-thio, (benzoyl or naphthoyl or mono- or bicyclic heterocyclyl)-thio, nitro, amino, di-((naphthyl or phenyl or mono- or bicyclic heterocyclyl)-$C_1$-$C_7$-alkyl)-amino, (benzoyl or naphthoyl or mono- or bicyclic heterocyclyl)-amino, (phenyl or naphthyl or mono- or bicyclic heterocyclyl)-sulfonylamino wherein phenyl or naphthyl is unsubstituted or substituted preferably by one or more, especially one to three, $C_1$-$C_7$-alkyl moieties, (phenyl or naphthyl or mono- or bicyclic heterocyclyl)-$C_1$-$C_7$-alkyl-sulfonylamino, (phenyl or naphthyl or mono- or bicyclic heterocyclyl)-aminocarbonylamino, (phenyl or naphthyl or mono- or bicyclic heterocyclyl)-oxycarbonylamino, (phenyl or naphthyl or mono- or bicyclic heterocyclyl)-$C_1$-$C_7$-alkyloxycarbonylamino, carboxyl, $C_1$-$C_7$-alkyl-carbonyl, halo-$C_1$-$C_7$-alkylcarbonyl, hydroxy-$C_1$-$C_7$-alkylcarbonyl, $C_1$-$C_7$-alkoxy-$C_1$-$C_7$-alkylcarbonyl, amino-$C_1$-$C_7$-alkylcarbonyl, (N-) mono- or (N,N-) di-($C_1$-$C_7$-alkyl)-amino-$C_1$-$C_7$-alkylcarbonyl, Cl-$C_7$-alkanoylamino-$C_1$-$C_7$-alkylcarbonyl, halo-$C_1$-$C_7$-alkoxycarbonyl, (phenyl or naphthyl or mono- or bicyclic heterocyclyl)-oxy-carbonyl, (phenyl or naphthyl or mono- or bicyclic heterocyclyl )-$C_1$-$C_7$-alkoxycarbonyl, (N,N-) di-($C_1$-$C_7$-alkyl)-amino-$C_1$-$C_7$-alkoxycarbonyl, carbamoyl, N-mono or N,N-di-(naphthyl or phenyl or mono- or bicyclic heterocyclyl)-aminocarbonyl, cyano, $C_1$-$C_7$-alkylene which is unsubstituted or substituted by up to four $C_1$-$C_7$-alkyl substituents and bound to two adjacent ring atoms of the aryl moiety, sulfenyl, sulfinyl, $C_1$-$C_7$-alkylsulfinyl, (phenyl or naphthyl or mono- or bicyclic heterocyclyl)-sulfinyl wherein phenyl or naphthyl is unsubstituted or substituted preferably by one or more, especially one to three, $C_1$-$C_7$-alkyl moieties, phenyl- or naphthyl-$C_1$-$C_7$-alkylsulfinyl, sulfonyl, (phenyl or naphthyl or mono- or bicyclic heterocyclyl)-sulfonyl wherein phenyl or naphthyl is unsubstituted or substituted preferably by one or more, especially one to three, $C_1$-$C_7$-alkyl moieties, (phenyl or naphthyl or mono- or bicyclic heterocyclyl)-$C_1$-$C_7$-alkylsulfonyl, sulfamoyl and N-mono or N,N-di-($C_1$-$C_7$-alkyl, phenyl-, naphthyl, mono- or bicyclic heterocyclyl, phenyl-$C_1$-$C_7$-alkyl, naphthyl-$C_1$-$C_7$-alkyl and/or mono- or bicyclic heterocyclyl-$C_1$-$C_7$-alkyl)-aminosulfonyl;

where any phenyl or naphthyl or mono- or bicyclic heterocyclyl—which mono- or bicyclic heterocyclyl is preferably as defined for mono- or bicyclic heterocyclyl, more preferably is selected from pyrrolyl, furanyl, tetrahydrofuranyl, tetrahydropyranyl and thienyl—mentioned as substituent of or as part of a substituent of mono- or bicyclic heterocyclyl, phenyl or naphthyl $R^1$ under (i) or (ii) is unsubstituted or substituted by one or more, preferably up to three, moieties independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycabonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfo, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro, or preferably, where preferred substituents are mentioned, by one or more of these mentioned substituents;

$R^2$ is phenyl, naphthyl, phenyl-$C_1$-$C_7$-alkyl or naphthyl-$C_1$-$C_7$-alkyl, wherein each phenyl or naphthyl mentioned so far in the definition of $R^2$ is unsubstituted or substituted as just described for substituted phenyl or naphthyl in the definition of $R^1$, or is preferably $C_1$-$C_7$-alkyl that is unsubstituted or substituted by one or more, especially up to three, e.g. one or two, substituents independently selected from the group consisting of $C_2$-$C_7$-alkenyl, $C_2$-$C_7$-alkinyl, halo, hydroxy, $C_1$-$C_7$-alkoxy, halo-$C_1$-$C_7$-alkoxy, such as trifluoromethoxy, hydroxy-$C_1$-$C_7$-alkoxy, $C_1$-$C_7$-alkoxy-$C_1$-$C_7$-alkoxy, phenyl- or naphthyloxy, phenyl- or naphthyl-$C_1$-$C_7$-alkyloxy, $C_1$-$C_7$-alkanoyloxy, ($C_1$-$C_7$-alkyl, hydroxy-$C_1$-$C_7$-alkyl, $C_1$-$C_7$-alkoxy-$C_1$-$C_7$-alkyl, phenyl and/or phenyl-$C_1$-$C_7$-alkyl)-aminocarbonyloxy, benzoyl- or naphthoyloxy, $C_1$-$C_7$-alkylthio, halo-$C_1$-$C_7$-alkthio, such as trifluoromethylthio, hydroxy-$C_1$-$C_7$-alkylthio, $C_1$-$C_7$-alkoxy-$C_1$-$C_7$-alkylthio, phenyl- or naphthylthio, phenyl- or naphthyl-$C_1$-$C_7$-alkylthio, nitro, amino, mono- or di-($C_1$-$C_7$-alkyl, phenyl, naphthyl, phenyl-$C_1$-$C_7$-alkyl, naphthyl-$C_1$-$C_7$-alkyl, hydroxy-$C_1$-$C_7$-alkyl and/or $C_1$-$C_7$-alkoxy-$C_1$-$C_7$-alkyl)-amino, $C_1$-$C_7$-alkanoylamino, benzoyl- or naphthoylamino, phenyl- or naphthyl-$C_1$-$C_7$-alkylcarbonylamino, $C_1$-$C_7$-alkylsulfonylamino, phenyl- or naphthylsulfonylamino wherein phenyl or naphthyl is unsubstituted or substituted by one or more, especially one to three, $C_1$-$C_7$-alkyl moieties, phenyl- or naphthyl-$C_1$-$C_7$-alkylsulfonylamino, carboxyl, $C_1$-$C_r$alkyl-carbonyl, $C_1$-$C_7$-alkoxycarbonyl, phenyl- or naphthyloxycarbonyl, phenyl- or naphthyl-$C_1$-$C_7$-alkoxycarbonyl, carbamoyl, N-mono- or N,N-di-($C_1$-$C_7$-alkyl)-aminocarbonyl, N-mono- or N,N-di-(naphthyl- or phenyl-$C_1$-$C_7$-alkyl)-aminocarbonyl, cyano, sulfenyl (—S—OH), sulfonyl (—S(═O)—OH), $C_1$-$C_7$-alkylsulfinyl ($C_1$-$C_7$-alkyl-S(═O)—), phenyl- or naphthylsulfinyl wherein phenyl or naphthyl is unsubstituted or substituted by one or more, especially one to three, $C_1$-$C_7$-alkyl moieties, phenyl- or naphthyl-$C_1$-$C_7$-alkylsulfinyl, sulfonyl, $C_1$-$C_7$-alkylsulfonyl, phenyl- or naphthylsulfonyl wherein phenyl or naphthyl is unsubstituted or substituted by one or more, especially one to three, $C_1$-$C_7$-alkyl moieties, phenyl- or naphthyl-$C_1$-$C_7$-alkylsulfonyl, sulfamoyl, N-mono or N,N-di-($C_1$-$C_7$-alkyl, phenyl-, naphthyl, phenyl-$C_1$-$C_7$-alkyl or naphthyl-$C_1$-$C_7$-alkyl)-aminosulfonyl, N-mono-, N'-mono-, N,N-di- or N,N,N'-tri-($C_1$-$C_7$-alkyl, hydroxy-$C_1$-$C_7$-alkyl, $C_1$-$C_7$-alkoxy-$C_1$-$C_7$-alkyl, phenyl and/or phenyl-$C_1$-$C_7$-alkyl)-aminocarbonyla or -aminocarbonyloxy and N-mono-, N'-mono-, N,N-di- or N,N,N'-tri-($C_1$-$C_7$-alkyl, hydroxy-$C_1$-$C_7$-alkyl and/or $C_1$-$C_7$-alkoxy-$C_1$-$C_7$-alkyl)aminosulfonylamino;

or $C_3$-$C_{10}$-cycloalkyl or $C_3$-$C_{10}$-cycloalkyl-$C_1$-$C_7$-alkyl;

$R^3$ is a moiety selected from the group of moieties of the formulae

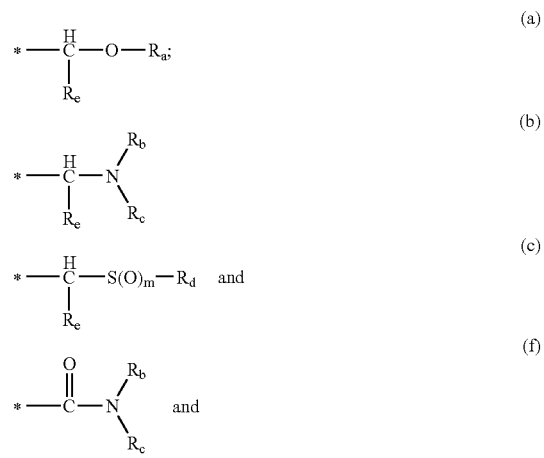

where in any of the moieties of the formulae given above under (a), (b), (c) and (f) the asterisk (*) shows the bond binding the respective moiety $R^3$ to the rest of the molecule in formula I, $R_a$ is acyl selected from the group consisting of $C_1$-$C_7$-alkanoyl, such as acetyl, 3,3-dimethyl-butyryl, 2,2-dimethyl-propionyl or 3,3-dimethyl-butyryl, unsubstituted (or with lower preference) mono-, di- or tri-(halo $C_1$-$C_7$-alkoxy, $C_1$-$C_7$-alkyloxy-$C_1$-$C_7$-alkyoxy, $C_1$-$C_7$-alkyloxy-$C_1$-$C_7$-alkyl and/or $C_1$-$C_7$-alkyl)-substituted) phenyl-$C_1$-$C_7$-alkanoyl, $C_3$-$C_8$-cycloalkylcarbonyl or $C_3$-$C_8$-cycloalkyl-$C_1$-$C_7$-alkyl-carbonyl, such as cyclopropylcarbonyl, cyclobutylcarbonyl, cyclohexylacetyl or cyclohexylcarbonyl, (tetrahydrofuranyl or tetrahydropyranyl)-carbonyl or (tetrahydrofuranyl or tetrahydropyranyl)-$C_1$-$C_7$-alkyl-carbonyl, such as tetrahydrofuranylcarbonyl, tetrahydropyranylcarbonyl, tetrahydrofuranylacetyl or tetrahydropyranylacetyl, N-mono- or N,N-di-($C_1$-$C_7$-alkyl)-aminocarbonyl, N-[phenyl or phenyl-$C_1$-$C_7$-alkyl (e.g. benzyl)]-aminocarbonyl, N-[$C_3$-$C_8$-cycloalkyl (e.g. cyclohexyl-) or $C_3$-$C_8$-cycloalkyl-$C_1$-$C_7$-alkyl]aminocarbonyl, $C_1$-$C_7$-alkylaminocarbonyl, or ($C_1$-$C_7$-alkyl, phenyl, naphthyl, phenyl-$C_1$-$C_7$-alkyl and/or napthyl-$C_1$-$C_7$-alkyl)-oxycarbonyl, e.g. $C_1$-$C_7$-alkoxycarbonyl, such as tert-butyloxycarbonyl or isobutyloxycarbonyl, or phenyl-$C_1$-$C_7$-alkyloxycarbonyl; or is hydrogen;

$R_b$ is $C_1$-$C_7$-alkyl or—in each case unsubstituted or substituted - phenyl, naphthyl, phenyl-$C_1$-$C_7$-alkyl or naphthyl-$C_1$-$C_7$-alkyl wherein in the case of a substituted moiety the substituents are one or more, especially up to three, substituents independently selected from the group consisting of $C_1$-$C_7$-alkyl, such as methyl, ethyl, n-propyl, isopropyl, n-butyl, isobutyl, sec-butyl or tert-butyl, $C_2$-$C_7$-alkenyl, $C_2$-$C_7$-alkinyl, hydroxy-$C_1$-$C_7$-alkyl, halo-$C_1$-$C_7$-alkyl, such as trifluoromethyl, $C_1$-$C_7$-alkoxy-$C_1$-$C_7$-alkyl, such as 3-methoxypropyl or 2-methoxyethyl, amino-$C_1$-$C_7$-alkyl, $C_1$-$C_7$-alkoxy, hydroxy-$C_1$-$C_7$-alkoxy, $C_1$-$C_7$-alkoxy-$C_1$-$C_7$-alkoxy, $C_1$-$C_7$-alkanoyloxy, amino, mono- or di-($C_1$-$C_7$-alkyl)-amino, $C_1$-$C_7$-alkanoylamino, $C_1$-$C_7$-alkylsulfonylamino, $C_1$-$C_7$-alkoxy-carbonyl, carboxy-$C_1$-$C_7$-alkyl, halo, hydroxy, halo-$C_1$-$C_7$-alkoxy, such as trifluoromethoxy, halo-$C_1$-$C_7$-alkylthio, such as trifluoromethylthio, nitro, carboxyl, $C_1$-$C_7$-alkyl-carbonyl, halo-$C_1$-$C_7$-alkylcarbonyl, hydroxy-$C_1$-$C_7$-alkylcarbonyl, $C_1$-$C_7$-alkoxy-$C_1$-$C_7$-alkylcarbonyl, halo-$C_1$-$C_7$- alkoxycarbonyl, carbamoyl, cyano, $C_1$-$C_7$-alkylsulfinyl, sulfonyl, $C_1$-$C_7$-alkylsulfonyl, halo-$C_1$-$C_7$-alkylsulfonyl, hydroxy-$C_1$-$C_7$-alkylsulfonyl, $C_1$-$C_7$-alkoxy-$C_1$-$C_7$-alkylsulfonyl, sulfamoyl and N-mono or N,N-di-($C_1$-$C_7$-alkyl)-aminosulfonyl; or is acyl as just defined under $R_a$ or selected from unsubstituted or mono-, di- or tri-(halo and/or $C_1$-$C_7$alkyl)-substituted (phenyl or phenyl-$C_1$-$C_7$-alkyl)-sulfonyl, such as phenylsulfonyl or phenylmethanesulfonyl, or $C_1$-$C_7$-alkylsulfonyl, such as methanesulfonyl;

$R_c$ is hydrogen, $C_1$-$C_7$-alkyl, $C_3$-$C_8$-cycloalkyl, hydroxy-$C_1$-$C_7$-alkyl or $C_1$-$C_7$-alkyloxy-$C_1$-$C_7$-alkyl, preferably hydrogen or $C_1$-$C_7$-alkyl;

$R_d$ is unsubstituted or substituted phenyl- or naphthyl-$C_1$-$C_7$-alkyl wherein in the case of a substituted moiety the substituents are one or more, especially up to three, substituents independently selected from those mentioned for unsubstituted of substituted phenyl- or naphthyl-$C_1$-$C_7$-alkyl under $R_b$, or is —N($R_b$)($R_c$);

$R_e$ is $C_1$-$C_7$-alkyl or preferably hydrogen; and m is 2;

each of $R^4$ and $R^5$ is selected, independently from the other, from $C_1$-$C_7$-alkyl, hydroxy, $C_1$-$C_7$-alkyloxy and preferably hydrogen;

and T is carbonyl or preferably methylene;

or a pharmaceutically acceptable salt thereof, for the treatment of a disease that depends on activity of renin, especially hypertension, or preferably for the manufacture of a pharmaceutical formulation for the treatment of a disease that depends on activity of renin, especially hypertension.

A quite preferred embodiment of the invention relates to a new compound of the formula I, wherein $R^1$, $R^3$, $R^4$, $R^5$, m and T are as defined in the preceding paragraph and $R^2$ is phenyl, naphthyl or (with lower preference) naphthyl-$C_1$-$C_7$-alkyl, wherein each phenyl or naphthyl mentioned so far in the definition of $R^2$ is unsubstituted or substituted as just described for substituted phenyl or naphthyl in the definition of $R^1$, or preferably $C_1$-$C_7$-alkyl that is unsubstituted or substituted by one or more, especially up to three, e.g. one or two, substituents independently selected from the group consisting of $C_2$-$C_7$-alkenyl, $C_2$-$C_7$-alkinyl, halo, hydroxy, $C_1$-$C_7$-alkoxy, halo-$C_1$-$C_7$-alkoxy, such as trifluoromethoxy, hydroxy-$C_1$-$C_7$-alkoxy, $C_1$-$C_7$-alkoxy-$C_1$-$C_7$-alkoxy, phenyl- or naphthyloxy, phenyl- or naphthyl-$C_1$-$C_7$-alkyloxy, $C_1$-$C_7$-alkanoyloxy, benzoyl- or naphthoyloxy, $C_1$-$C_7$-alkylthio, halo-$C_1$-$C_7$-alkthio, such as trifluoromethylthio, hydroxy-$C_1$-$C_7$-alkylthio, $C_1$-$C_7$-alkoxy-$C_1$-$C_7$-alkylthio, phenyl- or naphthylthio, phenyl- or naphthyl-$C_1$-$C_7$-alkylthio, $C_1$-$C_7$-alkanoylthio, benzoyl- or naphthoylthio, nitro, amino, mono- or di-($C_1$-$C_7$-alkyl, hydroxy-$C_1$-$C_7$-alkyl and/or $C_1$-$C_7$-alkoxy-$C_1$-$C_7$-alkyl)-amino, mono- or di-(naphthyl- or phenyl-$C_1$-$C_7$-alkyl)-amino, $C_1$-$C_7$-alkanoylamino, benzoyl- or naphthoylamino, $C_1$-$C_7$-alkylsulfonylamino, phenyl- or naphthylsulfonylamino wherein phenyl or naphthyl is unsubstituted or substituted by one or more, especially one to three, $C_1$-$C_7$-alkyl moieties, phenyl- or naphthyl-$C_1$-$C_7$-alkylsulfonylamino, carboxyl, $C_1$-$C_7$-alkyl-carbonyl, $C_1$-$C_7$-alkoxy-carbonyl, phenyl- or naphthyloxycarbonyl, phenyl- or naphthyl-$C_1$-$C_7$-alkoxycarbonyl, carbamoyl, N-mono- or N,N-di-($C_1$-$C_7$-alkyl)-aminocarbonyl, N-mono- or N,N-di-(naphthyl- or phenyl-$C_1$-$C_7$-alkyl)-aminocarbonyl, cyano, sulfenyl, (—S—OH) sulfonyl (—S(=O)—OH), $C_1$-$C_7$-alkylsulfinyl ($C_1$-$C_7$-alkyl-S(=O)—), phenyl- or naphthylsulfinyl wherein phenyl or naphthyl is unsubstituted or substituted by one or more, especially one to three, $C_1$-$C_7$-alkyl moieties, phenyl- or naphthyl-$C_1$-$C_7$-alkylsulfinyl, sulfonyl, $C_1$-$C_7$-alkylsulfonyl, phenyl- or naphthylsulfonyl wherein phenyl or naphthyl is unsubstituted or substituted by one or more, especially one to three, $C_1$-$C_7$-alkyl moieties, phenyl- or naphthyl-$C_1$-$C_7$-alkylsulfonyl, sulfamoyl, N-mono or N,N-di-($C_1$-$C_7$-alkyl, phenyl-, naphthyl, phenyl-$C_1$-$C_7$-alkyl or naphthyl-$C_1$-$C_7$-alkyl)-aminosulfonyl, N-mono-, N'-mono-, N,N-di- or N,N,N'-tri-($C_1$-$C_7$-alkyl, hydroxy-$C_1$-$C_7$-alkyl and/or $C_1$-$C_7$-alkoxy-$C_1$-$C_7$-alkyl)-aminocarbonylamino and N-mono-, N'-mono-, N,N-di- or N,N,N'-tri-($C_1$-$C_7$-alkyl, hydroxy-$C_1$-$C_7$-alkyl and/or $C_1$-$C_7$-alkoxy-$C_1$-$C_7$-alkyl) aminosulfonylamino; or is $C_3$-$C_{10}$-cycloalkyl or $C_3$-$C_{10}$-cycloalkyl-$C_1$-$C_7$-alkyl;

or a (preferably pharmaceutically acceptable) salt thereof.

In another very preferred embodiment, the invention relates to a new compound of the formula I wherein $R^1$ is phenyl-, indolyl- or quinolyl-$C_1$-$C_7$-alkanoyl (preferably -carbonyl or -acetyl) wherein the phenyl, indolyl or quinolyl is substituted by $C_1$-$C_7$-alkyloxy-$C_1$-$C_7$-alkyloxy, $C_1$-$C_7$-alkyloxy-$C_1$-$C_7$-alkyl or $C_1$-$C_7$-alkyloxy-$C_1$-$C_7$-alkyloxy-$C_1$-$C_7$-alkyl and may further be substituted by one or more, e.g. up to three, $C_1$-$C_7$-alkyl (especially methyl) and/or $C_1$-$C_7$-alkyloxy moieties;

$R^2$ is $C_1$-$C_7$-alkyl;

$R^3$ is a moiety selected from the group of moieties of the formulae

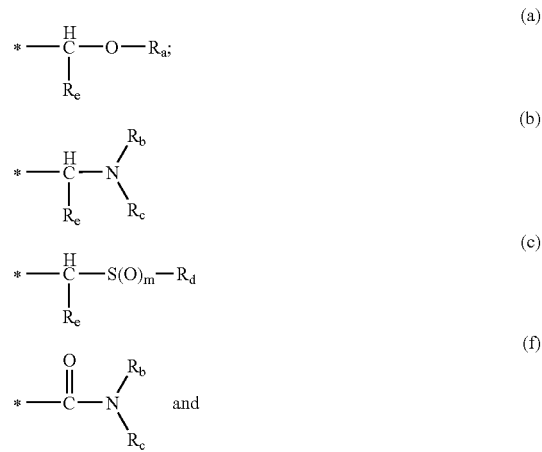

where in any of the moieties of the formulae given above under (a), (b), (c) and (f) the asterisk (*) shows the bond binding the respective moiety $R^3$ to the rest of the molecule in formula I, wherein $R_a$ is hydrogen or N-mono- or N,N-di-($C_1$-$C_7$-alkyl, (unsubstituted or halo-substituted) phenyl or naphthyl, phenyl-$C_1$-$C_7$-alkyl, naphthyl-$C_1$-$C_7$-alkyl or $C_3$-$C_8$-cycloalkyl)-aminocarbonyl;

each of $R_b$ and $R_c$ is, independently of the other, selected from hydrogen, $C_1$-$C_7$-alkyl, phenyl, naphthyl, naphthyl-$C_1$-$C_7$-alkyl, $C_3$-$C_8$-cycloalkylcarbonyl (=$C_3$-$C_8$-cycloalkyl-C(=O)—), $C_3$-$C_8$cycloalkyl-$C_1$-$C_7$-alkylcarbonyl, unsubstituted or mono-, di- or tri-(halo, $C_1$-$C_7$-alkoxy, $C_1$-$C_7$-alkyloxy-$C_1$-$C_7$-alkyoxy, $C_1$-$C_7$-alkyloxy-$C_1$-$C_7$-alkyl and/or $C_1$-$C_7$-alkyl)-substituted phenyl- or naphthyl-$C_1$-$C_7$-alkanoyl, preferably benzoyl or phenylacetyl, (tetrahydrofuranyl or tetrahydropyranyl)-carbonyl or (tetrahydrofuranyl or tetrahydropyranyl)-$C_1$-$C_7$-alkyl-carbonyl, such as tetrahydrofuranyl-carbonyl, tetrahydropyranylcarbonyl, tetrahydrofuranylacetyl or tetrahydropyranylacetyl, $C_1$-$C_7$-alkylsulfonyl (=$C_1$-$C_7$-alkanesulfonyl) or (unsubstituted or [$C_1$-$C_7$-alkyl-, halo-lower alkyl-, halo, $C_1$-$C_7$-alkyloxy-, cyano-, $C_1$-$C_7$-alkanoyl- and/or $C_1$-$C_7$-alkylsulfonyl-]substituted) (phenyl- or naphthyl)-$C_1$-$C_7$-alkylsulfonyl, with the proviso that if $R_c$ is hydrogen, $C_1$-$C_7$-alkyl, phenyl, naphthyl or naphthyl-$C_1$-$C_7$-alkyl, then $R_b$ can also be phenyl-$C_1$-$C_7$-alkyl; $R_d$ is unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, cyano-, $C_1$-$C_7$-alkanoyl- and/or $C_1$-$C_7$-alkylsulfonyl-]substituted (phenyl- or naphthyl)-$C_1$-$C_7$-alkyl;

$R_e$ is hydrogen; and m is 2;

each of $R^4$ and $R^5$ is hydrogen; and

T is carbonyl or preferably methylene;

or a (preferably pharmaceutically acceptable) salt thereof.

In the following, preferred definitions are provided individually for each variant. It should be noted that each of the preferred definitions for any variant can be combined with any preferred definition of another variant(s).

Preferred Definitions for $R^1$ $R^1$ is as defined in the claims, preferably $R^1$ is acyl as defined herein, more preferably bearing a carbonyl group.

In a first embodiment $R^1$ is unsubstituted or substituted aryl-carbonyl.

Preferred examples for the aryl moiety of the acyl substituent are phenyl and naphthyl, more preferably phenyl. When the aryl moiety is substituted, it is preferably preferably mono-, di- or tri-substituted, more preferably di-substituted. Suitable substituents for the aryl moiety are as defined herein, preferably —($C_0$-$C_7$-alkylene)-(X)$_r$—($C_1$-$C_7$-alkylene)-(Y)$_s$—($C_0$-$C_7$-alkylene)-H, wherein r and s are 0 or 1 and Y and X are independently O, NH or NH—CO—O—; or is halo, such as Cl or F, hydroxy, phenyl- or naphthyloxy, phenyl- or naphthyl-$C_1$-$C_7$-alkyloxy, monocyclic heterocyclyl-$C_1$-$C_7$-alkyloxy, wherein heterocyclyl is preferably a 5- or 6-membered ring containing a nitrogen atom, such as isoxazolyl; nitro, amino, amino-$C_1$-$C_7$-alkyl, carboxyl, and cyano, more preferably —($C_0$-$C_7$-alkylene)-(X)$_r$—($C_1$-$C_7$-alkylene)-(Y)$_s$—($C_0$-$C_7$-alkylene)-H, monocyclic heterocyclyl-$C_1$-$C_7$-alkyloxy, phenyl- or naphthyl-$C_1$-$C_7$-alkyloxy or halo. When the alkylene moieties of the formula —($C_0$-$C_7$-alkylene)-(X)$_r$—($C_1$-$C_7$-alkylene)-(Y)$_s$—($C_0$-$C_7$-alkylene)-H are substituted, they are preferably substituted by one or more, more preferably three halo such as F. Preferred examples of —($C_0$-$C_7$-alkylene)-(X)$_r$—($C_1$-$C_7$-alkylene)-(Y)$_s$—($C_0$-$C_7$-alkylene)-H include —(O or NH, preferably O)—$C_1$-$C_7$-alkyl, —$C_1$-$C_7$-alkyl, —(O or NH, preferably O)—$C_1$-$C_7$-alkylene-(O or NH, preferably O)—$C_1$-$C_7$-alkyl, —(O or NH, preferably O)—$C_1$-$C_7$-alkylene-(O or NH, preferably O)—H, —$C_1$-$C_7$-alkylene-(O or NH, preferably O)—$C_1$-$C_7$-alkylene-(O or NH, preferably O)—$C_1$-$C_7$-alkyl, -$C_1$-$C_7$-alkylene-(O or NH, preferably O)—$C_1$-$C_7$-alkyl, halo-$C_1$-$C_7$-alkyl, —(O or NH, preferably O)—halo-$C_1$-$C_7$-alkyl, or —(O or NH, preferably O)—$C_1$-$C_7$-alkylene-(O or NH, preferably O)—halo-$C_1$-$C_7$-alkyl, most preferably —OMe, —OC$_3$H$_6$OMe, methyl, ethyl, t-butyl, —CH$_2$OC$_2$H$_4$OMe, —OC$_2$H$_4$OC$_2$H$_4$, —OC$_3$H$_6$OH, —C$_4$H$_8$OMe, —CHF$_2$, —OCF$_3$, —OC$_2$H$_4$CF$_3$, —OC$_3$H$_6$CF$_3$, and —OC$_3$H$_6$OCF$_3$. In preferred embodiments, the aryl moiety is di-substituted whereby both substituents are —($C_0$-$C_7$-alkylene)-(X)$_r$—($C_1$-$C_7$-alkylene)-(Y)$_s$—($C_0$-$C_7$-alkylene)-H as defined herein, more preferably one substituent is —O—$C_1$-$C_7$-alkyl, such as OMe, or —$C_1$-$C_7$-alkyl, such as methyl or ethyl, and the other is —O—$C_1$-$C_7$-alkylene-O—$C_1$-$C_7$-alkyl, such as —OC$_3$H$_6$OMe.

In a second embodiment $R^1$ is unsubstituted or substituted heterocyclyl-carbonyl.

Preferred examples for the heterocyclyl moiety of the acyl substituent are mono- or bicyclic, preferably bicyclic, heterocyclyl. Preferred are aromatic ring systems, or in particular if a bicyclic moiety is contemplated, partially saturated ring systems, in particular whereby one of the rings is aromatic and the other is saturated. Most preferred are aromatic ring systems. The heterocyclyl moiety has preferably 1, 2 or 3, more preferably 1 or 2 heteroatoms selected from O, N or S, more preferably O or N. Particularly preferred examples include pyrrolyl, furanyl, thienyl (=thiophenyl), thiazolyl, pyrazolyl, triazolyl, tetrazolyl, oxetidinyl, 3-($C_1$-$C_7$-alkyl)-oxetidinyl, pyridyl, pyrimidinyl, morpholino, thiomorpholino, piperidinyl, piperazinyl, pyrrolidinyl, tetrahydrofuranyl, tetrahydrofuran-onyl, tetrahydro-pyranyl, 1H-indazolyl, benzofuranyl, benzothiophenyl, benzimidazolyl, benzopyrazolyl, benzo[1,2,5]oxadiazolyl, and 3,4-dihydro-2H-benzo[1,4]dioxinyl, or more preferably indolyl, isoquinolyl, quinolyl and 3,4-dihydro-2H-benzo[1,4]dioxinyl or especially indolyl, and 3,4-dihydro-2H-benzo[1,4]dioxinyl. When the heterocyclyl moiety is substituted, it is preferably mono- or di-substituted, most preferably di-substituted. Suitable substituents for the heterocyclyl moiety are as defined herein, preferably —($C_0$-$C_7$-alkylene)-(X)$_r$—($C_1$-$C_7$-alkylene)-(Y)$_s$—($C_0$-$C_7$-alkylene)-H, wherein r and s are 0 or 1 and Y and X are independently O, NH or NH—CO—O—, halo-$C_1$-$C_7$-alkyl, halo, hydroxy, phenyl- or naphthyloxy, phenyl- or naphthyl-$C_1$-$C_7$-alkyloxy, nitro, amino, amino-$C_1$-$C_7$-alkyl, carboxyl, and cyano. Preferred examples of —($C_0$-$C_7$-alkylene)-(X)$_r$—($C_1$-$C_7$-alkylene)-(Y)$_s$—($C_0$-$C_7$-alkylene)-H include —(O or NH, preferably O)—$C_1$-$C_7$-alkyl, —$C_1$-$C_7$-alkyl, —(O or NH, preferably O)—$C_1$-$C_7$-alkylene-(O or NH, preferably O)—$C_1$-$C_7$-alkyl, —(O or NH, preferably O)—$C_1$-$C_7$-alkylene-(O or NH, preferably O)—H, —$C_1$-$C_7$-alkylene-(O or NH, preferably O)—$C_1$-$C_7$-alkylene-(O or NH, preferably O)—$C_1$-$C_7$-alkyl, —$C_1$-$C_7$-alkylene-(O or NH, preferably O)—$C_1$-$C_7$-alkyl, more preferably —$C_1$-$C_7$-alkyl, —O—$C_1$-$C_7$-alkylene-O—$C_1$-$C_7$-alkyl, or —$C_1$-$C_7$-alkylene-O—$C_1$-$C_7$-alkyl, still more preferably methyl, ethyl, —C$_2$H$_4$—NH—CO—OMe, —CH$_2$OC$_2$H$_4$OMe, —OC$_2$H$_4$OC$_2$H$_4$, —OC$_3$H$_6$OH, —C$_2$H$_4$OMe, —C$_3$H$_6$OMe and —NH—C$_3$H$_6$OMe, yet more preferably—methyl, —OC$_3$H$_6$OMe and —C$_3$H$_6$OMe. Most preferably the heterocyclyl moiety is substituted by methyl and/or —C$_3$H$_6$OMe.

Preferred Definitions for $R^2$ $R^2$ is as defined in the claims, preferably $R^2$ is in a first embodiment unsubstituted or substituted alkyl as defined herein. Preferred examples are branched or straight chain $C_1$-$C_7$-alkyl which may be substituted or unsubstituted. In a preferred embodiment, $R^2$ is branched alkyl such as isopropyl, isobutyl, sec-butyl or tert-butyl, isopentyl, 1-ethylpropyl, and 1,2-dimethyl-propyl, most preferably isopropyl. Branched alkyl is preferably unsubstituted. If the alkyl moiety is substituted, suitable substituents are as defined herein, preferably O—$C_1$-$C_4$-alkyl, halo, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano.

Preferably in a second embodiment $R^2$ is cycloalkyl. Preferred examples for the cycloalkyl moiety are monocyclic rings, preferably $C_3$-$C_7$-cycloalkyl, more preferably $C_3$, $C_4$, $C_5$ and $C_6$-cycloalkyl, most preferably cyclopropyl. The cycloalkyl moiety may be substituted or unsubstituted. When the cycloalkyl moiety is substituted, it is preferably monosubstituted. Suitable substituents for the cycloalkyl moiety are as defined herein, preferably O—$C_1$-$C_4$-alkyl, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano, most preferably phenyl or naphthyl. Most preferably, the cycloalkyl moiety is unsubstituted.

Preferred Definitions for $R^3$ $R^3$ is as defined in the claims, preferably $R^3$ is a moiety selected from the group of moieties of the formulae

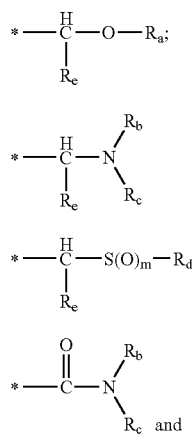

more preferably (a), (b) or (f), still more preferably (a) or (b), most preferably (b), where in any of the moieties of the formulae given above under (a), (b), (c) and (f) the asterisk (*) shows the bond binding the respective moiety $R^3$ to the rest of the molecule in formula I, wherein $R_a$ is acyl selected from $C_1$-$C_7$-alkanoyl, unsubstituted or mono-, di- or tri-(halo, $C_1$-$C_7$-alkoxy, $C_1$-$C_7$-alkyloxy-$C_1$-$C_7$-alkyoxy, $C_1$-$C_7$-alkyloxy-$C_1$-$C_7$-alkyl and/or $C_1$-$C_7$-alkyl)-substituted)phenyl-$C_1$-$C_7$-alkanoyl, $C_3$-$C_8$-cycloalkylcarbonyl or $C_3$-$C_8$-cycloalkyl-$C_1$-$C_7$-alkyl-carbonyl, (tetrahydrofuranyl or tetrahydropyranyl)-carbonyl or (tetrahydrofuranyl or tetrahydropyranyl)-$C_1$-$C_7$-alkyl-carbonyl, N-mono- or N,N-di-($C_1$-$C_7$-alkyl)-aminocarbonyl, N-[phenyl or phenyl-$C_1$-$C_7$-alkyl]-aminocarbonyl, N-[$C_3$-$C_8$-cycloalkyl or $C_3$-$C_8$-cycloalkyl-$C_1$-$C_7$-alkyl]-aminocarbonyl, $C_1$-$C_7$-alkylaminocarbonyl, N-(phenyl-$C_1$-$C_7$-alkyl)($C_1$-$C_7$-alkyl)-aminocarbonyl, N-(phenyl-$C_1$-$C_7$-alkyl)($C_3$-$C_8$-cycloalkyl-$C_1$-C7-alkyl)-aminocarbonyl, N-($C_1$-$C_7$-alkyl)($C_3$-$C_8$-cycloalkyl-$C_1$-$C_7$-alkyl)-aminocarbonyl, N-(phenyl-$C_1$-$C_7$-alkyl)($C_3$-$C_8$-cycloalkyl)-aminocarbonyl, N-(heterocyclyl-$C_1$-$C_7$-alkyl)($C_3$-$C_8$-cycloalkyl)-aminocarbonyl, N-(heterocyclyl)($C_3$-$C_8$-cycloalkyl)-aminocarbonyl; or is hydrogen;

$R_b$ is $C_1$-C7-alkyl or—in each case unsubstituted or substituted—phenyl, naphthyl, phenyl-$C_1$-$C_7$-alkyl or naphthyl-$C_1$-$C_7$-alkyl wherein in the case of a substituted moiety the substituents are one or more, especially up to three, substituents independently selected from the group consisting of $C_1$-$C_7$-alkyl, $C_2$-$C_7$-alkenyl, $C_2$-$C_7$-alkinyl, hydroxy-$C_1$-$C_7$-alkyl, halo-$C_1$-$C_7$-alkyl, such as trifluoromethyl, $C_1$-$C_7$-alkoxy-$C_1$-$C_7$-alkyl, amino-$C_1$-$C_7$-alkyl, $C_1$-$C_7$-alkoxy, hydroxy-$C_1$-$C_7$-alkoxy, $C_1$-$C_7$-alkoxy-$C_1$-$C_7$-alkoxy, $C_1$-$C_7$-alkanoyloxy, amino, mono- or di-($C_1$-$C_7$-alkyl)-amino, $C_1$-$C_7$-alkanoylamino, $C_1$-$C_7$-alkylsulfonylamino, $C_1$-$C_7$-alkoxy-carbonyl, carboxy-$C_1$-$C_7$-alkyl, halo, hydroxy, halo-$C_1$-$C_7$-alkoxy, halo-$C_1$-$C_7$-alkylthio, nitro, carboxyl, $C_1$-$C_7$-alkyl-carbonyl, halo-$C_1$-$C_7$-alkylcarbonyl, hydroxy-$C_1$-$C_7$-alkylcarbonyl, $C_1$-$C_7$-alkoxy-$C_1$-$C_7$-alkylcarbonyl, halo-$C_1$-$C_7$-alkoxycarbonyl, carbamoyl, cyano, $C_1$-$C_7$-alkylsulfinyl, sulfonyl, $C_1$-$C_7$-alkylsulfonyl, halo-$C_1$-$C_7$-alkylsulfonyl, hydroxy-$C_1$-$C_7$-alkylsulfonyl, $C_1$-$C_7$-alkoxy-$C_1$-$C_7$-alkylsulfonyl, sulfamoyl and N-mono or N,N-di-($C_1$-$C_7$-alkyl)-aminosulfonyl; or is acyl as just defined under $R_a$ or selected from unsubstituted mono-, di- or tri-(halo and/or $C_1$-$C_7$-alkyl)-substituted (phenyl- or phenyl-$C_1$-$C_7$-alkyl)-sulfonyl, $C_1$-$C_7$-alkylsulfonyl;

$R_c$ is, hydroxy-$C_1$-$C_7$-alkyl, $C_1$-$C_7$-alkyloxy-$C_1$-$C_7$-alkyl, unsubstituted or substituted $C_3$-$C_8$-cycloalkyl-$C_1$-$C_7$-alkyl, or preferably hydrogen, unsubstituted or substituted $C_3$-$C_8$-cycloalkyl or unsubstituted or substituted $C_1$-$C_7$-alkyl;

$R_d$ is unsubstituted or substituted phenyl- or naphthyl-$C_1$-$C_7$-alkyl wherein in the case of a substituted moiety the substituents are one or more, especially up to three, substituents independently selected from those mentioned for unsubstituted of substituted phenyl- or naphthyl-$C_1$-$C_7$-alkyl under $R_b$, or is —N($R_b$)($R_c$);

$R_e$ is $C_1$-$C_7$-alkyl or preferably hydrogen; and m is 2;

preferably $R_a$ is hydrogen or N-mono- or N,N-di-($C_1$-$C_7$-alkyl, (unsubstituted or halo-substituted) phenyl or naphthyl, phenyl-$C_1$-$C_7$-alkyl, naphthyl-$C_1$-$C_7$-alkyl $C_3$-$C_8$-cycloalkyl-$C_1$-$C_7$-alkyl, heterocyclyl-$C_1$-$C_7$-alkyl, heterocyclyl and/or $C_3$-$C_8$-cycloalkyl)-aminocarbonyl; each of $R_b$ and $R_c$ is, independently of the other, is selected from hydrogen, $C_1$-$C_7$-alkyl, $C_3$-$C_8$-cycloalkyl-$C_1$-$C_7$-alkyl, $C_3$-$C_8$-cycloalkyl, unsubstituted or substituted aryl such as phenyl, naphthyl, naphthyl-$C_1$-$C_7$-alkyl, or acyl such as $C_3$-$C_8$-cycloalkylcarbonyl, $C_3$-$C_8$cycloalkyl-$C_1$-$C_7$-alkylcarbonyl, unsubstituted or mono-, di- or tri-(halo, $C_1$-$C_7$-alkoxy, $C_1$-$C_7$-alkyloxy-$C_1$-$C_7$-alkyoxy, $C_1$-$C_7$-alkyloxy-$C_1$-$C_7$-alkyl and/or $C_1$-$C_7$-alkyl)-substituted phenyl- or naphthyl-$C_1$-$C_7$-alkanoyl, (tetrahydrofuranyl or tetrahydropyranyl)-carbonyl or (tetrahydrofuranyl or tetrahydropyranyl)-$C_1$-$C_7$-alkyl-carbonyl, $C_1$-$C_7$-alkylsulfonyl or (unsubstituted or [$C_1$-$C_7$-alkyl-, halo-lower alkyl-, halo, $C_1$-$C_7$-alkyloxy-, cyano-, $C_1$-$C_7$-alkanoyl- and/or $C_1$-$C_7$-alkylsulfonyl-]substituted) (phenyl- or naphthyl)-$C_1$-$C_7$-alkylsulfonyl, with the proviso that if $R_c$ is hydrogen, $C_1$-$C_7$-alkyl, phenyl, naphthyl or naphthyl-$C_1$-$C_7$-alkyl, then $R_b$ can also be phenyl-$C_1$-$C_7$-alkyl;

$R_d$ is unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, cyano-, $C_1$-$C_7$-alkanoyl- and/or $C_1$-$C_7$-alkylsulfonyl-]substituted (phenyl- or naphthyl)-$C_1$-$C_7$-alkyl;

$R_e$ is hydrogen; and m is 2.

$R^3$ is in a first embodiment a moiety of the formula (a)

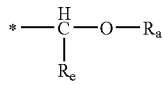

In this embodiment, $R_a$ is as defined herein, preferably, $R_a$ is hydrogen or acyl, preferably acyl. Acyl is preferably selected from $C_1$-$C_7$-alkanoyl, unsubstituted or mono-, di- or tri-(halo, $C_1$-$C_7$-alkoxy, $C_1$-$C_7$-alkyloxy-$C_1$-$C_7$-alkyoxy, $C_1$-$C_7$-alkyloxy-$C_1$-$C_7$-alkyl and/or $C_1$-$C_7$-alkyl)-substituted) phenyl-$C_1$-$C_7$-alkanoyl, $C_3$-$C_8$-cycloalkylcarbonyl or $C_3$-$C_8$-cycloalkyl-$C_1$-$C_7$-alkyl-carbonyl, (tetrahydrofuranyl or tetrahydropyranyl)-carbonyl or (tetrahydrofuranyl or tetrahydropyranyl)-$C_1$-$C_7$-alkyl-carbonyl, and ($C_1$-$C_7$-alkyl, phenyl, naphthyl, phenyl-$C_1$-$C_7$-alkyl and/or napthyl-$C_1$-$C_7$-alkyl)-oxycarbonyl, or preferably from N-mono- or N,N-di-substituted aminocarbonyl, in particular N-mono- or N,N-di-($C_1$-$C_7$-alkyl)-aminocarbonyl, such as N,N-di-($CH_2CHCH_3$)-aminocarbonyl or N-($CH_2CHCH_3$)(methyl)-aminocarbonyl, N-[phenyl or phenyl-$C_1$-$C_7$-alkyl, such as phenyl-$CH_2$— or as phenyl-$CH(CH_2CH_3)$-]-aminocarbonyl, N-[$C_3$-$C_8$-cycloalkyl or $C_3$-$C_8$-cycloalkyl-$C_1$-$C_7$-alkyl]-aminocarbonyl, $C_1$-$C_7$-alkylaminocarbonyl, N-(phenyl-$C_1$-$C_7$-alkyl)($C_1$-$C_7$-alkyl)-aminocarbonyl, such as N-(phenyl-$CH_2$—)(methyl or ethyl)aminocarbonyl, N-(phenyl-$C_1$-$C_7$-alkyl)($C_3$-$C_8$-cycloalkyl-$C_1$-$C_7$-alkyl)-aminocarbonyl, such as N-(phenyl-$CH_2$—)(cyclopropyl-$CH_2$—)aminocarbonyl, N-($C_1$-$C_7$-alkyl)($C_3$-$C_8$-cycloalkyl-$C_1$-$C_7$-alkyl)-aminocarbonyl, such as N-(methyl)(cyclohexyl-$CH_2$—)aminocarbonyl, N-(phenyl-$C_1$-$C_7$-alkyl)($C_3$-$C_8$-cycloalkyl)-aminocarbonyl, such as N-(phenyl-$CH_2$—) (cyclopropyl)-aminocarbonyl, N-(heterocyclyl-$C_1$-$C_7$-alkyl)($C_3$-$C_8$-cycloalkyl)-aminocarbonyl, such as N-(heterocyclyl-$C_1$-$C_7$-alkyl)(cyclopropyl)-aminocarbonyl and N-(heterocyclyl)($C_3$-$C_8$-cycloalkyl)-aminocarbonyl, such as N-(heterocyclyl)(cyclopropyl)-aminocarbonyl, whereby heterocyclyl is in each instance preferably a monocyclic, such as 5- or 6-membered monocyclic, preferably saturated ring systems or aromatic ring systems, in particular saturated ring systems. The heterocyclyl moiety has preferably 1, 2 or 3, more preferably 1 or 2 heteroatoms selected from O, N or S, more preferably O or N. Particularly preferred examples include 5- or 6-membered rings preferably containing an oxygen atom, in particular tetrahydropyranyl or tetrahydrofuranyl. When the heterocyclyl moiety is substituted, it is preferably mono-substituted. Suitable substituents for the heterocyclyl moiety are as defined herein, preferably halo, hydroxy, nitro, amino, amino-$C_1$-$C_7$-alkyl, carboxyl, and cyano, more preferably phenyl-$C_1$-$C_7$-alkyl. Suitable phenyl substituents include $C_1$-$C_7$-alkyl, —O—$C_1$-$C_7$-alkyl, halo-$C_1$-$C_7$-alkyl, halo, hydroxyl and amino. Most preferably the heterocyclyl moiety is unsubstituted.

In this embodiment, $R_e$ is as defined herein, preferably, $R_e$ is hydrogen.

When $R^3$ is a moiety of the formula (a), then one or more, preferably all of the following substituents have the following definition:

$R^1$ is substituted phenyl carbonyl as defined herein, in particular whereby one substituent is —O—$C_1$-$C_7$-alkyl, such as OMe, or —$C_1$-$C_7$-alkyl, such as methyl or ethyl, and the other is —O—$C_1$-$C_7$-alkylene-O—$C_1$-$C_7$-alkyl, such as —$OC_3H_6OMe$; or $R^1$ is substituted aromatic heterocyclyl-carbonyl, in particular bicyclic heterocyclylcarbonyl, such as indolyl-carbonyl, whereby the heterocyclyl moiety is substituted by methyl and/or —$C_3H_6OMe$;

$R^2$ is branched alkyl, such as isopropyl;

T is methylene, and $R^4$ and $R^5$ are hydrogen.

$R^3$ is in a second embodiment a moiety of the formula (b)

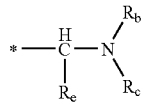

In this embodiment, $R_b$ is as defined herein, preferably $R_b$ is selected from hydrogen, $C_1$-$C_7$-alkyl, $C_3$-$C_8$-cycloalkyl-$C_1$-$C_7$-alkyl, $C_3$-$C_8$-cycloalkyl, unsubstituted or substituted aryl such as phenyl, naphthyl, naphthyl-$C_1$-$C_7$-alkyl, or acyl, more preferably unsubstituted or substituted aryl or acyl, most preferably acyl, each as defined herein.

When $R_b$ is unsubstituted or substituted aryl, preferred examples are phenyl or naphthyl, more preferably phenyl, which are each unsubstituted or substituted by a suitable substituent such as $C_1$-$C_7$-alkyl, —O—$C_1$-$C_7$-alkyl, halo-$C_1$-$C_7$-alkyl, halo, hydroxy, phenyl- or naphthyloxy, phenyl- or naphthyl-$C_1$-$C_7$-alkyloxy, nitro, amino, amino-$C_1$-$C_7$-alkyl, carboxyl, and cyano; preferably each are unsubstituted.

When $R_b$ is acyl, preferred examples are selected from the group consisting of (a) to (p), most preferably (e):

(a) Unsubstituted or substituted mono- or bicyclic aryl-carbonyl

Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl, indanyl, or 1,2,3,4-tetrahydronaphthyl. When the aryl moiety is substituted, it is preferably mono- or di-substituted. In particular, phenyl is preferably unsubstituted, mono- or di-substituted, and indanyl or 1,2,3, 4-tetrahydronaphthyl are preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, halo, such as Cl, —O—$C_1$-$C_7$-alkylene-O-alkyl, such as O—$C_3H_6OCH_3$, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano, unsubstituted or substituted, preferably unsubstituted, heterocyclyl or unsubstituted or substituted, preferably unsubstituted, heterocyclyl-$C_1$-$C_4$-alkyl, such as heterocyclyl-$CH_2$, whereby the heterocyclyl moiety in each case is preferably monocyclic 5- or 6-membered heterocyclyl, preferably containing an N and/or O atom, such as tetrahydrofuranyl or tetrahydropyranyl, piperidinyl, pyrrolidinyl, piperazinyl or morpholinyl, most preferably heterocyclyl, heterocyclyl-$CH_2$, 'O—$C_1$-$C_7$-alkyl, —O—$C_1$-$C_7$-alkylene-O-alkyl and/or halo.

(b) unsubstituted or substituted mono- or bicyclic heterocyclylcarbonyl

Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrrolidin-2-onyl, pyrrolyl, piperidyl, furanyl, pyrimidyl, pyridyl, pyrazinyl, isoxazolyl, pyrrolidin-2-onyl, tetrahydrofuranyl, or tetrahydropyranyl; or 9- to 11-membered bicyclic ring systems preferably containing at least one nitrogen and/or oxygen atom, in particular indolyl, 2,3-dihydro-benzo[1,4]dioxinyl, chromanyl, 2H-chromenyl, 3,4-dihydro-1H-quinolin-2-onyl, benzo[d]isoxazolyl, 4,5,6,7-tetrahydro-benzo[d]isoxazolyl, 3a,4,5,6,7,7a-hexahydro-benzo[d]isoxazolyl, 1,4,5,6,-tetrahydro-cyclopentapyrazolyl, 3,4-dihydro-2H-benzo[b][1,4]dioxepinyl, benzofuranyl, 4H-benzo[1,4]oxazin-3-onyl, benzooxazolyl, benzo[1,2,5]oxadiazolyl, benzimidazolyl or 3,4-dihydro-2H-benzo[1,4]oxazinyl, more preferably pyrazinyl, isoxazolyl, pyrrolidin-2-onyl, tetrahydrofuranyl, tetrahydropyranyl, indolyl, 2,3-dihydro-benzo[1,4]dioxinyl, chromanyl, 2H-chromenyl, 3,4-dihydro-1H-quinolin-2-onyl, benzo[d]isoxazolyl, 4,5,6,7-tetrahydro-benzo[d]isoxazolyl, 3a,4,5,6,7,7a-hexahydro-benzo[d]isoxazolyl, 1,4,5,6,-tetrahydro-cyclopentapyrazolyl, or 3,4-dihydro-2H-benzo[b][1,4]dioxepinyl. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, more preferably phenyl, —$C_1$-$C_7$-alkyl or $C_3$-$C_8$-cycloalkyl. Suitable phenyl and cycloalkyl substituents include $C_1$-$C_7$-alkyl, —O—$C_1$-$C_7$-alkyl, halo-$C_1$-$C_7$-alkyl, halo, hydroxyl and amino.

Most preferably the heterocyclyl moiety is unsubstituted or is mono-substituted with phenyl, —$C_1$-$C_7$-alkyl or $C_3$-$C_8$-cycloalkyl.

(c) unsubstituted or substituted mono- or bicyclic cycloalkylcarbonyl

Preferred examples for the cycloalkyl moiety are monocyclic rings, preferably $C_3$-$C_8$-cycloalkyl, more preferably $C_3$, $C_4$, $C_5$, $C_6$ and $C_7$-cycloalkyl. The cycloalkyl moiety may be substituted or unsubstituted. $C_3$, $C_4$, $C_5$, and $C_7$-cycloalkyl are preferably unsubstituted and $C_6$-cycloalkyl is preferably unsubstituted or substituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, carboxyl, and cyano, most preferably O—$C_1$-$C_4$-alkyl or hydroxy.

(d) unsubstituted or substituted alkylcarbonyl

Preferred examples for the alkyl moiety are branched or straight chain $C_1$-$C_7$-alkyl which may be substituted or unsubstituted. In one embodiment, the alkyl moiety is branched alkyl such as isopropyl, isobutyl, sec-butyl or tert-butyl, isopentyl, 1-ethylpropyl, 2,2-dimethyl-propyl and 1,2-dimethyl-propyl, most preferably isobutyl, isopentyl and 2,2-dimethyl-propyl. In another embodiment the alkyl moiety is straight chain alkyl such as methyl, ethyl, n-propyl, n-butyl or n-pentyl, preferably methyl, ethyl or n-propyl. Alkyl is preferably substituted. When the alkyl moiety is substituted, it is preferably mono-, di- or tri-substituted, more preferably mono-substituted. Suitable substituents for the alkyl moiety are as defined herein, preferably O—$C_1$-$C_4$-alkyl, such as OMe, halo, hydroxy, unsubstituted or substituted phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, aminocarbonyl, N-mono- or N,N-di-substituted aminocarbonyl, such as CONHMe, carboxyl, $C_1$-$C_7$-alkyloxycarbonyl, such as COOMe, and cyano, whereby suitable phenyl or naphthyl substituents include $C_1$-$C_7$-alkyl, such as methyl, —O—$C_1$-$C_7$-alkyl, halo-$C_1$-$C_7$-alkyl, halo, hydroxyl and amino, preferably $C_1$-$C_7$-alkyl, and whereby suitable amino substituents include $C_1$-$C_7$-alkyl, such as methyl, phenyl or cyclopropyl, preferably $C_1$-$C_7$-alkyl. Most preferably the alkyl moiety is mono-substituted by —O—$C_1$-$C_7$-alkyl, hydroxyl, $C_1$-$C_7$-alkanoylamino, unsubstituted or di-substituted phenyloxy, aminocarbonyl, N-mono- or N,N-di-substituted aminocarbonyl and $C_1$-$C_7$-alkyloxycarbonyl.

(e) unsubstituted or substituted mono- or bicyclic aryl-$C_1$-$C_7$-alkylcarbonyl Preferably aryl alkyl is aryl-$C_{1-6}$ alkyl, more preferably aryl-$C_{1-4}$ alkyl, in particular aryl-$CH_2$—, aryl-$CH_2CH_2$—, aryl-$CH(CH_3)$—, aryl-$CH_2CH(CH_3)$— or aryl-$C(CH_3)_2$—, most preferably aryl-$CH_2$—. The alkyl moiety, in particular when aryl alkyl is aryl-$CH_2$— or aryl-$CH_2CH_2$—, may be substituted, preferably mono-substituted. Examples of preferred substituents include O—$C_1$-$C_4$-alkyl, such as OMe, halo, hydroxy, nitro, amino, amino-$C_1$-$C_7$-alkyl, $C_1$-$C_7$-alkanoylamino, such as —NHCOMe, carboxyl, and cyano or unsubstituted or substituted, preferably unsubstituted, phenyl, whereby suitable phenyl substituents include $C_1$-$C_7$-alkyl, —O—$C_1$-$C_7$-alkyl, halo-$C_1$-$C_7$-alkyl, halo, hydroxyl and amino; most preferably unsubstituted phenyl, $C_1$-$C_7$-alkanoylamino, O—$C_1$-$C_4$-alkyl or hydroxyl.

Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl or naphthyl. When the aryl moiety is substituted, it is preferably mono-, di- or tri-substituted. In particular, phenyl is preferably unsubstituted, mono-, di- or tri-substituted, and naphthyl is preferably unsubstituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, unsubstituted or substituted, preferably substituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, carboxyl, and cyano. Suitable substituents for the phenyl and naphthyl substituent on the aryl moiety of aryl alkylcarbonyl include $C_1$-$C_7$-alkyl, —O—$C_1$-$C_7$-alkyl, halo-$C_1$-$C_7$-alkyl, halo, hydroxyl and amino. Most preferably the aryl alkyl moiety is unsubstituted or substituted by —O—$C_1$-$C_7$-alkyl, halo-$C_1$-$C_7$-alkyl, substituted phenyl, $C_1$-$C_7$-alkanoylamino and/or halo.

(f) unsubstituted or substituted mono- or bicyclic heterocyclyl-$C_1$-$C_7$-alkylcarbonyl Preferably heterocyclyl alkyl is heterocyclyl-$C_{1-6}$ alkyl, more preferably heterocyclyl-$C_{1-4}$ alkyl, in particular heterocyclyl-$CH_2$—, heterocyclyl-$CH_2CH_2$— or heterocyclyl-$CH_2C(CH_3)_2$—, most preferably heterocyclyl-$CH_2$—. Heterocyclyl-$CH_2C(CH_3)_2$— is particularly preferred when the heterocyclyl moiety is a 5- or 6-membered ring such as an aromatic ring, in particular pyrrolyl. Heterocyclyl-$CH_2CH_2$— is particularly preferred when the heterocyclyl moiety is a 5- or 6-membered ring such as an aromatic ring, in particular furanyl.

Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrimidyl, pyridyl, pyrazinyl, isoxazolyl, pyrrolidin-2-onyl, pyrrolyl, piperidyl, furanyl, tetrahydrofuranyl, or tetrahydropyranyl; or 9- to 11-membered bicyclic ring systems preferably containing at least one nitrogen and/or oxygen atom, in particular 4H-benzo[1,4]oxazin-3-onyl, benzooxazolyl, indolyl, 2,3-dihydro-benzo[1,4]dioxinyl, chromanyl, 2H-chromenyl, 3,4-dihydro-1H-quinolin-2-onyl, benzo[d]isoxazolyl, 4,5,6,7-tetrahydrobenzo[d]isoxazolyl, 3a,4,5,6,7,7a-hexahydro-benzo[d]isoxazolyl, 1,4,5,6,-tetrahydrocyclopentapyrazolyl, 3,4-dihydro-2H-benzo[b][1,4]dioxepinyl, benzofuranyl, benzo[1,2,5]oxadiazolyl, benzimidazolyl or 3,4-dihydro-2H-benzo[1,4]oxazinyl, more preferably pyrrolidinyl, pyrrolidin-2-onyl, pyrrolyl, piperidyl, furanyl, tetrahydrofuranyl, tetrahydropyranyl, 4H-benzo[1,4]oxazin-3-onyl or benzooxazolyl. When the heterocyclyl moiety is substituted, it is preferably mono-substituted. Suitable substituents for the heterocyclyl moiety are as defined herein, preferably -$C_1$-$C_7$-alkyl, such as methyl, halo, hydroxy, $C_1$-$C_7$-alkanoyl, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, more preferably —$C_1$-$C_7$-alkyl or $C_1$-$C_7$-alkanoyl. Suitable phenyl and cycloalkyl substituents include $C_1$-$C_7$-alkyl, —O—$C_1$-$C_7$-alkyl, halo-$C_1$-$C_7$-alkyl, halo, hydroxyl and amino. Most preferably the heterocyclyl moiety is unsubstituted or is mono-substituted with unsubstituted phenyl, —$C_1$-$C_7$-alkyl or $C_1$-$C_7$-alkanoyl.

(g) unsubstituted or substituted mono- or bicyclic cycloalkyl-$C_1$-$C_7$-alkylcarbonyl Preferably cycloalkyl alkyl is cycloalkyl-$C_{1-6}$ alkyl, more preferably cycloalkyl-$C_{1-4}$ alkyl, in particular cycloalkyl-$CH_2$—, cycloalkyl-$CH_2CH_2$— or cycloalkyl-$CH_2C(CH_3)_2$—, most preferably cycloalkyl-$CH_2$—. The alkyl moiety may be substituted, preferably mono-substituted, including on the carbon where the cycloalkyl moiety is attached. Examples of preferred substituents include O—$C_1$-$C_4$-alkyl, such as OMe, halo, hydroxy, nitro, amino, amino-$C_1$-$C_7$-alkyl, carboxyl, and cyano, most preferably O—$C_1$-$C_4$-alkyl or hydroxyl. Preferred examples for the cycloalkyl moiety are monocyclic rings, preferably $C_3$-$C_7$-cycloalkyl, more preferably $C_3$, $C_5$ and $C_6$-cycloalkyl. The cycloalkyl moiety may be substituted or unsubstituted. $C_3$-cycloalkyl is preferably unsubstituted and $C_5$ and $C_6$-cycloalkyl are preferably unsubstituted or substituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, —NHCOEt or —NHCOCHCH$_3$)$_2$, carboxyl, and cyano, most preferably amino, O—$C_1$-$C_4$-alkyl or hydroxy.

(h) unsubstituted or substituted alkyloxycarbonyl

Preferred examples for the alkyl moiety are branched or straight chain $C_1$-$C_7$-alkyl which may be substituted or unsubstituted. In one embodiment, the alkyl moiety is branched alkyl such as isopropyl, isobutyl, sec-butyl or tert-butyl, isopentyl, 1-ethylpropyl, 2,2-dimethyl-propyl and 1,2-dimethyl-propyl, most preferably isobutyl, isopentyl and 2,2-dimethyl-propyl. In another embodiment the alkyl moiety is straight chain alkyl such as methyl, ethyl, n-propyl, n-butyl or n-pentyl, preferably methyl or ethyl. When the alkyl moiety is substituted, it is preferably mono-, di- or tri-substituted, more preferably mono-substituted. Suitable substituents for the alkyl moiety are as defined herein, preferably O—$C_1$-$C_4$-alkyl, such as OMe, halo, hydroxy, unsubstituted or substituted phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, aminocarbonyl, N-mono- or N,N-di-substituted aminocarbonyl, such as CONHMe, carboxyl, $C_1$-$C_7$-alkyloxycarbonyl, such as COOMe, and cyano, whereby suitable phenyl or naphthyl substituents include $C_1$-$C_7$-alkyl, such as methyl, —O—$C_1$-$C_7$-alkyl, halo-$C_1$-$C_7$-alkyl, halo, hydroxyl and amino, preferably $C_1$-$C_7$-alkyl, and whereby suitable amino substituents include $C_1$-$C_7$-alkyl, such as methyl, phenyl or cyclopropyl, preferably $C_1$-$C_7$-alkyl. Most preferably the alkyl moiety is mono-substituted by —O—$C_1$-$C_7$-alkyl, $C_1$-$C_7$-alkanoylamino and N-mono- or N,N-di-substituted aminocarbonyl.

(i) unsubstituted or substituted mono- or bicyclic aryl-oxycarbonyl

Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl or naphthyl. When the aryl moiety is substituted, it is preferably mono- or di-substituted. In particular, phenyl is preferably unsubstituted, mono- or di-substituted, and naphthyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, halo, such as Cl, —O—$C_1$-$C_7$-alkylene-O-alkyl, such as —O—$C_3H_6OCH_3$, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano, unsubstituted or substituted, preferably unsubstituted, heterocyclyl or unsubstituted or substituted, preferably unsubstituted, heterocyclyl-$C_1$-$C_4$-alkyl, such as heterocyclyl-$CH_2$, whereby the heterocyclyl moiety in each case is preferably monocyclic 5- or 6-membered heterocyclyl, preferably containing an N and/or O atom, such as tetrahydrofuranyl, tetrahydropyranyl, piperidinyl, pyrrolidinyl, pyrrolidin-2-onyl, piperazinyl or morpholinyl, most preferably heterocyclyl or —O—$C_1$-$C_7$-alkyl.

(j) unsubstituted or substituted mono- or bicyclic heterocyclyloxycarbonyl

Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated, more preferably saturated, rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrrolidin-2-onyl, pyrrolyl, piperidyl, furanyl, pyrimidyl, pyridyl, pyrazinyl, isoxazolyl, pyrrolidin-2-onyl, tetrahydrofuranyl, or tetrahydropyranyl; more preferably tetrahydrofuranyl or tetrahydropyranyl. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, more preferably phenyl, —$C_1$-$C_7$-alkyl or $C_3$-$C_8$-cycloalkyl. Suitable phenyl and cycloalkyl substituents include $C_1$-$C_7$-alkyl, —O—$C_1$-$C_7$-alkyl, halo-$C_1$-$C_7$-alkyl, halo, hydroxyl and amino. Most preferably the heterocyclyl moiety is unsubstituted.

(k) unsubstituted or substituted mono- or bicyclic cycloalkyloxycarbonyl

Preferred examples for the cycloalkyl moiety are monocyclic rings, preferably $C_3$-$C_8$-cycloalkyl, more preferably $C_3$, $C_4$, $C_5$, $C_6$ and $C_7$-cycloalkyl, most preferably $C_6$-cycloalkyl. The cycloalkyl moiety may be substituted or unsubstituted, preferably unsubstituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, carboxyl, and cyano, most preferably O—$C_1$-$C_4$-alkyl or hydroxy.

(l) unsubstituted or substituted mono- or bicyclic aryl-$C_1$-$C_7$-alkyloxycarbonyl Preferably aryl alkyl is aryl-$C_{1-6}$ alkyl, more preferably aryl-$C_{1-4}$alkyl, in particular aryl-$CH_2$—, aryl-$CH_2CH_2$—, aryl-$CH(CH_3)$—, aryl-$CH_2CH(CH_3)$— or aryl-$CH(CH_2CH_3)$—, most preferably aryl-$CH_2$—. Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono-, di- or tri-substituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, unsubstituted or substituted, preferably substituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, carboxyl, and cyano. Suitable substituents for the phenyl and naphthyl substituent on the aryl moiety of aryl alkylcarbonyl include $C_1$-$C_7$-alkyl, —O—$C_1$-$C_7$-alkyl, halo-$C_1$-$C_7$-alkyl, halo, hydroxyl and amino.

(m) unsubstituted or substituted mono- or bicyclic heterocyclyl-$C_1$-$C_7$-alkyloxycarbonyl Preferably heterocyclyl alkyl is heterocyclyl-$C_{1-6}$ alkyl, more preferably heterocyclyl-$C_{1-4}$ alkyl, in particular heterocyclyl-$CH_2$—, heterocyclyl-$CH_2CH_2$— or heterocyclyl-$CH_2CH(CH_3)$—, most preferably heterocyclyl-$CH_2$—. Heterocyclyl-$CH_2CH(CH_3)$— is particularly preferred when the heterocyclyl moiety is a 5- or 6-membered ring such as a saturated ring, in particular 1,3-dioxane. Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrimidyl, pyridyl, pyrazinyl, isoxazolyl, pyrrolidin-2-onyl, pyrrolyl, piperidyl, furanyl, 1,3-dioxane, tetrahydrofuranyl, or tetrahydropyranyl; more preferably pyridyl, piperidyl, isoxazolyl, tetrahydrofuranyl, tetrahydropyranyl or 1,3-dioxane. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, such as COMe, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, more preferably —$C_1$-$C_7$-alkyl or $C_1$-$C_7$-alkanoyl. Suitable phenyl and cycloalkyl substituents include $C_1$-$C_7$-alkyl, —O—$C_1$-$C_7$-alkyl, halo-$C_1$-$C_7$-alkyl, halo, hydroxyl and amino. Most preferably the heterocyclyl moiety is unsubstituted or is mono-substituted with —$C_1$-$C_7$-alkyl or $C_1$-$C_7$-alkanoyl.

(n) unsubstituted or substituted mono- or bicyclic cycloalkyl-$C_1$-$C_7$-alkyloxycarbonyl Preferably cycloalkyl alkyl is cycloalkyl-$C_{1-6}$ alkyl, more preferably cycloalkyl-$C_{1-4}$ alkyl, in particular cycloalkyl-$CH_2$—, cycloalkyl-$CH_2CH_2$— or cycloalkyl-$CH_2CH(CH_3)$—, most preferably cycloalkyl-$CH_2$—. Preferred examples for the cycloalkyl moiety are monocyclic rings, preferably $C_3$-$C_7$-cycloalkyl, more preferably $C_3$ and $C_5$ -cycloalkyl. The cycloalkyl moiety may be substituted or unsubstituted. $C_3$-cycloalkyl is preferably unsubstituted and $C_5$-cycloalkyl are preferably unsubstituted or substituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, —NHCOEt or —NHCOCHCH$_3$)$_2$, carboxyl, and cyano, most preferably $C_1$-$C_7$-alkanoylamino.

(o) N-mono- or N,N-di-(unsubstituted or substituted mono- or bicyclic aryl, unsubstituted or substituted mono- or bicyclic cycloalkyl, unsubstituted or substituted mono- or bicyclic aryl-$C_1$-$C_7$-alkyl, unsubstituted or substituted mono- or bicyclic heterocyclyl-$C_1$-$C_7$-alkyl, unsubstituted or substituted mono- or bicyclic cycloalkyl-$C_1$-$C_7$-alkyl and/or unsubstituted or substituted alkyl)-aminocarbonyl Preferred examples for the alkyl moiety of the unsubstituted or substituted alkyl aminocarbonyl are branched or straight chain $C_1$-$C_7$-alkyl which may be substituted or unsubstituted. In one embodiment, the alkyl moiety is branched alkyl such as isopropyl, isobutyl, sec-butyl or tert-butyl, isopentyl, 1-ethylpropyl, 2,2-dimethyl-propyl and 1,2-dimethylpropyl, most preferably isopropyl or isobutyl. In another embodiment the alkyl moiety is straight chain alkyl such as methyl, ethyl, n-propyl, n-butyl or n-pentyl, preferably methyl or ethyl. When the alkyl moiety is substituted, it is preferably mono-, di- or tri-substituted, more preferably mono-substituted. Suitable substituents for the alkyl moiety are as defined herein, preferably O—$C_1$-$C_4$-alkyl, such as OMe, halo, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, aminocarbonyl, N-mono- or N,N-di-substituted aminocarbonyl, such as CONHMe, carboxyl, $C_1$-$C_7$-alkyloxycarbonyl, such as COOMe, and cyano. Most preferably the alkyl moiety is unsubstituted.

Preferred examples of the aryl moiety of the unsubstituted or substituted aryl aminocarbonyl include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl or naphthyl. When the aryl moiety is substituted, it is preferably mono- or di-substituted. Suitable substituents are as defined herein, preferably $C_1$-$C_7$-alkyl, —O—$C_1$-$C_7$-alkyl, such as OMe, halo-$C_1$-$C_7$-alkyl, halo, such as Cl, —O—$C_1$-$C_7$-alkylene-O-alkyl, such as O—$C_3H_6OCH_3$, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano. Most preferably aryl is unsubstituted.

Preferred examples for the cycloalkyl moiety moiety of the unsubstituted or substituted cycloalkyl aminocarbonyl are monocyclic rings, preferably $C_3$-$C_8$-cycloalkyl, more preferably $C_3$, $C_4$, $C_5$, $C_6$ and $C_7$-cycloalkyl, most preferably $C_3$ or $C_6$-cycloalkyl. The cycloalkyl moiety may be substituted or unsubstituted, preferably unsubstituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, carboxyl, and cyano, most preferably O—$C_1$-$C_4$-alkyl or hydroxy.

Preferably the aryl alkyl moiety of the unsubstituted or substituted aryl alkyl aminocarbonyl is aryl-$C_{1-6}$ alkyl, more preferably aryl-$C_{1-4}$ alkyl, in particular aryl-$CH_2$—, aryl-$CH_2CH_2$—, or aryl-$CH(CH_2CH_3)$—, most preferably aryl-$CH_2$—. The alkyl moiety, in particular when aryl alkyl is aryl-$CH_2$—, may be substituted, preferably mono-substituted. Examples of preferred substituents include O—$C_1$-$C_4$-alkyl, such as OMe, halo, hydroxy, nitro, amino, amino-$C_1$-$C_7$-alkyl, $C_1$-$C_7$-alkanoylamino, such as —NHCOMe, carboxyl, and cyano or unsubstituted or substituted, preferably unsubstituted, phenyl, whereby suitable phenyl substituents include $C_1$-$C_7$-alkyl, —O—$C_1$-$C_7$-alkyl, halo-$C_1$-$C_7$-alkyl, halo, hydroxyl and amino; most preferred is unsubstituted phenyl. Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono-, di- or tri-substituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, nitro, amino, amino-$C_1$-$C_7$-alkyl, $C_1$-$C_7$-alkanoylamino, such as —NHCOMe, carboxyl, and cyano, more preferably —O—$C_1$-$C_7$-alkyl or halo.

Preferably the heterocyclyl alkyl moiety of the unsubstituted or substituted heterocyclyl alkyl aminocarbonyl is heterocyclyl-$C_{1-6}$ alkyl, more preferably heterocyclyl-$C_{1-4}$ alkyl, in particular heterocyclyl-$CH_2$— or heterocyclyl-$CH_2CH_2$—, most preferably heterocyclyl-$CH_2$—. Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrimidyl, pyridyl, pyrazinyl, isoxazolyl, pyrrolidin-2-onyl, pyrrolyl, piperidyl, furanyl, 1,3-dioxane, tetrahydrofuranyl, or tetrahydropyranyl; more preferably furanyl or tetrahydropyranyl. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, such as COMe, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, more preferably —$C_1$-$C_7$-alkyl or $C_1$-$C_7$-alkanoyl. Suitable phenyl and cycloalkyl substituents include $C_1$-$C_7$-alkyl, —O—$C_1$-$C_7$-alkyl, halo-$C_1$-$C_7$-alkyl, halo, hydroxyl and amino. Most preferably the heterocyclyl moiety is unsubstituted.

Preferably the cycloalkyl alkyl moiety of the unsubstituted or substituted cycloalkyl alkyl aminocarbonyl is cycloalkyl-$C_{1-6}$ alkyl, more preferably cycloalkyl-$C_{1-4}$ alkyl, in particular cycloalkyl-$CH_2$—. Preferred examples for the cycloalkyl moiety are monocyclic rings, preferably $C_3$-$C_7$-cycloalkyl, more preferably $C_6$-cycloalkyl. The cycloalkyl moiety may be substituted or unsubstituted, preferably unsubstituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, —NHCOEt or —NHCOCHCH$_3$)$_2$, carboxyl, and cyano, most preferably $C_1$-$C_7$-alkanoylamino.

Preferred examples of N-mono- or N,N-di-(unsubstituted or substituted mono- or bicyclic aryl, unsubstituted or substituted mono- or bicyclic cycloalkyl, unsubstituted or substituted mono- or bicyclic aryl-$C_1$-$C_7$-alkyl, unsubstituted or substituted mono- or bicyclic heterocyclyl-$C_1$-$C_7$-alkyl, unsubstituted or substituted mono- or bicyclic cycloalkyl-$C_1$-$C_7$-alkyl and/or unsubstituted or substituted alkyl)-aminocarbonyl include (unsubstituted or substituted mono- or bicyclic aryl)(unsubstituted or substituted alkyl)aminocarbonyl,
unsubstituted or substituted mono- or bicyclic heterocyclyl-$C_1$-$C_7$-alkyl-aminocarbonyl,
unsubstituted or substituted mono- or bicyclic aryl-$C_1$-$C_7$-alkyl-aminocarbonyl,
unsubstituted or substituted mono- or bicyclic aryl-aminocarbonyl,
unsubstituted or substituted mono- or bicyclic cycloalkyl-$C_1$-$C_7$-alkyl-aminocarbonyl,
di-(unsubstituted or substituted mono- or bicyclic aryl)-aminocarbonyl,
di-(unsubstituted or substituted alkyl)-aminocarbonyl,
(unsubstituted or substituted mono- or bicyclic aryl-$C_1$-$C_7$-alkyl)(unsubstituted or substituted alkyl)-aminocarbonyl,
(unsubstituted or substituted mono- or bicyclic cycloalkyl)(unsubstituted or substituted mono- or bicyclic aryl-$C_1$-$C_7$-alkyl)-aminocarbonyl,
(unsubstituted or substituted mono- or bicyclic cycloalkyl)(unsubstituted or substituted mono- or bicyclic aryl)-aminocarbonyl, and
unsubstituted or substituted mono- or bicyclic cycloalkyl-aminocarbonyl.

(p) unsubstituted or substituted mono- or bicyclic aryl-$C_1$-$C_7$-alkylsulfonyl preferably aryl alkyl is aryl-$C_{1-6}$ alkyl, more preferably aryl-$C_{1-4}$ alkyl, in particular aryl-$CH_2$—, aryl-$CH_2CH_2$—, aryl-$CH(CH_3)$—, aryl-$CH_2CH(CH_3)$— or aryl-$CH(CH_2CH_3)$—, most preferably aryl-$CH_2$—. Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono-, di- or tri-substituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, unsubstituted or substituted, preferably substituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, carboxyl, and cyano. Suitable substituents for the phenyl and naphthyl substituent on the aryl moiety of aryl alkylcarbonyl include $C_1$-$C_7$-alkyl, —O—$C_1$-$C_7$-alkyl, halo-$C_1$-$C_7$-alkyl, halo, hydroxyl and amino.

When $R_b$ is acyl, $R_c$ is as defined herein, preferably, $R_c$ is hydroxy-$C_1$-$C_7$-alkyl, $C_1$-$C_7$-alkyloxy-$C_1$-$C_7$-alkyl, unsubstituted or substituted $C_3$-$C_8$-cycloalkyl-$C_1$-$C_7$-alkyl, or preferably hydrogen, unsubstituted or substituted $C_3$-$C_8$-cycloalkyl or unsubstituted or substituted $C_1$-$C_7$-alkyl, most preferably cyclopropyl or methyl. In particular, when $R_b$ is acyl as defined under (h) to (n), $R_c$ is preferably hydrogen, unsubstituted or substituted $C_3$-$C_8$-cycloalkyl or unsubstituted or substituted $C_1$-$C_7$-alkyl, most preferably cyclopropyl or methyl. In particular, when $R_b$ is acyl as defined under (o), $R_c$ is preferably unsubstituted or substituted $C_3$-$C_8$-cycloalkyl most preferably cyclopropyl. In particular, when $R_b$ is acyl as defined under (p), $R_c$ is preferably unsubstituted or substituted $C_3$-$C_8$-cycloalkyl most preferably methyl or isobutyl.

When $R_c$ is hydrogen, then one or more, preferably all of the following substituents have the following definition:

$R_b$ is unsubstituted or substituted aryl as defined herein, preferably unsubstituted phenyl, unsubstituted or substituted aryl alkylcarbonyl as defined herein, preferably unsubstituted phenyl-$C(CH_3)_2$—CO or unsubstituted phenyl-CH(OMe)—CO, unsubstituted or substituted aryl carbonyl as defined herein, preferably unsubstituted indanyl-CO—, unsubstituted or substituted heterocyclyl carbonyl as defined herein, preferably unsubstituted 2,3-dihydrobenzo[1,4]dioxinyl-CO—, unsubstituted or substituted heterocyclyl alkyl carbonyl as defined herein, preferably unsubstituted tetrahydropyranyl-$CH_2$—CO—

$R^1$ is substituted phenyl carbonyl as defined herein, in particular whereby one substituent is —O—$C_1$-$C_7$-alkyl, such as OMe, or —$C_1$-$C_7$-alkyl, such as methyl or ethyl, and the other is —O—$C_1$-$C_7$-alkylene-O—$C_1$-$C_7$-alkyl, such as —$OC_3H_6OMe$;

$R^2$ is branched alkyl, such as isopropyl;

T is methylene, and $R^4$ and $R^5$ are hydrogen.

When $R_c$ is unsubstituted or substituted $C_1$-$C_7$-alkyl, preferred examples are branched or straight chain $C_1$-$C_7$-alkyl which may be substituted or unsubstituted. In a preferred embodiment, $R_c$ is branched alkyl such as isopropyl, isobutyl, sec-butyl or tert-butyl, isopentyl, 1-ethylpropyl, and 1,2-dimethyl-propyl, most preferably isopropyl. In another preferred embodiment, $R_c$ is straight chain alkyl such as methyl, ethyl, n-propyl, n-butyl or n-pentyl, more preferably methyl or ethyl, most preferably ethyl If the alkyl moiety is substituted, suitable substituents are as defined herein, preferably O—$C_1$-$C_4$-alkyl, halo, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano. Most preferably, the alkyl moiety is unsubstituted.

When $R_c$ is unsubstituted or substituted $C_3$-$C_8$-cycloalkyl, preferred examples for the cycloalkyl moiety are monocyclic rings, preferably $C_3$-$C_7$-cycloalkyl, more preferably $C_3$, $C_4$, $C_5$ and $C_6$-cycloalkyl, more preferably cyclopropyl or cyclobutyl, most preferably cyclopropyl. The cycloalkyl moiety may be substituted or unsubstituted. When the cycloalkyl moiety is substituted, it is preferably mono-substituted. Suitable substituents for the cycloalkyl moiety are as defined herein, preferably O—$C_1$-$C_4$-alkyl, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano, most preferably phenyl or naphthyl. Most preferably, the cycloalkyl moiety is unsubstituted.

When $R_c$ is unsubstituted or substituted $C_3$-$C_8$-cycloalkyl-$C_1$-$C_7$-alkyl, such as $C_3$-$C_8$-cycloalkyl-$C_1$-$C_4$-alkyl, in particular $C_3$-$C_8$-cycloalkyl-$CH_2$, preferred examples for the cycloalkyl moiety are monocyclic rings, preferably $C_3$-$C_7$-cycloalkyl, more preferably $C_3$, $C_4$, $C_5$ and $C_6$-cycloalkyl, most preferably cyclopropyl. The cycloalkyl moiety may be substituted or unsubstituted. When the cycloalkyl moiety is substituted, it is preferably mono-substituted. Suitable substituents for the cycloalkyl moiety are as defined herein, preferably O—$C_1$-$C_4$-alkyl, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano, most preferably phenyl or naphthyl. Most preferably, the cycloalkyl moiety is unsubstituted.

When $R_c$ is unsubstituted or substituted $C_3$-$C_8$-cycloalkyl-$C_1$-$C_7$-alkyl, then one or more, preferably all of the following substituents have the following definition:

$R^1$ is substituted phenyl carbonyl as defined herein, in particular whereby one substituent is —O—$C_1$-$C_7$-alkyl, such as OMe, or —$C_1$-$C_7$-alkyl, such as methyl or ethyl, and the other is —O—$C_1$-$C_7$-alkylene-O—$C_1$-$C_7$-alkyl, such as —$OC_3H_6OMe$;

$R^2$ is branched alkyl, such as isopropyl;

T is methylene, and $R^4$ and $R^5$ are hydrogen.

When $R^3$ is a moiety of formula (b), $R_e$ is as defined herein, preferably, $R_e$ is hydrogen.

$R^3$ is in a third embodiment a moiety of the formula (c)

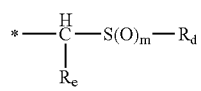

In this embodiment, $R_d$ is as defined herein, in particular $R_d$ is unsubstituted or substituted phenyl- or naphthyl-$C_1$-$C_7$-alkyl wherein in the case of a substituted moiety the substituents are one or more, especially up to three, substituents independently selected from those mentioned for unsubstituted of substituted phenyl- or naphthyl-$C_1$-$C_7$-alkyl under $R_b$, or is —$N(R_b)(R_c)$ wherein $R_b$ and $R_c$ are as defined for the second embodiment above, preferably is unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, cyano-, $C_1$-$C_7$-alkanoyl- and/or $C_1$-$C_7$-alkylsulfonyl-]substituted (phenyl- or naphthyl)-$C_1$-$C_7$-alkyl; most preferably benzyl.

$R^3$ is in a fourth embodiment a moiety of the formula (f)

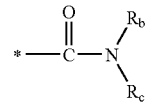

In this embodiment, $R_b$ is as defined herein, in particular as described with respect to the second embodiment where $R^3$ is a moiety of the formula (b). Preferably, $R_b$ is aryl-alkyl, such as phenyl-$C_1$-$C_4$-alkyl, whereby the aryl moiety is unsubstituted or substituted by a suitable substituent such as $C_1$-$C_7$-alkyl, —O—$C_1$-$C_7$-alkyl, halo-$C_1$-$C_7$-alkyl, halo, hydroxy, phenyl- or naphthyloxy, phenyl- or naphthyl-$C_1$-$C_7$-alkyloxy, nitro, amino, amino-$C_1$-$C_7$-alkyl, carboxyl, and cyano; preferably the aryl moiety is unsubstituted. Or $R_b$ is unsubstituted or substituted alkyl. Preferred examples are branched or straight chain $C_1$-$C_7$-alkyl which may be substituted or unsubstituted, preferably straight chain alkyl such as methyl, ethyl, n-propyl, n-butyl or n-pentyl, preferably methyl, whereby the alkyl moiety is unsubstituted or substituted by a suitable substituent such as O—$C_1$-$C_4$-alkyl, halo, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano; preferably the alkyl moiety is unsubstituted.

In this embodiment, $R_c$ is as defined herein, preferably, $R_c$ is hydrogen.

When $R^3$ is a moiety of the formula (f), then one or more, preferably all of the following substituents have the following definition:

$R^1$ is substituted phenyl carbonyl as defined herein, in particular whereby one substituent is —O—$C_1$-$C_7$-alkyl, such as OMe, or —$C_1$-$C_7$-alkyl, such as methyl or ethyl, and the other is —O—$C_1$-$C_7$-alkylene-O—$C_1$-$C_7$-alkyl, such as —$OC_3H_6OMe$;

$R^2$ is branched alkyl, such as isopropyl;

T is methylene, and $R^4$ and $R^5$ are hydrogen.

Particular embodiments of the invention, especially of compounds of the formula I and/or salts thereof, are provided in the Examples—the invention thus, in a very preferred embodiment, relates to a compound of the formula I, or a salt thereof, selected from the compounds given in the Examples, as well as the use thereof.

Process of Manufacture

A compound of formula I, or a salt thereof, is prepared analogously to methods that, for other compounds, are in principle known in the art, so that for the novel compounds of the formula I the process is novel at least as analogy process, especially as described or in analogy to methods described herein in the illustrative Examples, or modifications thereof, preferably in general by (A) for the synthesis of a compound of the formula I wherein $R^3$ is a moiety of the formula (a)

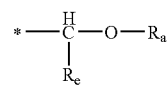

wherein $R_a$ and $R_e$ are as defined for a compound of the formula I and $R^1$, $R^2$, $R^4$, $R^5$ and T are as defined for a compound of the formula I, reducing a compound of the formula II,

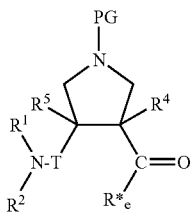

(II)

wherein $R^1$, $R^2$, $R^4$, $R^5$ and T are as just defined, $R^*_e$ is hydroxy or $R_e$ as defined for a compound of the formula I and PG is a protecting group, to the corresponding hydroxy compound of the formula III,

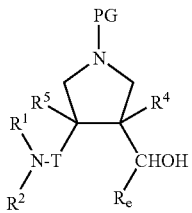

(III)

wherein $R_e$ is as defined for a compound of the formula I and the other moieties are as defined, which is then either deprotected to a corresponding compound of the formula I wherein $R_a$ in the moiety of the formula (a) is hydrogen or further reacted either (i) with a compound of the formula IV,

 (IV)

wherein $R_a^*$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or acyl and X is a leaving group, or (ii) in order to introduce a moiety $R_a$ which is N-(unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-$C_1$-$C_7$-alkyl, unsubstituted or substituted mono- or bicyclic heterocyclyl-$C_1$-$C_7$-alkyl, unsubstituted or substituted mono- or bicyclic cycloalkyl-$C_1$-$C_7$-alkyl or unsubstituted or substituted alkyl)-aminocarbonyl, with an isocyanato compound of the formula IV*,

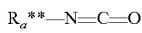 (IV*)

wherein $R_a^{**}$ is unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-$C_1$-$C_7$-alkyl, unsubstituted or substituted mono- or bicyclic heterocyclyl-$C_1$-$C_7$-alkyl, unsubstituted or substituted mono- or bicyclic cycloalkyl-$C_1$-$C_7$-alkyl or unsubstituted or substituted alkyl, where reaction (i) or (ii) is followed by removal of any protecting group(s) to give a corresponding compound of the formula I if no further conversion requiring the presence of protecting groups is desired; or (B) for the synthesis of a compound of the formula I wherein $R^3$ is a moiety of the formula (b)

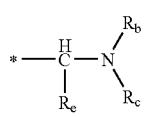

(b)

wherein $R_e$, $R_b$ and $R_c$ are as defined for a compound of the formula I, and wherein $R^1$, $R^2$, $R^4$, $R^5$ and T are as defined for a compound of the formula I, reacting an aldehyde compound of the formula V,

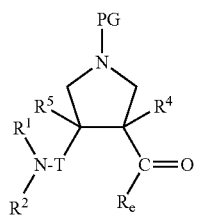

(V)

wherein $R_e$, $R^1$, $R^2$, $R^4$, $R^5$ and T are as defined for a compound of the formula I and PG is a protecting group, under conditions of reductive amination with a compound of the formula VI,

 (VI)

wherein $R_b$ and $R_c$ are as defined for a compound of the formula I, followed, if no further conversion requiring protecting groups is intended, by removal of any protecting group(s); or (C) for the synthesis of a compound of the formula I wherein $R^3$ is a moiety of the formula (f)

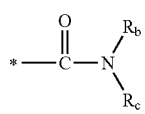

(f)

wherein $R_b$ and $R_c$ as well as $R^1$, $R^2$, $R^4$, $R^5$ and T are as defined for a compound of the formula I, condensing an acid of the formula IIB,

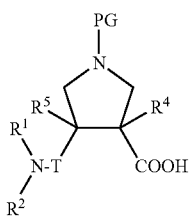

(IIB)

wherein $R^1$, $R^2$, $R^4$, $R^5$ and T are as defined for a compound of the formula I and PG is a protecting group, or a reactive derivative thereof, with an amine of the formula VI, $$R_b\text{—NH—}R_c \qquad \text{(VI)}$$

wherein $R_b$ and $R_c$ are as defined for a compound of the formula I, followed, if no further conversion requiring protecting groups is intended, by removal of any protecting group(s); or (D) for the synthesis of a compound of the formula I wherein $R^3$ is a moiety of the formula (g)

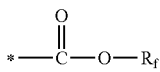

(g)

wherein $R_f$ is as defined for a compound of the formula I and wherein $R^1$, $R^2$, $R^4$, $R^5$ and T are as defined for a compound of the formula I, reacting an acid of the formula IIB,

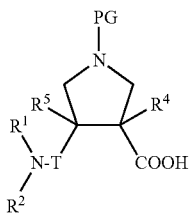

(IIB)

wherein $R^1$, $R^2$, $R^4$, $R^5$ and T are as defined for a compound of the formula I and PG is a protecting group, or a reactive derivative thereof, with an alcohol or alcohol derivative of the formula VII, $$R_f\text{—X} \qquad \text{(VII)}$$

wherein $R_f$ is as defined for a compound of the formula I and X is hydroxy or a leaving group, followed, if no further conversion requiring protecting groups is intended, by removal of any protecting group(s); or (E) for the synthesis of a compound of the formula I wherein $R^3$ is a moiety of the formula (d) or (e) as defined for a compound of the formula I and $R^1$, $R^2$, R $R^5$ and T are as defined for a compound of the formula I, reacting a compound of the formula IIA,

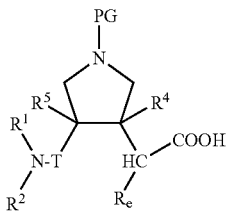

(IIA)

wherein $R^1$, $R^2$, $R^4$, $R^5$, T and $R_e$ are as defined for a compound of the formula I,
(i) for the synthesis of a compound of the formula I wherein $R^3$ is a moiety of the formula (d) with a compound of the formula VI, $$R_b\text{—NH—}R_c \qquad \text{(VI)}$$

wherein $R_a$ and $R_b$ are as defined for a compound of the formula I, or
(ii) for the synthesis of a compound of the formula I wherein $R^3$ is a moiety of the formula (e) with a compound of the formula VII, $$R_f\text{—X} \qquad \text{(VII);}$$

wherein $R_f$ is as defined for a compound of the formula I and X is hydroxy or a leaving group;

and, if desired, subsequent to any one or more of the processes (A), (B), (C),r (D) or (E) mentioned above, converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials (especially of the formulae II, IIA, IIB, III, IV, IV*, V, VI and VII), in addition to specific protecting groups mentioned, further protecting groups may be present, and any protecting groups are removed at an appropriate stage in order to obtain a corresponding compound of the formula I, or a salt thereof.

Preferred Reaction Conditions

The preferred reaction conditions for the reactions mentioned above, as well as for the transformations and conversions, are as follows (or analogous to methods used in the Examples or as described there):

The reduction under (A) preferably takes place under customary conditions for the reduction of carbonic acids to the corresponding alcohols, preferably in the presence of an appropriate complex hydride, such as borane-dimethylsulfide-complex, in an appropriate solvent, e.g. an ether, such as tetrahydrofurane, at preferred temperatures e.g. from −40 to 30° C., e.g. from −15 to 0° C., or e.g. with disiamylborane or LiAlH[OC(CH$_3$)]$_3$ in tetrahydrofurane or diethylether, sodium borohydride in ethanol or sodium borohydride in the presence of LiCl in diglycol, or the like, at preferred temperatures in the range from 0° C. to the reflux temperature of the reaction mixture.

The subsequent removal of a protecting group, e.g. PG, such as tert-butoxycarbonyl, methoxymethyl, benzyl, 2-(trimethylsilyl)-ethoxycarbonyl or tert-butyldimethylsilyl, if required, takes place under standard conditions, see also the literature mentioned below under General Process Conditions. For example, tert-butoxycarbonyl is removed in the presence of an acid, e.g. a hydrohalic acid, such as HCl, in an appropriate solvent, e.g. an ether, such as dioxane, or an alcohol, e.g. isopropanol, at customary temperatures, e.g. at room temperature, the removal of benzyl by treatment with hydrogen in the presence of a noble metal catalyst, such as palladium on charcoal, under customary reaction conditions, e.g. in an appropriate solvent, such as methanol or ethanol, and at customary temperatures, e.g. from 0 to 50° C., the removal of 2-(trimethylsilyl)-ethoxycarbonyl can be achieved, for example, by reaction with a tetra-lower alkylammonium fluoride, such as tetraethylammoniumfluoride, in an appropriate solvent or solvent mixture, e.g. a halogenated hydrocarbon, such as methylene chloride, and/or a nitrile, such as acetonitrile, preferably at elevated temperatures, e.g. under reflux conditions, and the removal of tert-butyldimethylsilyl in the presence of tetra-butyl ammonium fluoride, e.g. in the presence of a solvent such as tetrahydrofurane at preferred temperatures from 0 to 50° C., e.g. at about room temperature.

The further reaction under (A) (i) (preferably with a still protected compound of the formula III) with a compound of the formula IV then preferably takes place under customary conditions for substitution reaction, e.g. in an appropriate solvent, such as an ether, e.g. tetrahydrofurane, or a halogenated hydrocarbon, e.g. methylene chloride, at appropriate temperatures, e.g. in the range from −40° C. to the reflux temperature, if useful or required in the presence of a base, such as potassium carbonate. The leaving group X is preferably halo, especially chloro, bromo or iodo, alkanesulfonyloxy, such as methanesulfonyloxy, or arylsulfonyloxy, such as p-toluolsulfonyloxy.

The further reaction under (A) (ii) (preferably with a still protected compound of the formula III) with a compound of the formula IV*, alternatively, then preferably takes place under customary conditions for the reaction of hydroxy compounds with isocyanates, for example, the reaction preferably takes place in the presence of a Lewis Acid, such as aluminium chloride, in an appropriate solvent, such as diethyl-ether, at preferred temperatures e.g. from 0 to 50° C. Where required, subsequent removal of protecting groups takes place as described above or below, especially as described under the general process conditions.

The reductive amination under (B) preferably takes place place under customary conditions for reductive amination, e.g. in the presence of an appropriate reducing (e.g. hydrogenation) agent, such as hydrogen in the presence of a catalyst or a complex hydride, e.g. sodium triacetoxyborohydride or sodium cyanoborohydride, in an appropriate solvent, such as a halogenated hydrocarbon, e.g. methylene chloride or 1,2,-dichloroethane, and optionally a carbonic acid, e.g. acetic acid, at preferred temperatures between −10° C. and 50° C., e.g. from 0° C. to room temperature; if required, the subsequent removal of protecting groups takes place e.g. as described above under (A).

The condensation of an acid of the formula II, or a reactive derivative thereof, under (C) preferably takes place under customary condensation conditions, where among the possible reactive derivatives of an acid of the formula II reactive esters (such as the hydroxybenzotriazole (HOBT), pentafluorophenyl, 4-nitrophenyl or N-hydroxysuccinimide ester), acid halogenides (such as the acid chloride or bromide) or reactive anhydrides (such as mixed anhydrides with lower alkanoic acids or symmetric anhydrides) are preferred. Reactive carbonic acid derivatives can also and preferably be formed in situ. The reaction is carried out by dissolving the compounds of formulae II and VI in a suitable solvent, for example a halogenated hydrocarbon, such as methylene chloride, N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and, if the reactive derivative of the acid of the formula II is formed in situ, a suitable coupling agent that forms a preferred reactive derivative of the carbonic acid of formula III in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N', N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, *Synthesis* 1972, 453-463. The reaction mixture is preferably stirred at a temperature of between approximately −20 and 50° C., especially between 0° C. and 30° C., e.g. at room temperature. The reaction may preferably carried out under an inert gas, e.g. nitrogen or argon. If required, the subsequent removal of protecting groups takes place e.g. as described above under (A).

The esterification under (D) can be carried out under comparable reaction conditions as described for the condensation under (C) described in the preceding paragraph, and also the reactive derivatives of the acid of the formula II may be as described there, if in the compound of the formula VII X is hydroxy. Where X is a leaving group, especially halogen, the reaction takes place in the presence of a base. If required, the subsequent removal of protecting groups takes place e.g. as described above under (A).

The condensation under reaction (E) (i) preferably takes place under conditions as mentioned above for reaction (C), the esterification under reaction (E) (ii) with compounds of the formula VII wherein X is OH preferably takes place under conditions mentioned above for reaction (D), the reaction (e) (ii) with compounds of the formula VII wherein X is a leaving group, preferably halogen, can take place in the presence of a base.

Optional Reactions and Conversions

Compounds of the formula I, or protected forms thereof directly obtained according to any one of the preceding procedures (meaning that, if conversion is desired, a removal of protecting groups is not required under (A), (B), (C), (D) or (E) or after introducing protecting groups anew, which are included subsequently as starting materials for conversions as well even if not mentioned specifically, can be converted into different compounds of the formula I according to known procedures, where required after removal of protecting groups.

For example, a compound of the formula I wherein $R_1$, $R_2$, $R_4$, $R_5$ and T are as defined for compounds of the formula I above or below and wherein $R^3$ is a group of the formula (a) mentioned above wherein $R_e$ is as defined for a compound of the formula I and $R_a$ is hydrogen (which compound may be used in free or preferably in protected form, e.g. a compound of the formula III given above) may be converted into the corresponding compound of the formula VIII,

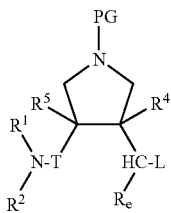

(VIII)

wherein $R_e$, $R_1$, $R_2$, $R_4$, $R_5$ and T are as just defined, PG is a protecting group and L is a leaving group, especially a $C_1$-$C_7$-alkanesulfonyloxy, such as methanesulfonyloxy, or arylsulfonyloxy, such as toluenesulfonyloxy, preferably by reaction with the corresponding alkane- or arylsulfonylhalogenide, e.g. -chloride, under customary conditions, e.g. in the absence or presence of an appropriate solvent, such as an ether or a halogenated hydrocarbon, in the presence of a tertiary nitrogen base, such as triethylamine, at temperatures e.g. from −20° C. to the reflux temperature of the reaction mixture, giving a corresponding compound of the formula VIII; the latter can then be deprotected to give the corresponding compound of the formula I, or reacted with a mercapto compound of the formula X,

wherein $R_d$ is a moiety as defined as for a compound of the formula I other than of the formula —N($R_a$)($R_b$), to give a corresponding compound of the formula XI,

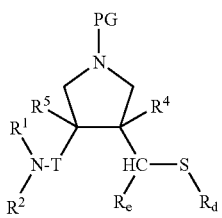

wherein $R_1$, $R_2$, $R_4$, $R_5$ and T are as just defined and PG is a protecting group, which may then be deprotected to give a compound of the formula I wherein $R^3$ is a moiety of the formula (c)

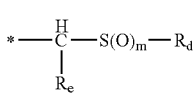

wherein $R_e$ is as defined for a compound of the formula I, m is 0 (zero) and $R_d$ is as defined for a compound of the formula X; or converted by oxidation, e.g. with an organic peroxide, such as m-chloro-perbenzoic acid, in an appropriate solvent, e.g. dimethylformamide, tetrahydrofurane or methylene chloride, to the corresponding compound wherein m is 2 which after deprotection gives the corresponding compound of the formula I.

Alternatively, a compound of the formula I wherein $R_1$, $R_2$, $R_4$, $R_5$ and T are as defined for compounds of the formula I above or below and wherein $R^3$ is a group of the formula (a) mentioned above wherein $R_e$ is as defined for a compound of the formula I and $R_a$ is hydrogen (which compound may be used in free or preferably in protected form, e.g. a compound of the formula III given above) may be converted into a compound of the formula VIII as described above which is then reacted with a $C_1$-$C_7$-alkanoyl-thiolate, e.g. an alkalimetal (such as sodium) thiolate, to the corresponding compound of the formula XI given above wherein $R_d$ is $C_1$-$C_7$-alkanoyl, such as acetyl, which is then hydrolyzed, e.g. with lithium hydroxide, under customary conditions to the corresponding free mercapto compound of the formula XIA,

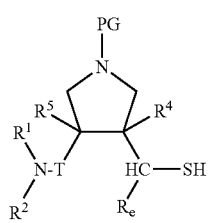

which is then either
(i) reacted with a compound of the formula XA,

wherein Hal is halo and $R_d$ has a meaning as defined herein other than —N($R_b$$R_c$), to a corresponding protected version of a compound of the formula I which can then be deprotected to give the corresponding compound of the formula I wherein $R_d$ is as defined for a compound of the formula XA, or which can first be oxidised to a protected version of a compound of the formula I wherein m is 1 or preferably 2, for example with a peroxide, such as m-chloro-perbenzoic acid, and then deprotected to give the corresponding compound of the formula I; or (ii) oxidized with a peroxide, such as hydrogen peroxide, and subsequently reacted with a halogenating agent, such as phosphorous oxychloride or oxalyl chloride, to the corresponding compound wherein instead of the SH group an $S(O)_2$-Hal group, e.g. wherein Hal is halo, especially chloro, is present, which can then be reacted with a compound of the formula VI

as defined above to give, after deprotection, a corresponding compound of the formula I wherein $R_d$ is a group of the formula —N($R_b$)($R_c$).

In a compound of the formula I wherein $R^3$ is a moiety of the formula (b)

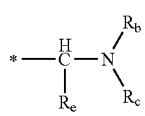

wherein $R_e$ is as defined for a compound of the formula I, $R_c$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl and $R_b$ is hydrogen, or preferably a protected derivative thereof, e.g. of the formula XII,

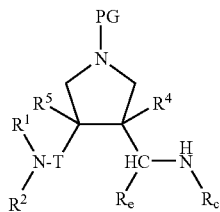

(XII)

wherein PG is a protecting group and the other moieties are as defined for a compound of the formula I, can be converted into the acylated compound of the formula XIII,

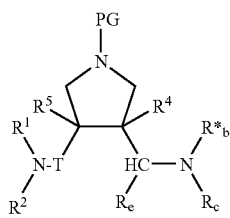

(XIII)

wherein $R^*_b$ is acyl and the other moieties are as defined for a compound of the formula XII, by reaction with a corresponding acid of the formula XIV, $$R^*_b\text{—OH} \qquad\qquad (XIV)$$

wherein $R^*_b$ is acyl, or a reactive derivative thereof. Removal of the protecting group(s) then leads to the corresponding compound of the formula I wherein $R^3$ is a moiety of the formula (b) as just given wherein $R_e$ and $R_c$ are as defined for a compound of the formula XII and $R_b$ is acyl.

An oxo group in a compound of the formula I, e.g. carbonyl as T, may be converted to the corresponding thioxo, e.g. thiocarbonyl, group by reaction with Lawesson's reagent under customary reaction conditions.

Salts of compounds of formula I having at least one salt-forming group may be prepared in a manner known per se. For example, salts of compounds of formula I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

A salt of a compound of the formula I can be converted in customary manner into the free compound; metal and ammonium salts can be converted, for example, by treatment with suitable acids, and acid addition salts, for example, by treatment with a suitable basic agent. In both cases, suitable ion exchangers may be used.

Stereoisomeric mixtures, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Intermediates and final products can be worked up and/or purified according to standard methods, e.g. using chromatographic methods, distribution methods, (re-) crystallization, and the like. Some possible methods that can also be used with other compounds analogously can be found in the Examples.

Starting Materials

In the subsequent description of starting materials (which term also includes intermediates) and their synthesis, $R^1$, $R^2$, $R^3$, $R^4$, $R^5$, T, m, $R_a$, $R_b$, $R_c$, $R_d$, $R_e$, $R_f$ and PG have the meanings given above or in the Examples for the respective starting materials or intermediates, if not indicated otherwise directly or by the context. Protecting groups, if not specifically mentioned, can be introduced and removed at appropriate steps in order to prevent functional groups, the reaction of which is not desired in the corresponding reaction step or steps, from participating in a reaction, employing protecting groups, methods for their introduction and their removal are as described above or below, e.g. in the references mentioned under "General Process Conditions". The person skilled in the art will readily be able to decide whether and which protecting groups are useful or required and at which stage it is appropriate to introduce, exchange and/or remove protecting groups.

A compound of the formula II wherein $R^*_e$ is hydrogen (which is a compound of the formula V wherein $R^*_e$ is hydrogen) can be obtained from a compound of the formula IIB or of the formula XV given below by reduction of the (in the case of formula XV esterified, e.g. by $C_1$-$C_7$-alkyloxy) carboxy function, e.g. with an appropriate complex hydride, such as borane-dimethylsulfide complex, in an appropriate solvent, such as an ether, e.g. tetrahydrofurane, at preferred temperatures between −50° C. and the reflux temperature of the reaction mixture, e.g. at −30 to 60° C.

A compound of the formula II wherein $R^*_e$ is unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (especially) substituted or preferably unsubstituted $C_1$-$C_7$-alkyl (which is a compound of the formula V wherein $R_e$ is unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (especially) substituted or preferably unsubstituted $C_1$-$C_7$-alkyl) can, for example, be obtained from a compound of the formula V wherein R*_e is hydrogen by reaction with a grignard reagent of the formula XXII,

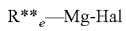  (XXII)

wherein R**_e is unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (especially) substituted or preferably unsubstituted $C_1$-$C_7$-alkyl and Hal is halo, especially chloro or bromo, under customary reaction conditions, e.g. in an ether, such as diethylether, at preferred temperatures from 0° C. to the reflux temperature of the reaction mixture, to give a compound of the formula IIIA,

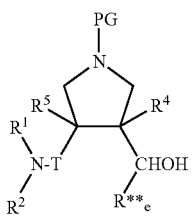 (IIIA)

wherein R**_e is as just described (which is a compound of the formula III wherein R*_e is as just defined for R**_e); which is then oxidized, e.g. in the presence of an appropriate oxidant, such as Dess-Martin-periodinane, in an appropriate solvent, e.g. a halogenated hydrocarbon, e.g. methylene chloride, at preferred temperatures from 0° C. to 50° C., e.g. at room temperature, to give the corresponding compound of the formula II or V.

Alternatively, a compound of the formula II wherein R*_e is unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or (especially) substituted or preferably unsubstituted $C_1$-$C_7$-alkyl can be reacted in the presence of a condensation agent, e.g. under reaction conditions and with reagents as described under process variants (C) and (D) above, with N,O-dimethyl hydroxylamine to form the corresponding Weinreb amide which can then directly be reacted with a Grignard reagent of the formula XXII as described above to a corresponding compound of the formula II or V.

A compound of the formula IIB (which is a compound of the formula II wherein R*_e is hydroxy) can be prepared from a corresponding ester of the formula XV,

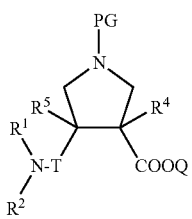 (XV)

wherein Q is an organic moiety, preferably substituted or especially unsubstituted $C_1$-$C_7$-alkyl, by hydrolysis in the presence of a base, e.g. an alkaline metal hydroxide, such as lithium hydroxide, in an appropriate solvent, e.g. a hydroxy lower alkane, such as methanol, in the presence of water and preferably at temperatures e.g. from 0 to 50° C.

A compound of the formula XV wherein T is methylene or methylene mono-substituted by alkyl (—[C(H)(alkyl)]-) can, for example, be obtained by reacting an aldehyde or keto compound of the formula XVI,

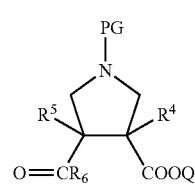 (XVI)

wherein Q is as described for a compound of the formula XV and $R_6$ is alkyl or preferably hydrogen with an amine of the formula XVII,

 (XVII)

under conditions of reductive amination, e.g. under the reaction conditions described for reaction (B) above. If instead of a compound of the formula XVII a compound of the formula XVII*,

 (XVII*)

is used, a compound of the formula XV* results,

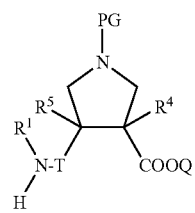 (XV*)

wherein Q is as defined for a compound of the formula XV, which can then be converted into a compound of the formula XV by reaction with a compound of the formula XVIII,

 (XVIII)

wherein Y, if $R_2$ is acyl, is either hydroxy or the compound is a reactive derivative, e.g. wherein Y is halo or an activating group formed in situ, preferably under conditions analogous to those in reaction (C) above; or Y, if $R_2$ is one of the moieties defined for $R_2$ in compounds of the formula I other than acyl, is a leaving group, e.g. as defined for X in a compound of the formula IV above and under reaction conditions analogous to those described above for the reaction under (A) (i).

A compound of the formula XVI wherein $R_6$ is alkyl or preferably hydrogen can, for example, be obtained from a hydroxy compound of the formula XIX,

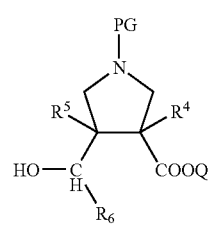 (XIX)

wherein $R_6$ is alkyl or preferably hydrogen and Q is as defined for a compound of the formula XV by oxidation to the corresponding oxo compound of the formula XVI which preferably takes place in the presence of an appropriate oxidant, such as Dess-Martin-periodinane, in an appropriate solvent, e.g. a halogenated hydrocarbon, e.g. methylene chloride, at preferred temperatures from 0° C. to 50° C., e.g. at room temperature.

A hydroxy compound of the formula XIX wherein $R_6$ is hydrogen can, for example, be obtained from a compound of the formula XX,

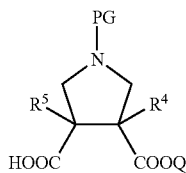

(XX)

wherein Q is as defined for a compound of the formula XV by reduction in the presence of an appropriate complex hydride, e.g. borane dimethylsulfide complex, in an appropriate solvent, such as an ether, e.g. tetrahydrofurane, at preferred temperatures between −50° and the reflux temperature of the reaction mixture, e.g. at −30 to 60° C.

A compound of the formula XX may, inter alia, be obtained by reacting a compound of the formula XXI,

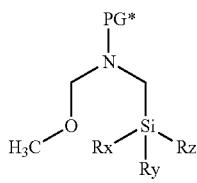

(XXI)

wherein PG* is a protecting group that withstands the reaction, e.g. benzyl, and each of Rx, Ry and Rz are alkyl, preferably C1-C7-alkyl, especially methyl, with a fumaric acid derivative of the formula XXII,

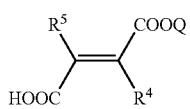

(XXII)

wherein each of $R^4$ and $R^5$ preferably has one of the meanings given for $R^4$ and $R^5$ other than hydroxy, more preferably is $C_1$-$C_7$-alkyl, e.g. methyl or ethyl, or is hydrogen, in the presence of an acid, e.g. trifluoroacetic acid, in an appropriate solvent, such as y halogenated hydrocarbon, e.g. methylene chloride, at preferred temperatures e.g. in the range from −30 to 50° C., yielding the corresponding compound of the formula XX wherein preferably the protecting group PG* can be replaced with a different protecting group PG useful for subsequent reactions, such as tert-butoxycarbonyl, for example benzyl PG* can be removed with hydrogen in the presence of a hydrogenation catalyst, especially a noble metal catalyst, preferably on a carrier material, such as charcoal, e.g. Pd/C, in an appropriate solvent, such as an alcohol, e.g. ethanol, at temperatures e.g. from −10 to 60° C., and tert-butoxycarbonyl may be introduced in the same step or subsequently by reaction with tert-butoxycarbonic anhydride.

A compound of the formula IIA can, for example, be prepared from a corresponding ester of the formula XVA,

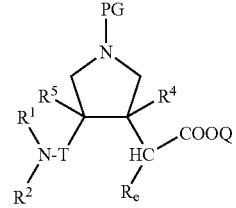

(XVA)

wherein Q is an organic moiety, preferably substituted or especially unsubstituted $C_1$-$C_7$-alkyl, by hydrolysis in the presence of a base, e.g. an alkaline metal hydroxide, such as lithium hydroxide, in an appropriate solvent, e.g. a hydroxy lower alkane, such as methanol, in the presence of water and preferably at temperatures e.g. from 0 to 50° C.

A compound of the formula XVA wherein T is methylene or methylene mono-substituted by alkyl (—[C(H)(alkyl)]-) can, for example, be obtained by reacting an aldehyde or keto compound of the formula XVIA,

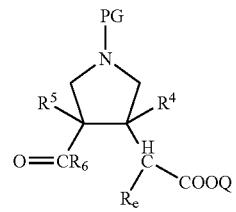

(XVIA)

wherein Q is as described for a compound of the formula XVA and $R_6$ is alkyl or preferably hydrogen with an amine of the formula XVII, $$R^1\text{—NH—}R^2 \quad \text{(XVII)}$$

under conditions of reductive amination, e.g. under the reaction conditions described for reaction (B) above. If instead of a compound of the formula XVII a compound of the formula XVII*, $$H_2\text{—N—}R_1 \quad \text{(XVII*)}$$

is used, a compound of the formula XVA* results,

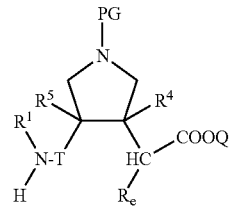

(XVA*)

wherein Q is as defined for a compound of the formula XVA, which can then be converted into a compound of the formula XVA by reaction with a compound of the formula XVIII,

R₂—Y    (XVIII)

wherein Y, if R₂ is acyl, is either hydroxy or the compound is a reactive derivative, e.g. wherein Y is halo or an activating group formed in situ, preferably under conditions analogous to those in reaction (C) above; or Y, if R₂ is one of the moieties defined for R₂ in compounds of the formula I other than acyl, is a leaving group, e.g. as defined for X in a compound of the formula IV above and under reaction conditions analogous to those described above for the reaction under (A) (i).

A compound of the formula XVIA wherein $R_6$ is alkyl or preferably hydrogen can, for example, be obtained from a hydroxy compound of the formula XIXA,

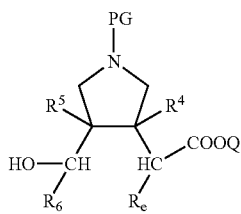

(XIXA)

wherein $R_6$ is alkyl or preferably hydrogen and Q is as defined for a compound of the formula XVA by oxidation to the corresponding oxo compound of the formula XVIA which preferably takes place in the presence of an appropriate oxidant, such as Dess-Martin-periodinane, in an appropriate solvent, e.g. a halogenated hydrocarbon, e.g. methylene chloride, at preferred temperatures from 0° C. to 50° C., e.g. at room temperature.

A hydroxy compound of the formula XIXA wherein $R_6$ is hydrogen can, for example, be obtained from a compound of the formula XXA,

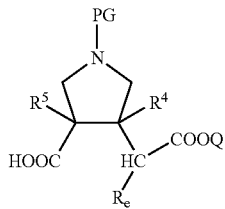

(XXA)

wherein Q is as defined for a compound of the formula XV by reduction in the presence of an appropriate complex hydride, e.g. borane dimethylsulfide complex, in an appropriate solvent, such as an ether, e.g. tetrahydrofurane, at preferred temperatures between −50° and the reflux temperature of the reaction mixture, e.g. at −30 to 60° C.

A compound of the formula XXA may, inter alia, be obtained by reacting a compound of the formula XXI, as described above, with a fumaric acid derivative of the formula XXIA,

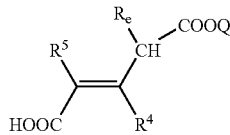

(XXIA)

wherein each of $R^4$ and $R^5$ preferably has one of the meanings given for $R^4$ and $R^5$ other than hydroxy, more preferably is $C_1$-$C_7$-alkyl, e.g. methyl or ethyl, or is hydrogen, in the presence of an acid, e.g. trifluoroacetic acid, in an appropriate solvent, such as y halogenated hydrocarbon, e.g. methylene chloride, at preferred temperatures e.g. in the range from −30 to 50° C., yielding the corresponding compound of the formula XXA wherein preferably the protecting group PG* can be replaced with a different protecting group PG useful for subsequent reactions, such as tert-butoxycarbonyl, for example benzyl PG* can be removed with hydrogen in the presence of a hydrogenation catalyst, especially a noble metal catalyst, preferably on a carrier material, such as charcoal, e.g. Pd/C, in an appropriate solvent, such as an alcohol, e.g. ethanol, at temperatures e.g. from −10 to 60° C., and tert-butoxycarbonyl may be introduced in the same step or subsequently by reaction with tert-butoxycarbonic anhydride.

A compound of the formula IIA may also be obtained by reacting a compound of the formula VIII as described above with a cyanide salt, e.g. an alkali metal cyanide, such as sodium or potassium cyanide, to the corresponding compound wherein instead of the —C(H)($R_e$)-L group a —C(H)($R_e$)—CN group is present, followed by hydrolysis with a base, such as sodium hydroxide, or under mild conditions by reaction first with $H_2S$ resulting in a corresponding thioamide which can then be hydrolysed under mild conditions to give a corresponding compound of the formula IIA.

A compound of the formula XV or XVA wherein T is carbonyl (and Q is as defined for compounds of the formula XV above) can, for example, be obtained by reacting a compound of the formula XX or XXA, respectively, as defined above, or a reactive derivative thereof, under conditions analogous to those described above for the condensation reaction under process variant (C) with a compound of the formula XVII as defined above.

In the preceding starting materials (and final products), $R^4$ and $R^5$ are preferably hydrogen, with less preference unsubstituted or substituted alkyl, esterified or etherified hydroxy, with still less preference (in the intermediates preferably protected) hydroxy.

Hydroxy $R^4$ and/or $R^5$ can be introduced into starting materials at various stages, e.g. in (preferably appropriately protected) compounds of the formula XV, for example by treatment with a strong base to remove the hydrogen to be substituted by $R^4$ or $R^5$, such as lithium hexamethyldisilazide (LHMDS) or preferably lithium diisopropylamide in tetrahydrofuran at low temperatures, e.g. from −100 to −50° C., such as at −78° C., followed by oxidation e.g. by addition of an oxaziridine derivative according to Davis (e.g. 2-tert-butoxycarbonyl-3-trichloromethyl-oxaziridine or 2-(phenylsulfonyl or tolylsulfonyl)-3-phenyl-oxaziridine or (e.g. for stereoselective synthesis) (+)- or (−)-(camphorsulfonyl)oxaziridine) to give the corresponding hydroxy compound.

An alternative is the transformation on the following 0-protected alcohol shown on the left (a compound of the formula XIX) to give an intermediate (shown on the right, also a compound of the formula XIX) that can be used either to build a final pyrrolidine where $R^5$ or $R^4$ are OH or etherified or esterified hydroxy depending on the sequence of reactions used:

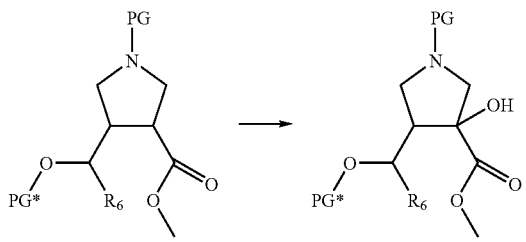

wherein in both formulae PG* is a hydroxy protecting group, under comparable reacrtion conditions as just mentioned or other customary conditions.

Hydroxy $R^4$ and/or $R^5$ may then further be esterified or etherified according to standard procedures to give the corresponding compounds wherein $R^4$ and/or $R^5$ is esterified or etherified hydroxy.

Other starting materials, such as also the starting materials of the formula IV, IV*, VI, VII, X and XIV are known in the art, can be prepared according to methods that are known in the art and/or are commercially available.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the processes in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the processes of the present invention those starting materials are preferably used which result in compounds of formula I described as being preferred. Special preference is given to reaction conditions that are identical or analogous to those mentioned in the Examples. The invention relates also to novel starting compounds and intermediates described herein, especially those leading to novel compounds of the formula I or compounds of the formula I mentioned as preferred herein.

Pharmaceutical use, Pharmaceutical Preparations and Methods

As described above, the compounds of the present invention are inhibitors of renin activity and, thus, may be of use for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like. Hypertension, at least as one component of the disease to be treated, is especially preferred, meaning that hypertension alone or in combination with one or more (especially of the mentioned) other diseases may be treated (prophylactically and/or therapeutically).

The present invention further provides pharmaceutical compositions comprising a therapeutically effective amount of a pharmacologically active compound of the instant invention, alone or in combination with one or more pharmaceutically acceptable carriers.

The pharmaceutical compositions according to the present invention are those suitable for enteral, such as oral or rectal, transdermal and parenteral administration to mammals, including man, to inhibit renin activity, and for the treatment of conditions associated with (especially inappropriate) renin activity. Such conditions include hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders and the like. Especially preferred is a disease which comprises hypertension, more especially hypertension itself, where treatment with a pharmaceutical composition or the use of a compound of the formula I for its synthesis is useful prophylactically and/or (preferably) therapeutically.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

Accordingly, the present invention provides pharmaceutical compositions as described above for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, as well as methods of their use.

The pharmaceutical compositions may contain a therapeutically effective amount of a compound of the formula I as defined herein, either alone or in a combination with another therapeutic agent, e.g., each at an effective therapeutic dose as reported in the art. Such therapeutic agents include:

a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) anti-obesity agents such as orlistat; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibittors; ACE/NEP inhibitors such as omapatrilat, sampatrilat and fasidotril; angiotensin II antagonists such as candesartan, eprosartan, irbesartan, losartan, telmisartan and valsartan, in particular valsartan; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs,* 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical products or compositions comprising a therapeutically effective amount of a compound of the invention alone or in combination with a therapeutically effective amount of another therapeutic agent, preferably selected from anti-diabetics, hypolipidemic agents, anti-obesity agents or anti-hypertensive agents, most preferably from antidiabetics, anti-hypertensive agents or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by (especially inappropriate) renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like.

Thus, the present invention also relates to a compound of formula I for use as a medicament, to the use of a compound of formula I for the preparation of a pharmaceutical composition for the prevention and/or treatment of conditions mediated by (especially inappropriate) renin activity, and to a pharmaceutical composition for use in conditions mediated by (especially inappropriate) renin activity comprising a compound of formula I, or a pharmaceutically acceptable salt thereof, in association with a pharmaceutically acceptable diluent or carrier material therefore.

The present invention further provides a method for the prevention and/or treatment of conditions mediated by (especially inappropriate) renin activity, which comprises administering a therapeutically effective amount of a compound of the present invention to a warm-blooded animal, especially a human, in need of such treatment.

A unit dosage for a mammal of about 50-70 kg may contain between about 1 mg and 1000 mg, advantageously between about 5-600 mg of the active ingredient. The therapeutically effective dosage of active compound is dependent on the species of warm-blooded animal (especially mammal, more especially human), the body weight, age and individual condition, on the form of administration, and on the compound involved.

In accordance with the foregoing the present invention also provides a pharmaceutical product comprising a therapeutic combination, e.g., a kit, kit of parts, e.g., for use in any method as defined herein, comprising a compound of formula I, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition comprising a compound of the formula I according to the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula I, or a pharmaceutically acceptable salt thereof, and at least a second drug substance, said second drug substance preferably being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to a modulation of (especially inappropriate) renin activity.

Preferably, the condition associated with (especially inappropriate) renin activity is selected from hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders.

Finally, the present invention provides a method or use which comprises administering a compound of formula I in combination with a therapeutically effective amount of an anti-diabetic agent, a hypolipidemic agent, an anti-obesity agent or an anti-hypertensive agent.

Ultimately, the present invention provides a method or use which comprises administering a compound of formula I in the form of a pharmaceutical composition as described herein.

The above-cited properties are demonstrable in vitro and in vivo tests using advantageously mammals, e.g., mice, rats, rabbits, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The concentration level in vitro may range between about $10^{-3}$ molar and $10^{-10}$ molar concentrations. A therapeutically effective amount in vivo may range depending on the route of administration, between about 0.001 and 500 mg/kg, preferably between about 0.1 and 100 mg/kg.

As described above, the compounds of the present invention have enzyme-inhibiting properties. In particular, they inhibit the action of the natural enzyme renin. Renin passes from the kidneys into the blood where it effects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

The action of renin inhibitors may be demonstrated inter alia experimentally by means of in vitro tests, the reduction in the formation of angiotensin I being measured in various systems (human plasma, purified human renin together with synthetic or natural renin substrate).

Inter Alia the Following In Vitro Tests may be Used:

Recombinant human renin (expressed in Chinese Hamster Ovary cells and purified using standard methods) at 7.5 nM concentration is incubated with test compound at various concentrations for 1 h at RT in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 2 µM and increase in fluorescence is recorded at an excitation wave-length of 350 nm and at an emission wave-length of 500 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 20 µM.

Alternatively, recombinant human renin (expressed in Chinese Hamster Ovary cells and purified using standard methods) at 0.5 nM concentration is incubated with test compound at various concentrations for 2 h at 37° C. in 0.1 M Tris-HCl buffer, pH 7.4, containing 0.05 M NaCl, 0.5 mM EDTA and 0.05% CHAPS. Synthetic peptide substrate Arg-Glu (EDANS)-Ile-His-Pro-Phe-His-Leu-Val-Ile_His_Thr-Lys (DABCYL)-Arg9 is added to a final concentration of 4 µM and increase in fluorescence is recorded at an excitation wavelength of 340 nm and at an emission wave-length of 485 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 20 µM.

In another assay, human plasma spiked with recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration.

Compounds of the formula I, in this assay, preferably can show $IC_{50}$ values in the range from 1 nM to 20 µM.

In another assay, recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I, in this assay, preferably show $IC_{50}$ values in the range from 1 nM to 20 µM.

In animals deficient in salt, renin inhibitors bring about a reduction in blood pressure. Human renin may differ from the renin of other species. In order to test inhibitors of human renin, primates, e.g.,marmosets (Callithrix jacchus) may be used, because human renin and primate renin are substantially homologous in the enzymatically active region. Inter alia the following in vivo tests may be used:

Compounds of the formula I can be tested in vivo in primates as described in the literature (see for example by Schnell C R et al. Measurement of blood pressure and heart rate by telemetry in conscious, unrestrained marmosets. Am J Physiol 264 (Heart Circ Physiol 33). 1993: 1509-1516; or Schnell C R et al. Measurement of blood pressure, heart rate, body temperature, ECG and activity by telemetry in conscious, unrestrained marmosets. Proceedings of the fifth FELASA symposium: Welfare and Science. Eds BRIGHTON. 1993.

The following Examples, while representing preferred embodiments of the invention, serve to illustrate the invention without limiting its scope.

Abbreviations:
abs. Absolute
Ac acetyl
AcOEt ethyl acetate
AcOH acetic acid
aq aqueous
Bz benzyl
cc concentrated
c-hexane cyclohexane
DIBAL-H diisobutylaluminium hydride
DMF dimethylformamide
DMSO dimethylsulfoxide
DPPA diphenylphosphoryl azide
EDCl 1-(3-dimethylaminopropyl)-3-ethylcarbodiimide hydrochloride
Ether diethylether
$Et_3N$ triethylamine
$Et_2O$ diethylether
EtOH ethanol
Flow flow rate
h hour(s)
HMPA hexamethylphosphoroamide
HOBt 1-hydroxybenzotriazole
HPLC High Performance Liquid Chromatography
iPrOH isopropanol
L liter(s)
KHMDS potassium hexamethyldisilazane
LC-MS Liquid Chromatography/Mass Spectrometry
LDA lithium diisopropylamine
Me methyl
MeI methyl iodide
MeOH methanol MesCl methanesulfonyl chloride
Min minute(s)
mL milliliter
MS Mass Spectrometry
NMM 4-methylmorpholine
NMR Nuclear Magnetic Resonance
Pd/C palladium on charcoal
Ph phenyl
Py BOP (benzotriazol-1-yloxy)-tripyrrolidinophosphonium-hexafluorophosphate
RT room temperature
TBAF tetra-butylammonium fluoride
TBDMS-Cl tert-butyldimethylsilyl chloride
TBDMS tert-butyldimethylsilyl
TBME tert-Butylmethylether
TEA triethylamine
TEMPO 2,2,6,6,-tetramethyl-1-piperidinyloxy free radical
TFA trifluoroacetic acid
THF tetrahydrofurane
RP reverse phase
Prep Preparative
sat. saturated
TLC Thin Layer Chromatography
$t_r$ retention time Trademarks
Celite=Celite® (The Celite Corporation)=filtering aid based on diatomaceous earth
$NH_2$ Isolute (=Isolute® $NH_2$, Isolute® is registered for Argonaut Technologies, Inc.)=ion exchanger with amino groups based on silica gel
Nucleosil=Nucleosil®, trademark of Machery & Nagel, Düren, FRG for HPLC materials Temperatures are measured in degrees Celsius. Unless otherwise indicated, the reactions take place at RT.

TLC conditions: $R_f$ values for TLC are measured on 5×10 cm TLC plates, silica gel $F_{254}$, Merck, Darmstadt, Germany.

Scheme 1

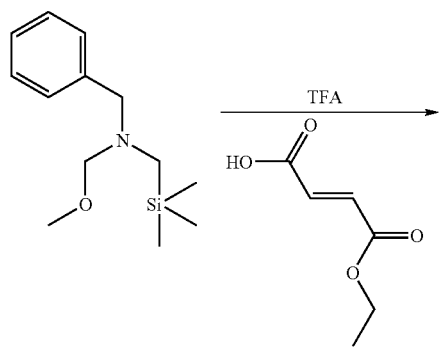

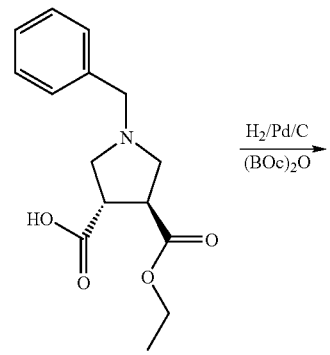

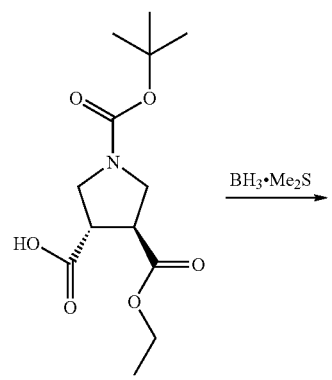

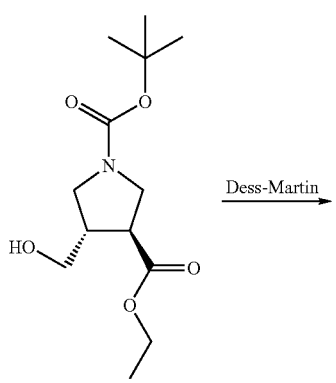

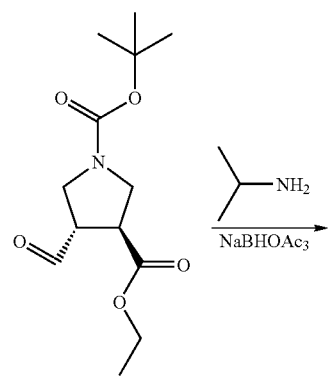

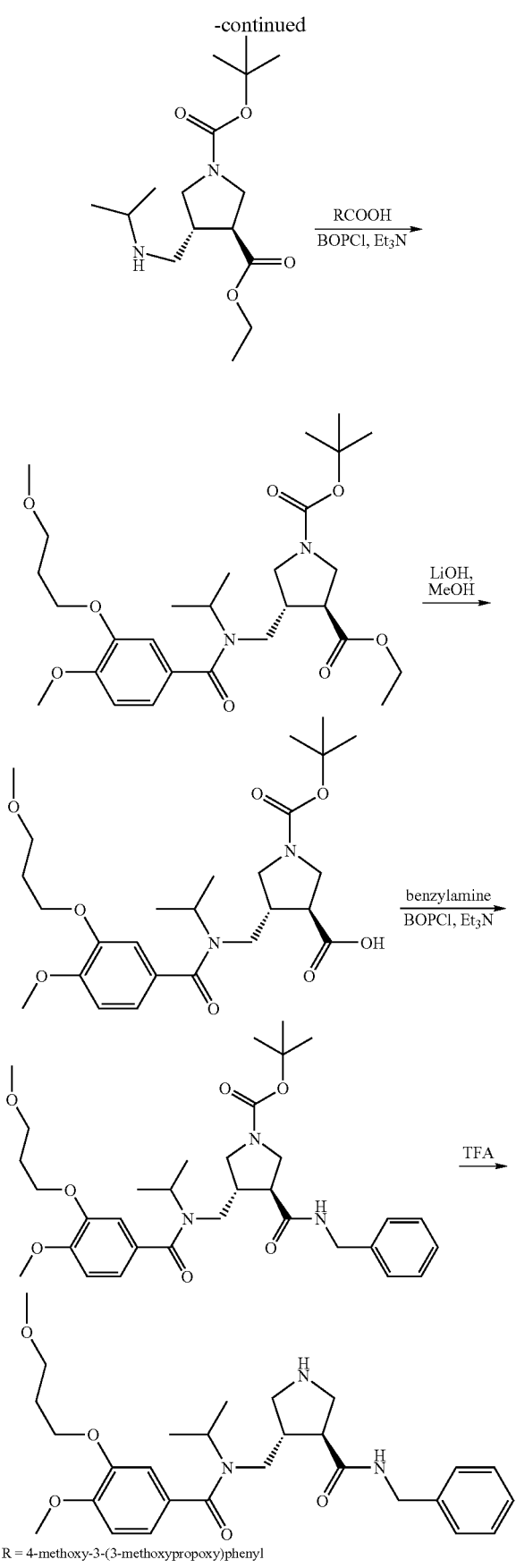

R = 4-methoxy-3-(3-methoxypropoxy)phenyl

EXAMPLE 1

(3S*,4S*)-4-({Isopropyl-[4-methoxy-3-(3-methoxy-propoxy)-benzoyl]-amino}-methyl)-pyrrolidine-3-carboxylic acid benzylamide

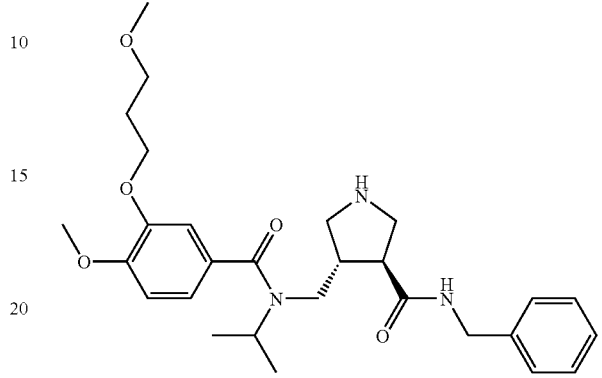

To a solution of (3S*,4R*)-3-benzylcarbamoyl-4-({iso-propyl-[4-methoxy-3-(3-methoxy-propoxy)-benzoyl]-amino}-methyl)-pyrrolidine-1-carboxylic acid tert-butyl ester (61 mg, 0.098 mmol) in 2 mL $CH_2Cl_2$, TFA (113 μL, 1.46 mmol) is added. The mixture is stirred at 30° C. for 2 h, then overnight at RT, and poured into a saturated solution of $NaHCO_3$. The layers are separated, and the aqueous one is back-extracted twice with $CH_2Cl_2$. The combined organic extracts are dried over $Na_2SO_4$, filtered and concentrated. The crude material is purified by flash chromatography on an $NH_2$ Isolute SPE Flash column (eluent: $CH_2Cl_2$:MeOH 100:0 to 95:5) to give the title product. TLC, $R_f$($CH_2Cl_2$/MeOH 9:1)= 0.2. MS (LC-MS): 498 $[M+H]^+$; $t_R$ (HPLC, Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 4.38 min.

To a solution of the free base in dioxane (2 mL), 4N HCl in dioxane (0.105 mmol, 26 μL) is added, and the resulting solution is lyophilized to afford the corresponding hydrochloride salt as a white powder.

The starting material is prepared as follows:

A. (3S*,4S*)-1-Benzyl-pyrrolidine-3,4-dicarboxylic acid monoethyl ester

To a stirred solution of mono ethyl fumarate (2.85 g, 19.8 mmol) and trifluoroacetic acid (1.98 mmol, 0.15 mL) in methylene chloride (50 mL), N-benzyl-N-(methoxymethyl)trimethylsilyl amine (Aldrich) (9.41 g, 39.6 mmol) is added at 0° C. under $N_2$. The mixture is stirred at 0° C. for 30 min and then at RT over 48 h. The crude material is concentrated and purified by flash chromatography on silica gel (eluent: $CH_2Cl_2$/MeOH 85:15 to 85:15+2% $NH_4OH$) to give the title compound. MS (LC-MS): 278.0 $[M+H]^+$. $^1$H-NMR ($CD_3OD$, 400 MHz): δ=1.29 (t, 3H), 3.28 (m, 5H), 3.60 (m, 1 H), 4.07 (m, 2H), 4.20 (m, 2H), 7.47 (m, 5H) ppm.

B. (3S*,4S*)-Pyrrolidine-1,3,4-tricarboxylic acid 1-tert-butyl ester 3-ethyl ester A mixture of (3S*,4S*)-1-benzyl-pyrrolidine-3,4-dicarboxylic acid monoethyl ester (10 g, 36.1 mmol), di-tert-butylcarbonate (7.9 g, 39.6 mmol) and Pd(OH)$_2$/C 20% (1 g, 50% wet) in EtOH (200 mL) is stirred under hydrogen atmosphere for 5 h. The crude material is filtered over a pad of Celite and concentrated. $^1$H-NMR indicates that the title compound is obtained cleanly. TLC, $R_f$(AcOEt)=0.17. MS (LC-MS): 286.1 [M–H]$^-$.

C. (3S*,4S*)4-Hydroxymethyl-pyrrolidine-1,3-dicarboxylic acid 1-tert-butylester 3-ethyl ester To a solution of (3S*,4S*)-pyrrolidine-1,3,4-tricarboxylic acid 1-tert-butyl ester 3-ethyl ester (10 g, 34.8 mmol) in THF (180 mL), a solution of borane dimethylsulfide complex (2N in THF, 24.4 mL, 48.7 mmol) is added slowly at −10° C. The mixture is stirred at −10° C. for 20 min, then allowed to reach RT and further stirred for 4 h. MeOH is carefully added (exothermic!), and the mixture is concentrated under reduced pressure. MeOH is again added, and the mixture is concentrated. This operation is repeated 3 times, then the mixture is finally taken up into a saturated aqueous solution of NaHCO$_3$ and extracted 3 times with CH$_2$Cl$_2$. The combined organic extracts are dried over Na$_2$SO$_4$, filtered and concentrated. The crude material is purified by flash chromatography on silica gel (eluent: CH$_2$Cl$_2$/MeOH from 100:0 to 95:5) to give the title compound as product. TLC, Rf (AcOEt)=0.52. MS (LC-MS): 174.1 [M+H-Boc]$^+$.

D. (3S*,4S*)-4-Formyl-pyrrolidine-1,3-dicarboxylic acid 1-tert-butyl ester 3-ethyl ester To a well stirred mixture of (3S*,4S*)-4-hydroxymethyl-pyrrolidine-1,3-dicarboxylic acid 1-tert-butylester 3-ethyl ester (3.21 g, 11.74 mmol) and Dess-Martin periodinane (2.63 g, 11.74 mmol) in CH$_2$Cl$_2$ (30 mL), slowly wet CH$_2$Cl$_2$ (232 µL of water in 10 mL of CH$_2$Cl$_2$) is added. The clear solution becomes cloudy toward the end of wet CH$_2$Cl$_2$ addition. The mixture is diluted with Et$_2$O, then concentrated to a few mL of solvent by rotary evaporation. The residue is taken up in Et$_2$O and then washed with a 1:1 10% Na$_2$S$_2$O$_3$ saturated aqueous NaHCO$_3$, followed by H$_2$O and brine. The aqueous washings are back-extracted with Et$_2$O, and this organic layer is washed with H$_2$O and brine. The combined organic layers are dried with Na$_2$SO$_4$, filtered and concentrated. The crude mixture is used in the next step without further purification. TLC, $R_f$(c-hexane/AcOEt 8:2)=0.2.

E. (3S*,4R*)-4-(Isopropylamino-methyl)-pyrrolidine-1,3-dicarboxylic acid 1-tert-butyl ester 3-ethyl ester A solution of (3S*,4S*)-4-formyl-pyrrolidine-1,3-dicarboxylic acid 1-tert-butyl ester 3-ethyl ester (2.87 g, 10.56 mmol) and isopropylamine (2.72 mL, 31.68 mmol) in 1,2-dichloroethane (150 mL) is stirred 25 min, before addition of NaBH(OAc)$_3$ (3.12 g, 14.78 mmol) follows. The solution is stirred for 4 h, then diluted with CH$_2$Cl$_2$ and washed with an aqueous saturated solution of NaHCO$_3$. The combined organic extracts are dried over Na$_2$SO$_4$ and concentrated. The crude material is purified by flash chromatography on silica gel (eluent: CH$_2$Cl$_2$/MeOH 100:0 to 80:20) to give the title product. TLC, $R_f$(CH$_2$Cl$_2$/MeOH 95:5)=0.1.

F. (3S*,4R*)-4-({Isopropyl-[4-methoxy-3-(3-methoxy-propoxy)-benzoyl]-amino}-methyl)-pyrrolidine-1,3-dicarboxylic acid 1-tert-butyl ester 3-ethyl ester A mixture of (3S*,4R*)-4-(isopropylamino-methyl)-pyrrolidine-1,3-dicarboxylic acid 1-tert-butyl ester 3-ethyl ester (2.58 g, 8.2 mmol), 3-(3-methoxy-propoxy)-4-methoxy-benzoic acid (1.93 g, 8.04 mmol), bis(2-oxo-3-oxazolidinyl) phosphinic chloride (2.3 g, 9.02 mmol) and triethylamine (4.57 µL, 32.81 mmol) in CH$_2$Cl$_2$ (50 mL) is refluxed for 2 h and then quenched by the addition of aqueous NaHCO$_3$ solution. The organic layer is separated, and the aqueous phase is extracted 3 times with AcOEt. The combined organic extracts are dried (Na$_2$SO$_4$), and the solvent is removed in vacuo. The crude product is purified by flash chromatography on silica gel (eluent: c-hexane/AcOEt 50:50 to 0:100 and then AcOEt/MeOH 95:5) to give the title product. TLC, $R_f$ (CH$_2$Cl$_2$/MeOH 95:5)=0.3. $t_R$ (HPLC, C18 column, 10-100% CH$_3$CN/H$_2$O/5 min, 100% CH$_3$CN/3 min, CH$_3$CN and H$_2$O containing 0.1% TFA, flow: 1.5 mL/min): 5.76 min.

G. (3S*,4R*)-4-({Isopropyl-[4-methoxy-3-(3-methoxy-propoxy)-benzoyl]-amino}-methyl)-pyrrolidine-1,3-dicarboxylic acid 1-tert-butyl ester To a solution of (3S*,4R*)-4-({isopropyl-[4-methoxy-3-(3-methoxy-propoxy)-benzoyl]-amino}-methyl)-pyrrolidine-1,3-dicarboxylic acid 1-tert-butyl ester 3-ethyl ester (1.41 g, 2.63 mmol) in MeOH (25 mL) cooled at 0° C., 662 mg of LiOH.H$_2$O is added. The reaction mixture is stirred overnight. The mixture is taken up in CH$_2$Cl$_2$, an aqueous HCl (5%) solution is added and the resulting mixture is extracted 3 times with CH$_2$Cl$_2$, dried over Na$_2$SO$_4$, filtered and concentrated. The crude material is used in the next step without purification. TLC, $R_f$ (CH$_2$Cl$_2$/MeOH 95:5)=0.15. MS (LC-MS): 409.0 [M-H-Boc]$^-$; $t_R$ (HPLC, C18 column, 10-100% CH$_3$CN/H$_2$O/5 min, 100% CH$_3$CN/3 min, CH$_3$CN and H$_2$O containing 0.1% TFA, flow: 1.5 mumin): 4.96 min.

H. (3S*,4R*)-3-Benzylcarbamoyl-4-({isopropyl-[4-methoxy-3-(3-methoxy-propoxy)-benzoyl]-amino}-methyl)-pyrrolidine-1-carboxylic acid tert-butyl ester To a stirring solution of (3S*,4R*)-4-({isopropyl-[4-methoxy-3-(3-methoxy-propoxy)-benzoyl]-amino}-methyl)-pyrrolidine-1,3-dicarboxylic acid 1-tert-butyl ester (70 mg, 0.138 mmol), bis(2-oxo-3-oxazolidinyl)phosphinic chloride (42 mg, 0.166 mmol) and triethylamine (77 µL, 0.552 mmol) in CH$_2$Cl$_2$ (3 mL), benzylamine (18 µL, 0.166 mmol) is added. The resulting solution is refluxed for 2 h and then quenched by the addition of aqueous NaHCO$_3$ solution. The organic layer is separated, and the aqueous phase is extracted 3 times with CH$_2$Cl$_2$. The combined organic extracts are dried (Na$_2$SO$_4$), and the solvent is removed in vacuo. The crude material is purified by preparative HPLC (C18-ODB-AQ, 5 µm, 20×50 mm, YMC, eluent: CH$_3$CN/H$_2$O+0.1 % HCOOH flow: 20 mL/min). The HPLC fractions are collected and lyophilized to afford the title product. TLC, $R_f$ (CH$_2$Cl$_2$/MeOH 95:5)=0.2. MS (LC-MS): 598.0 [M+H]$^+$; $t_R$ (HPLC, C18 column, 10-100% CH₃CN/H₂O/5 min, 100% CH₃CN/3 min, CH₃CN and H₂O containing 0.1% TFA, flow: 1.5 mL/min): 5.60 min.

4-Methoxy-3-(3-methoxy-propoxy)-benzoic acid

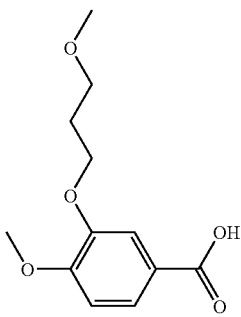

a. 4-Methoxy-3-(3-methoxy-propoxy)-benzoic acid methyl ester

A solution of methyl-3-hydroxy-4-methoxybenzoate (Aldrich) (89.3 g, 0.49 mol), K₂CO₃ (100.5 g, 0.727 mol) and 1-bromo-3-methoxy-propane (80 g, 0.523 mol) in CH₃CN (1100 mL) is refluxed for 6 h. After completion of the reaction, the mixture is cooled to RT and concentrated under reduced pressure. The residue is taken up into AcOEt (500 mL) and washed with water. The aqueous layer is back-extracted twice with AcOEt, and the combined organic extracts are dried over MgSO₄, filtered and concentrated to afford the title compound which is further used in the next step without purification. $t_R$ (HPLC, CC 70/4 Nucleosil 3 C18HD column, 20 to 100% CH₃CN in H₂O in 2, then 4 min with 100% CH₃CN, CH₃CN and H₂O with 0.1% TFA, flow: 1.5 mL/min): 3.07 min.

b. 4-Methoxy-3-(3-methoxy-propoxy)-benzoic acid

A solution of 4-methoxy-3-(3-methoxy-propoxy)-benzoic acid methyl ester (140 g, 0.55 mol) and NaOH (1N, 825 mL, 0.825 mol) in MeOH (840 mL) is stirred at RT for 18 h. After completion, the solvent is removed under reduced pressure, and the residue is diluted with water (200 mL) and extracted twice with AcOEt (250 mL). The aqueous layer is acidified by addition of aqueous HCl (2N, 470 mL) and extracted 3 times with AcOEt (1 L). The combined organic extracts are washed with brine, dried over Na₂SO₄, filtered and concentrated. The crude material is purified by crystallization in AcOEt to give the title compound. MS (LC-MS): 239.1 [M−H]⁻; $t_R$ (HPLC, CC 70/4 Nucleosil 3 C18HD column, 20 to 100% CH₃CN in H₂O in 2, then 4 min with 100% CH₃CN, CH₃CN and H₂O with 0.1% TFA, flow: 1.5 mL/min): 2.43 min.

EXAMPLE 2

(3S*,4S*)-4-({Isopropyl-[4-methoxy-3-(3-methoxy-propoxy)-benzoyl]-amino}-methyl)-pyrrolidine-3-carboxylic acid methylamide

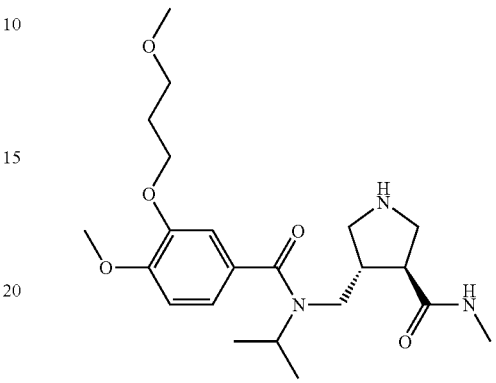

The title compound is prepared analogously as described for the title compound Example 1, starting from (3S*,4R*)-4-({isopropyl-[4-methoxy-3-(3-methoxy-propoxy)-benzoyl]-amino}-methyl)-pyrrolidine-1,3-dicarboxylic acid 1-tert-butyl ester and methylamine. MS (LC-MS): 422.1 [MH]⁺; $t_R$ (HPLC, nucleosil C18 column, 10-100% CH₃CN/H₂O/5 min, 100% CH₃CN/3 min, flow: 1.5 ml/min): 3.83 min.

Scheme 2

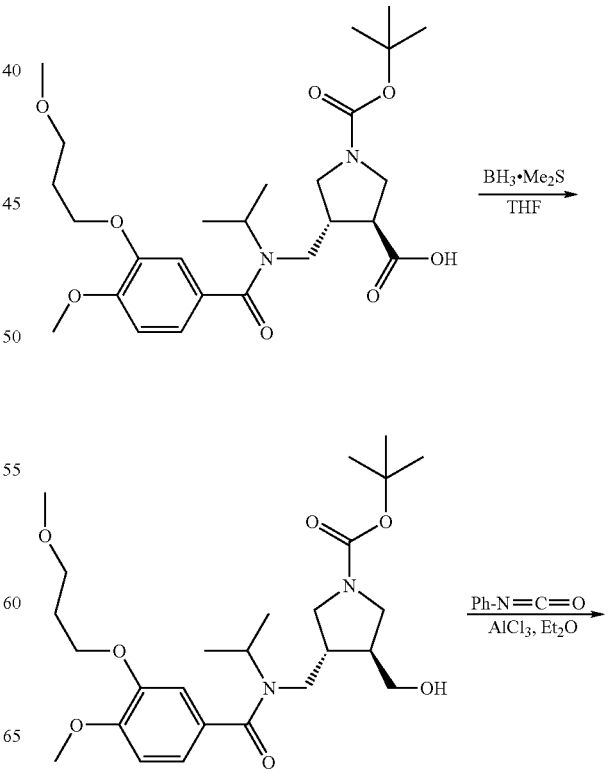

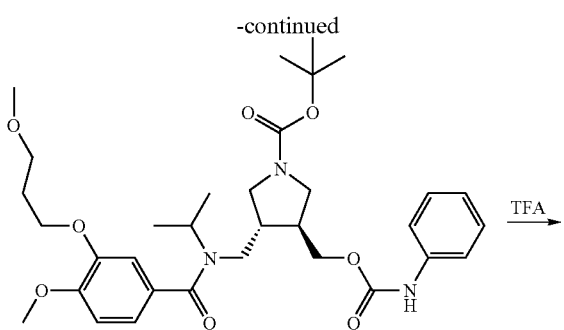

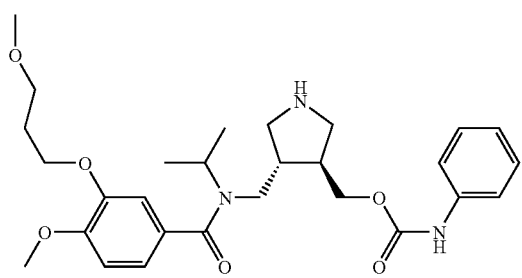

EXAMPLE 3

Phenyl-carbamic acid (3S*,4S*)-4-({isopropyl-[4-methoxy-3-(3-methoxy-propoxy)-benzoyl]-amino}-methyl)-pyrrolidin-3-ylmethyl ester

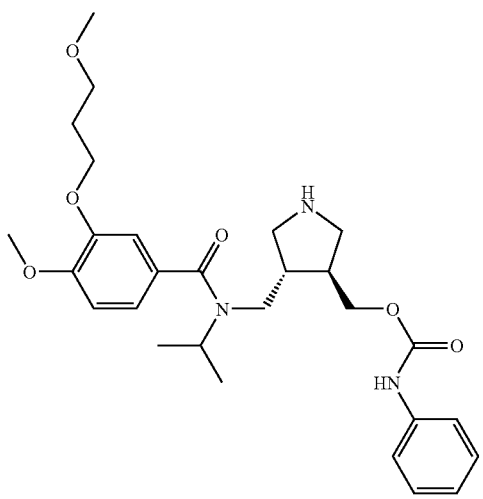

To a solution of (3R*,4S*)-3-({isopropyl-[4-methoxy-3-(3-methoxy-propoxy)-benzoyl]-amino}-methyl)-4-phenyl carbamoyloxymethyl-pyrrolidine-1-carboxylic acid tert-butyl ester (68 mg, 0.11 mmol) in 2 mL $CH_2Cl_2$, TFA (128 µL, 1.66 mmol) is added. The mixture is stirred at 30° C. for 2 h, then overnight at RT, and poured into a saturated solution of $NaHCO_3$. The layers are separated, and the aqueous one is back-extracted twice with $CH_2Cl_2$. The combined organic extracts are dried over $Na_2SO_4$, filtered and concentrated. The crude material is purified by flash chromatography on Isolute SPE Flash $NH_2$ column (eluent: $CH_2Cl_2$/MeOH 100:0 to 97:3) to give the title product. MS (LC-MS): 514.0 $[M+H]^+$; $t_R$ (HPLC, Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 4.52 min.

To a solution of the free base in dioxane (2 mL), 4N HCl in dioxane (0.099 mmol, 25 µL) is added, and the resulting solution is lyophilized to afford the corresponding hydrochloride salt as a white powder.

The starting material is prepared as follows:

A. (3S*,4R*)-3-Hydroxymethyl-4-({isopropyl-[4-methoxy-3-(3-methoxy-propoxy)-benzoyl]-amino}-methyl)-pyrrolidine-1-carboxylic acid tert-butyl ester To a solution of (3S*,4R*)-4-({isopropyl-[4-methoxy-3-(3-methoxy-propoxy)-benzoyl]-amino}-methyl)-pyrrolidine-1,3-dicarboxylic acid 1-tert-butyl ester (1.29 g, 2.54 mmol) (Example 1 G) in THF (25 mL), a solution of borane dimethylsulfide complex (2M in THF, 2.80 mL, 5.58 mmol) is slowly added at −10° C. The mixture is stirred for 20 min at −10° C., then allowed to reach RT and further stirred overnight. MeOH is carefully added (exothermic!), and the mixture is concentrated under reduced pressure. MeOH is again added, and the mixture is concentrated. This operation is repeated 3 times, and the mixture is finally taken up into a saturated aqueous solution of $NaHCO_3$ and extracted 3 times with $CH_2Cl_2$. The combined organic extracts are dried over $Na_2SO_4$, filtered and concentrated. The crude material is purified by flash chromatography on silica gel (eluent: $CH_2Cl_2$/MeOH from 100:0 to 95:5) to give the desired product. TLC, $R_f$ ($CH_2Cl_2$/MeOH 95:5)=0.3. MS (LC-MS): 395.1 $[M+H-Boc]^+$; $t_R$ (HPLC, C18 column, 10-100% $CH_3CN/H_2O$/5 min, 100% $CH_3CN$/3 min, $CH_3CN$ and $H_2O$ containing 0.1% TFA, flow: 1.5 mL/min): 5.01 min.

B. (3R*,4S*)-3-({Isopropyl-[4-methoxy-3-(3-methoxy-propoxy)-benzoyl]-amino}-methyl)-4-phenyl carbamoyloxymethyl-pyrrolidine-1-carboxylic acid tert-butyl ester Phenyl isocyanate (44 µL, 0.404 mmol) followed by $AlCl_3$ (27 mg, 0.202 mmol) are added to a solution of (3S*,4R*)-3-hydroxymethyl-4-({isopropyl-[4-methoxy-3-(3-methoxy-propoxy)-benzoyl]-amino}-methyl)-pyrrolidine-1-carboxylic acid tert-butyl ester (100 mg, 0.202 mmol) in $Et_2O$ (6 mL). The resulting mixture is stirred at RT overnight. For workup, a sat. solution of $NaHCO_3$ is added and the mixture is extracted with ethyl acetate. The combined extracts are dried ($Na_2SO_4$) and the solvent is evaporated. The crude product is purified by flash chromatography on silica gel (eluent: c-hexane/AcOEt 80:20 to 0:100) to give the title product. TLC, $R_f$ ($CH_2Cl_2$/MeOH 95:5)=0.5. MS (LC-MS): 514.0 $[M+H-Boc]^+$; $t_R$ (HPLC, C18 column, 10-100% $CH_3CN/H_2O$/5 min, 100% $CH_3CN$/3 min, CH3CN and $H_2O$ containing 0.1% TFA, flow: 1.5 ml/min): 5.91 min.

EXAMPLE 4

Benzyl-carbamic acid (3S*,4S*)-4-({isopropyl-[4-methoxy-3-(3-methoxy-propoxy)-benzoyl]-amino}-methyl)-pyrrolidin-3-ylmethyl ester

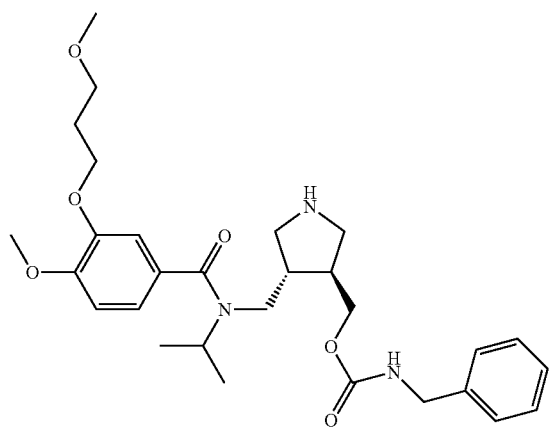

The title compound is prepared analogously as described in Example 3 from (3S*,4R*)-3-hydroxymethyl-4-({isopropyl-[4-methoxy-3-(3-methoxy-propoxy)-benzoyl]-amino}-methyl)-pyrrolidine-1-carboxylic acid tert-butyl ester and benzylisocyanate. MS (LC-MS): 528.3 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 4.52 min.

EXAMPLE 5

N-((3S*,4S*)-4-Hydroxymethyl-pyrrolidin-3-ylmethyl)-N-isopropyl-4-methoxy-3-(3-methoxy-propoxy)-benzamide

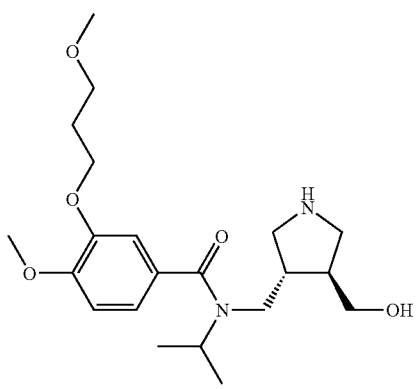

To a solution of (3S*,4R*)-3-hydroxymethyl-4-({isopropyl-[4-methoxy-3-(3-methoxy-propoxy)-benzoyl]-amino}-methyl)-pyrrolidine-1-carboxylic acid tert-butyl ester (85 mg, 0.172 mmol) in 2 mL CH$_2$Cl$_2$, TFA (85 µL, 2.23 mmol) is added. The mixture is stirred 4.5 h at RT, and poured into a saturated solution of NaHCO$_3$. The layers are separated, and the aqueous one is back-extracted twice with CH$_2$Cl$_2$. The combined organic extracts are dried over Na$_2$SO$_4$, filtered and concentrated. The crude material is purified by flash chromatography on Isolute SPE Flash NH$_2$ column (eluent: CH$_2$Cl$_2$/MeOH 100:0 to 99:1) to give the title product. MS (LC-MS): 395.1 [M+H]$^+$; $t_R$ (HPLC, Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 3.75 min.

To a solution of the free base in dioxane (2 mL), 4N HCl in dioxane (0.009 mmol, 2.2 µL) is added, and the resulting solution is lyophilized to afford the corresponding hydrochloride salt as a white powder.

Scheme 3

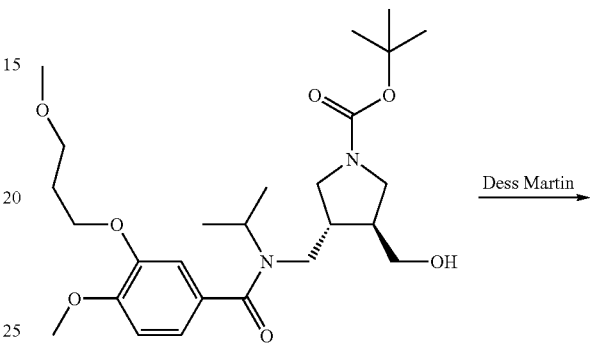

Dess Martin

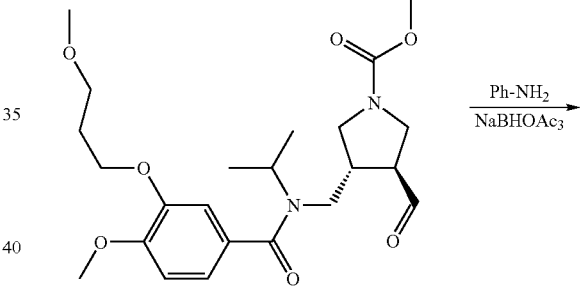

Ph-NH$_2$
NaBHOAc$_3$

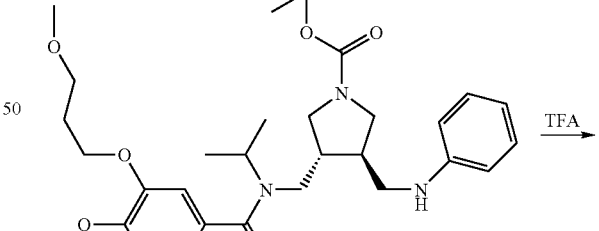

TFA

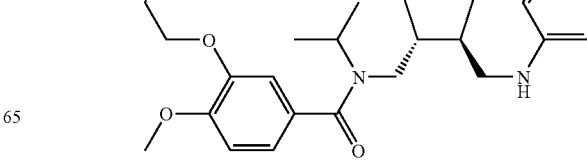

EXAMPLE 6

N-Isopropyl-4-methoxy-3-(3-methoxy-propoxy)-N-((3S*,4S*)-4-phenylamino methyl-pyrrolidin-3-ylmethyl)-benzamide

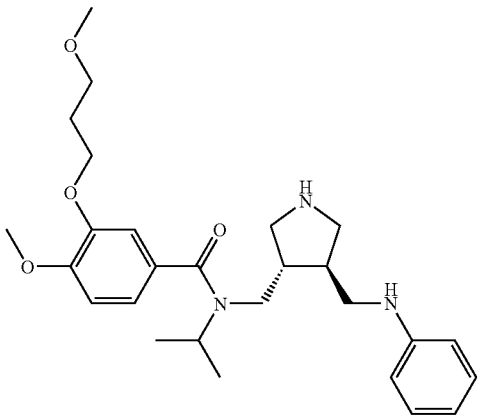

To a solution of (3R*,4R*)-3-({isopropyl-[4-methoxy-3-(3-methoxy-propoxy)-benzoyl]-amino}-methyl)-4-phenylaminomethyl-pyrrolidine-1-carboxylic acid tert-butyl ester (65 mg, 0.12 mmol) in 2 mL $CH_2Cl_2$, TFA (139 µL, 1.8 mmol) is added. The mixture is stirred 2 h at RT, and poured into a saturated solution of $NaHCO_3$. The layers are separated, and the aqueous one is back-extracted twice with $CH_2Cl_2$. The combined organic extracts are dried over $Na_2SO_4$, filtered and concentrated. The crude material is purified by flash chromatography on an Isolute SPE Flash $NH_2$ column (eluent: $CH_2Cl_2$/MeOH 100:0 to 97:3) to give the title product. TLC, $R_f$ ($SiO_2$—$NH_2$, $CH_2Cl_2$/MeOH 95:5)=0.6. MS (LC-MS): 470.0 $[M+H]^+$; $t_R$ (HPLC, Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 3.37 min.

To a solution of the free base in dioxane (2 mL), (0.242 mmol, 60 µL) of 4N HCl in dioxane is added, and the resulting solution is lyophilized to afford the corresponding dihydrochloride salt as a white powder.

The starting material is prepared as follows:

A. (3S*,4R*)-3-Formyl-4-({isopropyl-[4-methoxy-3-(3-methoxy-propoxy)-benzoyl]-amino}-methyl)-pyrrolidine-1-carboxylic acid tert-butyl ester To a well-stirred mixture of (3S*,4R*)-3-hydroxymethyl-4-({isopropyl-[4-methoxy-3-(3-methoxy-propoxy)-benzoyl]-amino}-methyl)-pyrrolidine-1-carboxylic acid tert-butyl ester (600 mg, 1.21 mmol) and Dess-Martin periodinane (272 mg, 1.21 mmol) in $CH_2Cl_2$ (10 mL), slowly wet $CH_2Cl_2$ (24 µL of water in 2 mL of $CH_2Cl_2$) is added. The clear solution becomes cloudy towards the end of wet $CH_2Cl_2$ addition. The mixture is diluted with $Et_2O$ and concentrated to a few mL of solvent by rotary evaporation. The residue is taken up in $Et_2O$, and washed with a 1:1 10% $Na_2S_2O_3$/saturated aqueous solution of $NaHCO_3$, followed by $H_2O$ and brine. The aqueous washings are back-extracted with $Et_2O$, and this organic layer is washed with $H_2O$ and brine. The combined organic layers are dried over $Na_2SO_4$, filtered and concentrated under reduced pressure. The crude material is used without further purification in the next step. TLC, $R_f$ ($CH_2Cl_2$/MeOH 95:5)=0.3. $t_R$ (HPLC, Nucleosil C18 column, 10-100% $CH_3CN/H_2O$/5 min, 100% $CH_3CN$/3 min, $CH_3CN$ and $H_2O$ containing 0.1% TFA, flow: 1.5 ml/min): 5.16 min.

B. (3R*,4R*)-3-({Isopropyl-[4-methoxy-3-(3-methoxy-propoxy)-benzoyl]-amino}-methyl)-4-phenylaminomethyl-pyrrolidine-1-carboxylic acid tert-butyl ester A solution of (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester (100 mg, 0.20 mmol) and aniline (26 µL, 0.28 mmol) in 1,2-dichloroethane (5 mL) is stirred 25 min, before the addition of $NaBH(OAc)_3$ (60 mg, 0.28 mmol) follows. The solution is stirred overnight at RT, then diluted with $CH_2Cl_2$ and washed with an aqueous saturated solution of $NaHCO_3$. The combined organic extracts are dried over $Na_2SO_4$ and concentrated. The crude material is purified by flash chromatography on silica gel (eluent: $CH_2Cl_2$/MeOH 100:0 to 97:3) to give the title product. TLC, $R_f$ ($CH_2Cl_2$/MeOH 95:5)=0.25. MS (LC-MS): 570.0 $[M+H]^+$; $t_R$ (HPLC, nucleosil C18 column, 10-100% $CH_3CN/H_2O$/ 5 min, 100% $CH_3CN$/3 min, $CH_3CN$ and $H_2O$ containing 0.1% TFA, flow: 1.5 ml/min): 5.31 min.

EXAMPLE 7

N-Isopropyl-4-methoxy-3-(3-methoxy-propoxy)-N-((3S*,4S*)-4-piperidin-1-ylmethyl-pyrrolidin-3-ylmethyl)-benzamide

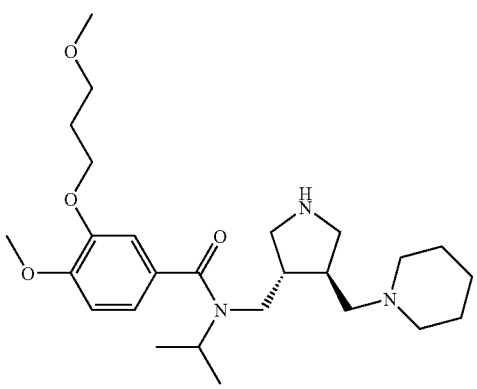

The title compound is prepared analogously as described in Example 5 from (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester and piperidine. MS (LC-MS): 462.1 $[M+H]^+$; $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 3.74 min.

EXAMPLE 8

N-{(3S*,4S*)-4-[(Cyclopropanecarbonyl-methyl-amino)-methyl]-pyrrolidin-3-ylmethyl}-N-isopropyl-4-methoxy-3-(3-methoxy-propoxy)-benzamide

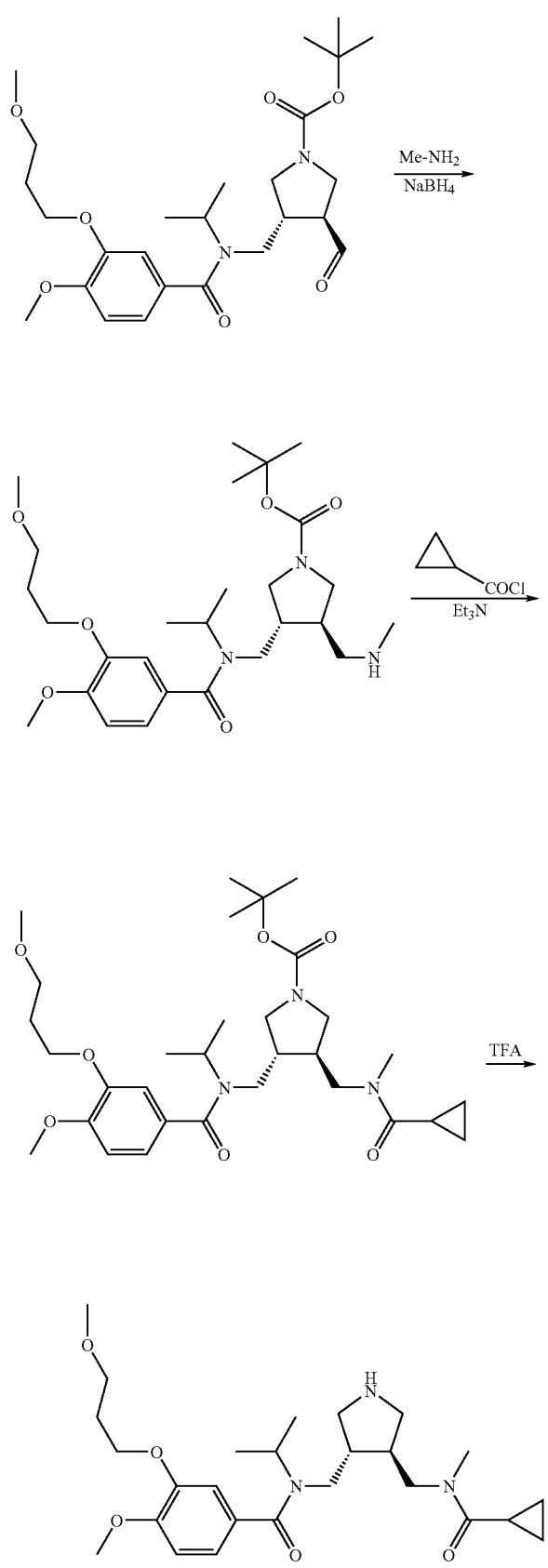

To a solution of (3R*,4R*)-3-[(cyclopropanecarbonyl-methyl-amino)-methyl]-4-({isopropyl-[4-methoxy-3-(3-methoxy-propoxy)-benzoyl]-amino}-methyl)-pyrrolidine-1-carboxylic acid tert-butyl ester (154 mg, 0.267 mmol) in 3 mL CH$_2$Cl$_2$, TFA (309 μL, 4.01 mmol) is added. The mixture is stirred 4 h at RT, and poured into a saturated solution of NaHCO$_3$. The layers are separated, and the aqueous one is back-extracted twice with CH$_2$Cl$_2$. The combined organic extracts are dried over Na$_2$SO$_4$, filtered and concentrated. The crude material is purified by flash chromatography on Isolute SPE Flash NH$_2$ column (eluent: CH$_2$Cl$_2$/MeOH 100:0 to 95:5) to give the title product. TLC, R$_f$(SiO$_2$—NH$_2$, CH$_2$Cl$_2$/MeOH 95:5)=0.1. MS (LC-MS): 476.1 [M+H]$^+$; t$_R$ (HPLC, Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 4.10 min.

To a solution of the free base in dioxane (2 mL), 4N HCl in dioxane (0.198 mmol, 50 μL) is added, and the resulting solution is lyophilized to afford the corresponding dihydrochloride salt as a white powder.

The starting material is prepared as follows:

A. (3R*,4R*)-3-({Isopropyl-[4-methoxy-3-(3-methoxy-propoxy)-benzoyl]-amino}-methyl)-4-methylaminomethyl-pyrrolidine-1-carboxylic acid tert-butyl ester To a solution of (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester (150 mg, 0.304 mmol) and magnesium sulfate (92 mg, 0.373 mmol) in THF (4 mL), methylamine (1.52 mL, 3.044 mmol, 2M in THF) is added. The solution is stirred at RT overnight under nitrogen atmosphere and NaBH$_4$ (23 mg, 0.608 mmol) is added. The resulting mixture is stirred for 1 h and the excess reducing agent quenched with water, CH$_2$Cl$_2$ is added and the reaction mixture is poured into an aqueous saturated solution of NaHCO$_3$. The organic layer is separated and the aqueous phase extracted twice with CH$_2$Cl$_2$, dried over Na$_2$SO$_4$, filtered, and concentrated in vacuo. The crude material is purified by flash chromatography on silica gel (eluent: CH$_2$Cl$_2$/MeOH 100:0 to 95:5+1% NH$_4$OH ) to give the title product. TLC, R$_f$ (CH$_2$Cl$_2$/MeOH 95:5)=0.05. MS (LC-MS) [M−H]$^+$= 508.1. t$_R$ (HPLC, Nucleosil C18 column, 10-100%

CH₃CN/H₂O/5 min, 100% CH₃CN/3 min, CH₃CN and H₂O containing 0.1% TFA, flow: 1.5 ml/min): 4.53 min.

B. (3R*,4R*)-3-[(Cyclopropanecarbonyl-methyl-amino)-methyl]-4-({isopropyl-[4-methoxy-3-(3-methoxy-propoxy)-benzoyl]-amino}-methyl)-pyrrolidine-1-carboxylic acid tert-butyl ester To a solution of (3R*,4R*)-3-({isopropyl-[4-methoxy-3-(3-methoxy-propoxy)-benzoyl]-amino}-methyl)-4-methylaminomethyl-pyrrolidine-1-carboxylic acid tert-butyl ester (134 mg, 0.264 mmol) in CH₂Cl₂ (2 mL), cyclopropanecarbonyl chloride (29 µL, 0.317 mmol) and triethylamine (44 µL, 0.317 mmol) are added under N₂ atmosphere. The mixture is stirred overnight at RT, diluted with CH₂Cl₂ and poured into an aqueous saturated solution of NaHCO₃. The organic layer is separated, and the aqueous one is extracted twice with CH₂Cl₂. The combined organic extracts are dried over Na₂SO₄, filtered and concentrated. The crude product is used in the next step without purification. TLC, $R_f$(CH₂Cl₂/MeOH 95:5)=0.2. MS (LC-MS): 476.1 [M+H-Boc]⁺. $t_R$ (HPLC, Nucleosil C18 column, 10-100% CH₃CN/H₂O/5 min, 100% CH₃CN/3 min, CH₃CN and H₂O containing 0.1% TFA, flow: 1.5 ml/min): 5.42 min.

EXAMPLE 9

N-Isopropyl-4-methoxy-3-(3-methoxy-propoxy)-N-{(3S,4S)-4-[(methyl-phenylacetyl-amino)-methyl]-pyrrolidin-3-ylmethyl}-benzamide

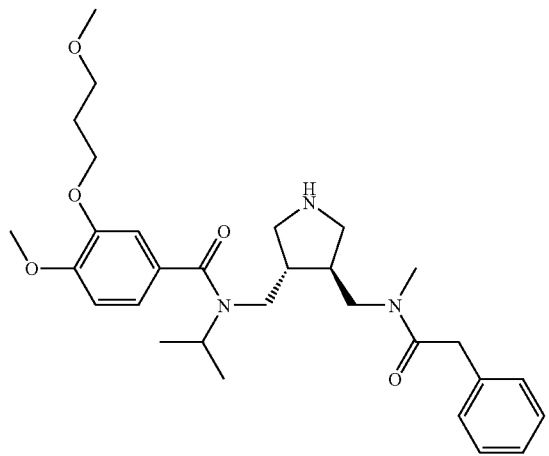

To a solution of (3R,4R)-3-({isopropyl-[4-methoxy-3-(3-methoxy-propoxy)-benzoyl]-amino}-methyl)-4-[(methyl-phenylacetyl-amino)-methyl]-pyrrolidine-1-carboxylic acid tert-butyl ester (0.36 g, 0.575 mmol) in 12 mL CH₂Cl₂, TFA (0.664 mL, 8.62 mmol) is added. The mixture is stirred 2 h at 30° C., and poured into a saturated solution of NaHCO₃. The layers are separated, and the aqueous one is back-extracted twice with CH₂Cl₂. The combined organic extracts are dried over Na₂SO₄, filtered and concentrated. To a solution of the free base in dioxane (3 mL), 4N HCl in dioxane (0.144 mL) is added, and the resulting solution is lyophilized to afford the corresponding hydrochloride salt. TLC, $R_f$(CH₂Cl₂/MeOH 95:5)=0.1. MS (LC-MS): 526.1 [M+H]⁺; $t_R$ (Macherey-Nagel Nucleosil C18 column, 10-100% CH₃CN/H₂O/5 min, 100% CH₃CN/3 min, CH₃CN and H₂O containing 0.1% TFA, flow: 1.5 mL/min): 4.41 min.

The starting material is prepared as follows:

A. (3R,4R)-3-({Isopropyl-[4-methoxy-3-(3-methoxy-propoxy)-benzoyl]-amino}-methyl)-4-[(methyl-phenylacetyl-amino)-methyl]-pyrrolidine-1-carboxylic acid tert-butyl ester Racemic (3R*,4R*)-3-({isopropyl-[4-methoxy-3-(3-methoxy-propoxy)-benzoyl]-amino}-methyl)-4-[(methyl-phenylacetyl-amino)-methyl]-pyrrolidine-1-carboxylic acid tert-butyl ester is separated into the single enantiomers by preparative chiral HPLC on a Chiralpak AD-H column (4.6× 250 mm, 5 µM particle size; flow rate 1 mL/min, UV=210 nM, injection=1.7 g in 5 mL ethanol and using ethanol as the eluent to give the enantiomerically pure title compound: $t_R$ (HPLC, Chiralpak AD-H, HPLC 250×4.6 mm, ethanol, flow: 0.5 ml/min): 26.46 min; and (3S,4S)-3-({isopropyl-[4-methoxy-3-(3-methoxy-propoxy)-benzoyl]-amino}-methyl)-4-[(methyl-phenylacetyl-amino)-methyl]-pyrrolidine-1-carboxylic acid tert-butyl ester: $t_R$ (HPLC, Chiralpak AD-H, HPLC 250×4.6 mm, ethanol, flow: 0.5 ml/min): 13.53 min.

B. (3R*,4R)-3-({Isopropyl-[4-methoxy-3-(3-methoxy-propoxy)-benzoyl]-amino}-methyl)-4-methylaminomethyl-pyrrolidine-1-carboxylic acid tert-butyl ester The title compound is prepared from (3R*,4R*)-3-({isopropyl-[4-methoxy-3-(3-methoxy-propoxy)-benzoyl]-amino}-methyl)-4-methylaminomethyl-pyrrolidine-1-carboxylic acid tert-butyl ester (79 mg, 0.165 mmol) and phenylacetyl chloride according to Example 8, reaction step B. $R_f$ (CH₂Cl₂/MeOH 95:5)=0.4. MS (LC-MS): 526.1 [M+H]⁺; $t_R$ (Macherey-Nagel Nucleosil C18 column, 10-100% CH₃CN/H₂O/5 min, 100% CH₃CN/3 min, CH₃CN and H₂O containing 0.1% TFA, flow: 1.5 mL/min): 4.71 min.

Alternatively, the starting material (3R,4R)-3-({isopropyl-[4-methoxy-3-(3-methoxy-propoxy)-benzoyl]-amino}-methyl)-4-[(methyl-phenylacetyl-amino)-methyl]-pyrrolidine-1-carboxylic acid tert-butyl ester is prepared according to scheme 5 as follows:

Scheme 5

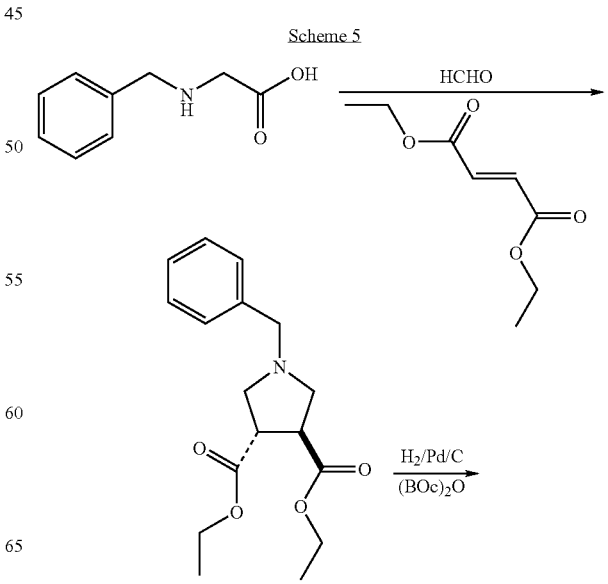

-continued
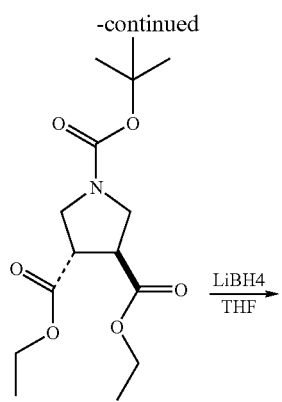
LiBH4
THF
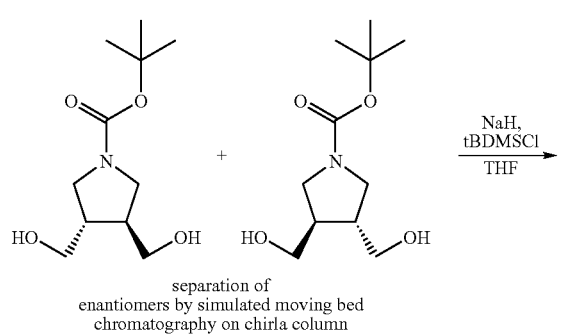
separation of
enantiomers by simulated moving bed
chromatography on chirla column
NaH,
tBDMSCl
THF
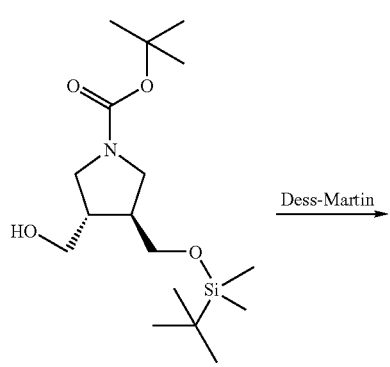
Dess-Martin
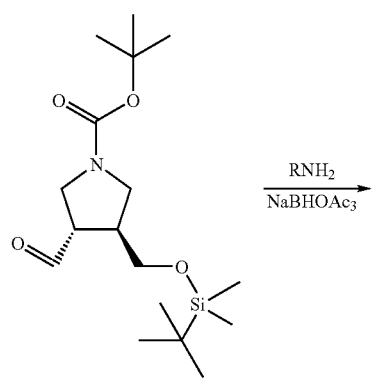
RNH2
NaBHOAc3
-continued
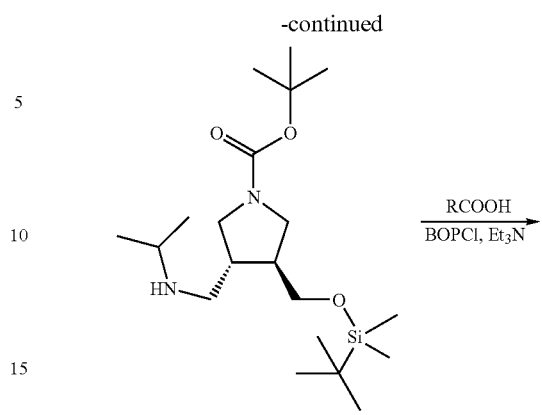
RCOOH
BOPCl, Et3N
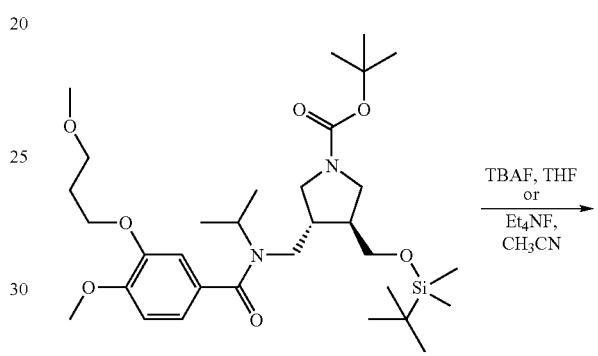
TBAF, THF
or
Et4NF,
CH3CN
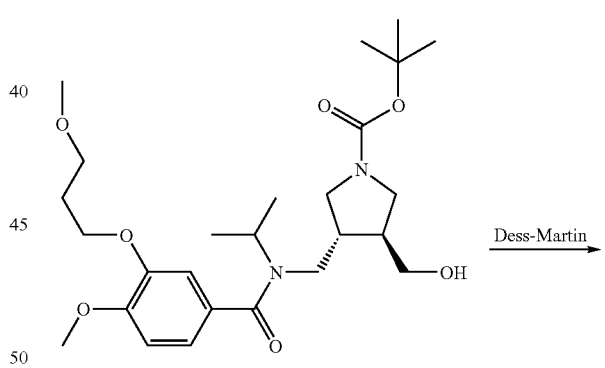
Dess-Martin
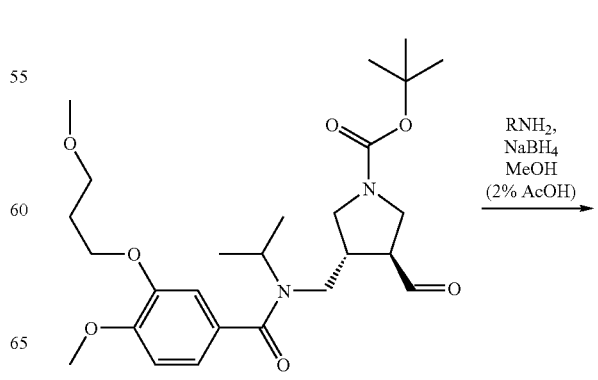
RNH2,
NaBH4
MeOH
(2% AcOH)

-continued

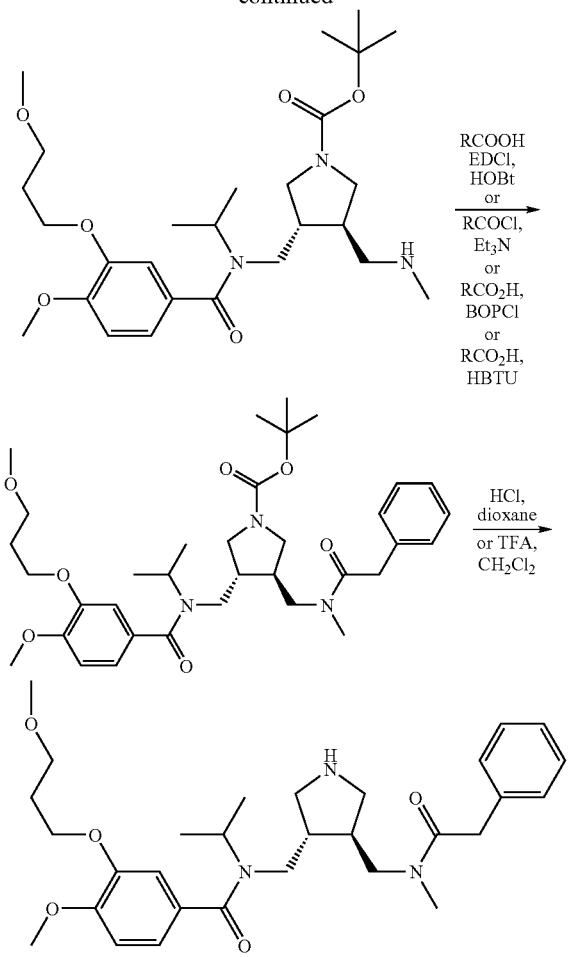

A. (3S*,4S*)-1-Benzyl-pyrrolidine-3,4-dicarboxylic acid diethyl ester

A mixture of N-benzylglycine (51.3 g, 310.55 mmol), diethylfumarate (51.85 mL, 316.76 mmol) and paraformaldehyde powder (10.25 g, 341.6 mmol) in toluene (500 mL) is heated at reflux for 2 h, while collecting water using a dean-stark apparatus. The solvent is concentrated and the mixture purified by distillation under vacuum (~50 mbar), the desired title compound distilling at 80-85° C. TLC, $R_f$ (CH$_2$Cl$_2$/acetone 95:5)=0.56. MS (LC-MS): 306.2 [M+H]$^+$; $t_R$ (HPLC, RP8 column, 10-100% CH$_3$CN/H$_2$O/5 min, 100% CH$_3$CN/2.5 min, CH$_3$CN and H$_2$O containing 0.1% TFA, flow: 1.5 mL/min): 4.35 min.

B. (3S*,4S*)-Pyrrolidine-1,3,4-tricarboxylic acid 1-tert-butyl ester 3,4-diethyl ester A mixture of (3S*,4S*)-1-benzyl-pyrrolidine-3,4-dicarboxylic acid diethyl ester (82.8 g, 271.14 mmol), di-tert-butylcarbonate (88.76 g, 406.71 mmol) and Pd/C 10% (8 g) in EtOH (1.5 L) is stirred under hydrogen atmosphere. The crude material is filtered over a pad of Celite and concentrated. The crude material is purified by flash chromatography on silica gel (eluent: CH$_2$Cl$_2$/acetone 100:0 to 95:5). TLC, $R_f$ (CH$_2$Cl$_2$/acetone 95:5)=0.51. MS (LC-MS): 216.2 [M+H-Boc]$^+$.

C. (3S*,4S*)-3,4-Bis-hydroxymethyl-pyrrolidine-1-carboxylic acid tert-butyl ester To a ice-cooled solution of (3S*,4S*)-pyrrolidine-1,3,4-tricarboxylic acid 1-tert-butyl ester 3,4-diethyl ester (36 g, 114.15 mmol) in THF (1 L), is added dropwise a solution of LiBH$_4$ (228.3 mmol) in THF (250 mL). The reaction mixture is stirred overnight at room temperature and quenched with an aqueous solution of NaOH 2N (400 mL). Ether is added, the layers are separated and the aqueous one back extracted twice with ether. The combined organic extracts are dried over Na$_2$SO$_4$, filtered and concentrated to give the title compound which is used without further purification in the next step. TLC, $R_f$ (CH$_2$Cl$_2$/MeOH 95:5)=0.14. MS (LC-MS): 232.2 [M+H]$^+$; $t_R$ (HPLC, C18 column, 5-100% CH$_3$CN/H$_2$O/6 min, 100% CH$_3$CN/2 min, CH$_3$CN and H$_2$O containing 0.1% TFA, flow: 1 mL/min): 3.37 min.

(3S,4S)-3,4-Bis-hydroxymethyl-pyrrolidine-1-carboxylic acid tert-butyl ester and (3R,4R)-3,4-Bis-hydroxymethyl-pyrrolidine-1-carboxylic acid tert-butyl ester The two enantiomers are separated via chiral preparative HPLC using simulated moving bed chromatography (SMB) "UOP SORBEX Prep." Technology with 16 columns "Princeton Chromatography Inc." (7.5×2.12 cm), stationary phase: Chiralpak AD Prep. 20 μm, (eluent: hexane/EtOH/MeOH 90:5:5).

(3S,4S)-3,4-Bis-hydroxymethyl-pyrrolidine-1-carboxylic acid tert-butyl ester: $t_R$ (Chiralpak AD-H, 250×4.6 mm, flow rate 1 mL/min) (eluent: hexane/EtOH 90:10): 6.4 min. $[\alpha]_D$=−11.1 (c=1.795, CHCl$_3$).

(3R,4R)-3,4-Bis-hydroxymethyl-pyrrolidine-1-carboxylic acid tert-butyl ester: $t_R$ (Chiralpak AD-H, 250×4.6 mm, flow rate 1 mL:min) (eluent: hexane/EtOH 90:10): 8.58 min. $[\alpha]_D$=+10.2 (c=1.795, CHCl$_3$).

D. (3S,4S)-3-(tert-Butyl-dimethyl-silanyloxymethyl)-4-hydroxymethyl-pyrrolidine-1-carboxylic acid tert-butyl ester To a suspension of sodium hydride (60% in oil, 0.996 g, 24.9 mmol) (previously washed with pentane) in THF (40 mL) is added dropwise under a nitrogen atmosphere a solution of (3S,4S)-3,4-bis-hydroxymethyl-pyrrolidine-1-carboxylic acid tert-butyl ester (4.8 g, 20.75 mmol) in THF (40 mL) at 0° C. The mixture is stirred for 1.5 h at 0° C. before the dropwise addition of a solution of tert-butyl(chloro)dimethylsilane (3.44 g, 22.83 mmol) in THF (40 mL). The resulting mixture is further stirred 1 h at 0° C. and 1 h at RT, then poured into an aqueous solution of NaHCO$_3$ (5%) (150 mL) and extracted 3 times with Et$_2$O. The combined organic extracts are dried over Na$_2$SO$_4$, filtered and concentrated. The crude material is purified by flash chromatography on silica gel (eluent: CH$_2$Cl$_2$/MeOH 99:1 to 93:7). TLC, $R_f$ (CH$_2$Cl$_2$/MeOH 95:5)=0.33. MS (LC-MS): 346.2 [M+H]$^+$.

E. (3S,4S)-3-(tert-Butyl-dimethyl-silanyloxymethyl) 4-formyl-pyrrolidine-1-carboxylic acid tert-butyl ester To a well stirred mixture of (3S,4S)-3-(tert-butyl-dimethyl-silanyloxymethyl)-4-hydroxymethyl-pyrrolidine-1-carboxylic acid tert-butyl ester (8.2 g, 23.73 mmol) and Dess-Martin periodinane (10.06 g, 23.73 mmol) in CH$_2$Cl$_2$ (60 mL), slowly wet CH$_2$Cl$_2$ (0.47 mL of water in 60 mL of $CH_2Cl_2$) is added. The clear solution becomes cloudy toward the end of wet $CH_2Cl_2$ addition and is further stirred overnight. Then concentrated to a few mL of solvent by rotary evaporation and taken up in $Et_2O$. A solution of 1:1 10% $Na_2S_2O_3$/saturated aqueous $NaHCO_3$ is added. The layers are separated and the organic extract is washed successively with $H_2O$ and brine. The aqueous washings are back-extracted with $Et_2O$, and this organic layer is washed with $H_2O$ and brine. The combined organic layers are dried with $Na_2SO_4$, filtered and concentrated. The crude mixture is used in the next step without further purification. TLC, $R_f$ ($CH_2Cl_2$/MeOH 95:5)=0.42. MS (LC-MS): 244.2 $[M+H-Boc]^+$; $t_R$ (HPLC, C18 column, 5-100% $CH_3CN/H_2O$/6 min, 100% $CH_3CN$/2 min, $CH_3CN$ and $H_2O$ containing 0.1% TFA, flow: 1 mL/min): 6.45 min.

F. (3S,4R)-3-(tert-Butyl-dimethyl-silanyloxymethyl)-4-(isopropylamino-methyl)-pyrrolidine-1-carboxylic acid tert-butyl ester A solution of (3S,4S)-3-(tert-butyl-dimethyl-silanyloxymethyl)-4-formyl-pyrrolidine-1-carboxylic acid tert-butyl ester (7.7 g, 22.41 mmol) and isopropylamine (5.78 mL, 67.24 mmol) in 1,2-dichloroethane (200 mL) is stirred 25 min before the addition of $NaBH(OAc)_3$ (11.88 g, 56.03 mmol). The solution is stirred for 5 h, then diluted with $CH_2Cl_2$ and washed with an aqueous saturated solution of $NaHCO_3$. The aqueous layer is back extracted twice with $CH_2Cl_2$ and the combined organic extracts are dried over $Na_2SO_4$, filtered and concentrated. The crude material is used in the next step without further purification. TLC, $R_f$($CH_2Cl_2$/MeOH 9:1)=0.39. MS (LC-MS): 387.2 $[M+H]^+$.

G. (3S,4R)-3-(tert-Butyl-dimethyl-silanyloxymethyl)-4-({isopropyl-[4-methoxy-3-(3-methoxy-propoxy)-benzoyl]-amino}-methyl)-pyrrolidine-1-carboxylic acid tert-butyl ester A mixture of ((3S,4R)-3-(tert-butyl-dimethyl-silanyloxymethyl)-4-(isopropylamino-methyl)-pyrrolidine-1-carboxylic acid tert-butyl ester (8.9 g, 23.02 mmol), 3-(3-methoxy-propoxy)-4-methoxy-benzoic acid (6.08 g, 25.32 mmol), bis(2-oxo-3-oxazolidinyl)phosphinic chloride (6.45 g, 25.32 mmol) and triethylamine (7.62 mL, 92.07 mmol) in $CH_2Cl_2$ (230 mL) is refluxed for 3 h. The reaction is quenched by the addition of an aqueous saturated solution of $NaHCO_3$. The organic layer is separated, and the aqueous phase is extracted 3 times with AcOEt. The combined organic extracts are dried ($Na_2SO_4$), and the solvent is removed in vacuo. The crude product is purified by flash chromatography on silica gel (eluent: $CH_2Cl_2$/acetone 95:5 to $CH_2Cl_2$/MeOH 95:5) to give the title product. TLC, $R_f$ ($CH_2Cl_2$/MeOH 95:5)=0.47. MS (LC-MS): 609.4 $[M+H]^+$; $t_R$ (HPLC, C18 column, 5-100% $CH_3CN/H_2O$/6 min, 100% $CH_3CN$/2 min, $CH_3CN$ and $H_2O$ containing 0.1% TFA, flow: 1 mL/min): 7.05 min.

H. (3S,4R)-3-Hydroxymethyl-4-({isopropyl-[4-methoxy-3-(3-methoxy-propoxy)-benzoyl]-amino}-methyl)-pyrrolidine-1-carboxylic acid tert-butyl ester To a solution of (3S,4R)-3-(tert-butyl-dimethyl-silanyloxymethyl)-4-({isopropyl-[4-methoxy-3-(3-methoxy-propoxy)-benzoyl]-amino}-methyl)-pyrrolidine-1-carboxylic acid tert-butyl ester (8.75 g, 14.37 mmol) in THF (50 mL) is added tetrabutylammonium fluoride trihydrate (6.8 g, 24.55 mmol) under a nitrogen atmosphere. The reaction mixture is stirred overnight. Water and AcOEt are added, the layers are separated and the aqueous one extracted twice with AcOEt. The combined organic extracts are dried ($Na_2SO_4$), and the solvent is removed in vacuo. The crude product is purified by flash chromatography on silica gel (eluent: $CH_2Cl_2$/MeOH 97:3 to 95:5) to give the title product. TLC, Rf ($CH_2Cl_2$/MeOH 95:5)=0.3. MS (LC-MS): 395.1 $[M+H-Boc]^+$; $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 5.01 min.

I. (3S,4R)-3-Formyl-4-({isopropyl-[4-methoxy-3-(3-methoxy-propoxy)-benzoyl]-amino}-methyl)-pyrrolidine-1-carboxylic acid tert-butyl ester The title compound is prepared analogously as described for the title compound under E in Scheme 5 from (3S,4R)-3-hydroxymethyl-4-({isopropyl-[4-methoxy-3-(3-methoxy-propoxy)-benzoyl]-amino}-methyl)-pyrrolidine-1-carboxylic acid tert-butyl ester. TLC, $R_f$($CH_2CO_2$/MeOH 95:5)=0.3. $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 ml/min): 5.16 min.

J. (3R,4R)-3-({Isopropyl-[4-methoxy-3-(3-methoxy-propoxy)-benzoyl]-amino}-methyl)-4-methylaminomethyl-pyrrolidine-1-carboxylic acid tert-butyl ester To a solution of (3S,4R)-3-formyl-4-({isopropyl-[4-methoxy-3-(3-methoxy-propoxy)-benzoyl]-amino}-methyl)-pyrrolidine-1-carboxylic acid tert-butyl ester (2.7 g, 5.48 mmol) in MeOH (containing 2% AcOH, 25 mL), methylamine (13.7 mL, 27.41 mmol, 2M in MeOH) is added. The solution is stirred at RT for 1 h under nitrogen atmosphere and cooled to 10° C., before the careful addition of $NaBH_4$ (0.415 g, 10.96 mmol) (exothermic !!). The resulting mixture is allowed to reach RT and stirred for 1.5 h. The excess reducing agent is quenched with water, AcOEt is added and the reaction mixture is poured into an aqueous saturated solution of $NaHCO_3$. The organic layer is separated and the aqueous layer extracted twice with AcOEt, dried over $Na_2SO_4$, filtered, and concentrated in vacuo. The crude material is used in the next step without further purification. TLC, $R_f$($CH_2Cl_2$/MeOH 95:5)=0.05. MS (LC-MS) $[M+H]+=508.1$. $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 ml/min): 4.53 min.

K. (3R,4R)-3-({Isopropyl-[4-methoxy-3-(3-methoxy-propoxy)-benzoyl]-amino}-methyl)-4-[(methyl-phenylacetyl-amino)-methyl]-pyrrolidine-1-carboxylic acid tert-butyl ester To a solution of (3R,4R)-3-({isopropyl-[4-methoxy-3-(3-methoxy-propoxy)-benzoyl]-amino}-methyl)-4-methylaminomethyl-pyrrolidine-1-carboxylic acid tert-butyl ester (2 g, 3.35 mmol) in $CH_2Cl_2$ (25 mL), phenylacetyl chloride (0.53 mL, 4.02 mmol) and triethylamine (0.56 mL, 4.02 mmol) are added under $N_2$ atmosphere at 0° C. The mixture is stirred 30 min at 0° C., then allowed to reach RT and further stirred for 1 h. The reaction mixture is diluted with $CH_2Cl_2$ and poured into an aqueous saturated solution of $NaHCO_3$. The organic layer is separated, and the aqueous one is extracted twice with $CH_2Cl_2$. The combined organic extracts are dried over $Na_2SO_4$, filtered and concentrated. The crude product is purified by flash chromatography on silica gel (eluent: c-hexane/AcOEt 20:80 to 0:100) to give the title compound. TLC, $R_f$ (CH₂Cl₂/MeOH 95:5)=0.4. MS (LC-MS): 526 [M-Boc+H]⁺; t$_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 ml/min): 5.71 min.

In a similar fashion as described above for Example 9/reaction step J, (3R,4R*)-3-({isopropyl-[4-methoxy-3-(3-methoxy-propoxy)-benzoyl]-amino}-methyl)-4-methylaminomethyl-pyrrolidine-1-carboxylic acid tert-butyl ester is prepared from racemic (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester by reductive amination with methylamine in presence of NaBH₄: TLC, R$_f$(CH₂Cl₂/MeOH 95:5)=0.05. MS (LC-MS) [M+H]⁺=508.1. t$_R$ (HPLC, Nucleosil C18 column, 10-100% CH3CN/H₂O/5 min, 100% CH₃CN/3 min, CH₃CN and H₂O containing 0.1% TFA, flow: 1.5 ml/min): 4.53 min.

A. (3S*,4S*)-3-(tert-Butyl-dimethyl-silanyloxymethyl)-4-hydroxymethyl-pyrrolidine-1-carboxylic acid tert-butyl ester The title compound is prepared in a similar manner as described for Example 9/reaction step D, from (3S*,4S*)-3,4-bis-hydroxymethyl-pyrrolidine-1-carboxylic acid tert-butyl ester (25.0 g, 108 mmol), tert-butyl(chloro)dimethylsilane (17.9 g, 119 mmol) and NaH (3.11 g, 130 mmol; 55-65% dispersion in oil) in THF (0.6 L) as a yellowish oil. MS: 346.2 [M+H]⁺.

B. (3S*,4S*)-3-(tert-Butyl-dimethyl-silanyloxymethyl)-4-formyl-pyrrolidine-1-carboxylic acid tert-butyl ester The title compound is prepared in a similar manner as described for Example 9/reaction step E, from (3S*,4S*)-3-(tert-butyl-dimethyl-silanyloxymethyl)-4-hydroxymethyl-pyrrolidine-1-carboxylic acid tert-butyl ester (10.4 g, 58.9 mmol) and Dess-Martin periodinane (25.0 g, 58.9 mmol) in CH₂Cl₂ (150 mL), slowly wet CH₂Cl₂ (1.17 mL of water in 150 mL of CH₂Cl₂) as colorless oil. MS: 244.2 [M+H-Boc]⁺. t$_R$ (HPLC, C18 column, 5-100% CH₃CN/H₂O/6 min, 100% CH₃CN/2 min, CH₃CN and H₂O containing 0.1% TFA, flow: 1 mL/min): 6.46 min.

C. (3S*,4R*)-3-(tert-Butyl-dimethyl-silanyloxymethyl)-4-(isopropylamino-methyl)-pyrrolidine-1-carboxylic acid tert-butyl ester The title compound is prepared in a similar manner as described for Example 9/reaction step F, from (3S*,4S*)-3-(tert-butyl-dimethyl-silanyloxymethyl)-4-formyl-pyrrolidine-1-carboxylic acid tert-butyl ester (19.3 g, 56.1 mmol), isopropylamine (14.5 mL, 168 mmol) and NaBH(OAc)₃ (29.7 g, 140 mmol) in 1,2-dichloroethane (0.5 L) as a yellowish oil. MS: 387.2 [M+H]⁺. t$_R$ (HPLC, C18 column, 5-100% CH₃CN/H₂O/6 min, 100% CH₃CN/2 min, CH₃CN and H₂O containing 0.1% TFA, flow: 1 mL/min): 5.34 min.

D. (3S*,4R*)-3-(tert-Butyl-dimethyl-silanyloxymethyl)-4-({isopropyl-[4-methoxy-3-(3-methoxy-propoxy)-benzoyl]-amino}-methyl)-pyrrolidine-1-carboxylic acid tert-butyl ester The title compound is prepared in a similar manner as described for Example 9/reaction step G, from ((3S*,4R)-3-(tert-butyl-dimethyl-silanyloxymethyl)-4-(isopropylamino-methyl)-pyrrolidine-1-carboxylic acid tert-butyl ester (22.9 g, 59.1 mmol), 3-(3-methoxy-propoxy)-4-methoxy-benzoic acid (15.6 g, 65.1 mmol), bis(2-oxo-3-oxazolidinyl)phosphinic chloride (16.6 g, 65.1 mmol) and triethylamine (19.6 mL, 237 mmol) in CH₂Cl₂ (0.6 L) as a yellowish oil. MS: 609.4 [M+H]⁺; t$_R$ (HPLC, C18 column, 5-100% CH₃CNIH₂O/6 min, 100% CH₃CN/23 min, CH₃CN and H₂O containing 0.1% TFA, flow: 1 mL/min): 7.06 min.

E. (3S*,4R*)-3-Hydroxymethyl-4-({isopropyl-[4-methoxy-3-(3-methoxy-propoxy)-benzoyl]-amino}-methyl)-pyrrolidine-1-carboxylic acid tert-butyl ester The title compound is prepared in a similar manner as described for Example 9/reaction step H, from (3S*,4R*)-3-(tert-butyl-dimethyl-silanyloxymethyl)-4-({isopropyl-[4-methoxy-3-(3-methoxy-propoxy)-benzoyl]-amino}-methyl)-pyrrolidine-1-carboxylic acid tert-butyl ester (25.0 g, 41.1 mmol) and tetrabutylammonium fluoride trihydrate (19.4 g, 61.6 mmol) in THF (150 mL) as a colorless oil. MS: 495.2 [M+H]+; t$_R$ (HPLC, C18 column, 5-100% CH₃CN/H₂O/6 min, 100% CH₃CN/1.5 min, CH₃CN and H₂O containing 0.1% TFA, flow: 1.5 mL/min): 4.84 min.

F. (3S*,4R*)-3-Formyl-4-({isopropyl-[4-methoxy-3-(3-methoxy-propoxy)-benzoyl]-amino}-methyl)-pyrrolidine-1-carboxylic acid tert-butyl ester The title compound is prepared in a similar manner as described for Example 9/reaction step I, from (3S*,4R*)-3-hydroxymethyl-4-({isopropyl-[4-methoxy-3-(3-methoxy-propoxy)-benzoyl]-amino}-methyl)-pyrrolidine-1-carboxylic acid tert-butyl ester (4.9 g, 9.95 mmol) and Dess-Martin periodinane (4.22 g, 9.95 mmol) in CH₂Cl₂ (30 mL), slowly wet CH₂Cl₂ (0.20 mL of water in 30 mL of CH₂Cl₂) as colorless oil. MS: 437.2 [M+H-BOC]+. t$_R$ (HPLC, Nucleosil C18 column, 5-100% CH₃CN/H₂O/6 min, 100% CH₃CN/1.5 min, CH₃CN and H₂O containing 0.1% TFA, flow: 1.5 ml/min): 4.99 min.

EXAMPLE 10

N-{(3S,4S)-4-[(Cyclopropyl-phenylacetyl-amino)-methyl]-pyrrolidin-3-ylmethyl}-N-isopropyl-4-methoxy-3-(3-methoxy-propoxy)-benzamide

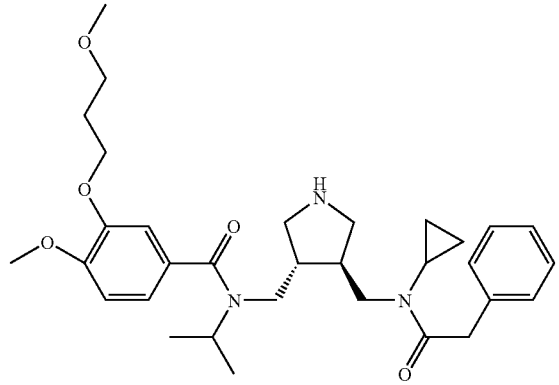

A solution of (3R,4R)-3-[(cyclopropyl-phenylacetyl-amino)-methyl]-4-({isopropyl-[4-methoxy-3-(3-methoxy-propoxy)-benzoyl]-amino}-methyl)-pyrrolidine-1-carboxylic acid tert-butyl ester (0.32 g, 0.48 mmol) in a 4N HCl solution in dioxane (2.0 mL) is stirred at room temperature overnight. The reaction mixture is then freeze-dried to afford the corresponding hydrochloride salt as white solid. MS: 552.2 [M]+; $t_R$ (HPLC, Nucleosil C18HD column, 5-100% $CH_3CN/H_2O/6$ min, 100% $CH_3CN/1.5$ min, $CH_3CN$ and $H_2O$ containing 0.1% TFA flow: 1 mL/min): 4.72 min.

The starting material is prepared as follows:

A. (3R,4R)-3-Cyclopropylaminomethyl-4-({isopropyl-[4-methoxy-3-(3-methoxy-propoxy)-benzoyl]-amino}-methyl)-pyrrolidine-1-carboxylic acid tert-butyl ester A solution of (3S,4R)-3-formyl-4-({isopropyl-[4-methoxy-3-(3-methoxy-propoxy)-benzoyl]-amino}-methyl)-pyrrolidine-1-carboxylic acid tert-butyl ester (7.45 g, 15.1 mmol; Example 9/reaction step 1) and cycloproylamine (5.30 mL, 75.6 mmol) in MeOH (containing 2% AcOH, 90 mL) is stirred for 1 h at room temperature, followed by portionwise addition of NaBH4 (1.14 g, 30.2 mmol). After stirring for 1 h, the reaction mixture is concentrated to one third of its volume, water and a saturated NaHCO3 solution are added and the aqueous layer is extracted with AcOEt. The combined organics are dried (Na2SO4) and evaporated to dryness to afford the title compound as colorless oil. The crude material is used in the next step without further purification. MS (LC-MS) [M+H]+=534.2. $t_R$ (HPLC, Nucleosil C18HD column, 5-100% $CH_3CN/H_2O/6$ min, 100% $CH_3CN/1.5$ min, $CH_3CN$ and $H_2O$ containing 0.1% TFA, flow: 1 mL/min): 4.79 min.

B. (3R,4R)-3-[(Cyclopropyl-phenylacetyl-amino)-methyl]-4-({isopropyl-[4-methoxy-3-(3-methoxy-propoxy)-benzoyl]-amino}-methyl)-pyrrolidine-1-carboxylic acid tert-butyl ester To a solution of (3R,4R)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester (0.30 g, 0.56 mmol) in CH2Cl2 (6 mL) are subsequently added Et3N (0.094 mL, 0.67 mmol), 1-hydroxy-benzotriazol hydrate (0.09 g, 0.67 mmol), N-(3-dimethylaminopropyl)-N'-ethyl-carbodiimide hydrochloride (0.129 g, 0.67 mmol) and phenylacetic acid (0.09 g, 0.67 mmol), followed by stirring overnight. The reaction mixture is diluted with CH2Cl2 and then washed with 1N HCl (5 mL), saturated aqueous NaHCO3 and brine, the organic layer is dried over MgSO4 and concentrated. Purification by flash chromatography (eluent: hexane/AcOEt 25:75, then AcOEt 100%) gives the title compound as colorless oil. MS (LC-MS): 652.4 [M+H]+. $t_R$ (HPLC, Nucleosil C18HD column, 5-100% $CH_3CN/H_2O/6$ min, 100% $CH_3CN/1.5$ min, $CH_3CN$ and $H_2O$ containing 0.1% TFA, flow: 1 mL/min): 5.80 min.

EXAMPLE 11

N-[(3S*,4S*)-4-({Cyclopropyl-[2-(4-methoxy-phenyl)-acetyl]-amino}-methyl)-pyrrolidin-3-ylmethyl]-N-isopropyl-4-methoxy-3-(3-methoxy-propoxy)-benzamide

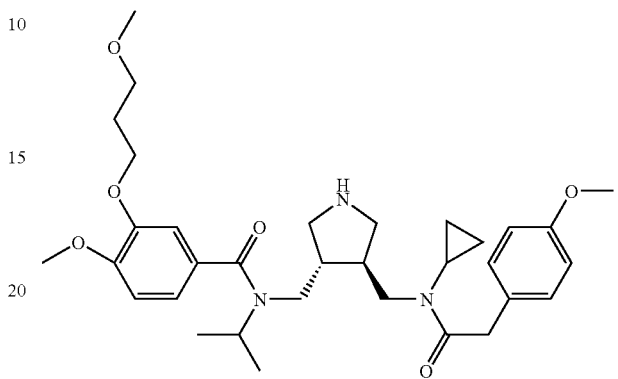

To a solution of (3R*,4R*)-3-({cyclopropyl-[2-(4-methoxy-phenyl)-acetyl]-amino}-methyl)-4-({isopropyl-[4-methoxy-3-(3-methoxy-propoxy)-benzoyl]-amino}-methyl)-pyrrolidine-1-carboxylic acid tert-butyl ester (0.17 g, 0.26 mmol) in dioxane (1 mL), 4N HCl in dioxane (0.647 mL) is added, and the resulting solution is lyophilized to afford the corresponding hydrochloride salt. TLC, $R_f$ ($CH_2Cl_2$/MeOH 9:1+10% $NH_4OH$)=0.2. MS (LC-MS): 582.4 [M+H]+; $t_R$ (HPLC, Macherey-Nagel Nucleosil C18 column, 5-100% $CH_3CN/H_2O/6$ min, 100% $CH_3CN/2$ min, $CH_3CN$ and $H_2O$ containing 0.1% TFA, flow: 1 mL/min): 4.06 min.

The starting material is prepared as follows:

A. (3R*,4R*)-3-Cyclopropylaminomethyl-4-({isopropyl-[4-methoxy-3-(3-methoxy-propoxy)-benzoyl]-amino}-methyl)-pyrrolidine-1-carboxylic acid tert-butyl ester The title compound is prepared analogously as described for the title compound under J in Example 9 from (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester and cyclopropylamine. TLC, $R_f$($CH_2Cl_2$/MeOH 9:1+10 % $NH_4OH$)=0.48. MS (LC-MS): 534.4 [M+H]+; $t_R$ (HPLC, Macherey-Nagel Nucleosil C18 column, 5-100% $CH_3CN/H_2O/6$ min, 100% $CH_3CN/2$ min, $CH_3CN$ and $H_2O$ containing 0.1% TFA, flow: 1 mL/min): 4.53 min.

B. (3R*,4R*)-3-({cyclopropyl-[2-(4-methoxy-phenyl)-acetyl]-amino}-methyl)-4-({isopropyl-[4-methoxy-3-(3-methoxy-propoxy)-benzoyl]-amino}-methyl)-pyrrolidine-1-carboxylic acid tert-butyl ester To a solution of 4-methoxyphenylacetic acid (0.075 g, 0.45 mmol) in $CH_2Cl_2$ (3 mL), are added triethylamine (0.063 mL, 0.45 mmol), 1-hydroxy-benzotriazol hydrate (0.061 g, 0.45 mmol) and N-(3-dimethylaminopropyl)-N'-ethyl-carbodiimide hydrochloride (EDC) (0.086 g, 0.45 mmol) followed by (3R*,4R*)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester (0.2 g, 0.375 mmol). The resulting mixture is stirred for 2 days at RT,

EXAMPLE 12

N-[(3S*,4S*)-4-({[2-(3-Acetylamino-phenyl)-acetyl]-cyclopropyl-amino}-methyl)-pyrrolidin-3-ylmethyl]-N-isopropyl-4-methoxy-3-(3-methoxy-propoxy)-benzamide

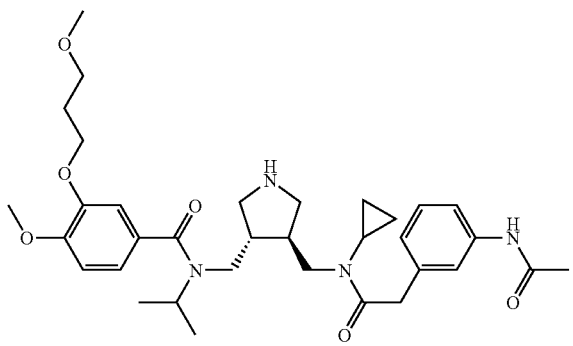

To a solution of (3R*,4R*)-3-({[2-(3-acetylamino-phenyl)-acetyl]-cyclopropyl-amino}-methyl)-4-({isopropyl-[4-methoxy-3-(3-methoxy-propoxy)-benzoyl]-amino}-methyl)-pyrrolidine-1-carboxylic acid tert-butyl ester (0.31 g, 0.44 mmol) in dioxane (15 mL), 4N HCl in dioxane (6 mL) is added, the resulting solution is stirred at RT for 8 h and then lyophilized to afford the corresponding hydrochloride salt. MS (LC-MS): 609.1 [M+H]$^+$; $t_R$ (HPLC, Macherey Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 5.03 min.

The starting material is prepared as follows:

A. (3R*,4R*)-3-({Cyclopropyl-[2-(3-nitro-phenyl)-acetyl]-amino}-methyl)-4-({isopropyl-[4-methoxy-3-(3-methoxy-propoxy)-benzoyl]-amino}-methyl)-pyrrolidine-1-carboxylic acid tert-butyl ester At 0° C. HBTU (426 mg, 1.12 mmol) is added to a solution of 3-nitrophenylacetic acid (187 mg, 1.03 mmol) in CH$_3$CN (10 mL) and the resulting solution is stirred for 10 min. Then a solution of (3R*,4R*)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester (0.2 g, 0.375 mmol). (500 mg, 0.94 mmol) and triethylamine (1.04 mL, 7.5 mmol) in CH$_3$CN (10 mL) is added at 0° C. and the reaction mixture is stirred at RT for another 2 h. For workup a sat. solution of NaHCO$_3$ is added and the mixture is extracted with ethyl acetate. Washing of the combined extracts with brine, drying (Na$_2$SO$_4$), filtration and evaporation of the solvent affords the crude product which is purified by flash chromatography on silica gel (eluent: CH$_2$Cl$_2$ to CH$_2$Cl$_2$/MeOH 9:1) to give the title compound. MS (LC-MS): 597.0 [M+H-Boc]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mumin): 6.47 min.

B. (3R*,4R*)-3-({[2-(3-Amino-phenyl)-acetyl]-cyclopropyl-amino}-methyl)-4-({isopropyl-[4-methoxy-3-(3-methoxy-propoxy)-benzoyl]-amino}-methyl)-pyrrolidine-1-carboxylic acid tert-butyl ester At RT H$_2$ is passed through a suspension of (3R*,4R*)-3-({cyclopropyl-[2-(3-nitro-phenyl)-acetyl]-amino}-methyl)-4-({isopropyl-[4-methoxy-3-(3-methoxy-propoxy)-benzoyl]-amino}-methyl)-pyrrolidine-1-carboxylic acid tert-butyl ester (660 mg, 0.95 mmol) and Raney-Ni (100 mg) for several hours. After completion of the reaction the mixture is filtered over Celite and the solvent is evaporated to give the title compound which is used without further purification. MS (LC-MS): 667.0 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 5.33 min.

C. (3R*,4R*)-3-({[2-(3-Acetylamino-phenyl)-acetyl]-cyclopropyl-amino}-methyl)-4-({isopropyl-[4-methoxy-3-(3-methoxy-propoxy)-benzoyl]-amino}-methyl)-pyrrolidine-1-carboxylic acid tert-butyl ester Triethylamine (67 µL, 0.48 mmol), DMAP (0.4 mg, 0.003 mmol) and acetic anhydride (46 µL, 0.48 mmol) are added to a solution of (3R*,4R*)-3-({[2-(3-amino-phenyl)-acetyl]-cyclopropyl-amino}-methyl)-4-({isopropyl-[4-methoxy-3-(3-methoxy-propoxy)-benzoyl]-amino}-methyl)-pyrrolidine-1-carboxylic acid tert-butyl ester (215 mg, 0.32 mmol) in THF (20 mL). The reaction mixture is stirred at RT for 16 h before water is added for workup. Extraction with ethyl acetate, drying of the combined extracts (Na$_2$SO$_4$), filtration and evaporation of the solvent affords the crude product which is purified by flash chromatography on silica gel (eluent: CH$_2$Cl$_2$ to CH$_2$Cl$_2$/MeOH 9:1) to give the title compound. MS (LC-MS): 709.1 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 6.04 min.

An alternative method for the N-Boc deprotection reaction is described in the following example:

EXAMPLE 13

N-((3S,4S)-4-{[(3-Acetylamino-3-methyl-butyryl)-cyclopropyl-amino]-methyl}-pyrrolidin-3-ylmethyl)-N-isopropyl-4-methoxy-3-(3-methoxy-propoxy)-benzamide

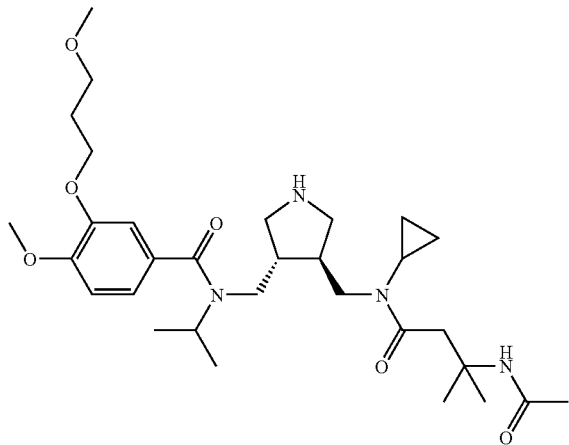

ZnBr$_2$ (110 mg, 0.49 mmol) is added to a solution of (3R,4R)-3-{[(3-acetylamino-3-methyl-butyryl)-cyclopropyl-amino]-methyl}-4-({isopropyl-[4-methoxy-3-(3-methoxy-propoxy)-benzoyl]-amino}-methyl)-pyrrolidine-1-carboxylic acid tert-butyl ester (150 mg, 0.22 mmol) in 1,2-dichloroethane (5 mL) and the resulting suspension is stirred at 55° C. for 16 h. In order to drive the reaction to completion another portion of ZnBr$_2$ (50 mg, 0.22 mmol) is added and heating is continued for another 24 h. For workup a sat. solution of NaHCO$_3$ is added and the mixture is extracted with CH$_2$Cl$_2$. Drying (Na$_2$SO$_4$) of the combined extracts, filtration and evaporation of the solvent affords the desired product as free base. The free base is dissolved in dioxane (2 mL) and fumaric acid (11 mg, 0.11 mmol) is added. Lyophilization yields the title compound as hemifumarate salt. MS (LC-MS): 575.0 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 4.90 min.

The following Examples are prepared according to the procedures described above in Examples 8, 9, 10, 11, 12 and 13:

TABLE 1

| Example | configuration | structure | [M + H]$^+$ | t$_R$ (HPLC) |
|---|---|---|---|---|
| 14 | (3S*, 4S*) | 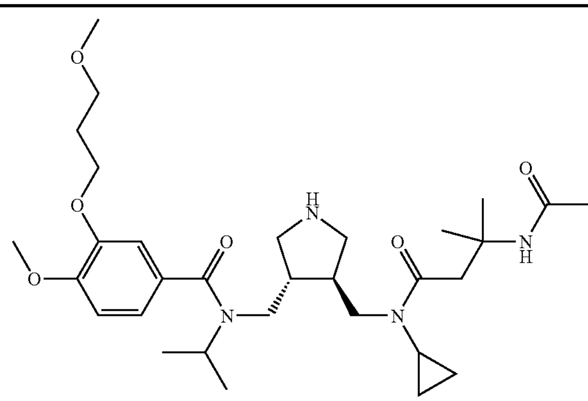 | 575.1 | 4.18[a] |
| 15 | (3S*, 4S*) | 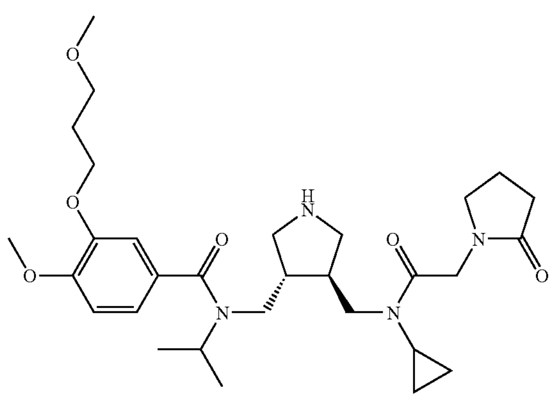 | 559.1 | 4.04[a] |

TABLE 1-continued

| Example | configuration | structure | [M + H]+ | t$_R$ (HPLC) |
|---|---|---|---|---|
| 16 | (3S*, 4S*) | 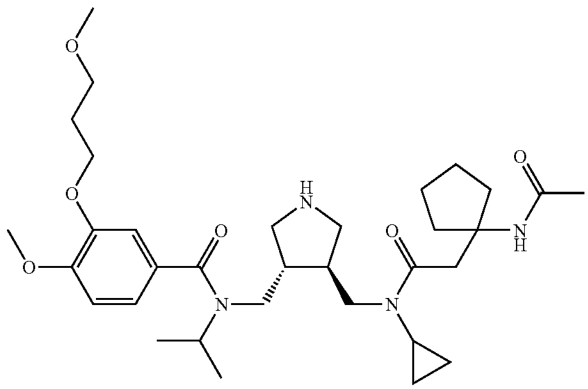 | 601.2 | 4.34[a] |
| 17 | (3S*, 4S*) | 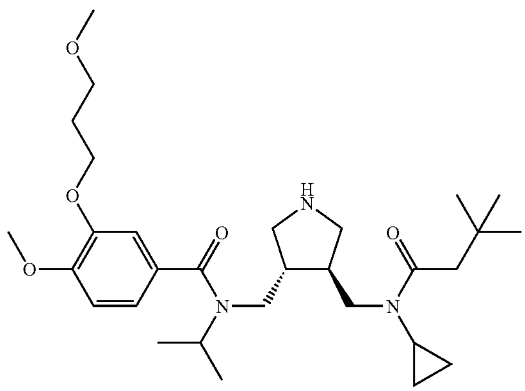 | 532.1 | 4.72[a] |
| 18 | (3S*, 4S*) | 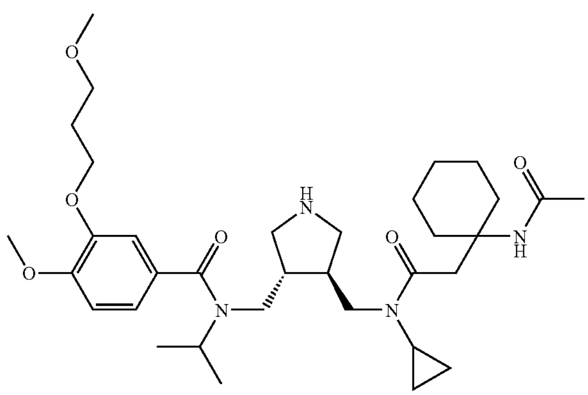 | 615.2 | 4.52[a] |
| 19 | (3S*, 4S*) | 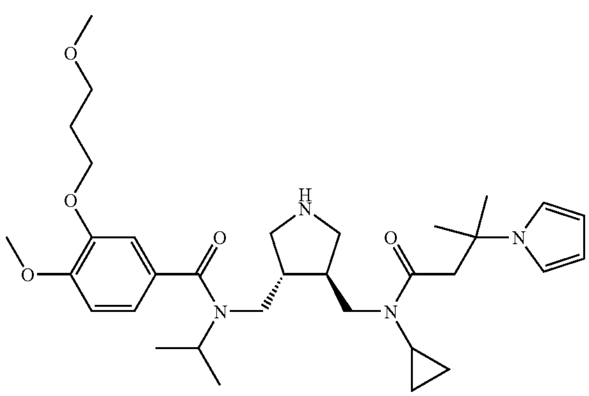 | 583.3 | 4.82[a] |

TABLE 1-continued

| Example | configuration | structure | [M + H]+ | t_R (HPLC) |
|---|---|---|---|---|
| 20 | (3S*, 4S*) | 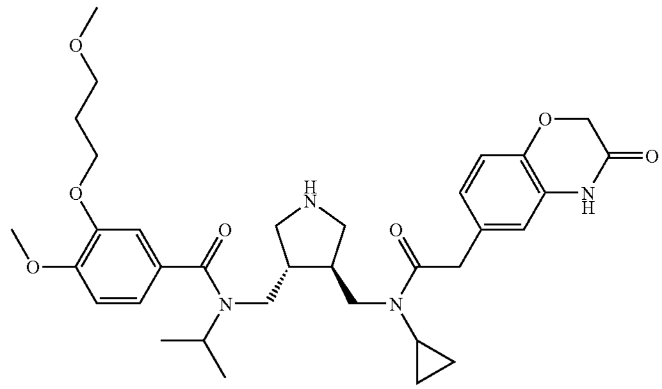 | 623.4 | 4.49[a] |
| 21 | (3S*, 4S*) | 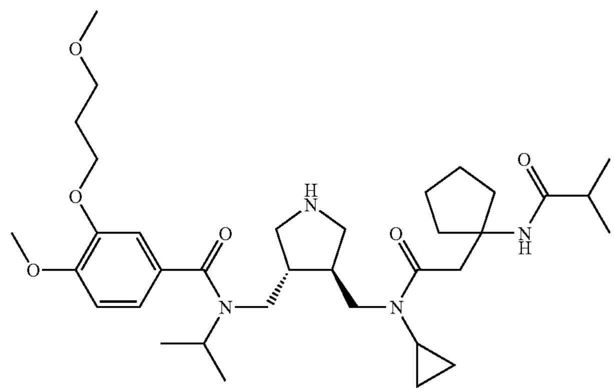 | 629.7 | 4.80[a] |
| 22 | (3S*, 4S*) | 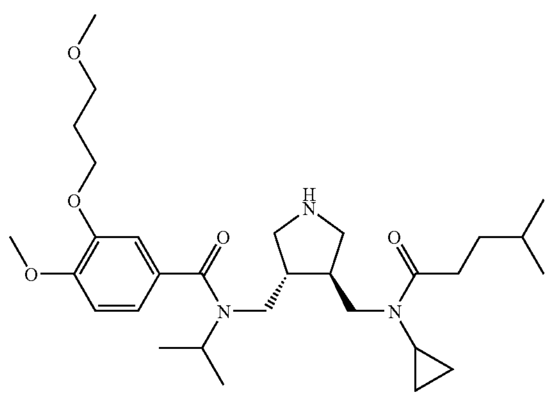 | 532.3 | 5.12[a] |
| 23 | (3S*, 4S*) | 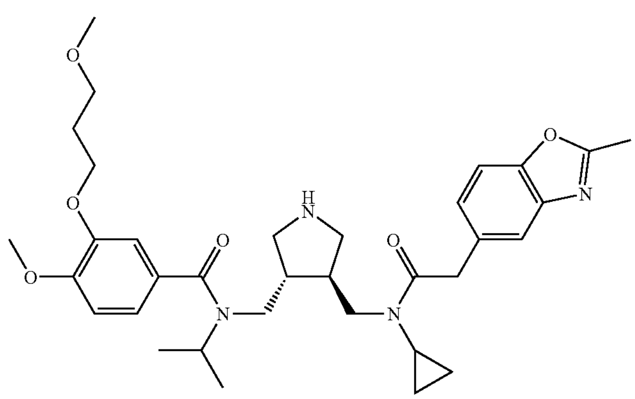 | 607.2 | 5.19[a] |

TABLE 1-continued

| Example | configuration | structure | [M + H]+ | t$_R$ (HPLC) |
|---|---|---|---|---|
| 24 | (3S*, 4S*) | 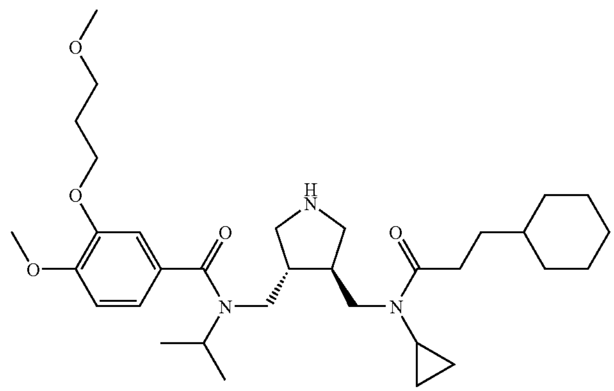 | 572.3 | 5.99[a] |
| 25 | (3S, 4S) | 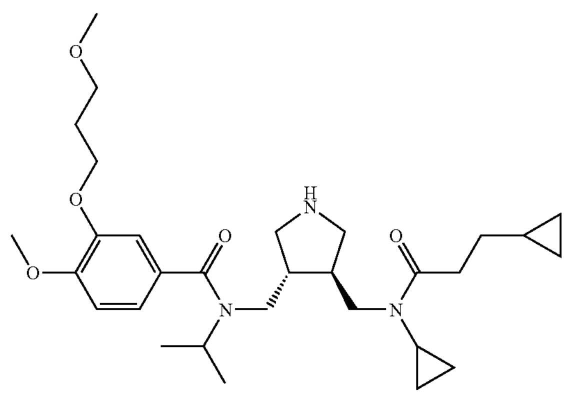 | 530.2 | 5.87[a] |
| 26 | (3S, 4S) | 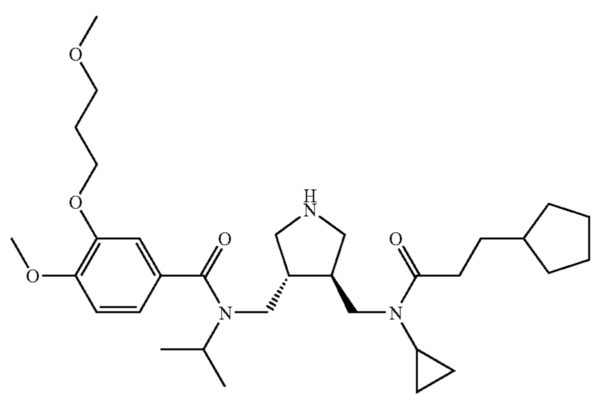 | 558.3 | 6.19[a] |
| 27 | (3S, 4S) | 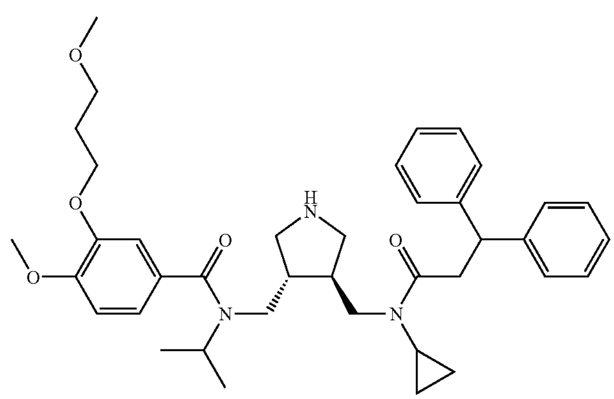 | 642.3 | 5.51[a] |

TABLE 1-continued

| Example | configuration | structure | [M + H]+ | t_R (HPLC) |
|---|---|---|---|---|
| 28 | (3S, 4S) | 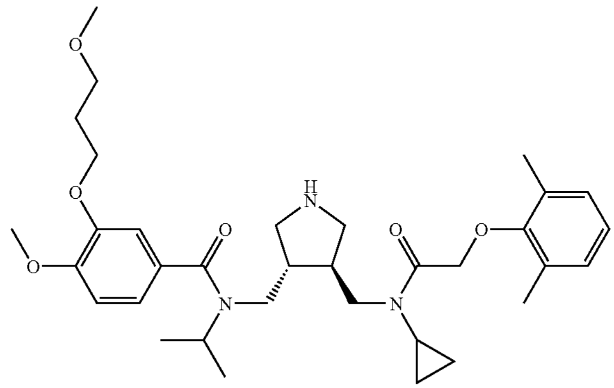 | 596.3 | 5.44[a] |
| 29 | (3S, 4S) | 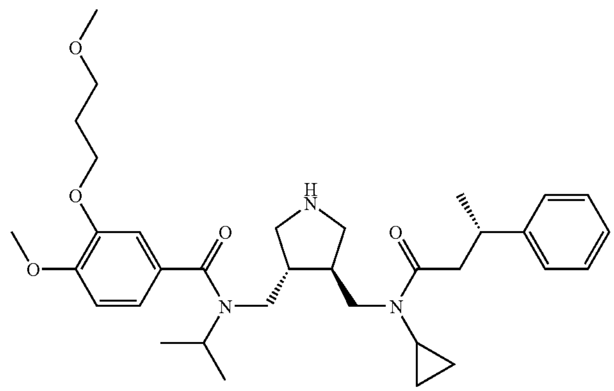 | 580.0 | 4.95[a] |
| 30 | (3S, 4S) | 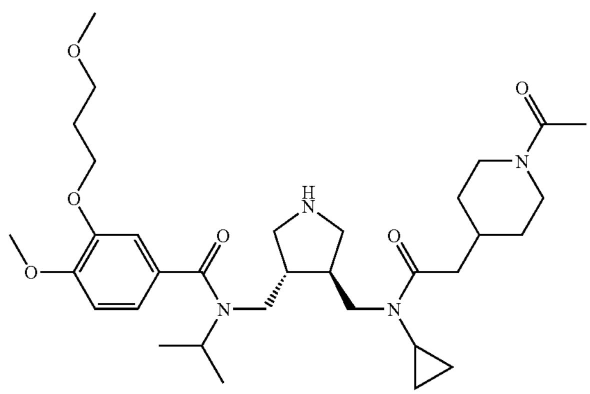 | 601.5 | 3.04[b] |
| 31 | (3S, 4S) | 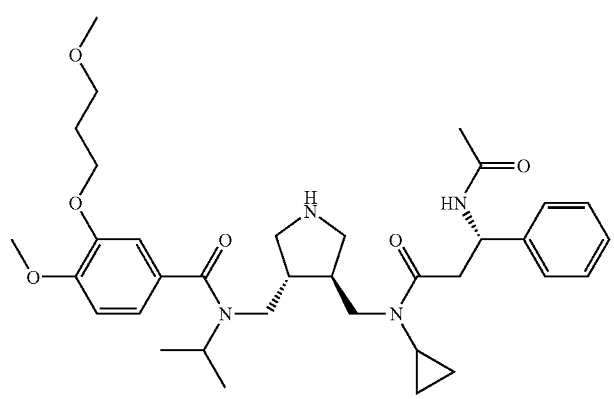 | 623.5 | 0.36[b] |

TABLE 1-continued

| Example | configuration | structure | [M + H]+ | t_R (HPLC) |
|---|---|---|---|---|
| 32 | (3S, 4S) | 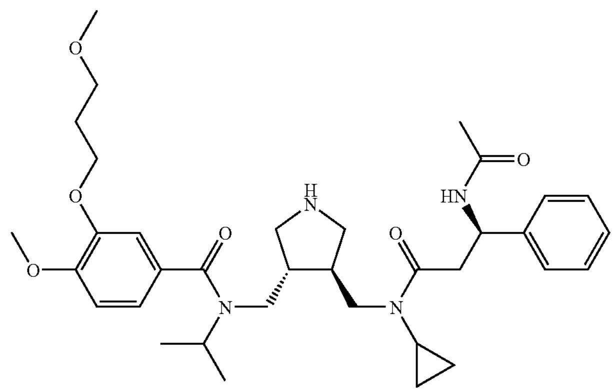 | 623.5 | 0.35[b] |
| 33 | (3S, 4S) | 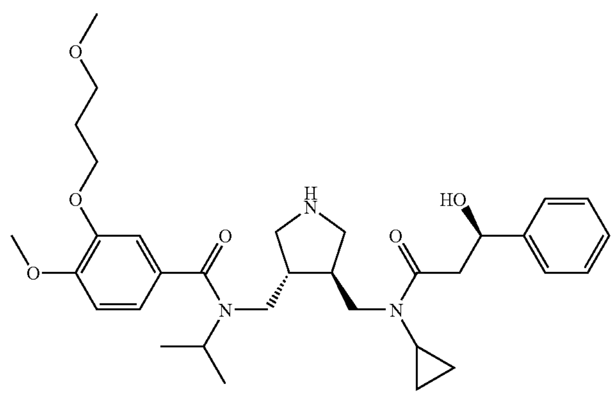 | 582.2 | 4.46[a] |
| 34 | (3S, 4S) | 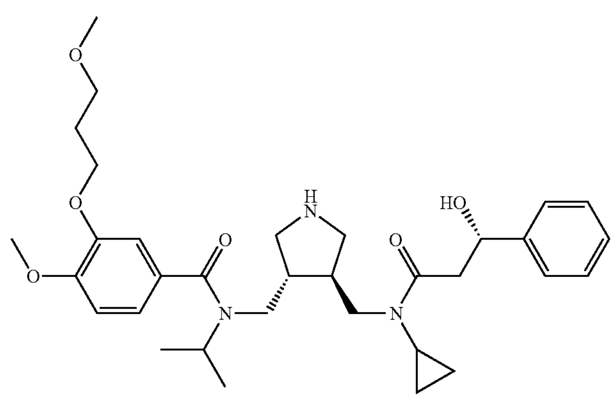 | 582.2 | 4.50[a] |
| 35 | (3S, 4S) | 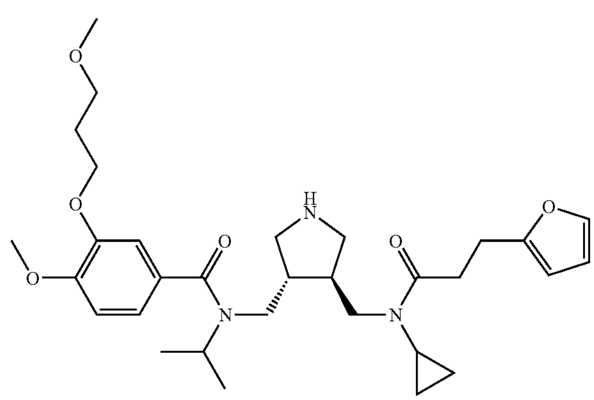 | 556.3 | 4.67[a] |

TABLE 1-continued

| Example | configuration | structure | [M + H]+ | t_R (HPLC) |
|---|---|---|---|---|
| 36 | (3S, 4S) | 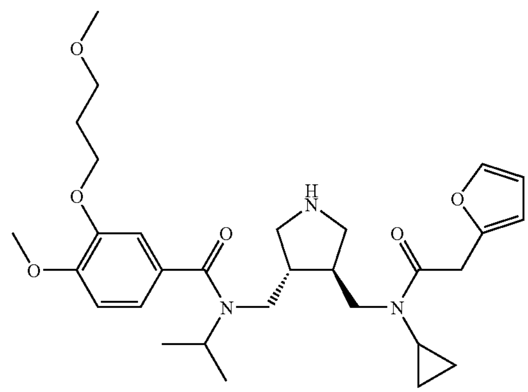 | 542.2 | 4.48[a] |
| 37 | (3S, 4S) | 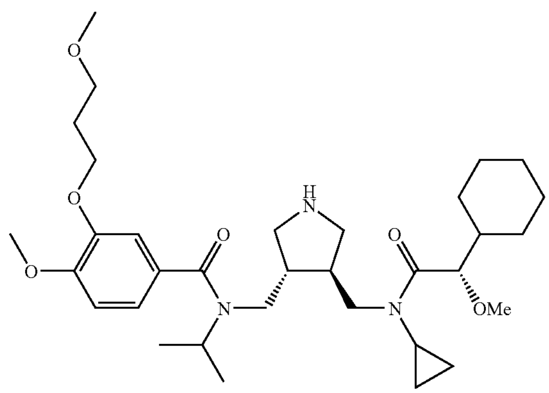 | 588.3 | 2.89[c] |
| 38 | (3S, 4S) | 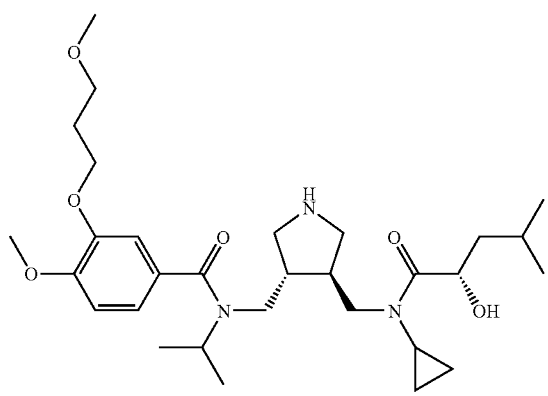 | 548.2 | 2.41[d] |
| 39 | (3S*, 4S*) | 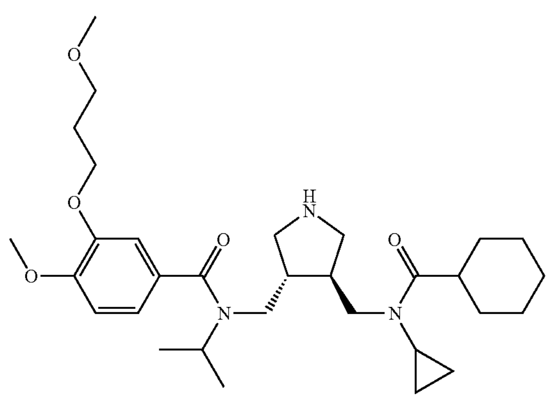 | 544.4 | 4.69[e] |

TABLE 1-continued

| Example | configuration | structure | [M + H]+ | t_R (HPLC) |
|---|---|---|---|---|
| 40 | (3S, 4S) | 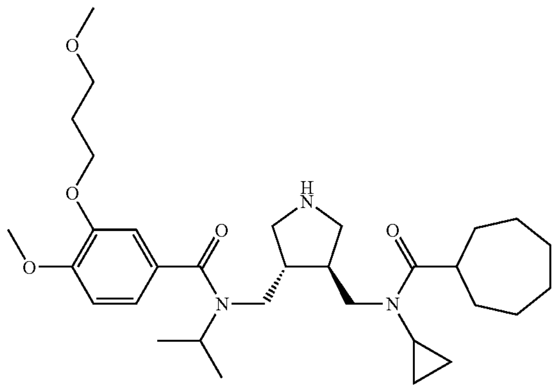 | 558.2 | 4.48[f] |
| 41 | (3S, 4S) | 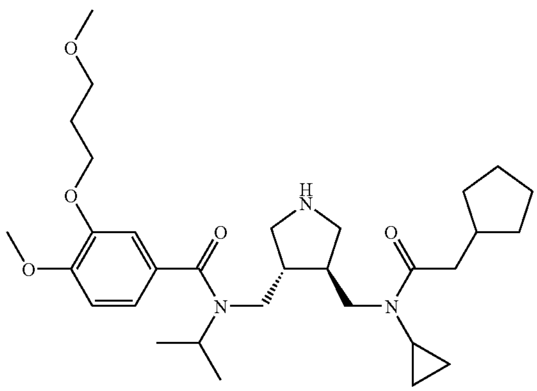 | 544.3 | 4.97[e] |
| 42 | (3S*, 4S*) | 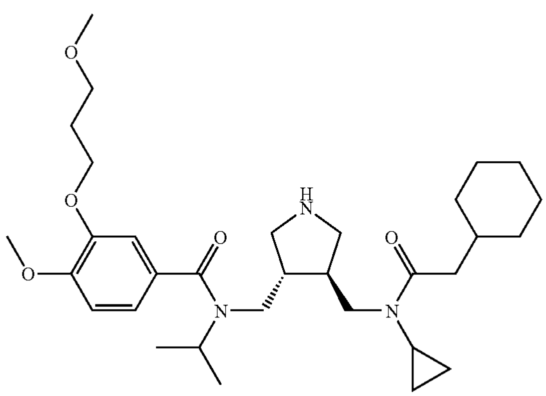 | 558.4 | 5.28[e] |
| 43 | (3S*, 4S*) | 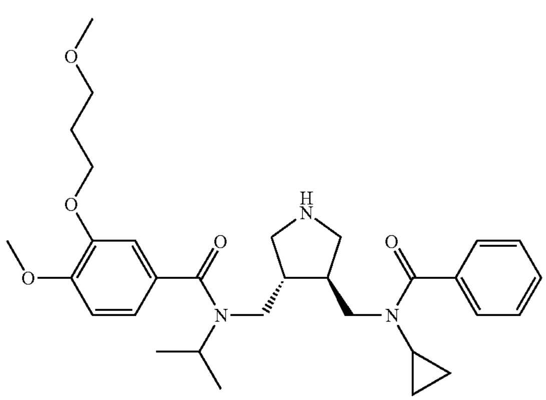 | 538.2 | 4.61[e] |

TABLE 1-continued

| Example | configuration | structure | [M + H]+ | t$_R$ (HPLC) |
|---|---|---|---|---|
| 44 | (3S*, 4S*) | 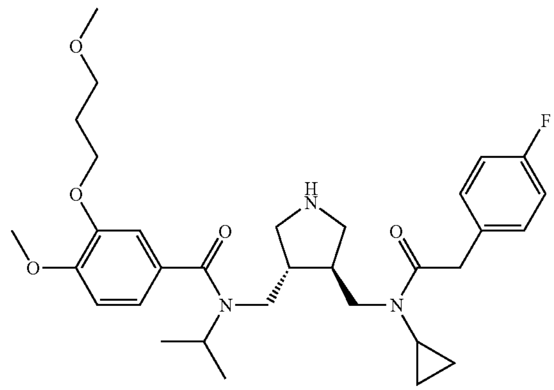 | 570.2 | 4.85$^e$ |
| 45 | (3S, 4S) | 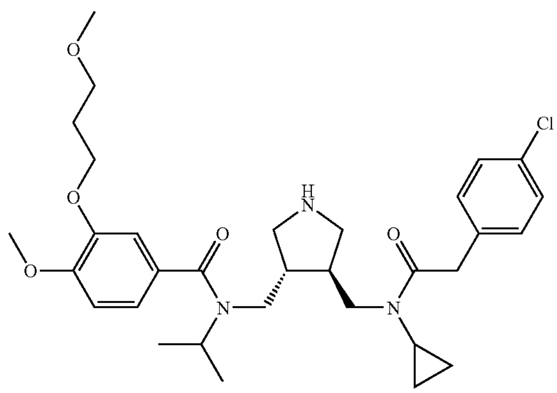 | 586.2 | 5.04$^e$ |
| 46 | (3S*, 4S*) | 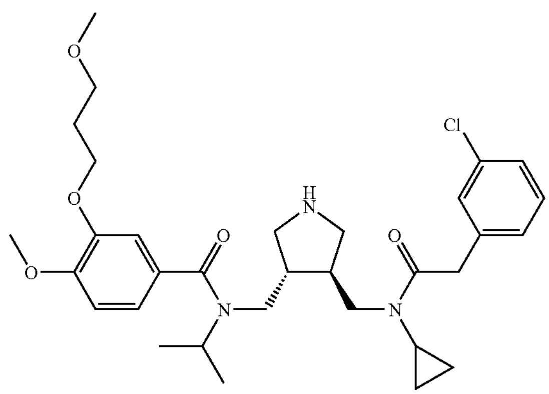 | 587.3 | 4.79$^e$ |
| 47 | (3S*, 4S*) | 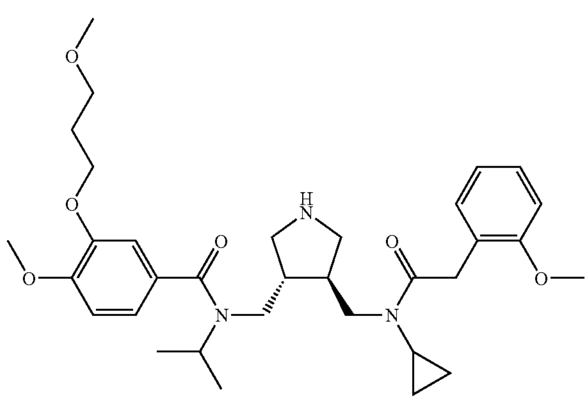 | 582.3 | 4.58$^e$ |

TABLE 1-continued
| Example | configuration | structure | [M + H]+ | t_R (HPLC) |
|---|---|---|---|---|
| 48 | (3S*, 4S*) | 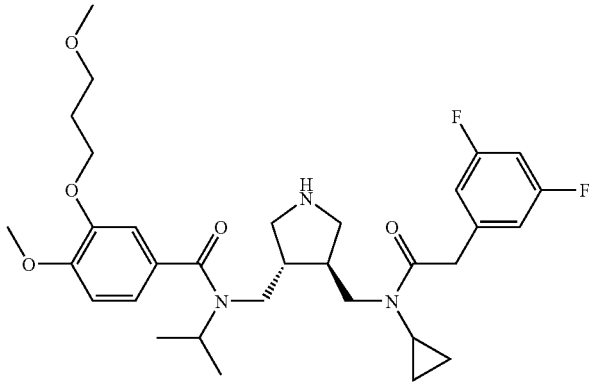 | 588.2 | 4.36[f] |
| 49 | (3S*, 4S*) | 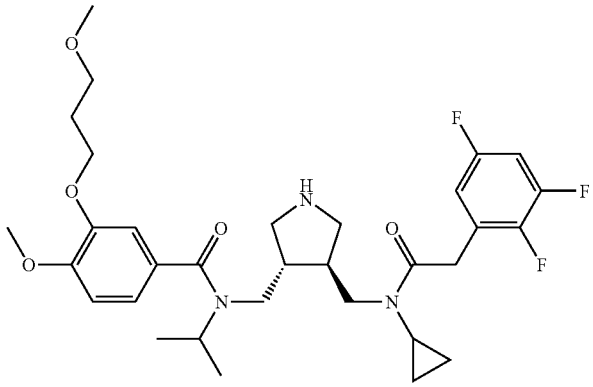 | 606.2 | 4.99[e] |
| 50 | (3S*, 4S*) | 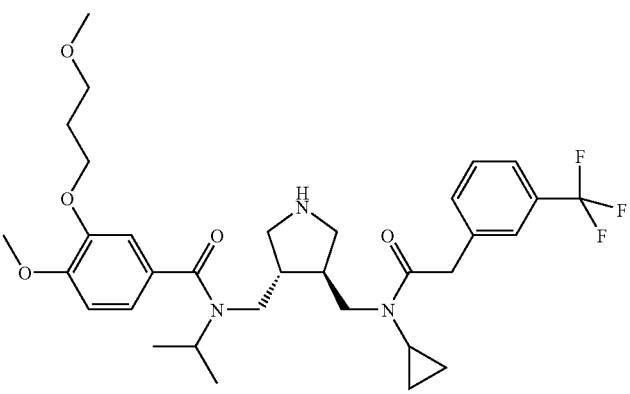 | 620.2 | 4.67[f] |
| 51 | (3S*, 4S*) | 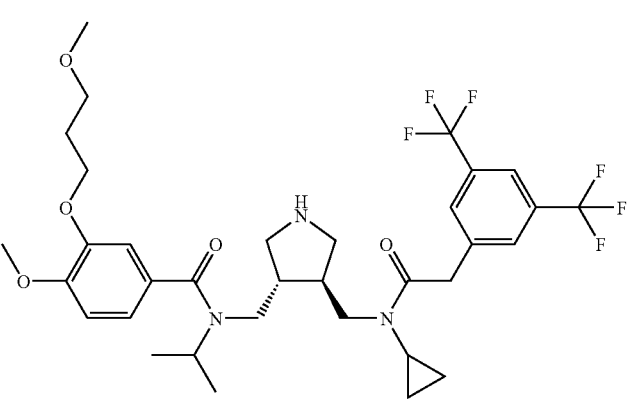 | 688.2 | 5.58[e] |

TABLE 1-continued

| Example | configuration | structure | [M + H]+ | tR (HPLC) |
|---|---|---|---|---|
| 52 | (3S*, 4S*) | 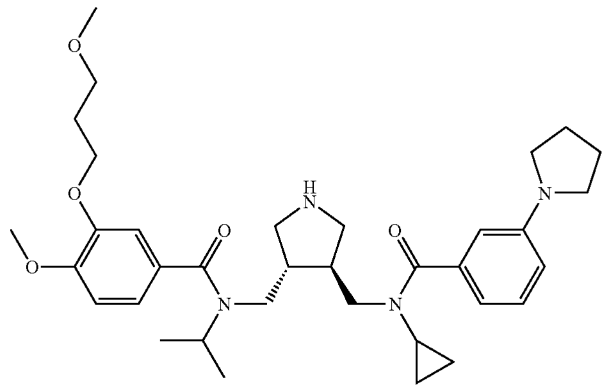 | 607.4 | 3.96[e] |
| 53 | (3S*, 4S*) | 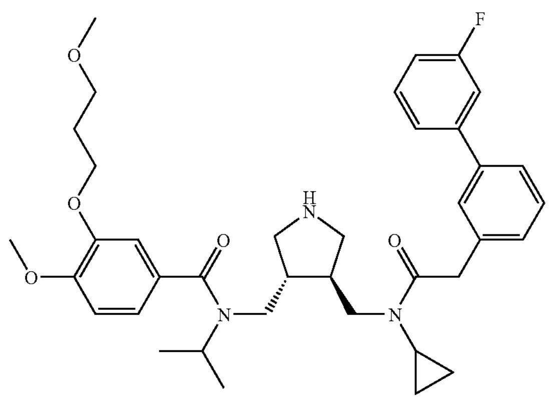 | 646.4 | 5.18[e] |
| 54 | (3S*, 4S*) | 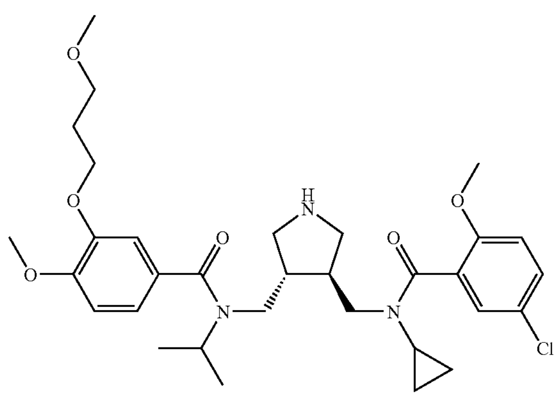 | 602.2 | 4.30[f] |
| 55 | (3S*, 4S*) | 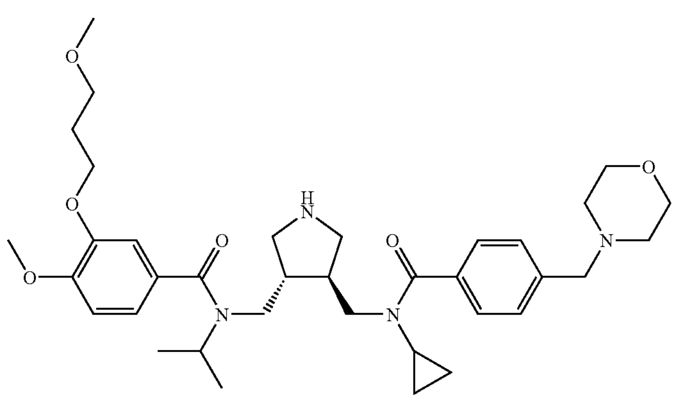 | 637.3 | 2.93[f] |

TABLE 1-continued
| Example | configuration | structure | [M + H]+ | t_R (HPLC) |
|---|---|---|---|---|
| 56 | (3S*, 4S*) | 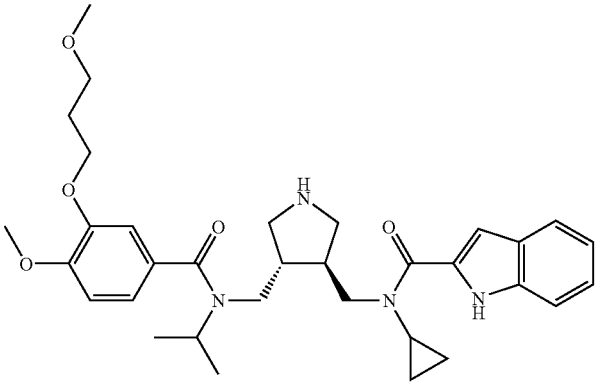 | 577.3 | 4.91[e] |
| 57 | (3S*, 4S*) | 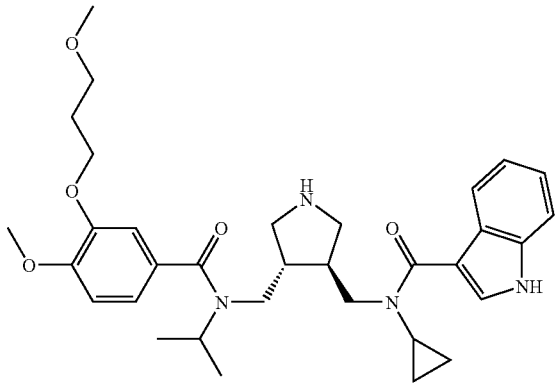 | 577.3 | 4.54[e] |
| 58 | (3S, 4S) | 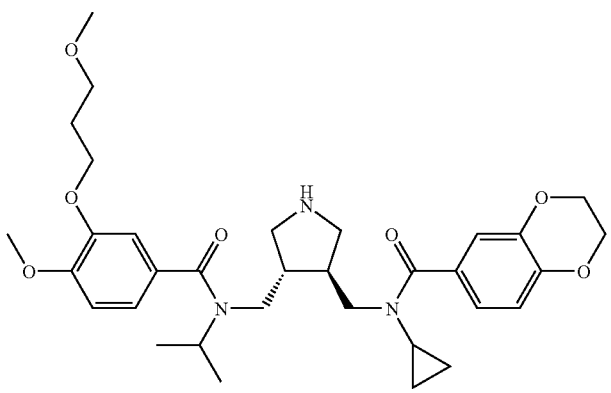 | 596.2 | 3.76[f] |
| 59 | (3S*, 4S*) | 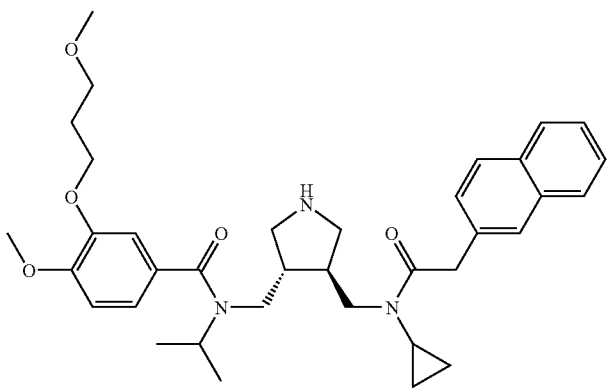 | 602.2 | 5.11[f] |

TABLE 1-continued

| Example | configuration | structure | [M + H]+ | t_R (HPLC) |
|---|---|---|---|---|
| 60 | (3S, 4S) | 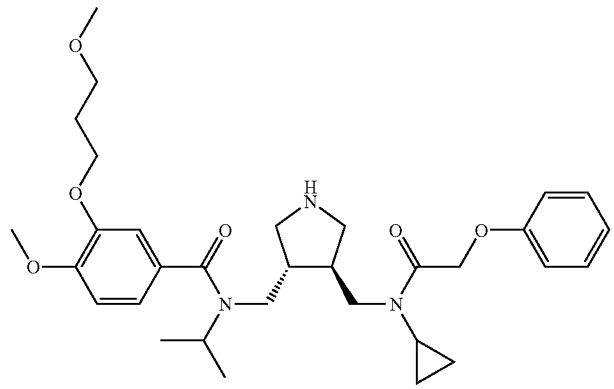 | 568.2 | 4.04[f] |
| 61 | (3S*, 4S*) | 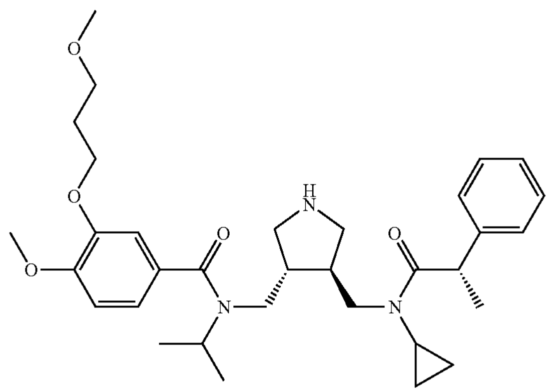 | 566.4 | 4.96[e] |
| 62 | (3S*, 4S*) | 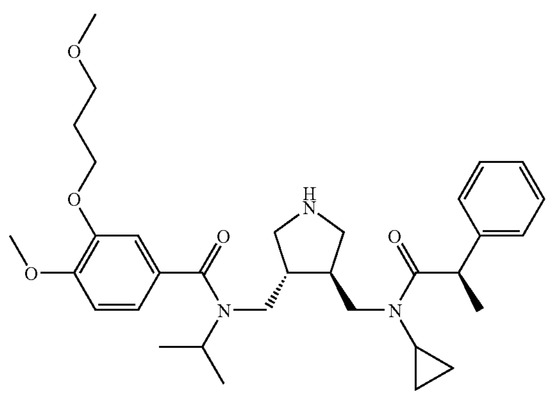 | 566.4 | 4.92[e] |
| 63 | (3S, 4S) | 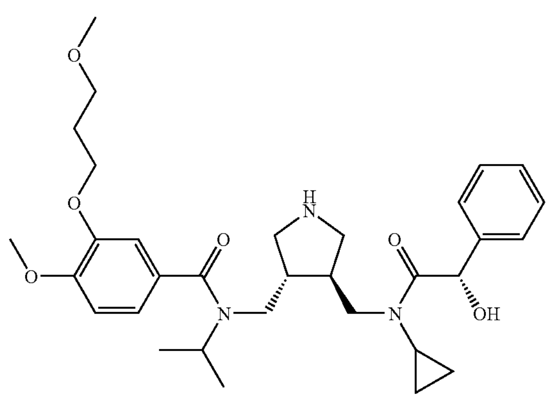 | 568.2 | 3.54[f] |

TABLE 1-continued

| Example | configuration | structure | [M + H]+ | t_R (HPLC) |
|---|---|---|---|---|
| 64 | (3S, 4S) | 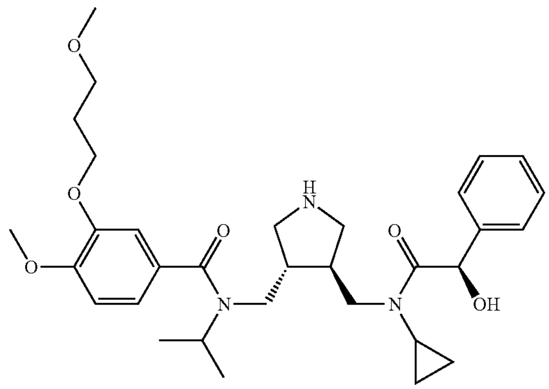 | 568.2 | 3.52[f] |
| 65 | (3S, 4S) | 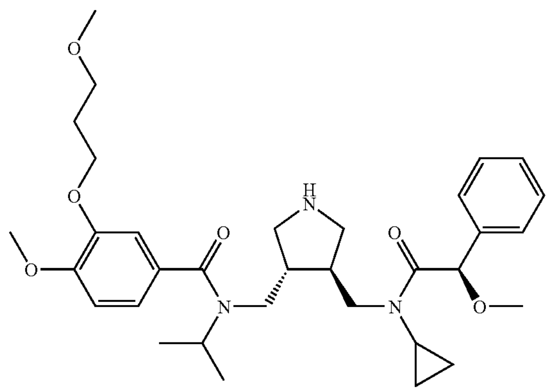 | 582.2 | 3.78[f] |
| 66 | (3S, 4S) | 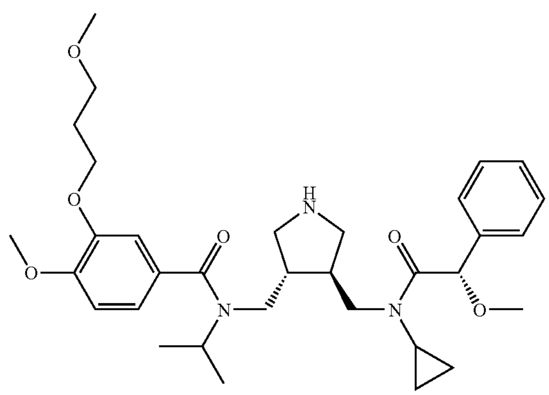 | 582.2 | 3.80[f] |
| 67 | (3S*, 4S*) | 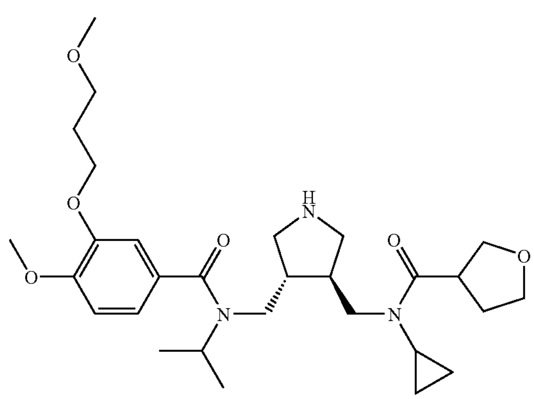 | 532.2 | 3.29[f] |

TABLE 1-continued

| Example | configuration | structure | [M + H]+ | t_R (HPLC) |
|---|---|---|---|---|
| 68 | (3S*, 4S*) | 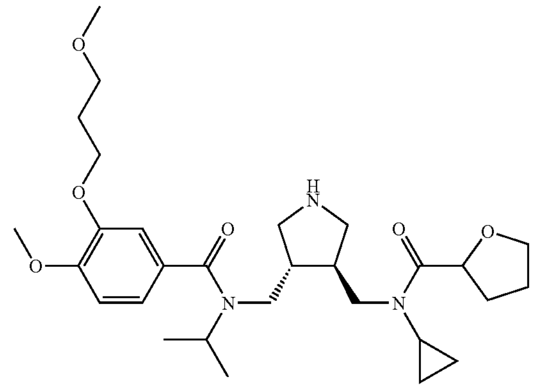 | 532.2 | 3.32[f] |
| 69 | (3S, 4S) | 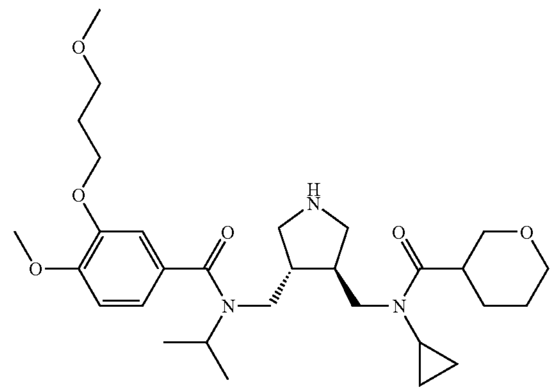 | 546.2 | 3.40[f] |
| 70 | (3S, 4S) | 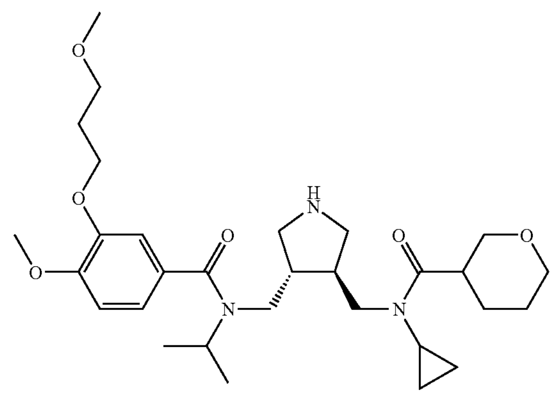 | 546.2 | 3.41[f] |
| 71 | (3S*, 4S*) | 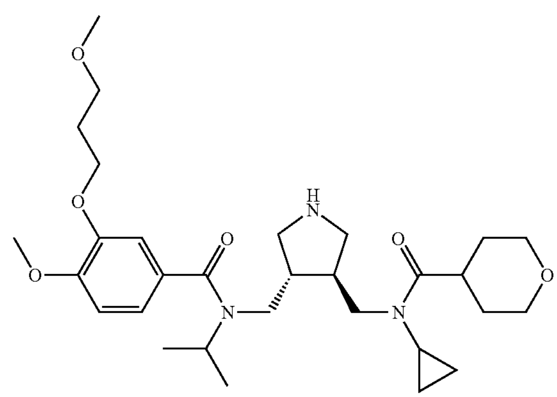 | 546.4 | 4.21[e] |

TABLE 1-continued

| Example | configuration | structure | [M + H]+ | t_R (HPLC) |
|---|---|---|---|---|
| 72 | (3S, 4S) | 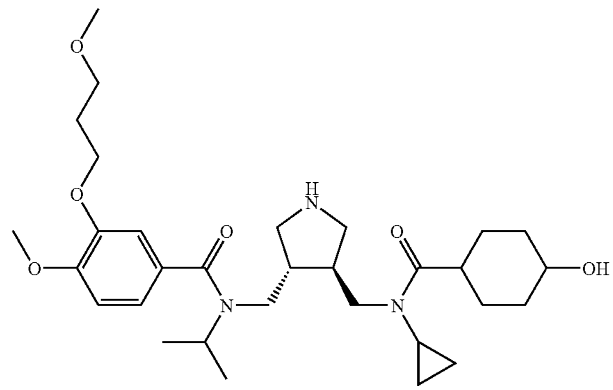 | 560.2 | 3.10[f] |
| 73 | (3S, 4S) | 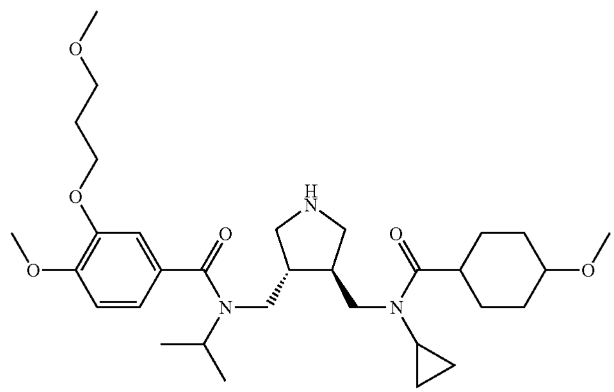 | 574.2 | 3.82[f] |
| 74 | (3S, 4S) | 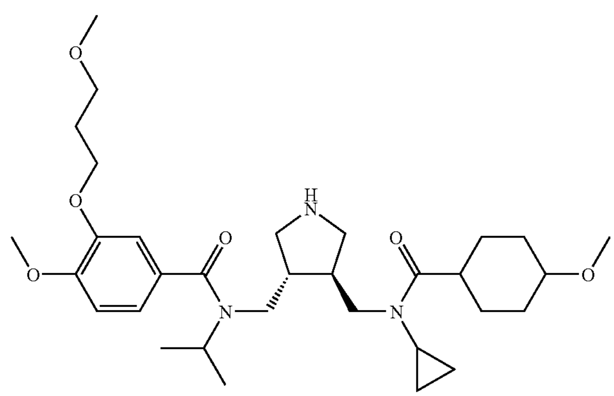 | 574.2 | 3.60[f] |
| 75 | (3S, 4S) | 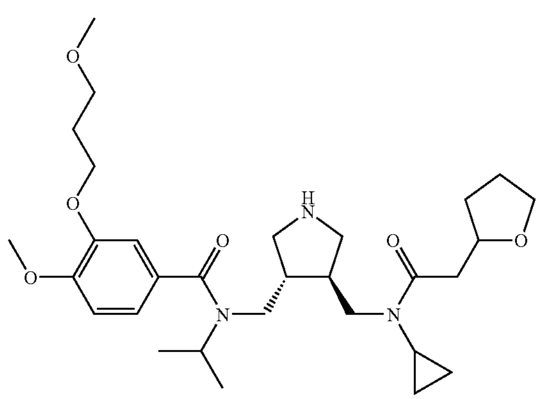 | 546.2 | 3.46[f] |

TABLE 1-continued

| Example | configuration | structure | [M + H]+ | t_R (HPLC) |
|---|---|---|---|---|
| 76 | (3S, 4S) | 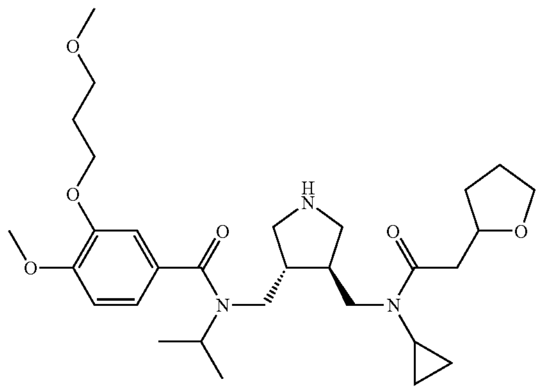 | 546.2 | 3.48[f] |
| 77 | (3S, 4S) | 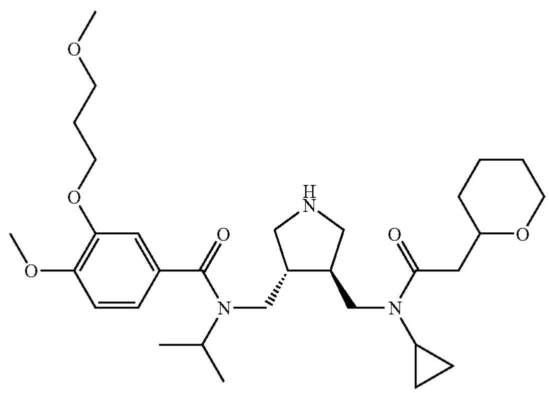 | 560.2 | 3.75[f] |
| 78 | (3S, 4S) | 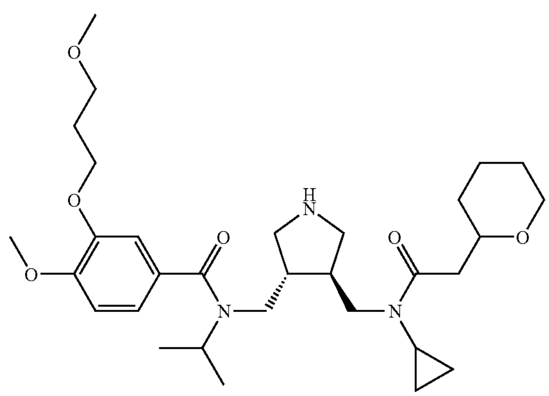 | 560.2 | 3.72[f] |
| 79 | (3S, 4S) | 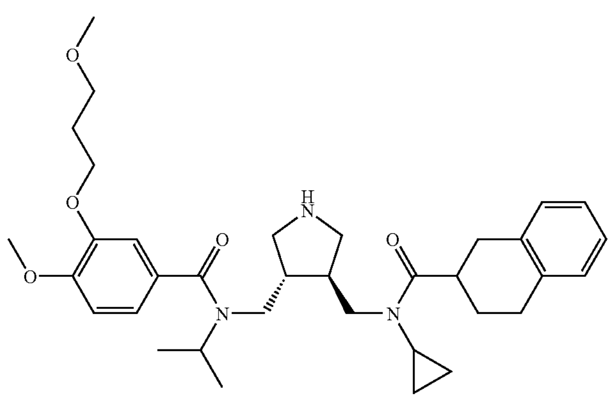 | 592.2 | 4.47[f] |

TABLE 1-continued
| Example | configuration | structure | [M + H]+ | t_R (HPLC) |
|---|---|---|---|---|
| 80 | (3S, 4S) | 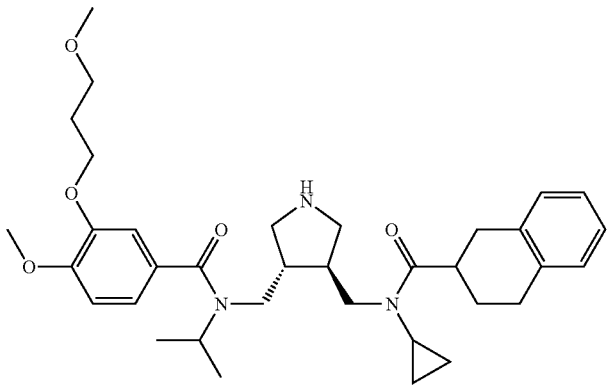 | 592.2 | 4.46[f] |
| 81 | (3S*, 4S*) | 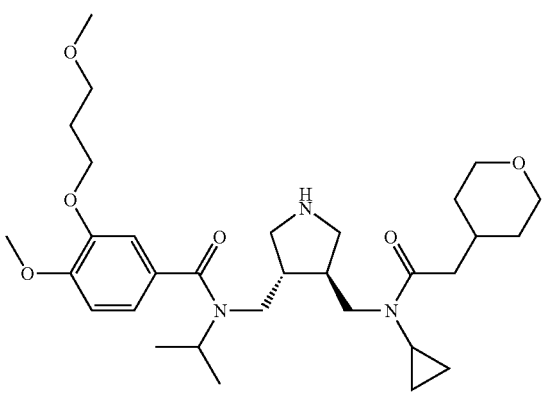 | 560.4 | 4.08[e] |
| 82 | (3S, 4S) | 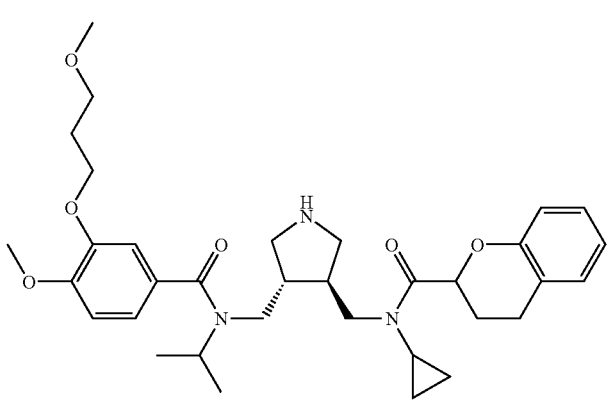 | 594.2 | 4.28[f] |
| 83 | (3S, 4S) | 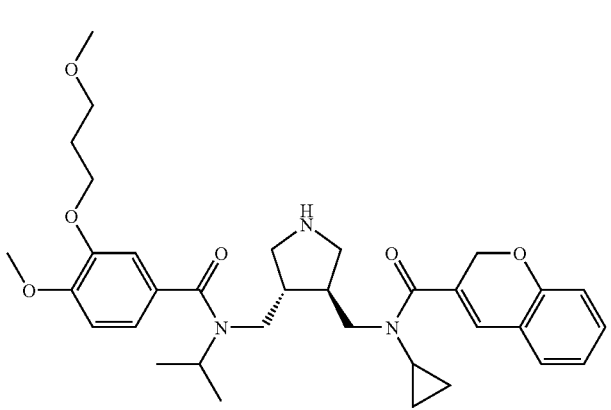 | 592.2 | 4.20[f] |

TABLE 1-continued

| Example | configuration | structure | [M + H]+ | t_R (HPLC) |
|---|---|---|---|---|
| 84 | (3S, 4S) | 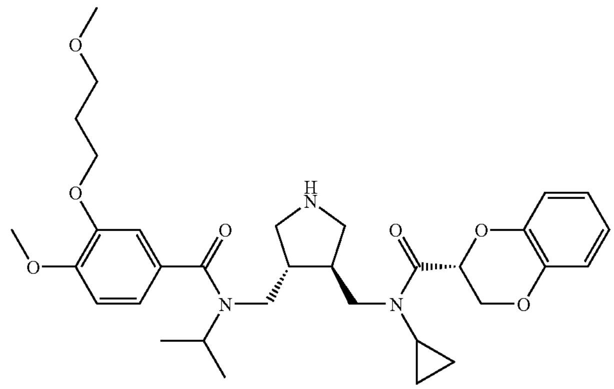 | 596.2 | 4.80[e] |
| 85 | (3S, 4S) | 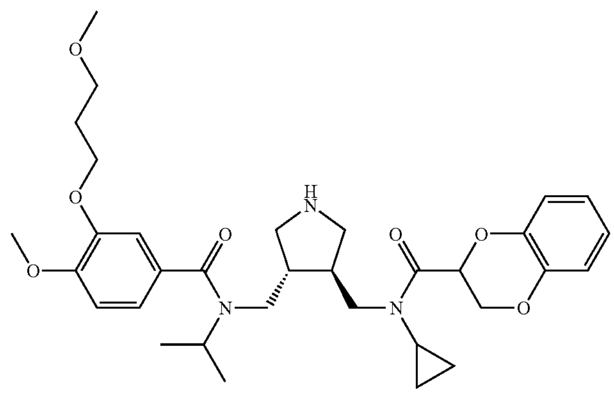 | 596.2 | 4.80[e] |
| 86 | (3S, 4S) | 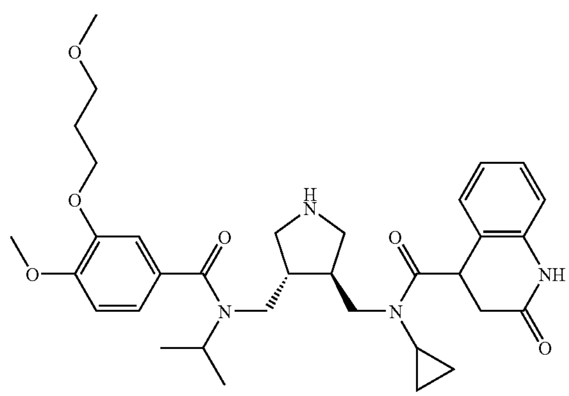 | 607.2 | 3.43[f]/ 3.50[f] |
| 87 | (3S, 4S) | 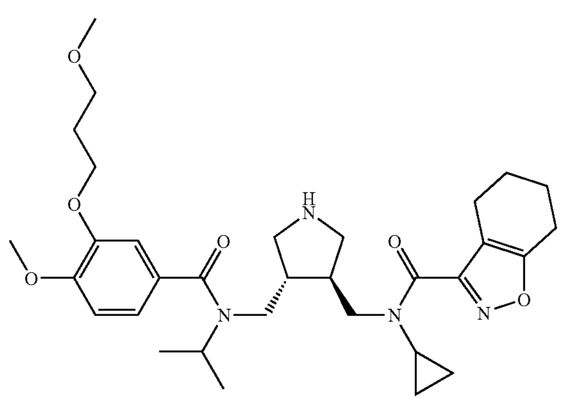 | 583.2 | 4.00[f] |

TABLE 1-continued

| Example | configuration | structure | [M + H]⁺ | $t_R$ (HPLC) |
|---|---|---|---|---|
| 88 | (3S, 4S) | 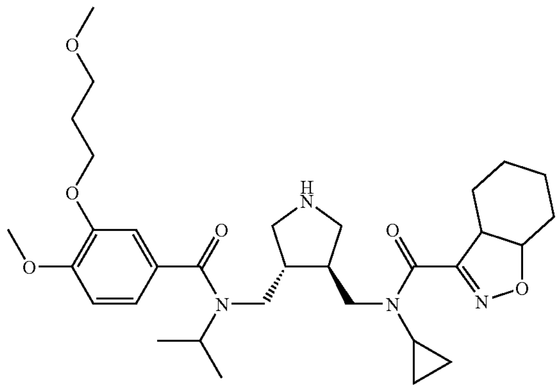 | 585.3 | 4.73[e] |
| 89 | (3S, 4S) | 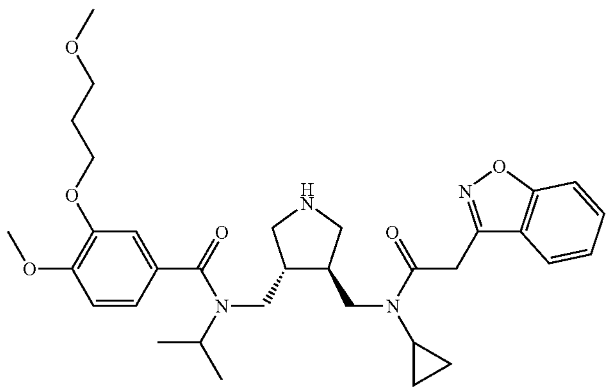 | 593.2 | 4.02[f] |
| 90 | (3S*, 4S*) | 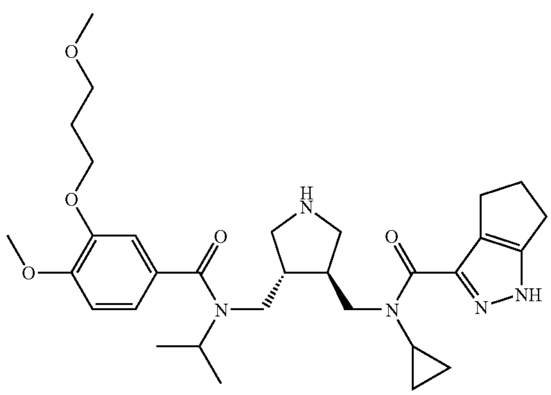 | 568.3 | 4.21[e] |
| 91 | (3S*, 4S*) | 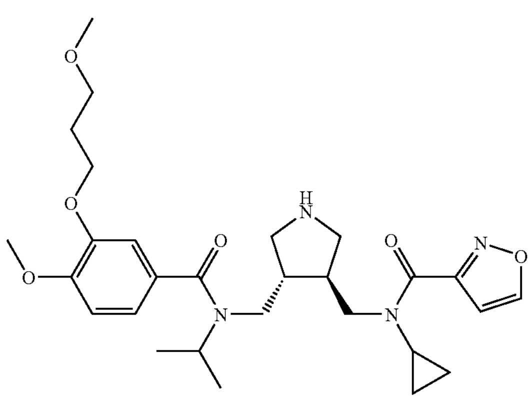 | 529.2 | 3.37[f] |

TABLE 1-continued
| Example | configuration | structure | [M + H]+ | $t_R$ (HPLC) |
|---|---|---|---|---|
| 92 | (3S*, 4S*) | 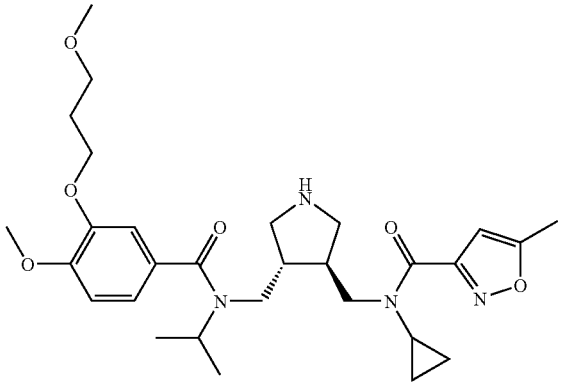 | 543.2 | 4.39[e] |
| 93 | (3S*, 4S*) | 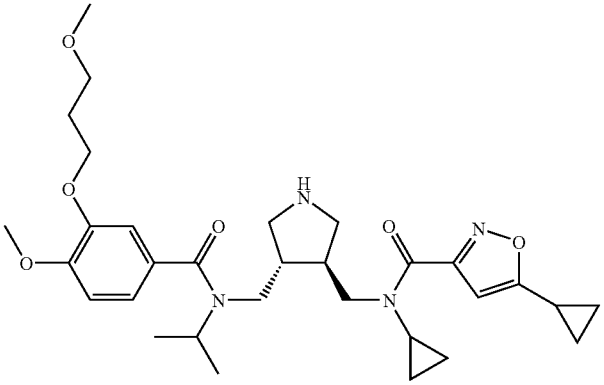 | 569.2 | 3.88[f] |
| 94 | (3S, 4S) | 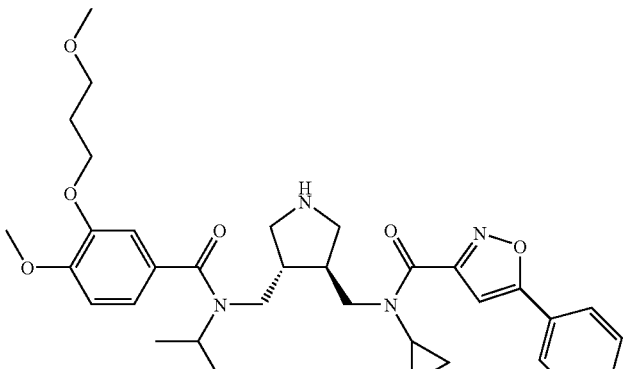 | 605.2 | 4.97[e] |
| 95 | (3S*, 4S*) | 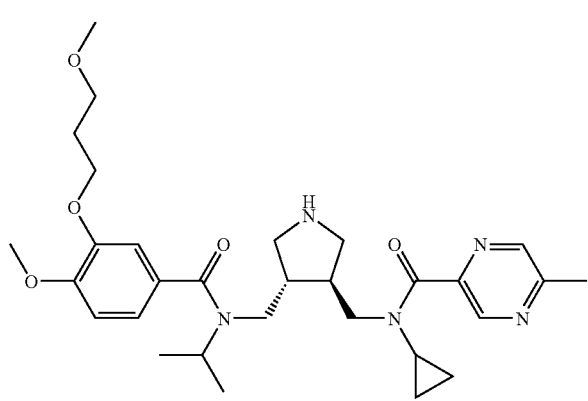 | 554.2 | 4.15[e] |

TABLE 1-continued
| Example | configuration | structure | [M + H]+ | tR (HPLC) |
|---|---|---|---|---|
| 96 | (3S, 4S) | 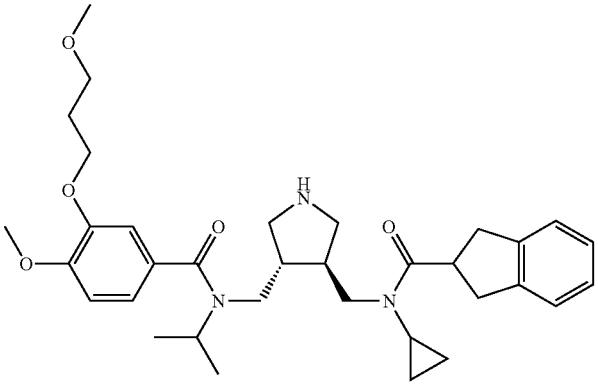 | 578.2 | 4.38f |
| 97 | (3S*, 4S*) | 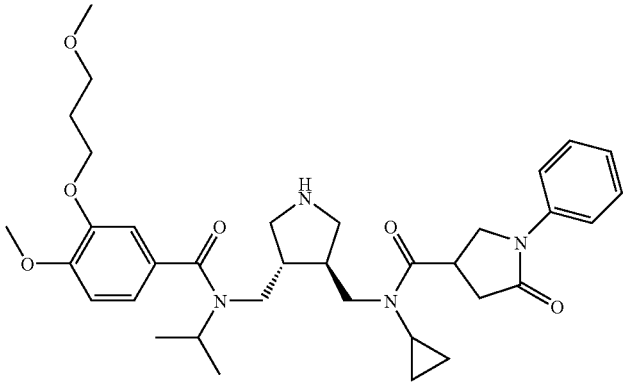 | 621.3 | 4.52e |
| 98 | (3S*, 4S*) | 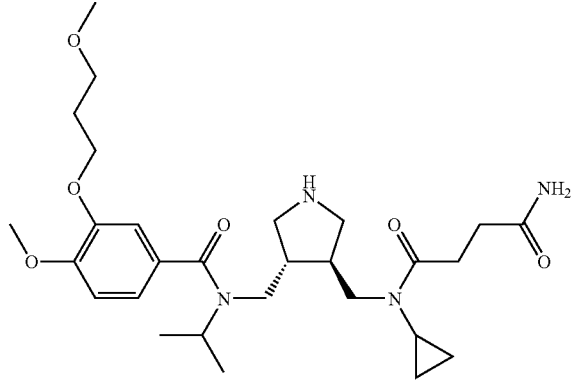 | 533.2 | 2.91f |
| 99 | (3S*, 4S*) | 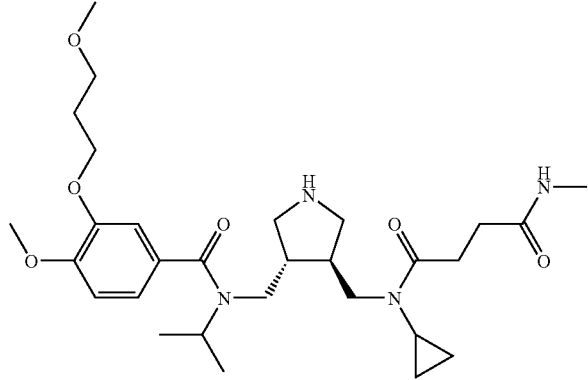 | 547.2 | 3.00f |

TABLE 1-continued

| Example | configuration | structure | [M + H]+ | tR (HPLC) |
|---|---|---|---|---|
| 100 | (3S*, 4S*) | 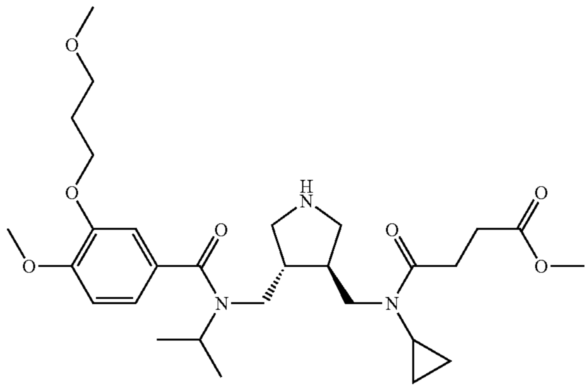 | 548.2 | 3.49[f] |
| 101 | (3S, 4S) | 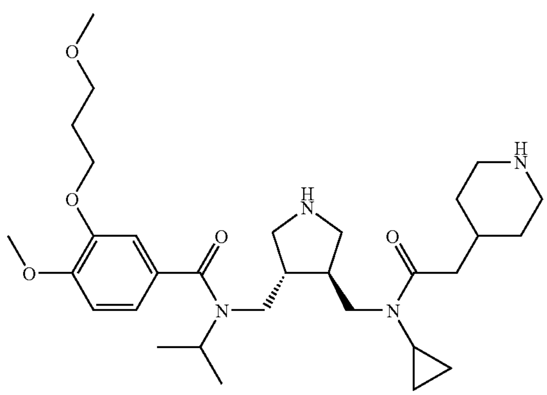 | 559.4 | 3.75[e] |
| 102 | (3S, 4S) | 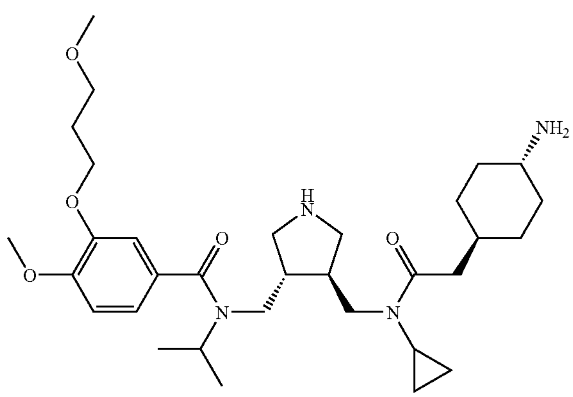 | 573.4 | 3.81[e] |

TABLE 1-continued

| Example | configuration | structure | [M + H]⁺ | $t_R$ (HPLC) |
|---|---|---|---|---|
| 103 | (3S, 4S) | 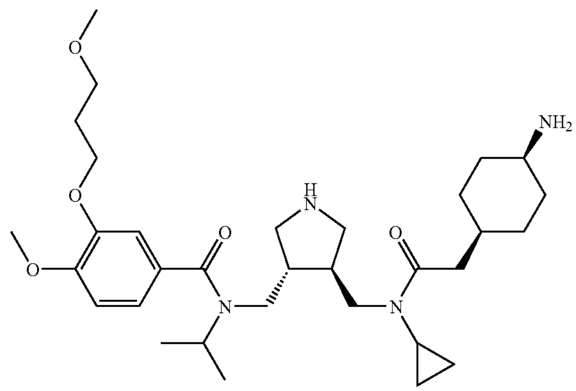 | 573.4 | 3.81[e] |
| 104 | (3S, 4S) | 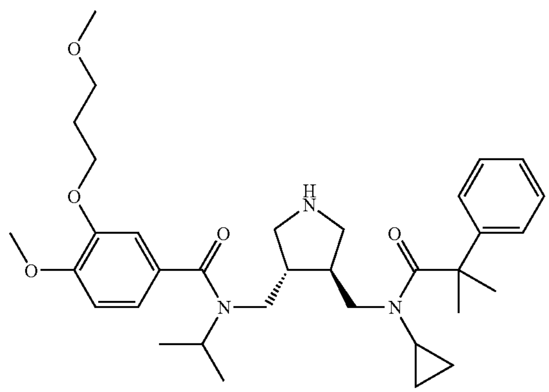 | 580.2 | 4.35[f] |

[a] $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
[b] $t_R$ (Waters Symmetry C18 column, 10-95% CH₃CN/H₂O/3.5 min, 95% CH₃CN/H₂O, 2 min, CH₃CN and H₂O containing 0.1% TFA, flow: 0.6 mL/min).
[c] $t_R$ (Waters Symmetry C18 column, 5-95% CH₃CN/H₂O/3.5 min, 95% CH₃CN/H₂O, 2 min, CH₃CN and H₂O containing 0.1% TFA, flow: 0.6 mL/min).
[d] $t_R$ (Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min).
[e] $t_R$ (HPLC, Nucleosil C18HD column, 5-100% CH₃CN/H₂O/6 min, 100% CH₃CN/2 min, CH₃CN and H₂O containing 0.1% TFA, flow: 1 mL/min).
[f] $t_R$ (HPLC, Nucleosil C18HD column, 20-100% CH₃CN/H₂O/6 min, 100% CH₃CN/2 min, CH₃CN and H₂O containing 0.1% TFA, flow: 1 mL/min).

The starting materials are prepared as follows:

For Examples 73 and 74: (3R,4R)-3-{[Cyclopropyl-cis-(4-methoxy-cyclohexanecarbonyl)-amino]-methyl}-4-({isopropyl-[4-methoxy-3-(3-methoxy-propoxy)-benzoyl]-amino}-methyl)-pyrrolidine-1-carboxylic acid tert-butyl ester and (3R,4R)-3-{[cyclopropyl-trans-(34-methoxy-cyclohexanecarbonyl)-amino]-methyl}-4-({isopropyl-[4-methoxy-3-(3-methoxy-propoxy)-benzyl]-amino}-methyl)-pyrrolidine-1-carboxylic acid tert-butyl ester are separated by chiral HPLC of the diastereoisomeric mixture (0.77 g) on a Chiralpak AD (20 µM; column 50×500 mm) using n-hexane/isopropanol 4:1 as eluent (flow rate: 100 mL/min, UV 210 nm).

For Examples 75 and 76: (3R,4R)-3-{[Cyclopropyl-(2-tetrahydro-furan-2(R)-yl-acetyl)-amino]-methyl}-4-({isopropyl-[4-methoxy-3-(3-methoxy-propoxy)-benzoyl]-amino}-methyl)-pyrrolidine-1-carboxylic acid tert-butyl ester and (3R,4R)-3-{[cyclopropyl-(2-tetrahydro-furan-2(S)-yl-acetyl)-amino]-methyl}-4-({isopropyl-[4-methoxy-3-(3-methoxy-propoxy)-benzoyl]-amino}-methyl)-pyrrolidine-1-carboxylic acid tert-butyl ester are separated by chiral HPLC of the diastereoisomeric mixture (0.34 g) on a Chiralpak AD (20 µM; column 50×500 mm) using n-hexane/EtOH/MeOH 70:25:5 as eluent (flow rate: 100 mL/min, UV 210 nm).

For Examples 77 and 78: (3R,4R)-3-{[Cyclopropyl-(2-tetrahydro-pyran-2(R)-yl-acetyl)-amino]-methyl}-4-({isopropyl-[4-methoxy-3-(3-methoxy-propoxy)-benzoyl]-amino}-methyl)-pyrrolidine-1-carboxylic acid tert-butyl ester and (3R,4R)-3-{[cyclopropyl-(2-tetrahydro-pyran-2(S)-yl-acetyl)-amino]-methyl}-4-({isopropyl-[4-methoxy-3-(3-methoxy-propoxy)-benzoyl]-amino}-methyl)-pyrrolidine-1-carboxylic acid tert-butyl ester are separated by chiral HPLC of the diastereoisomeric mixture (0.32 g) on a Chiralpak AD (20 µM; column 50×500 mm) using a gradient n-hexane/EtOH 90:10 to 85:15 (after 30 min) as eluent (flow rate: 120 mL/min, UV 210 nm).

For Examples 79 and 80: (3R,4R)-3-{[Cyclopropyl-(1,2,3,4-tetrahydro-naphthalene-2(R)-carbonyl)-amino]-methyl}-4-({isopropyl-[4-methoxy-3-(3-methoxy-propoxy)-benzoyl]-amino}-methyl)-pyrrolidine-1-carboxylic acid tert-butyl ester and (3R,4R)-3-{[cyclopropyl-(1,2,3,4-tetrhydro-naphthalene-2(S)-carbonyl)-amino]-methyl}-4-({isopropyl-[4-methoxy-3-(3-methoxy-propoxy)-benzoyl]-amino}-methyl)-pyrrolidine-1-carboxylic acid tert-butyl ester are separated by chiral HPLC of the diastereoisomeric mixture (0.42 g) on a Chiralpak AD (20 µM; column 50×500 mm) using n-hexane/EtOH 4:1 as eluent (flow rate: 50 mL/min, UV 210 nm).

The following Examples are prepared according to the procedures described above in Examples 8, 9, 10, 11, 12 and 13:

TABLE 2

| Example | configuration | structure | [M + H]+ | $t_R$ (HPLC) |
|---|---|---|---|---|
| 105 | (3S, 4S) | 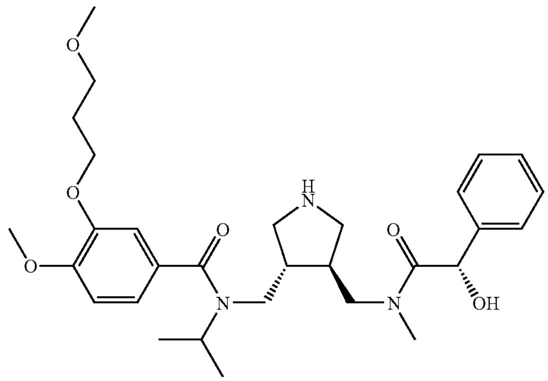 | 542.2 | 4.29[a] |
| 106 | (3S, 4S) | 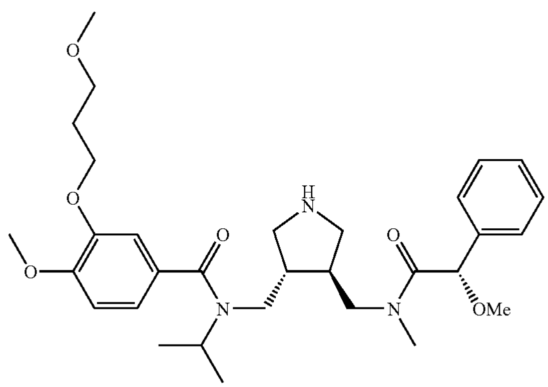 | 556.3 | 4.43[a] |
| 107 | (3S, 4S) | 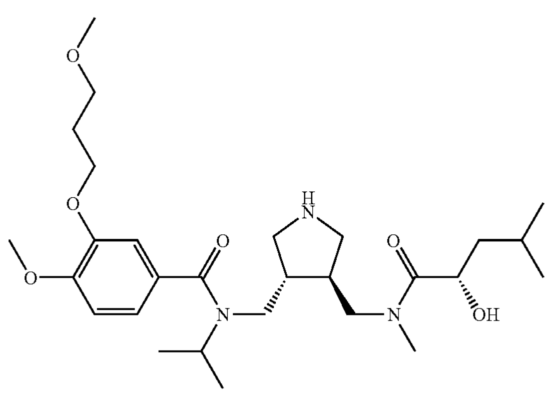 | 522.2 | 3.48[d] |

TABLE 2-continued

| Example | configuration | structure | [M + H]+ | t_R (HPLC) |
|---|---|---|---|---|
| 108 | (3S, 4S) | 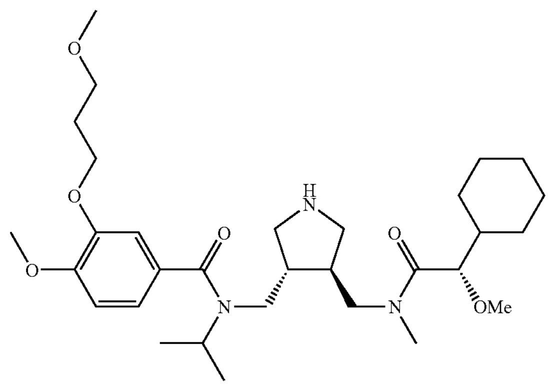 | 562.3 | 2.83[c] |
| 109 | (3S, 4S) | 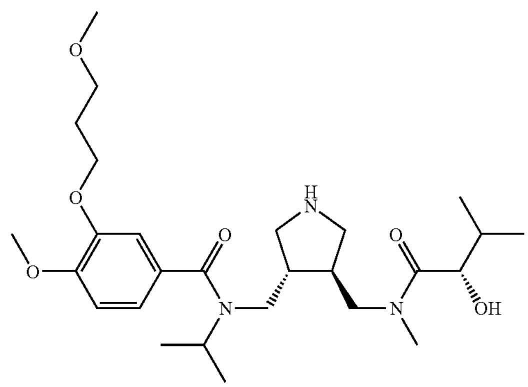 | 508.3 | 2.59[c] |
| 110 | (3S, 4S) | 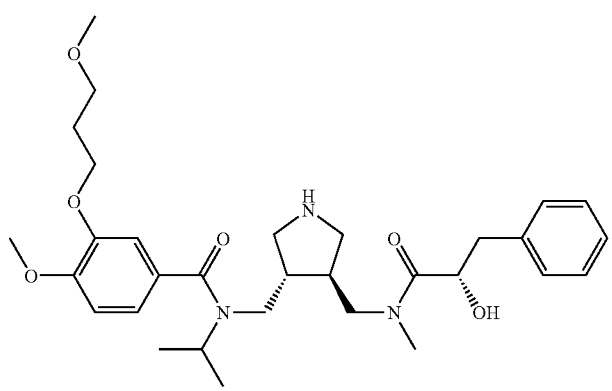 | 556.3 | 2.17 minb[c] |
| 111 | (3S, 4S) | 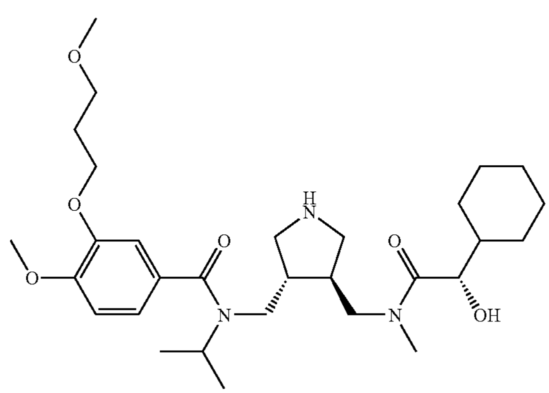 | 548.3 | 2.79[c] |

TABLE 2-continued

| Example | configuration | structure | [M + H]⁺ | t_R (HPLC) |
|---|---|---|---|---|
| 112 | (3S, 4S) | 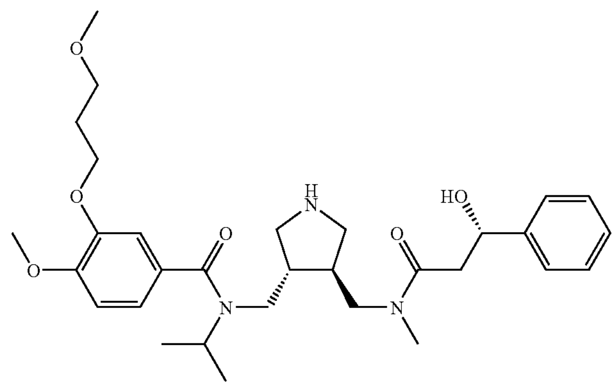 | 556.3 | 1.98[b] |
| 113 | (3S, 4S) | 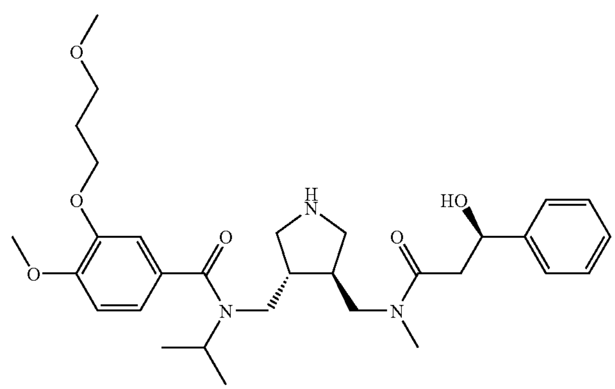 | 556.3 | 1.77[b] |
| 114 | (3S, 4S) | 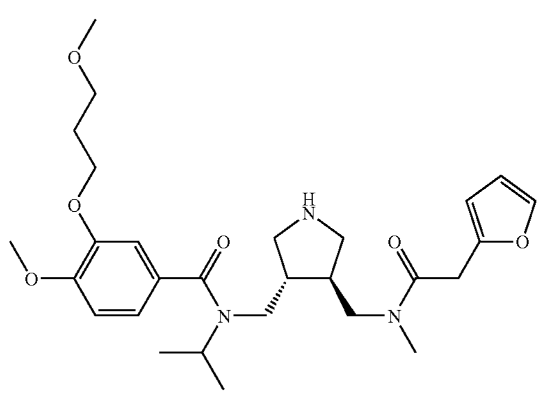 | 516.3 | 2.60[c] |
| 115 | (3S, 4S) | 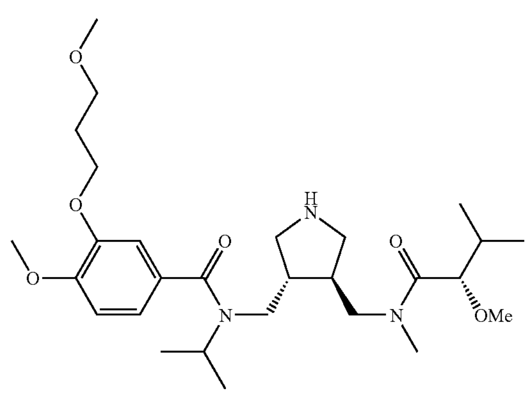 | 522.3 | 1.75[b] |

TABLE 2-continued

| Example | configuration | structure | [M + H]+ | t$_R$ (HPLC) |
|---|---|---|---|---|
| 116 | (3S, 4S) | 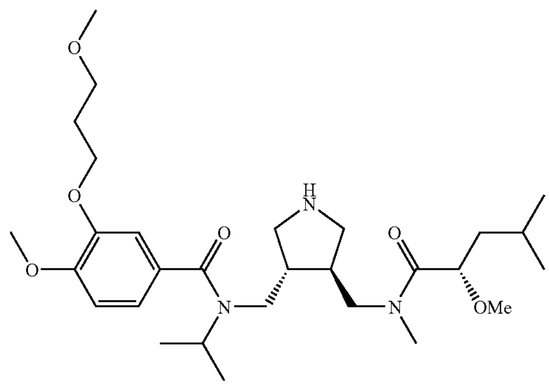 | 536.3 | 2.39[b] |
| 117 | (3S*, 4S*) | 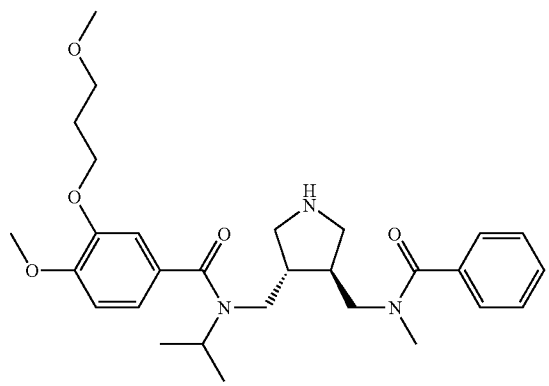 | 512.2 | 4.09[e] |
| 118 | (3S, 4S) | 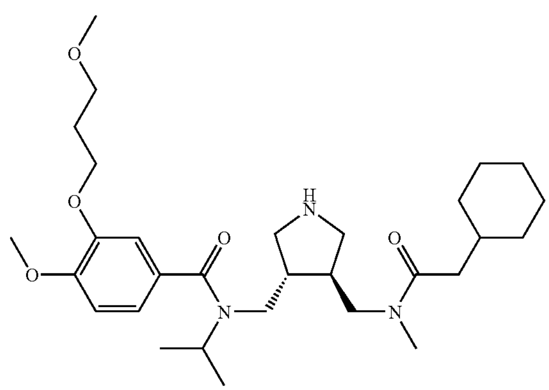 | 532.4 | 4.86[e] |
| 119 | (3S*, 4S*) | 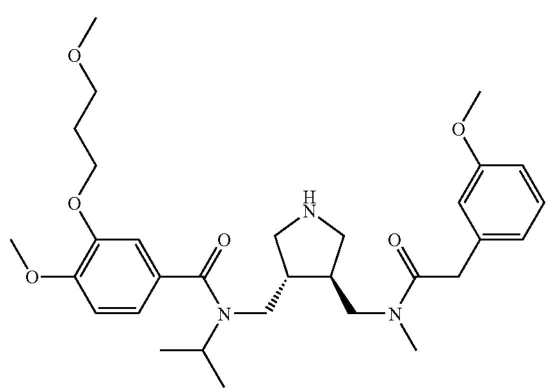 | 556.3 | 4.29[e] |

TABLE 2-continued

| Example | configuration | structure | [M + H]+ | t_R (HPLC) |
|---|---|---|---|---|
| 120 | (3S, 4S) | 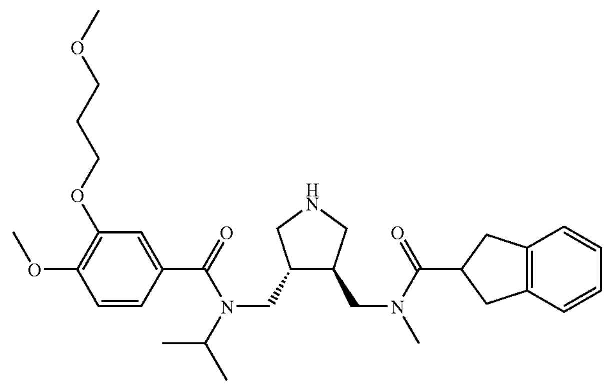 | 552.2 | 4.04[f] |
| 121 | (3S, 4S) | 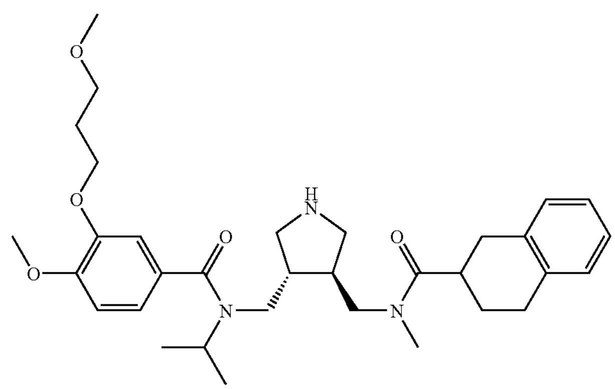 | 566.2 | 4.16[f] |
| 122 | (3S, 4S) | 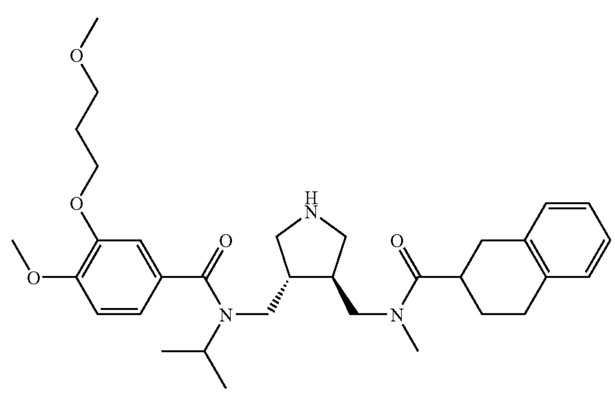 | 566.2 | 4.17[f] |
| 123 | (3S*, 4S*) | 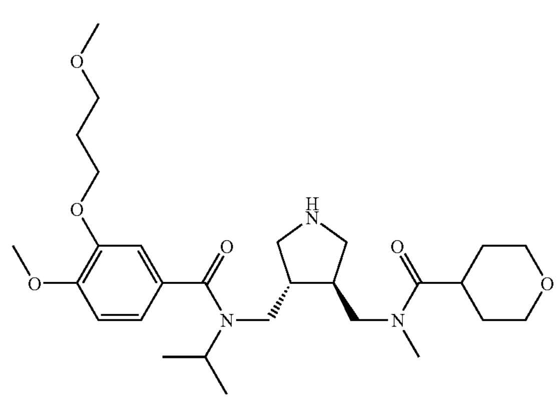 | 520.3 | 3.74[e] |

TABLE 2-continued
| Example | configuration | structure | [M + H]⁺ | t_R (HPLC) |
|---|---|---|---|---|
| 124 | (3S, 4S) | 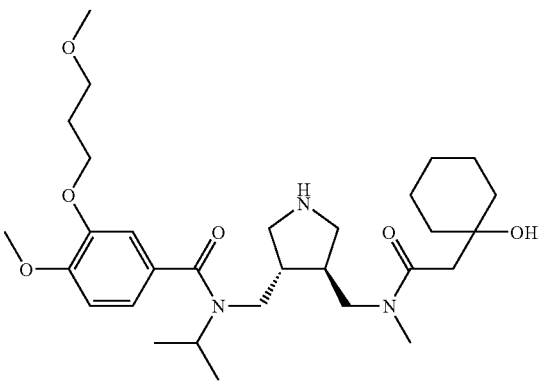 | 548.2 | 3.63ᶠ |
| 125 | (3S, 4S) | 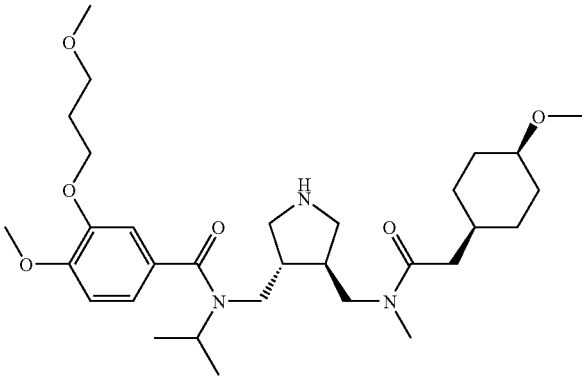 | 562.3 | 3.55ᶠ |
| 126 | (3S, 4S) | 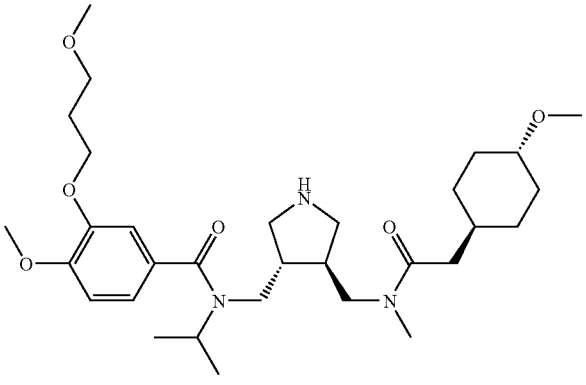 | 562.2 | 3.47ᶠ |
| 127 | (3S, 4S) | 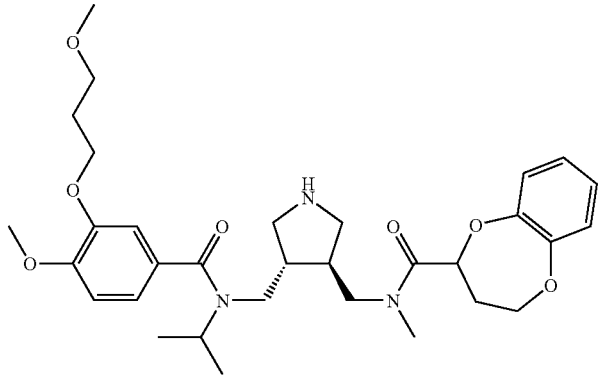 | 584.3 | 5.11ᶠ |

TABLE 2-continued

| Example | configuration | structure | [M + H]⁺ | t_R (HPLC) |
|---|---|---|---|---|
| 128 | (3S, 4S) | | 548.2 | 3.25^f |
| 129 | | | | 3.41^f |

<sup>a</sup>t_R (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
<sup>b</sup>t_R (Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min).
<sup>c</sup>t_R (Waters Symmetry C18 column, 5-95% CH₃CN/H₂O/3.5 min, 95% CH₃CN/H₂O, 2 min, CH₃CN and H₂O containing 0.1% TFA, flow: 0.6 mL/min).
<sup>d</sup>t_R (Nucleosil C18 HD column, 20-95% CH₃CN/H₂O/3.5 min, 95% CH₃CN/H₂O, 2 min, CH₃CN and H₂O containing 0.1% TFA, flow: 0.6 mL/min).
<sup>e</sup>t_R (HPLC, Nucleosil C18HD column, 5-100% CH₃CN/H₂O/6 min, 100% CH₃CN/2 min, CH₃CN and H₂O containing 0.1% TFA, flow: 1 mL/min).
<sup>f</sup>t_R (HPLC, Nucleosil C18HD column, 20-100% CH₃CN/H₂O/6 min, 100% CH₃CN/2 min, CH₃CN and H₂O containing 0.1% TFA, flow: 1 mL/min).

The starting materials are prepared as follows:

For Examples 121 and 122: (3R,4R)-3-({Isopropyl-[4-methoxy-3-(3-methoxy-propoxy)-benzoyl]-amino}-methyl)-4-{[methyl-(1,2,3,4-tetrahydro-naphthalene-2(R)-carbonyl)-amino]-methyl}-pyrrolidine-1-carboxylic acid tert-butyl ester and (3R,4R)-3-({isopropyl-[4-methoxy-3-(3-methoxy-propoxy)-benzoyl]-amino}-methyl)-4-{[methyl-(1,2,3,4-tetrahydro-naphthalene-2(S)-carbonyl)-amino]-methyl}-pyrrolidine-1-carboxylic acid tert-butyl ester are separated by chiral HPLC of the diastereoisomeric mixture (0.32 g) on a Chiralpak AD (20 μM, column 50×500 mm) using n-hexane/EtOH 1:1 as eluent (flow rate: 50 mL/min, UV 210 nm).

For Examples 128 and 129: (3R,4R)-3-({Isopropyl-[4-methoxy-3-(3-methoxy-propoxy)-benzoyl]-amino}-methyl)-4-{[cis-(4-methoxy-cyclohexanecarbonyl)-methyl-amino-]-methyl}-pyrrolidine-1-carboxylic acid tert-butyl ester and (3R,4R)-3-({isopropyl-[4-methoxy-3-(3-methoxy-propoxy)-benzoyl]-amino}-methyl)-4-{[trans-(4-methoxy-cyclohexanecarbonyl)-methyl-amino]-methyl}-pyrrolidine-1-carboxylic acid tert-butyl ester are separated by chiral HPLC of the diastereoisomeric mixture (0.32 g) on a Chiralpak AD (20 μM, column 50×500 mm) using n-hexane/EtOH 1:1 as eluent (flow rate: 50 mL/min, UV 210 nm).

The following intermediates are prepared accordingly:

3-Acetylamino-3-methyl-butyric acid

Triethylamine (1.8 mL, 12.8 mmol), acetic anhydride (1.2 mL, 12.8 mL) and DMAP (10 mg, 0.09 mmol) are subsequentially added to a suspension of 3-amino-3-methyl-butyric acid (1.00 g, 8.5 mmol) in THF (100 mL). After heating at 60° C. for 3 h AcOEt is added and the organic phase is washed with 1N HCl. Drying (Na₂SO₄), filtration and evaporation of the solvent yields the desired product. MS (LC-MS): [M+H]⁺= 160.1. t_R (HPLC, Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min): 0.40 min.

(1-Acetylamino-cyclopentyl)-acetic acid

Triethylamine (1.2 mL, 8.4 mmol), acetic anhydride (0.8 mL, 8.4 mL) and DMAP (10 mg, 0.09 mmol) are subsequentially added to a suspension of (1-amino-cyclopentyl)-acetic acid (1.00 g, 5.6 mmol) in THF (30 mL). After heating at 60° C. for 2 h AcOEt is added and the organic phase is washed with 1N HCl. Drying (Na₂SO₄), filtration and evaporation of the solvent yields the desired product. MS (LC-MS): [M+H]⁺= 186.1. t_R (HPLC, Waters Symmetry C18 column, 80-95% CH₃CN/H₂O/3.5 min, 95% CH₃CN/H₂O, 2 min, CH₃CN and H₂O containing 0.1% TFA, flow: 0.6 mL/min): 0.53 min.

(1-Acetylamino-cyclohexyl)-acetic acid

The title compound is prepared analogously as described for (1-acetylamino-cyclopentyl)-acetic acid from (1-amino-cyclohexyl)-acetic acid. MS (LC-MS): [M+H]⁺=200.1. (HPLC, Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min): 0.81 min.

(1-Isobutyrylamino-cyclopentyl)-acetic acid

The title compound is prepared analogously as described for (1-acetylamino-cyclopentyl)-acetic acid from (1-amino-cyclopentyl)-acetic acid. MS (LC-MS): [M+H]⁺=214.2. t_R (HPLC, Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min): 3.08 min.

(S)-3-Acetylamino-3-phenyl-propionic acid

The title compound is prepared analogously as described for (1-acetylamino-cyclopentyl)-acetic acid from (S)-3- amino-3-phenylpropionic acid. MS (LC-MS): [M+H]+=208.2. $t_R$ (HPLC, -Waters Symmetry C18 column, 10-95% CH$_3$CN/H$_2$O/3.5 min, 95% CH$_3$CNlH$_2$O, 2 min, CH$_3$CN and H$_2$O containing 0.1% TFA, flow: 0.6 mL/min): 0.79 min.

(R)-3-Acetylamino-3-phenyl-propionic acid

The title compound is prepared analogously as described for (1-acetylamino-cyclopentyl)-acetic acid from (R)-3-amino-3-phenylpropionic acid. MS (LC-MS): [M+H]+=208.2. $t_R$ (HPLC, Waters Symmetry C18 column, 10-95% CH$_3$CN/H$_2$O/3.5 min, 95% CH$_3$CN/H$_2$O, 2 min, CH$_3$CN and H$_2$O containing 0.1% TFA, flow: 0.6 mL/min): 1.16 min.

Scheme 6

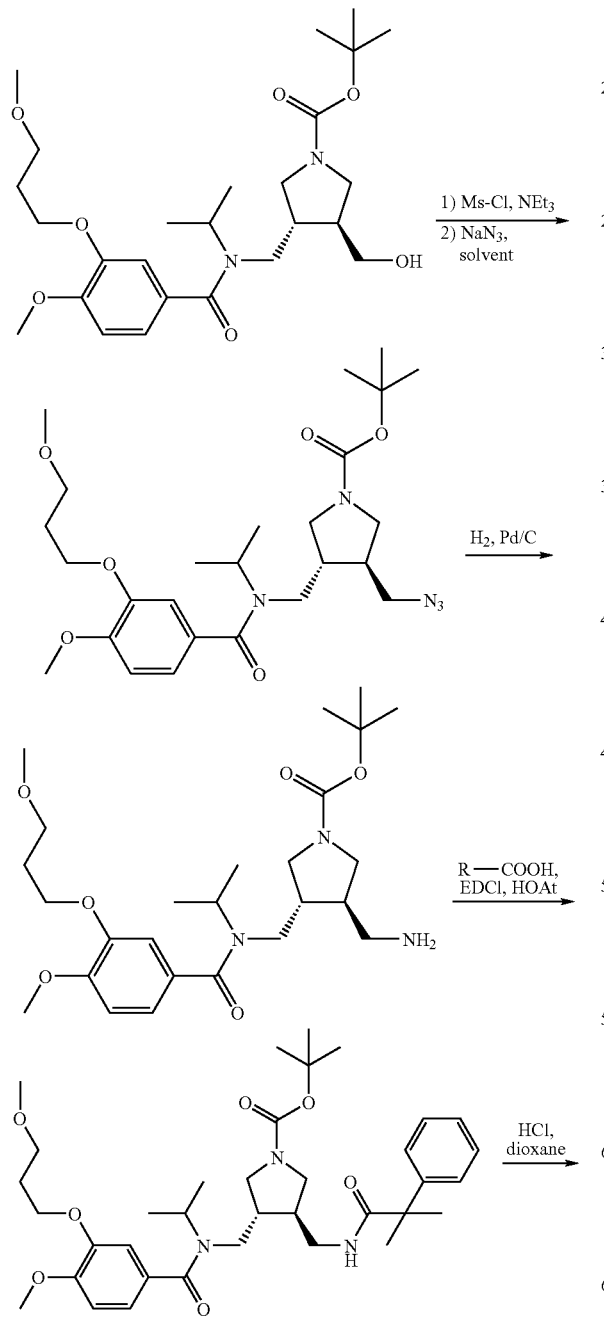

-continued

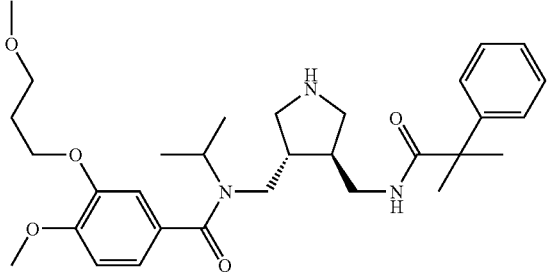

EXAMPLE 130

N-Isopropyl-4-methoxy-3-(3-methoxy-propoxy)-N-{(3S,4S)-4-[(2-methyl-2-phenyl-propionylamino)-methyl]-pyrrolidin-3-ylmethyl}-benzamide

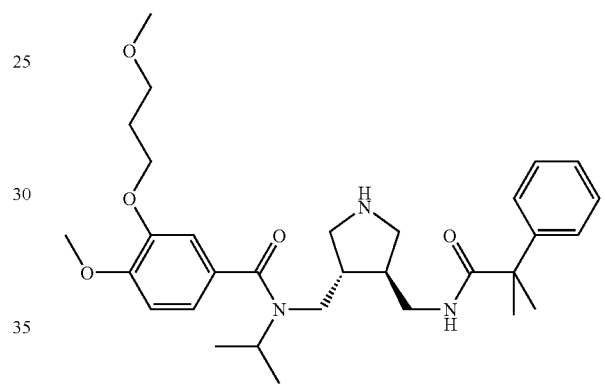

The title compound is prepared according to Scheme 6 as follows: The solution of (3R,4R)-3-({isopropyl-[4-methoxy-3-(3-methoxy-propoxy)-benzoyl]-amino}-methyl)-4-[(2-methyl-2-phenyl-propionylamino)-methyl]-pyrrolidine-1-carboxylic acid tert-butyl ester (227 mg, 0.319 mmol) in 4N HCl in dioxane (2 mL) is stirred for 6 hrs at room temperature. The volatiles are removed by freeze-drying to give the title compound as white solid. MS [M+H]+=540.2. $t_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 3.91 min.

The starting material is prepared as follows:

A. (3R,4S)-3-({Isopropyl-[4-methoxy-3-(3-methoxy-propoxy)-benzoyl]-amino}-methyl)-4-methanesulfonyloxymethyl-pyrrolidine-1-carboxylic acid tert-butyl ester To a solution of (3S,4R)-3-hydroxymethyl-4-({isopropyl-[4-methoxy-3-(3-methoxy-propoxy)-benzoyl]-amino}-methyl)-pyrrolidine-1-carboxylic acid tert-butyl ester (2.32 g, 4.69 mmol; Example 10, reaction step H) is subsequently added at −20° C. with stirring NEt$_3$ (1.95 mL, 14.1 mmol) and in a dropwise fashion methane sulfonylchloride (0.423 mL, 5.39 mmol). Stirring is continued for 20 min at −20° C., the mixture is then diluted with CH$_2$Cl$_2$ and the organic layer is washed with 2N HCl, dried (Na$_2$SO$_4$) and evaporated to dryness to give the crude title compound as yellowish oil. TLC, $R_f$(hexane/AcOEt 1:3)=0.13.

B. (3S,4R)-3-Azidomethyl-4-({isopropyl-[4-methoxy-3-(3-methoxy-propoxy)-benzoyl]-amino}-methyl)-pyrrolidine-1-carboxylic acid tert-butyl ester To a solution of (3R,4S)-3-({isopropyl-[4-methoxy-3-(3-methoxy-propoxy)-benzoyl]-amino}-methyl)-4-methanesulfonyloxymethyl-pyrrolidine-1-carboxylic acid tert-butyl ester (2.7 g, 4.71 mmol) in DMF (20 mL) is added in one portion $NaN_3$ (774 mg, 11.8 mmol) and the mixture is stirred at 70° C. overnight. After cooling to room temperature, a saturated aqueous $NaHCO_3$ solution is added, followed by extraction with diethyl ether. The combined organics are washed with brine, dried over $Na_2SO_4$ and concentrated. The crude product is purified by RP-HPLC on a $PrepC_{18}$ OBD column (dimensions: 30×100 mm; 5 µM particle size, Sun-Fire Ltd) and using a 95-5% gradient of $MeCN/H_2O$ 5:95 (containing 0.1% TFA) to $MeCN/H_2O$ 95:5 (containing 0.1% TFA) over 20 min gives the title compound as colorless oil. TLC, $R_f$ (hexane/AcOEt 1:3)=0.31. MS: 520.2 $[M+H]^+$. $t_R$ (HPLC, Nucleosil C18HD column, 20-100% $CH_3CN/H_2O/6$ min, 100% $CH_3CN/2$ min, $CH_3CN$ and $H_2O$ containing 0.1% TFA, flow: 1 mL/min): 5.04 min.

C. (3R,4R)-3-Aminomethyl-4-({isopropyl-[4-methoxy-3-(3-methoxy-propoxy)-benzoyl]-amino}-methyl)-pyrrolidine-1-carboxylic acid tert-butyl ester A solution of (3S,4R)-3-azidomethyl-4-({isopropyl-[4-methoxy-3-(3-methoxy-propoxy)-benzoyl]-amino}-methyl)-pyrrolidine-1-carboxylic acid tert-butyl ester (1.86 g, 3.58 mmol) in MeOH (40 mL) is hydrogenated overnight in the presence of Pd/C 10% (0.6 g; Engelhard 4505) at room temperature under atmospheric pressure to give, after filtration and drying in vacuo, the title compound as colorless oil. MS: 494.2 $[M+H]^+$. $t_R$ (HPLC, Nucleosil C18HD column, 20-100% $CH_3CN/H_2O/6$ min, 100% $CH_3CN/2$ min, $CH_3CN$ and $H_2O$ containing 0.1% TFA, flow: 1 mL/min): 3.73 min.

D. (3R,4R)-3-({Isopropyl-[4-methoxy-3-(3-methoxy-propoxy)-benzoyl]-amino}-methyl)-4-[(2-methyl-2-phenyl-propionylamino)-methyl]-pyrrolidine-1-carboxylic acid tert-butyl ester To a solution of (3R,4R)-3-aminomethyl-4-({isopropyl-[4-methoxy-3-(3-methoxy-propoxy)-benzoyl]-amino}-methyl)-pyrrolidine-1-carboxylic acid tert-butyl ester (200 mg, 0.405 mmol) and α,α-dimethylphenylacetic acid (101 mg, 0.608 mmol) in $CH_2Cl_2$ (3 mL) is subsequently added $Et_3N$ (0.085 mL, 0.608 mmol), 1-hydroxy-7-azabenzotriazole (84 mg, 0.608 mmol; commercially available from ABCR, AV24631) and N-(3-dimethylaminopropyl)-N'-ethyl-carbodiimide HCl (118 mg, 0.608 mmol). Stirring is continued overnight at room temperature, the mixture is then diluted with $CH_2Cl_2$, and the organic layer is subsequently washed with 2N HCl, saturated aqueous $NaHCO_3$ and brine, dried ($MgSO_4$) and concentrated. Purification by RP-HPLC on a $PrepC_{18}$ OBD column (dimensions: 30×100 mm; 5 µM particle size, SunFire Ltd) and using a 95-5% gradient of MeCN/$H_2O$ 5:95 (containing 0.1% TFA) to MeCN/$H_2O$ 95:5 (containing 0.1% TFA) over 20 min gives the title compound as colorless oil. MS $[M]^+$=640.2. $t_R$ (HPLC, Nucleosil C18HD column, 20-100% $CH_3CN/H_2O/6$ min, 100% $CH_3CN/2$ min, $CH_3CN$ and $H_2O$ containing 0.1% TFA, flow: 1 mL/min): 5.2 min.

In a similar manner as described in Example 9 for the reaction step J, the following starting materials are prepared, which are used for the preparation of the Examples 137-148 listed in Table 3:

N-((3S*,4R*)-4-Ethylaminomethyl-pyrrolidin-3-ylmethyl)-N-isopropyl4-methoxy-3-(3-methoxy-propoxy)-benzamide: The title compound is prepared from (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester (0.75 g, 1.52 mmol), 2N solution of ethylamine in MeOH (3.805 mL, 7.61 mmol) and $NaBH_4$ (0.115 g, 3.04 mmol) and purification by flash chromatography on silica gel ($CH_2Cl_2$/MeOH 96:4, then $CH_2Cl_2$/MeOH (10% $NH_3$ conc.) gradient from 9:1 to 8:2) to give a colorless oil. MS: 522.4 $[M+H]^+$. $t_R$ (HPLC, Nucleosil C18HD column, 5-100% $CH_3CN/H_2O/6$ min, 100% $CH_3CN/2$ min, $CH_3CN$ and $H_2O$ containing 0.1% TFA, flow: 1 mL/min): 4.47 min.

The corresponding enantiomer N-((3S,4R)-4-Ethylaminomethyl-pyrrolidin-3-ylmethyl)-N-isopropyl-4-methoxy-3-(3-methoxy-propoxy)-benzamide is obtained as follows: A solution of (3S,4R)-3-formyl-4-({isopropyl-[4-methoxy-3-(3-methoxy-propoxy)-benzoyl]-amino}-methyl)-pyrrolidine-1-carboxylic acid tert-butyl ester (1.27 g, 2.58 mmol) and gaseous ethylamine (0.704 g, 15.5 mmol; Fluka 02940) in 1,2-dichloroethane (10 mL) is stirred at room temperature for 30 min, then sodium triacetoxyborohydride (1.37 g, 6.45 mmol) is added in one portion and the mixture is stirred overnight. The organic phase is washed with saturated aqueous $NaHCO_3$ solution, the water layers are re-extracted with $CH_2Cl_2$, and the combined organics are dried ($Na_2SO_4$) and evaporated to dryness to give the title compound. MS: 522.2 $[M+H]^+$.

N-((3S*,4S*)-4-Cyclobutylaminomethyl-pyrrolidin-3-ylmethyl)-N-isopropyl-4-methoxy-3-(3-methoxy-propoxy)-benzamide: from (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester (1.00 g, 2.03 mmol), cyclobutylamine (0.74 g, 10.2 mmol) and $NaBH_4$ (0.154 g, 4.06 mmol) to give the title compound as oil. TLC, $R_f$ (hexane/AcOEt )=0.31. MS: 548.3 $[M+H]^+$. $t_R$ (HPLC, Nucleosil C18HD column, 20-100% $CH_3CN/H_2O/6$ min, 100% $CH_3CN/2$ min, $CH_3CN$ and $H_2O$ containing 0.1% TFA, flow: 1 mL/min): 4.28 min.

N-Isopropyl-N-[(3S*,4S*)-4-(isopropylamino-methyl)-pyrrolidin-3-ylmethyl]-4-methoxy-3-(3-methoxy-propoxy)-benzamide: from (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester (0.75 g, 1.52 mmol), isopropylamine (0.654 mL, 7.61 mmol) and $NaBH_4$ (0.115 g, 3.04 mmol) and purification by flash chromatography on silica gel ($CH_2Cl_2$/MeOH 96:4, then $CH_2Cl_2$/MeOH (10% $NH_3$ conc.) gradient from 9:1 to 8:2) to give the title compound as colorless oil. MS: 536.4 $[M+H]^+$. $t_R$ (HPLC, Nucleosil C18HD column, 5-100% $CH_3CN/H_2O/6$ min, 100% $CH_3CN/2$ min, $CH_3CN$ and $H_2O$ containing 0.1% TFA, flow: 1 mL/min): 4.58 min.

N-[(3S*,4R*)-4-(Isobutylamino-methyl)-pyrrolidin-3-ylmethyl]-N-isopropyl-4-methoxy-3-(3-methoxy-propoxy)-benzamide: from (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester (0.75 g, 1.52 mmol), isobutylamine (0.756 mL, 7.61 mmol) and $NaBH_4$ (0.115 g, 3.04 mmol) and purification by flash chromatography on silica gel ($CH_2Cl_2$/MeOH 96:4, then $CH_2Cl_2$/MeOH (10% $NH_3$ conc.) gradient from 9:1 to 8:2) to give the title compound as colorless oil. MS: 550.4 $[M+H]^+$. $t_R$ (HPLC, Nucleosil C18HD column, 5-100% $CH_3CN/H_2O/6$ min, 100% $CH_3CN/2$ min, $CH_3CN$ and $H_2O$ containing 0.1% TFA, flow: 1 mL/min): 4.74 min.

N-{(3S*,4R*)-4-[(Cyclopropylmethyl-amino)-methyl]-pyrrolidin-3-ylmethyl}-N-isopropyl-4-methoxy-3-(3-methoxy-propoxy)-benzamide: from (3S*,4R*)-3-formyl-4-({isopropyl-[4-methoxy-3-(3-methoxy-propoxy)-benzoyl]-amino}-methyl)-pyrrolidine-1-carboxylic acid tert-butyl ester (0.75 g, 1.52 mmol), cyclopropanemethylamine (0.652 mL, 7.61 mmol) and NaBH$_4$ (0.115 g, 3.04 mmol) and purification by flash chromatography on silica gel (CH$_2$Cl$_2$/MeOH 96:4, then CH$_2$Cl$_2$/MeOH (10% NH$_3$ conc.) gradient from 9:1 to 8:2) to give the title compound as colorless oil. MS: 548.4 [M+H]$^+$. t$_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 4.66 min.

The title compounds in Table 3 are prepared accordingly from the starting materials described above:

TABLE 3

| Example | configuration | structure | [M + H]$^+$ | t$_R$ (HPLC) |
|---------|---------------|-----------|-------------|--------------|
| 131 | (3S, 4S) | 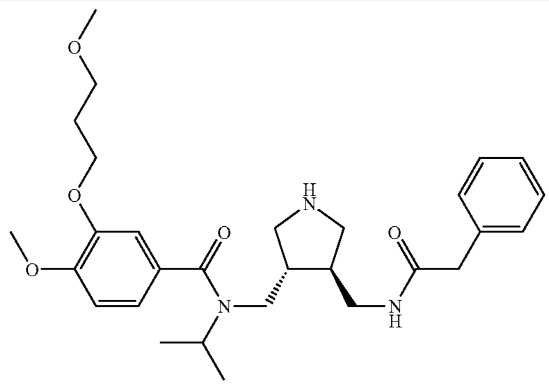 | 512.2 | 3.47$^b$ |
| 132 | (3S, 4S) | 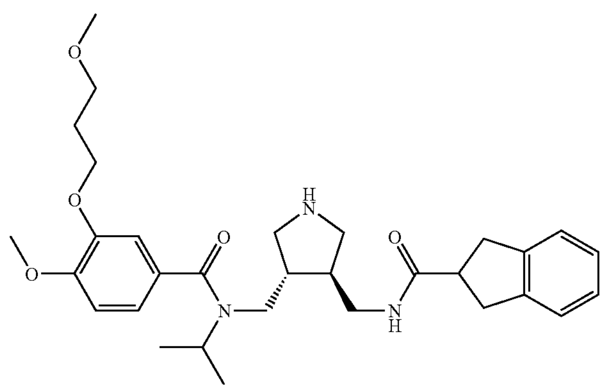 | 538.2 | 3.83$^b$ |
| 133 | (3S, 4S) | 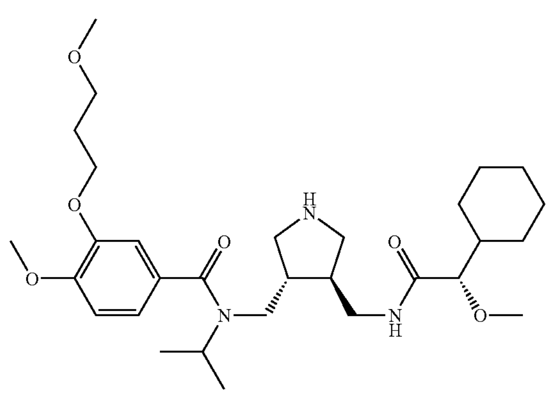 | 548.2 | 4.00$^b$ |

TABLE 3-continued

| Example | configuration | structure | [M + H]+ | $t_R$ (HPLC) |
|---|---|---|---|---|
| 134 | (3S, 4S) | 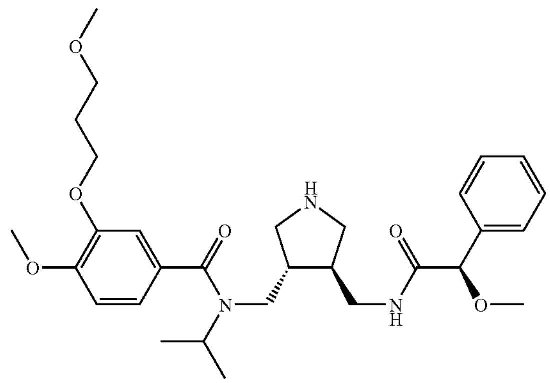 | 542.2 | 3.59[b] |
| 135 | (3S, 4S) | 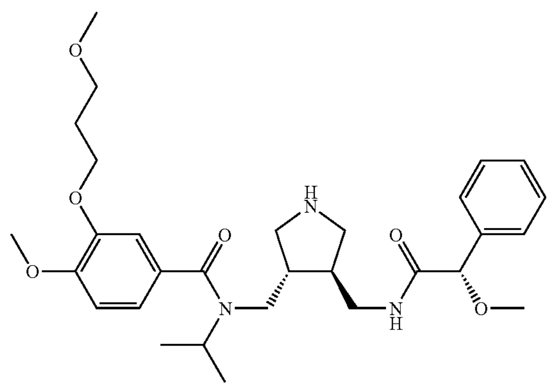 | 542.2 | 3.57[b] |
| 136 | (3S, 4S) | 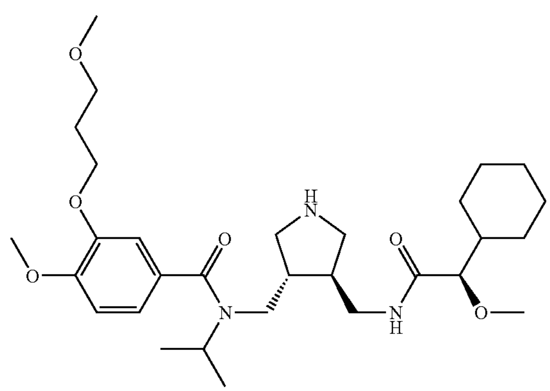 | 548.2 | 3.98[b] |
| 137 | (3S, 4S) | 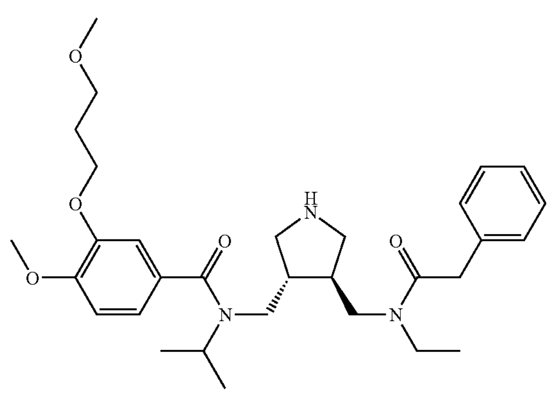 | 540.2 | 3.86[b] |

TABLE 3-continued

| Example | configuration | structure | [M + H]+ | t<sub>R</sub> (HPLC) |
|---|---|---|---|---|
| 138 | (3S, 4S) | 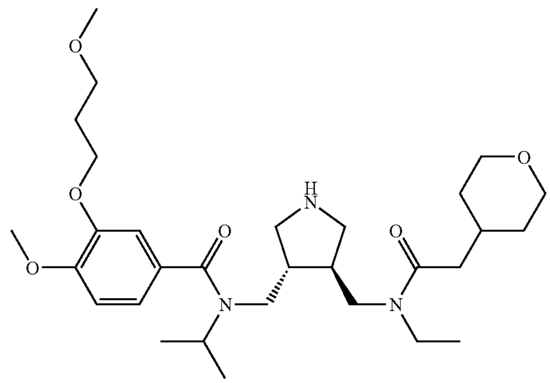 | 548.3 | 4.11[a] |
| 139 | (3S*, 4S*) | 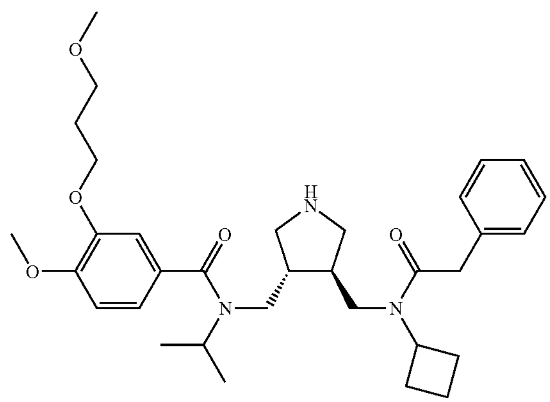 | 566.2 | 4.32[b] |
| 140 | (3S*, 4S*) | 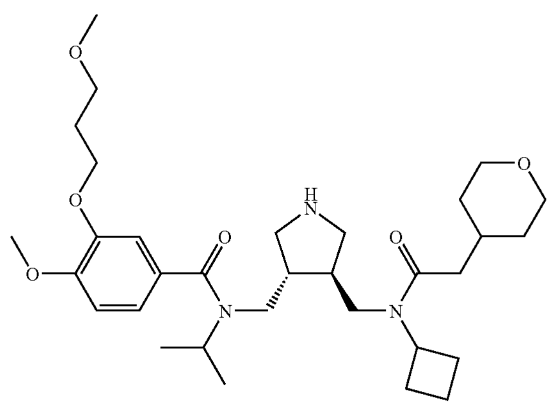 | 574.2 | 3.74[b] |
| 141 | (3S*, 4S*) | 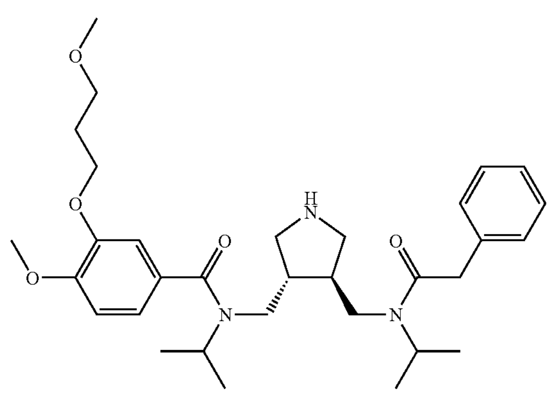 | 554.4 | 4.58[a] |

TABLE 3-continued

| Example | configuration | structure | [M + H]⁺ | t_R (HPLC) |
|---------|---------------|-----------|----------|------------|
| 142 | (3S*, 4S*) | 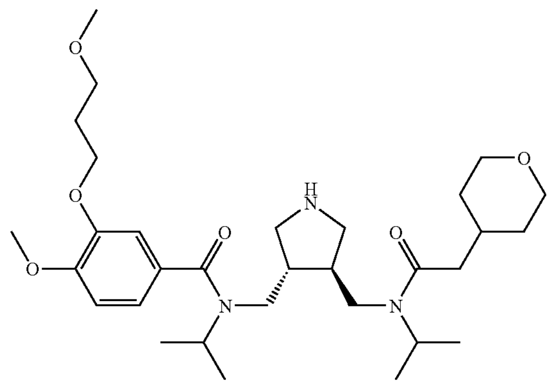 | 562.4 | 4.14[a] |
| 143 | (3S*, 4S*) | 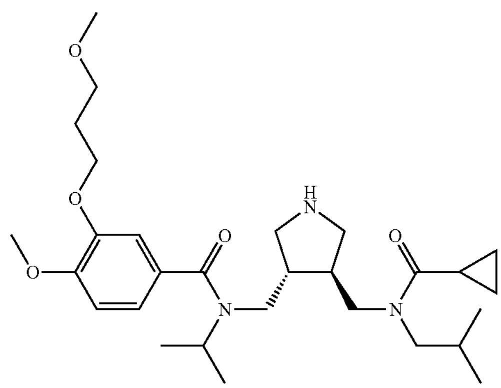 | 532.4 | 4.88[a] |
| 144 | (3S*, 4S*) | 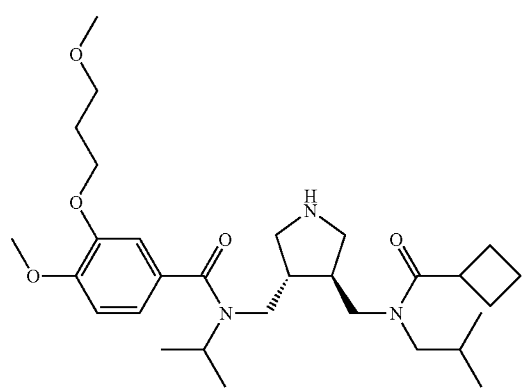 | 518.4 | 4.64[a] |
| 145 | (3S*, 4S*) | 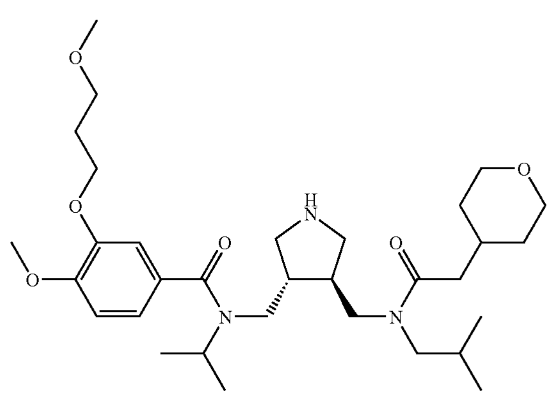 | 576.4 | 4.33[a] |

TABLE 3-continued

| Example | configuration | structure | [M + H]⁺ | t_R (HPLC) |
|---------|---------------|-----------|----------|------------|
| 146 | (3S*, 4S*) | 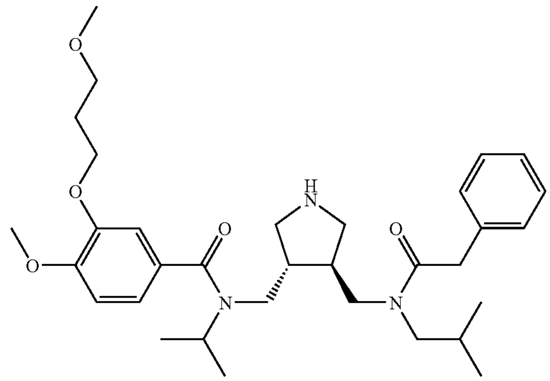 | 568.4 | 4.76[a] |
| 147 | (3S*, 4S*) | 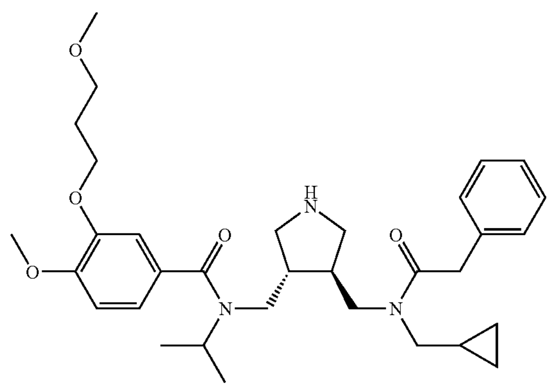 | 566.4 | 4.66[a] |
| 148 | (3S*, 4S*) | 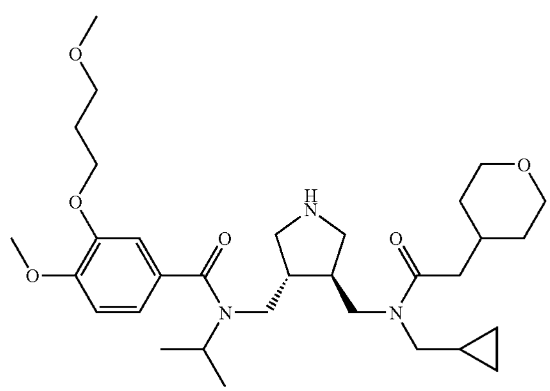 | 574.4 | 4.23[a] |

[a] t_R (HPLC, Nucleosil C18HD column, 5-100% CH₃CN/H₂O/6 min, 100% CH₃CN/2 min, CH₃CN and H₂O containing 0.1% TFA, flow: 1 mL/min).
[b] t_R (HPLC, Nucleosil C18HD column, 20-100% CH₃CN/H₂O/6 min, 100% CH₃CN/2 min, CH₃CN and H₂O containing 0.1% TFA, flow: 1 mL/min).

EXAMPLE 149

1-(3-Methoxy-propyl)-3-methyl-1H-indole-6-carboxylic acid {(3S,4S)-4-[(cyclopropyl-phenylacetyl-amino)-methyl]-pyrrolidin-3-ylmethyl}-isopropyl-amide

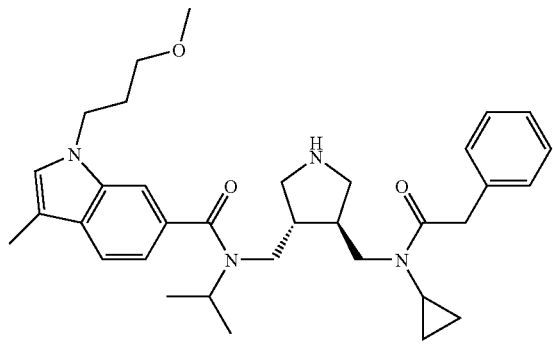

To a solution of (3R,4R)-3-[(cyclopropyl-phenylacetyl-amino)-methyl]-4-({isopropyl-[1-(3-methoxy-propyl)-3-methyl-1H-indole-6-carbonyl]-amino}-methyl)-pyrrolidine-1-carboxylic acid tert-butyl ester (0.26 g, 0.395 mmol) in dioxane (1 mL), 4N HCl in dioxane (1 mL) is added, and the resulting solution is lyophilized to afford the corresponding hydrochloride salt. MS (LC-MS): 559 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 5.35 min.

The starting material is prepared as follows:

A. (3S,4R)-3-(tert-Butyl-dimethyl-silanyloxymethyl)-4-({isopropyl-[1-(3-methoxy-propyl)-3-methyl-1H-indole-6-carbonyl]-amino}-methyl)-pyrrolidine-1-carboxylic acid tert-butyl ester A mixture of (3S,4R)-3-(tert-butyl-dimethyl-silanyloxymethyl)-4-(isopropylamino-methyl)-pyrrolidine-1-carboxylic acid tert-butyl ester (8.5 g, 22 mmol), 1-(3-methoxy-propyl)-3-methyl-1H-indole-6-carboxylic acid (7.6 g, 30.8 mmol), bis(2-oxo-3-oxazolidinyl)phosphinic chloride (7.84 g, 30.8 mmol) and triethylamine (12.3 mL, 88 mmol) in CH$_2$Cl$_2$ (425 mL) is refluxed overnight under a nitrogen atmosphere and then quenched by the addition of an aqueous saturated solution of NaHCO$_3$. The organic layer is separated, and the aqueous phase is extracted 3 times with AcOEt. The combined organic extracts are concentrated in vacuo. The residual oil is taken up in a mixture of THF and MeOH, NaOH 1N is added to cleave the anhydride side product and the mixture stirred for 3 h. The solvents are concentrated, CH$_2$Cl$_2$ is added and the layers are separated. The aqueous one is then back extracted twice with CH$_2$Cl$_2$ and the combined organic extracts are washed with brine, dried over Na$_2$SO$_4$, filtered and concentrated. The crude product is used in the next step without further purification. TLC, R$_f$(AcOEt)=0.6. MS (LC-MS): 516.3 [M-Boc+H]$^+$; $t_R$ (HPLC, Macherey-Nagel Nucleosil C18 column, 10-100% CH$_3$CN/H$_2$O/5 min, 100% CH$_3$CN/3 min, CH$_3$CN an H$_2$O containing 0.1% TFA, flow: 1.5 mL/min): 8.60 min.

B. (3S,4R)-3-Hydroxymethyl-4-({isopropyl-[1-(3-methoxy-propyl)-3-methyl-1H-indole-6-carbonyl]-amino}-methyl)-pyrrolidine-1-carboxylic acid tert-butyl ester To a solution of (3S,4R)-3-(tert-butyl-dimethyl-silanyloxymethyl)-4-({isopropyl-[4-methoxy-3-(3-methoxy-propoxy)-benzoyl]-amino}-methyl)-pyrrolidine-1-carboxylic acid tert-butyl ester (13.8 g, 22 mmol) in MeCN (350 mL) is added tetraethylammonium fluoride hydrate (6.6 g, 44 mmol) under a nitrogen atmosphere. The reaction mixture is refluxed for 3 h. Water and AcOEt are added, the layers are separated and the aqueous one extracted twice with AcOEt. The combined organic extracts are dried (Na$_2$SO$_4$), filtered and the solvent is removed in vacuo. The crude product is purified by flash chromatography on silica gel (eluent: CH$_2$Cl$_2$/MeOH 100:0 to 90:10) to give the title product. TLC, Rf (CH$_2$Cl$_2$/MeOH 95:5)=0.2. MS (LC-MS): 402.2 [M+H-Boc]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 6.85 min.

C. (3S,4R)-3-Formyl-4-({isopropyl-[1-(3-methoxy-propyl)-3-methyl-1H-indole-6-carbonyl]-amino}-methyl)-pyrrolidine-1-carboxylic acid tert-butyl ester The title compound is prepared analogously as described for the title compound under I in Scheme 5 from (3S,4R)-3-hydroxymethyl-4-({isopropyl-[1-(3-methoxy-propyl)-3-methyl-1H-indole-6-carbonyl]-amino}-methyl)-pyrrolidine-1-carboxylic acid tert-butyl ester. TLC, R$_f$ (CH$_2$Cl$_2$/MeOH 95:5)=0.6. $t_R$ (HPLC, C18 column, 5-100% CH$_3$CN/H$_2$O/6 min, 100% CH$_3$CN/2 min, CH$_3$CN and H$_2$O containing 0.1% TFA, flow: 1 mL/min): 5.11 min.

D. (3R,4R)-3-Cyclopropylaminomethyl-4-({isopropyl-[1-(3-methoxy-propyl)-3-methyl-1H-indole-6-carbonyl]-amino}-methyl)-pyrrolidine-1-carboxylic acid tert-butyl ester To a solution of (3S,4R)-3-formyl-4-({isopropyl-[1-(3-methoxy-propyl)-3-methyl-1H-indole-6-carbonyl]-amino}-methyl)-pyrrolidine-1-carboxylic acid tert-butyl ester (6 g, 10.9 mmol) in dichloroethane (100 mL), cyclopropylamine (0.85 mL, 12 mmol) and NaBH(OAc)$_3$ (4.32 g, 15.3 mmol) are added. The solution is stirred at RT overnight, then diluted with CH$_2$Cl$_2$. A saturated solution of NaHCO$_3$ is added, the layers are separated and the aqueous one extracted twice with CH$_2$Cl$_2$. The combined organic extracts are dried over Na$_2$SO$_4$, filtered, and concentrated in vacuo. The crude material is purified by flash chromatography on silica gel (eluent: AcOEt/MeOH 100:0 to 85:15) to give the title compound. TLC, Rf (AcOEt)=0.1. MS (LC-MS): 541.3 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 5.52 min.

E. (3R,4R)-3-[(Cyclopropyl-phenylacetyl-amino)-methyl]-4-({isopropyl-[1-(3-methoxy-propyl)-3-methyl-1H-indole-6-carbonyl]-amino}-methyl)-pyrrolidine-1-carboxylic acid tert-butyl ester The title compound is prepared analogously as described for the title compound under K in Example 9 (Scheme 5) from (3R,4R)-3-cyclopropylaminomethyl-4-({isopropyl-[1-(3-methoxy-propyl)-3-methyl-1H-indole-6-carbonyl]-amino}-methyl)-pyrrolidine-1-carboxylic acid tert-butyl ester. MS (LC-MS): 658.9 [M-Boc+H]⁺. $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 ml/min): 6.69 min.

1-(3-Methoxy-propyl)-3-methyl-1H-indole-6-carboxylic acid

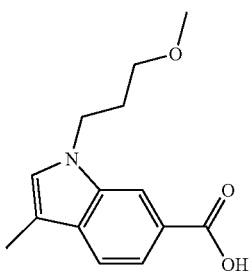

3-Methyl-1H-indole-6-carboxylic acid methyl ester

A mixture of 3-formyl-1H-indole-6-carboxylic acid methyl ester (5 g, 24.6 mmol), p-toluene-sulfonic acid (704 mg, 3.7 mmol) and p-toluenesulfonylhydrazide (5.49 g, 29.5 mmol) in a mixture of dimethylformamide (50 mL) and sulfolane (25 mL) is heated at 100° C. for 15 min. Then cooled to RT, before the addition of sodium cyanoborohydride (6.2 g, 98.4 mmol, 2 g portions after 10 min intervals). The resulting mixture is heated at 100° C. for 2 h, cooled to RT and poured into a mixture of ice and water (250 mL) leading to a white precipitate. Water (500 mL) is added, and the mixture is stirred for 30 min before filtration. The off-white solid is washed with warm water. Toluene is added and removed by rotary evaporation to afford the title compound as a yellow solid. TLC, $R_f$ (hexane/AcOEt 4:1)=0.3. MS (LC-MS): [M+H]+=188.1. $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 5.13 min.

1-(3-Methoxy-propyl)-3-methyl-1H-indole-6-carboxylic acid methyl ester

To a solution of 3-methyl-1H-indole-6-carboxylic acid methyl ester (2.5 g, 13.2 mmol) in DMF (25 mL), a solution of NaH (580 mg, 14.5 mmol, 60% dispension in grease) in DMF (25 mL) is slowly added under a $N_2$ atmosphere. The mixture is stirred at 80° C. for 20 min, and cooled to RT before the addition of 1-bromo-3-methoxypropane (4.04 g, 26.4 mmol). The resulting mixture is stirred for 24 h. 1-Bromo-3-methoxypropane (2.02 g, 13.2 mmol) and NaH (580 mg, 14.5 mmol) are added and the mixture further stirred for 24 h to complete the reaction. The solvent is concentrated under reduced pressure and the mixture diluted with AcOEt. An aqueous saturated solution of $NaHCO_3$ is added, the layers are separated, and the aqueous one is back-extracted with AcOEt. The combined organic extracts are dried over $Na_2SO_4$, filtered and concentrated. The crude residue is purified by flash chromatography on silica gel (eluent: c-hexane/AcOEt 80:20) to give the title compound. MS (LC-MS): 262.0 [M+H]⁺; $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 mumin): 5.80 min.

1-(3-Methoxy-propyl)-3-methyl-1H-indole-6-carboxylic acid

To a solution of 1-(3-methoxy-propyl)-3-methyl-1H-indole-6-carboxylic acid methyl ester (1.56 g, 6.3 mmol) in MeOH (20 mL) and $H_2O$ (1 mL) is added NaOH (756 mg, 18.9 mmol) and the mixture is stirred at 50° C. overnight. Then neutralized by the addition of water and HCl 1.0 M (3 eq, 18.9 mmol). $CH_2Cl_2$ is added, the layers are separated, and the aqueous one is extracted twice with $CH_2Cl_2$. The combined organic layers are dried over $Na_2SO_4$, filtered and concentrated under reduced pressure. The crude material is obtained in a pure form and is used in the next step without purification. MS (LC-MS): 248.0 [M+H]⁺; $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 4.93 min.

The following Examples are prepared according to the procedures described above for Example 149:

TABLE 4

| Example | configuration | structure | [M + H]⁺ | $t_R$ (HPLC) |
|---|---|---|---|---|
| 150 | (3S, 4S) | 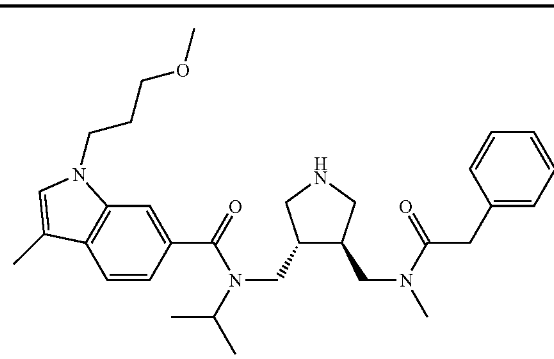 | 533 | 5.20[a] |

TABLE 4-continued

| Example | configuration | structure | [M + H]⁺ | $t_R$ (HPLC) |
|---|---|---|---|---|
| 151 | (3S, 4S) | 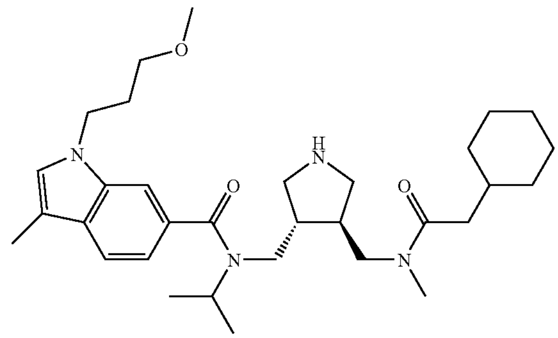 | 539 | 5.64[a] |

[a] $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).

The starting materials of the title compounds in Table 4 are prepared as follows:

1-(3-Methoxy-propyl)-3-methyl-1H-indole-6-carboxylic acid {(3S,4S)-4-[(methyl-phenylacetyl-amino)-methyl]-pyrrolidin-3-ylmethyl}-isopropyl-amide In a similar manner as described in Example 9 for the reaction step J, the following starting material is prepared from (3S,4R)-3-formyl-4-({isopropyl-[1-(3-methoxy-propyl)-3-methyl-1H-indole-6-carbonyl]-amino}-methyl)-pyrrolidine-1-carboxylic acid tert-butyl ester (prepared under C in example 151) (3 g, 5.4 mmol), 2N solution of methylamine in MeOH (13.5 mL, 27 mmol) and NaBH₄ (0.408 g, 10.8 mmol) and purification by flash chromatography on silica gel (CH₂Cl₂/MeOH 90:10, then AcOEt/MeOH/NH₄OH 89:10:1) to give a colorless oil. MS: 515.0 [M+H]⁺. ]⁺; $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 ml/min): 5.41 min.

EXAMPLE 152

4-Ethyl-N-isopropyl-3-(3-methoxy-propoxy)-N-{(3S,4S)-4-[(methyl-phenylacetyl-amino)-methyl]-pyrrolidin-3-ylmethyl}-benzamide

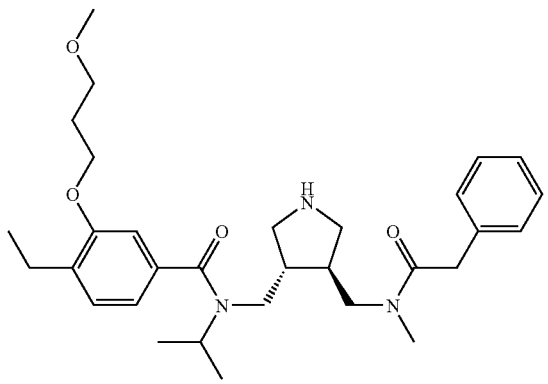

To a solution of (3R,4R)-3-({[4-Ethyl-3-(3-methoxy-propoxy)-benzoyl]-isopropyl-amino}-methyl)-4-[(methyl-phenylacetyl-amino)-methyl]-pyrrolidine-1-carboxylic acid tert-butyl ester (0.330 g, 0.529 mmol) in dioxane (2 mL), 4N HCl in dioxane (2 mL) is added, and the resulting solution is lyophilized to afford the corresponding hydrochloride salt. MS (LC-MS): 524.3 [M+H]⁺; $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 ml/min): 5.94 min.

The starting material is prepared in a similar manner as described in Example 149, reaction steps A to E, as follows:

A. (3S,4R)-3-(tert-Butyl-dimethyl-silanyloxymethyl)-4-({[4-ethyl-3-(3-methoxy-propoxy)-benzoyl]-isopropyl-amino}-methyl)-pyrrolidine-1-carboxylic acid tert-butyl ester From (3S,4R)-3-(tert-butyl-dimethyl-silanyloxymethyl)-4-(isopropylamino-methyl)-pyrrolidine-1-carboxylic acid tert-butyl ester (8.5 g, 22 mmol), 4-ethyl-3-(3-methoxy-propoxy)-benzoic acid (5.76 g, 24.2 mmol), BOPCl (6.16 g, 24.2 mmol) and triethylamine (12.3 g, 88 mmol). TLC, Rf (CH₂Cl₂/MeOH 95:5)=0.32. $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 ml/min): 8.81 min. MS (LC-MS): [M+H-BOC]+507.3

B. (3R,4S)-3-({[4-Ethyl-3-(3-methoxy-propoxy)-benzoyl]-isopropyl-amino}-methyl)-4-hydroxymethyl-pyrrolidine-1-carboxylic acid tert-butyl ester From (3S,4R)-3-(tert-butyl-dimethyl-silanyloxymethyl)-4-({[4-ethyl-3-(3-methoxy-propoxy)-benzoyl]-isopropyl-amino}-methyl)-pyrrolidine-1-carboxylic acid tert-butyl ester (13.1 g, 21.6 mmol) and TBAF (17 g, 54 mmol), and purification by flash chromatography on silica gel (CH₂Cl₂/MeOH 95:5) to give the title compound as yellow oil. TLC, Rf (AcOEt)=0.4,MS (LC-MS): 437.3 [M+H-tBu]⁺; $t_R$ (HPLC, Macherey-Nagel Nucleosil C18 column, 10-100% CH3CN/H2O/5 min, 100% CH₃CN/3 min, CH₃CN and H2O containing 0.1% TFA, flow: 1.5 mL/min): 6.74 min.

C. (3R,4S)-3-({[4-Ethyl-3-(3-methoxy-propoxy)-benzoyl]-isopropyl-amino}-methyl)-4-formyl-pyrrolidine-1-carboxylic acid tert-butyl ester From (3R,4S)-3-({[4-ethyl-3-(3-methoxy-propoxy)-benzoyl]-isopropyl-amino}-methyl)-4-hydroxymethyl-pyrroli-

D. (3R,4R)-3-({[4-Ethyl-3-(3-methoxy-propoxy)-benzoyl]-isopropyl-amino}-methyl)-4-methylaminomethyl-pyrrolidine-1-carboxylic acid tert-butyl ester In a similar manner as described in Example 9 for the reaction step J, the following starting materials is prepared from (3R,4S)-3-({[4-ethyl-3-(3-methoxy-propoxy)-benzoyl]-isopropyl-amino}-methyl)-4-formyl-pyrrolidine-1-carboxylic acid tert-butyl ester (3.5 g, 6 mmol), methyl amine (0.93 mL, 30 mmol) and NaBH$_4$ (0.454 g, 12 mmol) and purification by flash chromatography on silica gel (CH$_2$Cl$_2$/MeOH 1:1) to (CH$_2$Cl$_2$/MeOH/NH$_4$OH 89:10:1) to give the title compound as colorless oil. TLC, Rf (CH2Cl2/MeOH/NH4OH 89:10:1)=0.29. MS (LC-MS): 506.2 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 5.38 min.

E. (3R,4R)-3-({[4-Ethyl-3-(3-methoxy-propoxy)-benzoyl]-isopropyl-amino}-methyl)-4-[(methyl-phenylacetyl-amino)-methyl]-pyrrolidine-1-carboxylic acid tert-butyl ester From (3R,4R)-3-({[4-ethyl-3-(3-methoxy-propoxy)-benzoyl]-isopropyl-amino}-methyl)-4-methylaminomethyl-pyrrolidine-1-carboxylic acid tert-butyl ester (0.7 g, 1.38 mmol), phenylacetyl chloride (0.22 mL, 1.66 mmol) and triethylamine (0.21 mL, 2.1 mmol) in CH$_2$Cl$_2$ (40 mL) and purification by flash chromatography on silica gel (c-hexane/AcOEt 1:1 to 0:1) to give the title compound as colorless oil. TLC, Rf (AcOEt)=0.30. MS (LC-MS): 624.0 [M+H]$^+$; t$_R$ (Waters Symmetry C18 column, 20-100% CH$_3$CN/H$_2$O/5 min, CH$_3$CN and H$_2$O containing 0.1% TFA, flow: 0.6 mL/min): 4.41 min.

4-Ethyl-3-(3-methoxy-propoxy)-benzoic acid

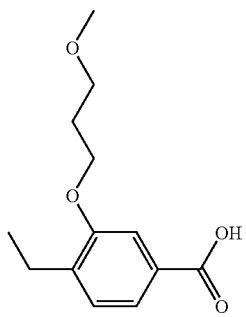

a. 4-Bromo-3-hydroxy-benzoic acid methyl ester

To a solution of 4-bromo-3-hydroxy-benzoic acid (prepared according to J. Amer. Chem Soc. 1946, 68, 574) (5 g, 32.8 mmol) in MeOH (100 mL), conc. H$_2$SO$_4$ (1 mL) is added. The solution is refluxed for 14 h, then concentrated to about 30 mL and poured into a water. The aqueous layer is extracted with ether (50 mL×4) and the combined organic extracts are neutralized with a saturated aqueous solution of NaHCO$_3$ (50 mL×2), washed with brine (50 mL), dried over Na$_2$SO$_4$, filtered and concentrated to give the title compound as a white powder. TLC, R$_f$ (AcOEt)=0.9. $^1$H-NMR (CDCl$_3$, 300 MHz): δ=5.8 (bs, 1H), 7.45 (d, 1H), 7.55 (d, 1H), 7.7 (s, 1H) ppm.

b. 4-Bromo-3-(3-methoxy-propoxy)-benzoic acid methyl ester

A solution of 4-bromo-3-hydroxy-benzoic acid methyl ester (12 g, 51.9 mmol), potassium carbonate (10.77 g, 77.9 mmol) and 1-iodo-3-methoxy propane (11.42 g, 57.1 mmol) in acetonitrile (250 mL) is stirred at reflux for 16 h. The solvent is concentrated under reduced pressure, H$_2$O (100 mL) is added, and the aqueous layer extracted with ether (50 mL×4). The combined organic extracts are washed with brine, dried over anhydrous sodium sulfate and concentrated under reduced pressure to afford the title which was used without further purification in the next step. TLC, R$_f$ (hexane/AcOEt 2:1)=0.65. $^1$H-NMR (CDCl$_3$, 300 MHz): δ=2.12 (p, 2H), 3.38 (s, 3H), 3.63 (t, 2H), 3.9 (s, 3H), 4.2 (t, 2H), 7.5 (d, 1H), 7.55 (m, 1H), 7.6 (d, 1H) ppm.

c. 3-(3-Methoxy-propoxy)-4-trimethylsilanylethynyl-benzoic acid methyl ester To a stirred solution of 4-bromo-3-(3-methoxy-propoxy)-benzoic acid methyl ester (5 g, 16.49 mmol) and trimethylsilyl actetylene (2.74 mL, 19.8 mmol) in triethylamine (60 mL), Cl$_2$Pd(PPh$_3$)$_2$ (2.31 g, 3.29 mmol) and CuI (0.314 g, 1.65 mmol) are added. The resulting mixture is stirred at RT for 15 h and concentrated under reduced pressure. The crude residue is purified by flash chromatography on silica gel (eluent: hexane/AcOEt 10:1 to 5:1) to give the desired title product as a brown oil. $^1$H-NMR (CDCl$_3$, 300 MHz): δ=0.25 (s, 9H), 2.12 (p, 2H), 3.38 (s, 3H), 3.65 (t, 2H), 3.9 (s, 3H), 4.18 (t, 2H), 7.45 (d, 1H), 7.52 (s, 1H), 7.58 (d, 1H) ppm.

d. 4-Ethynyl-3-(3-methoxy-propoxy)-benzoic acid

To a solution of 3-(3-methoxy-propoxy)-4-trimethylsilanylethynyl-benzoic acid methyl ester (16.49 mmol) in MeOH (40 mL) is added KOH (1 N, 24.7 mL, 24.7 mmol). The resulting mixture is stirred at RT for 15 h and concentrated under reduced pressure. The residue was taken up in HCl (2 N, 100 mL) and extracted with AcOEt (100 mL×3). The combined organic extracts are washed with brine, dried over anhydrous sodium sulfate and concentrated under reduced pressure to afford the title as a yellow oil which is used without further purification in the next step. MS (FAB): 235.0 [M+H]$^+$. $^1$H-NMR (CDCl$_3$, 300 MHz): δ=2.15 (p, 2H), 3.38 (s, 3H), 3.41 (s, 1H), 3.62 (t, 2H), 4.22 (t, 2H), 7.5 (d, 1H), 7.65 (s, 1H), 7.68 (d, 1H) ppm.

e. 4-Ethyl-3-(3-methoxy-propoxy)-benzoic acid

To a solution of 4-ethynyl-3-(3-methoxy-propoxy)-benzoic acid (1 g, 4.11 mmol) in EtOH (20 mL), Pd(OH)$_2$ (0.1 g) is added. The resulting mixture is stirred under an hydrogen atmosphere for 15 min, then filtered and concentrated. The crude material is purified by flash chromatography on silica gel (eluent: hexane/AcOEt 2:1) to give the title compound as white powder. $^1$H-NMR (CDCl$_3$, 300 MHz): δ=1.2 (t, 3H), 2.15 (p, 2H), 2.7 (q, 2H), 3.38 (s, 3H), 3.62 (t, 2H), 4.15 (t, 2H), 7.25 (d, 1H), 7.55 (s, 1H), 7.68 (d, 1H) ppm.

The following Examples are prepared according to the procedures described above for Example 152:

TABLE 5

| Example | configuration | structure | [M + H]+ | t<sub>R</sub> (HPLC) |
|---------|---------------|-----------|----------|----------------------|
| 153 | (3S, 4S) | 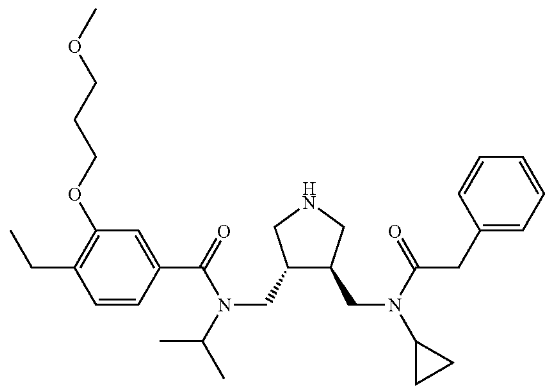 | 550.2 | 6.13<sup>a</sup> |
| 154 | (3S, 4S) | 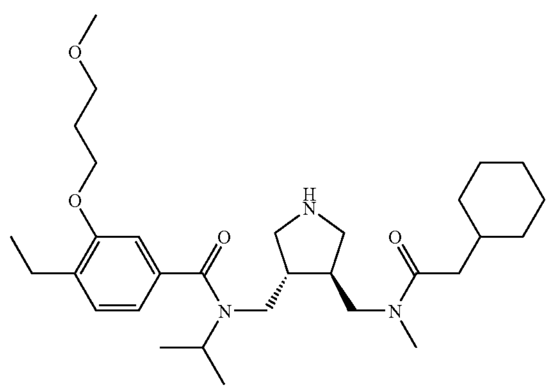 | 530 | 5.55<sup>a</sup> |
| 155 | (3S, 4S) | 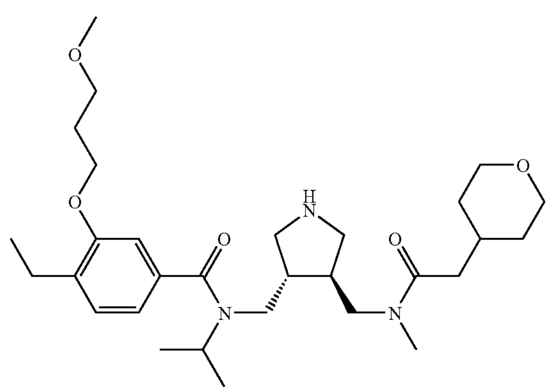 | 532 | 4.10<sup>b</sup> |

TABLE 5-continued
| Example | configuration | structure | [M + H]+ | tR (HPLC) |
|---|---|---|---|---|
| 156 | (3S, 4S) | 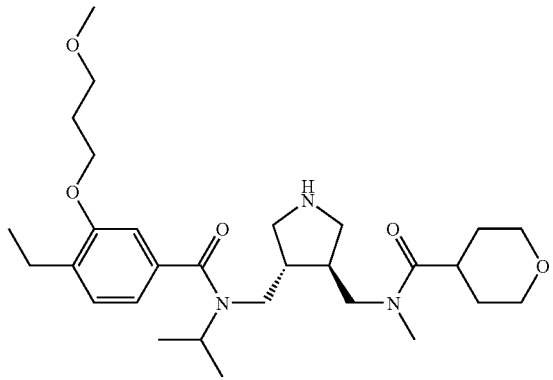 | 518 | 3.97[b] |
| 157 | (3S, 4S) | 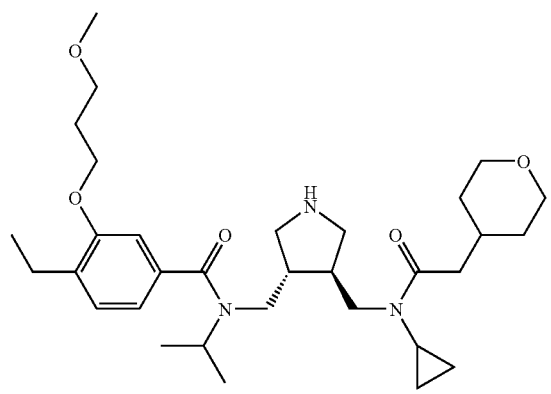 | 558.3 | 4.37[b] |
| 158 | (3S, 4S) | 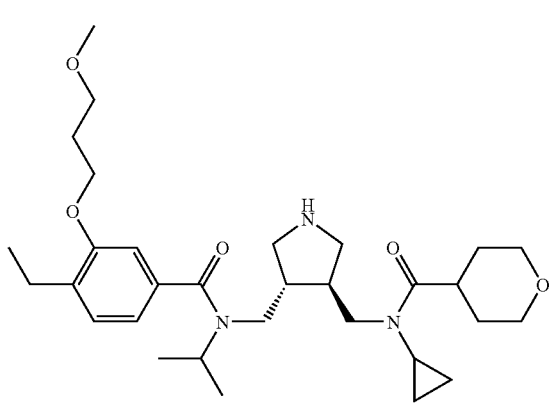 | 544.3 | 4.25[b] |
| 159 | (3S, 4S) | 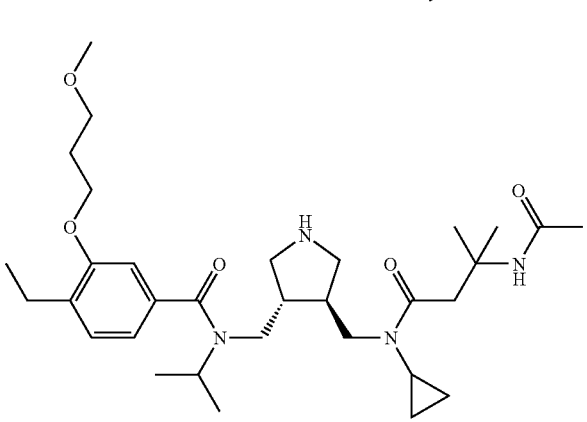 | 573.3 | 2.63[c] |

TABLE 5-continued

| Example | configuration | structure | [M + H]⁺ | $t_R$ (HPLC) |
|---|---|---|---|---|
| 160 | (3S, 4S) | 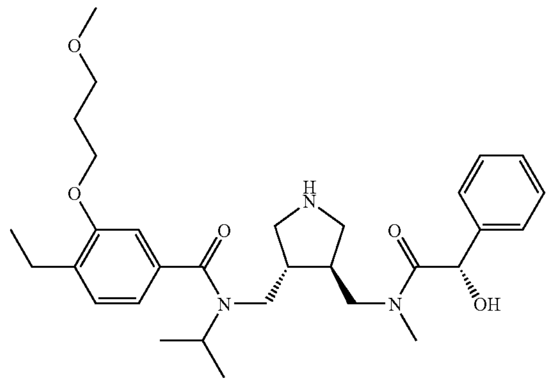 | 540.3 | 4.88[a] |
| 161 | (3S, 4S) | 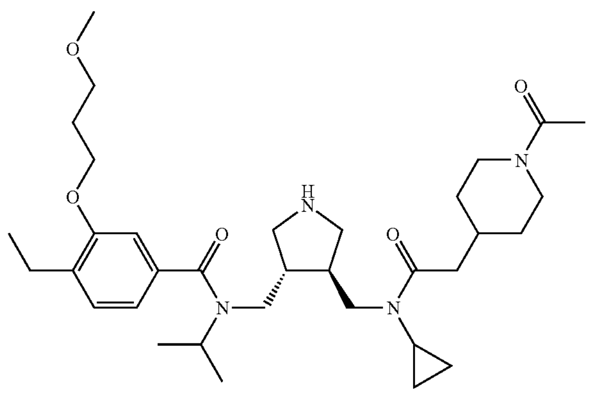 | 599.2 | 2.60[c] |
| 162 | (3S, 4S) | 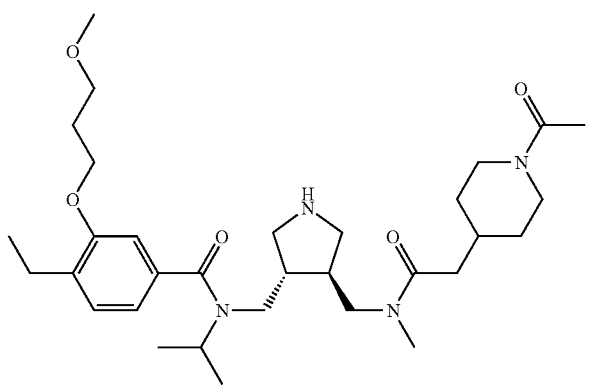 | 573.2 | 2.20[c] |
| 163 | (3S, 4S) | 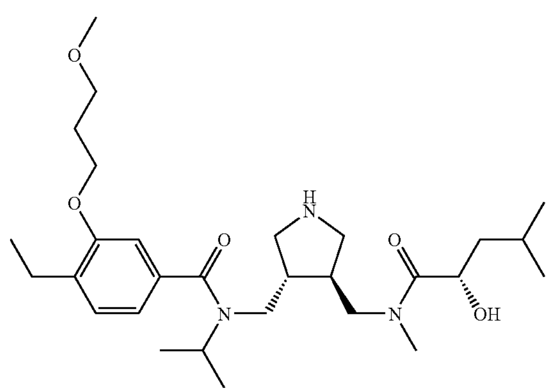 | 520.3 | 2.94[d] |

TABLE 5-continued

| Example | configuration | structure | [M + H]⁺ | $t_R$ (HPLC) |
|---|---|---|---|---|
| 164 | (3S, 4S) | 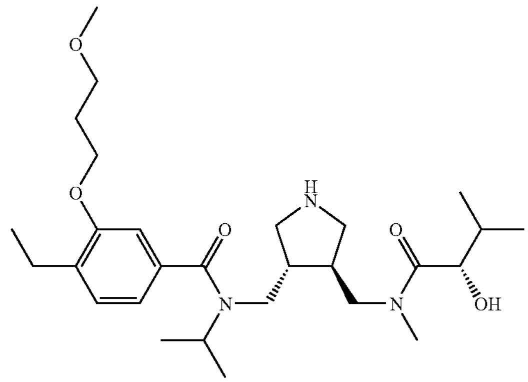 | 506.4 | 2.86 min[d] |
| 165 | (3S, 4S) | 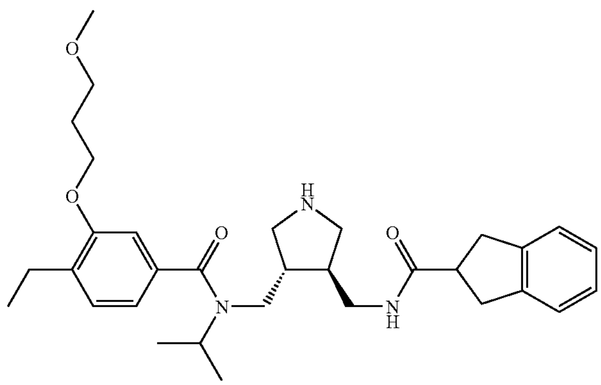 | 536.2 | 4.71[f] |
| 166 | (3S, 4S) | 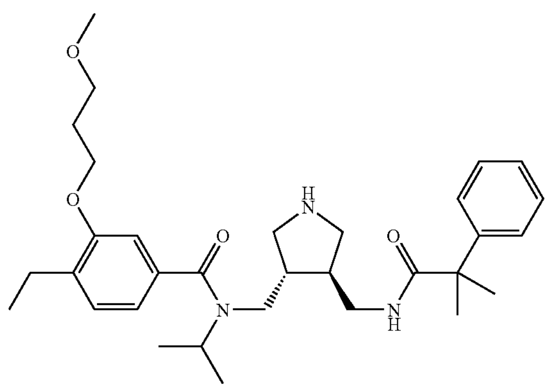 | 538.2 | 4.76[f] |
| 167 | (3S, 4S) | 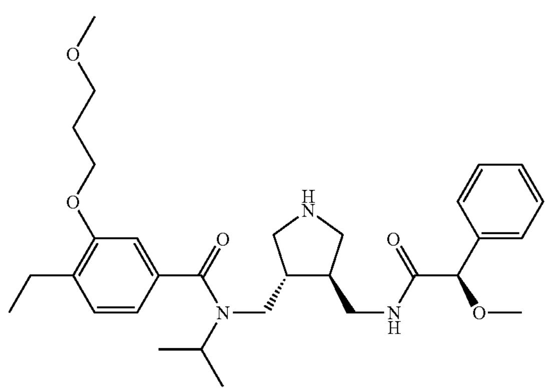 | 540.2 | 4.47[f] |

TABLE 5-continued

| Example | configuration | structure | [M + H]+ | t$_R$ (HPLC) |
|---|---|---|---|---|
| 168 | (3S, 4S) | 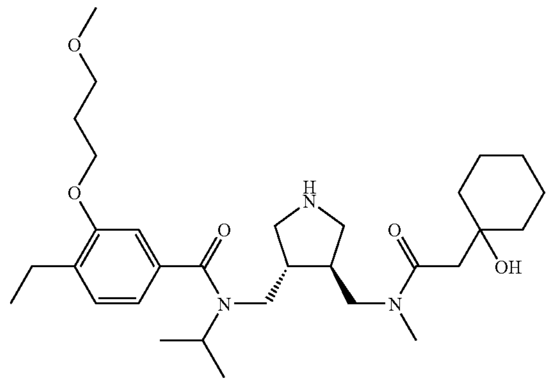 | 546.2 | 4.52$^f$ |
| 169 | (3S, 4S) | 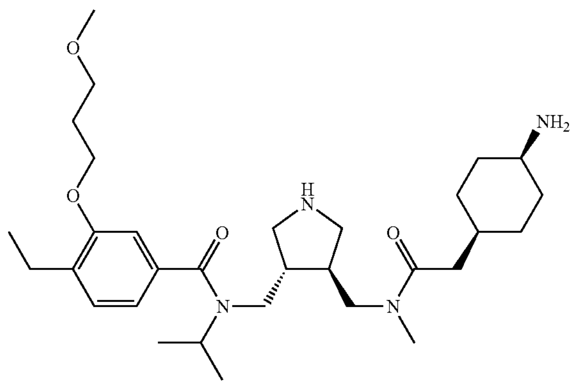 | 545.5 | 4.26$^e$ |
| 170 | (3S, 4S) | 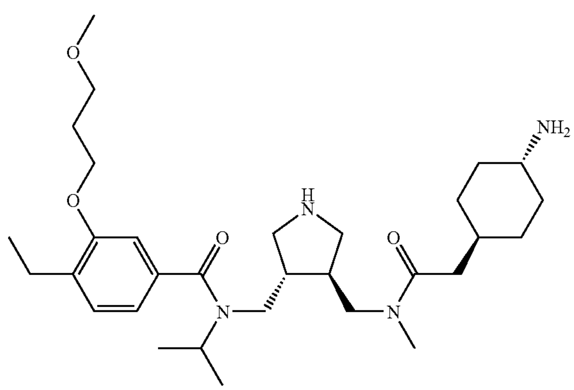 | 545.5 | 4.25$^e$ |
| 171 | (3S, 4S) | 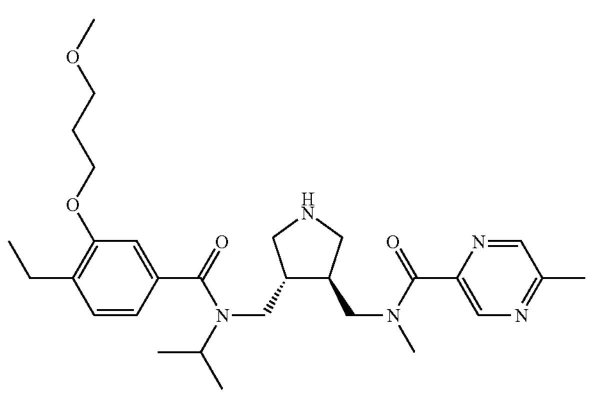 | 526.3 | 4.69$^e$ |

TABLE 5-continued
| Example | configuration | structure | [M + H]+ | tR (HPLC) |
|---|---|---|---|---|
| 172 | (3S, 4S) | 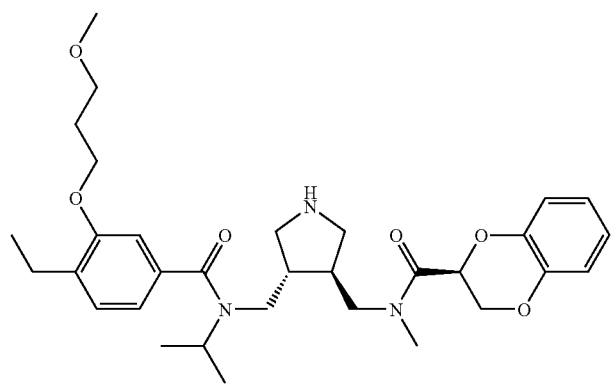 | 568.2 | 5.24e |
| 173 | (3S, 4S) | 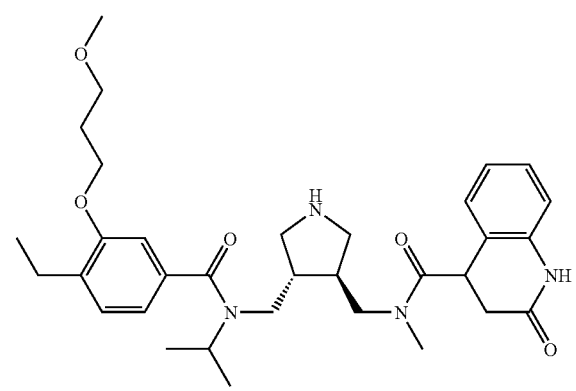 | 579.3 | 4.78e |
| 174 | | | 579.3 | 4.67e |
| 175 | (3S, 4S) | 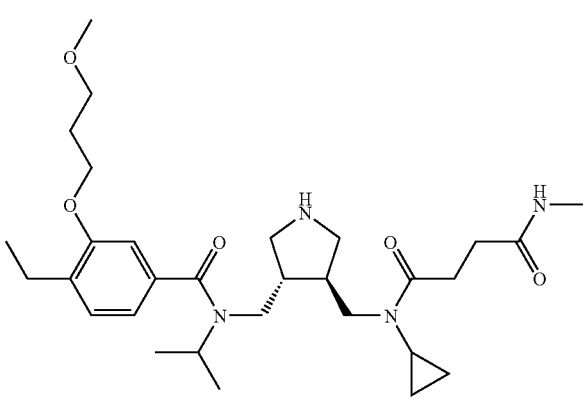 | 545.3 | 4.62e |
| 176 | (3S, 4S) | 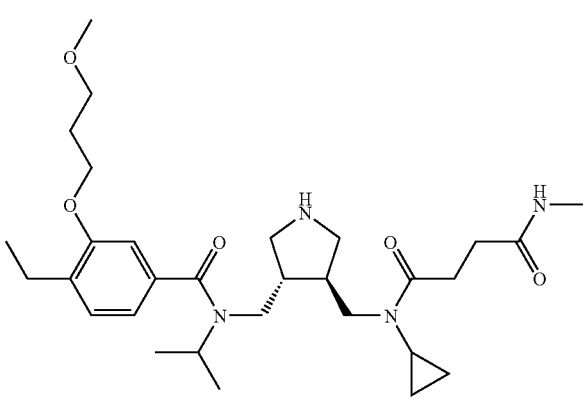 | 552.3 | 4.86e |

TABLE 5-continued

| Example | configuration | structure | [M + H]+ | t_R (HPLC) |
|---------|---------------|-----------|----------|------------|
| 177 | (3S, 4S) | 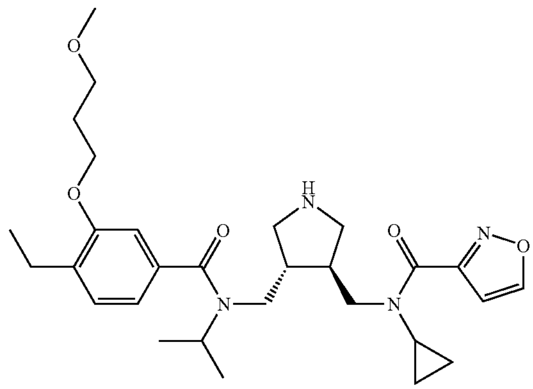 | 527.2 | 4.89[e] |
| 178 | (3S, 4S) | 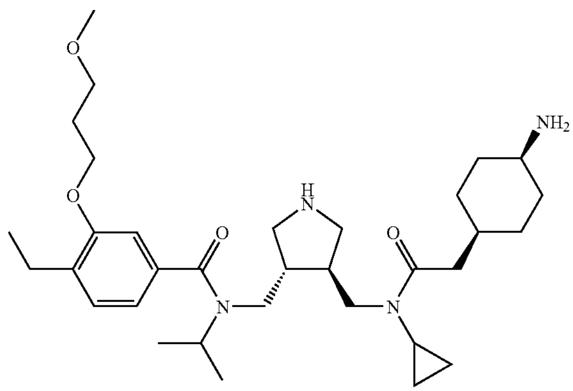 | 571.4 | 4.35[e] |
| 1791 | (3S, 4S) | 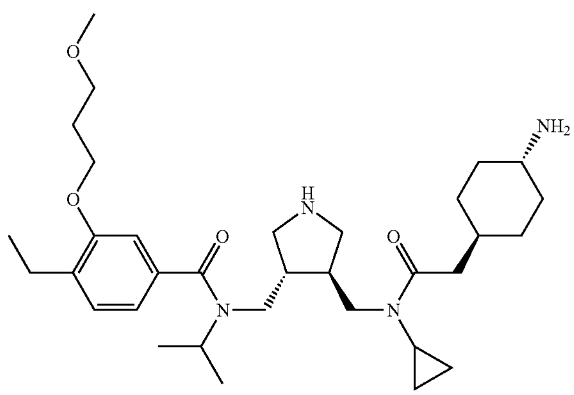 | 571.4 | 4.41[e] |
| 180 181 | (3S, 4S) | | 530.2 | 4.16[f] 4.16[f] |

TABLE 5-continued

| Example | configuration | structure | [M + H]+ | t_R (HPLC) |
|---|---|---|---|---|
| 182 183 | (3S, 4S) | | 544.2 | 4.28[f] 4.32[f] |
| 184 185 | (3S, 4S) | | 558.3 | 3.98[f] 4.20[f] |
| 186 187 | (3S, 4S) | | 518.2 | 4.00[f] 4.04[f] |

[a] t_R (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
[b] t_R (HPLC, Nucleosil C-18HD (4 × 70 mm, 3 μm), 20-100% CH₃CN/H₂O/6 min, 100% CH₃CN/1.5 min; flow: 1 mL/min).
[c] t_R (Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min).
[d] t_R (Waters Symmetry C18 column, 5-95% CH₃CN/H₂O/3.5 min, 95% CH₃CN/H₂O, 2 min, CH₃CN and H₂O containing 0.1% TFA, flow: 0.6 mL/min).
[e] t_R (HPLC, Nucleosil C18HD column, 5-100% CH₃CN/H₂O/6 min, 100% CH₃CN/2 min, CH₃CN and H₂O containing 0.1% TFA, flow: 1 mL/min).
[f] t_R (HPLC, Nucleosil C18HD column, 20-100% CH₃CN/H₂O/6 min, 100% CH₃CN/2 min, CH₃CN and H₂O containing 0.1% TFA, flow: 1 mL/min).

The starting materials of the title compounds in Table 5 are prepared as follows:

(3R,4R)-3-Aminomethyl-4-({[4-ethyl-3-(3-methoxy-propoxy)-benzoyl]-isopropyl-amino}-methyl)-pyrrolidine-1-carboxylic acid tert-butyl ester:

According to the procedure described for Example 130/ reaction step C, by hydrogenation of (3S,4R)-3-azidomethyl-4-({[4-ethyl-3-(3-methoxy-propoxy)-benzoyl]-isopropyl-amino}-methyl)-pyrrolidine-1-carboxylic acid tert-butyl ester (3.95 g, 7.48 mmol), dissolved in absolute EtOH (100 mL), in the presence of Pd/C 10% (0.8 g; Engelhard 4505) at room temperature under atmospheric pressure to give, after filtration and drying in vacuo, the title compound as colorless oil. MS: 492.2 [M+H]+. t_R (HPLC, Nucleosil C18HD column, 20-100% CH₃CN/H₂O/6 min, 100% CH₃CN/2 min, CH₃CN and H₂O containing 0.1% TFA, flow: 1 mL/min): 4.62 min.

a. (3R,4S)-3-({[4-Ethyl-3-(3-methoxy-propoxy)-benzoyl]-isopropyl-amino}-methyl)-4-methanesulfonyloxymethyl-pyrrolidine-1-carboxylic acid tert-butyl ester: prepared from (3R,4S)-3-({[4-Ethyl-3-(3-methoxy-propoxy)-benzoyl]-isopropyl-amino}-methyl)-4-hydroxymethyl-pyrrolidine-1-carboxylic acid tert-butyl ester (4.00 g, 8.12 mmol), methane sulfonylchloride (0.733 mL, 9.34 mmol) and NEt$_3$ (3.40 mL, 24.4 mmol) in CH$_2$Cl$_2$ (50 mL) similar to the procedure described for Example 130/reaction step A, to give the title compound as yellowish oil. TLC, R$_f$ (hexane/AcOEt 1:3)=0.32.

b. (3S,4R)-3-Azidomethyl-4-({[4-ethyl-3-(3-methoxy-propoxy)-benzoyl]-isopropyl-amino}-methyl)-pyrrolidine-1-carboxylic acid tert-butyl ester: prepared from (3R,4S)-3-({[4-ethyl-3-(3-methoxy-propoxy)-benzoyl]-isopropyl-amino}-methyl)-4-methanesulfonyloxymethyl-pyrrolidine-1-carboxylic acid tert-butyl ester (5.50 g, 8.10 mmol) and NaN$_3$ (2.13 g, 32.4 mmol) in DMF (40 mL) similar to the procedure described for Example 130/reaction step B, and purification by flash chromatography on silica gel (hexane/AcOEt 1:1) to give the title compound as colorless oil. TLC, R$_f$ (hexane/AcOEt 1:3)=0.47. MS: 518.2 [M+H]$^+$. t$_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 5.89 min.

(3R,4R)-3-Cyclopropylaminomethyl-4-({[4-ethyl-3-(3-methoxy-propoxy)-benzoyl]-isopropyl-amino}-methyl)-pyrrolidine-1-carboxylic acid tert-butyl ester To a solution of (3R,4S)-3-({[4-ethyl-3-(3-methoxy-propoxy)-benzoyl]-isopropyl-amino}-methyl)-4-formyl-pyrrolidine-1-carboxylic acid tert-butyl ester (described under step C in example 152) (6.9 g, 11.88 mmol) in dichloroethane (112 mL), cyclopropylamine (0.92 mL, 13.1 mmol) and NaBH(OAc)$_3$ (3.52 g, 16.63 mmol) are added. The solution is stirred at RT overnight, then diluted with CH$_2$Cl$_2$. A saturated solution of NaHCO$_3$ is added, the layers are separated and the aqueous one extracted twice with CH$_2$Cl$_2$. The combined organic extracts are dried over Na$_2$SO$_4$, filtered, and concentrated in vacuo. The crude material is purified by flash chromatography on silica gel (eluent: AcOEt/MeOH 100:0 to 85:15) to give the title compound. MS (LC-MS): 532.3 [M+H]+; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 5.58 min.

The starting materials of Examples 173 and 174 are prepared as follows:

The two diastereomers (3R,4R)-3-({[4-ethyl-3-(3-methoxy-propoxy)-benzoyl]-isopropyl-amino}-methyl)-4(R)-{[methyl-(2-oxo-1,2,3,4-tetrahydro-quinoline-4-carbonyl)-amino]-methyl}-pyrrolidine-1-carboxylic acid tert-butyl ester and (3R,4R)-3-({[4-ethyl-3-(3-methoxy-propoxy)-benzoyl]-isopropyl-amino}-methyl)-4(S)-{[methyl-(2-oxo-1,2,3,4-tetrahydro-quinoline-4-carbonyl)-amino]-methyl}-pyrrolidine-1-carboxylic acid tert-butyl ester are separated by chiral HPLC of the diastereoisomeric mixture (0.5 g) on a Chiralcel OD column (20 mM; 5×50 cm) using n-hexane/EtOH/MeOH 90:7.5:2.5 as eluent (flow 90 mL/min, UV detection 210 nm).

The starting materials of Examples 180 and 181 are prepared as follows:

The two diastereomers (3R,4R)-3-{[cyclopropyl-(tetrahydro-furan-3(R)-carbonyl)-amino]-methyl}-4-({[4-ethyl-3-(3-methoxy-propoxy)-benzoyl]-isopropyl-amino}-methyl)-pyrrolidine-1-carboxylic acid tert-butyl ester and (3R,4R)-3-{[cyclopropyl-(tetrahydro-furan-3(S)-carbonyl)-amino]-methyl}-4-({[4-ethyl-3-(3-methoxy-propoxy)-benzoyl]-isopropyl-amino}-methyl)-pyrrolidine-1-carboxylic acid tert-butyl ester are separated by chiral HPLC of the diastereoisomeric mixture (0.33 g) on a Chiralpak AD column (20 μM; 50×500 mm) using n-hexane/EtOH/MeOH 80:17.5:2.5 (flow rate: 110 mL/min, UV 210 nm).

The starting materials of Examples 182 and 183 are prepared as follows:

The two diastereomers (3R,4R)-3-{[cyclopropyl-(tetrahydro-pyran-3(R)-carbonyl)-amino]-methyl}-4-({[4-ethyl-3-(3-methoxy-propoxy)-benzoyl]-isopropyl-amino}-methyl)-pyrrolidine-1-carboxylic acid tert-butyl ester and (3R,4R)-3-{[cyclopropyl-(tetrahydro-pyran-3-carbonyl)-amino]-methyl}-4-({[4-ethyl-3-(3-methoxy-propoxy)-benzoyl]-isopropyl-amino}-methyl)-pyrrolidine-1-carboxylic acid tert-butyl ester are separated by chiral HPLC of the diastereoisomeric mixture (0.33 g) on a Chiralpak OD column (20 μM; 50×500 mm) using n-hexane/EtOH/MeOH 97:1.5:1.5 (flow rate: 120 mL/min, UV 210 nm).

The starting materials of Examples 184 and 185 are prepared as follows:

The two diastereomers (3R,4R)-3-{[cyclopropyl-cis-(4-hydroxy-cyclohexanecarbonyl)-amino]-methyl}-4-({[4-ethyl-3-(3-methoxy-propoxy)-benzoyl]-isopropyl-amino}-methyl)-pyrrolidine-1-carboxylic acid tert-butyl ester and (3R,4R)-3-{[cyclopropyl-trans-(4-hydroxy-cyclohexanecarbonyl)-amino]-methyl}-4-({[4-ethyl-3-(3-methoxy-propoxy)-benzoyl]-isopropyl-amino}-methyl)-pyrrolidine-1-carboxylic acid tert-butyl ester are separated by chiral HPLC of the diastereoisomeric mixture (0.32 g) on a Chiralpak OD column (20 μM; 5×50 cm) using n-hexane/EtOH/MeOH 97:1.5:1.5 as eluent (flow 120 mL/min, UV detection 210 nm).

The starting materials of Examples 186 and 187 are prepared as follows:

The two diastereomers (3R,4R)-3-({[4-ethyl-3-(3-methoxy-propoxy)-benzoyl]-isopropyl-amino}-methyl)-4-{[methyl-(tetrahydro-pyran-3(R)-carbonyl)-amino]-methyl}-pyrrolidine-1-carboxylic acid tert-butyl ester and (3R,4R)-3-({[4-ethyl-3-(3-methoxy-propoxy)-benzoyl]-isopropyl-amino}-methyl)-4-{[methyl-(tetrahydro-pyran-3(S)-carbonyl)-amino]-methyl}-pyrrolidine-1-carboxylic acid tert-butyl ester are separated by chiral HPLC of the diastereoisomeric mixture (0.28 g) on a Chiralcel AD-H column (30×250 cm) using a gradient 2-propanol/CO$_2$ (flow 130 mL/min, UV detection 220 nm).

EXAMPLE 188

N-{(3S,4S)-4-[(Cyclopropyl-phenylacetyl-amino)-methyl]-pyrrolidin-3-ylmethyl}-N-isopropyl-3-(3-methoxy-propoxy)-4-methyl-benzamide

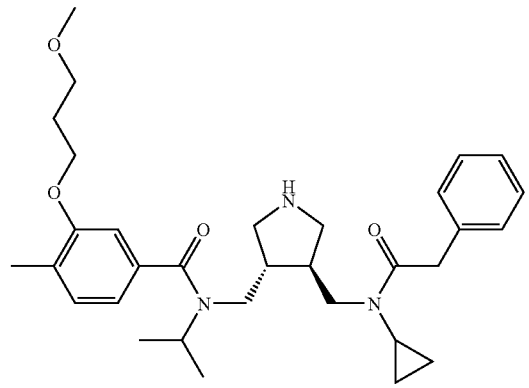

To a solution of (3R,4R)-3-[(cyclopropyl-phenylacetyl-amino)-methyl]-4-({[4-methyl-3-(3-methoxy-propoxy)-benzoyl]-isopropyl-amino}-methyl)-pyrrolidine-1-carboxylic acid tert-butyl ester (0.280 g, 0.44 mmol) in dioxane (3 mL), 4N HCl in dioxane (2.5 mL) is added, and the resulting solution is lyophilized to afford the corresponding hydrochloride salt. MS (LC-MS): 536.2 [M+H]$^+$; t$_R$ (HPLC, Nucleosil C-18HD (4×70 mm, 3 µm), 20-100% CH$_3$CN/H$_2$O/6 min, 100% CH$_3$CN/1.5 min; flow: 1 mL/min): 4.56 min.

The starting material is prepared in a similar manner as described in Example 149, reaction steps A to E, as follows:

A. (3S,4R)-3-(tert-Butyl-dimethyl-silanyloxymethyl)-4-({[4-methyl-3-(3-methoxy-propoxy)-benzoyl]-isopropyl-amino}-methyl)-pyrrolidine-1-carboxylic acid tert-butyl ester From (3S,4R)-3-(tert-butyl-dimethyl-silanyloxymethyl)-4-(isopropylamino-methyl)-pyrrolidine-1-carboxylic acid tert-butyl ester (5 g, 12.9 mmol), 4-methyl-3-(3-methoxy-propoxy)-benzoic acid (4.06 g, 18.1 mmol), BOPCl (4.6 g, 18.1 mmol) and triethylamine (7.2 mL, 51.7 mmol). TLC, Rf (AcOEt)=0.7. MS (LC-MS): 493 [M+H-Boc]$^+$.

B. (3R,4S)-3-({[4-Methyl-3-(3-methoxy-propoxy)-benzoyl]-isopropyl-amino}-methyl)-4-hydroxymethyl-pyrrolidine-1-carboxylic acid tert-butyl ester From (3S,4R)-3-(tert-butyl-dimethyl-silanyloxymethyl)-4-({[4-methyl-3-(3-methoxy-propoxy)-benzoyl]-isopropyl-amino}-methyl)-pyrrolidine-1-carboxylic acid tert-butyl ester (6.79 g, 11.5 mmol) and TBAF (5.42 g, 17.2 mmol) to give the title compound as yellow oil which was used in the next step without purification. TLC, Rf (AcOEt)=0.4. MS (LC-MS): 423 [M+H-tBu]$^+$; t$_R$ (HPLC, Macherey-Nagel Nucleosil C18 column, 10-100% CH3CN/H2O/5 min, 100% CH$_3$CN/3 min, CH$_3$CN and H2O containing 0.1% TFA, flow: 1.5 mUmin): 6.05 min.

C. (3R,4S)-3-({[4-Methyl-3-(3-methoxy-propoxy)-benzoyl]-isopropyl-amino}-methyl)-4-formyl-pyrrolidine-1-carboxylic acid tert-butyl ester From (3R,4S)-3-({[4-methyl-3-(3-methoxy-propoxy)-benzoyl]-isopropyl-amino}-methyl)-4-hydroxymethyl-pyrrolidine-1-carboxylic acid tert-butyl ester (5.7 g, 11.9 mmol) and Dess Martin Periodinane (5.1 g, 11.9 mmol) to give the title product as a yellow oil which was used in the next step without purification. TLC, Rf (AcOEt)=0.49.

D. (3R,4R)-3-({[4-Methyl-3-(3-methoxy-propoxy)benzoyl]-isopropyl-amino}-methyl)-4-cyclopropylaminomethyl-pyrrolidine-1-carboxylic acid tert-butyl ester From (3R,4S)-3-({[4-methyl-3-(3-methoxy-propoxy)-benzoyl]-isopropyl-amino}-methyl)-4-formyl-pyrrolidine-1-carboxylic acid tert-butyl ester (3 g, 6.29 mmol), cyclopropyl amine (0.395 mL, 6.92 mmol) and NaBHOAc$_3$ (1.87 g, 8.81 mmol) and purification by flash chromatography on silica gel (AcOEt/MeOH 100:0 to 85:15) to give the title compound as colorless oil. TLC, Rf (AcOEt)=0.63. MS (LC-MS): 518.3 [M+H]$^+$; t$_R$ (HPLC, Nucleosil C-18HD (4×70 mm, 3 µm), 20-100% CH$_3$CN/H$_2$O/6 min, 100% CH$_3$CN/1.5 min; flow: 1 mL/min): 5.37 min.

E. (3R,4R)-3-[(Cyclopropyl-phenylacetyl-amino)-methyl]-4-({[4-methyl-3-(3-methoxy-propoxy)-benzoyl]-isopropyl-amino}-methyl)-pyrrolidine-1-carboxylic acid tert-butyl ester From (3R,4R)-3-({[4-methyl-3-(3-methoxy-propoxy)-benzoyl]-isopropyl-amino}-methyl)-4-cyclopropylaminomethyl-pyrrolidine-1-carboxylic acid tert-butyl ester (0.3 g, 0.579 mmol), phenylacetyl chloride (0.092 mL, 0.695 mmol) and triethylamine (0.12 mL, 0.869 mmol) and purification by flash chromatography (c-hexane/AcOEt 1:1 to 0:1) to give the title compound as colorless oil. TLC, R$_f$ (AcOEt/c-hexane 4:1)=0.15. MS (LC-MS): 610.3 [M+H]$^+$; (LC-MS Waters Symmetry C18, 2.1×30 mm, 20-100% CH$_3$CN/5 min): 4.63 min.

3-(3-Methoxy-propoxy)-4-methyl-benzoic acid

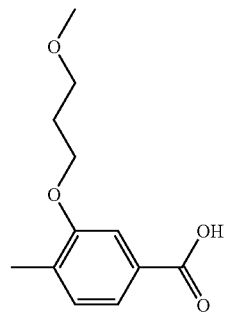

a. 3-Hydroxy-4-methyl-benzoic acid methyl ester

To a solution of 3-hydroxy-4-methyl-benzoic acid (5 g, 32.8 mmol) in MeOH (100 mL) cc H$_2$SO$_4$ (1 mL) is added. The solution is refluxed for 14 h, then concentrated to about 30 mL and poured into water. The aqueous layer is extracted with ether (50 mL×4) and the combined organic extracts are neutralized with a saturated aqueous solution of NaHCO$_3$ (50 mL×2), washed with brine (50 mL), dried over Na$_2$SO$_4$, filtered and concentrated to give the title compound as a white powder. TLC, R$_f$ (hexane/AcOEt 2:1 )=0.55. $^1$H-NMR (CDCl$_3$, 300 MHz): δ=2.3 (s, 3H), 3.9 (s, 3H), 7.15 (d, 1H), 7.5 (d, 1H), 7.6 (s, 1H) ppm.

b. 3-(3-Methoxy-propoxy)-4-methyl-benzoic acid methyl ester

A solution of 3-hydroxy-4-methyl-benzoic acid methyl ester (7.7 g, 32.43 mmol), potassium carbonate (6.72 g, 48.65 mmol) and 1-iodo-3-methoxy propane (7.14 g, 35.68 mmol) in acetonitrile (125 mL) is stirred at reflux for 26 h. The solvent is concentrated under reduced pressure, H$_2$O (100 mL) is added, and the aqueous layer is extracted with ether (50 mL×4). The combined organic extracts are washed with brine, dried over anhydrous sodium sulfate and concentrated under reduced pressure to afford the title which is used without further purification in the next step. TLC, Rf (hexane/AcOEt 2:1)=0.65. $^1$H-NMR (CDCl$_3$, 300 MHz): δ=2.10 (p, 2H), 2.3 (s, 3H), 3.38 (s, 3H), 3.62 (t, 2H), 3.9 (s, 3H), 4.15 (t, 2H), 7.15 (d, 1H), 7.45 (s, 1H), 7.55 (d, 1H) ppm.

c. 3-(3-Methoxy-propoxy)-4-methyl-benzoic acid

A solution of 3-(3-methoxy-propoxy)-4-methyl-benzoic acid methyl ester (7.12 g, 32.86 mmol) and NaOH (1 N in water, 100 mL, 100 mmol) in EtOH (100 mL) is refluxed for 1 h. The reaction mixture is allowed to reach RT, and the solvent is concentrated under reduced pressure. The residue is dissolved in water (200 mL) and washed with ether (50 mL×3). The pH is adjusted to 2 by addition of cc HCl and the aqueous layer extracted with AcOEt (150 mL×2). The combined organic extracts are dried over $Na_2SO_4$, filtered and concentrated in vacuo. The crude material is recrystallized in diethyl ether/hexane to afford the desired title product. TLC, $R_f$ (hexane/AcOEt 2:1)=0.15. MS (LC-MS): 224.0 [M–H]$^+$. $^1$H-NMR (CDCl$_3$, 300 MHz): δ=2.10 (p, 2H), 2.3 (s, 3H), 3.38 (s, 3H), 3.62 (t, 2H), 4.15 (t, 2H), 7.2 (d, 1H), 7.55 (s, 1H), 7.65 (d, 1H) ppm.

The following Examples are prepared according to the procedures described above for Example 188:

TABLE 6

| Example | configuration | structure | [M + H]$^+$ | $t_R$ (HPLC) |
|---|---|---|---|---|
| 189 | (3S, 4S) | 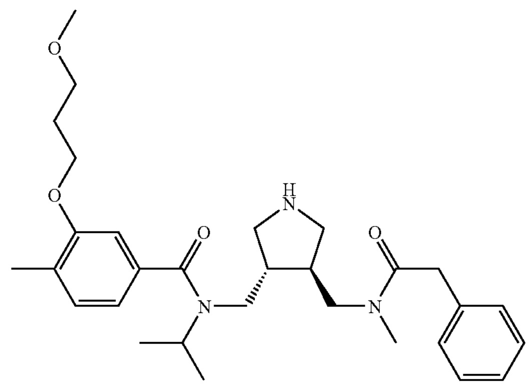 | 510.2 | 4.21$^a$ |
| 190 | (3S, 4S) | 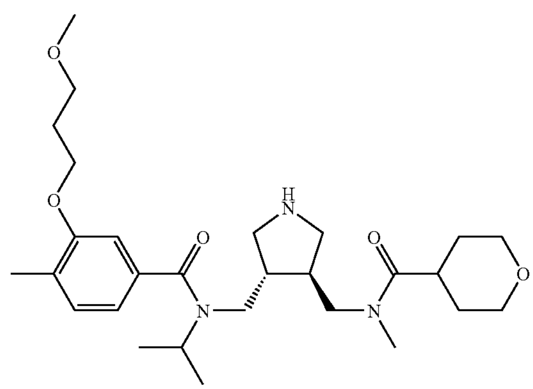 | 504.4 | 4.45$^a$ |
| 191 | (3S, 4S) | 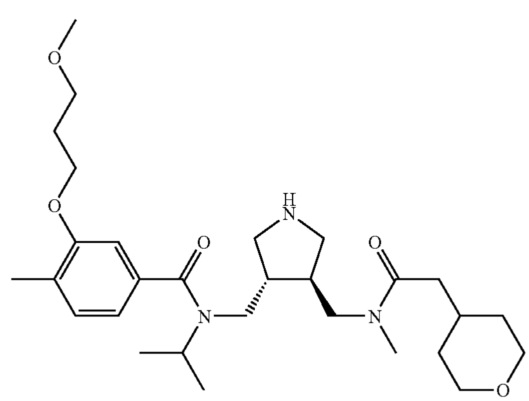 | 518.3 | 4.47$^a$ |

TABLE 6-continued

| Example | configuration | structure | [M + H]⁺ | t_R (HPLC) |
|---------|---------------|-----------|----------|------------|
| 192 | (3S, 4S) | 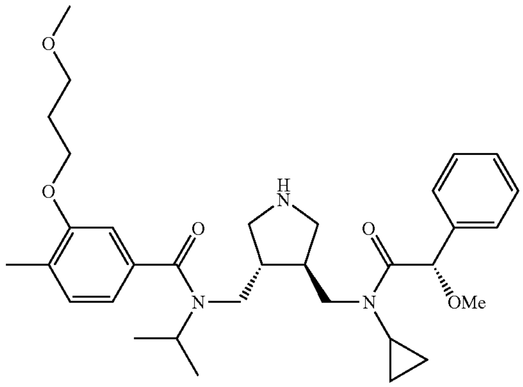 | 566.2 | 4.92ᵃ |
| 193 | (3S, 4S) | 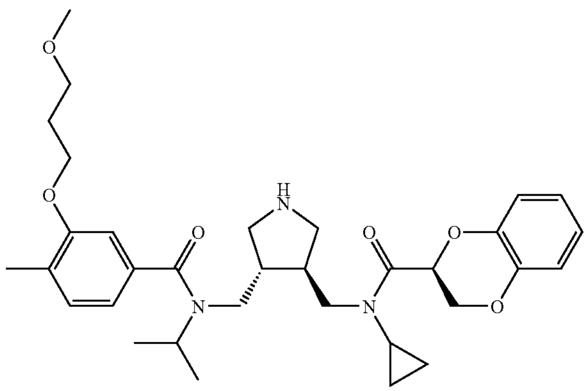 | 580.3 | 5.14ᵃ |
| 194 | (3S, 4S) | 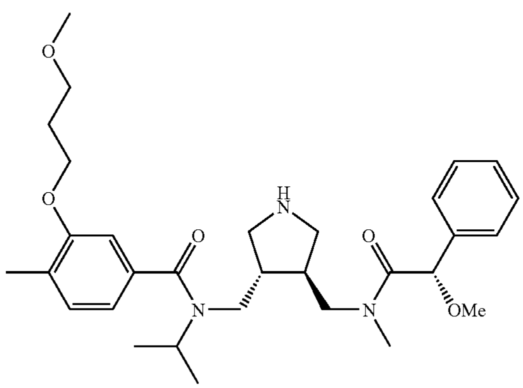 | 540.3 | 4.81ᵃ |
| 195 | (3S, 4S) | 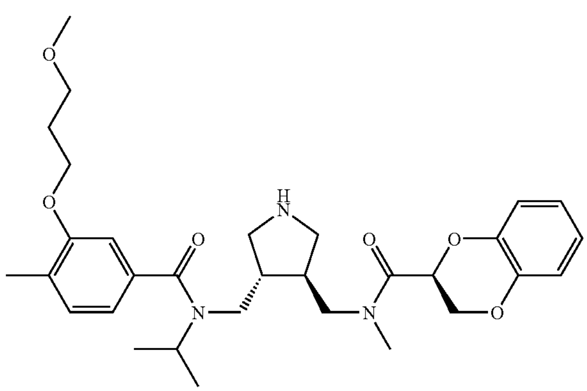 | 554.2 | 4.96ᵃ |

TABLE 6-continued

| Example | configuration | structure | [M + H]+ | t_R (HPLC) |
|---|---|---|---|---|
| 196 | (3S, 4S) | 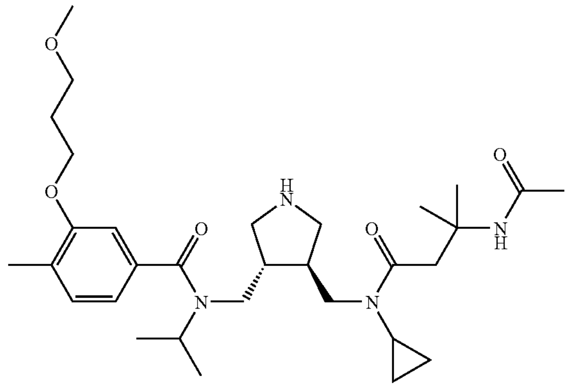 | 559.3 | 4.69[a] |
| 197 | (3S, 4S) | 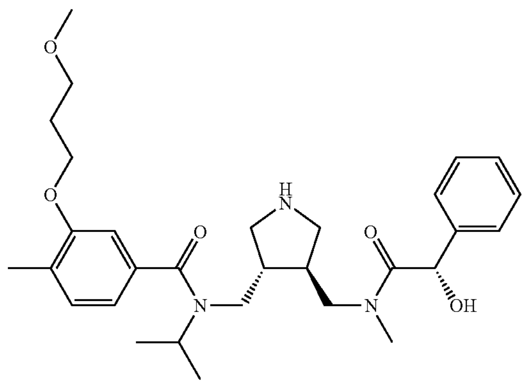 | 526.3 | 4.71[a] |
| 198 | (3S, 4S) | 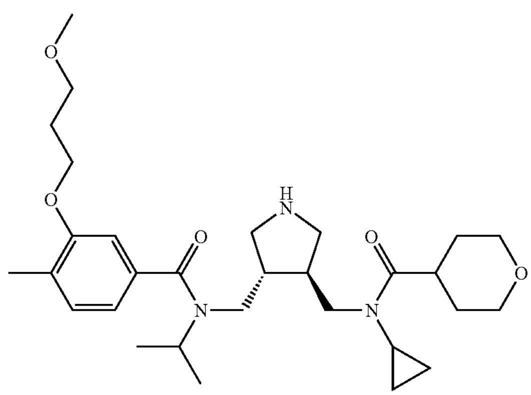 | 530.3 | 4.64[a] |
| 199 | (3S, 4S) | 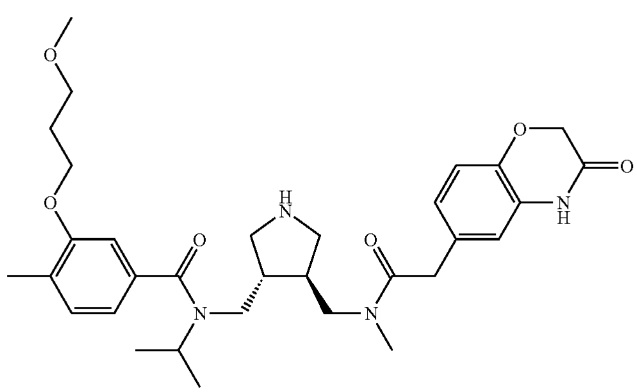 | 581.2 | 2.45[b] |

TABLE 6-continued
| Example | configuration | structure | [M + H]+ | $t_R$ (HPLC) |
|---|---|---|---|---|
| 200 | (3S, 4S) | 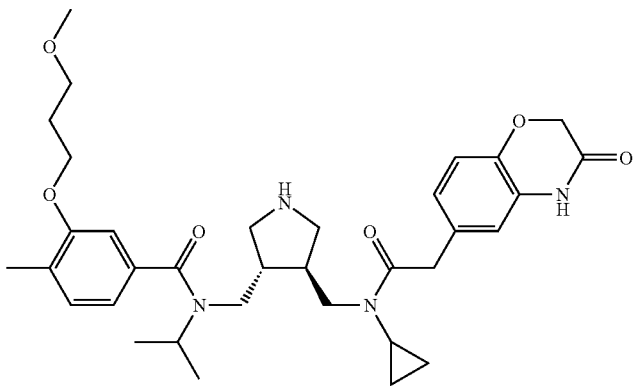 | 607.2 | 2.60[b] |
| 201 | (3S, 4S) | 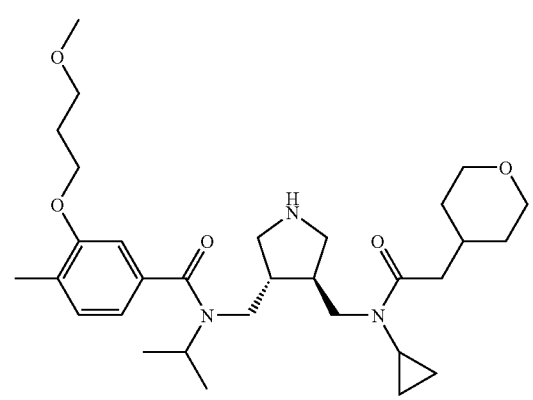 | 544.2 | 2.30[b] |
| 202 | (3S, 4S) | 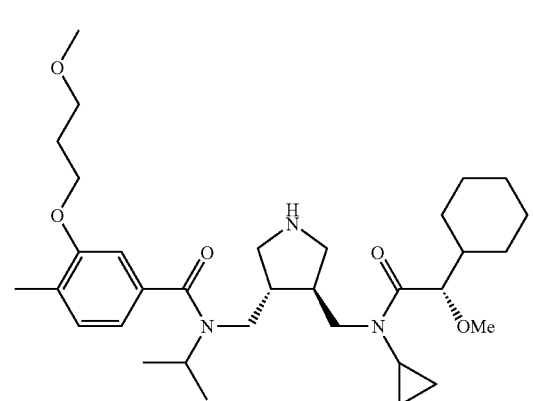 | 572.3 | 3.05[c] |
| 203 | (3S, 4S) | 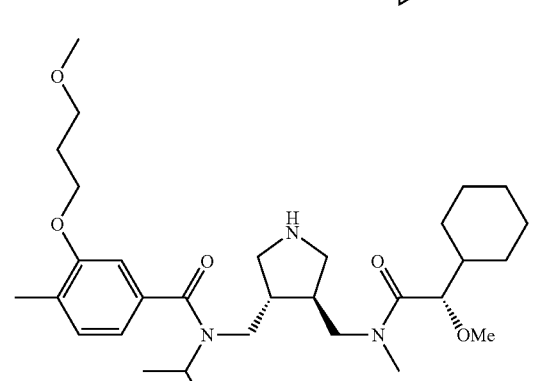 | 546.3 | 3.02[c] |

TABLE 6-continued
| Example | configuration | structure | [M + H]+ | tR (HPLC) |
|---|---|---|---|---|
| 204 | (3S, 4S) | 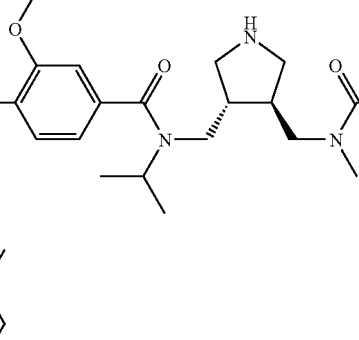 | 492.3 | 2.46[b] |
| 205 | (3S, 4S) | 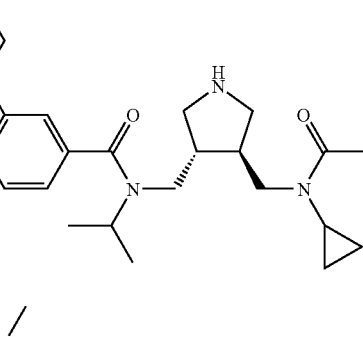 | 585.3 | 2.47[b] |
| 206 | (3S, 4S) | 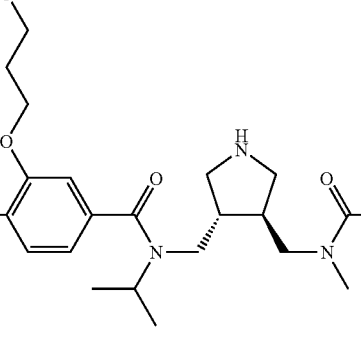 | 506.4 | 2.82[c] |
| 207 | (3S, 4S) | 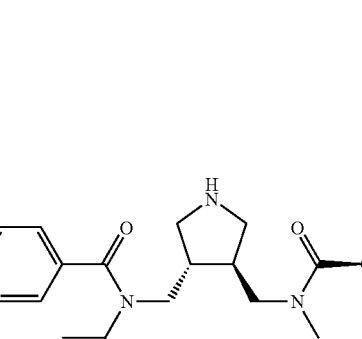 | 518.3 | 2.67[c] |

TABLE 6-continued

| Example | configuration | structure | [M + H]+ | tR (HPLC) |
|---|---|---|---|---|
| 208 | (3S, 4S) | 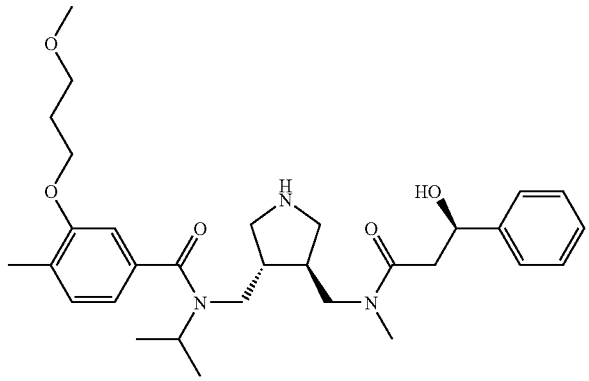 | 540.3 | 2.57[b] |
| 209 | (3S, 4S) | 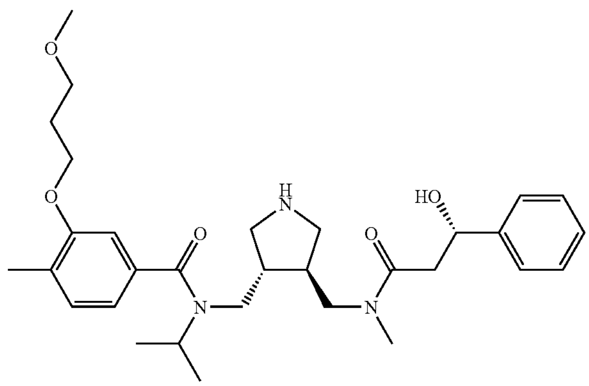 | 540.3 | 2.61[b] |
| 210 | (3S, 4S) | 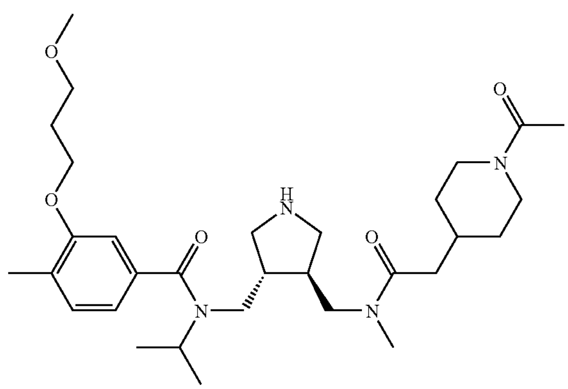 | 559.2 | 1.87[b] |
| 211 | (3S, 4S) | 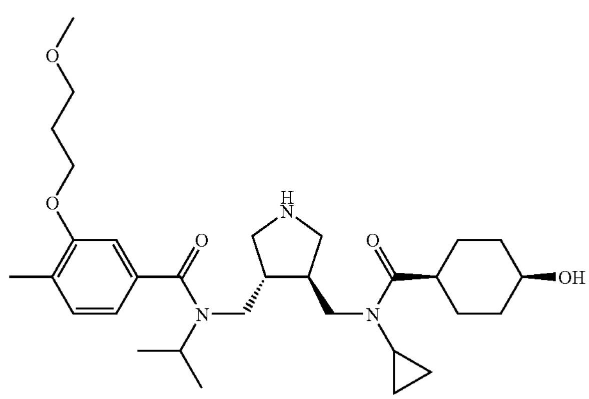 | 544.3 | 2.79[c] |

TABLE 6-continued

| Example | configuration | structure | [M + H]+ | $t_R$ (HPLC) |
|---|---|---|---|---|
| 212 | (3S, 4S) | 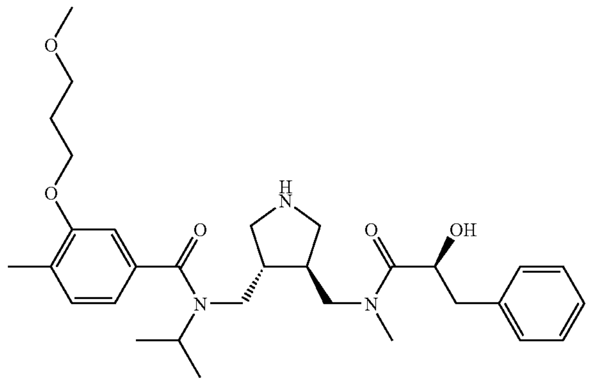 | 540.3 | 2.66[b] |
| 213 | (3S, 4S) | 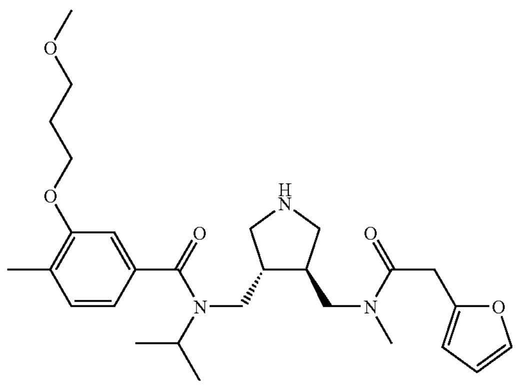 | 500.2 | 2.52[b] |
| 214 | (3S, 4S) | 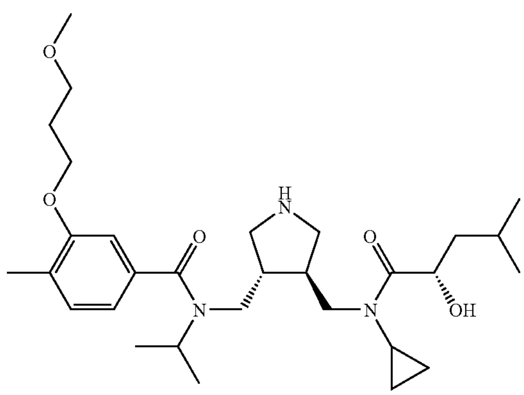 | 532.3 | 2.89[c] |
| 215 | (3S, 4S) | 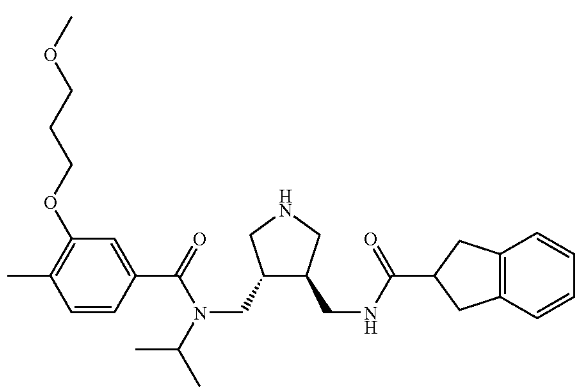 | 522.2 | 4.45[e] |

TABLE 6-continued

| Example | configuration | structure | [M + H]+ | tR (HPLC) |
|---|---|---|---|---|
| 216 | (3S, 4S) | 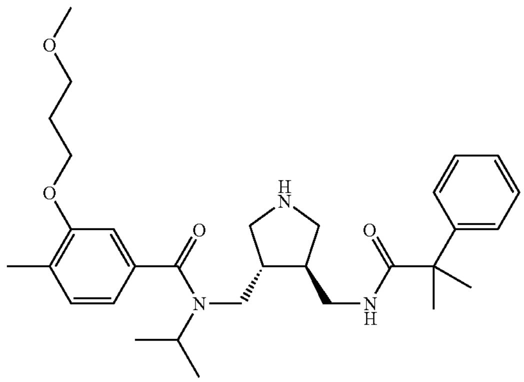 | 524.2 | 4.53e |
| 217 | (3S, 4S) | 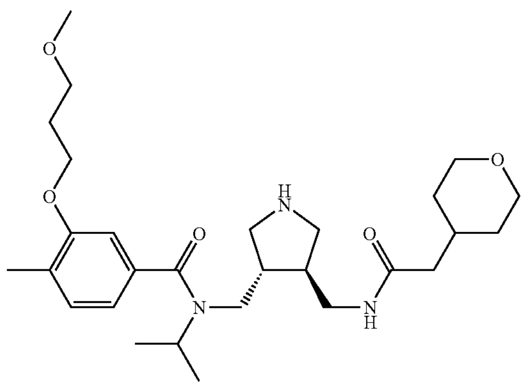 | 504.2 | 3.53e |
| 218 | (3S, 4S) | 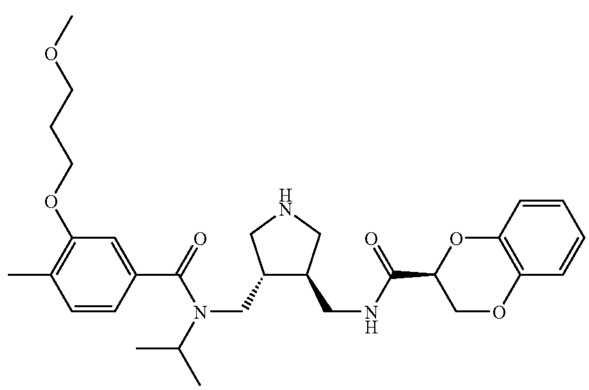 | 540.2 | 4.94d |
| 219 220 | (3S, 4S) | | 518.3 | 3.97e 3.99e |

TABLE 6-continued

| Example | configuration | structure | [M + H]⁺ | $t_R$ (HPLC) |
|---|---|---|---|---|
| 221<br>222 | (3S, 4S) | 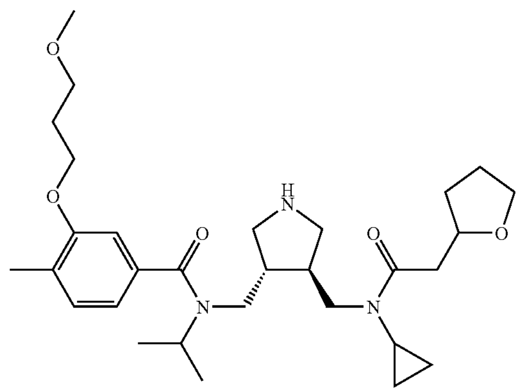 | 530.2 | 4.07$^e$<br>4.09$^e$ |
| 223<br>224 | (3S, 4S) | 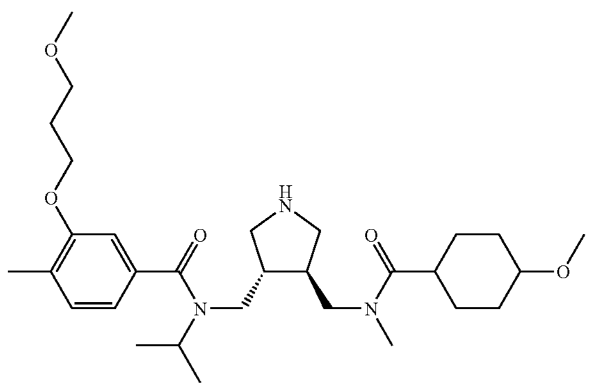 | 532.2 | 3.92$^e$<br>4.08$^e$ |
| 225<br>226 | (3S, 4S) | 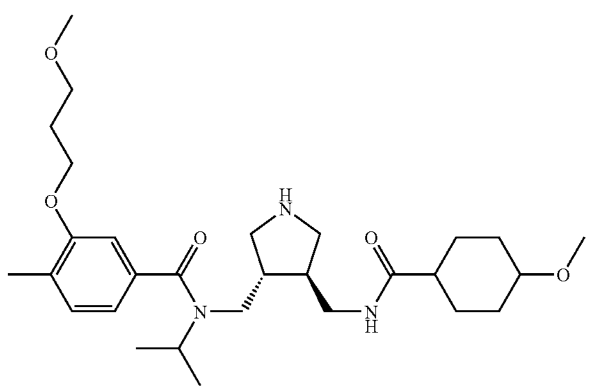 | 518.2 | 3.76$^e$<br>3.90$^e$ |

$^a$ $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
$^b$ $t_R$ (Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min).
$^c$ $t_R$ (Waters Symmetry C18 column, 5-95% CH₃CN/H₂O/3.5 min, 95% CH₃CN/H₂O, 2 min, CH₃CN and H₂O containing 0.1% TFA, flow: 0.6 mL/min).
$^d$ $t_R$ (HPLC, Nucleosil C18HD column, 5-100% CH₃CN/H₂O/6 min, 100% CH₃CN/2 min, CH₃CN and H₂O containing 0.1% TFA, flow: 1 mL/min).
$^e$ $t_R$ (HPLC, Nucleosil C18HD column, 20-100% CH₃CN/H₂O/6 min, 100% CH₃CN/2 min, CH₃CN and H₂O containing 0.1% TFA, flow: 1 mL/min).

The starting materials of the title compounds in Table 6 are prepared as follows:

(3R,4R)-3-Aminomethyl-4-({isopropyl-[3-(3-methoxy-propoxy)-4-methyl-benzoyl]-amino}-methyl)-pyrrolidine-1-carboxylic acid tert-butyl ester According to the procedure described for Example 130/reaction step C, by hydrogenation of (3S,4R)-3-azidomethyl-4-({isopropyl-[3-(3-methoxy-propoxy)-4-methyl-benzoyl]-amino}-methyl)-pyrrolidine-1-carboxylic acid tert-butyl ester (3.68 g, 7.31 mmol), dissolved in MeOH (80 mL), in the presence of Pd/C 10% (1.0 g; Engelhard 4505) at room temperature under atmospheric pressure to give, after filtration and drying in vacuo, the title compound as oil. MS: 478.2 [M+H]⁺. $t_R$ (HPLC, Nucleosil C18HD column, 20-100% CH₃CN/H₂O/6 min, 100% CH₃CN/2 min, CH₃CN and H₂O containing 0.1% TFA, flow: 1 mL/min): 4.28 min.

a. (3R,4S)-3-({Isopropyl-[3-(3-methoxy-propoxy)-4-methyl-benzoyl]-amino}-methyl)-4-methanesulfonyloxymethyl-pyrrolidine-1-carboxylic acid tert-butyl ester: prepared from (3S,4R)-3-hydroxymethyl-4-({isopropyl-[3-

(3-methoxy-propoxy)-4-methyl-benzoyl]-amino}-methyl)-pyrrolidine-1-carboxylic acid tert-butyl ester (3.80 g, 7.94 mmol), methane sulfonylchloride (0.717 mL, 9.13 mmol) and NEt$_3$ (3.32 mL, 23.8 mmol) in CH$_2$Cl$_2$ (50 mL) similar to the procedure described for Example 130/reaction step A, to give the title compound as yellowish oil. TLC, R$_f$ (hexane/AcOEt 1:3)=0.21.

b. (3S,4R)-3-Azidomethyl-4-({isopropyl-[3-(3-methoxy-propoxy)-4-methyl-benzoyl]-amino}-methyl)-pyrrolidine-1-carboxylic acid tert-butyl ester: prepared from (3R,4S)-3-({isopropyl-[3-(3-methoxy-propoxy)-4-methyl-benzoyl]-amino}-methyl)-4-methane-sulfonyloxymethyl-pyrrolidine-1-carboxylic acid tert-butyl ester (4.42 g, 7.94 mmol) and NaN$_3$ (2.09 g, 31.8 mmol) in DMF (40 mL) similar to the procedure described for Example 130/reaction step B, and purification by flash chromatography on silica gel (hexane/AcOEt 1:1) to give the title compound as oil. TLC, R$_f$ (hexane/AcOEt 1:3)=0.45. MS: 504.2 [M+H]$^+$. t$_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 5.65 min.

(3R,4R)-3-({[4-Methyl-3-(3-methoxy-propoxy)-benzovyl]-isopropyl-amino}-methyl)-4-methylaminomethyl-pyrrolidine-1-carboxylic acid tert-butyl ester In a similar manner as described in Example 9 for the reaction step J, the following starting materials is prepared from (3R,4S)-3-({[4-methyl-3-(3-methoxy-propoxy)-benzoyl]-isopropyl-amino}-methyl)-4-formyl-pyrrolidine-1-carboxylic acid tert-butyl ester (prepared under C in example 190) (2 g, 4.2 mmol), 2N solution of methylamine in MeOH (10.5 mL, 21 mmol) and NaBH$_4$ (0.318 g, 8.40 mmol) and purification by flash chromatography on silica gel (AcOEt/MeOH 90:10, then AcOEt/MeOH/NH$_4$OH 89:10:1) to give a colorless oil. MS: 492.1 [M+H]$^+$.

The starting materials of Examples 219 and 220 are prepared as follows:

The two diastereomers (3R,4R)-3-({isopropyl-[3-(3-methoxy-propoxy)-4-methyl-benzoyl]-amino}-methyl)-4-{[methyl-(2-tetrahydro-pyran-2(R)-yl-acetyl)-amino]-methyl}-pyrrolidine-1-carboxylic acid tert-butyl ester and (3R,4R)-3-({isopropyl-[3-(3-methoxy-propoxy)-4-methyl-benzoyl]-amino}-methyl)-4-{[methyl-(2-tetrahydro-pyran-2(S)-yl-acetyl)-amino]-methyl}-pyrrolidine-1-carboxylic acid tert-butyl ester are separated by chiral HPLC of the diastereoisomeric mixture (0.59 g) on a Chiralpak AD column (20 µM; 5×50 cm) using n-hexane/isopropanol 8:2, containing 0.1% TFA, as eluent (flow 100 mL/min, UV detection 210 nm).

The starting materials of Examples 221 and 222 are prepared as follows:

The two diastereomers (3R,4R)-3-{[cyclopropyl-(2-tetrahydro-furan-2(R)-yl-acetyl)-amino]-methyl}-4-({isopropyl-[3-(3-methoxy-propoxy)-4-methyl-benzoyl]-amino}-methyl)-pyrrolidine-1-carboxylic acid tert-butyl ester and (3R,4R)-3-{[cyclopropyl-(2-tetrahydro-furan-2(S)-yl-acetyl)-amino]-methyl}-4-({isopropyl-[3-(3-methoxy-propoxy)-4-methyl-benzoyl]-amino}-methyl)-pyrrolidine-1-carboxylic acid tert-butyl ester are separated by chiral HPLC of the diastereoisomeric mixture (0.33 g) on a Chiralpak aD column (20 µM; 5×50 cm) using n-hexane/EtOH/MeOH 80:15:15 as eluent (flow 120 mL/min, UV detection 210 nm).

The starting materials of Examples 223 and 224 are prepared as follows:

The two diastereomers (3R,4R)-3-({isopropyl-[3-(3-methoxy-propoxy)-4-methyl-benzoyl]-amino}-methyl)-4-{[cis-(4-methoxy-cyclohexanecarbonyl)-methyl-amino]-methyl}-pyrrolidine-1-carboxylic acid tert-butyl ester and (3R,4R)-3-({isopropyl-[3-(3-methoxy-propoxy)-4-methyl-benzoyl]-amino}-methyl)-4-{[trans-(4-methoxy-cyclohexanecarbonyl)-methyl-amino]-methyl}-pyrrolidine-1-carboxylic acid tert-butyl ester are separated by chiral HPLC of the diastereoisomeric mixture (0.50 g) on a Chiralpak OD (20 µM; column 5×50 cm) using n-hexane/EtOH/MeOH 97:1.5:1.5 as eluent (flow 120 mL/min, UV detection 210 nm).

The starting materials of Examples 225 and 226 are prepared as follows:

The two diastereomers (3R,4R)-3-({isopropyl-[3-(3-methoxy-propoxy)-4-methyl-benzoyl]-amino}-methyl)-4-{[cis-(4-methoxy-cyclohexanecarbonyl)-amino]-methyl}-pyrrolidine-1-carboxylic acid tert-butyl ester and (3R,4R)-3-({isopropyl-[3-(3-methoxy-propoxy)-4-methyl-benzoyl]-amino}-methyl)-4-{[trans-(4-methoxy-cyclohexanecarbonyl)-amino]-methyl}-pyrrolidine-1-carboxylic acid tert-butyl ester are separated by chiral HPLC of the diastereoisomeric mixture (0.29 mg) on a Chiralpak OD (20 µM; column 5×50 cm) using n-hexane/EtOH/MeOH 97:1.5:1.5 as eluent (flow 120 mL/min, UV detection 210 nm).

EXAMPLE 227

1-(3-Methoxy-propyl)-1H-indole-6-carboxylic acid {(3S,4S)-4-[(cyclopropyl-phenylacetyl-amino)-methyl]-pyrrolidin-3-ylmethyl}-isopropyl-amide

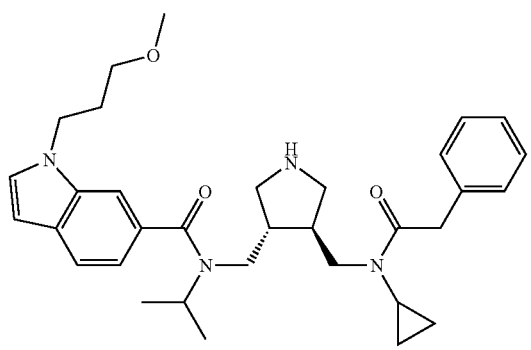

To a solution of (3R,4R)-3-[(cyclopropyl-phenylacetyl-amino)-methyl]-4-({isopropyl-[1-(3-methoxy-propyl)-1H-indole-6-carbonyl]-amino}-methyl)-pyrrolidine-1-carboxylic acid tert-butyl ester (0.15 g, 0.232 mmol) in dioxane (3 mL), 4N HCl in dioxane (1 mL) is added, and the resulting solution is lyophilized to afford the corresponding hydrochloride salt. MS (LC-MS): 545.2 [M+H]$^+$; t$_R$ (HPLC, Waters Symmetry C18, 3.5 um, 2.1×50 mm, 20-95% CH$_3$CN/H$_2$O/ 3.5 min, 95% CH$_3$CN/2 min, CH$_3$CN and H$_2$O containing 0.1% HCOOH, flow: 0.6 mL/min): 2.46 min.

The starting material is prepared in a similar manner as described in Example 149, reaction steps A to E, as follows:

A. (3S,4R)-3-(tert-Butyl-dimethyl-silanyloxymethyl)-4-({isopropyl-[1-(3-methoxy-propyl)-1H-indole-6-carbonyl]-amino}-methyl)-pyrrolidine-1-carboxylic acid tert-butyl ester From (3S,4R)-3-(tert-butyl-dimethyl-silanyloxymethyl)-4-(isopropylamino-methyl)-pyrrolidine-1-carboxylic acid tert-butyl ester (5 g, 12.9 mmol), 1-(3-methoxy-propyl)-1H-indole-6-carboxylic acid (4.22 g, 18.1 mmol), BOPCl (4.6 g, 18.1 mmol) and triethylamine (7.2 mL, 51.7 mmol). TLC, Rf (AcOEt)=0.32.

B. (3S,4R)-3-Hydroxymethyl-4-({isopropyl-[1-(3-methoxy-propyl)-1H-indole-6-carbonyl]-amino}-methyl)-pyrrolidine-1-carboxylic acid tert-butyl ester From (3S,4R)-3-(tert-butyl-dimethyl-silanyloxymethyl)-4-({isopropyl-[1-(3-methoxy-propyl)-1H-indole-6-carbonyl]-amino}-methyl)-pyrrolidine-1-carboxylic acid tert-butyl ester (6.79 g, 11.3 mmol) and TBAF (5.35 g, 17.0 mmol) and purification by flash chromatography on silivca gel (chexane/AcOEt 50:50 to 0:100 to AcOEt/MeOH 90:10). TLC, Rf (AcOEt)=0.34. MS (LC-MS): 432 [M+H-tBu]$^+$; t$_R$ (HPLC, Macherey-Nagel Nucleosil C18 column, 10-100% CH3CN/H2O/15 min, 100% CH$_3$CN/3 min, CH$_3$CN and H$_2$O containing 0.1% TFA, flow: 1.5 mL/min): 5.73 min.

C. (3S,4R)-3-Formyl-4-({isopropyl-[1-(3-methoxy-propyl)-1H-indole-6-carbonyl]-amino}-methyl)-pyrrolidine-1-carboxylic acid tert-butyl ester From (3S,4R)-3-hydroxymethyl-4-({isopropyl-[1-(3-methoxy-propyl)-1H-indole-6-carbonyl]-amino}-methyl)-pyrrolidine-1-carboxylic acid tert-butyl ester (4.3 g, 8.82 mmol) and Dess Martin Periodinane (4.11 g, 9.70 mmol) to give the title product as a yellow oil which was used in the next step without purification.

D. (3R,4R)-3-Cyclopropylaminomethyl-4-({isopropyl-[1-(3-methoxy-propyl)-1H-indole-6-carbonyl]-amino}-methyl)-pyrrolidine-1-carboxylic From (3S,4R)-3-formyl-4-({isopropyl-[1-(3-methoxy-propyl)-1H-indole-6-carbonyl]-amino}-methyl)-pyrrolidine-1-carboxylic acid tert-butyl ester (2 g, 4.12 mmol), cyclopropyl amine (0.318 mL, 4.53 mmol) and NaBHOAc$_3$ (1.2 g, 5.77 mmol) and purification by flash chromatography on silica gel (CH$_2$Cl$_2$/MeOH 95:5 to CH$_2$Cl$_2$/MeOH/NH$_4$OH 90:10:1). MS (LC-MS): 527.3 [M+H]$^+$; t$_R$ (Waters Symmetry C18, 3.5 um, 2.1×50 mm, 20-95% CH$_3$CN/H$_2$O/3.5 min, 95% CH$_3$CN/2 min, CH$_3$CN and H$_2$O containing 0.1% HCOOH, flow: 0.6 mL/min): 2.45 min.

E. (3R,4R)-3-[(Cyclopropyl-phenylacetyl-amino)-methyl]-4-({isopropyl-[1-(3-methoxy-propyl)-1H-indole-6-carbonyl]-amino}-methyl)-pyrrolidine-1-carboxylic acid tert-butyl ester From (3R,4R)-3-cyclopropylaminomethyl-4-({isopropyl-[1-(3-methoxy-propyl)-1H-indole-6-carbonyl]-amino}-methyl)-pyrrolidine-1-carboxylic (0.25 g, 0.475 mmol), phenylacetyl chloride (0.069 mL, 0.522 mmol) and triethylamine (0.079 mL, 0.569 mmol) and purification by preparative HPLC (C18-ODB-5 µm, 19×50 mm, eluent: CH$_3$CN/H$_2$O+0.1% HCOOH). MS (LC-MS): 645.3 [M+H]$^+$; t$_R$ (HPLC, Waters Symmetry C18, 3.5 um, 2.1×50 mm, 20-95% CH$_3$CN/H$_2$O/3.5 min, 95% CH$_3$CN/2 min, CH$_3$CN and H$_2$O containing 0.1% HCOOH, flow: 0.6 mL/min): 4.11 min.

1-(3-Methoxy-propyl)-1H-indole-6-carboxylic acid

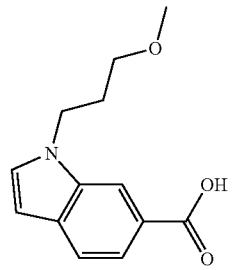

a. 1-(3-Methoxy-propyl)-1H-indole-6-carboxylic acid methyl ester

To a solution of methyl indole-6-carboxylate (5.0 g, 28.5 mmol) in DMF (25 mL) is added under nitrogen, NaH-60% dispersion in oil (1.25 g, 31.3 mmol), the mixture is heated at 60° C. for 2 h, cooled to RT and 1-bromo-3-methoxypropane (8.7 g, 57.0 mmol) is added. The mixture is further stirred at 60° C. overnight. The crude mixture is poured into an aqueous solution of NH$_4$Cl and diluted with CH$_2$Cl$_2$. The layers are separated and the aqueous one extracted twice with CH$_2$Cl$_2$. The combined organic extracts are washed with water, dried over Na$_2$SO$_4$, filtered and concentrated to give the title product. MS (LC-MS): 248.0 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 5.69 min.

b. 1-(3-Methoxy-propyl)-1H-indole-6-carboxylic acid

To a solution of 1-(3-methoxy-propyl)-1H-indole-6-carboxylic acid methyl ester (7 g, 28.5 mmol) in MeOH (50 mL) is added NaOH 2N (28.5 mL), and the mixture is stirred for 3 h. The solvent is concentrated and the remaining aqueous residue is acidified with HCl 1N and extracted twice with CH$_2$Cl$_2$. The combined organic extracts are dried over Na$_2$SO$_4$, filtered and concentrated to give title product. TLC, R$_f$ (c-hexane/AcOEt 2:1)=0.25. MS (LC-MS): 232.0 [M+H]$^+$, t$_R$ (HPLC, Macherey-Nagel Nucleosil C18 column, 10-100% CH$_3$CN/H$_2$O/5 min, 100% CH$_3$CN/3 min, flow: 1.5 ml/min): 5.04 min.

The following Example is prepared according to the procedures described above for Example 227:

TABLE 7

| Example | configuration | structure | [M + H]+ | t_R (HPLC) |
|---------|---------------|-----------|----------|------------|
| 228 | (3S, 4S) | | 519.3 | 2.32 | t_R (HPLC, Waters Symmetry C18, 3.5 um, 2.1 × 50 mm, 20-95% CH₃CN/H₂O/3.5 min, 95% CH₃CN/2 min, CH₃CN and H₂O containing 0.1% HCOOH, flow: 0.6 mL/min).

The starting material of the title compound in Table 7 is prepared as follows:

(3R,4R)-3-({Isopropyl-[1-(3-methoxy-propyl)-1H-indole-6-carbonyl]-amino}-methyl)-4-methylaminomethyl-pyrrolidine-1-carboxylic acid tert-butyl ester In a similar manner as described in Example 9 for the reaction step J, the following starting material is prepared from (3S,4R)-3-formyl-4-({isopropyl-[1-(3-methoxy-propyl)-1H-indole-6-carbonyl]-amino}-methyl)-pyrrolidine-1-carboxylic acid tert-butyl ester (2 g, 4.12 mmol) (prepared under C in example 229), 2N solution of methylamine in MeOH (10.3 mL, 20.6 mmol) and NaBH₄ (0.156 g, 4.12 mmol) and purification by flash chromatography on silica gel (CH₂Cl₂/MeOH 95:5 to CH₂Cl₂/MeOH/NH₄OH 90:10:1). MS (LC-MS): 501.3 [M+H]+; t_R (Waters Symmetry C18, 3.5 um, 2.1×50 mm, 20-95% CH₃CN/H₂O/3.5 min, 95% CH₃CN/2 min, CH₃CN and H₂O containing 0.1% HCOOH, flow: 0.6 mL/min): 2.40 min.

The following Examples are prepared according to the procedures described above for Examples 227, 233 and 282 using (3R,4R)-3-cyclopropylaminomethyl-4-({cyclopropyl-[4-methoxy-3-(3-methoxy-propoxy)-benzoyl]-amino}-methyl)-pyrrolidine-1-carboxylic acid tert-butyl ester:

TABLE 8

| Example | configuration | structure | [M + H]+ | t_R (HPLC) |
|---------|---------------|-----------|----------|------------|
| 229 | (3S, 4S) | 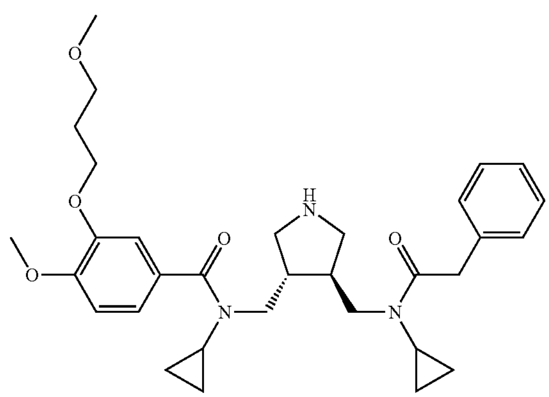 | 550 | 3.86 |

TABLE 8-continued

| Example | configuration | structure | [M + H]⁺ | t$_R$ (HPLC) |
|---|---|---|---|---|
| 230 | (3S, 4S) | 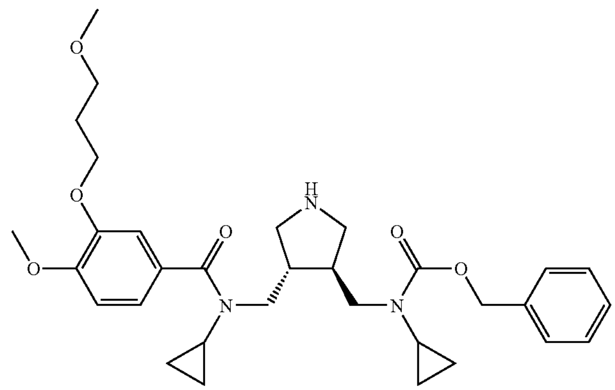 | 565.9 | 5.16 |
| 231 | (3S, 4S) | 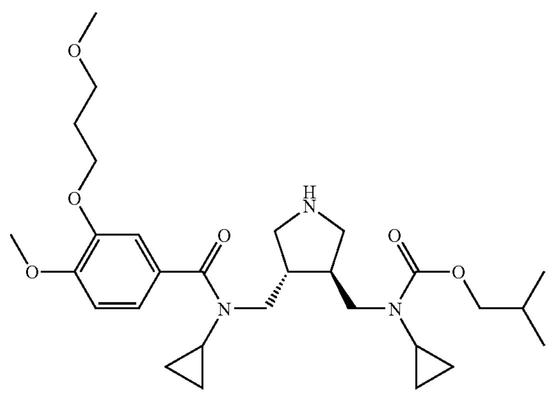 | 532 | 5.23 |
| 232 | (3S, 4S) | | 560.2 | 3.33 | t$_R$ (HPLC, Nucleosil C-18HD, 20-100% CH$_3$CN/H$_2$O/6 min, 100% CH$_3$CN/1.5 min, flow: 1 ml/min).

The starting material of the title compounds in Table 8 is prepared as follows:

(3R,4R)-3-Cyclopropylaminomethyl-4-({cyclopropyl-[4-methoxy-3-(3-methoxy-propoxy)-benzoyl]-amino}-methyl)-pyrrolidine-1-carboxylic acid tert-butyl ester In a similar manner as described in Example 149 for the reaction step D, the following starting material is prepared from (3R,4S)-3-({cyclopropyl-[4-methoxy-3-(3-methoxy-propoxy)-benzoyl]-amino}-methyl)-4-formyl-pyrrolidine-1-carboxylic acid tert-butyl ester (1.79 g, 3.65 mmol) (prepared according to example 9 using cyclopropyl amine instead of isopropyl amine under F), cyclopropyl amine (0.287 mL, 4.01 mmol) and NaBHOAc$_3$ (1.14 g, 5.11 mmol) to give the title compound which is used in the next steps without further purification. TLC, R$_f$ (CH$_2$Cl$_2$/AcOEt 9:1)= 0.35. MS (LC-MS): 532.0 [M+H]$^+$.

EXAMPLE 233

Cyclopropyl-[(3S*,4S*)4-({isopropyl-[4-methoxy-3-(3-methoxy-propoxy)-benzoyl]-amino}-methyl)-pyrrolidin-3-ylmethyl]-carbamic acid cyclopropylmethyl ester

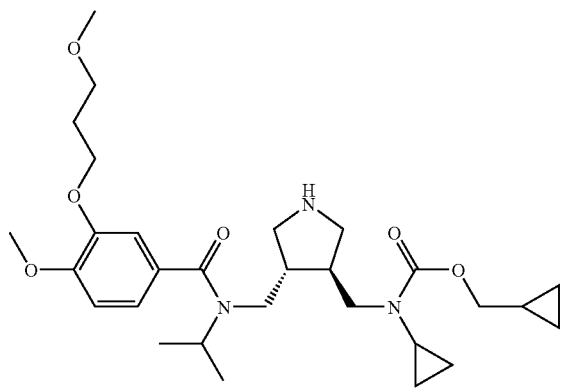

To a solution of (3S*,4R*)-3-[(cyclopropyl-cyclopropyl-methoxycarbonyl-amino)-methyl]-4-({isopropyl-[4-methoxy-3-(3-methoxy-propoxy-benzoyl]-amino}-methyl)-pyrrolidine-1-carboxylic acid tert-butyl ester (140 mg, 0.222 mmol) in dioxane (4 mL), 4N HCl in dioxane (2 mL) is added and the resulting solution is stirred at RT for 7 h. Lyophilization affords the corresponding hydrochloride salt. MS (LC-MS): 532.1 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 5.37 min.

The starting material is prepared as follows:

(3S*,4R*)-3-[(Cyclopropyl-cyclopropylmethoxycarbonyl-amino)-methyl]-4-({isopropyl-[4-methoxy-3-(3-methoxy-propoxy)-benzoyl]-amino}-methyl)-pyrrolidine-1-carboxylic acid tert-butyl ester To a solution of cyclopropylmethanol (29 μL, 0.366 mmol) in CH$_2$Cl$_2$ (5 mL) bis(trichloromethyl) carbonate (40 mg, 0.136 mmol) followed by DMAP (143 mg, 1.170 mmol) are added and the resulting milky suspension is stirred at RT for 15 min. Then a solution of ((3R*,4R*)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester (215 mg, 0.403 mmol) in CH$_2$Cl$_2$ (5 mL) is added and the resulting clear solution is stirred at RT for another 3.5 h. Evaporation of the solvent affords the crude product which is purified by preparative HPLC (Waters C$_{18}$ ODB, eluent: H$_2$O/CH$_3$CN 20 to 100%) to give the title compound. MS (LC-MS): 532.0 [M+H-Boc]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 6.48 min.

The following Examples are prepared according to the procedures described above for Example 233 or described below for Example 282:

TABLE 9

| Example | configuration | structure | [M + H]+ | $t_R$ (HPLC) |
|---------|---------------|-----------|----------|--------------|
| 234 | (3S*, 4S*) | 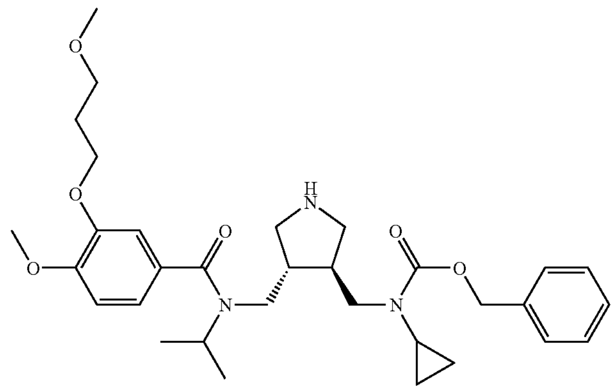 | 568.0 | 5.27[a] |
| 235 | (3S, 4S) | 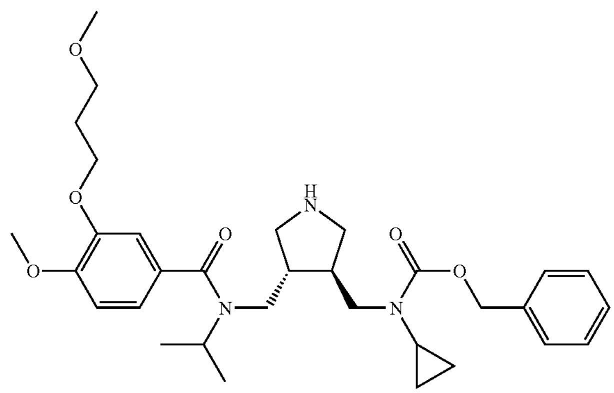 | 568.2 | 5.17[a] |
| 236 | (3S*, 4S*) | 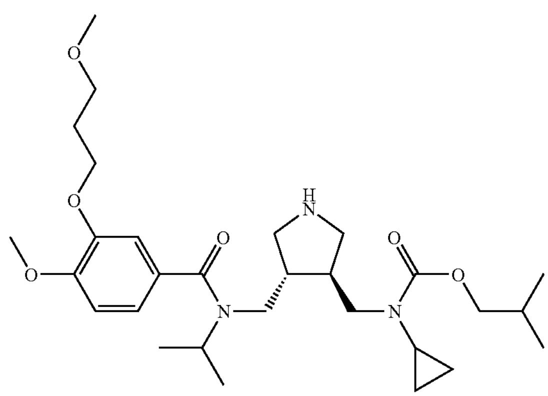 | 534.1 | 5.35[a] |
| 237 | (3S*, 4S*) | 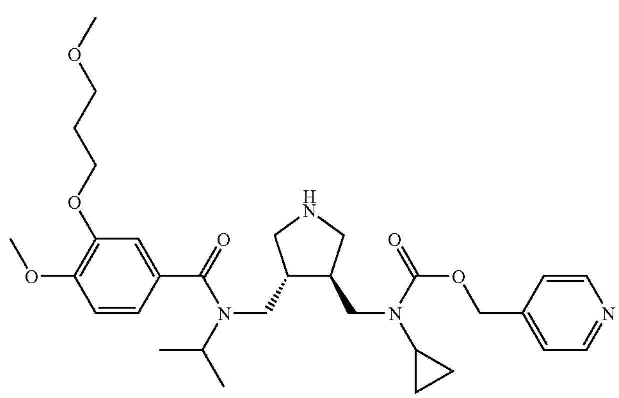 | 285.1 [M + 2H]$^{2+}$ | 4.70[a] |

TABLE 9-continued
| Example | configuration | structure | [M + H]+ | tR (HPLC) |
|---|---|---|---|---|
| 238 | (3S*, 4S*) | 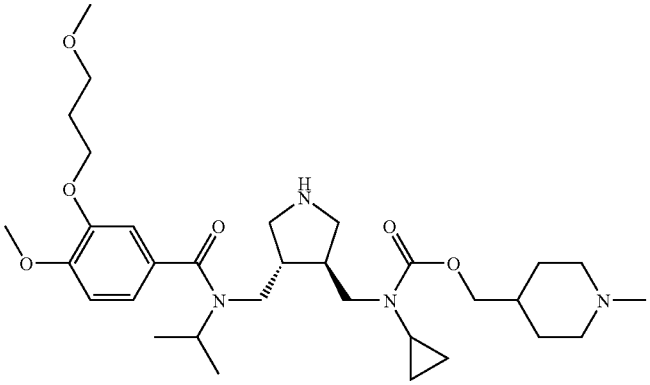 | 295.1 [M + 2H]2+ | 4.72[a] |
| 239 | (3S*, 4S*) | 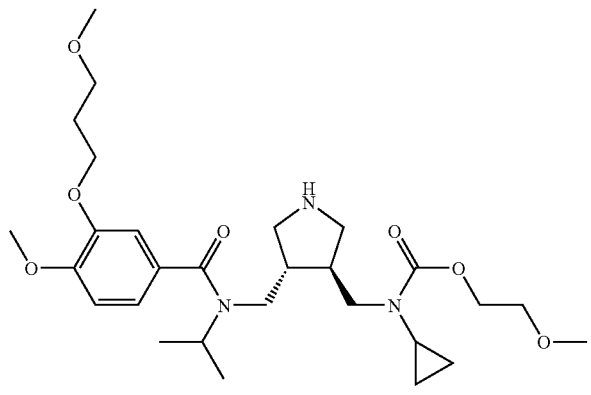 | 536.0 | 5.10[a] |
| 240 | (3S*, 4S*) | 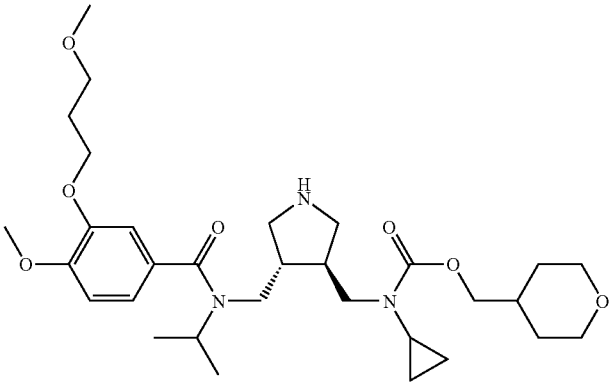 | 576.1 | 5.25[a] |
| 241 | (3S*, 4S*) | 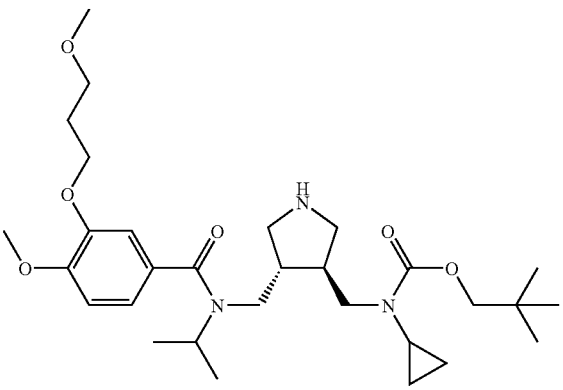 | 548.1 | 5.83[a] |

TABLE 9-continued

| Example | configuration | structure | [M + H]+ | t_R (HPLC) |
|---|---|---|---|---|
| 242 | (3S*, 4S*) | 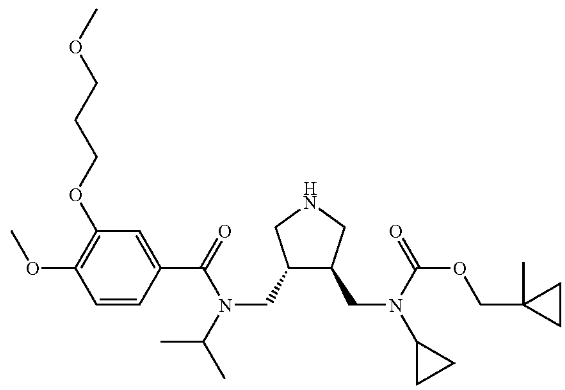 | 546.1 | 4.76[a] |
| 243 | (3S*, 4S*) | 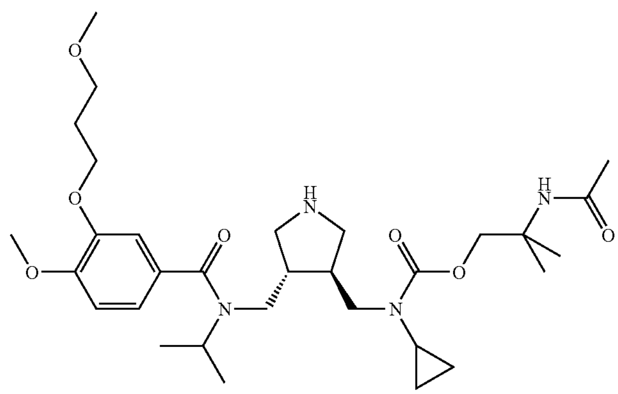 | 591.4 | 4.25[a] |
| 244 | (3S*, 4S*) | 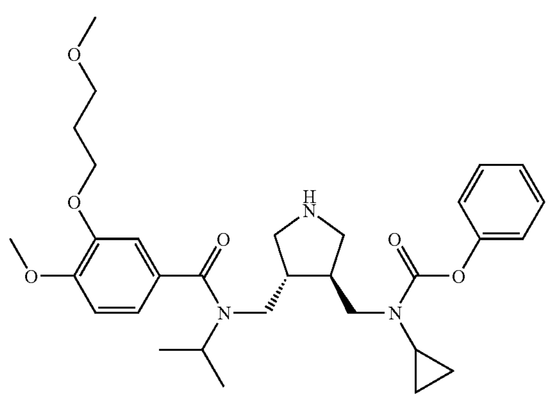 | 554.3 | 4.70[a] |
| 245 | (3S*, 4S*) | 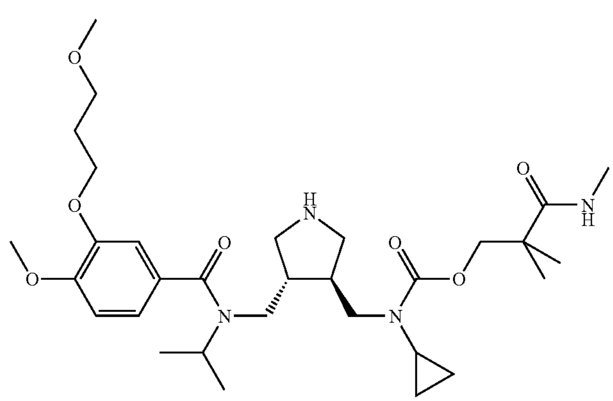 | 591.4 | 4.19[a] |

TABLE 9-continued

| Example | configuration | structure | [M + H]+ | t$_R$ (HPLC) |
|---|---|---|---|---|
| 246 | (3S*, 4S*) | 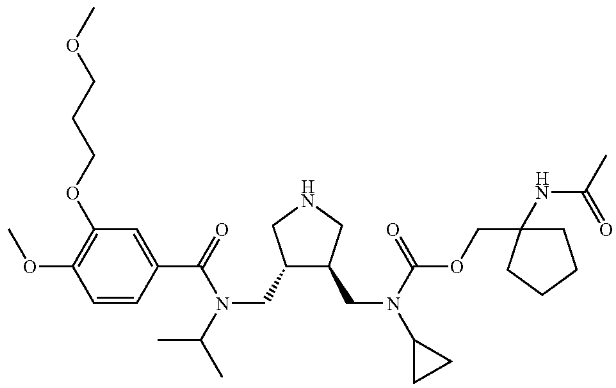 | 617.4 | 4.41$^a$ |
| 247 | (3S*, 4S*) | 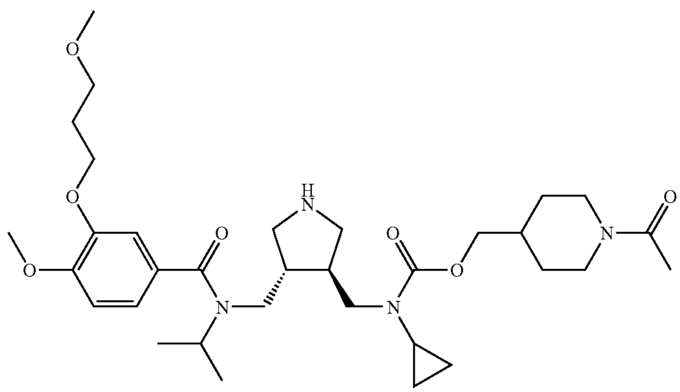 | 617.5 | 4.26$^a$ |
| 248 | (3S*, 4S*) | 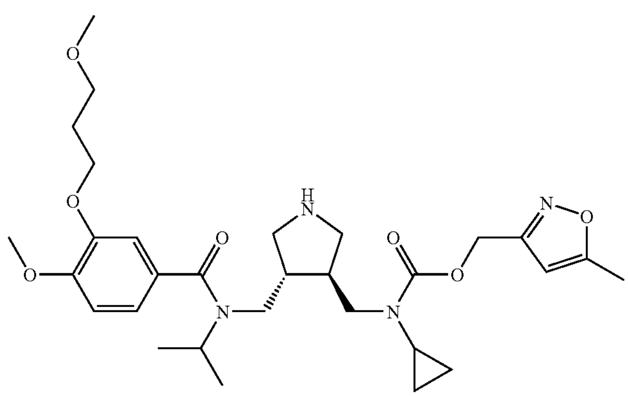 | 573.4 | 4.54$^a$ |
| 249 | (3S*, 4S*) | 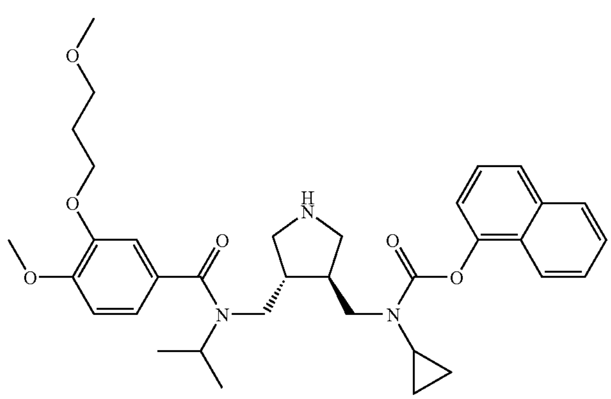 | 604.2 | 5.14$^a$ |

TABLE 9-continued

| Example | configuration | structure | [M + H]⁺ | $t_R$ (HPLC) |
|---|---|---|---|---|
| 250 | (3S, 4S) | 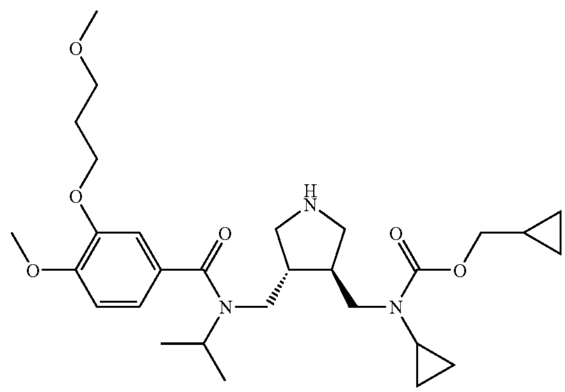 | 532.3 | 4.87[a] |
| 251 | (3S, 4S) | 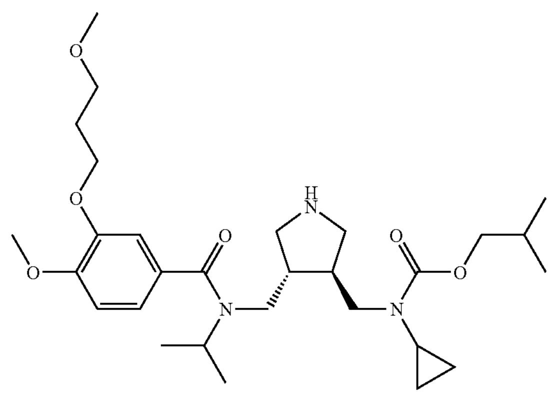 | 534.2 | 5.11[a] |
| 252 | (3S, 4S) | 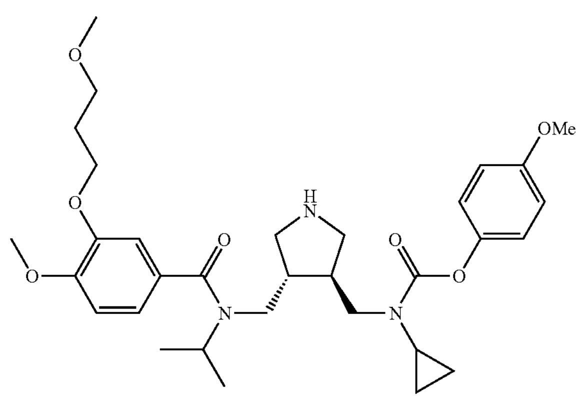 | 584.2 | 5.69[a] |
| 253 | (3S, 4S) | 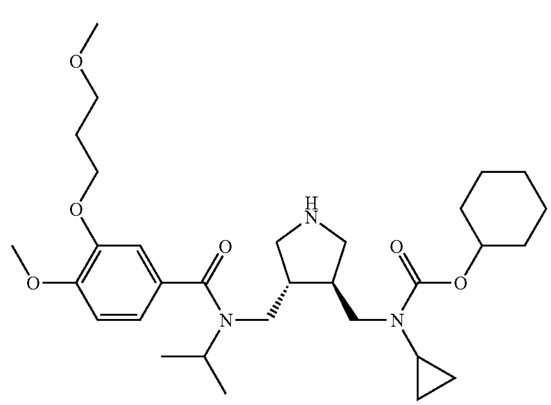 | 560.2 | 5.92[a] |

TABLE 9-continued

| Example | configuration | structure | [M + H]+ | t_R (HPLC) |
|---|---|---|---|---|
| 254 | (3S, 4S) | 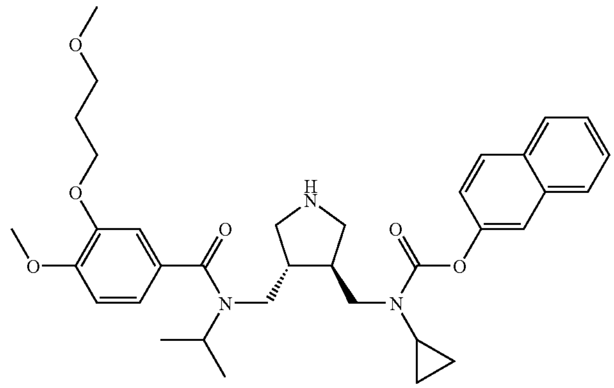 | 604.2 | 6.01[a] |
| 255 | (3S, 4S) | 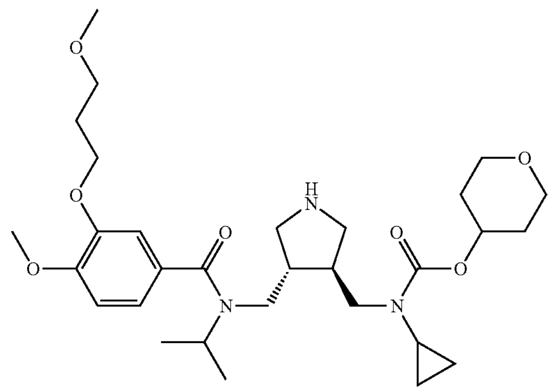 | 562.3 | 5.42[a] |
| 256 | (3S, 4S) | 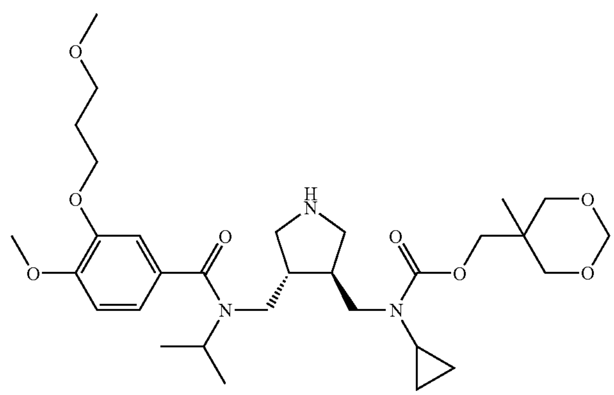 | 592.3 | 5.58[a] |
| 257 | (3S, 4S) | 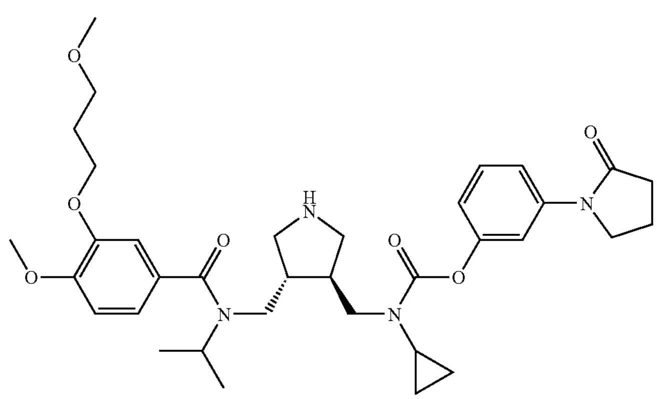 | 637.5 | 5.88[a] |

TABLE 9-continued

| Example | configuration | structure | [M + H]+ | t_R (HPLC) |
|---|---|---|---|---|
| 258 | (3S, 4S) | 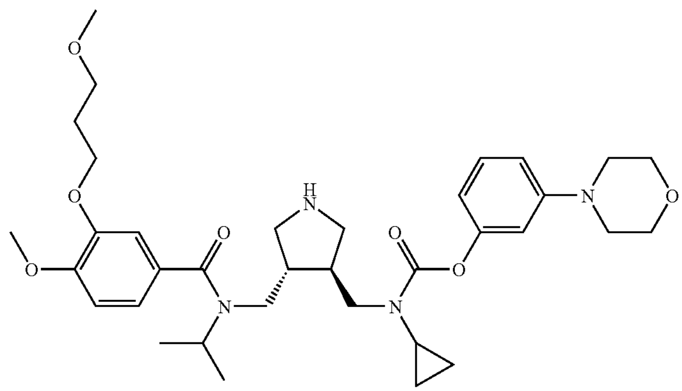 | 639.2 | 5.90[a] |
| 259 | (3S, 4S) | 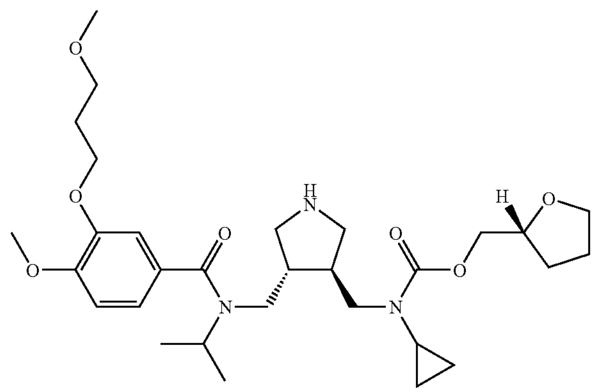 | 562.5 | 5.41[a] |
| 260 | (3S, 4S) | 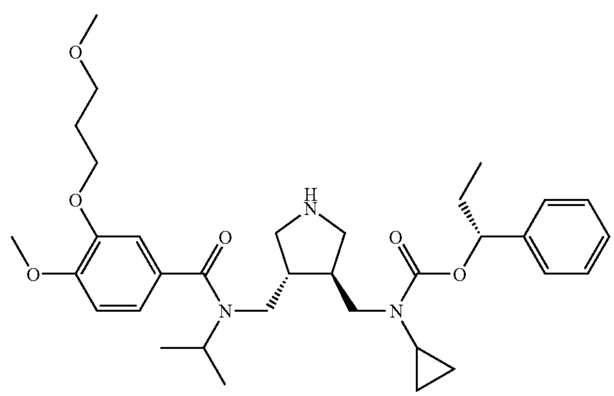 | 596.0 | 6.35[a] |
| 261 | (3S, 4S) | 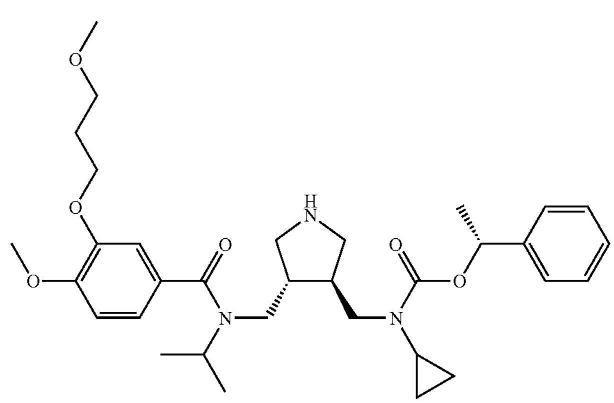 | 582.0 | 5.03[a] |

TABLE 9-continued

| Example | configuration | structure | [M + H]+ | t_R (HPLC) |
|---|---|---|---|---|
| 262 | (3S, 4S) | 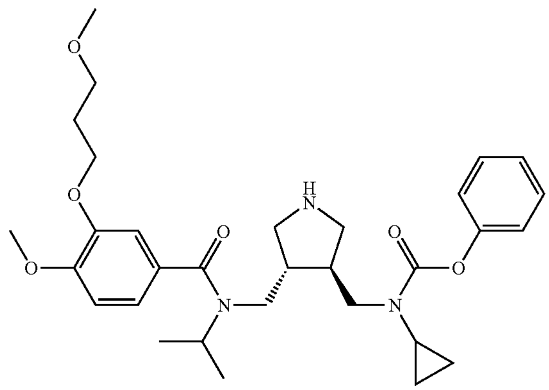 | 554.0 | 4.83[a] |
| 263 | (3S, 4S) | 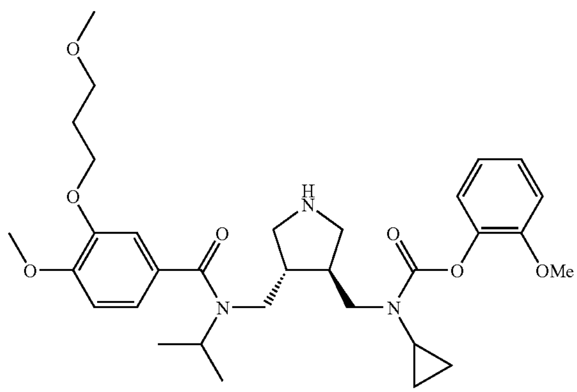 | 584.0 | 4.85[a] |
| 264 | (3S, 4S) | 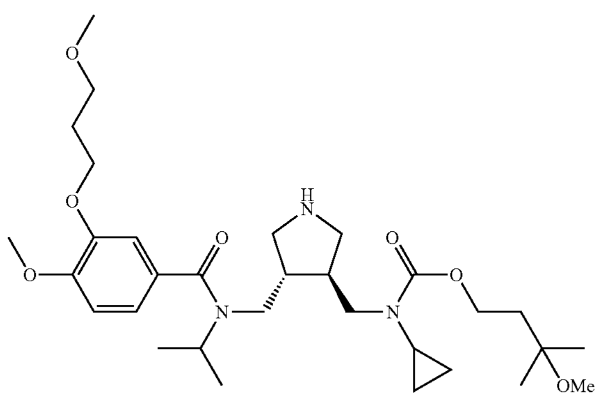 | 578.5 | 3.36[b] |
| 265 | (3S, 4S) | 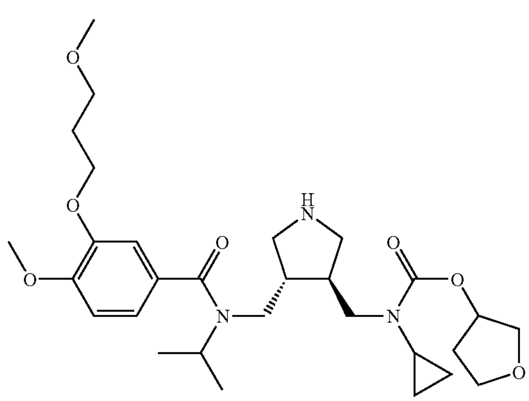 | 548.5 | 3.08[b] |

TABLE 9-continued

| Example | configuration | structure | [M + H]+ | t_R (HPLC) |
|---|---|---|---|---|
| 266 | (3S, 4S) | 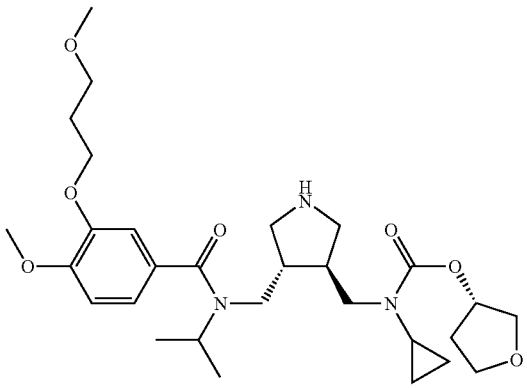 | 548.4 | 0.38[b] |
| 267 | (3S, 4S) | 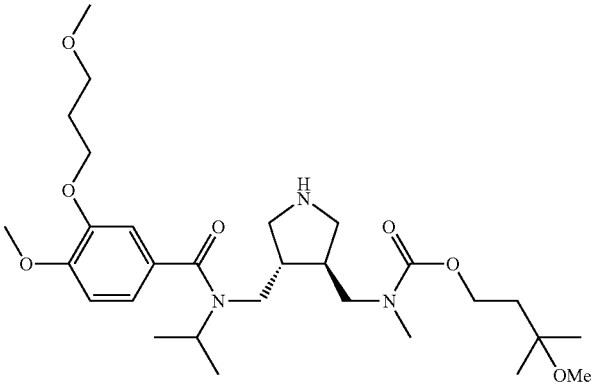 | 552.2 | 4.44[a] |
| 268 | (3S, 4S) | 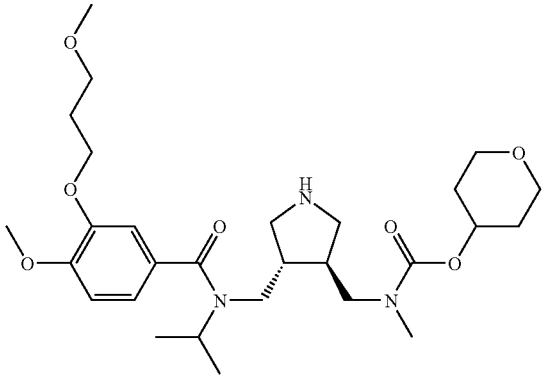 | 536.2 | 2.58[c] |

[a] t_R (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min).
[b] t_R (Waters Symmetry C18 column, 10-95% CH$_3$CN/H$_2$O/3.5 min, 95% CH$_3$CN/H$_2$O, 2 min, CH$_3$CN and H$_2$O containing 0.1% TFA, flow: 0.6 mL/min).
[c] t_R (Waters Symmetry C18 column, 5-95% CH$_3$CN/H$_2$O/3.5 min, 95% CH$_3$CN/H$_2$O, 2 min, CH$_3$CN and H$_2$O containing 0.1% TFA, flow: 0.6 mL/min).

The starting material of Example 245 is prepared as follows:

(3S*,4R*)-3-{[Cyclopropyl-(2-methyl-2-methylcarbamoyl-propoxycarbonyl)-amino]-methyl}-4-({isopropyl-[4-methoxy-3-(3-methoxy-propoxy)-benzoyl]-amino}-methyl)-pyrrolidine-1-carboxylic acid tert-butyl ester

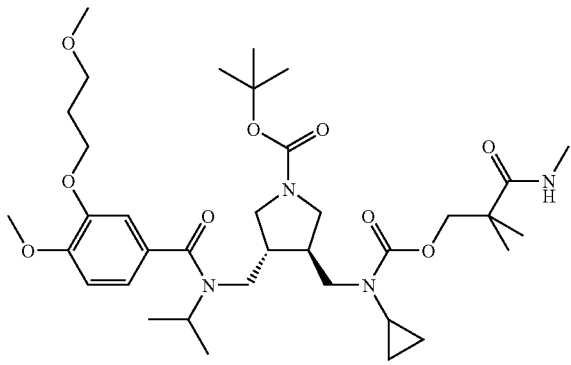

HBTU (161 mg, 0.43 mmol) is added to a solution of (3S*,4R*)-3-{[(2-carboxy-2-methyl-propoxycarbonyl)-cyclopropyl-amino]-methyl}-4-({isopropyl-[4-methoxy-3-(3-methoxy-propoxy)-benzoyl]-amino}-methyl)-pyrrolidine-1-carboxylic acid tert-butyl ester (240 mg, 0.35 mmol) in $CH_3CN$ (10 mL) at 0° C. After 5 min a solution of methylamine (44 µL, 0.35 mmol, 8M in EtOH) and triethylamine (493 µL, 3.54 mmol) in $CH_3CN$ (10 mL) is added at 0° C. and the reaction solution is stirred at RT for 5 h. Another portion of methylamine (0.22 mL, 1.75 mmol) is added and stirring is continued for another 16 h. Then, triethylamine (247 µL, 1.77 mmol) and HBTU (268 mg, 1.02 mmol) are added and the reaction mixture is stirred at 50° C. for another 16 h. The solvent is evaporated and the crude product purified by HPLC (Interchrom $C_{18}$ ODB 10 µm, 28×250 mm, eluent: $CH_3CN$/$H_2O$ 5%/2.5 min, $CH_3CN$/$H_2O$ 5-100%/23 min, 100% $CH_3CN$/4.5 min, flow 40 mL/min) to give the title compound. MS (LC-MS): 691.4 $[M+H]^+$; $t_R$ (HPLC, Macherey-Nagel Nucleosil C18 column, 10-100% $CH_3CN$/$H_2O$/5 min, 100% $CH_3CN$/3 min, $CH_3CN$ and $H_2O$ containing 0.1% TFA, flow: 1.5 ml/min): 5.38 min.

The starting material is prepared as follows:

A. (3S*,4R*)-3-{[Cyclopropyl-(2-methoxycarbonyl-2-methyl-propoxycarbonyl)-amino]-methyl}-4-({isopropyl-[4-methoxy-3-(3-methoxy-propoxy)-benzoyl]-amino}-methyl)-pyrrolidine-1-carboxylic acid tert-butyl ester The title compound is prepared analogously as described above for NVP-BGW706 from ((3R*,4R*)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester and methyl 2,2-dimethyl-3-hydroxypropionate using bis(trichloromethyl) carbonate. MS (LC-MS): 592.1 $[M+H-Boc]^+$; $t_R$ (HPLC, Macherey-Nagel Nucleosil C18 column, 10-100% $CH_3CN$/$H_2O$/5 min, 100% $CH_3CN$/3 min, $CH_3CN$ and $H_2O$ containing 0.1% TFA, flow: 1.5 ml/min): 5.92 min.

B. (3S*,4R*)-3-{[(2-Carboxy-2-methyl-propoxycarbonyl)-cyclopropyl-amino]-methyl}-4-({isopropyl-[4-methoxy-3-(3-methoxy-propoxy)-benzoyl]-amino}-methyl)-pyrrolidine-1-carboxylic acid tert-butyl ester A mixture of (3S*,4R*)-3-{[cyclopropyl-(2-methoxycarbonyl-2-methyl-propoxycarbonyl)-amino]-methyl}-4-({isopropyl-[4-methoxy-3-(3-methoxy-propoxy)-benzoyl]-amino}-methyl)-pyrrolidine-1-carboxylic acid tert-butyl ester (290 mg, 0.42 mmol) and LiOH·$H_2O$ (44 mg, 1.05 mmol) in $H_2O$ (2 mL) and THF (6 mL) is stirred at RT for 3 d. After evaporation of the solvent 1N HCl is added and the mixture is extracted with ethyl acetate. Drying ($Na_2SO_4$) of the combined extracts, filtration and evaporation of the solvent affords the title compound which is used without further purification. MS (LC-MS): 578.0 $[M+H-Boc]^+$; $t_R$ (HPLC, Macherey-Nagel Nucleosil C18 column, 10-100% $CH_3CN$/H20/5 min, 100% $CH_3CN$/3 min, $CH_3CN$ and $H_2O$ containing 0.1% TFA, flow: 1.5 ml/min): 5.44 min.

The following Examples are prepared according to the procedures described above for Example 233 or below for Example 282 using (3R,4R)-3-cyclopropylaminomethyl-4-({isopropyl-[3-(3-methoxy-propoxy)-4-methyl-benzoyl]-amino}-methyl)-pyrrolidine-1-carboxylic acid tert-butyl ester or (3R,4R)-3-({isopropyl-[3-(3-methoxy-propoxy)-4-methyl-benzoyl]-amino}-methyl)-4-methylaminomethyl-pyrrolidine-1-carboxylic acid tert-butyl ester:

TABLE 10

| Example | configuration | structure | [M + H]+ | t_R (HPLC) |
|---|---|---|---|---|
| 269 | (3S, 4S) | 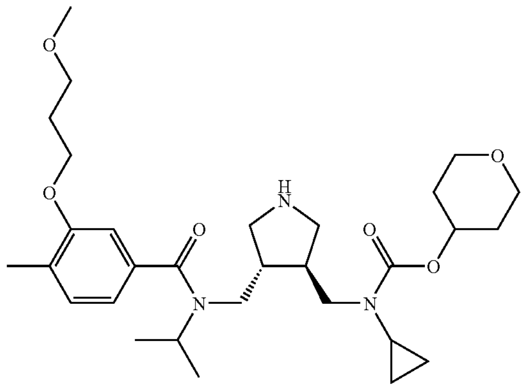 | 546.3 | 5.76[a] |
| 270 | (3S, 4S) | 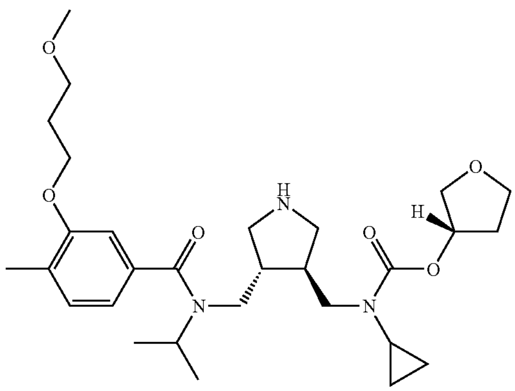 | 532.3 | 4.71[a] |
| 271 | (3S, 4S) | 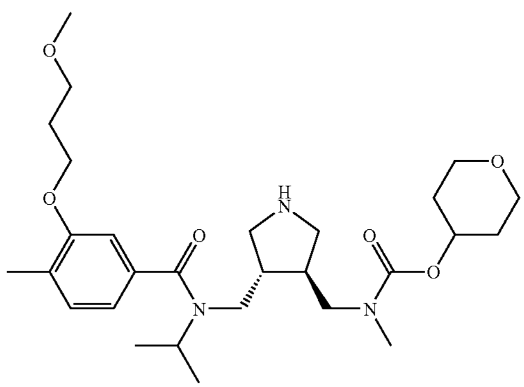 | 520.3 | 4.57[a] |
| 272 | (3S, 4S) | 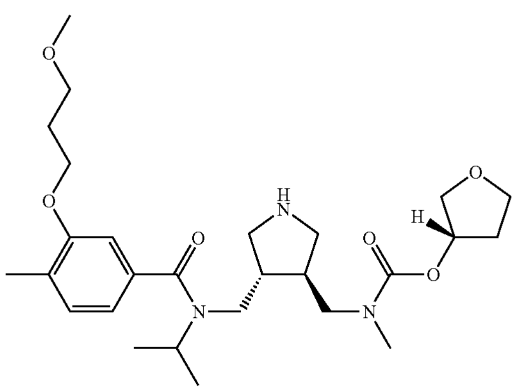 | 506.2 | 4.52[a] |

TABLE 10-continued

| Example | configuration | structure | [M + H]⁺ | t_R (HPLC) |
|---------|---------------|-----------|----------|------------|
| 273 | (3S, 4S) | 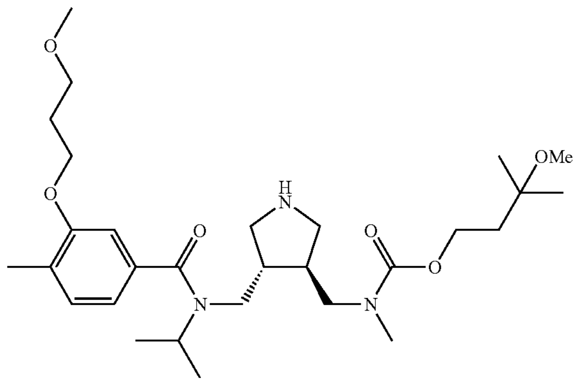 | 536.3 | 2.64[b] |
| 274 | (3S, 4S) | 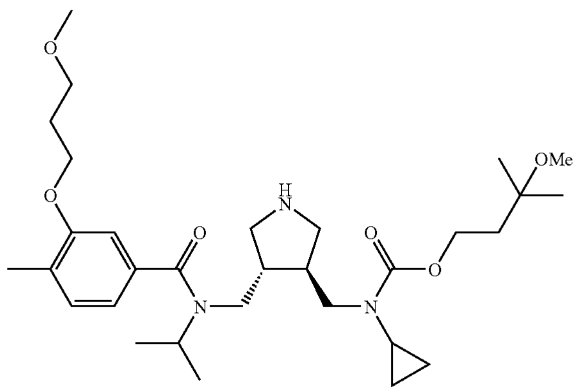 | 562.3 | 5.03[a] |
| 275 | (3S, 4S) | 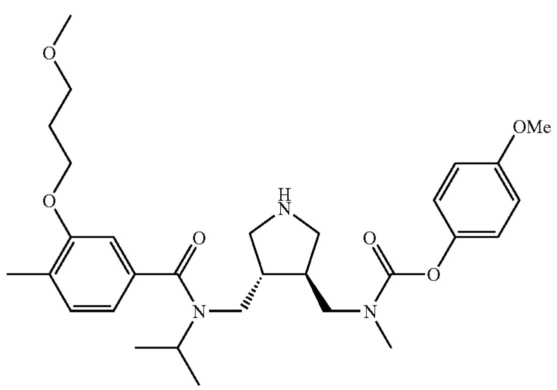 | 542.2 | 5.00[a] |
| 276 | (3S, 4S) | 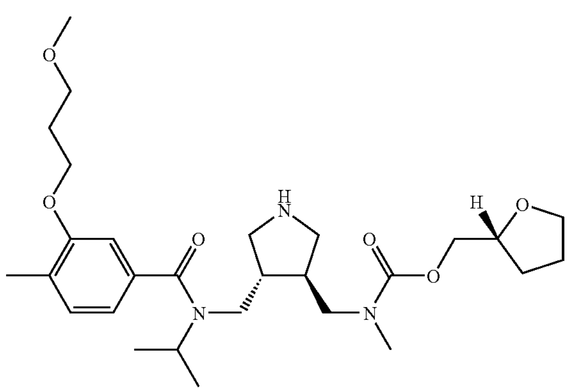 | 520.3 | 4.67[a] |

TABLE 10-continued

| Example | configuration | structure | [M + H]+ | t_R (HPLC) |
|---|---|---|---|---|
| 277 | (3S, 4S) | 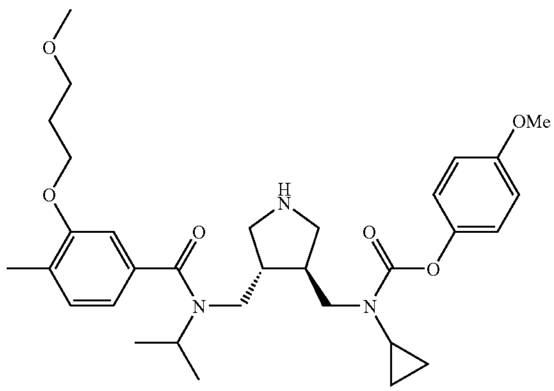 | 568.3 | 5.18[a] |
| 278 | (3S, 4S) | 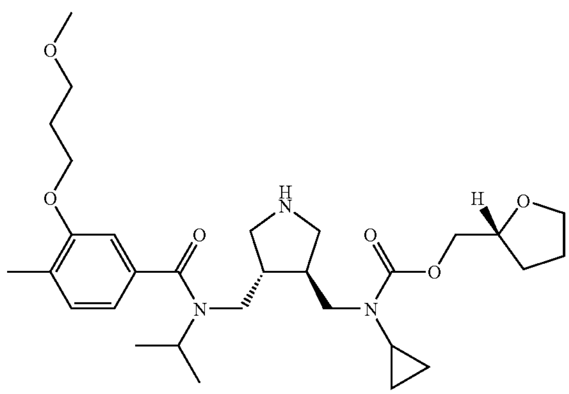 | 546.3 | 4.85[a] |
| 279 | (3S, 4S) | 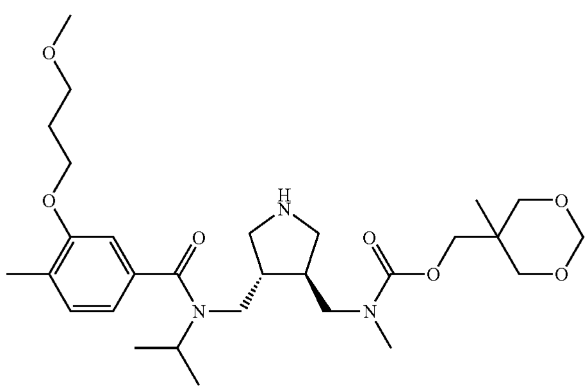 | 550.3 | 4.74[a] |
| 280 | (3S, 4S) | 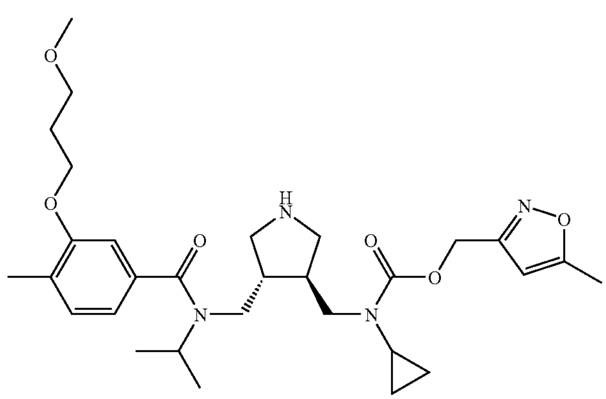 | 557.2 | 2.68[b] |

TABLE 10-continued

| Example | configuration | structure | [M + H]+ | $t_R$ (HPLC) |
|---|---|---|---|---|
| 281 | (3S, 4S) | 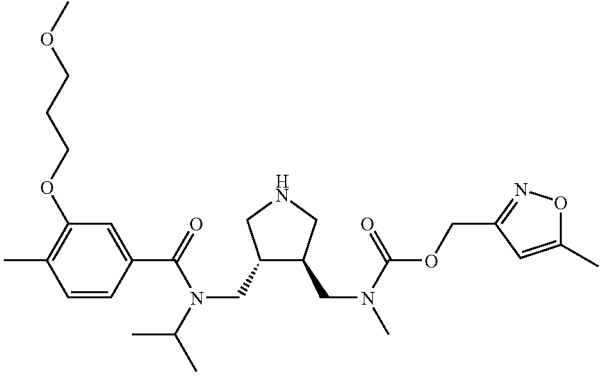 | 531.1 | 2.51[b] |

[a] $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
[b] $t_R$ (Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min).

EXAMPLE 282

Cyclopropyl-[(3S,4S)-4-({[4-ethyl-3-(3-methoxy-propoxy)-benzoyl]-isopropyl-amino}-methyl)-pyrrolidin-3-ylmethyl]-carbamic acid isobutyl ester

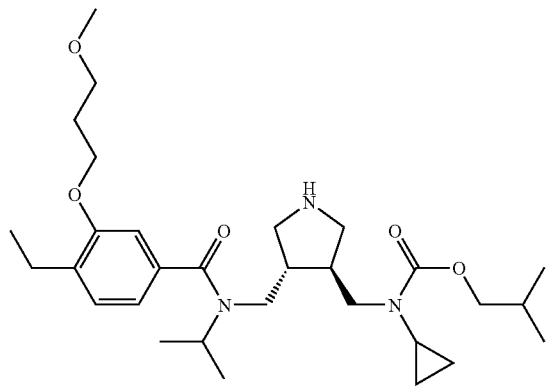

To a solution of (3S,4R)-3-[(cyclopropyl-isobutoxycarbonyl-amino)-methyl]-4-({[4-ethyl-3-(3-methoxy-propoxy)-benzoyl]-isopropyl-amino}-methyl)-pyrrolidine-1-carboxylic acid tert-butyl ester (0.280 g, 0.443 mmol) in dioxane (2 mL), 4N HCl in dioxane (2 mL) is added, and the resulting solution is lyophilized to afford the corresponding hydrochloride salt. MS (LC-MS): 532 [M+H]+; $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 ml/min): 5.52 min.

The starting material is prepared as follows:

(3S,4R)-3-[(Cyclopropyl-isobutoxycarbonyl-amino)-methyl]-4-({[4-ethyl-3-(3-methoxy-propoxy)-benzoyl]-isopropyl-amino}-methyl)-pyrrolidine-1-carboxylic acid tert-butyl ester To a solution of (3R,4R)-3-cyclopropylaminomethyl-4-({[4-ethyl-3-(3-methoxy-propoxy)-benzoyl]-isopropyl-amino}-methyl)-pyrrolidine-1-carboxylic acid tert-butyl ester (250 mg, 0.470 mmol) in CH₂Cl₂ (3 mL) are added isobutylchloroformate (84 mg, 0.611 mmol) and triethylamine (85 µL, 0.611 mmol) under a N₂ atmosphere. The mixture is stirred overnight at RT, diluted with CH₂Cl₂ and poured into an aqueous saturated solution of NaHCO₃. The layers are separated and the aqueous one extracted twice with CH₂Cl₂. The combined organic extracts are dried over Na₂SO₄, filtered and concentrated. The crude residue is purified by flash chromatography on silica gel (eluent: CH₂Cl₂/MeOH 100:0 to 90:10) to give the title compound. MS (LC-MS): 532 [M+H-Boc]+; $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 ml/min): 8.22 min.

The following Examples are prepared according to the procedures described above for Example 233 or Example 282:

TABLE 11

| Example | configuration | structure | [M + H]+ | tR (HPLC) |
|---|---|---|---|---|
| 283 | (3S, 4S) | 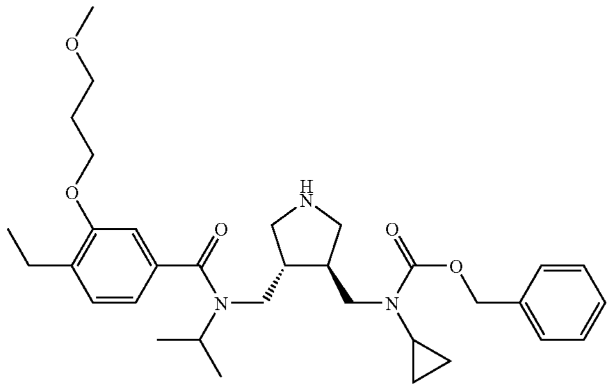 | 556 | 5.53[a] |
| 284 | (3S, 4S) | 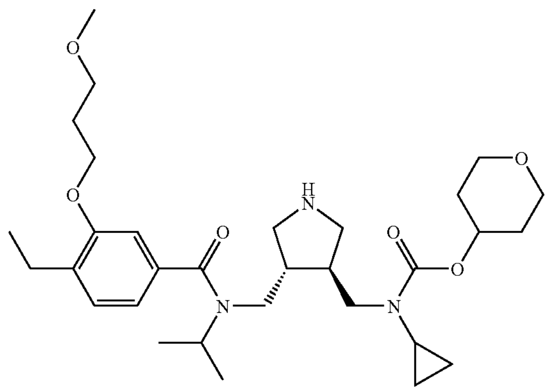 | 560.3 | 2.68[b] |
| 285 | (3S, 4S) | 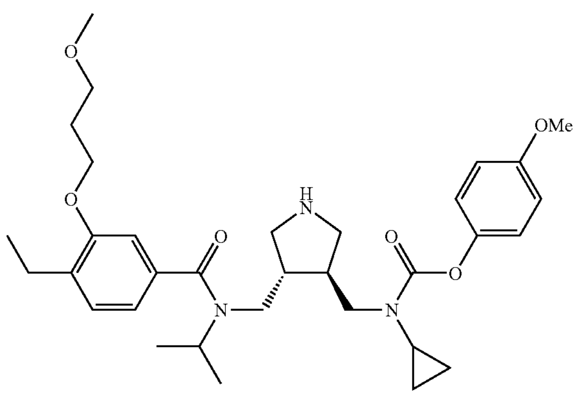 | 582.2 | 2.95[b] |
| 286 | (3S, 4S) | 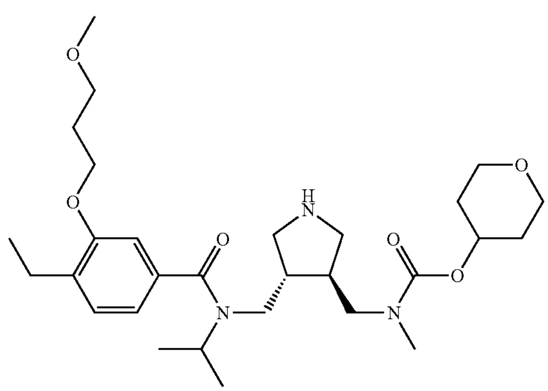 | 534.2 | 4.80[a] |

TABLE 11-continued

| Example | configuration | structure | [M + H]+ | tR (HPLC) |
|---|---|---|---|---|
| 287 | (3S, 4S) | 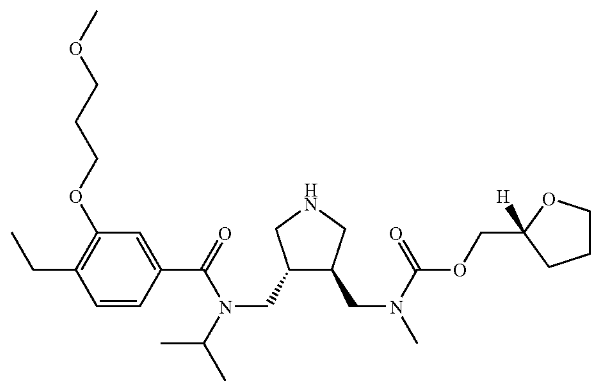 | 534.2 | 4.87[a] |
| 288 | (3S, 4S) | 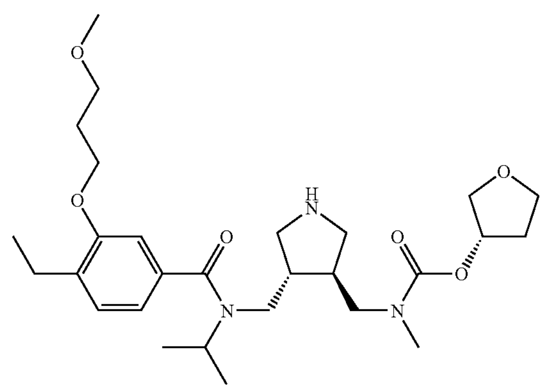 | 520.3 | 4.73[a] |
| 289 | (3S, 4S) | 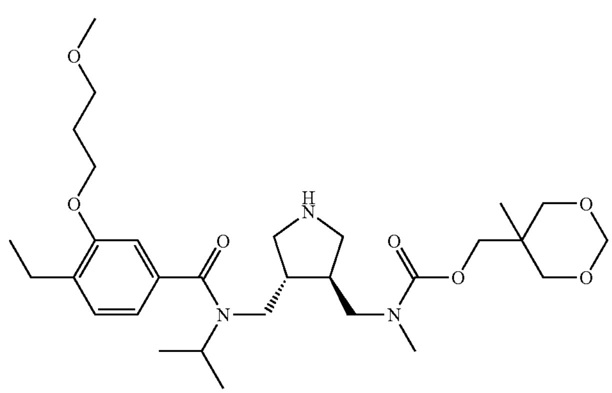 | 564.3 | 4.91[a] |

TABLE 11-continued

| Example | configuration | structure | [M + H]+ | $t_R$ (HPLC) |
|---|---|---|---|---|
| 290 | (3S, 4S) | 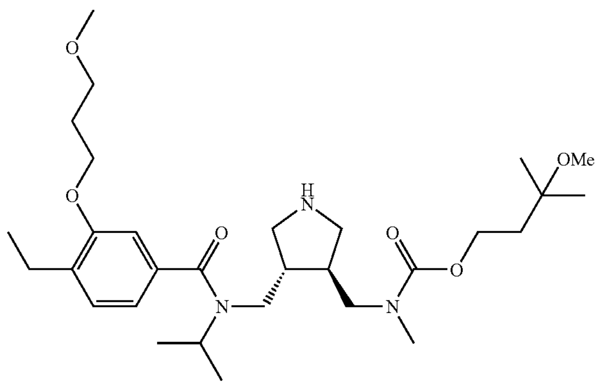 | 550.2 | 2.80[b] |

[a] $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min).
[b] $t_R$ (Waters Symmetry C18 column, 20-95% $CH_3CN/H_2O$/3.5 min, 95% $CH_3CN/H_2O$, 2 min, $CH_3CN$ and $H_2O$ containing 0.1% TFA, flow: 0.6 mL/min).

The following Examples are prepared according to the procedures described above for Example 233 or Example 282 using (3R,4R)-3-cyclopropylaminomethyl-4-({isopropyl-[1-(3-methoxy-propyl)-3-methyl-1H-indole-6-carbonyl]-amino}-methyl)-pyrrolidine-1-carboxylic acid tert-butyl ester:

TABLE 12

| Example | configuration | structure | [M + H]+ | $t_R$ (HPLC) |
|---|---|---|---|---|
| 291 | (3S, 4S) | 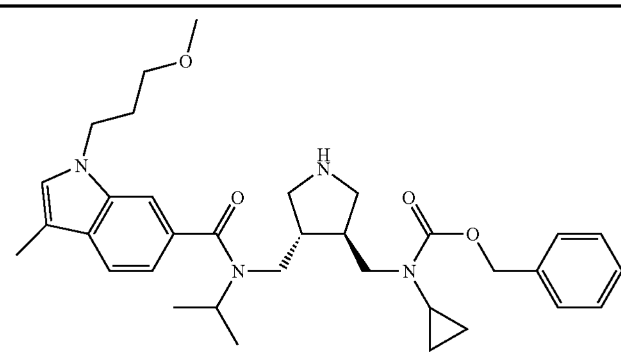 | 575 | 5.67[a] |
| 292 | (3S, 4S) | 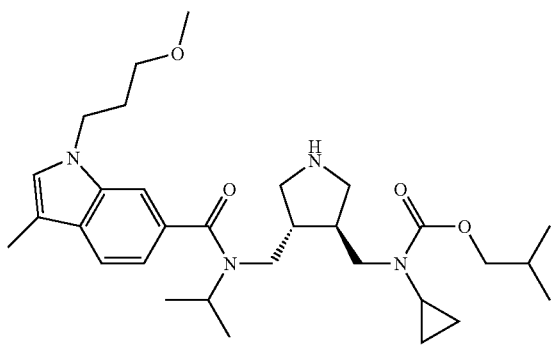 | 541 | 5.66[a] |

TABLE 12-continued

| Example | configuration | structure | [M + H]⁺ | $t_R$ (HPLC) |
|---|---|---|---|---|
| 293 | (3S, 4S) | 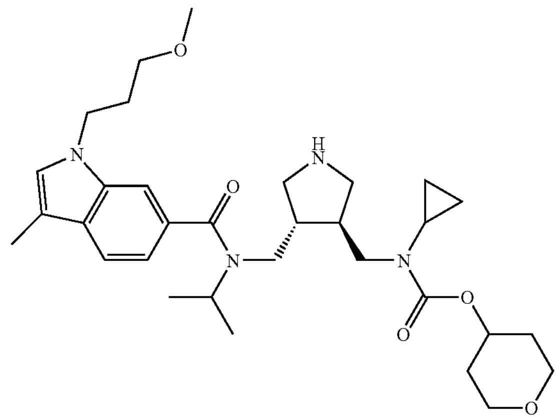 | 569.3 | 4.22[b] |

[a]$t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
[b]$t_R$ (HPLC, Nucleosil C-18HD (4 × 70 mm, 3 μm), 20-100% CH₃CN/H₂O/6 min, 100% CH₃CN/1.5 min; flow: 1 mL/min).

N-(2-Hydroxy-1,1-dimethyl-ethyl)-acetamide

A mixture of 2-amino-2-methyl-propan-1-ol (2.0 mL, 20.4 mmol), acetanhydride (1.9 mL, 20.4 mmol) and NaHCO₃ (2.6 g, 30.6 mmol) in H₂O (20 mL) is stirred at RT for 16 h. For workup 1N HCl is added and the mixture is extracted with ethyl acetate. Drying (Na₂SO₄) of the combined extracts, filtration and evaporation of the solvent yields the title compound as a colorless solid. MS (LC-MS): [M+H]⁺=132.2. $t_R$ (HPLC, Waters Symmetry C18 column, 20-95% CH₃CN/H₂O/3.5 min, 95% CH₃CN/H₂O, 2 min, CH₃CN and H₂O containing 0.1% TFA, flow: 0.6 mL/min): 0.38 min.

N-(1-Hydroxymethyl-cyclopentyl)-acetamide

The title compound is prepared analogously as described for N-(2-hydroxy-1,1-dimethyl-ethyl)-acetamide from (1-amino-cyclopentyl)-methanol. MS (LC-MS): [M+H]⁺=158.2. $t_R$ (HPLC, Waters sun fire C18 column, 5-95% CH₃CN/H₂O/3.5 min, 95% CH₃CN/H₂O, 2 min, CH₃CN and H₂O containing 0.1% TFA, flow: 0.8 mL/min): 1.76 min.

1-(4-Hydroxymethyl-piperidin-1-yl)-ethanone

The title compound is prepared analogously as described for N-(2-hydroxy-1,1-dimethyl-ethyl)-acetamide from piperidin-4-yl-methanol. MS (LC-MS): [M+H]⁺=158.3. $t_R$ (HPLC, Waters Symmetry C18 column, 5-95% CH₃CN/H₂O/3.5 min, 95% CH₃CN/H₂O, 2 min, CH₃CN and H₂O containing 0.1% TFA, flow: 0.6 mL/min): 0.39 min.

EXAMPLE 294

Benzyl-ethyl-carbamic acid (3S,4S)4-({isopropyl-[4-methoxy-3-(3-methoxy-propoxy)-benzoyl]-amino}-methyl)-pyrrolidin-3-ylmethyl ester

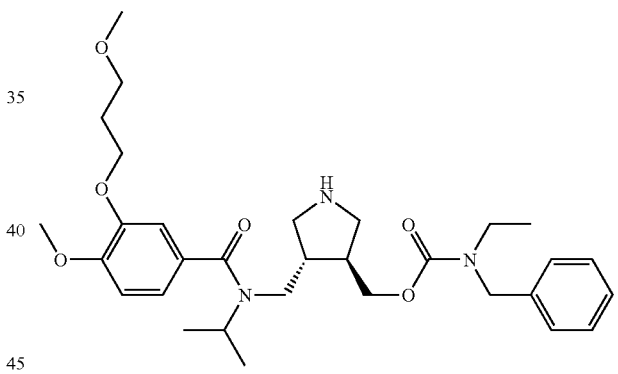

To a solution of (3S,4R)-3-[(benzyl-ethyl-carbamoyloxy)-methyl]-4-({isopropyl-[4-methoxy-3-(3-methoxy-propoxy)-benzoyl]-amino}-methyl)-pyrrolidine-1-carboxylic acid tert-butyl ester (83 mg, 0.127 mmol) in 2 mL dioxane, 4 N HCl in dioxane (1 mL, 4 mmol) is added. The mixture is stirred at RT for 2 h, and the resulting solution is lyophilized to afford the corresponding hydrochloride salt. MS (LC-MS): 556.1 [M+H]⁺; $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min): 4.89 min.

The starting material is prepared as follows:

(3S,4R)-3-[(Benzyl-ethyl-carbamoyloxy)-methyl]-4-({isopropyl-[4-methoxy-3-(3-methoxy-propoxy)-benzoyl]-amino}-methyl)-pyrrolidine-1-carboxylic acid tert-butyl ester To a stirred solution of (3S,4R)-3-hydroxymethyl-4-({isopropyl-[4-methoxy-3-(3-methoxy-propoxy)-benzoyl]- amino}-methyl)-pyrrolidine-1-carboxylic acid tert-butyl ester (250 mg, 0.505 mmol) in CH$_2$Cl$_2$ (10 mL) is added triphosgen (56 mg, 0.187 mmol) and DMAP (197 mg, 1.62 mmol). The resulting solution is stirred 30 min before the addition of commercially available N-ethylbenzylamine (113 μL, 0.758 mmol). The mixture is further stirred overnight, then diluted with CH$_2$Cl$_2$ and poured into an aqueous saturated solution of NaHCO$_3$. The layers are separated and the aqueous one extracted twice with CH$_2$Cl$_2$. The combined organic extracts are dried over Na$_2$SO$_4$, filtered and concentrated. The crude material is purified by flash chromatography on silica gel (eluent: CH$_2$Cl$_2$/MeOH 100:0 to 98:2). TLC, R$_f$ (CH$_2$Cl$_2$/MeOH 95:5)=0.2. MS (LC-MS): 655.9 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 6.36 min.

EXAMPLE 295

Benzyl-cyclopropylmethyl-carbamic acid (3S,4S)-4-({isopropyl-[4-methoxy-3-(3-methoxy-propoxy)-benzoyl]-amino}-methyl)-pyrrolidin-3-ylmethyl ester

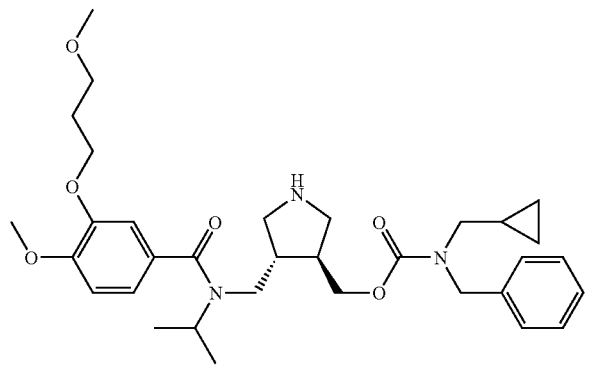

The title compound is prepared analogously as described in Example 294 from (3S,4R)-3-hydroxymethyl-4-({isopropyl-[4-methoxy-3-(3-methoxy-propoxy)-benzoyl]-amino}-methyl)-pyrrolidine-1-carboxylic acid tert-butyl ester and benzyl-cyclopropylmethyl-amine. MS (LC-MS): 582.0 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 5.15 min.

The starting material is prepared as follows:

Benzyl-cyclopropylmethyl-amine

A mixture of benzaldehyde (3 mL, 29.55 mmol), cyclopropanemethylamine (2.53 mL, 29.55 mmol), AcOH (1.7 mL, 29.55 mmol) in 1,2-dichloroethane (150 mL) is stirred at RT for 25 minutes. Sodium triacetoxyborohydride (8.8 g, 41.37 mmol) is added and the mixture further stirred overnight at RT. Sodium triacetoxyborohydride (3.13 g, 15 mmol) is again added to complete the reaction. The mixture is quenched by the addition of NaOH 1N (50 mL), the layers are separated and the aqueous phase is extracted twice with ether. The combined organic extracts are dried (Na$_2$SO$_4$), filtered and concentrated. The crude material is purified by flash chromatography on silica gel (eluent: CH$_2$Cl$_2$/MeOH 95:5 to 80:20+5% NH$_3$) to give the title product. t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 4.91 min.

EXAMPLE 296

Cyclohexylmethyl-methylcarbamic acid (3S,4S)4-({isopropyl-[4-methoxy-3-(3-methoxypropoxy)-benzoyl]-amino}-methyl)-pyrrolidin-3-yl-methyl ester

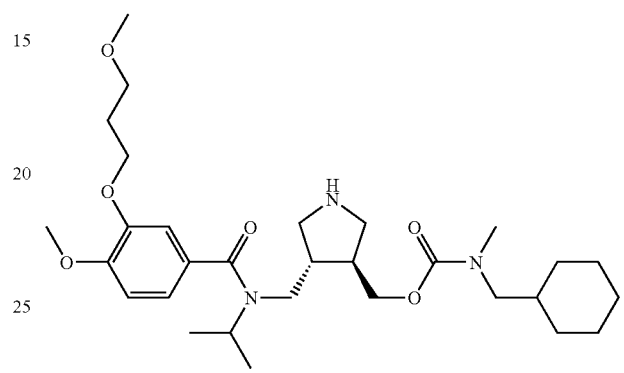

To a solution of (3S,4R)-3-[(cyclohexylmethyl-methyl-carbamoyloxy)-methyl]-4-({isopropyl-[4-methoxy-3-(3-methoxy-propoxy)-benzoyl]-amino}-methyl)-pyrrolidine-1-carboxylic acid tert-butyl ester (182 mg, 0.281 mmol) in 1 mL dioxane, 4 N HCl in dioxane (2 mL, 8 mmol) is added. The mixture is stirred at RT for 2 h, and the resulting solution is lyophilized to afford the corresponding hydrochloride salt. MS (LC-MS): 548 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 5.14 min.

The starting material is prepared as follows:

(3S,4R)-3-[(cyclohexylmethyl-methyl-carbamoyloxy)-methyl]-4-({isopropyl-[4-methoxy-3-(3-methoxy-propoxy)-benzoyl]-amino}-methyl)-pyrrolidine-1-carboxylic acid tert-butyl ester To a stirred suspension of NaH (60% oily dispersion, 17 mg, 0.42 mmol) in THF (2 mL) is added at 0° C. (3S,4R)-3-hydroxymethyl-4-({isopropyl-[4-methoxy-3-(3-methoxy-propoxy)benzoyl]-amino}-methyl)-pyrrolidine-1-carboxylic acid tert-butyl ester (160 mg, 0.303 mmol) in THF (3 mL). The resulting solution is stirred 30 min before the addition of a solution of cyclohexylmethyl-methyl-carbamoyl chloride (80 mg, 0.421 mmol) in THF (3 mL). The mixture is further stirred overnight at RT and poured into an aqueous solution of NH$_4$Cl. AcOEt is added, the layers are separated and the aqueous one extracted twice with AcOEt. The combined organic extracts are dried over Na$_2$SO$_4$, filtered and concentrated. The crude material is purified by flash chromatography on silica gel (eluent: CH$_2$Cl$_2$/MeOH 100:0 to 95:5). TLC, R$_f$ (CH$_2$Cl$_2$/MeOH 95:5)=0.25. MS (LC-MS): 648 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 6.83 min.

Intermediates are prepared as described by the following methods:

Cyclohexylmethyl-methyl-carbamoyl chloride

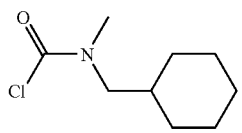

a Cyclohexylmethyl-methyl-amine

A solution of cyclohexancarbaldehyde (4 mL, 33.24 mmol) and methylamine (50.0 mL, 99.8 mmol) in MeOH (160 mL containing 2% AcOH) is stirred at RT for 1 h. Sodium borohydride (2.515 g, 66.48 mmol) is added portionwise at 0° C. and stirring is continued, at RT for 1 h. A solution of NaOH 1N is added and the methanol is concentrated. $CH_2Cl_2$ is added, the layers are separated and the aqueous one extracted twice with $CH_2Cl_2$. The combined organic extracts are dried over $Na_2SO_4$, filtered and concentrated. The crude material is purified by flash chromatography (eluent: $CH_2Cl_2$/MeOH 95:5 to 80:20+5% $NH_3$) to give the title product. TLC, $R_f$ ($CH_2Cl_2$/MeOH 95:5)=0.1; $t_R$ (HPLC, Macherey-Nagel Nucleosil C18 column, 10-100% $CH_3CN/H_2O$/5 min, 100% $CH_3CN$/3 min, flow: 1.5 ml/min): 7.09 min.

b. Cyclohexylmethyl-methyl-carbamoyl chloride

To a solution of triphosgene (77 mg, 0.259 mmol) in $CH_2Cl_2$ (1 mL) at −78° C. is added dropwise pyridine (63 μl, 0.786 mmol) followed by a solution of cyclohexylmethyl-methylamine (100 mg, 0.786 mmol) in $CH_2Cl_2$ (1 mL). The yellow mixture is allowed to reach RT and stirred overnight. The solvent is concentrated, and the residue taken up in AcOEt. An aqueous saturated solution of $NaHCO_3$ is added, the layers are separated and the aqueous one is extracted twice with AcOEt. The combined organic extracts are washed with brine, dried over $Na_2SO_4$, filtered and concentrated to afford the title compound as a yellow oil. TLC, $R_f$ ($CH_2Cl_2$/MeOH 95:5)=0.95. MS (LC-MS): 189.1 $[M+H]^+$.

The following Examples are prepared according to the procedures described above for Example 296:

TABLE 13

| Example | configuration | structure | $[M + H]^+$ | $t_R$ (HPLC) |
|---|---|---|---|---|
| 297 | (3S*, 4S*) | 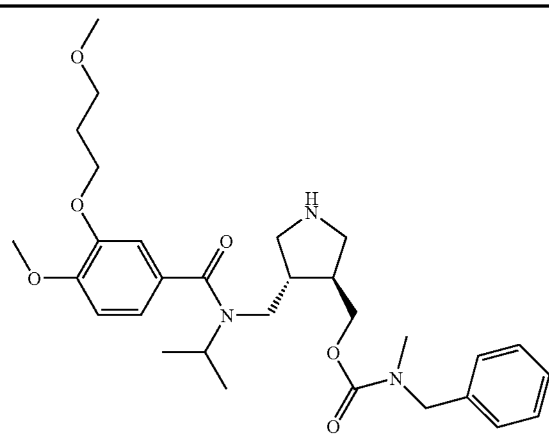 | 542.5 | 4.70$^a$ |
| 298 | (3S, 4S) | 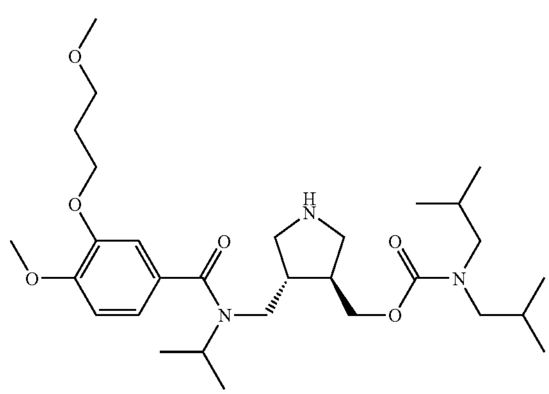 | 550 | 5.33$^a$ |

TABLE 13-continued

| Example | configuration | structure | [M + H]+ | $t_R$ (HPLC) |
|---|---|---|---|---|
| 299 | (3S, 4S) | 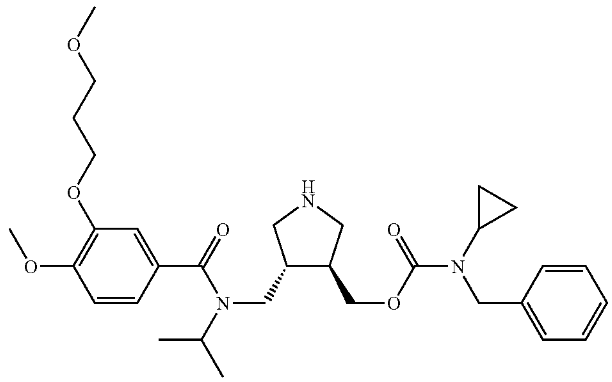 | 568 | 4.15[a] |
| 300 | (3S, 4S) | 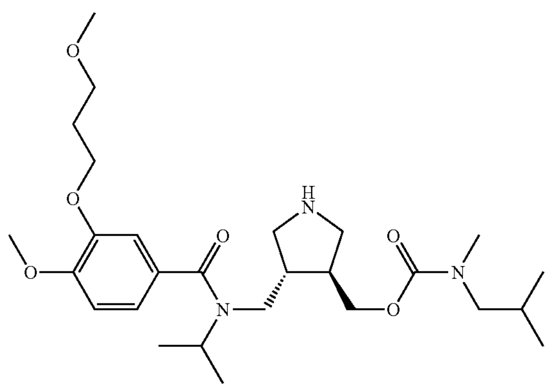 | 508 | 5.13[a] |
| 301 | (3S, 4S) | 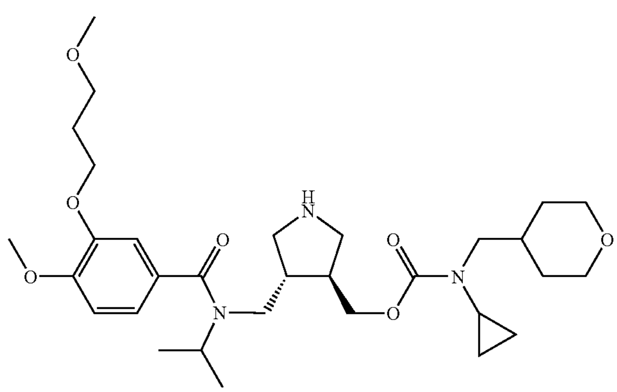 | 576.3 | 4.44[a] |

TABLE 13-continued

| Example | configuration | structure | [M + H]+ | t_R (HPLC) |
|---------|---------------|-----------|----------|------------|
| 302 | (3S, 4S) | 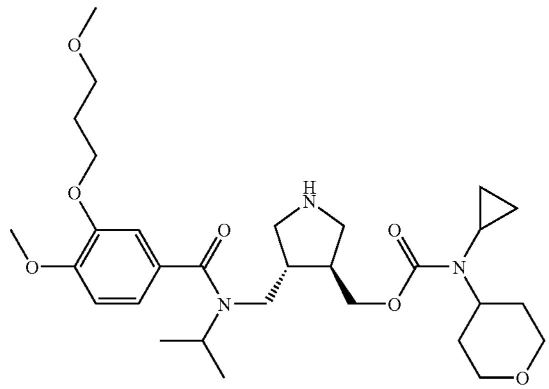 | 562.3 | 1.07[b] |

[a] t_R (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
[b] t_R (HPLC Zorbax SB C18, 10-95% CH₃CN/H₂O/0.8 min, 95% CH₃CN/0.7 min, CH₃CN and H₂O containing 0.1% HCOOH, flow: 1.5 ml/min).

The following Examples are prepared according to the procedures described above for Example 296 using (3R,4S)-3-({[4-ethyl-3-(3-methoxy-propoxy)-benzoyl]-isopropyl-amino}-methyl)-4-hydroxymethyl-pyrrolidine-1-carboxylic acid tert-butyl ester:

TABLE 14

| Example | configuration | structure | [M + H]+ | t_R (HPLC) |
|---------|---------------|-----------|----------|------------|
| 303 | (3S, 4S) | 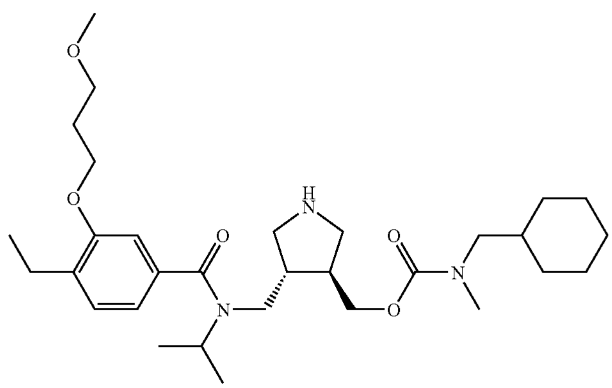 | 546.6 | 5.41[b] |
| 304 | (3S, 4S) | 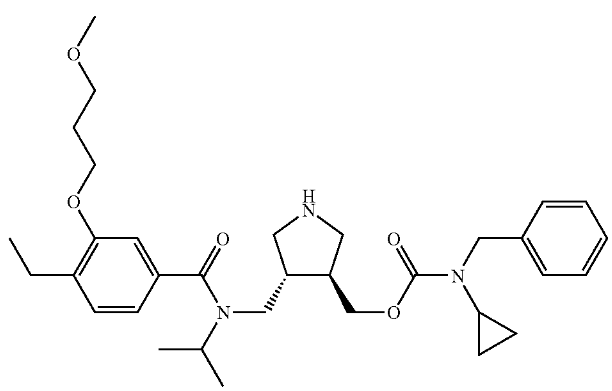 | 566.6 | 5.10[b] |

TABLE 14-continued

| Example | configuration | structure | [M + H]⁺ | t$_R$ (HPLC) |
|---|---|---|---|---|
| 305 | (3S, 4S) | 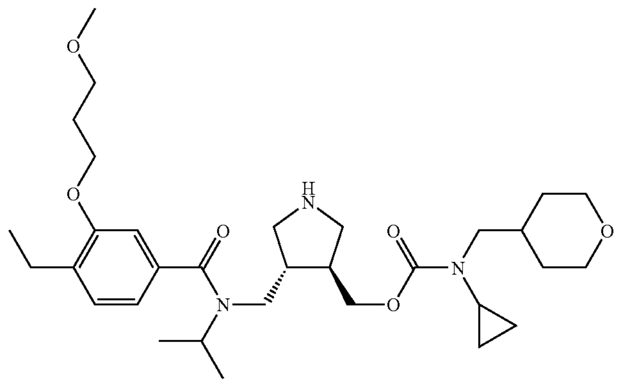 | 574.4 | 5.02$^a$ |
| 306 | (3S, 4S) | 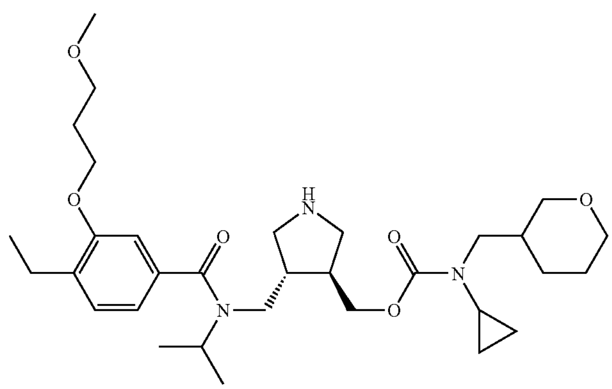 | 574.2 | 5.04$^b$ <br> 5.13$^b$ |
| 307 | (3S, 4S) | 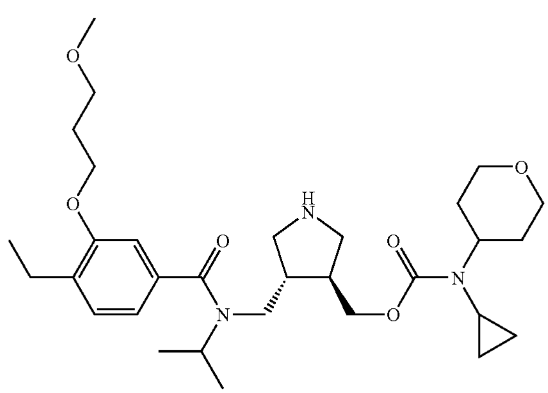 | 560.3 | 4.94$^a$ |

TABLE 14-continued

| Example | configuration | structure | [M + H]+ | tR (HPLC) |
|---|---|---|---|---|
| 308 | (3S, 4S) | 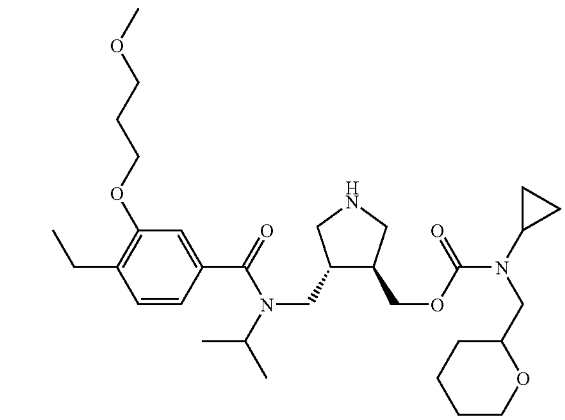 | 574.2 | 4.87[b] |

[a] tR (HPLC, Macherey-Nagel Nucleosil C18 column, 10-100% CH3CN/H2O/5 min, 100% CH3CN/3 min, CH3CN and H2O containing 0.1% TFA, flow: 1 mL/min). ou 1.5 de flux attendre response anne
[b] tR (HPLC, Nucleosil C18-HD column, 20-100% CH3CN/H2O/6 min, 100% CH3CN/1.5 min, flow: 1 ml/min).

The following Examples are prepared according to the procedures described above for Example 296 starting from (3S,4R)-3-hydroxymethyl-4-({isopropyl-[1-(3-methoxy-propyl)-3-methyl-1H-indole-6-carbonyl]-amino}-methyl)-pyrrolidine-1-carboxylic acid tert-butyl ester:

TABLE 15

| Example | configuration | structure | [M + H]+ | tR (HPLC) |
|---|---|---|---|---|
| 309 | (3S, 4S) | | 569.3 | 2.39 | tR (HPLC, Waters Symmetry C18 column, 20-100% CH3CN/H2O/6 min, 100% CH3CN/1.5 min).

Intermediates are prepared as described by the following methods:

Benzyl-cyclopropyl-carbamoyl chloride

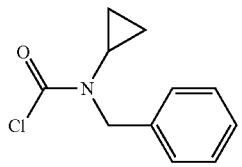

a. Benzyl-cyclopropyl-amine

The title compound is prepared analogously as described for benzyl-cyclopropylmethylamine. TLC, R$_f$ (CH$_2$Cl$_2$/MeOH 95:5)=0.1, MS (LC-MS): 148.2 [M+H]+.

b. Benzyl-cyclopropyl-carbamoyl chloride

The title compound is prepared analogously as described for cyclohexylmethyl-methylcarbamoyl chloride. TLC, R$_f$ (CH$_2$Cl$_2$/MeOH 95:5)=0.9. MS (LC-MS): [M+H]+=210.2. t$_R$ (HPLC, Waters Symmetry C18 column, 20-100% CH$_3$CN/H$_2$O/5 min, CH$_3$CN and H$_2$O containing 0.1% TFA, flow: 0.6 mL/min): 4.67 min.

Cyclopropyl-(tetrahydro-pyran-4-ylmethyl)-carbamoyl chloride

The title compound is prepared analogously as described for benzyl-cyclopropyl-carbamoyl chloride starting from cyclopropyl-(tetrahydro-pyran-4-ylmethyl)-amine (prepared analogously as described for benzyl-cyclopropylmethyl-amine). TLC, R$_f$(CH$_2$Cl$_2$/MeOH 95:5)=0.9.

Cyclopropyl-(tetrahydro-pyran-3-ylmethyl)-carbamoyl chloride

The title compound is prepared analogously as described for benzyl-cyclopropyl-carbamoyl chloride starting from cyclopropyl-(tetrahydro-pyran-3-ylmethyl)-amine (prepared analogously as described for benzyl-cyclopropylmethyl-amine). TLC, Rf (CH$_2$Cl$_2$/MeOH 95:5)=0.9.

Cyclopropyl-(tetrahydro-pyran-2-ylmethyl)-carbamoyl chloride

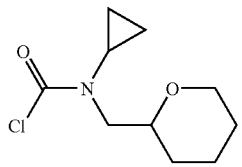

a. Toluene-4-sulfonic acid tetrahydro-pyran-2-ylmethyl ester

To a suspension of tetrahydropyran-2-methanol (2 g, 17.2 mmol) cooled at 0° C. is added toluene-4-sulfonyl chloride (3.6 g, 18.92 mmol), followed by (2.63 mL, 18.92 mmol) of triethylamine. The mixture is allowed to reach RT and stirred overnight. Then poured into an aqueous saturated solution of NaHCO$_3$. The layers are separated and the aqueous one extracted twice with CH$_2$Cl$_2$. The combined organic extracts are dried over Na$_2$SO$_4$, filtered and concentrated. The crude material is purified by flash chromatography on silica gel (eluent: c-hexane/AcOEt 80:20) to give the title product. TLC, R$_f$ (CH$_2$Cl$_2$/MeOH 95:5)=0.9. MS (LC-MS): 271.1 [M+H]$^+$, t$_R$ (HPLC, Macherey-Nagel Nucleosil C18 column, 10-100% CH$_3$CN/H$_2$O/5 min, 100% CH$_3$CN/3 min, flow: 1.5 ml/min): 5.32 min.

b. Cyclopropyl-(tetrahydro-pyran-2-ylmethyl)-amine

A mixture of toluene-4-sulfonic acid tetrahydro-pyran-2-ylmethyl ester (500 mg, 1.85 mmol) and cyclopropylamine (2 mL, 15 mmol) is heated overnight at 110° C. in a sealed tube. The crude mixture is concentrated and taken up in CH$_2$Cl$_2$. Water is added, the layers are separated and the aqueous one back extracted twice with CH$_2$Cl$_2$. The combined organic extracts are washed with brine, dried over Na$_2$SO$_4$, filtered and concentrated. TLC, R$_f$ (CH$_2$Cl$_2$/MeOH 95:5)=0.3, MS (LC-MS): 156.2 [M+H]$^+$.

c. Cyclopropyl-(tetrahydro-pyran-2-ylmethyl)-carbamoyl chloride

To a stirred solution of cyclopropyl-(tetrahydro-pyran-2-ylmethyl)-amine (200 mg, 0.74 mmol) in THF (4 mL) is added triethylamine (144 µL, 1.036 mmol) and 4-dimethylaminopyridine (1.81 mg, 0.015 mmol). The mixture is cooled to 0° C., and triphosgene (88 mg, 0.296 mmol) is added in one portion. After stirring for 30 min at 0° C. and overnight at RT, water is cautiously added and the solution is extracted with AcOEt. The combined organic extracts are washed with brine, dried over Na$_2$SO$_4$, filtered and concentrated. TLC, R$_f$ (CH$_2$Cl$_2$/MeOH 95:5)=0.9.

Cyclopropyl-(tetrahydro-pyran-4-yl)-carbamoyl chloride

The title compound is prepared analogously as described for cyclopropyl-(tetrahydro-pyran-2-ylmethyl)-carbamoyl chloride starting from commercially available cyclopropyl-(tetrahydro-pyran-4-yl)-amine. TLC, R$_f$ (CH$_2$Cl$_2$/MeOH 95:5)=0.9.

EXAMPLE 310

((S)-1-Phenyl-propyl)-carbamic acid (3S,4S)-4-({isopropyl-[4-methoxy-3-(3-methoxy-propoxy)-benzoyl]-amino}-methyl)-pyrrolidin-3-ylmethyl ester

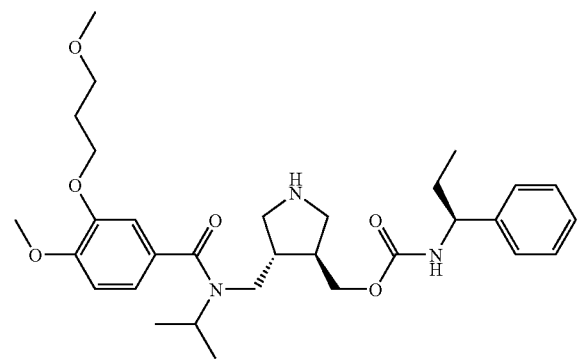

To a solution of (3R,4S)-3-({isopropyl-[4-methoxy-3-(3-methoxy-propoxy)-benzoyl]-amino}-methyl)-4-((S)-1-phenyl-propylcarbamoyloxymethyl)-pyrrolidine-1-carboxylic acid tert-butyl ester (49 mg, 0.075 mmol) in 1 mL dioxane, 4 N HCl in dioxane (0.5 mL, 2 mmol) is added. The mixture is stirred at RT for 2 h, and the resulting solution is lyophilized to afford the corresponding hydrochloride salt. MS (LC-MS): 556.3 [M+H]$^+$; t$_R$ (HPLC, Nucleosil C18-HD column, 20-100% CH$_3$CN/H$_2$O/6 min, 100% CH$_3$CN/1.5 min, flow: 1 ml/min): 4.11 min.

The starting material is prepared as follows:

(3R,4S)-3-({isopropyl-[4-methoxy-3-(3-methoxy-propoxy)-benzoyl]-amino}-methyl)-4-((S)-1-phenyl-propylcarbamoyloxymethyl)-pyrrolidine-1-carboxylic acid tert-butyl ester To a solution of (3S,4R)-3-hydroxymethyl-4-({isopropyl-[4-methoxy-3-(3-methoxy-propoxy)-benzoyl]-amino}-methyl)-pyrrolidine-1-carboxylic acid tert-butyl ester (200 mg, 0.404 mmol) in ether (12 mL) are successively added (S)-1-phenylpropyl isocyanate (130.4 mg, 0.809 mmol) and AlCl$_3$ (54 mg, 0.404 mmol). The mixture is stirred at RT under nitrogen overnight. (S)-1-phenylpropyl isocyanate (150 µL) and AlCl$_3$ (54 mg, 0.404 mmol) are again added and the mixture further stirred for 5 h. AcOEt is added and the reaction mixture quenched by the addition of an aqueous saturated solution of NaHCO$_3$. The layers are separated and the aqueous one back extracted twice with AcOEt. The combined organic extracts are dried over Na$_2$SO$_4$, filtered and concentrated under reduced pressure. The crude mixture is purified by flash chromatography on silica gel (eluent: CH$_2$Cl$_2$/MeOH 100:0 to 95:5) to give the title product TLC, R$_f$ (CH$_2$Cl$_2$/MeOH 95:5)=0.35. MS (LC-MS): 656.2 [M+H]$^+$; t$_R$ (HPLC, Nucleosil C18-HD column, 20-100% CH$_3$CN/H$_2$O/6 min, 100% CH$_3$CN/1.5 min, flow: 1 ml/min): 3.94 min.

The following Examples are prepared according to the procedures described above for Example 310:

The starting material is prepared as follows:
(3R*,4R*)-3-(3-Benzyl-1-cyclopropyl-ureidomethyl)-4-({isopropyl-[4-methoxy-3-(3-methoxy-propoxy)-benzoyl]-amino}-methyl)-pyrrolidine-1-carboxylic acid tert-butyl Ester To a solution of ((3R*,4R*)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester (235 mg, 0.440 mmol) in THF (6 mL) is added

TABLE 16

| Example | configuration | structure | [M + H]$^+$ | t$_R$ (HPLC) |
|---|---|---|---|---|
| 311 | (3S, 4S) | 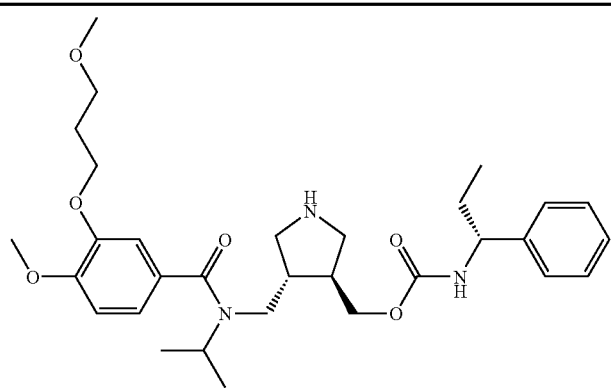 | 556.3 | 4.13 | t$_R$ (HPLC, Nucleosil C18-HD column, 20-100% CH$_3$CN/H$_2$O/6 min, 100% CH$_3$CN/1.5 min, flow: 1 ml/min).

EXAMPLE 312

N-[(3S*,4S*)-4-(3-Benzyl-1-cyclopropyl-ureidomethyl)-pyrrolidin-3-ylmethyl]-N-isopropyl-4-methoxy-3-(3-methoxy-propoxy)-benzamide

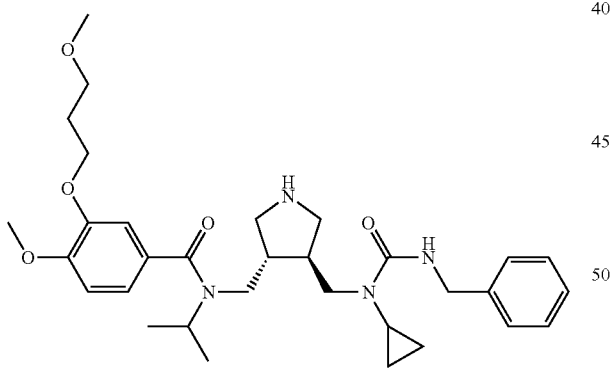

To a solution of (3R*,4R*)-3-(3-benzyl-1-cyclopropyl-ureidomethyl)-4-({isopropyl-[4-methoxy-3-(3-methoxy-propoxy)-benzoyl]-amino}-methyl)-pyrrolidine-1-carboxylic acid tert-butyl ester (270 mg, 0.405 mmol) in dioxane (5 mL), 4N HCl in dioxane (3 mL) is added and the resulting solution is stirred at RT for 5 h. Lyophilization affords the corresponding hydrochloride salt as a colorless powder. MS (LC-MS): 567.0 [M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 5.18 min.

triethylamine (123 µL, 0.880 mmol) followed by benzylisocyanate (54 µL, 0.440 mmol). The mixture is stirred at RT for 2 h before water is added. Extraction with ethyl acetate, drying of the combined extracts (Na$_2$SO$_4$), filtration and evaporation of the solvent affords the crude product which is purified by flash chromatography on silica gel (eluent gradient: CH$_2$Cl$_2$ 100% to CH$_2$Cl$_2$/MeOH 9:1) to give the title compound. MS (LC-MS): 667.1M+H]$^+$; t$_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 6.26 min.

EXAMPLE 313

Pyrrolidine-1-carboxylic acid cyclopronpyl-[(3S*,4S*)-4-({isopropyl-[4-methoxy-3-(3-methoxy-propoxy)-benzoyl]-amino}-methyl)-pyrrolidin-3-ylmethyl]-amide

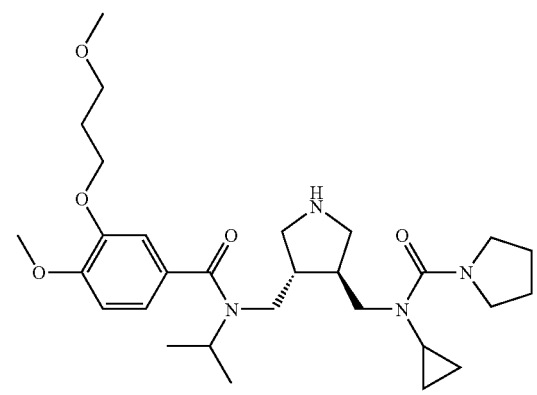

To a solution of (3R*,4R*)-3-{[cyclopropyl-(pyrrolidine-1-carbonyl)-amino]-methyl}4-({isopropyl-[4-methoxy-3-(3-methoxy-propoxy)-benzoyl]-amino}-methyl)-pyrrolidine-1-carboxylic acid tert-butyl ester (165 mg, 0.262 mmol) in dioxane (5 mL), 4N HCl in dioxane (3 mL) is added and the resulting solution is stirred at RT for 4.5 h. Lyophilization affords the corresponding hydrochloride salt as a colorless solid. MS (LC-MS): 531.1 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 5.11 min.

The starting material is prepared as follows:

(3R*,4R*)-3-{[Cyclopropyl-(pyrrolidine-1-carbonyl)-amino]-methyl}-4-({isopropyl-[4-methoxy-3-(3-methoxy-propoxy)-benzoyl]-amino}-methyl)-pyrrolidine-1-carboxylic acid tert-butyl ester Triethylamine (99 µL, 0.714 mmol) followed by 1-pyrrolidinecarbonyl chloride is added to a solution of ((3R*,4R*)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester (254 mg, 0.476 mmol) in CH$_2$Cl$_2$ (20 mL). The resulting solution is stirred at RT for 2 h and at 60° C. for another 24 h. Evaporation of the solvent affords the crude product which is purified by preparative HPLC (Waters C$_{18}$ ODB, eluent: H$_2$O/CH$_3$CN 20 to 100%) to give the title compound. MS (LC-MS): 631.1 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 6.31 min.

EXAMPLE 314

N-[(3S*,4S*)-4-(1-Cyclopropyl-3-methyl-3-phenyl-ureidomethyl)-pyrrolidin-3-ylmethyl]-N-isopropyl-4-methoxy-3-(3-methoxy-propoxy)-benzamide

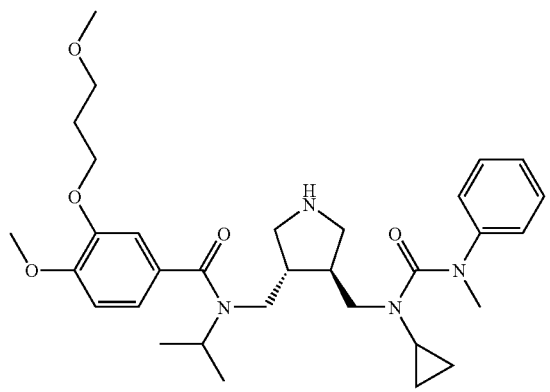

A solution of (3R*,4R*)-3-(1-cyclopropyl-3-methyl-3-phenyl-ureidomethyl)-4-({isopropyl-[4-methoxy-3-(3-methoxy-propoxy)-benzoyl]-amino}-methyl)-pyrrolidine-1-carboxylic acid tert-butyl ester (195 mg, 0.29 mmol) in 4N HCl/dioxane (8 mL) is stirred at RT until the reaction is complete. Lyophilization affords the title compound as a colorless foam. MS (LC-MS): 567.1 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 4.57 min.

The starting material is prepared as follows:

(3R*,4R*)-3-(1-Cyclopropyl-3-methyl-3-phenyl-ureidomethyl)-4-({isopropyl-[4-methoxy-3-(3-methoxy-propoxy)-benzoyl]-amino}-methyl)-pyrrolidine-1-carboxylic acid tert-butyl ester A mixture of (3R*,4R*)-3-cyclopropylaminomethyl-4-({isopropyl-[4-methoxy-3-(3-methoxy-propoxy)-benzoyl]-amino}-methyl)-pyrrolidine-1-carboxylic acid tert-butyl ester (216 mg, 0.41 mmol), N-methyl-N-phenyl carbamoylchloride (274 mg, 1.62 mmol), triethylamine (0.45 mL, 3.24 mmol) and DMAP (1 mg, 0.008 mmol) in THF (15 mL) is heated at 60° C. for 4 h. After cooling to RT 1N HCl is added and the mixture is extracted with ethyl acetate, the combined organic extracts are dried (Na$_2$SO$_4$), filtered and the solvent is evaporated. Purification by flash chromatography on silica gel (eluent gradient: CH$_2$Cl$_2$ 100% CH$_2$Cl$_2$/MeOH 9:1) affords the title compound. MS (LC-MS): 667.1 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 6.02 min.

EXAMPLE 315

N-{(3S,4S)-4-[1-Cyclopropyl-3-(tetrahydro-pyran-4-ylmethyl)-ureido-methyl]-pyrrolidin-3-ylmethyl}-N-isopropyl-4-methoxy-3-(3-methoxy-propoxy)-benzamide

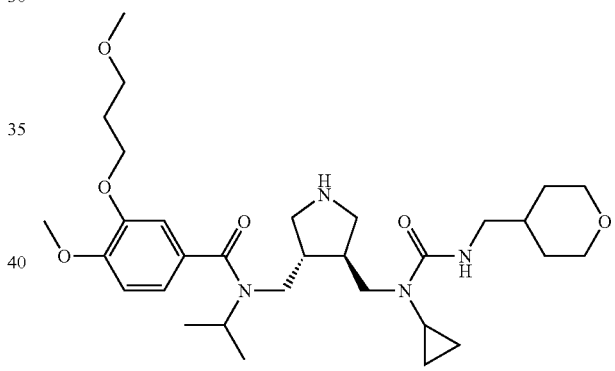

To a solution of (3R*,4R*)-3-[1-cyclopropyl-3-(tetrahydro-pyran-4-ylmethyl)-ureidomethyl]-4-({isopropyl-[4-methoxy-3-(3-methoxy-propoxy)-benzoyl]-amino}-methyl)-pyrrolidine-1-carboxylic acid tert-butyl ester (50 mg, 0.074 mmol) in dioxane (3 mL), 4N HCl in dioxane (1 mL) is added and the resulting solution is stirred at RT for 5 h. Lyophilization affords the corresponding hydrochloride salt as a colorless solid. MS (LC-MS): 575.1 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 ml/min): 5.29 min.

The starting material is prepared as follows:

(3R*,4R*)-3-[1-Cyclopropyl-3-(tetrahydro-pyran-4-ylmethyl)-ureidomethyl]-4-({isopropyl-[4-methoxy-3-(3-methoxy-propoxy)-benzoyl]-amino}-methyl)-pyrrolidine-1-carboxylic acid tert-butyl ester 4-Aminomethyl tetrahydropyrane (50 mg, 0.435 mmol) is added to a suspension of bis(trichloromethyl) carbonate (155 mg, 0.522 mmol) and charcoal (10 mg) in AcOEt(8 mL) at RT. The mixture is stirred at RT for 5 min and heated under reflux for another 10 min before it is allowed to cool to RT.

Filtration and evaporation of the solvent affords the corresponding isocyanate which is used without further purification and dissolved in CH₃CN (10 mL). ((3R*,4R*)-3-Cyclopropylaminomethyl-4-({isopropyl-[4-methoxy-3-(3-methoxy-propoxy)-benzoyl]-amino}-methyl)-pyrrolidine-1-carboxylic acid tert-butyl ester (232 mg, 0.435 mmol) is added and the mixture is heated under reflux for 16 h. For workup the solvent is evaporated and purified by preparative HPLC (Interchrom C18 ODB, eluent: CH₃CN/H₂O 5%/2.5 min, CH₃CN/H₂O 5-100%/22.5 min, 100% CH₃CN/4.5 min, flow 40 mL/min) to give the title compound. MS (LC-MS): 675.1 [M+H]⁺; $t_R$ (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 ml/min): 6.19 min.

The following Examples are prepared according to the procedures described above for Example 312 or Example 314:

TABLE 17

| Example | configuration | structure | [M + H]⁺ | $t_R$ (HPLC) |
|---|---|---|---|---|
| 316 | (3S*, 4S*) | 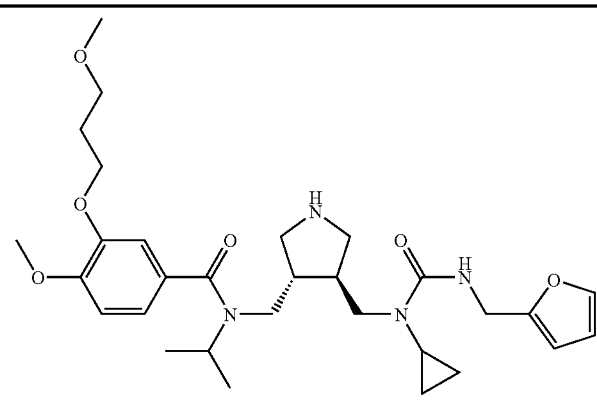 | 557.0 | 5.17ᵃ |
| 317 | (3S, 4S) | 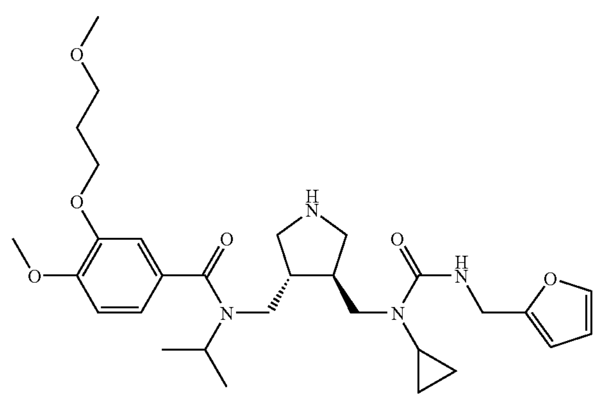 | 557.5 | 4.77ᵃ |
| 318 | (3S*, 4S*) | 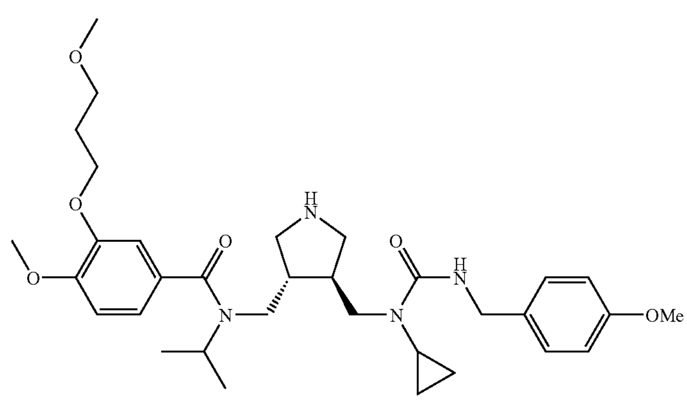 | 597.1 | 5.35ᵃ |

TABLE 17-continued

| Example | configuration | structure | [M + H]⁺ | $t_R$ (HPLC) |
|---|---|---|---|---|
| 319 | (3S*, 4S*) | 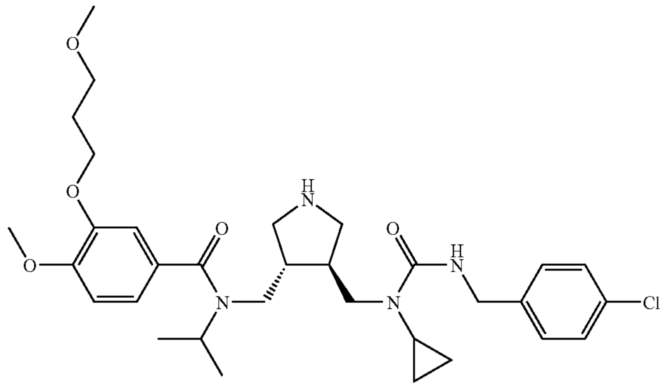 | 601.0 | 5.58[a] |
| 320 | (3S*, 4S*) | 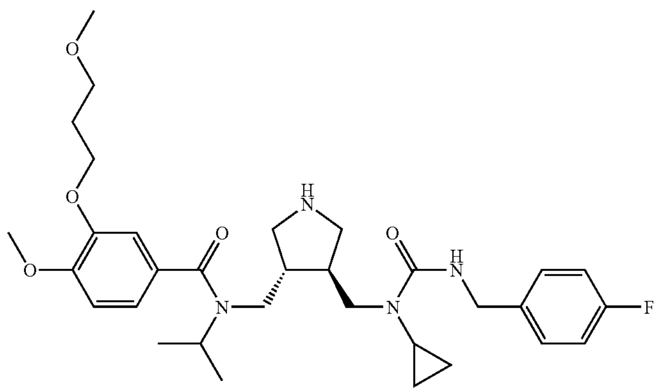 | 585.0 | 5.42[a] |
| 321 | (3S*, 4S*) | 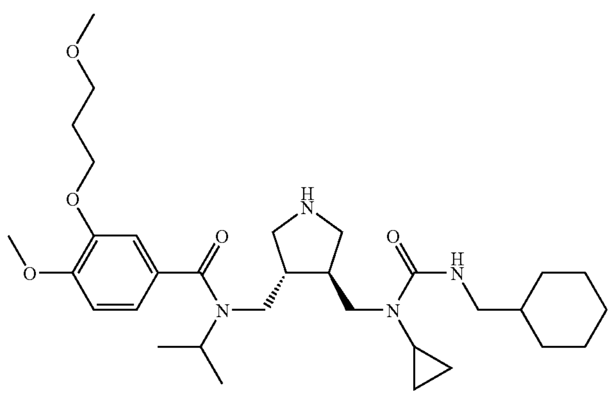 | 573.1 | 5.73[a] |
| 322 | (3S*, 4S*) | 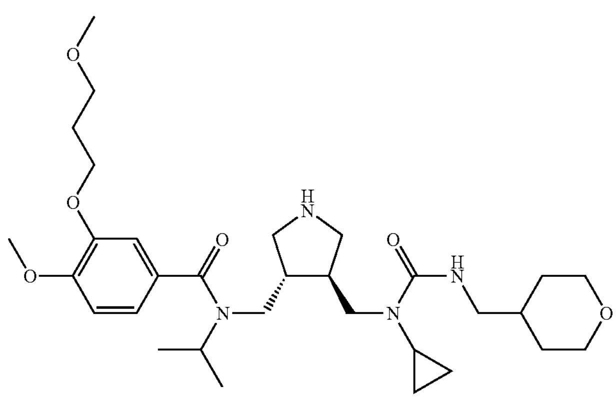 | 575.1 | 5.29[a] |

TABLE 17-continued

| Example | configuration | structure | [M + H]+ | tR (HPLC) |
|---|---|---|---|---|
| 323 | (3S*, 4S*) | 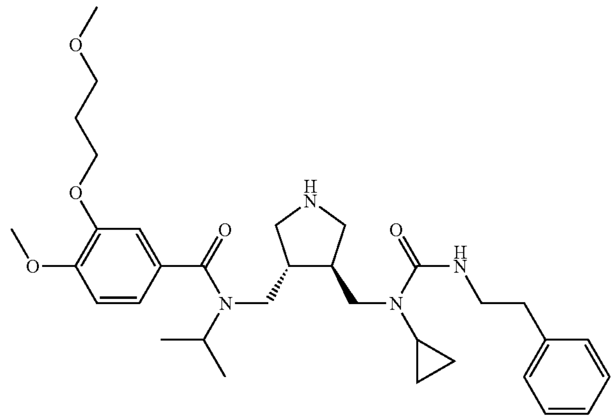 | 581.1 | 5.67a |
| 324 | (3S*, 4S*) | 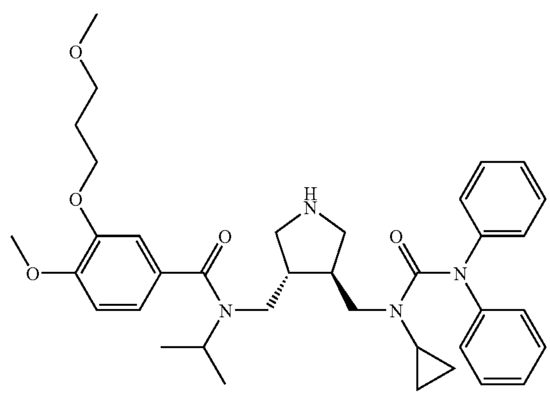 | 629.1 | 5.85a |
| 325 | (3S*, 4S*) | 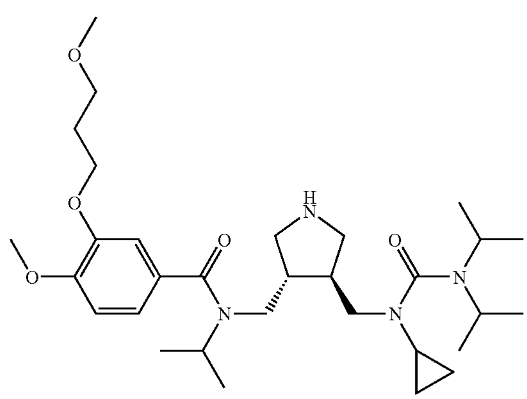 | 561.1 | 5.70a |

TABLE 17-continued

| Example | configuration | structure | [M + H]+ | t_R (HPLC) |
|---|---|---|---|---|
| 326 | (3S*, 4S*) | 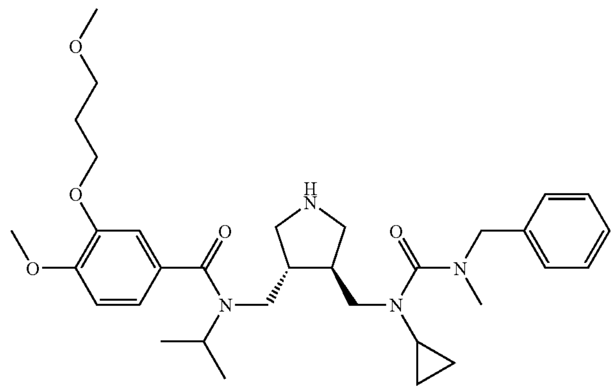 | 581.1 | 4.66[a] |
| 327 | (3S*, 4S*) | 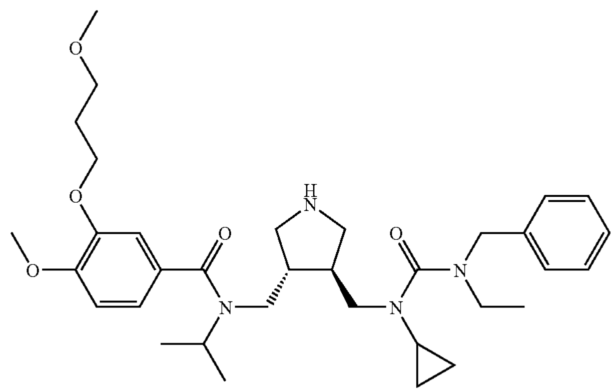 | 595.1 | 4.78[a] |
| 328 | (3S, 4S) | 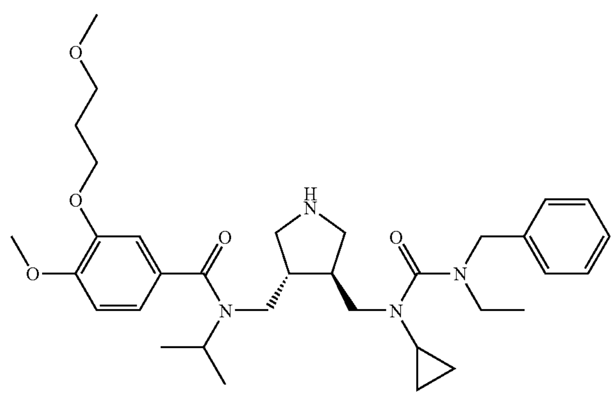 | 595.0 | 5.04[a] |
| 329 | (3S*, 4S*) | 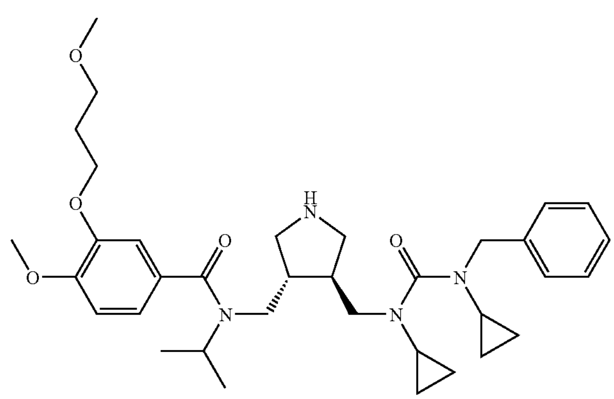 | 607.5 | 4.96[a] |

TABLE 17-continued

| Example | configuration | structure | [M + H]+ | t_R (HPLC) |
|---|---|---|---|---|
| 330 | (3S*, 4S*) | 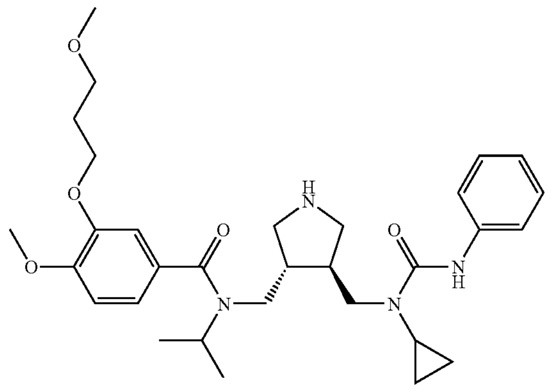 | 553.3 | 4.74[a] |
| 331 | (3S*, 4S*) | 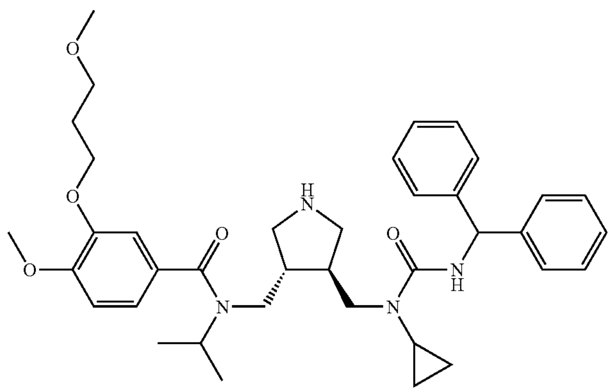 | 643.2 | 5.17[a] |
| 332 | (3S, 4S) | 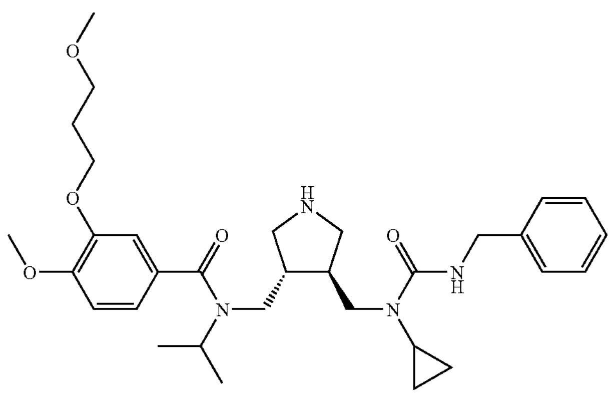 | 567.3 | 4.82[a] |
| 333 | (3S*, 4S*) | 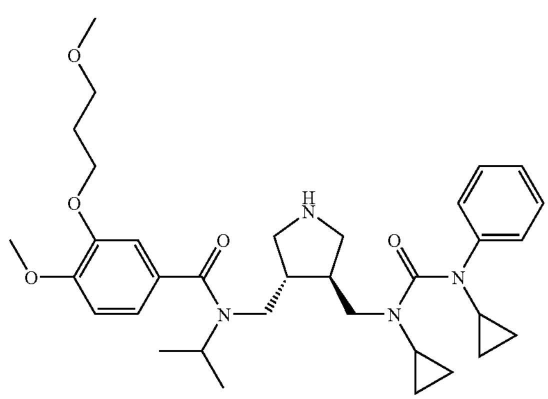 | 593.3 | 4.94[a] |

TABLE 17-continued
| Example | configuration | structure | [M + H]+ | $t_R$ (HPLC) |
|---|---|---|---|---|
| 334 | (3S*, 4S*) | 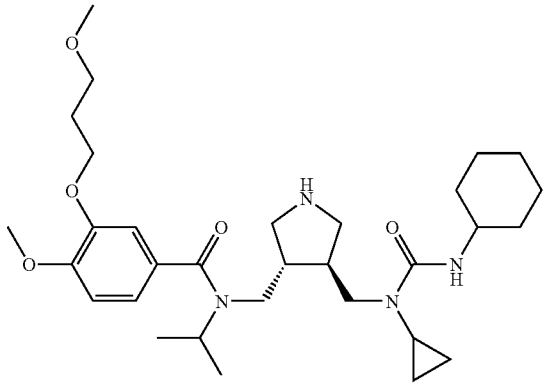 | 559.5 | 5.05[a] |
| 335 | (3S*, 4S*) | 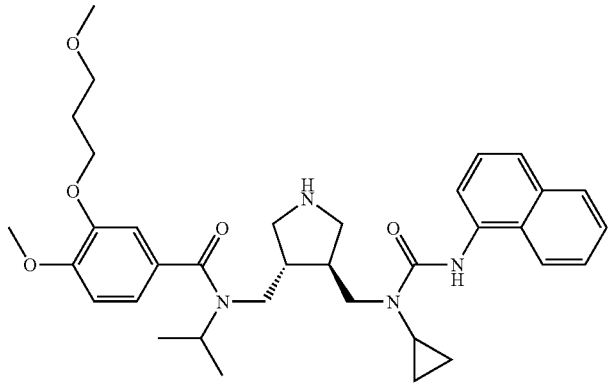 | 603.3 | 5.52[a] |
| 336 | (3S, 4S) | 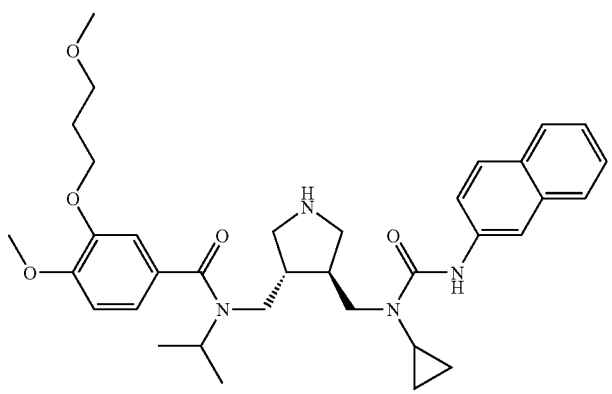 | 603.3 | 5.95[a] |
| 337 | (3S, 4S) | 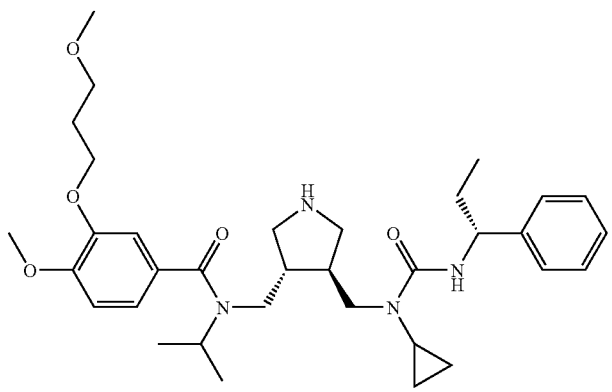 | 595.2 | 5.85[a] |

TABLE 17-continued

| Example | configuration | structure | [M + H]+ | $t_R$ (HPLC) |
|---|---|---|---|---|
| 338 | (3S, 4S) | 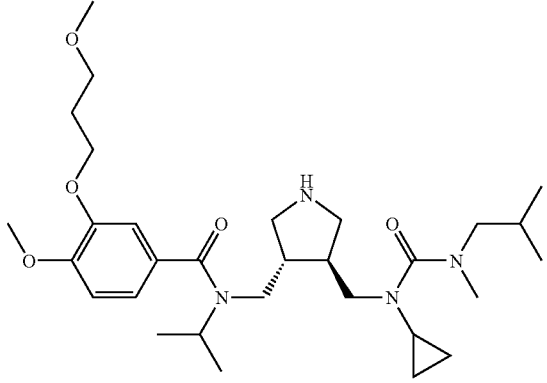 | 547.2 | 5.91[a] |
| 339 | (3S, 4S) | 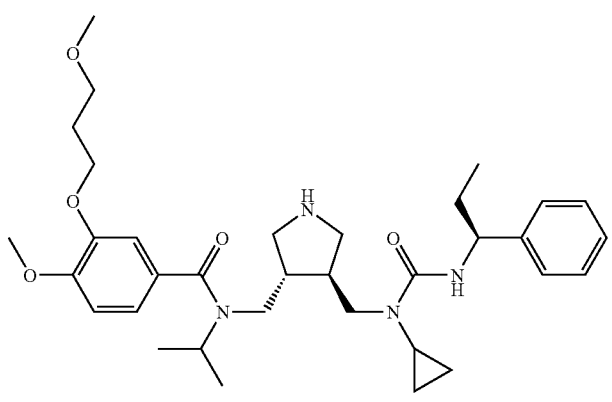 | 595.2 | 5.13[a] |
| 340 | (3S, 4S) | 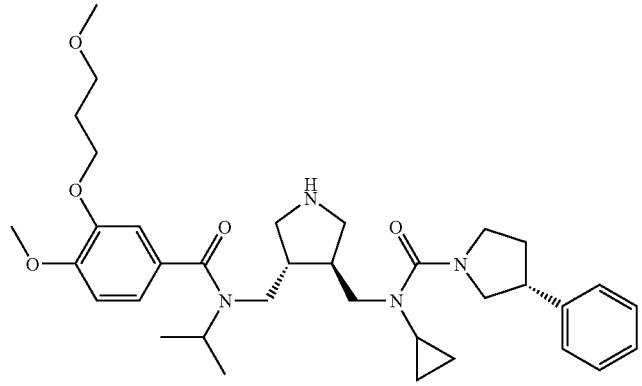 | 607.5 | 3.47[b] |

[a] $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min).
[b] $t_R$ (HPLC, Waters Symmetry C18 column, 10-95% CH$_3$CN/H$_2$O/3.5 min, 95% CH$_3$CN/H$_2$O, 2 min, CH$_3$CN and H$_2$O containing 0.1% TFA, flow: 0.6 mL/min).

Benzyl-methyl-carbamoyl chloride

At −78° C. pyridine (1.25 mL, 15.5 mmol) followed by methyl benzylamine (2.0 mL, 15.5. mmol) are added to a solution of bis(trichloromethyl) carbonate (1.55 g, 5.2 mmol) in CH$_2$Cl$_2$ (20 mL). The reaction mixture is allowed to warm to RT and stirred for another 1.5 h. For workup 1N HCl is added to the yellow suspension and the mixture is extracted with ethyl acetate. Drying (Na$_2$SO$_4$) of the combined organic exctracts, filtration and evaporation of the solvent affords the title compound. MS (LC-MS): [M+H]+=184.1. $t_R$ (HPLC, Waters Symmetry C18 column, 20-95% CH$_3$CN/H$_2$O/3.5 min, 95% CH$_3$CN/H$_2$O, 2 min, CH$_3$CN and H$_2$O containing 0.1% TFA, flow: 0.6 mL/min): 3.84 min.

Benzyl-ethyl-carbamoyl chloride

The title compound is prepared analogously as described for benzyl-methyl-carbamoyl chloride from benzyl ethylamine. MS (LC-MS): [M+H]+=198.1. $t_R$ (HPLC, Waters Symmetry C18 column, 20-95% $CH_3CN/H_2O$/3.5 min, 95% $CH_3CN/H_2O$, 2 min, $CH_3CN$ and $H_2O$ containing 0.1% TFA, flow: 0.6 mL/min): 4.12 min.

Phenyl-cyclopropyl-carbamoyl chloride

The title compound is prepared analogously as described for benzyl-methyl-carbamoyl chloride from cyclopropyl-phenyl-amine prepared according to 0 *Synlett* 2003, 14, 2139. MS (LC-MS): $[M+H]^+$=196.2. $t_R$ (HPLC, Waters Symmetry C18 column, 20-95% $CH_3CN/H_2O$/3.5 min, 95% $CH_3CN$/$H_2O$, 2 min, $CH_3CN$ and $H_2O$ containing 0.1% TFA, flow: 0.6 mL/min): 4.44 min.

Scheme 6

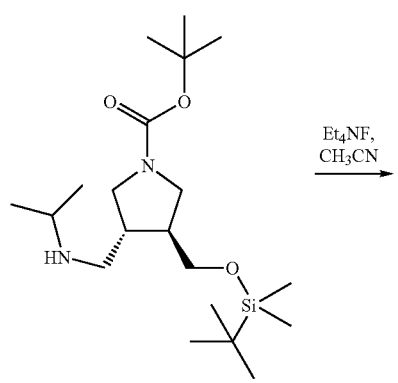

Et$_4$NF, CH$_3$CN →

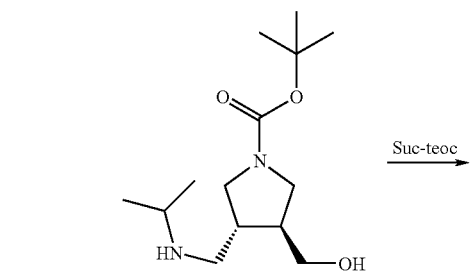

Suc-teoc →

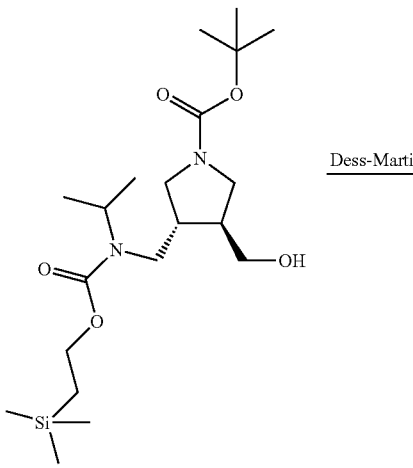

Dess-Martin →

-continued

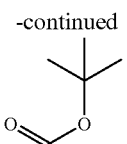

RNH$_2$ / NaBHOAc$_3$ →

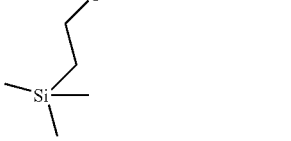

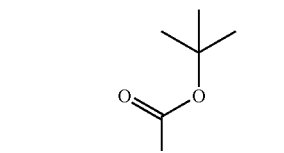

RCOOH / EDCl, HOAt →

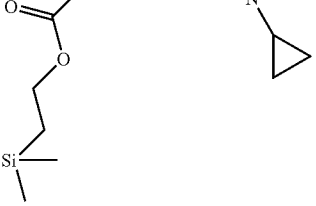

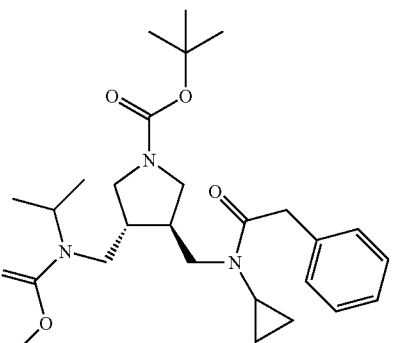

TBAF / CH$_3$CN →

311

-continued

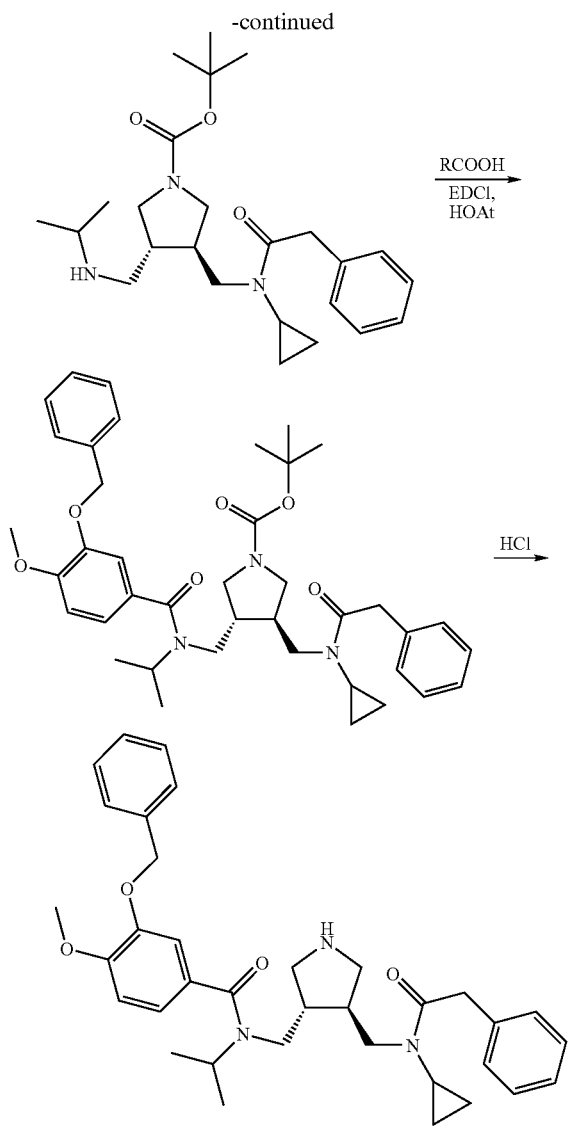

EXAMPLE 341

3-Benzyloxy-N-{(3S,4S)-4-[(cyclopropyl-phenylacetyl-amino)-methyl]-pyrrolidin-3-ylmethyl}-N-isopropyl-4-methoxy-benzamide

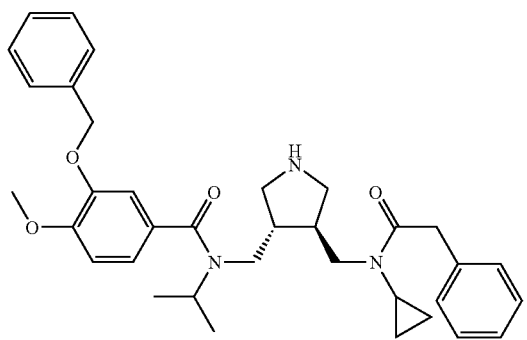

312

To a solution of (3R,4R)-3-{[(3-benzyloxy-4-methoxybenzoyl)-isopropyl-amino]-methyl}-4-[(cyclopropyl-phenylacetyl-amino)-methyl]-pyrrolidine-1-carboxylic acid tert-butyl ester (0.191 g, 0.285 mmol) in dioxane (2 mL), 4N HCl in dioxane (1.07 mL) is added, and the resulting solution is stirred for 2 h, then lyophilized to afford the corresponding hydrochloride salt. MS (LC-MS): 570.2 [M+H]$^+$; $t_R$ (HPLC, C18 column, 20-100% $CH_3CN/H_2O$/6 min, 100% $CH_3CN$/1.5 min, $CH_3CN$ and $H_2O$ containing 0.1% TFA, flow: 1 mL/min): 4.60 min.

The starting material is prepared as follows:

A. (3S,4R)-3-Hydroxymethyl-4-(isopropylamino-methyl)-pyrrolidine-1-carboxylic acid tert-butyl ester To a solution of (3S,4R)-3-(tert-butyl)-dimethyl-silanyloxymethyl)-4-(isopropylamino-methyl)-pyrrolidine-1-carboxylic acid tert-butyl ester (prepared under F in Example 9, Scheme 5) (19.5 g, 47.4 mmol) in MeCN (250 ml) is added $Et_4NF$ (14.4 g, 94.8 mmol) and the resulting is refluxed for 3 h. The solvent is concentrated under reduced pressure and the crude material is taken up in AcOEt, a saturated aqueous solution of $NaHCO_3$ is added and the layers are separated. The aqueous layer is back extracted twice with AcOEt and the combined organic extracts are dried over $Na_2SO_4$, filtered and concentrated. The compound was used in the next step without further purification. TLC, $R_f$ (MeOH/$CH_2Cl_2$ 1:9): 0.22. MS (LC-MS): 273.0 [M+H]$^+$.

B. (3S,4S)-3-Hydroxymethyl-4-{[isopropyl-(2-trimethylsilanyl-ethoxycarbonyl)-amino]-methyl}-pyrrolidine-1-carboxylic acid tert-butyl ester To a solution of (3S,4R)-3-hydroxymethyl-4-(isopropylamino-methyl)-pyrrolidine-1-carboxylic acid tert-butyl ester (13.6 g, 47.4 mmol) in dioxane (200 ml) are added $Et_3N$ (6.64 ml, 47.4 mmol) and 1-[(2-trimethylsilyl)ethoxycarbonyloxy]pyrrolidin-2,5-dione (12.3 g, 47.4 mmol). The mixture is stirred overnight at RT under nitrogen. The solvent is concentrated under reduced pressure and the crude material is taken up in AcOEt, a saturated aqueous solution of $NaHCO_3$ is added and the layers are separated. The aqueous layer is back extracted twice with AcOEt and the combined organic extracts are dried over $Na_2SO_4$, filtered and concentrated. The crude residue is purified by flash chromatography on silica gel (eluent: $CH_2Cl_2$/MeOH 95:5) to afford the title compound as a yellow oil. TLC, $R_f$(MeOH/$CH_2Cl_2$ 2:8): 0.65. MS (LC-MS): 417.0 [M+H]$^+$.

C. (3S,4S)-3-Formyl-4-{[isopropyl-(2-trimethylsilanyl-ethoxycarbonyl)-amino]-methyl}-pyrrolidine-1-carboxylic acid tert-butyl ester To a well stirred mixture of (3S,4S)-3-hydroxymethyl-4-{[isopropyl-(2-trimethylsilanyl-ethoxycarbonyl)-amino]-methyl}-pyrrolidine-1-carboxylic acid tert-butyl ester (16.6 g, 39.8 mmol) and Dess-Martin periodinane (16.9 g, 39.8 mmol) in $CH_2Cl_2$ (110 mL), slowly wet $CH_2Cl_2$ (0.79 mL of water in 110 mL of $CH_2Cl_2$) is added. The clear solution becomes cloudy toward the end of wet $CH_2Cl_2$ addition and is further stirred overnight. Then concentrated to a few mL of solvent by rotary evaporation and taken up in $Et_2O$. A solution of 1:1 10% $Na_2S_2O_3$ saturated aqueous $NaHCO_3$ is added. The layers are separated and the organic extract is washed successively with $H_2O$ and brine. The aqueous washings are back-extracted with $Et_2O$, and this organic layer is washed with $H_2O$ and brine. The combined organic layers are dried with Na₂SO₄, filtered and concentrated. The crude mixture is used in the next step without further purification. TLC, $R_f$ (CH₂Cl₂/MeOH 9:1)=0.48. MS (LC-MS): 437.0 [M+Na]⁺.

D. (3R,4S)-3-Cyclopropylaminomethyl-4-{[(isopropyl-(2-trimethylsilanyl-ethoxycarbonyl)-amino]-methyl}-pyrrolidine-1-carboxylic acid tert-butyl ester To a solution of (3S,4S)-3-formyl-4-{[isopropyl-(2-trimethylsilanyl-ethoxycarbonyl)-amino]-methyl}-pyrrolidine-1-carboxylic acid tert-butyl ester (8.1 g, 19.5 mmol) and cyclopropylamine (1.54 mL, 21.5 mmol) in 1,2-dichloroethane (200 mL) is added NaBH(OAc)₃ (6.1 g, 27.3 mmol) and the mixture is stirred overnight. Then diluted with CH₂Cl₂ and washed with an aqueous saturated solution of NaHCO₃. The aqueous layer is back extracted twice with CH₂Cl₂ and the combined organic extracts are dried over Na₂SO₄, filtered and concentrated. The crude material is used in the next step without further purification. TLC, $R_f$(CH₂Cl₂/MeOH 9:1)= 0.45. MS (LC-MS): 456.2 [M+H]⁺.

E. (3R,4S)-3-[(Cyclopropyl-phenylacetyl-amino)-methyl]-4-{[isopropyl-(2-trimethylsilanyl-ethoxycarbonyl)-amino]-methyl}-pyrrolidine-1-carboxylic acid tert-butyl ester To a solution of phenylacetic acid (1.45 g, 10.53 mmol) and (3R,4S)-3-cyclopropylaminomethyl-4-{[isopropyl-(2-trimethylsilanyl-ethoxycarbonyl)-amino]-methyl}-pyrrolidine-1-carboxylic acid tert-butyl ester (3.2 g, 7.022 mmol) in CH₂Cl₂ (10 mL), are added triethylamine (1.47 mL, 10.53 mmol) and 1-hydroxy-7-azabenzotriazol hydrate (1.46 g, 10.53 mmol) followed 15 min later by N-(3-dimethylaminopropyl)-N'-ethyl-carbodiimide hydrochloride (3.06 g, 15.78 mmol). The resulting mixture is stirred for 2 days at RT, then diluted with CH₂Cl₂ and poured into an aqueous 2M HCl solution. The layers are separated and the aqueous one extracted twice with CH₂Cl₂. The combined organic extracts are neutralized with an aqueous saturated solution of NaHCO₃, dried over Na₂SO₄, filtered and concentrated. The crude product is purified by flash chromatography on silica gel (eluent: hexane/AcOEt 2:1). TLC, $R_f$ (hexane/AcOEt 1:1)= 0.42. MS (LC-MS): 574.2 [M+H]⁺; $t_R$ (HPLC, C18 column, 20-100% CH₃CN/H₂O/6 min, 100% CH₃CN/1.5 min, CH₃CN and H₂O containing 0.1% TFA, flow: 1 mL/min): 6.49 min.

F. (3R,4R)-3-[(Cyclopropyl-phenylacetyl-amino)-methyl]-4-(isopropylamino-methyl)-pyrrolidine-1-carboxylic acid tert-butyl ester To a solution of (3R,4S)-3-[(cyclopropyl-phenylacetyl-amino)-methyl]-4-{[isopropyl-(2-trimethylsilanyl-ethoxycarbonyl)-amino]-methyl}-pyrrolidine-1-carboxylic acid tert-butyl ester (2.55 g, 4.44 mmol) in CH₃CN (30 mL) is added tetrabutylammonium fluoride trihydrate (4.34 g, 13.33 mmol) under a nitrogen atmosphere. The reaction mixture is stirred overnight at reflux. The solvent is removed under vacuum and Water and CH₂Cl₂ are added, the layers are separated and the aqueous one extracted twice with CH₂Cl₂. The combined organic extracts are dried (Na₂SO₄), and the solvent is removed in vacuo. The crude product is purified by flash chromatography on silica gel (eluent: CH₂Cl₂/MeOH/ NH₄OH 98:2:1) to give the title product. TLC, $R_f$(CH₂Cl₂/ MeOH/NH₄OH 98:2:1)=0.11. MS (LC-MS): 430.2 [M+H]⁺; $t_R$ (HPLC, C18 column, 20-100% CH₃CN/H₂O/16 min, 100% CH₃CN/1.5 min, CH₃CN and H₂O containing 0.1% TFA, flow: 1 mL/min): 3.90 min.

G. (3R,4R)-3-{[(3-Benzyloxy-4-methoxy-benzoyl)-isopropyl-amino]-methyl}-4-[(cyclopropyl-phenylacetyl-amino)-methyl]-pyrrolidine-1-carboxylic acid tert-butyl ester To a solution of 3-benzyloxy-4-methoxy-benzoic acid (0.19 g, 0.734 mmol) and (3R,4R)-3-[(cyclopropyl-phenylacetyl-amino)-methyl]-4-(isopropylamino-methyl)-pyrrolidine-1-carboxylic acid tert-butyl ester (0.3 g, 0.489 mmol) in CH₂Cl₂ (10 mL), are added triethylamine (0.102 mL, 0.734 mmol) and 1-hydroxy-7-azabenzotriazol hydrate (0.102 g, 0.734 mmol) followed 15 min later by N-(3-dimethylaminopropyl)-N'-ethyl-carbodiimide hydrochloride (0.142 g, 0.734 mmol). The resulting mixture is stirred for 2 days at RT, then diluted with CH₂Cl₂ and poured into an aqueous 2M HCl solution. The layers are separated and the aqueous one extracted twice with CH₂Cl₂. The combined organic extracts are neutralized with an aqueous saturated solution of NaHCO₃, dried over Na₂SO₄, filtered and concentrated. The crude product is purified by preparative HPLC. MS (LC-MS): 670.2 [M+H]⁺; $t_R$ (HPLC, C18 column, 20-100% CH₃CN/ H₂O/6 min, 100% CH₃CN/1.5 min, CH₃CN and H₂O containing 0.1% TFA, flow: 1 mL/min): 5.76 min.

The following Examples are prepared according to the procedures as described above for Example 341, by starting from (3R,4R)-3-[(benzyl-cyclopropyl-amino)-methyl]-4-(isopropylamino-methyl)-pyrrolidine-1-carboxylic acid tert-butyl ester (or its racemate) and the corresponding substituted benzoic acid.

TABLE 18

| Example | configuration | structure | [M + H]⁺ | $t_R$ (HPLC) |
|---|---|---|---|---|
| 342 | (3S, 4S) | 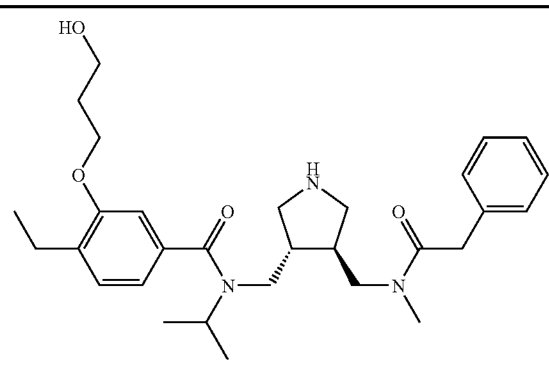 | 510.4 | 4.63ᵃ |

TABLE 18-continued

| Example | configuration | structure | [M + H]+ | t_R (HPLC) |
|---|---|---|---|---|
| 343 | (3S, 4S) | 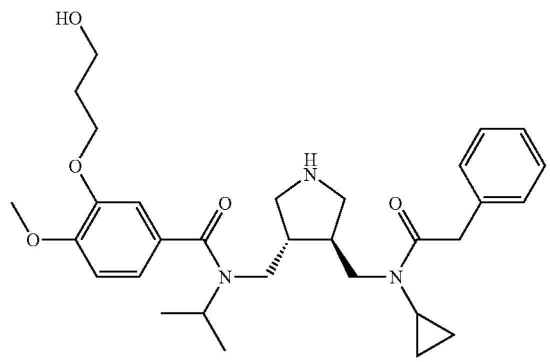 | 538.2 | 3.47[c] |
| 344 | (3S*, 4S*) | 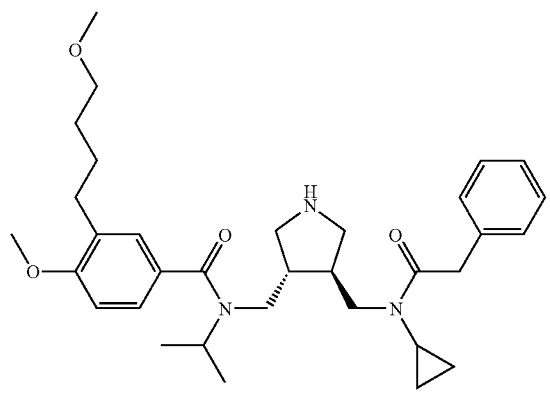 | 550.2 | 4.66[c] |
| 345 | (3S*, 4S*) | 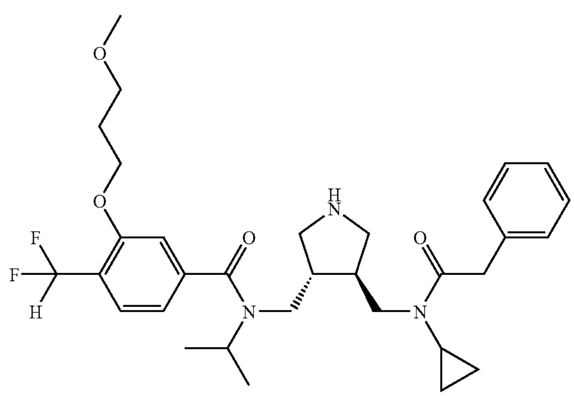 | 572.2 | 4.71[c] |
| 346 | (3S*, 4S*) | 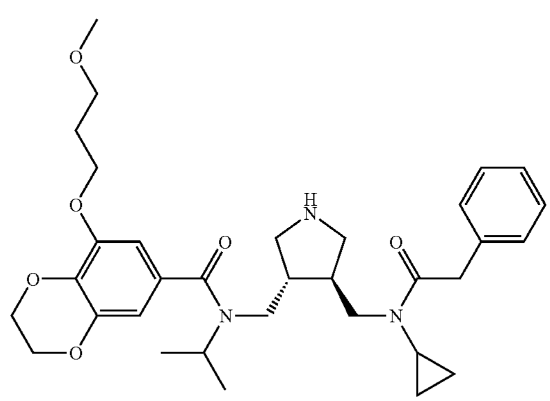 | 580.2 | 4.14[c] |

TABLE 18-continued
| Example | configuration | structure | [M + H]+ | t_R (HPLC) |
|---|---|---|---|---|
| 347 | (3S*, 4S*) | 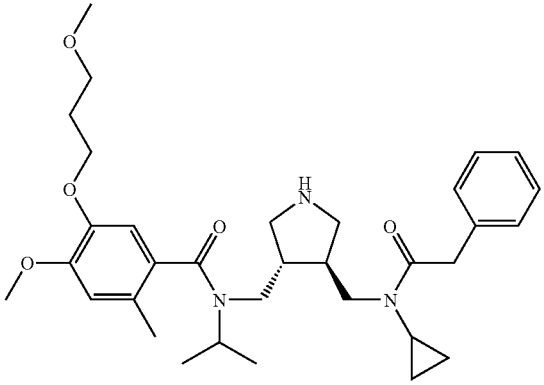 | 566.2 | 4.23[c] |
| 348 | (3S*, 4S*) | 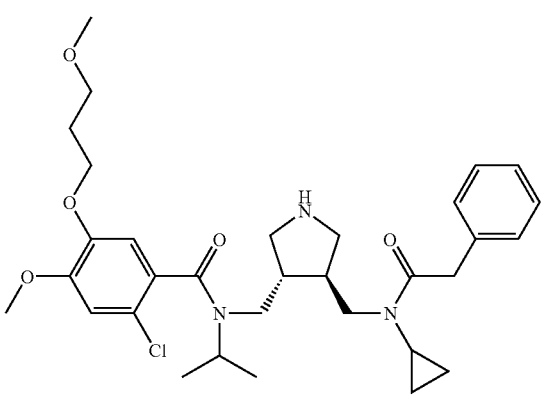 | 586.2 | 4.46[c] |
| 349 | (3S*, 4S*) | 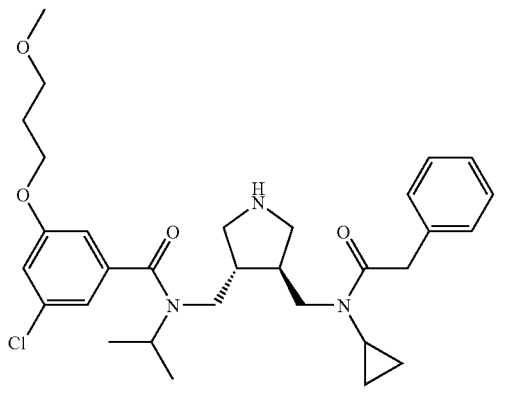 | 556.2 | 4.79[c] |
| 350 | (3S*, 4S*) | 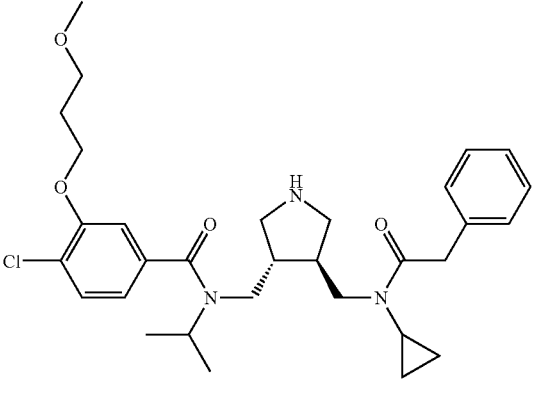 | 556.2 | 4.86[c] |

TABLE 18-continued

| Example | configuration | structure | [M + H]+ | t_R (HPLC) |
|---|---|---|---|---|
| 351 | (3S, 4S) | 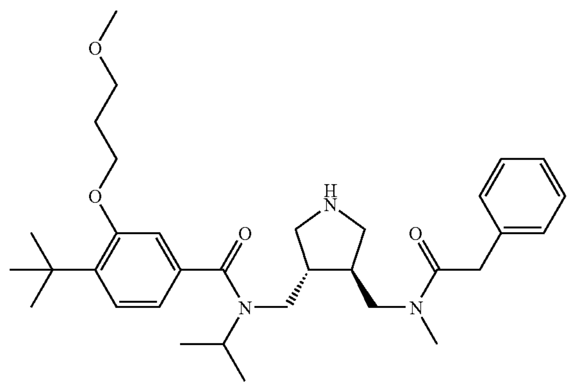 | 552.4 | 5.56[b] |
| 352 | (3S, 4S) | 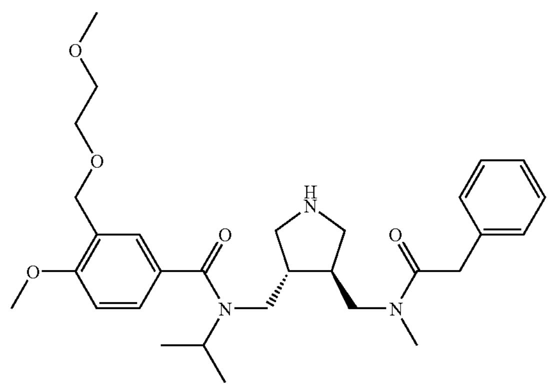 | 526.2 | 3.66[c] |
| 353 | (3S, 4S) | 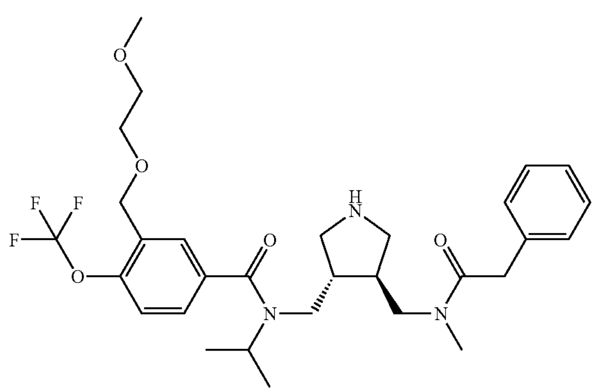 | 580.2 | 4.88[b] |
| 354 | (3S, 4S) | 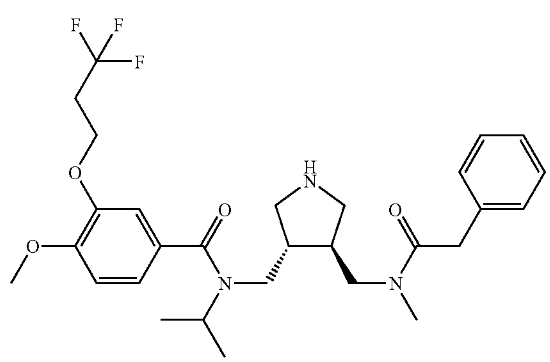 | 550.2 | 4.06[c] |

| Example | configuration | structure | [M + H]+ | tR (HPLC) |
|---|---|---|---|---|
| 355 | (3S, 4S) | 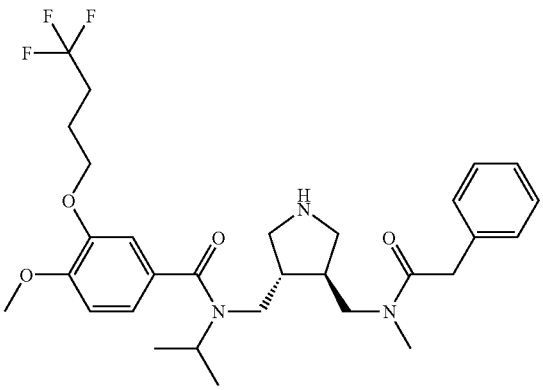 | 564.2 | 4.30[c] |
| 356 | (3S, 4S) | 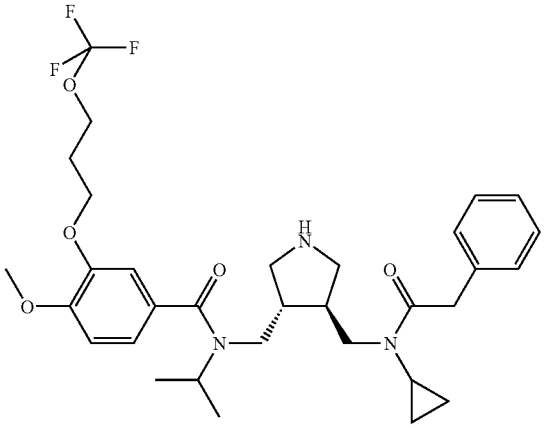 | 606.2 | 4.63[c] |
| 357 | (3S, 4S) | 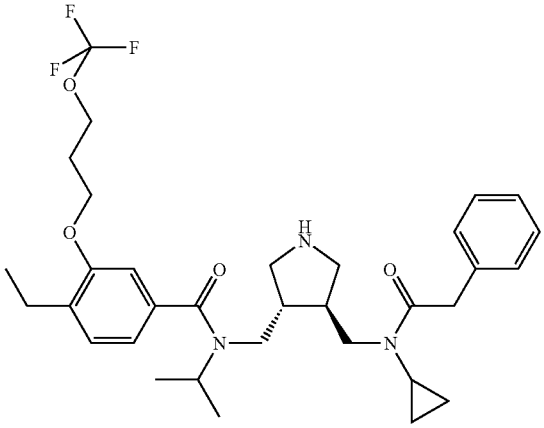 | 604.2 | 5.30[b] |

TABLE 18-continued

| Example | configuration | structure | [M + H]+ | t_R (HPLC) |
|---|---|---|---|---|
| 358 | (3S, 4S) | 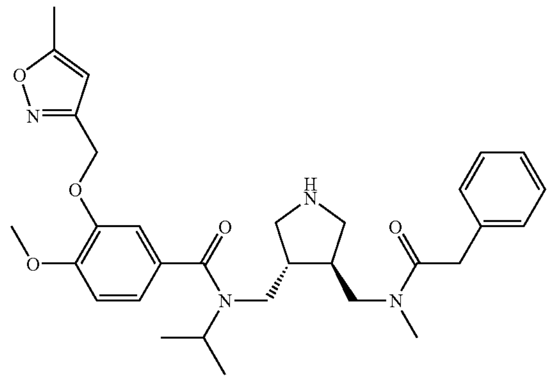 | 549.2 | 4.48[b] |
| 359 | (3S, 4S) | 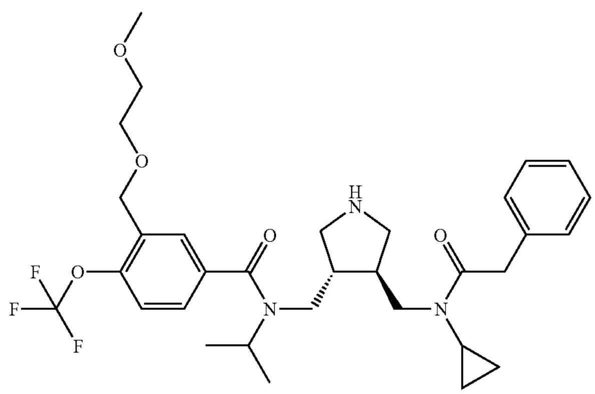 | 606.2 | 5.07[a] |
| 360 | (3S, 4S) | 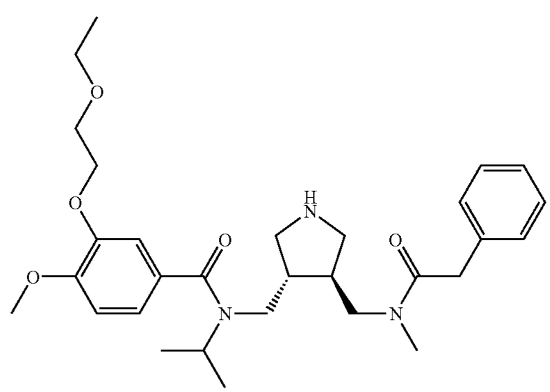 | 526.2 | 4.40[a] |

[a] t_R (HPLC, Macherey-Nagel Nucleosil C18 column, 10-100% CH₃CN/H₂O/5 min, 100% CH₃CN/3 min, CH₃CN and H₂O containing 0.1% TFA, flow: 1.5 mL/min).
[b] t_R (HPLC, Nucleosil C18HD column, 5-100% CH₃CN/H₂O/6 min, 100% CH₃CN/2 min, CH₃CN and H₂O containing 0.1% TFA, flow: 1 mL/min).
[c] t_R (HPLC, Nucleosil C18HD column, 20-100% CH₃CN/H₂O/6 min, 100% CH₃CN/2 min, CH₃CN and H₂O containing 0.1% TFA, flow: 1 mL/min).

The following intermediates are prepared:

4-Ethyl-3-(3-hydroxy-propoxy)-benzoic acid

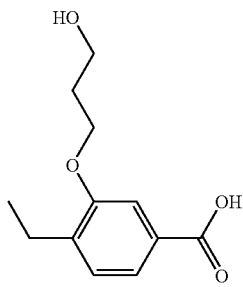

a. 4-Ethyl-3-hydroxy-benzoic acid

To a solution of 4-ethyl-3-(3-methoxy-propoxy)-benzoic acid (6.44 g, 27.03 mmol) in $CH_2Cl_2$ (150 mL) at −78° C. is slowly added $BBr_3$ (9 mL, 93.41 mmol). The reaction mixture is allowed to reach RT and stirred for 3 hours, then poured into ice/water and filtrated to afford the title product as a white solid. TLC, $R_f$ ($CH_2Cl_2$/MeOH 95:5)=0.2.

b. 4-Ethyl-3-hydroxy-benzoic acid methyl ester

To a solution of 4-ethyl-3-hydroxy-benzoic acid (3.76 g, 22.6 mmol) in MeOH (70 mL), cc $H_2SO_4$ (0.7 mL) is added. The solution is refluxed overnight, then concentrated to about 30 mL and poured into water. The aqueous layer is extracted with ether (50 mL×4) and the combined organic extracts are neutralized with a saturated aqueous solution of $NaHCO_3$ (50 mL×2), washed with brine (50 mL), dried over $Na_2SO_4$, filtered and concentrated to give the title compound as a white powder. TLC, $R_f$ ($CH_2Cl_2$/MeOH 95:5)=0.7, MS (LC-MS): 179.2 $[M-H]^-$, $t_R$ (HPLC, Nucleosil C18 column, 10-100% $CH_3CN/H_2O$/5 min, 100% $CH_3CN$/2.8 min, flow: 1 ml/min): 4.86 min.

c. 4-Ethyl-3-(3-hydroxy-propoxy)-benzoic acid methyl ester

To a solution of 4-ethyl-3-hydroxy-benzoic acid methyl ester (3.21 g, 17.81 mmol) in acetonitrile (35 mL) are added 3-bromo-1-propanol (1.85 mL, 21.37 mmol) and $K_2CO_3$ (3.69 g, 26.7 mmol). The solution is refluxed for 4 h, then poured into water and extracted three times with AcOEt. The combined organic extracts are washed with brine, dried over $Na_2SO_4$, filtered and concentrated to give the title product. TLC, $R_f$ (c-hexane/AcOEt 8:2)=0.15, MS (LC-MS): 239.2 $[M+H]^+$, $t_R$ (HPLC, Macherey-Nagel Nucleosil C18 column, 10-100% $CH_3CN/H_2O$/5 min, 100% $CH_3CN$/3 min, flow: 1.5 ml/min): 5.10 min.

d. 4-Ethyl-3-(3-hydroxy-propoxy)-benzoic acid

A solution of 4-ethyl-3-(3-hydroxy-propoxy)-benzoic add methyl ester (4.68 g, 19.63 mmol) in MeOH (90 mL) and $H_2O$ (5 mL) is treated with NaOH (2.35 g, 58.89 mmol), and heated at reflux for 5 h. The reaction mixture is extracted with AcOEt and the aqueous layer is acidified with HCl 4N and extracted three times with $CH_2Cl_2$. The combined organic extracts are dried over Na2SO4, filtered and concentrated in vacuo to give the title product. TLC, $R_f$ ($CH_2Cl_2$/MeOH 95:5)= 0.1, MS (LC-MS): 223.1 $[M-H]^-$, $t_R$ (HPLC, Macherey-Nagel Nucleosil C18 column, 10-100% $CH_3CN/H_2O$/5 min, 100% $CH_3CN$/3 min, flow: 1.5 ml/min): 4.47 min.

3-(3-Hydroxy-propoxy)-4-methoxy-benzoic acid

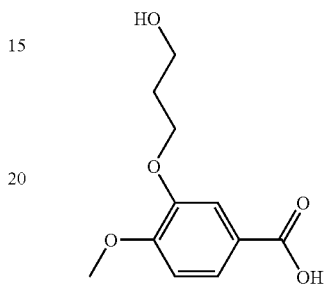

a. 3-(3-Hydroxy-propoxy)-4-methoxy-benzoic acid methyl ester

A mixture of methyl 3-hydroxy-4-methoxybenzoate (4.94 g, 26.6 mmol), 3-bromo-1-propanol (2.86 mL, 31.9 mmol) and anhydrous $K_2CO_3$ (5.51 g, 39.9 mmol) in MeCN (50 mL) is refluxed with stirring overnight, and after cooling is poured into ice/water. The aqueous layer is extracted with AcOEt, and the combined organics are washed with brine, dried ($Na_2SO_4$) and concentrated. Purification by flash chromatography on silica gel (hexane/AcOEt 1:2) gives a solid residue which is stirred in a 9:1 mixture of hexane/AcOEt over 30 min. Filtration of the suspension and drying in vacuo gives the title compound as white solid. TLC, $R_f$(hexane/AcOEt 1:1)= 0.09. MS: 241.2 $[M+H]^+$. $t_R$ (HPLC, Nucleosil C18HD column, 20-100% $CH_3CN/H_2O$/6 min, 100% $CH_3CN$/2 min, $CH_3CN$ and $H_2O$ containing 0.1% TFA, flow: 1 mL/min): 2.86 min. $^1$H-NMR ($CDCl_3$): δ 2.13 (m, 2H), 2.59 (m, 1H), 3.92 (s, 3H), 3.93 (s, 3H), 4.29 (m, 2H), 6.92 (m, 1H), 7.60 (s, 1H), 7.73 (m, 1H) ppm.

b. 3-(3-Hydroxy-propoxy)-4-methoxy-benzoic acid

A solution of 3-(3-hydroxy-propoxy)-4-methoxy-benzoic acid methyl ester (1.00 g, 4.16 mmol) in THF (3.0 mL) and 2N NaOH (3.1 mL) is stirred at room temperature over 6 hrs. The mixture is adjusted to pH 1 by addition of 2N aqueous HCl to afford a white suspension. The precipitate is filtered, washed with water and dried in vacuo at 50° C. to give the title compound as white solid. MS: 225.0 $[M-H]^+$. $^1$H-NMR ($CDCl_3$): δ 1.88 (m, 2H), 3.57 (m, 2H), 3.83 (s, 3H), 4.07 (m, 2H), 4.56 (s, br, 1H), 7.06 (dd, 1H), 7.46 (d, 1H), 7.57 (dd, 1H), 12.7 (s, br, 1H) ppm.

327
4-Methoxy-3-(4-methoxy-butyl)-benzoic acid

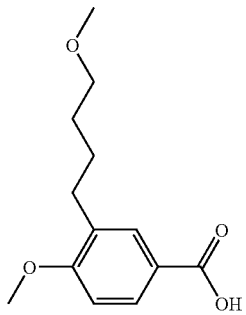

a. 4-Methoxy-3-(4-methoxy-butyl)-benzaldehyde

To a solution of 4-bromo-1-methoxy-2-(4-methoxy-butyl)-benzene (8.10 g, 29.7 mmol; described in EP0678 503 B1) in absolute THF (170 mL), cooled to −78° C., is added dropwise over 30 min and under an argon atmosphere a 1.6M solution of n-butyllithium in hexane (20.4 mL, 32.6 mmol). After stirring for 5 min, a mixture of DMF (5.03 mL, 65.2 mmol) in THF (20 mL) is added over 30 min at −78° C. Stirring is continued over 15 min at −78° C., and the reaction mixture is gradually warmed and stirred for an additional hour at room temperature before quenching with 1N HCl. The aqueous layer is extracted with diethyl ether (3×200 mL), the combined organics are dried ($Na_2SO_4$) and concentrated. Purification by flash chromatography on silica gel (hexane/AcOEt 4:1) gives the title compound as yellowish oil. TLC, $R_f$ (hexane/AcOEt 4:1)=0.27. MS: 223.2 [M+H]$^+$. $^1$H-NMR (CDCl$_3$): δ 1.6-1.74 (m, 4H) 2.70 (t, 2H), 3.37 (s, 3H), 3.43 (t, 2H), 3.96 (s, 3H), 6.99 (dd, 1H), 7.73 (d, 1H), 7.76 (dd, 1H), 9.70 (s, 1H) ppm.

b. 4-Methoxy-3-(4-methoxy-butyl)-benzoic acid

To a stirred suspension of 4-methoxy-3-(4-methoxy-butyl)-benzaldehyde (300 mg, 1.35 mmol) and sulfamic acid (176 mg, 1.81 mmol) in 80% acetic acid (2.3 mL) is added dropwise a solution of 80% $NaClO_2$ (127 mg, 1.40 mmol; dissolved in 170 μL of $H_2O$) in water (0.65 mL) over 5 min and by keeping the temperature at 18-20° C. Stirring of the yellow slurry is continued over 3 hrs at 20° C. before adding another aliquot of 80% $NaClO_2$ (151 mg, 1.67 mmol; dissolved in 205 μL of $H_2O$), dissolved in water (0.8 mL), and sulfamic acid (130 mg, 1.34 mmol) in 80% aqueous acetic acid. After stirring overnight, the reaction mixture is diluted by adding water (2.3 mL), the resulting suspension is stirred for 30 min and filtered. The precipitate is dried to give the title product as white solid. TLC, $R_f$ ($CH_2Cl_2$/MeOH 98:2)=0.5. MS: 239.0 [M+H]$^+$. $^1$H-NMR (CD$_3$OD): δ 1.55-1.7 (m, 4H), 2.65 (t, 2H), 3.31 (s, 3H), 3.41 (t, 2H), 3.89 (s, 3H), 4.87 (s, 1H+D$_2$O), 6.98 (m, 1H), 7.78 (s, 1H), 7.87 (m, 1H) ppm.

328
4-Difluoromethyl-3-(3-methoxy-propoxy)-benzoic acid

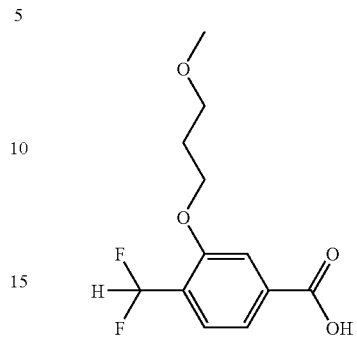

a. 4-Methyl-benzenesulfinic acid 3-methoxy-propyl ester

Toluene-4-sulfonyl chloride (25.4 g, 133.2 mmol) is slowly added to a solution of 3-methoxy-1-propanol (8.49 mL, 88.8 mmol) and triethylamine (14.8 mL, 106.5 mmol) in $CH_2Cl_2$ (80 mL) at 0° C. The reaction mixture is then allowed to warm to RT and stirred for another 16 h. The solvent is evaporated, water is added and the mixture is extracted with $CH_2Cl_2$. Drying ($Na_2SO_4$) of the combined organic extracts, filtering and evaporation of the solvent affords the crude product which is purified by flash chromatography on silica gel (eluent: c-hexane/AcOEt 5:1) to give the desired product. MS (LC-MS): 262.1 [M+18]$^+$; $t_R$ (HPLC, Macherey-Nagel Nucleosil C18 column, 10-100% $CH_3CN/H_2O$/5 min, 100% $CH_3CN$/3 min, $CH_3CN$ and $H_2O$ containing 0.1% TFA, flow: 1.5 mL/min): 5.12 min.

b. 4-Formyl-3-(3-methoxy-propoxy)-benzoic acid 3-methoxy-propyl ester

A mixture of 4-formyl-3-hydroxybenzoic acid (1.5 g, 8.8 mmol), 4-methyl-benzenesulfinic acid 3-methoxy-propyl ester (4.5 g, 18.4 mmol), diisopropylethylamine (3.4 mL, 19.3 mmol) and NaI (2.63 g, 17.5 mmol) in DMF (20 mL) is stirred at 80° C. for 60 h and at 130° C. for another 5 h. The solvent is partially removed under reduced pressure, water is added and the mixture is extracted with ethyl acetate. Washing (brine) and drying ($Na_2SO_4$) of the combined organic extracts, filtration and evaporation of the solvent affords the crude product. The desired product is obtained by flash chromatography on silica gel (eluent: c-hexane/AcOEt 3:1). MS (LC-MS): 311.1 [M+H]$^+$; $t_R$ (Zorbax SB C18 column, 10-95% $CH_3CN/H_2O$/0.8 min, 95% $CH_3CN/H_2O$, 0.7 min, $CH_3CN$ and $H_2O$ containing 0.1% TFA, flow: 1.5 mL/min): 1.20 min.

c. 4-Difluoromethyl-3-(3-methoxy-propoxy)-benzoic acid 3-methoxy-propyl ester DEOXO-FLUOR (2.8 mL, 15.0 mmol) is slowly added to a solution of 4-formyl-3-(3-methoxy-propoxy)-benzoic acid 3-methoxy-propyl ester (1.81 g, 5.8 mmol) in $CH_2Cl_2$ (15 mL) at 0° C. under Ar. The reaction mixture is then stirred at RT for 4.5 h, recooled to 0° C. before ethanol (7 mL) is added.

The mixture is then stirred at RT for another 16 h. The solvent is removed under reduced pressure and the crude product is purified by flash chromatography on silica gel (eluent: c-hexane/AcOEt 3:1) to afford the title compound. MS (LC-MS): 333.1 [M+H]$^+$; $t_R$ (Zorbax SB C18 column, 10-95% CH$_3$CN/H$_2$O/0.8 min, 95% CH$_3$CN/H$_2$O, 0.7 min, CH$_3$CN and H$_2$O containing 0.1% TFA, flow: 1.5 mL/min): 1.26 min.

d. 4-Difluoromethyl-3-(3-methoxy-propoxy)-benzoic acid 1N aqueous KOH (6.7 mL, 6.7 mmol) is slowly added to a solution of 4-difluoromethyl-3-(3-methoxy-propoxy)-benzoic acid 3-methoxy-propyl ester (1.48 g, 4.45 mmol) in MeOH (5 mL) and the reaction mixture is stirred at RT for 60 h. For workup the mixture is concentrated under reduced pressure, the residue is taken up in 2N HCl (until a pH=1 is obtained) and extracted with ethyl acetate. The combined organic extracts are washed with brine, dried (Na$_2$SO$_4$), filtered and the solvent is evaporated to give the title compound. MS (LC-MS): 259.1 [M–H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 4.89 min.

8-(3-Methoxy-propoxy)-2,3-dihydro-benzo[1,4]dioxine-6-carboxylic acid

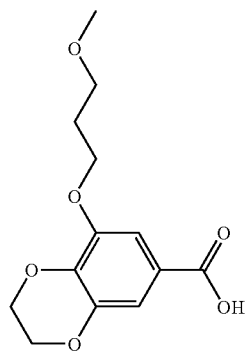

a. 8-Hydroxy-2,3-dihydro-benzo[1,4]dioxine-6-carboxylic acid ethyl ester

To a solution of 3,4,5-trihydroxy-benzoic acid ethyl ester (5.00 g, 24.2 mmol) in DMF (70 mL) are added 1,2-dibromoethane (2.13 mL, 24.2 mmol) and CsCO$_3$ (16.9 g, 50.9 mmol) and the mixture is stirred overnight at room temperature and for 5 hrs at 60° C. Extractive work-up with diethyl ether, washing of the organic phase with brine and evaporation gives the crude product as brown oil which is purified by silica gel chromatography (hexane/AcOEt 3:2). The title compound is obtained as a white solid. TLC, R$_f$ (hexane/AcOEt 1:1)=0.27. MS: 223.0 [M–H]$^+$. $^1$H-NMR (CDCl$_3$): δ 1.40 (t, 3H), 4.3-4.42 (m, 6H), 5.45 (s, 1H), 7.23 (s, 1H), 7.29 (s, 1H) ppm.

b. 8-(3-Methoxy-propoxy)-2,3-dihydro-benzo[1,4]dioxine-6-carboxylic acid ethyl ester The mixture of 8-hydroxy-2,3-dihydro-benzo[1,4]dioxine-6-carboxylic acid ethyl ester (1.65 g, 7.36 mmol), 1-bromo-3-methoxypropane (1.38 g, 8.83 mmol) and anhydrous K$_2$CO$_3$ (1.53 g, 11.0 mmol) in acetone (40 mL) is refluxed overnight. After cooling to room temperature, the mixture is poured into ice water and extracted with AcOEt. The organic layer is washed with brine, dried (Na$_2$SO$_4$) and concentrated. Purification by flash chromatography on silica gel (hexane/AcOEt 3:1) yields the title compound as white solid. TLC, R$_f$ (hexane/AcOEt 1:1)=0.32. MS: 297.0 [M+H]$^+$. $^1$H-NMR (CDCl$_3$): δ 1.41 (t, 3H), 2.16 (m, 2H), 3.40 (s, 3H), 3.61 (m, 2H), 4.20 (m, 2H), 4.31 (m, 2H), 4.35-4.45 (m, 4H), 7.27 (d, 1H), 7.31 (d, 1H) ppm.

c. 8-(3-Methoxy-propoxy)-2,3-dihydro-benzo[1,4]dioxine-6-carboxylic acid

The mixture of 8-hydroxy-2,3-dihydro-benzo[1,4]dioxine-6-carboxylic acid ethyl ester (1.85 g, 6.24 mmol) in dioxane (10 mL) and 2N NaOH (5.0 mL) is stirred at 60° C. over 1 h, then cooled to room temperature and acidified (pH 1) with 2N HCl. Volatiles are removed under reduced pressure to afford a suspension. The precipitate is filtered, washed with ice-water and dried in vacuo overnight to give the title product as white solid. TLC, R$_f$ (hexane/AcOEt 2:1+1% AcOH)= 0.07. MS: 267.0 [M–H]$^+$. $^1$H-NMR (DMSO-d$_6$): δ 1.96 (m, 2H), 3.26 (s, 3H), 3.48 (m, 2H), 4.05 (m, 2H), 4.27 (m, 2H), 4.31 (m, 2H), 7.07 (d, 1H9, 7.11 (d, 1H), 12.8 (s, br, 1H) ppm.

4-Methoxy-5-(3-methoxy-propoxy)-2-methyl-benzoic acid

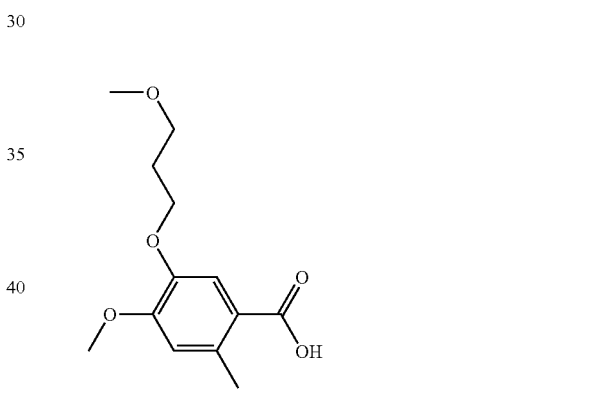

a. 2-Methoxy-1-(3-methoxy-propoxy)4-methyl-benzene

A stirred solution of 2-methoxy-4-methylphenol (5.00 g, 36.2 mmol), 1-bromo-3-methoxypropane (7.06 g, 45.2 mmol) and anhydrous K$_2$CO$_3$ (7.50 g, 64.3 mmol) is refluxed overnight. After cooling, volatiles are removed under reduced pressure, the residue is taken up in water and extracted with AcOEt. The combined organics are washed with brine, dried (Na$_2$SO$_4$) and concentrated. After silica gel chromatography (hexane/AcOEt 3:1) the title compound is obtained as colorless liquid. TLC, R$_f$ (hexane/AcOEt 2:1)=0.34. MS: 211.0 [M+H]$^+$. $^1$H-NMR (CDCl$_3$): δ 2.13 (m, 2H), 2.33 (s, 3H), 3.38 (s, 3H), 3.61 (m, 2H), 3.88 (s, 3H), 4.12 (m, 2H), 6.7-6.85 (m, 3H) ppm.

b. 1-Bromo-4-methoxy-5-(3-methoxy-propoxy)-2-methyl-benzene

To a solution of 2-methoxy-1-(3-methoxy-propoxy)-4-methyl-benzene (2.00 g, 9.51 mmol) in MeCN (30 mL) is added N-bromosuccinimide (1.96 g, 10.5 mmol) at room temperature. Stirring is continued for 2 hrs, followed by evaporation of the solvent. The title compound is obtained after flash chromatography on silica gel (hexane/AcOEt 6:1) as an oil. MS: 289.0/291.0 [M]$^+$. $t_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 5.04 min. $^1$H-NMR (CDCl$_3$): δ 2.13 (m, 2H), 2.36 (s, 3H), 3.39 (s, 3H), 3.58 (m, 2H), 3.87 (s, 3H), 4.12 (m, 2H), 6.77 (s,1H), 7.08 (s, 1H) ppm.

c. 4-Methoxy-5-(3-methoxy-propoxy)-2-methyl-benzaldehyde

To a solution of 1-bromo-4-methoxy-5-(3-methoxy-propoxy)-2-methyl-benzene (2.50 g, 8.65 mmol) in THF (25 mL), cooled to −70° C., is added a 1.6M solution of n-buthyllithium in hexane (5.94 mL, 9.51 mmol). After 30 min, DMF (1.05 mL, 13.0 mmol) is added and stirring is continued overnight while the reaction mixture is gradually warmed to room temperature. Quenching with ice-cold 1N aqueous HCl is followed by extraction with diethyl ether. The combined organic layers are washed with brine, dried (Na$_2$SO$_4$) and concentrated. Purification by flash chromatography on silica gel (hexane/AcOEt 7:2) gives the title compound as oil. TLC, R$_f$ (hexane/AcOEt 1:1)=0.29. MS: 239.2 [M+H]$^+$. $^1$H-NMR (CDCl$_3$): δ 2.16 (m, 2H), 2.66 (s, 3H), 3.39 (s, 3H), 3.60 (m, 2H), 3.97 (s, 3H), 4.18 (m, 2H), 6.73 (s, 1H), 7.40 (s, 1H), 10.2 (s, 1H) ppm.

d. 4-Methoxy-5-(3-methoxy-propoxy)-2-methyl-benzoic acid

To a solution of 4-methoxy-5-(3-methoxy-propoxy)-2-methyl-benzaldehyde (1.25 g, 5.25 mmol) in a 3:1 mixture of tert-butanol/CH$_2$Cl$_2$ (60 mL) is added 2-methyl-2-butene (25.0 mL), followed by dropwise addition of a solution of NaClO$_2$ (5.81 g, 51.4 mmol) and NaH$_2$PO$_4$ (4.07 g, 33.6 mmol) in water (45 mL) over 15 min at room temperature, and stirring is continued overnight. The reaction mixture is poured into ice/saturated aqueous NaHCO$_3$ solution, the water phase is washed with AcOEt, then acidified and extracted with AcOEt. The combined organics are washed with brine, dried (Na$_2$SO$_4$) and concentrated to give a yellow solid. The crude product is stirred for 30 min in a 95:5 mixture of hexane/diisopropyl ether (25 mL), the precipitate is filtered off, washed with a 95:5 mixture of hexane/diisopropyl ether and dried to give the title compound as yellowish solid. MS: 253.0 [M−H]$^+$. $t_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 3.23 min.

$^1$H-NMR (CDCl$_3$): δ 1.96 (m, 2H), 2.51 (s, 3H), 3.27 (s, 3H), 3.48 (m, 2H), 3.84 (s, 3H), 4.00 (m, 2H), 6.89 (s, 1H), 7.41 (s, 1H) ppm.

2-Chloro-4-methoxy-5-(3-methoxy-propoxy)-benzoic acid

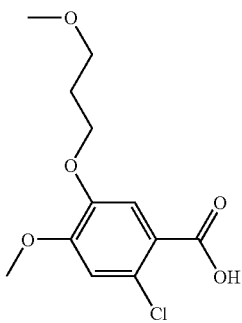

a. 2-Chloro-5-hydroxy-4-methoxy-benzaldehyde

2-Chloro-4,5-dimethoxybenzaldehyde (5.00 g, 24.9 mmol; commercially available from Akos Consulting) is dissolved at room temperature in conc. H$_2$SO$_4$ (23 mL; Riedel) at room temperature. The deeply colored mixture is heated at 65° C. overnight with stirring, and after cooling is poured with caution into ice-water containing 38 g of solid NaOH (pH 14). The water phase is washed twice with AcOEt, and then is adjusted to pH 1 by addition of HCl 37% with ice-cooling to form a white suspension. Extraction with AcOEt, drying of the organics over MgSO$_4$ and evaporation gives the crude product in a mixture with unreacted starting material. The title compound is obtained after silica gel chromatography (hexane/AcOEt gradient from 3:1 to 1:1) as white solid. TLC, R$_f$ (hexane/AcOEt 1:1)=0.35. MS: 187.0 [M+H]$^+$. ]$^+$. $^1$H-NMR (DMSO-d$_6$): δ 3.41 (s, 3H), 7.14 (s, 1H), 7.45 (s, 1H), 9.83 (s, 1H), 10.2 (s, 1H) ppm.

b. 2-Chloro-4-methoxy-5-(3-methoxy-propoxy)-benzaldehyde

A mixture of crude 2-chloro-5-hydroxy-4-methoxy-benzaldehyde (1.79 g, 8.15 mmol), 1-bromo-3-methoxypropane (1.53 g, 9.79 mmol) and anhydrous K$_2$CO$_3$ (1.69 g, 12.2 mmol) in MeCN (30 mL) is refluxed overnight. Ice water is added to the mixture, followed by extraction with AcOEt. The combined organics are washed with brine, dried (Na$_2$SO$_4$) and concentrated. The title compound is obtained after purification by RP-HPLC on a PrepC$_{18}$ OBD column (dimensions: 30×100 mm; 5 μM particle size, SunFire Ltd), and using a 95-5% gradient of MeCN/H$_2$O 5:95 (containing 0.1% TFA) to MeCN/H$_2$O 95:5 (containing 0.1% TFA) over 20 min, as white solid. TLC, R$_f$ (hexane/AcOEt 1:1)=0.42. MS: 259.0 [M+H]$^+$. ]$^+$. $t_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 4.15 min.

¹H-NMR (CDCl₃): δ 2.15 (m, 2H), 3.39 (s, 3H), 3.59 (m, 2H), 3.99 (s, 3H), 4.19 (m, 2H), 6.91 (s, 1H), 7.45 (s, 1H), 10.4 (s, 1H) ppm.

c.
2-Chloro-4-methoxy-5-(3-methoxy-propoxy)-benzoic acid

To a solution of 2-chloro-4-methoxy-5-(3-methoxy-propoxy)-benzaldehyde (1.08 g, 3.55 mmol) in a 3:1 mixture of tert-butanol/CH₂Cl₂ (20 mL) is added 2-methyl-2-butene (0.74 g, 5.32 mmol), followed by dropwise addition of a solution of NaClO₂ (0.67g, 7.10 mmol) and NaH₂PO₄ (0.67 g, 4.26 mmol) in water (14 mL) over 15 min at room temperature, and stirring is continued overnight. The reaction mixture is poured into ice/saturated aqueous NaHCO₃ solution, the water phase is washed with AcOEt. The ice-cold aqueous layer is acidified with HCl 37% to form a white precipitate which is filtered off, washed with ice-cold water and dried in vacuo. The compound is obtained as white solid. MS: 273.0 [M−H]⁺. $t_R$ (HPLC, Nucleosil C18HD column, 20-100% CH₃CN/H₂O/6 min, 100% CH₃CN/2 min, CH₃CN and H₂O containing 0.1% TFA, flow: 1 mL/min): 3.25 min. ¹H-NMR (CDCl₃): δ 1.96 (m, 2H), 3.25 (s, 3H), 3.47 (m, 2H), 3.85 (s, 3H), 4.03 (m, 2H), 7.10 (s, 1H), 7.39 (s, 1H) ppm.

4-Chloro-3-(3-methoxy-propoxy)-benzoic acid

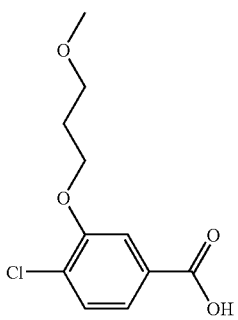

a. 4-Chloro-3-(3-methoxy-propoxy)-benzoic acid 3-methoxy-propyl ester

A mixture of 4-chloro-3-hydroxy-benzoic acid (4.02 g, 23.3 mmol; commercially available from Frinton Laboratories), 1-bromo-3-methoxypropane (8.73 g, 55.9 mmol) and anhydrous K₂CO₃ (9.66 g, 69.9 mmol) in MeCN (80 mL) is refluxed overnight. A further amount of 1-bromo-3-methoxypropane (1.82 g, 0.5 equiv.) is added under reflux conditions. After 2 hrs, the mixture is poured into ice-water and extracted with AcOEt. The combined organics are washed with brine, dried (Na₂SO₄) and concentrated. Flash-chromatography on silica gel (hexane/AcOEt 7:2) affords the title compound as an oil. TLC, $R_f$ (hexane/AcOEt 3:1)=0.17. MS: 317.2 [M−H]⁺. $t_R$ (HPLC, Nucleosil C18HD column, 20-100% CH₃CN/H₂O/6 min, 100% CH₃CN/2 min, CH₃CN and H₂O containing 0.1% TFA, flow: 1 mL/min): 5.13 min. ¹H-NMR (CDCl₃): δ 2.08 (m, 2H), 2.16 (m, 2H), 3.40 (s, 6H), 3.57 (m, 2H), 3.65 (m, 2H), 4.23 (m, 2H), 4.45 (m, 2H), 7.45 (m, 1H), 7.61 (m, 1H), 7.64 (s, 1H) ppm.

b. 4-Chloro-3-(3-methoxy-propoxy)-benzoic acid

A solution of 4-chloro-3-(3-methoxy-propoxy)-benzoic acid 3-methoxy-propyl ester (1.58 g, 4.99 mmol) in aqueous 2N NaOH (3.23 mL, 6.48 mmol) and dioxane (10 mL) is stirred at room temperature for 3.5 hrs. The mixture is acidified by addition of 2N HCl, the volatiles are removed by evaporation and the obtained suspension is filtered. The precipitate is washed with ice-cold water and dried in vacuo to give the title compound as white solid. MS: 243.0 [M−H]⁺. $t_R$ (HPLC, Nucleosil C18HD column, 20-100% CH₃CN/H₂O/6 min, 100% CH₃CN/2 min, CH₃CN and H₂O containing 0.1% TFA, flow: 1 mL/min): 3.93 min. ¹H-NMR (DMSO-d₆): δ 2.00 (m, 2H), 3.27 (s, 3H), 3.34 (s, br, 1H), 3.53 (m, 2H), 4.19 (m, 2H), 7.5-7.6 (m, 3H) ppm.

3-Chloro-5-(3-methoxy-propoxy)-benzoic acid

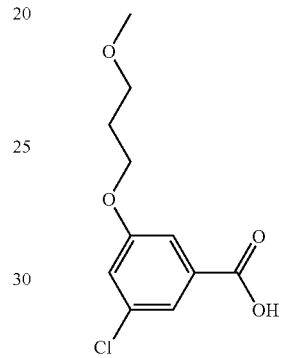

a. 3-Chloro-5-(3-methoxy-propoxy)-benzoic acid 3-methoxy-propyl ester

The title compound is obtained from 3-chloro-5-hydroxy-benzoic acid (1.96 g, 11.4 mmol; commercially available from J&W Pharm Lab), 1-bromo-3-methoxypropane (4.25 g, 27.3 mmol) and anhydrous K₂CO₃ (4.71 g, 34.1 mmol), as described above for the 4-chloro regioisomer, as oil. TLC, $R_f$ (hexane/AcOEt 3:1)=0.21. MS: 317.0 [M+H]⁺. ¹H-NMR (CDCl₃): δ 2.07 (m, 2H), 2.10 (m, 2H), 3.39 (s, 3H), 3.41 (s, 3H), 3.56 (m, 2H), 3.59, (m, 2H), 4.13 (m, 2H), 4.45 (m, 2H), 7.13 (m, 1H), 7.49 (m, 1H), 7.63 (m, 1H) ppm.

b. 3-Chloro-5-(3-methoxy-propoxy)-benzoic acid

The title compound is obtained from 3-chloro-5-(3-methoxy-propoxy)-benzoic acid 3-methoxy-propyl ester (1.70 g, 5.37 mmol), dissolved in dioxane (10 mL), by hydrolysis with 2N aqueous NaOH as a white solid. MS: 243.0 [M−H]⁺. $t_R$ (HPLC, Nucleosil C18HD column, 20-100% CH₃CN/H₂O/6 min, 100% CH₃CN/2 min, CH₃CN and H₂O containing 0.1% TFA, flow: 1 mL/min): 4.04 min. ¹H-NMR (DMSO-d₆): δ 1.96 (m, 2H), 3.25 (s, 3H), 3.36 (s, br, 1H), 3.48 (m, 2H), 4.11 (m, 2H), 7.31 (s, 1H), 7.40 (s, 1H), 7.49 (s, 1H) ppm.

4-tert-Butyl-3-(3-methoxy-propoxy)-benzoic acid

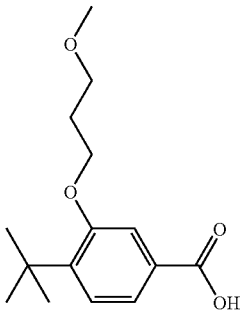

a. 4-tert-Butyl-3-methoxy-benzoic acid methyl ester

To a solution of 4-tert-butyl-3-methoxy-benzoic acid (3.00 g, 14.4 mmol; commercially available from Apin, 41226B) in MeOH (30 mL) is added $H_2SO_4$ conc. (3 mL) and the mixture is refluxed for 5 hrs. After cooling, the mixture is diluted with water, extracted twice with diethyl ether, the combined organics are dried ($Na_2SO_4$) and evaporated to dryness to give the title compound as yellowish oil. MS: 223.0 $[M+H]^+$. $t_R$ (HPLC, Nucleosil C18HD column, 5-100% $CH_3CN/H_2O/6$ min, 100% $CH_3CN/2$ min, $CH_3CN$ and $H_2O$ containing 0.1% TFA, flow: 1 mL/min): 6.12 min. $^1$H-NMR ($CDCl_3$): δ 1.41 (s, 9H), 3.91 (s, 3H), 3.92 (s, 3H), 7.36 (dd, 1H), 7.54 (d, 1H), 7.60 (dd, 1H) ppm.

b. 4-tert-Butyl-3-hydroxy-benzoic acid methyl ester

To a solution of borontribromide (3.38 mL, 35.1 mmol) in $CH_2Cl_2$ (35 mL), cooled to −60° C., is added under an argon atmosphere a solution of 4-tert-butyl-3-methoxy-benzoic acid methyl ester (2.60 g, 11.7 mmol) in $CH_2Cl_2$ (65 mL). The reaction is warmed to room temperature and stirring is continued overnight. Another aliquot of $BBr_3$ (1.13 mL, 11.7 mmol) is added, and the mixture is stirred for 6 hrs at ambient temperature before quenching by careful addition of water. The aqueous layer is extracted with $CH_2Cl_2$, the combined organics are washed with 1N aqueous NaOH, dried ($Na_2SO_4$) and concentrated. Purification by flash chromatography on silica gel (eluents: $CH_2Cl_2$ 100%, then $CH_2Cl_2$/acetone 97:3) gives the title compound as yellowish solid. MS: 209.0 $[M+H]^+$. $t_R$ (HPLC, Nucleosil C18HD column, 5-100% $CH_3CN/H_2O/6$ min, 100% $CH_3CN/2$ min, $CH_3CN$ and $H_2O$ containing 0.1% TFA, flow: 1 mL/min): 5.37 min. $^1$H-NMR ($CDCl_3$): δ 1.46 (s, 9H), 3.94 (s, 3H), 5.60 (s, 1H), 7.36 (dd, 1H), 7.50 (d, 1H), 7.57 (dd, 1H) ppm.

The alkaline aqueous layers obtained above are acidified with HCl conc., extracted with $CH_2Cl_2$, the organics are dried ($Na_2SO_4$) and evaporated to dryness to give 4-tert-butyl-3-hydroxy-benzoic acid: MS: 193.0 $[M+H]^+$. $^1$H-NMR (DMSO-$d_6$): δ 1.37 (s, 9H), 7.26 (m, 1H), 7.33 (m, 1H), 7.40 (m, 1H), 9.71 (s, 1H), 12.7 (s, 1H) ppm.

c. 4-tert-Butyl-3-(3-methoxy-propoxy)-benzoic acid methyl ester

A mixture of 4-tert-butyl-3-hydroxy-benzoic acid methyl ester (1.56 g, 7.49 mmol), 3-bromopropyl methyl ether (1.72 g, 11.2 mmol) and anhydrous $K_2CO_3$ (1.55 g, 11.2 mmol) in MeCN (30 mL) is refluxed overnight. After cooling, the mixture is filtered, the filtrate is diluted with $CH_2Cl_2$ and the organics are washed with aqueous 0.5M NaOH, aqueous 0.5M HCl and water, dried ($Na_2SO_4$) and concentrated. Purification by flash chromatography on silica gel (hexane/AcOEt 97:3) gives the title compound as colorless oil. MS: 281.1 $[M+H]^+$. $t_R$ (HPLC, Nucleosil C18HD column, 5-100% $CH_3CN/H_2O/6$ min, 100% $CH_3CN/2$ min, $CH_3CN$ and $H_2O$ containing 0.1% TFA, flow: 1 mL/min): 6.22 min. $^1$H-NMR ($CDCl_3$): δ 1.43 (s, 9H), 2.17 (m, 2H), 3.41 (s, 3H), 3.65 (m, 2H), 3.93 (s, 3H), 4.18 (m, 2H), 7.36 (dd, 1H), 7.96 (d, 1H), 7.60 (dd, 1H) ppm.

d. 4-tert-Butyl-3-(3-methoxy-propoxy)-benzoic acid

The title compound is obtained by hydrolysis of 4-tert-butyl-3-(3-methoxy-propoxy)-benzoic acid methyl ester (1.60 g, 5.14 mmol), dissolved in EtOH (15 mL), in the presence of aqueous 2N NaOH (3.85 mL, 7.70 mmol) as off-white powder. MS: 284.1 $[M+H_2O]^+$. $t_R$ (HPLC, Nucleosil C18HD column, 5-100% $CH_3CN/H_2O/6$ min, 100% $CH_3CN/2$ min, $CH_3CN$ and $H_2O$ containing 0.1% TFA, flow: 1 mL/min): 5.42. $^1$H-NMR (DMSO-$d_6$): δ 1.36 (s, 9H), 2.04 (m, 2H), 3.26 (s, 3H), 3.94 (m, 2H), 4.09 (m, 2H), 7.34 (m, 1H), 7.49 (s, 1H), 7.48 (m, 1H), 12.8 (s, br, 1H) ppm.

4-Methoxy-3-(2-methoxy-ethoxymethyl)-benzoic acid

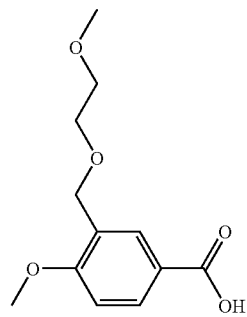

a. (5-Bromo-2-methoxy-phenyl)-methanol

To a suspension of 5-bromo-2-methoxy-benzaldehyde (7.00 g, 32.2 mmol) in MeOH (40 mL), cooled to 0 to 5° C., is added $NaBH_4$ (1.40 g, 35.4 mmol). After stirring for 1 h, the mixture is poured into ice-water, followed by extraction with AcOEt. The combined organics are washed with brine, dried ($Na_2SO_4$) and concentrated to give the title product as off-white solid. TLC, $R_f$ (hexane/AcOEt 3:1)=0.19. $^1$H-NMR ($CDCl_3$): δ 2.24 (m, 2H), 3.88 (s, 3H), 4.68 (d, 2H), 6.79 (dd, 1H), 7.41 (dd, 1H), 7.45 (d, 1H) ppm.

b. 4-Bromo-1-methoxy-2-(2-methoxy-ethoxymethyl)-benzene

To a solution of (5-bromo-2-methoxy-phenyl)-methanol (3.38 g, 14.8 mmol) and 2-bromoethyl methyl ether (2.06 g, 14.8 mmol) in DMF (30 mL) is added NaH (55% dispersion in oil; 1.36 g, 31.1 mmol) in three portions at room temperature, followed by stirring overnight. The mixture is poured into ice-cooled aqueous 2N HCl, the water phase is extracted with diethyl ether, the combined organic phase is washed with brine, dried ($Na_2SO_4$) and concentrated. Purification by flash chromatography (hexane/AcOEt 3:1) gives the title compound as liquid. TLC, $R_f$ (hexane/AcOEt 1:1)=0.44. $^1$H-NMR (CDCl$_3$): δ 3.45 (s, 3H), 3.64 (m, 2H), 3.71 (m, 2H), 3.83 (s, 3H), 4.60 (s, 2H), 6.76 (d, 1H), 7.37 (dd, 1H), 7.56 (d, 1H) ppm.

c. 4-Methoxy-3-(2-methoxy-ethoxymethyl)-benzoic acid ethyl ester

To a solution of 4-bromo-1-methoxy-2-(2-methoxy-ethoxymethyl)-benzene (2.88 g, 10.5 mmol) in absolute THF (30 mL) is added at −70° C. a 1.6N solution of n-butyllithium in hexane (7.20 mL, 11.5 mmol) with stirring. After 40 min, ethyl chloroformate (1.14 g, 10.5 mmol) is added, and the mixture is stirred overnight while gradually warming up to room temperature. The mixture is poured into 2N aqueous HCl, extracted with CH$_2$Cl$_2$, the organic layers are dried (Na$_2$SO$_4$) and concentrated. The crude product is purified by flash chromatography on silica gel (hexane/AcOEt 2:1) to give the title compound as liquid. TLC, $R_f$ (hexane/AcOEt 1:1)=0.13.

d. 4-Methoxy-3-(2-methoxy-ethoxymethyl)-benzoic acid

A solution of 4-methoxy-3-(2-methoxy-ethoxymethyl)-benzoic acid ethyl ester (0.87 g, 3.24 mmol) in a 1:1 mixture of THF and 4N NaOH (10 mL) is stirred at 50° C. overnight. After cooling, the volatiles are removed at reduced pressure, the remaining aqueous phase is acidified to pH 1 by dropwise addition of HCl 37%, and the resulting suspension is filtered off. The precipitate is washed with water, dried overnight in vacuo to give the title compound. TLC, $R_f$ (hexane/AcOEt 1:1)=0.07. MS: 239.0 [M−H]$^+$. $t_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 2.71 min. $^1$H-NMR (DMSO-d$_6$): δ 3.29 (s, 3H), 3.52 (m, 2H), 3.64 (m, 2H), 3.88 (s, 3H), 4.51 (s, 2H), 7.10 (m, 1H), 7.90 (m, 1H), 7.94 (m, 1H), 12.6 (s, br, 1H) ppm.

3-(2-Methoxy-ethoxymethyl)-4-trifluoromethoxy-benzoic acid

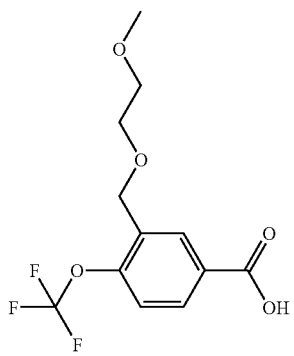

a. (5-Bromo-2-trifluoromethoxy-phenyl)-methanol

To a solution of 5-bromo-2-trifluoromethoxy-benzoic acid (2.00 g, 7.02 mmol, commercially available from Rare Chemicals, AL BE 0523) and NEt$_3$ (1.47 mL, 10.5 mmol) in THF (50 mL), cooled to −15° C. and under an argon atmosphere, is added dropwise isobutylchloroformate (1.15 mL, 8.77 mmol). The mixture is stirred for 1 hr after warming to room temperature, followed by addition of AcOEt (20 mL). The organic layer is subsequently washed with 0.5M HCl (20 mL), saturated aqueous NaHCO$_3$ solution (20 mL) and water (20 mL), then dried over Na$_2$SO$_4$ and concentrated to give the mixed anhydride intermediate. To a solution of the mixed anhydride obtained above (1.50 g, 3.90 mmol) in THF (40 mL), cooled to 0-5° C., is added dropwise a solution of LiBH$_4$ (0.17 g, 7.79 mmol) in THF (5 mL). After warming to room temperature, the reaction mixture is stirred overnight and then quenched by adding aqueous 2N NaOH (30 mL). Extraction of the water phase with AcOEt, drying of the combined organics (Na$_2$SO$_4$) and evaporation to dryness gives the title compound as white powder. $t_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 5.04 min. $^1$H-NMR (DMSO-d$_6$): δ 4.56 (d, 2H), 5.51 (t, 1H), 7.31 (dd, 1H), 7.59 (dd, 1H), 7.73 (d, 1H) ppm.

b. 4-Bromo-2-(2-methoxy-ethoxymethyl)-1-trifluoromethoxy-benzene

In a 3-neck flask under argon, a 55-65% dispersion of NaH in oil (0.097 g, 2.44 mmol) is washed with n-pentane, the organics are removed and DMF (10 mL) is added. The mixture is cooled to 0-5° C., and a solution of (5-bromo-2-trifluoromethoxy-phenyl)-methanol (0.60 g, 2.21 mmol) in DMF (3.0 mL) is added dropwise. After warming to room temperature, stirring is continued for 1 h before this mixture is added to a solution of 2-bromoethyl methyl ether (0.312 mL, 3.32 mmol) in DMF (3mL). After 4 hrs at room temperature, the reaction is still incomplete by TLC. Another aliquot of NaH (1 equiv; oil dispersion washed with pentane) and 2-bromoethyl methyl ether (0.312 mL, 3.32 mmol) are added, followed by stirring for 18 hrs at room temperature. The mixture is poured into ice-water and extracted with AcOEt, the combined organics are dried (Na$_2$SO$_4$) and evaporated to dryness to give the title compound as yellowish oil. MS: 346.0/348.0 [M+H$_{2l\ o}$]$^+$. $t_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 5.80 min. $^1$H-NMR (CDCl$_3$): δ 3.49 (s, 3H), 3.64 (m, 2H), 3.72 (m, 2H), 4.69 (s, 2H), 7.13 (dd, 1H), 7.46 (dd, 1H), 7.77 (d, 1H) ppm.

c. 3-(2-Methoxy-ethoxymethyl)-4-trifluoromethoxy-benzoic acid

To a solution of 4-bromo-2-(2-methoxy-ethoxymethyl)-1-trifluoromethoxy-benzene (0.28 g, 0.85 mmol) in absolute diethyl ether (2.0 mL), cooled to −70° C., is dropwise added under an argon atmosphere a 1.7M solution of tert.-butyllithium in pentane (0.50 mL, 0.85 mmol). After stirring for 30 min, CO$_2$ gas is bubbled into the solution for 2 min followed by stirring the yellow solution at −70° C. for additional 30 min. The reaction is quenched by addition of a saturated aqueous NH$_4$Cl solution (2 mL). The basic aqueous layer is washed with AcOEt and, after acidification to pH 1, is extracted twice with AcOEt. The combined organics are dried over Na$_2$SO$_4$ and evaporated to dryness to give the title compound as colorless oil. MS: 293.0 [M−H]$^+$. $t_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 4.62 min. $^1$H-NMR (CDCl$_3$): δ 3.46

(s, 3H), 3.67 (m, 2H), 3.76 (m, 2H), 4.71 (s, 2H), 7.35 (dd, 1H), 8.09 (dd, 1H), 8.35 (dd, 1H) ppm.

4-Methoxy-3-(3,3,3-trifluoro-propoxy)-benzoic acid

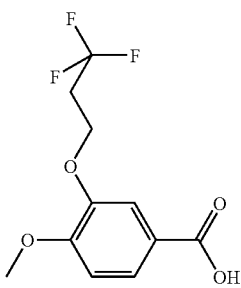

a. 4-Methoxy-3-(3,3,3-trifluoro-propoxy)-benzoic acid ethyl ester

The mixture of 3-hydroxy-4-methoxy-benzoic acid ethyl ester (1.75 g, 8.92 mmol), methanesulfonic acid 3,3,3-trifluoro-propyl ester (2.06 g, 10.7 mmol) and anhydrous $K_2CO_3$ (2.49 g, 17.8 mmol) in acetone (20 mL) is heated with stirring at reflux temperature overnight. After cooling, the mixture is diluted with AcOEt followed by washing of the organic phase with 2N aqueous NaOH and brine. The organic layer is dried over $Na_2SO_4$ and evaporated, and the crude product is purified by silica gel chromatography (eluent: hexane/AcOEt 5:1) to give the title compound as oil. TLC, $R_f$ (hexane/AcOEt 1:1)=0.59. MS: 293.0 [M+H]$^+$. $^1$H-NMR (CDCl$_3$): δ 1.42 (t, 3H), 2.74 (m, 2H), 3.96 (s, 3H), 4.33 (m, 2H), 4.40 (m, 2H), 6.94 (m, 1H), 7.59 (s, 1H), 7.77 (m, 1H) ppm.

b. 4-Methoxy-3-(3,3,3-trifluoro-propoxy)-benzoic acid

The title compound is obtained as white solid from 4-methoxy-3-(3,3,3-trifluoro-propoxy)-benzoic acid ethyl ester (0.62 g, 2.12 mmol), dissolved in THF (3.0 mL), after hydrolysis in the presence of 2N NaOH (1.6 mL) at 60° C. overnight. The ice-cold reaction mixture is acidified (pH 1) with HCl 37% to form a white precipitate which is filtered off, washed with water and dried in vacuo. TLC, $R_f$ (hexane/AcOEt 1:1)=0.17. MS: 263.0 [M−H]$^+$. $t_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 3.50 min. $^1$H-NMR (CDCl$_3$): δ 2.81 (m, 2H), 3.85 (s, 3H), 4.25 (m, 2H), 7.10 (dd, 1H), 7.49 (d, 1H), 7.63 (dd, 1H), 12.6 (s, br, 1H) ppm.

The methanesulfonic acid 3,3,3-trifluoro-propyl ester is prepared according to the following procedure:

To the mixture of 3,3,3-trifluoro-1-propanol (1.28 g, 10.8 mmol) and NEt$_3$ (4.53 mL, 32.7 mmol) in CH$_2$Cl$_2$ (10 mL) is added dropwise at −20° C. methanesulfochloride (1.03 mL, 13.1 mmol). The mixture is slowly warmed over 90 min to 5° C. with stirring, followed by addition of CH$_2$Cl$_2$ and washing of the organic layer with 2N aqueous HCl. The organics are dried over Na$_2$SO$_4$ and concentrated in vacuo to give the crude title product as yellowish liquid which was used without further purification. $^1$H-NMR (CDCl$_3$): δ 2.64 (m, 2H), 3.09 (s, 3H), 4.47 (t, 2H) ppm.

4-Methoxy-3-(4,4,4-trifluoro-butoxy)-benzoic acid

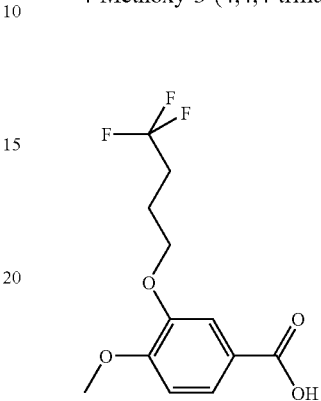

a. 4-Methoxy-3-(4,4,4-trifluoro-butoxy)-benzoic acid ethyl ester

A suspension of 3-hydroxy-4-methoxy-benzoic acid ethyl ester (1.00 g, 5.10 mmol), 1-bromo-4,4,4-trifluorobutane (1.12 g, 5.86 mmol) and anhydrous K$_2$CO$_3$ (2.14 g, 15.3 mmol) in MeCN (10 mL) is refluxed with stirring overnight. After cooling, the mixture is filtered, and the filtrates are evaporated to drying to give the title compound as white solid. TLC, R$_f$ (hexane/AcOEt 1:1)=0.62. MS: 307.0 [M+H]$^+$. $^1$H-NMR (CDCl$_3$): δ 1.42 (m, 3H), 2.1-2. (m, 2H), 2.3-2.45 (m, 2H), 3.95 (s, 3H), 4.14 (m, 2H), 4.39 (m, 2H), 6.93 (dd, 1H), 7.58 (d, 1H), 7.74 (dd, 1H) ppm.

b. 4-Methoxy-3-(4,4,4-trifluoro-butoxy)-benzoic acid

A mixture of 4-methoxy-3-(4,4,4-trifluoro-butoxy)-benzoic acid ethyl ester (0.93 g, 3.04 mmol) in THF (3 mL) and 2N NaOH (2.28 mL, 4.55 mmol) is heated with stirring at 60° C. overnight. After cooling, ice water is added and the pH is adjusted to 1 by addition of HCl 37% to form a white precipitate which is filtered off. The title compound is obtained after drying as white solid. TLC, R$_f$ (hexane/AcOEt 1:1)=0.17. MS: 277.0 [M−H]$^+$. $t_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 3.90 min. $^1$H-NMR (CDCl$_3$): δ 1.98 (m, 2H), 2.45 (m, 2H), 3.85 (s, 3H), 4.08 (m, 2H), 7.08 (dd, 1H), 7.46 (d, 1H), 7.60 (dd, 1H), 12.7 (s, br, 1H) ppm.

4-Methoxy-3-(3-trifluoromethoxy-propoxy)-benzoic acid

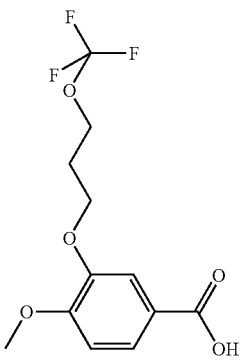

a. Dithiocarbonic acid O-(3-ethoxy-propyl) ester S-methyl ester

The title compound is prepared by the method described in Bull. Chem. Soc. Jpn. (2000), 73, 477f.: To a cooled solution of 3-ethoxy-1-propanol (24.4 g, 0.227 mol) in DMF (150 mL) is added NaH (60% dispersion in oil; 10.0 g, 0.250 mol) in portions over 1 hour, keeping the reaction temperature below 5° C. Stirring is continued for 5 hrs at room temperature, the mixture is cooled to 5 to 10° C. followed by dropwise addition of $CS_2$ (27.5 mL, 0.454 mol). The mixture is gradually warmed to ambient temperature overnight and then cooled to <10° C. before adding iodomethane (17.9 mL, 0.284 mol). Stirring is continued for 18 hrs at room temperature, the mixture is then poured into ice-cold diluted aqueous HCl and extracted with diethyl ether. The combined organic layers are washed with brine, dried over $MgSO_4$ and concentrated to give a yellow oil. Purification by flash chromatography on silica gel (hexane/AcOEt 20:1) gives the title compound as yellow liquid. TLC, $R_f$ (hexane/AcOEt 3:1)=0.56. $^1$H-NMR ($CDCl_3$): δ 1.23 (t, 3H), 2.11 (m, 2H), 2.60 (s, 3H), 3.52 (t, 2H), 3.58 (t, 2H), 4.79 (t, 2H) ppm.

b. 1-Ethoxy-3-trifluoromethoxy-propane

Following the method described in Tetrahedron Letters (1992), 33, 4173-4176, a suspension of 1,3-dibromo-5,5-dimethylhydantoin (78.5 g, 0.266 mol) in $CH_2Cl_2$ (0.8 L) is cooled to −70° C., followed by dropwise addition of hydrogen fluoride/pyridine (99.2 mL, 3.82 mol; Fluka No 47586). To this mixture is then slowly added a solution of dithiocarbonic acid O-(3-ethoxy-propyl) ester S-methyl ester (23.0 g, 0.089 mol) in $CH_2Cl_2$ (200 mL). The yellow reaction mixture is warmed to ambient temperature over 3.5 hrs and then quenched by addition of an ice-cold aqueous solution of $NaHSO_3/NaHCO_3/NaOH$ until the red-brownish color of the mixture disappears. The aqueous phase is adjusted to pH>10 by addition of solid sodium hydroxide with stirring, the organic phase is separated, washed with brine and filtered. Removal of the solvent ($CH_2Cl_2$) is achieved by distillation at atmospheric pressure (<35° C. boiling temperature). Fractions boiling between 37° C. and 110° C. are combined, taken up in $CH_2Cl_2$ (100 mL) and washed with 2N aqueous HCl. The aqueous layer is re-extracted with $CH_2Cl_2$ (40 mL), the combined organics are dried ($Na_2SO_4$) and filtered. The solvent is removed in a distillation apparatus at normal pressure (oil bath at 50° C.) to obtain the title compound as a pale yellow liquid. $^1$H-NMR ($CDCl_3$): δ 1.23 (t, 3H), 1.98 (m, 2H), 3.48-3.57 (m, 4H), 4.12 (t, 2H) ppm. $^{19}$F-NMR ($CDCl_3$): δ −60.8 ppm.

c. Trifluoro-methanesulfonic acid 3-trifluoromethoxy-propyl ester

Following a similar procedure as described in J. Org. Chem. (2001), 66, 1061-1063, 1-ethoxy-3-trifluoromethoxy-propane (1.50 g, 6.10 mmol) is added to a mixture of trifluoromethanesulfonic anhydride (4.04 mL, 23.8 mmol) and trifluoromethanesulfonic acid (0.15 mL, 1.65 mmol) with stirring. The mixture is heated at 60° C. overnight, cooled to room temperature and poured into ice-water. The aqueous layer is extracted with $CH_2Cl_2$, the combined organics are dried over $Na_2SO_4$ and filtered. Volatiles are removed by distillation at normal pressure (bath temperature at 65° C.) to give a mixture of trifluoro-methanesulfonic acid ethyl ester and the title compound as pale yellow liquid (used without further purification). $^1$H-NMR ($CDCl_3$): δ 2.25 (m, 2H), 4.16 (m, 2H), 4.70 (m, 2H) ppm.

d. 4-Bromo-1-methoxy-2-(3-trifluoromethoxy-propoxy)-benzene

A mixture of 5-bromo-2-methoxy-phenol (1.20 g, 5.62 mmol), crude trifluoro-methanesulfonic acid 3-trifluoromethoxy-propyl ester (2.52 g, 6.74 mmol; purity of 74%) and anhydrous $K_2CO_3$ (1.18 g, 8.42 mmol) in MeCN (8 mL) is stirred in a sealed flask at room temperature overnight and then filtered. The combined filtrates are concentrated and the crude product is chromatographed over silica gel (eluent: toluene) to give the title compound as oil. TLC, $R_f$ (toluene/AcOEt 10:1)=0.63. $^1$H-NMR ($CDCl_3$): δ 2.25 (m, 2H), 3.87 (s, 3H), 4.13 (m, 2H), 4.23 (m, 2H), 6.79 (dd, 1H), 7.04 (d,1H), 7.09 (dd, 1H) ppm. $^{19}$F-NMR ($CDCl_3$): zδ −60.7 ppm.

e. 4-Methoxy-3-(3-trifluoromethoxy-propoxy)-benzoic acid

To a solution of 4-bromo-1-methoxy-2-(3-trifluoromethoxy-propoxy)-benzene (1.11 g, 3.20 mmol) in THF (10 mL), cooled to −60 to −70° C., is added dropwise a 1.6M solution of n-butyllithium in hexane (2.30 mL, 3.69 mmol). After stirring for 30 min, a stream of $CO_2$ gas is bubbled into the yellow solution for 10 min. The reaction is quenched by adding 2N aqueous HCl and volatiles are removed by evaporation. The water phase is alkalized by addition of 4N NaOH, washed with AcOEt and then acidified with HCl 37% to form a white suspension. Extraction with $CH_2Cl_2$, drying of the organics over $Na_2SO_4$ and evaporation gives the title product as white solid. TLC, $R_f$ (hexane/AcOEt 1:1)=0.09. MS: 293.0 [M−H]$^+$. $t_R$ (HPLC, Nucleosil C18HD column, 20-100% $CH_3CN/H_2O$/6 min, 100% $CH_3CN$/2 min, $CH_3CN$ and $H_2O$ containing 0.1% TFA, flow: 1 mL/min): 4.00 min. $^1$H-NMR ($CDCl_3$): δ 2.15 (m, 2H), 3.85 (s, 3H), 4.10 (m, 2H), 4.27 (m, 2H), 7.08 (dd, 1H), 7.48 (d, 1H), 7.60 (dd, 1H) ppm. $^{19}$F-NMR (DMSO-d$_6$): δ −58.2 ppm.

4-Ethyl-3-(3-trifluoromethoxy-propoxy)-benzoic acid

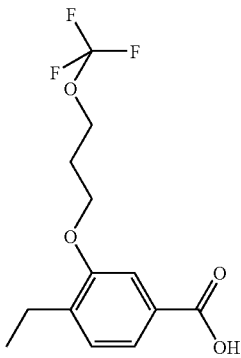

a. 4-Ethyl-3-(3-trifluoromethoxy-propoxy)-benzoic acid methyl ester

A mixture of 4-ethyl-3-hydroxy-benzoic acid methyl ester (250 mg, 1.32 mmol), crude trifluoro-methanesulfonic acid 3-trifluoromethoxy-propyl ester (590 mg, 1.58 mmol; purity of 74%) and anhydrous K$_2$CO$_3$ (276 mg, 1.98 mmol) in MeCN (2.0 mL) is stirred in a sealed glass vial overnight at room temperature. The crude product obtained after filtration and evaporation is purified by flash chromatography (hexane/AcOEt 1:1) to give the title compound as oil. TLC, R$_f$ (hexane/AcOEt 3:1)=0.38. $^1$H-NMR (CDCl$_3$): δ 1.24 (t, 3H), 2.25 (m, 2H), 2.70 (q, 2H), 3.94 (s, 3H), 4.18 (t, 2H), 4.24 (t, 2H), 7.25 (d, 1H), 7.52 (s, 1H), 7.64 (d, 1H) ppm. $^{19}$F-NMR (CDCl$_3$): δ −61.1 ppm.

b. 4-Ethyl-3-(3-trifluoromethoxy-propoxy)-benzoic acid

The title compound is obtained from 4-ethyl-3-(3-trifluoromethoxy-propoxy)-benzoic acid methyl ester (155 mg, 0.506 mmol) by hydrolysis in THF (3 mL) in the presence of aqueous 2N NaOH (0.38 mL, 0.76 mmol) at 60° C. overnight. After cooling to room temperature, volatiles are removed in vacuo and the residue is portioned between 2N aqueous HCl and CH$_2$Cl$_2$. The combined organics are dried (Na$_2$SO$_4$) and evaporated to dryness to give the title compound as a white solid. TLC, R$_f$ (hexane/AcOEt 1:1)=0.17. MS: 291.0 [M−H]$^+$. t$_R$ (HPLC, Nucleosil C18HD column, 20-100% CH$_3$CN/H$_2$O/6 min, 100% CH$_3$CN/2 min, CH$_3$CN and H$_2$O containing 0.1% TFA, flow: 1 mL/min): 4.99 min. $^1$H-NMR (DMSO-d$_6$): δ 1.15 (t, 3H), 2.18 (m, 2H), 2.64 (q, 2H), 4.13 (t, 2H), 4.29 (t, 2H), 7.28 (d, 1H), 7.45 (s, 1H), 7.51 (d, 1H), 12.65 (s, br, 1H) ppm. $^{19}$F-NMR (DMSO-d$_6$): δ −59.1 ppm.

4-Methoxy-3-(5-methyl-isoxazol-3-ylmethoxy)-benzoic acid

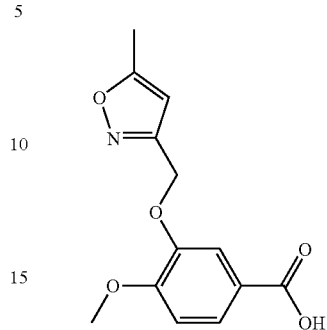

a. 4-Methoxy-3-(5-methyl-isoxazol-3-ylmethoxy)-benzoic acid ethyl ester

A mixture of 3-hydroxy-4-methoxy-benzoic acid (2.00 g, 10.2 mmol), 3-(chloromethyl)-5-methylisoxazole (1.61 g, 12.2 mmol; commercially available from Maybridge, SPB01262DA), anhydrous K$_2$CO$_3$ (2.11 g, 15.3 mmol) and NaI (0.31 g, 2.04 mmol) in MeCN (35 mL) is refluxed overnight. After cooling to room temperature, the mixture is filtered, the filtrate is diluted with CH$_2$Cl$_2$ and the organics are washed with aqueous 0.5M NaOH, water and brine. Drying over Na$_2$SO$_4$ and evaporation to dryness affords the crude title compound as oil. MS: 292.0 [M+H]$^+$. t$_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 4.14 min. $^1$H-NMR (CDCl$_3$): δ 1.39 (t, 3H), 2.45 (s, 3H), 3.93 (s, 3H), 4.35 (q, 2H), 5.20 (s, 2H), 6.15 (s, 1H), 6.15 (dd, 1H), 6.90 (d, 1H), 7.70 (dd, 1H) ppm.

b. 4-Methoxy-3-(5-methyl-isoxazol-3-ylmethoxy)-benzoic acid

The title compound is obtained by hydrolysis of 4-methoxy-3-(5-methyl-isoxazol-3-ylmethoxy)-benzoic acid ethyl ester (2.90 g, 8.96 mmol), dissolved in EtOH (25 mL), in the presence of 2N NaOH (6.72 mL, 13.4 mmol) at 70° C. for 3 hrs. After cooling to room temperature, volatiles are removed in vacuo, the aqueous phase is washed with CH$_2$Cl$_2$ and then acidified to pH 1 by addition of conc. HCl. The precipitate is filtered off and dried to give an off-white powder. MS: 264.0 [M+H]$^+$. t$_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 3.98 min. $^1$H-NMR (DMSO-d$_6$): δ 2.39 (s, 3H), 3.82 (s, 3H), 5.15 (s, 2H), 6.30 (s, 1H), 7.06 (dd,1H), 7.54 (d, $_1$H), 7.59 (dd, 1H), 12.7 (s, br, 1H) ppm.

3-(2-Ethoxy-ethoxy)4-methoxy-benzoic acid

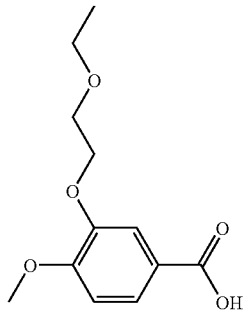

a. 3-(2-Ethoxy-ethoxy)-4-methoxy-benzoic acid ethyl ester

A mixture of 3-hydroxy-4-methoxy-benzoic acid ethyl ester (1.60 g, 8.16 mmol), 2-bromoethyl ethyl ether (1.38 mL, 12.2 mmol) and anhydrous K2CO$_3$ (1.69 g, 12.2 mmol) in MeCN (35 mL) is refluxed overnight. In order to complete the reaction, an additional aliquot of 2-bromoethyl ethyl ether (1.38 mL, 12.2 mmol) and a catalytic amount of NaI are added, and reflux is continued overnight. After cooling, the mixture is filtered and the filtrates are concentrated. The residue is taken up in CH$_2$Cl$_2$, the organic layer is washed with 0.5M NaOH and water, dried (Na$_2$SO$_4$) and concentrated. The title compound is obtained after flash chromatography (hexane/AcOEt 8:2) as colorless oil. MS: 269.0 [M+H]$^+$. t$_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 4.92 min. $^1$H-NMR (CDCl$_3$): δ 1.27 (m, 3H), 1.41 (m, 3H), 3.64 (m, 2H), 3.87 (m, 2H), 3.94 (s, 3H), 4.26 (m, 2H), 4.38 (m, 2H), 9.91 (dd, 1H), 7.63 (d, 1H), 7.72 (dd, 1H) ppm.

b. 3-(2-Ethoxy-ethoxy)-4-methoxy-benzoic acid

The title compound is obtained from 3-(2-ethoxy-ethoxy)-4-methoxy-benzoic acid ethyl ester (1.41 g, 5.26 mmol) by hydrolysis in EtOH (15 mL) in the presence of aqueous 2N NaOH (3.94 mL, 7.88 mmol) at 50° C. overnight as a white powder. MS: 239.0 [M−H]$^+$. t$_R$ (HPLC, Nucleosil C18HD column, 5-100% CH$_3$CN/H$_2$O/6 min, 100% CH$_3$CN/2 min, CH$_3$CN and H$_2$O containing 0.1% TFA, flow: 1 mL/min): 3.78 min. $^1$H-NMR (DMSO-d$_6$): δ 1.11 (t, 3H), 3.48 (q, 2H), 3.68 (m, 2H), 3.80 (s, 3H), 4.08 (m, 2H), 7.03 (dd, 1H), 7.43 (d, 1H), 7.55 (dd, 1H), 12.6 (s, br, 1H) ppm.

Scheme 7

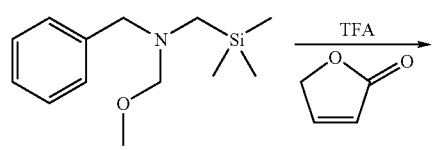

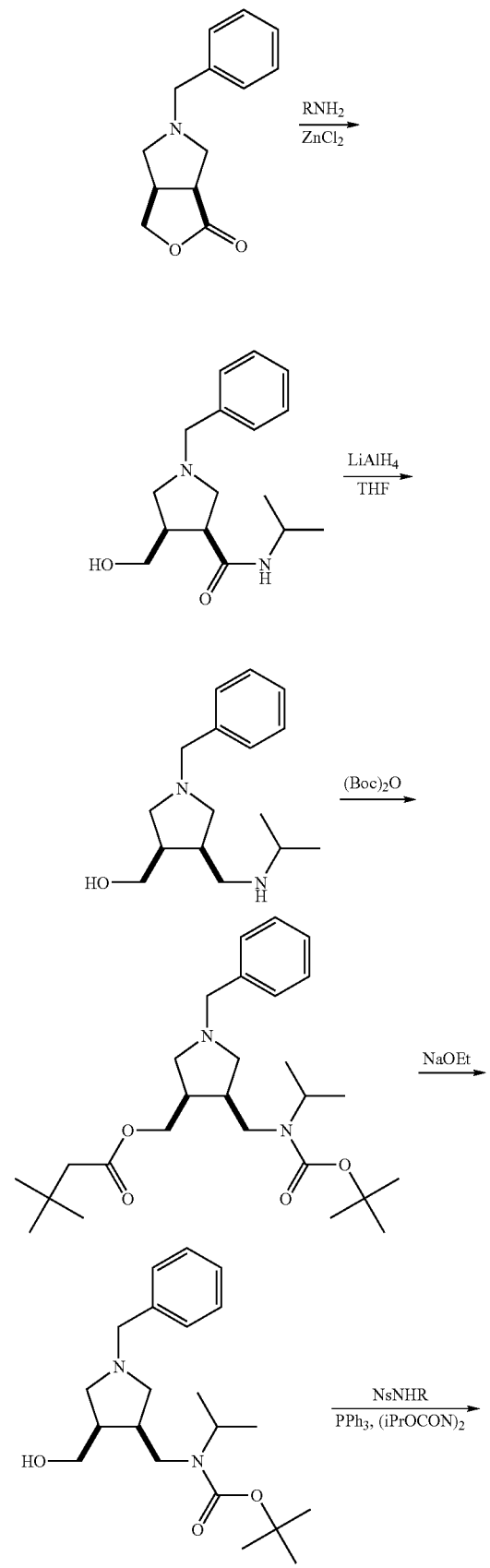

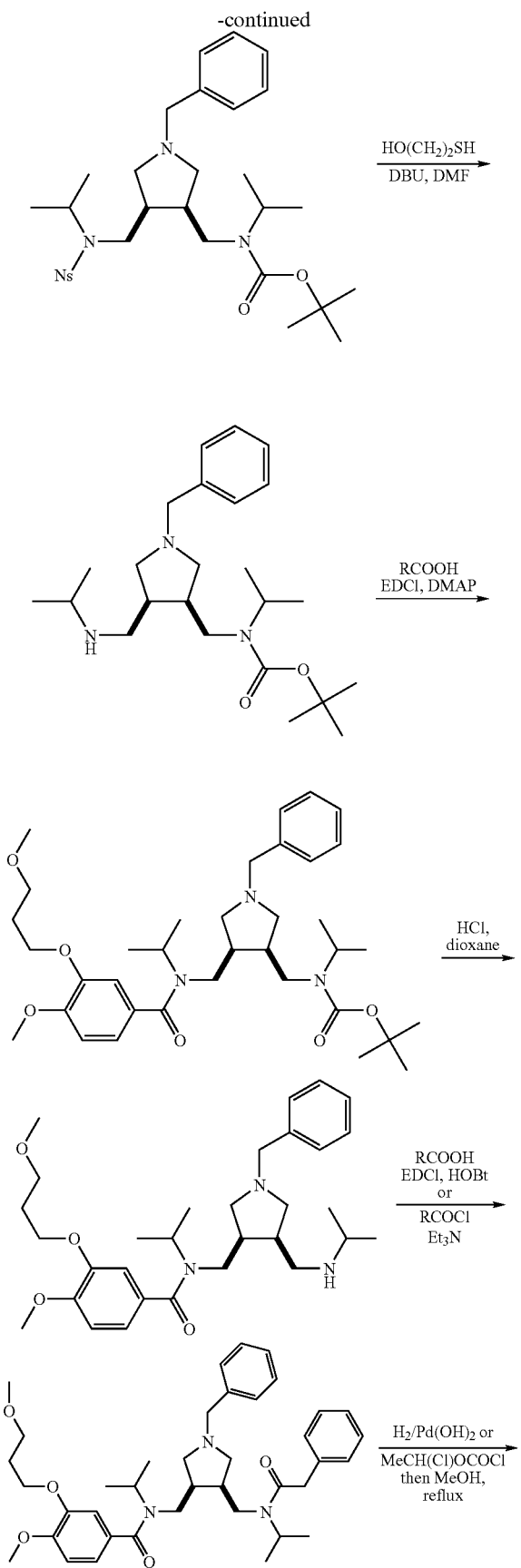

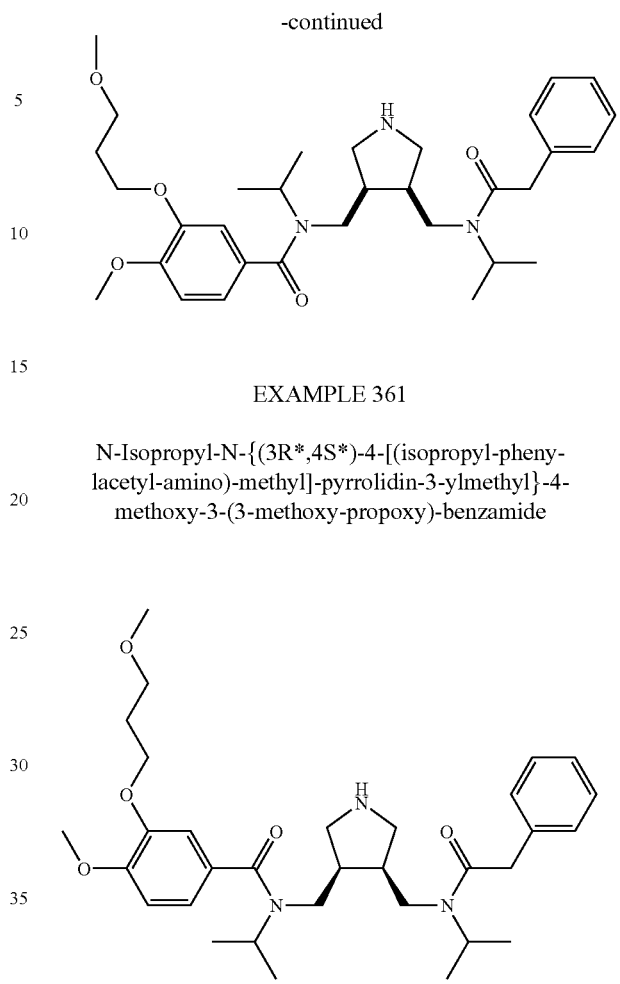

EXAMPLE 361

N-Isopropyl-N-{(3R*,4S*)-4-[(isopropyl-phenylacetyl-amino)-methyl]-pyrrolidin-3-ylmethyl}-4-methoxy-3-(3-methoxy-propoxy)-benzamide A solution of N-{((3R*,4S*)-1-benzyl-4-[(isopropyl-phenylacetyl-amino)-methyl]-pyrrolidin-3-ylmethyl}-N-isopropyl-4-methoxy-3-(3-methoxy-propoxy)-benzamide (0.15 g, 0.24 mmol) and 1-chloroethyl chloroformate (0.10 mL, 0.97 mmol) in ClCH$_2$CH$_2$Cl is refluxed for 2 h under a nitrogen atmosphere, and MeOH (10 mL) is then added at room temperature. The mixture is heated for 2 h at 80° C., and concentrated to give the title product. For purification, the N-Boc protected compound, (3S*,4R*)-3-({isopropyl-[4-methoxy-3-(3-methoxy-propoxy)-benzoyl]-amino}-methyl)-4-[(isopropyl-phenylacetyl-amino)-methyl]-pyrrolidine-1-carboxylic acid tert-butyl ester, is prepared analogously as described for the title compound D in Example 361, Scheme 7. The crude product is purified by flash chromatography on silica gel (eluent: cHexane/AcOEt 50/50) to give the product. MS (LC-MS): 654.4 [M+H]$^+$; tR (HPLC, C18 column, 10-100% CH$_3$CN/H$_2$O/5 min, 100% CH$_3$CN/2.5 min, CH$_3$CN and H$_2$O containing 0.1% TFA, flow: 1.5 mL/min): 5.92 min.

The pure title compound is prepared analogously as described for the title compound under I in Example 361, Scheme 7. MS (LC-MS): 554.4 [M+H]$^+$; $t_R$ (HPLC, C18 column, 10-100% CH$_3$CN/H$_2$O/5 min, 100% CH$_3$CN/3 min, CH$_3$CN and H$_2$O containing 0.1% TFA, flow: 1.5 mL/min): 5.23 min.

A. (3aR*,6aS*)-5-Benzyl-hexahydro-furo[3,4-c]pyrrol-1-one

To a mixture of y-crotonolactone (0.99 mL, 13.5 mmol) and N-(methoxymethyl)-N-(trimethylsilylmethyl)benzylamine (5.0 g, 20.2 mmol) in $CH_2Cl_2$ (50 mL) is added dropwise TFA (0.10 mL, 1.30 mmol) at 0° C. The reaction mixture is stirred overnight at room temperature and quenched with an aqueous saturated solution of $NaHCO_3$ (30 mL). $CH_2Cl_2$ is added, the layers are separated and the aqueous one back extracted twice with $CH_2Cl_2$. The combined organic extracts are dried over $MgSO_4$, filtered and concentrated. The crude material is purified by flash chromatography on silica gel (eluent: AcOEt/hexane 10:90 to 20:80) to give the titled product. TLC, Rf (AcOEt/hexane 3:7)=0.73. MS (LC-MS): 218.1 $[M+H]^+$; $t_R$ (HPLC, C18 column, 10-100% $CH_3CN/H_2O/5$ min, 100% $CH_3CN/2.5$ min, $CH_3CN$ and $H_2O$ containing 0.1% TFA, flow: 1.5 mL/min): 2.95 min.

B. (3S*,4R*)-1-Benzyl-4-hydroxymethyl-pyrrolidine-3-carboxylic acid isopropyl-amide A suspension of (3aR*,6aS*)-5-benzyl-hexahydro-furo[3,4-c]pyrrol-1-one (1.50 g, 6.90 mmol) and $ZnCl_2$ (0.94 g, 6.90 mmol) in $iPrNH_2$ (20 mL) is refluxed overnight under a nitrogen atmosphere. The crude material is filtered over a pad of Celite and concentrated. The crude material is purified by flash chromatography on silica gel (eluent: $CH_2Cl_2$/MeOH/$NH_4OH$ 70:25:5) to give the title product. TLC, $R_f$($CH_2Cl_2$/MeOH 95:5)=0.38. MS (LC-MS): 277.2 $[M+H]^+$.

C. [(3R*,4R*)-1-Benzyl-4-(isopropylamino-methyl)-pyrrolidin-3-yl]-methanol

To a ice-cooled solution of $LiAlH_4$ (0.56 g, 14.76 mmol) in THF (25 mL), is added dropwise a solution of (3S*,4R*)-1-benzyl-4-hydroxymethyl-pyrrolidine-3-carboxylic acid isopropylamide (1.02 g, 3.69 mmol) in THF (5 mL). The reaction mixture is refluxed overnight and quenched with $Na_2SO_4.10H_2O$ (4 g) at 0° C. Ether is added, the mixture is stirred for 2 h at room temperature. The crude material is filtered over a pad of Celite and concentrated to give the title compound which is used without further purification in the next step. TLC, $R_f$ ($CH_2Cl_2$/MeOH 95:5)=0.28. MS (LC-MS): 263.2 $[M+H]^+$; ]$^+$; $t_R$ (HPLC, C18 column, 10-100% $CH_3CN/H_2O/5$ min, 100% $CH_3CN/2.5$ min, $CH_3CN$ and $H_2O$ containing 0.1% TFA, flow: 1.5 mL/min): 2.94 min.

D. Carbonic acid (3R*,4S*)-1-benzyl-4-[(tert-butoxycarbonyl-isopropyl-amino)-methyl]-pyrrolidin-3-ylmethyl ester tert-butyl ester A suspension of [(3R*,4R*)-1-benzyl-4-(isopropylamino-methyl)-pyrrolidin-3-yl]-methanol (1.13 g, 4.31 mmol), $NaHCO_3$ (1.45 g, 17.24 mmol), and $Boc_2O$ (1.88 g, 8.62 mmol) in MeOH (50 mL) is stirred overnignt at room temperature. The mixture is heated for 1 h at 65° C., and then concentrated to a few mL of solvent by rotary evaporation. Water and $CH_2Cl_2$ are added, the layers are separated and the aqueous one extracted twice with $CH_2Cl_2$. The combined organic extracts are dried ($MgSO_4$), and concentrated to give the title compound which is used without further purification in the next step. TLC, $R_f$(AcOEt)=0.81. MS (LC-MS): 463.3 $[M+H]^+$; $t_R$ (HPLC, C18 column, 10-100% $CH_3CN/H_2O/5$ min, 100% $CH_3CN/2.5$ min, $CH_3CN$ and $H_2O$ containing 0.1% TFA, flow: 1.5 mL/min): 6.08 min.

E. ((3S*,4R*)-1-Benzyl-4-hydroxymethyl-pyrrolidin-3-ylmethyl)-isopropyl-carbamic acid tert-butyl ester A mixture of carbonic acid (3R*,4S*)-1-benzyl-4-[(tert-butoxycarbonyl-isopropyl-amino)-methyl]-pyrrolidin-3-ylmethyl ester tert-butyl ester (2.02 g, 4.31 mmol) and NaOEt (0.59 g, 8.62 mmol) in EtOH (35 mL) is stirred for 2 h at room temperature. The solvent is concentrated and the residue is diluted by $CH_2Cl_2$ and $H_2O$. The layers are separated and the organic extract is washed successively with $H_2O$ and brine. The combined organic layers are dried with $MgSO_4$, filtered and concentrated. The crude material is purified by flash chromatography on silica gel (eluent: $CH_2Cl_2$/MeOH 95:5) to give the title product. TLC, $R_f$ (AcOEt)=0.23. MS (LC-MS): 363.3 $[M+H]^+$; $t_R$ (HPLC, C18 column, 10-100% $CH_3CN/H_2O/5$ min, 100% $CH_3CN/2.5$ min, $CH_3CN$ and $H_2O$ containing 0.1% TFA, flow: 1.5 mL/min): 5.06 min.

F. ((3S*,4R*)-1-Benzyl-4-{[isopropyl-(2-nitro-benzenesulfonyl)-amino]-methyl}-pyrrolidin-3-ylmethyl)-isopropyl-carbamic acid tert-butyl ester To a solution of ((3S*,4R*)-1-benzyl-4-hydroxymethyl-pyrrolidin-3-ylmethyl)-isopropyl-carbamic acid tert-butyl ester (0.60 g, 1.66 mmol), N-isopropyl-2-nitro-benzenesulfonamide (0.49 g, 1.99 mmol), and $PPh_3$ (0.52 g, 1.99 mmol) in toluene (15 mL), is added dropwise diisopropyl azodicarboxylate (0.39 mL, 1.99 mmol) at 0° C. under a nitrogen atmosphere. The solution is stirred for 1 h at room temperature, and then heated at 65° C. for 1 h. The reaction mixture is concentrated. The crude material is used purified by flash chromatography on silica gel (eluent: c-hexane/AcOEt 3:7) to give the crude product. To the solid product is added a mixture of $Et_2O$/hexane (1:1) and the resulting suspension is filtered. The solid is washed with $Et_2O$/hexane (1:1) solution, and then the combined filtrate is concentrated to give a titled product. TLC, $R_f$ (AcOEt)=0.61. MS (LC-MS): 589.3 $[M+H]^+$; $t_R$ (HPLC, C18 column, 10-100% $CH_3CN/H_2O/5$ min, 100% $CH_3CN/2.5$ min, $CH_3CN$ and $H_2O$ containing 0.1% TFA, flow: 1.5 mL/min): 6.39 min.

G. [(3S*,4S*)-1-Benzyl-4-(isopropylamino-methyl)-pyrrolidin-3-ylmethyl]-isopropyl-carbamic acid tert-butyl ester A solution of((3S*,4R*)-1-benzyl-4-{[isopropyl-(2-nitrobenzenesulfonyl)-amino]-methyl}-pyrrolidin-3-ylmethyl)-isopropyl-carbamic acid tert-butyl ester (8.9 g, 23.02 mmol), 2-mercaptoethanol (0.81 mL, 11.60 mmol), and DBU (0.79 mL, 5.27 mmol) in $CH_3CN$ (10 mL) is stirred for 2 h at room temperature. The mixture is concentrated and then diluted with $Et_2O$ and $H_2O$. The organic layer is separated, and the aqueous phase is extracted 3 times with $Et_2O$. The combined organic extracts are dried ($MgSO_4$), and the solvent is concentrated to give the title compound which is used without further purification in the next step. TLC, $R_f$(AcOEt)=0.61. MS (LC-MS): 404.3 $[M+H]^+$; $t_R$ (HPLC, C18 column, 10-100% $CH_3CN/H_2O/5$ min, 100% $CH_3CN/2.5$ min, $CH_3CN$ and $H_2O$ containing 0.1% TFA, flow: 1.5 mL/min): 4.45 min.

H. [(3S*,4R*)-1-Benzyl-4-({isopropyl-[4-methoxy-3-(3-methoxy-propoxy)-benzoyl]-amino}-methyl)-pyrrolidin-3-ylmethyl]-isopropyl-carbamic acid tert-butyl ester To a solution of [(3S*,4S*)-1-benzyl-4-(isopropylamino-methyl)-pyrrolidin-3-ylmethyl]-isopropyl-carbamic acid tert-butyl ester (0.32 g, 0.55 mmol), 4-methoxy-3-(3-methoxy-propoxy)-benzoic acid (0.23 g, 0.96 mmol), DMAP (0.12 g, 0.96 mmol), and triethyl-amine (0.56 mL, 0.96 mmol) in DMF (10 mL), is added EDCl-HCl (0.19 g, 0.96 mmol) at 0° C. The reaction mixture is stirred overnight at room temperature. Water and Et$_2$O are added, the layers are separated and the aqueous one is extracted twice with Et$_2$O. The combined organic extracts are dried (MgSO$_4$), and the solvent is removed in vacuo. The crude product is purified by flash chromatography on silica gel (eluent: CH$_2$Cl$_2$/MeOH 90:10) to give the title product. TLC, R$_f$ (CH$_2$Cl$_2$/MeOH 9:1)=0.72. MS (LC-MS): 626.4 [M+H]$^+$; t$_R$ (HPLC, C18 column, 10-100% CH$_3$CN/H$_2$O/5 min, 100% CH$_3$CN/2.5 min, CH$_3$CN and H$_2$O containing 0.1% TFA, flow: 1.5 mL/min): 6.28 min.

I. N-[(3R*,4R*)-1-Benzyl-4-(isopropylamino-methyl)-pyrrolidin-3-ylmethyl]-N-isopropyl-4-methoxy-3-(3-methoxy-propoxy)-benzamide To a solution of [(3S*,4R*)-1-benzyl-4-({isopropyl-[4-methoxy-3-(3-methoxy-propoxy)-benzoyl]-amino}-methyl)-pyrrolidin-3-ylmethyl]-isopropyl-carbamic acid tert-butyl ester (0.41 g, 0.66 mmol), is added a dioxane solution of HCl 4N (10 mL). The reaction mixture is stirred for 2 h at room temperature. The solvent is concentrated and water (20 mL), an aqueous solution of NaOH 4N (5 mL) and Et$_2$O (25 mL) are added. The layers are separated and the aqueous one extracted twice with Et$_2$O. The combined organic extracts are dried (MgSO$_4$), and the solvent is removed in vacuo to give the title compound which is used without further purification in the next step. MS (LC-MS): 526.4 [M+H]$^+$; t$_R$ (HPLC, C18 column, 10-100% CH$_3$CN/H$_2$O/5 min, 100% CH$_3$CN/2.53 min, CH$_3$CN and H$_2$O containing 0.1% TFA, flow: 1.5 mL/min): 4.78 min.

J. N-{(3R*,4S*)-1-Benzyl4-[(isopropyl-phenylacetyl-amino)-methyl]-pyrrolidin-3-ylmethyl}-N-isopropyl-4-methoxy-3-(3-methoxy-propoxy)-benzamide To a solution of N-[(3R*,4R*)-1-benzyl-4-(isopropylamino-methyl)-pyrrolidin-3-ylmethyl]-N-isopropyl-4-methoxy-3-(3-methoxy-propoxy)-benzamide (0.19 g, 0.36 mmol), triethyl-amine (0.15 mL, 1.09 mmol), and DMAP (0.013 g, 0.11 mmol) in CH$_2$Cl$_2$, is added dropwise phenylacetyl chloride (0.058 mL, 0.44 mmol) at 0° C. under a nitrogen atmosphere. The solution is stirred overnight at room temperature. The mixture is added an aqueous solution of NaOH 0.1N (50 mL) and CH$_2$Cl$_2$ (50 mL). The organic layer is separated and the aqueous phase extracted twice with CH$_2$Cl$_2$, dried over MgSO$_4$, filtered, and concentrated in vacuo. The crude product is purified by flash chromatography on silica gel (eluent: CH$_2$Cl$_2$/MeOH 90:10) to give the title product. TLC, R$_f$ (CH$_2$Cl$_2$/MeOH 9:1)=0.23. MS (LC-MS): [M+H]$^+$; 644.4 t$_R$ (HPLC, C18 column, 10-100% CH$_3$CN/H$_2$O/5 min, 100% CH$_3$CN/2.5 min, CH$_3$CN and H$_2$O containing 0.1% TFA, flow: 1.5 mL/min): 5.95 min.

The following Examples are prepared according to the procedures described above for Example 361:

EXAMPLE 362

N-Isopropyl-N-{(3R*,4S*)-4-[(isopropyl-4-methoxy-3-(3-methoxy-propoxy)-benzoyl-amino)-methyl]-pyrrolidin-3-ylmethyl}-4-methoxy-3-(3-methoxy-propoxy)-benzamide

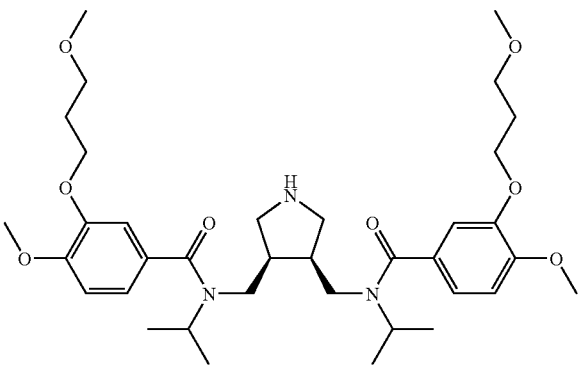

The title compound is prepared analogously as described in Example 361 by coupling N-[(3R*,4R*)-1-benzyl-4-(isopropylamino-methyl)-pyrrolidin-3-ylmethyl]-N-isopropyl4-methoxy-3-(3-methoxy-propoxy)-benzamide and 3-(3-methoxy-propoxy)-4-methoxy-benzoic acid in step J. MS (LC-MS): 658.3 [M+H]$^+$; t$_R$ (HPLC, Nucleosil C18 column, 10-100% CH$_3$CN/H$_2$O/5 min, 100% CH$_3$CN/2.5 min, CH$_3$CN and H$_2$O containing 0.1% TFA, flow: 1.5 mL/min): 5.20 min.

EXAMPLE 363

N-Isopropyl-4-methoxy-3-(3-methoxy-propoxy)-N-{(3R,4S)4-[(phenethyl-propionyl-amino)-methyl]-pyrrolidin-3-ylmethyl}-benzamide

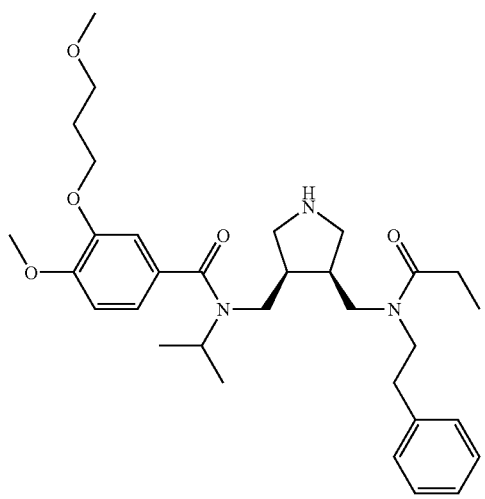

The title compound is prepared analogously as described in Example 361 using ((3S*,4R*)-1-benzyl-4-hydroxymethylpyrrolidin-3-ylmethyl)-isopropyl-carbamic acid tert-butyl ester and 2-nitro-N-phenethyl-benzenesulfonamide in step F, then propionyl chloride as the acylating agent in step H and 3-(3-methoxy-propoxy)-4-methoxy-benzoic acid as acylating agent in step J. MS (LC-MS): 554.4 [M+H]$^+$; $t_R$ (HPLC, Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 5.26 min.

EXAMPLE 364

N-[(3S,4S)-4-(1,3-Dioxo-1,3-dihydro-isoindol-2-ylmethyl)-pyrrolidin-3-ylmethyl]-N-isopropyl-3-(3-methoxy-propoxy)-4-methyl-benzamide

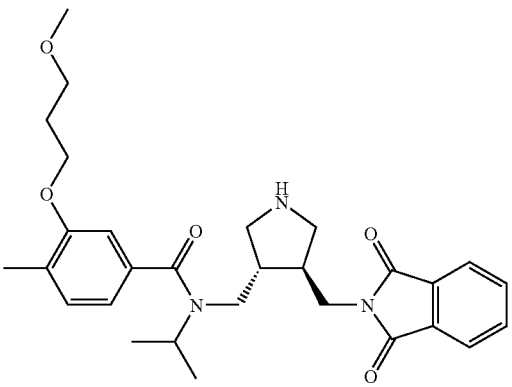

(3R,4R)-3-(1,3-Dioxo-1,3-dihydro-isoindol-2-ylmethyl)-4-({isopropyl-[3-(3-methoxy-propoxy)-4-methyl-benzoyl]-amino}-methyl)-pyrrolidine-1-carboxylic acid tert-butyl ester (180 mg, 0.30 mmol) is dissolved 4N HCl in dioxane (5 mL) and stirred at RT for 30 min. Lyophilization affords the corresponding hydrochloride salt. MS (LC-MS): 508.1 [M+H]$^+$; $t_R$ (HPLC, Waters Symmetry C18 column, 20-95% CH$_3$CN/H$_2$O/3.5 min, 95% CH$_3$CN/H$_2$O, 2 min, CH$_3$CN and H$_2$O containing 0.1% TFA, flow: 0.6 mL/min): 2.58 min.

The starting material is prepared as follows:

(3R,4R)-3-(1,3-Dioxo-1,3-dihydro-isoindol-2-ylmethyl)-4-({isopropyl-[3-(3-methoxy-propoxy)-4-methyl-benzoyl]-amino}-methyl)-pyrrolidine-1-carboxylic acid tert-butyl ester DEAD is slowly added to a solution of (3S,4R)-3-hydroxymethyl-4-({isopropyl-[3-(3-methoxy-propoxy)-4-methyl-benzoyl]-amino}-methyl)-pyrrolidine-1-carboxylic acid tert-butyl ester (210 mg, 0.44 mmol), phthalimide (07 mg, 0.66 mmol) and PPh$_3$ (173 mg, 0.66 mmol) in THF (5 mL) at RT. The resulting yellow solution is stirred for another 2 h before H$_2$O is added and the mixture is extracted with ethyl acetate. Drying (Na$_2$SO$_4$) of the extracts, filtration and evaporation of the solvent affords the crude product which is purified by preparative HPLC (Waters C$_{18}$ ODB, eluent: CH$_3$CN/H$_2$O 5%/2 min, CH$_3$CN/H$_2$O 5-100%/10 min, 100% CH$_3$CN/2.5 min, flow 20 mL/min) to give the desired product. MS (LC-MS): 630.2 [M+Na]$^+$; $t_R$ (HPLC, Waters Symmetry C18 column, 20-95% CH$_3$CN/H$_2$O/3.5 min, 95% CH$_3$CN/H$_2$O, 2 min, CH$_3$CN and H$_2$O containing 0.1% TFA, flow: 0.6 mL/min): 4.40 min.

Scheme 8

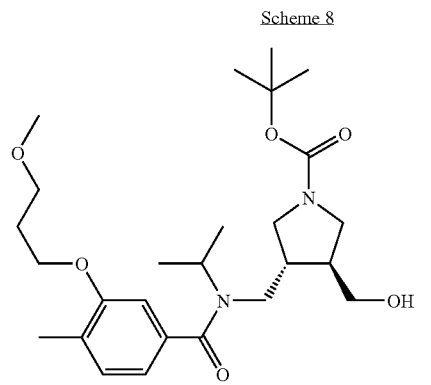

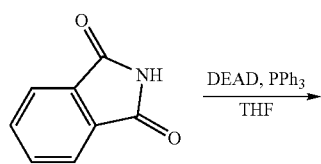

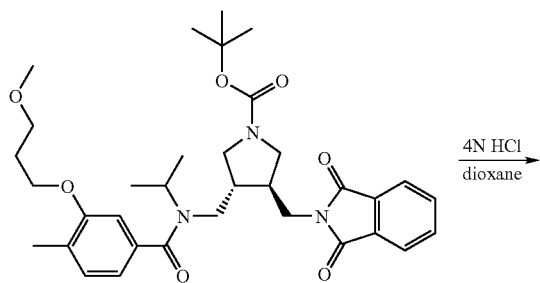

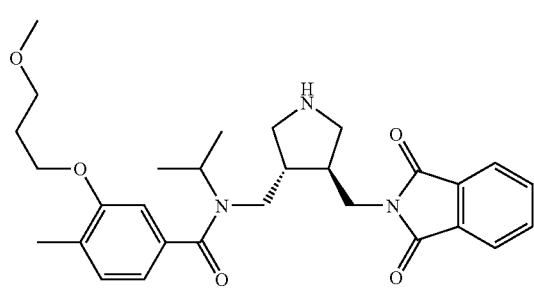

Scheme 9:

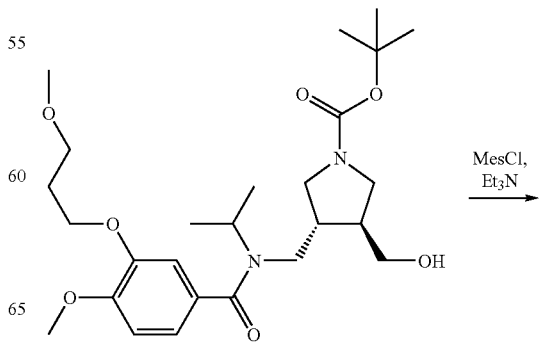

-continued

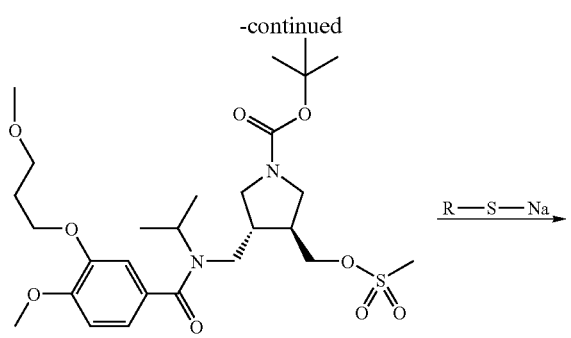

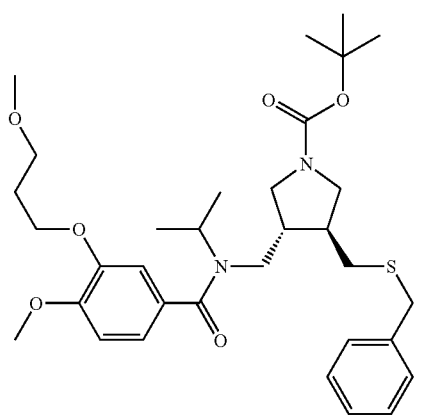

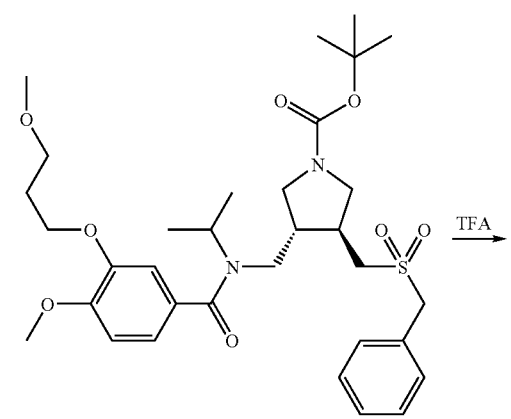

EXAMPLE 365

N-Isopropyl-4-methoxy-3-(3-methoxy-propoxy)-N-((3S*,4S*)-4-Phenyl-methanesulfonyl methyl-pyrrolidin-3-ylmethyl)-benzamide

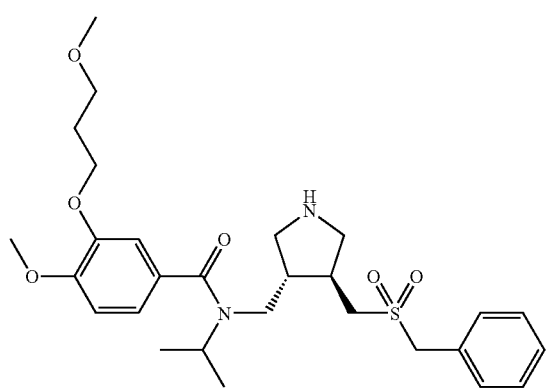

The title compound is prepared as shown in Scheme 9.

EXAMPLE 366

N-Isopropyl-4-methoxy-3-(3-methoxy-propoxy)-N-{(3S*,4S*)-4-[(methyl-phenylmethanesulfonyl-amino)-methyl]-pyrrolidin-3-ylmethyl}-benzamide

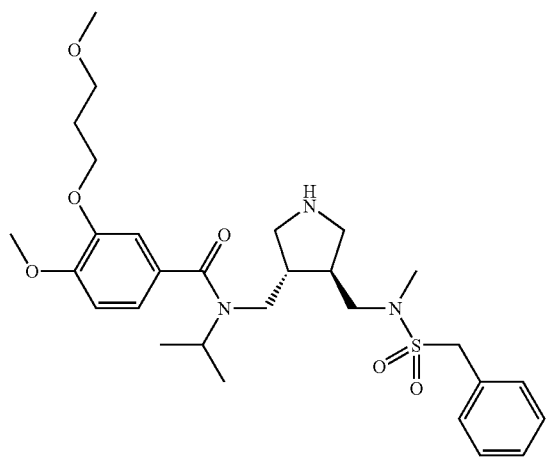

To a solution of (3R*,4S*)-3-({isopropyl-[4-methoxy-3-(3-methoxy-propoxy)-benzoyl]-amino}-methyl)-4-[(methyl-phenylmethanesulfonyl-amino)-methyl]-pyrrolidine-1-carboxylic acid tert-butyl ester (49 mg, 0.074 mmol) in 2 mL CH$_2$Cl$_2$, TFA (86 µL, 1.11 mmol) is added. The mixture is stirred 4 h at RT and then poured into a saturated solution of NaHCO$_3$. The layers are separated, and the aqueous one is back-extracted twice with CH$_2$Cl$_2$. The combined organic extracts are dried over Na$_2$SO$_4$, filtered and concentrated. The crude material is purified by flash chromatography on an Isolute SPE Flash NH$_2$ column (eluent: CH$_2$Cl$_2$/MeOH 100:0 to 95:5) to give the title product. TLC, R$_f$ (CH$_2$Cl$_2$/MeOH 9:1)=0.2. MS (LC-MS): 563.0 [M+H]$^+$; t$_R$ (HPLC, Nucleosil C18 column, 10-100% CH₃CN/H₂O/5 min, 100% CH₃CN/3 min, CH₃CN and H₂O containing 0.1% TFA, flow: 1.5 mL/min): 4.55 min.

To a solution of the free base in dioxane (2 mL), 4N HCl in dioxane (0.074 mmol, 19 µL) is added, and the resulting solution is lyophilized to afford the corresponding hydrochloride salt as a white powder.

The starting material is prepared as follows:

(3R*,4S*)-3-({Isopropyl-[4-methoxy-3-(3-methoxy-propoxy)-benzoyl]-amino}-methyl)-4-[(methyl-phenylmethanesulfonyl-amino)-methyl]-pyrrolidine-1-carboxylic acid tert-butyl ester To a solution of (3R*,4R*)-3-({isopropyl-[4-methoxy-3-(3-methoxy-propoxy)-benzoyl]-amino}-methyl)-4-methylaminomethyl-pyrrolidine-1-carboxylic acid tert-butyl ester (89 mg, 0.175 mmol) in CH₂Cl₂ (3 mL), alpha-toluenesulfonyl chloride (40 mg, 0.21 mmol) and triethylamine (30 µL, 0.21 mmol) are added under N₂ atmosphere. The mixture is stirred overnight at RT, diluted with CH₂Cl₂ and poured into an aqueous saturated solution of NaHCO₃. The organic layer is separated, and the aqueous one is extracted twice with CH₂Cl₂. The combined organic extracts are dried over Na₂SO₄, filtered and concentrated. The crude product is purified by preparative HPLC (C18-ODB-AQ, 5 µm, 20×50 mm, YMC, eluent: CH₃CN /H₂O+0.1% HCOOH flow: 20 mL/min). The HPLC fractions are collected, and the resulting solution is lyophilized to afford the title product. TLC, R_f (CH₂Cl₂/MeOH 95:5)=0.3. t_R (HPLC, Nucleosil C18 column, 10-100% CH₃CN/H₂O/5 min, 100% CH₃CN/3 min, CH₃CN and H₂O containing 0.1% TFA, flow: 1.5 ml/min): 5.81 min.

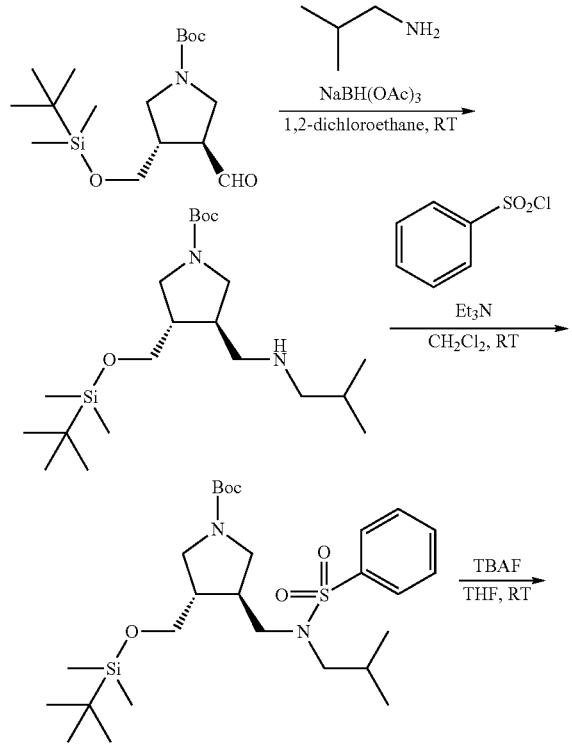

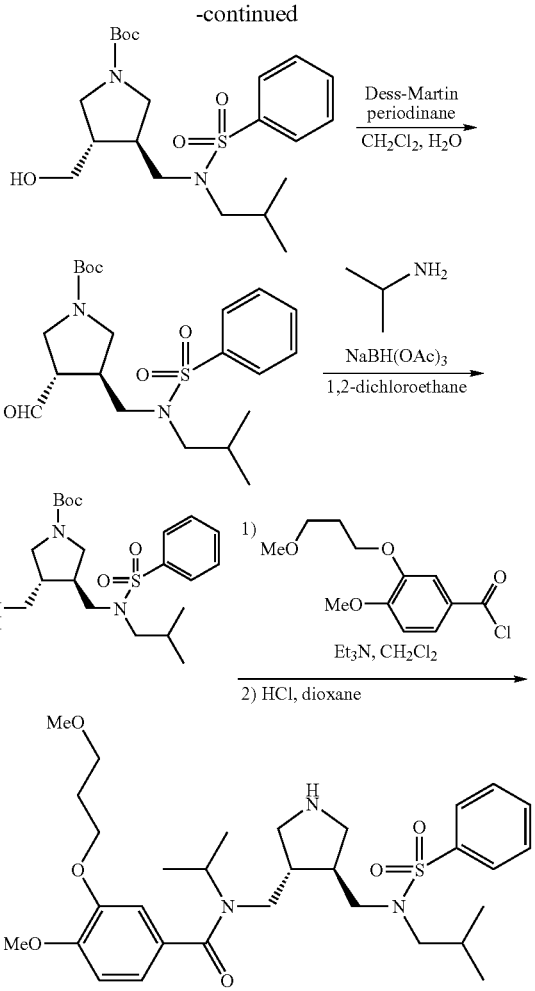

EXAMPLE 367

N-Isopropyl-4-methoxy-3-(3-methoxy-propoxy)-N-{(3S*,4S*)-4-[(isobutyl-phenylsulfonyl-amino)-methyl]-pyrrolidin-3-ylmethyl}-benzamide

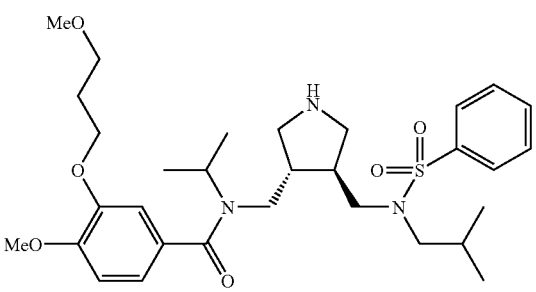

4N HCl/dioxane (4 mL) is added to a solution of (3R*,4R*)-3-({isopropyl-[4-methoxy-3-(3-methoxy-propoxy)-benzoyl]-amino}-methyl)-4-[(isobutyl-phenylsulfonyl-amino)-methyl]-pyrrolidine-1-carboxylic acid tert-butyl ester (0.804 g, 1.17 mmol) in dioxane (5 mL). After 3 h the solution is lyophilized to give the title compound a colorless powder. MS (LC-MS): 590.3 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 4.91 min.

The starting material is prepared as follows:

A. (3S*,4R*)-3-(tert-Butyl-dimethyl-silanyloxymethyl)-4-(isobutylamino-methyl)-pyrrolidine-1-carboxylic acid tert-butyl ester The title compound is prepared as described above for Example 9/step F (Scheme 5) from (3S*,4S*)-3-(tert-butyl-dimethyl-silanyloxymethyl)-4-formyl-pyrrolidine-1-carboxylic acid tert-butyl ester and isobutylamine. MS (LC-MS): 401.1 [M+H]$^+$; $t_R$ (HPLC, Waters Symmetry C18 column, 20-95% CH$_3$CN/H$_2$O/3.5 min, 95% CH$_3$CN/H$_2$O, 2 min, CH$_3$CN and H$_2$O containing 0.1% TFA, flow: 0.6 mL/min): 3.70 min.

B. N-[(3S*,4S*)4-(tert-Butyl-dimethyl-sianyloxymethyl)-pyrrolidin-3-ylmethyl]-N-isobutyl-benzenesulfonamide The title compound is prepared as described above in Example 366/step A from (3S*,4R*)-3-(tert-butyl-dimethyl-silanyloxymethyl)-4-(isobutylamino-methyl)-pyrrolidine-1-carboxylic acid tert-butyl ester and phenylsulfonyl chloride. TLC, R$_f$(CH$_2$Cl$_2$/MeOH 98:2)=0.42; $t_R$ (HPLC, Waters Symmetry C18 column, 20-95% CH$_3$CN/H$_2$O/3.5 min, 95% CH$_3$CN/H$_2$O, 2 min, CH$_3$CN and H$_2$O containing 0.1% TFA, flow: 0.6 mL/min): 5.58 min.

C. N-((3S*,4S*)-4-Hydroxymethyl-pyrrolidin-3-ylmethyl)-N-isobutyl-benzenesulfonamide The title compound is prepared as described above for Example 9/step H (Scheme 5) from N-[(3S*,4S*)-4-(tert-butyl-dimethyl-silanyloxymethyl)-pyrrolidin-3-ylmethyl]-N-isobutyl-benzenesulfonamide. MS (LC-MS): 327.1 [M-Boc+H]$^+$; $t_R$ (HPLC, Waters Symmetry C18 column, 20-95% CH$_3$CN/H$_2$O/3.5 min, 95% CH$_3$CN/H$_2$O, 2 min, CH$_3$CN and H$_2$O containing 0.1% TFA, flow: 0.6 mL/min): 4.17 min.

D. N-((3S*,4S*)-4-Formyl-pyrrolidin-3-ylmethyl)-N-isobutyl-benzenesulfonamide The title compound is prepared as described above for Example 9/step E (Scheme 5) from N-((3S*,4S*)-4-Hydroxymethyl-pyrrolidin-3-ylmethyl)-N-isobutyl-benzenesulfonamide. MS (LC-MS): 325.0 [M-Boc+H]$^+$; $t_R$ (HPLC, Waters Symmetry C18 column, 20-95% CH$_3$CN/H$_2$O/3.5 min, 95% CH$_3$CN/H$_2$O, 2 min, CH$_3$CN and H$_2$O containing 0.1% TFA, flow 0.6 mL/min): 4.24 min.

E. (3S*,4R)-3-[(Benzenesulfonyl-isobutyl-amino)-methyl]-4-(isopropylamino-methyl)-pyrrolidine-1-carboxylic acid tert-butyl ester The title compound is prepared as described above for Example 9/step F (Scheme 5) from N-((3S*,4S*)-4-formyl-pyrrolidin-3-ylmethyl)-N-isobutyl-benzenesulfonamide and isopropylamine. MS (LC-MS): 468.1 [M+H]$^+$; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 4.94 min.

F. (3R*,4R*)-3-({Isopropyl-[4-methoxy-3-(3-methoxy-propoxy)-benzoyl]-amino}-methyl)-4-[(isobutyl-phenylsulfonyl-amino)-methyl]-pyrrolidine-1-carboxylic acid tert-butyl ester Triethylamine (0.48 mL, 3.43 mmol) followed by 3-(3-methoxy-propoxy)-4-methoxy-benzoic acid chloride (621 mg, 2.4 mmol) (prepared from 3-(3-methoxy-propoxy)-4-methoxy-benzoic acid and SOCl$_2$ in CH$_2$Cl$_2$) is added to a solution of (3S*,4R*)-3-[(benzenesulfonyl-isobutyl-amino)-methyl]-4-(isopropylamino-methyl)-pyrrolidine-1-carboxylic acid tert-butyl ester (1.07 g, 2.3 mmol) in CH$_2$Cl$_2$ (30 mL) and stirred at RT for 16 h. For workup a sat. solution of NaHCO$_3$ is added and the mixture is extracted with ethyl acetate. The combined organic extracts are dried (Na$_2$SO$_4$), filtered and the solvent is evaporated. Purification of the crude product by flash chromatography on silica gel (eluent gradient: c-hexane/AcOEt 1:1 to 3:7) yields the title compound. TLC, R$_f$ (c-hexane/AcOEt 3:7)=0.40; $t_R$ (HPLC, Macherey-Nagel Nucleosil C18 column, 10-100% CH$_3$CN/H$_2$O/5 min, 100% CH$_3$CN/3 min, CH$_3$CN and H$_2$O containing 0.1% TFA, flow: 1.5 mL/min): 6.10 min.

The following Examples are prepared according to the procedures described above in Examples 8, 9, 10, 11, 12 and 13:

TABLE 19

| Example | configuration | structure | [M + H]$^+$ | $t_R$ (HPLC) |
|---|---|---|---|---|
| 368 | (3S*, 4S*) | 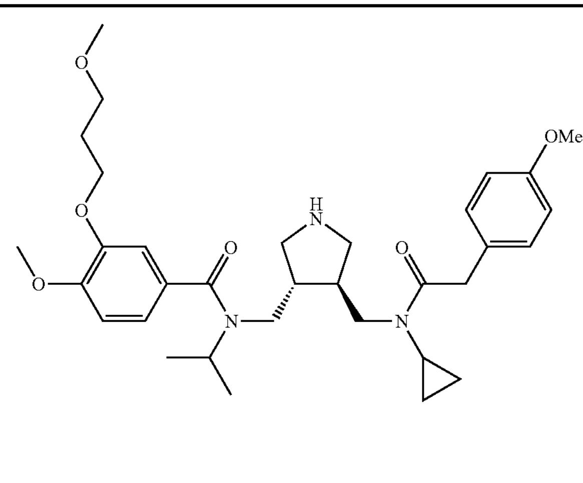 | 582.4 | 4.51 |

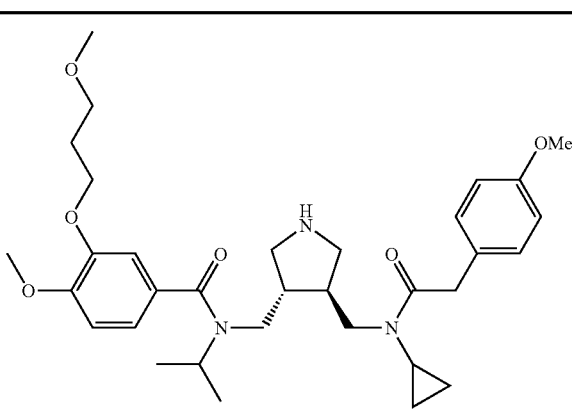

TABLE 19-continued

| Example | configuration | structure | [M + H]⁺ | $t_R$ (HPLC) |
|---|---|---|---|---|
| 369 | (3S, 4S) | 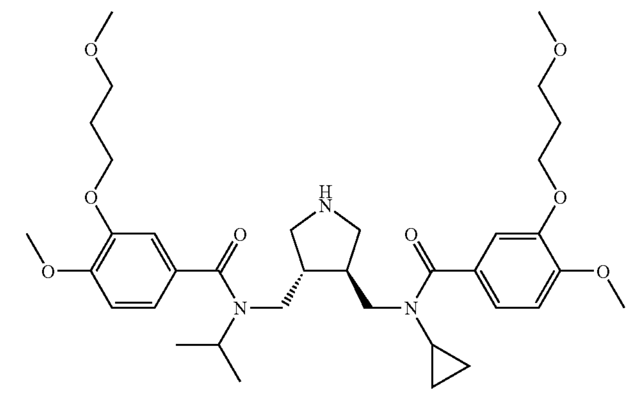 | 656.4 | 4.37 |

Conditions RP-HPLC: column: Nucleosil C18-HD (4×70 mm, 3 µM); solvent A: H₂O/0.1% TFA, solvent B: MeCN/0.1% TFA; gradient: 5-100% solvent B over 6 min, then 100% solvent B over 1.5 min, then 100 to 5% solvent B over 0.5 min; flow: 1.0 mL/min.

EXAMPLE 370

Soft Capsules 5000 soft gelatin capsules, each comprising as active ingredient 0.05 g of any one of the compounds of formula I mentioned in any one of the preceding Examples, are prepared as follows:

1. Composition

| Active ingredient | 250 g |
|---|---|
| Lauroglycol | 2 liters |

Preparation process: The pulverized active ingredient is suspended in Lauroglykol® (propylene glycol laurate, Gattefossé S. A., Saint Priest, France) and ground in a wet pulverizer to produce a particle size of about 1 to 3 µm. 0.419 g portions of the mixture are then introduced into soft gelatin capsules using a capsule-filling machine.

EXAMPLE 371

Tablets Comprising Compounds of the Formula I

Tablets, comprising, as active ingredient, 100 mg of any one of the compounds of formula I in any one of the preceding Examples are prepared with the following composition, following standard procedures:

Composition

| Active Ingredient | 100 mg |
|---|---|
| crystalline lactose | 240 mg |
| Avicel | 80 mg |
| PVPPXL | 20 mg |

-continued

| Aerosil | 2 mg |
|---|---|
| magnesium stearate | 5 mg |
| | 447 mg |

Manufacture: The active ingredient is mixed with the carrier materials and compressed by means of a tabletting machine (Korsch EKO, stamp diameter 10 mm).

Avicel® is microcrystalline cellulose (FMC, Philadelphia, USA). PVPPXL is polyvinyl-polypyrrolidone, cross-linked (BASF, Germany). Aerosil® is silicon dioxide (Degussa, Germany).

EXAMPLE 372

Renin Inhibiting Activity of the Compounds in Examples 1 to 369

Using the test systems mentioned above, IC₅₀ values for the compounds in the preceding examples 1 to 369 can be found in the range from 1 nM to 20 µM.

What is claimed is:
1. A compound of the formula I,

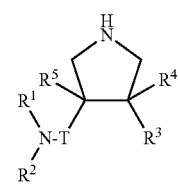

(I)

wherein
$R^1$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl, substituted or unsubstituted alkynyl or acyl;

$R^2$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted bicyclic aryl-alkyl, unsubstituted or substituted mono- or bicyclic heterocyclyl-alkyl, unsubstituted or substituted mono- or bicyclic cycloalkyl-alkyl, unsubstituted or substituted alkenyl, substituted or unsubstituted alkynyl; with the proviso that if $R^1$ is one of the moieties mentioned in the definition of $R^1$ other than acyl then $R^2$ can also be unsubstituted or substituted monocyclic aryl-alkyl;

$R^3$ is a moiety selected from the group consisting of moieties of the formulae

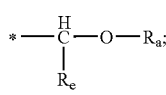
(a)

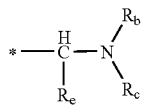
(b)

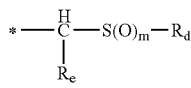
(c)

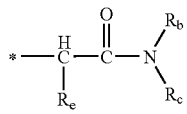
(d)

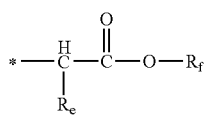
(e)

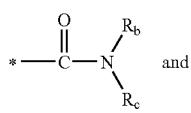
(f)

and

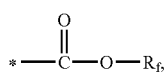
(g)

where in any of the moieties of the formulae given above under (a), (b), (c), (d), (e), (f) and (g) the asterisk (*) shows the bond binding the respective moiety $R^3$ to the rest of the molecule in formula I, $R_a$ is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl, acyl or hydrogen;

$R_b$ and $R_c$ are independently selected from the group consisting of unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted bicyclic aryl-alkyl, unsubstituted or substituted mono- or bicyclic heterocyclyl-alkyl, unsubstituted or substituted mono- or bicyclic cycloalkyl-alkyl, acyl or hydrogen, with the proviso that not more than one of $R_b$ and $R_c$ is acyl, and with the proviso that if $R_c$ is one of the mentioned moieties other than acyl then $R_b$ can also be unsubstituted or substituted monocyclic aryl-alkyl; or $R_b$ and $R_c$ may form together a 3 to 7 membered nitrogen containing ring which can be unsubstituted or substituted;

$R_d$ in a moiety of the formula (c) is unsubstituted or substituted alkyl, unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl or acyl, or can have one of these meanings or can be —N($R_b$)($R_c$) if m is 1 or 2;

$R_e$ is hydrogen, unsubstituted or substituted mono- or bicyclic aryl-alkyl, unsubstituted or substituted mono- or bicyclic cycloalkyl-alkyl or substituted or unsubstituted $C_1$-$C_7$-alkyl; and $R_f$ is substituted alkyl or unsubstituted or substituted mono- or bicyclic aryl, unsubstituted or substituted mono- or bicyclic heterocyclyl, unsubstituted or substituted mono- or bicyclic cycloalkyl, unsubstituted or substituted mono- or bicyclic aryl-alkyl, unsubstituted or substituted mono- or bicyclic heterocyclyl-alkyl, unsubstituted or substituted mono- or bicyclic cycloalkyl-alkyl;

m is 0, 1 or 2;

each of $R^4$ and $R^5$ is selected, independently from the other, from hydrogen, unsubstituted or substituted alkyl, hydroxy or esterified or etherified hydroxy;

and T is methylene, methylene mono-substituted by alkyl, carbonyl or thiocarbonyl;

or a salt thereof.

2. The compound of the formula I according to claim 1, wherein $R^1$ is acyl;

$R^2$ is unsubstituted or substituted cycloalkyl or unsubstituted or substituted alkyl, $R^3$ is a moiety selected from the group consisting of moieties of the formulae

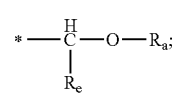
(a)

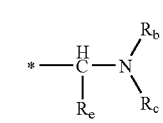
(b)

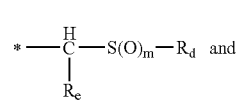
(c)

and

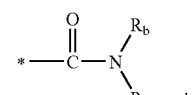
(f)

and where in any of the moieties of the formulae given above under (a), (b), (c) and (f) the asterisk (*) shows the bond binding the respective moiety $R^3$ to the rest of the molecule in formula I, $R_a$ is acyl or hydrogen;

$R_b$ is unsubstituted or substituted alkyl, unsubstituted or substituted mono- or bicyclic aryl, unsubstituted or substituted mono- or bicyclic aryl-$C_1$-$C_7$alkyl or acyl;

$R_c$ is hydroxy-$C_1$-$C_7$alkyl, $C_1$-$C_7$alkyloxy-$C_1$-$C_7$alkyl or preferably $C_3$-$C_8$-cycloalkyl, hydrogen or $C_1$-$C_7$-alkyl;

$R_d$ is unsubstituted or substituted mono- or bicyclic aryl-$C_1$-$C_7$alkyl;

$R_e$ is hydrogen or $C_1$-$C_7$-alkyl; and m is 2;

each of $R^4$ and $R^5$ is selected, independently from the other, from hydrogen, unsubstituted or substituted alkyl, hydroxy or esterified or etherified hydroxy;

and T is methylene, methylene mono-substituted by alkyl, carbonyl or thiocarbonyl;

or a pharmaceutically acceptable salt thereof.

3. The compound of the formula I according to claim 1, wherein $R^1$ is phenyl-, indolyl-, quinolyl- or 2,3-dihydro-benzo[1,4]dioxinyl-$C_1$-$C_7$-alkanoyl wherein the phenyl, indolyl, quinolyl or 2,3-dihydro-benzo[1,4]dioxinyl is substituted by halo, $C_1$-$C_7$-alkyloxy-$C_1$-$C_7$-alkyloxy, $C_1$-$C_7$-alkylene-O—$C_1$-$C_7$-alkyl or $C_1$-$C_7$-alkyloxy-$C_1$-$C_7$-alkyloxy-$C_1$-$C_7$-alkyl and may further be substituted by one or more $C_1$-$C_7$-alkyl and/or $C_1$-$C_7$-alkyloxy moieties;

$R^2$ is $C_3$-$C_8$-cycloalkyl or $C_1$-$C_7$-alkyl;

$R^3$ is a moiety selected from the group of moieties of the formulae

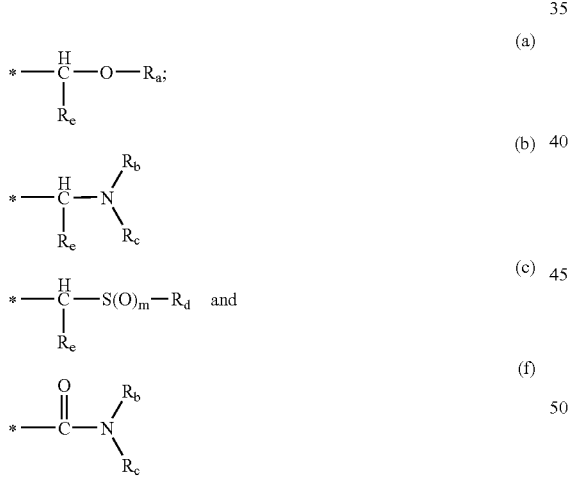

where in any of the moieties of the formulae given above under (a), (b), (c) and (f) the asterisk (*) shows the bond binding the respective moiety $R^3$ to the rest of the molecule in formula I, wherein $R_a$ is hydrogen or N-mono- or N,N-di-($C_1$-$C_7$-alkyl, (unsubstituted or halo-substituted) phenyl or naphthyl, phenyl-$C_1$-$C_7$alkyl, naphthyl-$C_1$-$C_7$-alkyl $C_3$-$C_8$-cycloalkyl-$C_1$-$C_7$alkyl, heterocyclyl-$C_1$-$C_7$-alkyl, heterocyclyl and/or $C_3$-$C_8$-cycloalkyl)-aminocarbonyl;

each of $R_b$ and $R_c$ is, independently of the other, is selected from hydrogen, $C_1$-$C_7$-alkyl, $C_3$-$C_8$-cycloalkyl-$C_1$-$C_7$-alkyl, $C_3$-$C_8$-cycloalkyl, unsubstituted or substituted aryl, naphthyl-$C_1$-$C_7$-alkyl, or acyl, unsubstituted or mono-, di- or tri-(halo, $C_1$-$C_7$-alkoxy, $C_1$-$C_7$-alkyloxy-$C_1$-$C_7$-alkyoxy, $C_1$-$C_7$-alkyloxy-$C_1$-$C_7$-alkyl and/or $C_1$-$C_7$-alkyl)-substituted phenyl- or naphthyl-$C_1$-$C_7$-alkanoyl, (tetrahydrofuranyl or tetrahydropyranyl)-carbonyl or (tetrahydrofuranyl or tetrahydropyranyl)-$C_1$-$C_7$-alkyl-carbonyl, $C_1$-$C_7$-alkylsulfonyl or (unsubstituted or [$C_1$-$C_7$-alkyl-, halo-lower alkyl-, halo, $C_1$-$C_7$-alkyloxy-, cyano-, $C_1$-$C_7$-alkanoyl- and/or $C_1$-$C_7$-alkylsulfonyl-]substituted) (phenyl- or naphthyl)-$C_1$-$C_7$-alkylsulfonyl, in particular acyl is selected from (a) unsubstituted or substituted mono- or bicyclic arylcarbonyl, wherein the aryl moiety is selected from phenyl, indanyl, or 1,2,3,4-tetrahydronaphthyl which is unsubstituted, mono- or di-substituted by heterocyclyl, heterocyclyl-$CH_2$, —O—$C_1$-$C_7$-alkyl, —O—$C_1$-$C_7$-alkylene-O-alkyl and/or halo, whereby the heterocyclyl moiety in each case is monocyclic 5- or 6-membered heterocyclyl, containing an N and/or O atom;

(b) unsubstituted or substituted mono- or bicyclic heterocyclylcarbonyl, wherein the heterocyclyl moiety is selected from 5 to 11 membered ring systems which may be saturated, partially saturated or aromatic, and having 1 or 2 heteroatoms selected from O and/or N, including pyrazinyl, isoxazolyl, pyrrolidin-2-onyl, tetrahydrofuranyl, tetrahydropyranyl, indolyl, 2,3-dihydro-benzo[1,4]dioxinyl, chromanyl, 2H-chromenyl, 3,4-dihydro-1H-quinolin-2-onyl, benzo[d]isoxazolyl, 4,5,6,7-tetrahydro-benzo[d]isoxazolyl, 3a,4,5,6,7,7a-hexahydro-benzo[a]isoxazolyl, 1,4,5,6,-tetrahydrocyclopentapyrazolyl, or 3,4-dihydro-2H-benzo[b][1,4] dioxepinyl, whereby the heterocyclyl moiety is unsubstituted or is mono-substituted with phenyl, —$C_1$-$C_7$-alkyl or $C_3$-$C_8$-cycloalkyl;

(c) unsubstituted or substituted mono or bicyclic cycloalkylcarbonyl wherein the cycloalkyl moiety is selected from $C_3$, $C_4$, $C_5$, $C_6$ and $C_7$-cycloalkyl which may be unsubstituted or mono-substituted with O—$C_1$-$C_4$-alkyl or hydroxy;

(d) unsubstituted or substituted alkylcarbonyl wherein the alkyl moiety is selected from branched or straight chain $C_1$-$C_7$-alkyl, whereby the alkyl moiety is mono-substituted with —O—$C_1$-$C_7$-alkyl, hydroxyl, $C_1$-$C_7$-alkanoylamino, unsubstituted or di-substituted phenyloxy, aminocarbonyl, N -mono- or N,N-di-substituted aminocarbonyl and $C_1$-$C_7$-alkyloxycarbonyl;

(e) unsubstituted or substituted mono or bicyclic aryl-$C_1$-$C_7$-alkylcarbonyl, wherein the alkyl moiety may be mono-substituted with unsubstituted phenyl, $C_1$-$C_7$-alkanoylamino, O—$C_1$-$C_4$-alkyl or hydroxyl, and wherein the aryl moiety is selected from phenyl or naphthyl, which may be unsubstituted or substituted by —O—$C_1$-$C_7$-alkyl, halo-$C_1$-$C_7$-alkyl, substituted phenyl, $C_1$-$C_7$-alkanoylamino and/or halo;

(f) unsubstituted or substituted mono- or bicyclic heterocyclyl-$C_1$-$C_7$-alkylcarbonyl, wherein the Heterocyclyl moiety is selected from 5 to 11 membered ring systems which may be saturated, partially saturated or aromatic, and having 1 or 2 heteroatoms selected from O and/or N, whereby the heterocyclyl moiety is unsubstituted or is mono-substituted with unsubstituted phenyl, —$C_1$-$C_7$-alkyl or $C_1$-$C_7$-alkanoyl;

(g) unsubstituted or substituted mono or bicyclic cycloalkyl-$C_1$-$C_7$-alkylcarbonyl, whereby the alkyl moiety may be mono-substituted, including on the carbon where the cycloalkyl moiety is attached, with —$C_1$-

$C_4$-alkyl or hydroxyl, and wherein the cycloalkyl moiety is selected from $C_3$, $C_5$ and $C_6$-cycloalkyl, which may be unsubstituted or mono-substituted with amino, O—$C_1$-$C_4$-alkyl or hydroxy;

(h) unsubstituted or substituted alkyloxycarbonyl, wherein the alkyl moiety is from branched or straight chain $C_1$-$C_7$-alkyl and which may be mono-substituted with by —O—$C_1$-$C_7$-alkyl, $C_1$-$C_7$-alkanoylamino and N-mono- or N,N-di-substituted aminocarbonyl;

(i) unsubstituted or substituted mono- or bicyclic aryloxycarbonyl, wherein the aryl moiety is selected from phenyl or naphthyl, which may be unsubstituted, mono-substituted with heterocyclyl or —O—$C_1$-$C_7$-alkyl, whereby the heterocyclyl moiety is monocyclic 5- or 6-membered heterocyclyl, containing an N and/or O atom;

(j) unsubstituted or substituted mono- or bicyclic heterocyclyloxycarbonyl, wherein the heterocyclyl moiety is selected from 5 to 7 membered ring systems which may be saturated, partially saturated or aromatic, and having 1 or 2 heteroatoms selected from O and/or N, in particular tetrahydrofuranyl or tetrahydropyranyl, wherein the heterocyclyl moiety is unsubstituted;

(k) unsubstituted or substituted mono- or bicyclic cycloalkyloxycarbonyl wherein the cycloalkyl moiety is selected from $C_6$-cycloalkyl which is unsubstituted;

(l) unsubstituted or substituted mono- or bicyclic aryl-$C_1$-$C_7$-alkyloxycarbonyl, wherein the aryl moiety is selected from phenyl which is unsubstituted;

(m) unsubstituted or substituted mono- or bicyclic heterocyclyl-$C_1$-$C_7$-alkyloxycarbonyl, wherein the cycloalkyl moiety is selected from 5 to 7 membered ring systems which may be saturated, partially saturated or aromatic, and having 1 or 2 heteroatoms selected from O and/or N, which is unsubstituted or is mono-substituted with —$C_1$-$C_7$-alkyl or $C_1$-$C_7$-alkanoyl;

(n) unsubstituted or substituted mono- or bicyclic cycloalkyl-$C_1$-$C_7$-oxycarbonyl, such as cycloalkyl-$CH_2$—, wherein the cycloalkyl moiety is selected from $C_3$ and $C_5$-cycloalkyl, and may be unsubstituted or substituted with $C_1$-$C_7$-alkanoylamino, (o) N-mono- or N,N-di-(unsubstituted or substituted mono- or bicyclic aryl, unsubstituted or substituted mono- or bicyclic cycloalkyl, unsubstituted or substituted mono- or bicyclic aryl-$C_1$-$C_7$-alkyl, unsubstituted or substituted mono- or bicyclic heterocyclyl-$C_1$-$C_7$-alkyl, unsubstituted or substituted mono- or bicyclic cycloalkyl-$C_1$-$C_7$-alkyl and/or unsubstituted or substituted alkyl) -aminocarbonyl, whereby the alkyl moiety of the unsubstituted or substituted alkyl aminocarbonyl is branched or straight chain $C_1$-$C_7$-alkyl which is unsubstituted;

the aryl moiety of the unsubstituted or substituted aryl aminocarbonyl is phenyl or naphthyl, which is unsubstituted, the cycloalkyl moiety of the unsubstituted or substituted cycloalkyl aminocarbonyl is $C_3$ or $C_6$-cycloalkyl which is unsubstituted;

the aryl alkyl moiety of the unsubstituted or substituted aryl alkyl aminocarbonyl is aryl-$CH_2$—, aryl-$CH_2CH_2$—, or aryl-$CH(CH_2CH_3)$—, whereby the alkyl moiety may be mono-substituted with unsubstituted phenyl, and whereby the aryl moiety is phenyl, which is unsubstituted;

the heterocyclyl alkyl moiety of the unsubstituted or substituted heterocyclyl alkyl aminocarbonyl is heterocyclyl-$CH_2$— whereby the heterocyclyl moiety is selected from 5 to 7 membered ring systems which may be aromatic, and having 1 or 2 heteroatoms selected from O and/or N; which is unsubstituted;

the cycloalkyl alkyl moiety of the unsubstituted or substituted cycloalkyl alkyl aminocarbonyl is cycloalkyl-$CH_2$—, whereby the cycloalkyl moiety is selected from $C_6$-cycloalkyl which is unsubstituted;

with the proviso that if $R_c$ is hydrogen, $C_1$-$C_7$-alkyl, phenyl, naphthyl or naphthyl-$C_1$-$C_7$-alkyl, then $R_b$ can also be phenyl-$C_1$-$C_7$-alkyl;

$R_d$ is unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, cyano-, $C_1$-$C_7$-alkanoyl- and/or $C_1$-$C_7$-alkylsulfonyl-]substituted (phenyl- or naphthyl)-$C_1$-$C_7$-alkyl;

$R_e$ is hydrogen; and m is 2;

each of $R^4$ and $R^5$ is hydrogen; and

T is carbonyl or methylene;

or a salt thereof.

4. The compound of the formula I according to claim 1, selected from the group of compounds consisting of:

N-((3S*,4S*)-4-{[(3-Acetylamino-3-methyl-butyryl)-cyclopropyl-amino]-methyl}-pyrrolidin-3-ylmethyl)-N-isopropyl-4-methoxy-3-(3-methoxy-propoxy)-benzamide N-[(3S*,4S*)-4-({Cyclopropyl-[2-(2-oxo-pyrrolidin-1-yl)-acetyl]-amino}-methyl)-pyrrolidin-3-ylmethyl]-N-isopropyl-4-methoxy-3-(3-methoxy-propoxy)-benzamide N-[(3S*,4S*)-4-({[2-(1-Acetylamino-cyclopentyl)-acetyl]-cyclopropyl-amino}-methyl)-pyrrolidin-3-ylmethyl]-N-isopropyl-4-methoxy-3-(3-methoxy-propoxy)-benzamide N-((3S*,4S*)-4-{[Cyclopropyl-(3,3-dimethyl-butyryl)-amino]-methyl}-pyrrolidin-3-ylmethyl)-N-isopropyl-4-methoxy-3-(3-methoxy-propoxy)-benzamide N-[(3S*,4S*)-4-({[2-(1-Acetylamino-cyclohexyl)-acetyl]-cyclopropyl-amino}-methyl)-pyrrolidin-3-ylmethyl]-N-isopropyl-4-methoxy-3-(3-methoxy-propoxy)-benzamide N-((3S*,4S*)-4-{[Cyclopropyl-(3-methyl-3-pyrrol-1-yl-butyryl)-amino]-methyl}-pyrrolidin-3-ylmethyl)-N-isopropyl-4-methoxy-3-(3-methoxy-propoxy)-benzamide N-[(3S*,4S*)-4-({Cyclopropyl-[2-(3-oxo-3,4-dihydro-2H-benzo[1,4]oxazin-6-yl)-acetyl]-amino}-methyl)-pyrrolidin-3-ylmethyl]-N-isopropyl-4-methoxy-3-(3-methoxy-propoxy)-benzamide N-[(3S*,4S*)-4-({Cyclopropyl-[2-(1-isobutyrylamino-cyclopentyl)-acetyl]-amino}-methyl) -pyrrolidin-3-ylmethyl]-N-isopropyl-4-methoxy-3-(3-methoxy-propoxy)-benzamide N-((3S*,4S*)-4-{[Cyclopropyl-(4-methyl-pentanoyl)-amino]-methyl}-pyrrolidin-3-ylmethyl)-N-isopropyl-4-methoxy-3-(3-methoxy-propoxy)-benzamide N-[(3S*,4S*)-4-({Cyclopropyl-[2-(2-methyl-benzooxazol-5-yl)-acetyl]-amino}-methyl)-pyrrolidin-3-ylmethyl]-N-isopropyl-4-methoxy-3-(3-methoxy-propoxy)-benzamide N-((3S*,4S*)-4-{[(3-Cyclohexyl-propionyl)-cyclopropyl-amino]-methyl}-pyrrolidin-3-ylmethyl)-N-isopropyl-4-methoxy-3-(3-methoxy-propoxy)-benzamide N-((3S,4S)-4-{[Cyclopropyl-(3-cyclopropyl-propionyl)-amino]-methyl}-pyrrolidin-3-ylmethyl)-N-isopropyl-4-methoxy-3-(3-methoxy-propoxy)-benzamide N-((3S,4S)-4-{[(3-Cyclopentyl-propionyl)-cyclopropyl-amino]-methyl}-pyrrolidin-3-ylmethyl)-N-isopropyl-4-methoxy-3-(3-methoxy-propoxy)-benzamide N-((3S,4S)-4-{[Cyclopropyl-(3,3-diphenyl-propionyl)-amino]-methyl}-pyrrolidin-3-ylmethyl)-N-isopropyl-4-methoxy-3-(3-methoxy-propoxy)-benzamide N-[(3S,4S)-4-({Cyclopropyl-[2-(2,6-dimethyl-phenoxy)-acetyl]-amino}-methyl)-pyrrolidin-3-ylmethyl]-N-isopropyl-4-methoxy-3-(3-methoxy-propoxy)-benzamide N-((3S,4S)-4-{[Cyclopropyl-((S)-3-phenyl-butyryl)-amino]-methyl}-pyrrolidin-3-ylmethyl)-N-isopropyl-4-methoxy-3-(3-methoxy-propoxy)-benzamide N-[(3S,4S)-4-(([2-(1-Acetyl-piperidin-4-yl)-acetyl]-cyclopropyl-amino}-methyl]-pyrrolidin-3-ylmethyl]-N-isopropyl-4-methoxy-3-(3-methoxy-propoxy)-benzamide N-((3S,4S)-4-{[((S)-3-Acetylamino-3-phenyl-propionyl)-cyclopropyl-amino]-methyl}-pyrrolidin-3-ylmethyl)-N-isopropyl-4-methoxy-3-(3-methoxy-propoxy)-benzamide N-((3S,4S)-4-{[((R)-3-Acetylamino-3-phenyl-propionyl) cyclopropyl-amino]-methyl}-pyrrolidin-3-ylmethyl)-N-isopropyl-4-methoxy-3-(3-methoxy-propoxy)-benzamide N-((3S,4S)-4-{[Cyclopropyl-((R)-3-hydroxy-3-phenyl-propionyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((S)-3-hydroxy-3-phenyl-propionyl)-amino]-methyl}-pyrrolidin-3-ylmethyl)-N-isopropyl-4-methoxy-3-(3-methoxy-propoxy)-benzamide N-((3S,4S)-4-{[Cyclopropyl-(3-furan-2-yl-propionyl)-amino]-methyl}-pyrrolidin-3-ylmethyl)-N-isopropyl-4-methoxy-3-(3-methoxy-propoxy)-benzamide N-((3S,4S)-4-{[Cyclopropyl-(2-furan-2-yl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((S)-2-methoxy-2-cyclohexyl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((S)-2-hydroxy-4-methyl-pentanoyl)-amino]-methyl}-pyrrolidin-3-ylmethyl)-N-isopropyl-4-methoxy-3-(3-methoxy-propoxy)-benzamide N-{(3S*,4S*)-4-[(Cyclohexanecarbonyl-cyclopropyl-amino)-methyl]-pyrrolidin-3-ylmethyl}-N-isopropyl-4-methoxy-3-(3-methoxy-propoxy)-benzamide Cycloheptanecarboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide N-((3S,4S)-4-{[(2-Cyclopentyl-acetyl)-cyclopropyl-amino]-methyl}-pyrrolidin-3-ylmethyl)-N-isopropyl-4-methoxy-3-(3-methoxy-propoxy)-benzamide N-((3S*,4S*)-4-{[(2-Cyclohexyl-acetyl)-cyclopropyl-amino]-methyl}-pyrrolidin-3-ylmethyl)-N-isopropyl-4-methoxy-3-(3-methoxy-propoxy)-benzamide N-{(3S*,4S*)-4-[(Benzoyl-cyclopropyl-amino)-methyl]-pyrrolidin-3-ylmethyl}-N-isopropyl-4-methoxy-3-(3-methoxy-propoxy)-benzamide N-[(3S*,4S*)-4-({Cyclopropyl-[2-4-fluoro-phenyl)-acetyl]-amino}-methyl)-pyrrolidin-3-ylmethyl]-N-isopropyl-4-methoxy-3-(3-methoxy-propoxy)-benzamide N-[(3S,4S)-4-({[2-(4-Chloro-phenyl)-acetyl]-cyclopropyl-amino}-methyl)-pyrrolidin-3-ylmethyl]-N-isopropyl-4-methoxy-3-(3-methoxy-propoxy)-benzamide N-[(3S*,4S*)-4-({[2-(3-Chloro-phenyl)-acetyl]-cyclopropyl-amino}-methyl)-pyrrolidin-3-ylmethyl]-N-isopropyl-4-methoxy-3-(3-methoxy-propoxy)-benzamide N-[(3S*,4S*)-4-({Cyclopropyl-[2-(2-methoxy-phenyl)-acetyl]-amino}-methyl)-pyrrolidin-3-ylmethyl]-N-isopropyl-4-methoxy-3-(3-methoxy-propoxy)-benzamide N-[(3S*,4S*)-4-({Cyclopropyl-[2-(3,5-difluoro-phenyl)-acetyl]-amino}-methyl)-pyrrolidin-3ylmethyl]-N-isopropyl-4-methoxy-3-(3-methoxy-propoxy)-benzamide N-[(3S*,4S*)-4-({Cyclopropyl-[2-2,3,5-trifluoro-phenyl)-acetyl]-amino}-methyl)-pyrrolidin-3-ylmethyl]-N-isopropyl-4-methoxy-3-(3-methoxy-propoxy)-benzamide N-[(3S*,4S*)-4-({Cyclopropyl-[2-(3-trifluoromethyl-phenyl)-acetyl]-amino}-methyl)-pyrrolidin-3-ylmethyl]-N-isopropyl-4-methoxy-3-(3-methoxy-propoxy)-benzamide N-[(3S*,4S*)-4-{[Cyclopropyl-(3-pyrrolidin-1yl-benzoyl)-amino]-methyl}-pyrrolidin-3-ylmethyl]-N-isopropyl-4-methoxy-3-(3-methoxy-propoxy)-benzamide N-[(3S*,4S*)-4-({Cyclopropyl-[2-(3'-fluoro-biphenyl-3-yl)-acetyl]-amino}-methyl)-pyrrolidin-3-ylmethyl]-N-isopropyl-4-methoxy-3-(3-methoxy-propoxy)-benzamide N-((3S*,4S*)-4-{[Cyclopropyl-(3-chloro-6-methoxy-1-yl-benzoyl)-amino]-methyl}-pyrrolidin-3-ylmethyl)-N-isopropyl-4-methoxy-3-(3-methoxy-propoxy)-benzamide N-((3S,4S)-4-{[Cyclopropyl-(4-morpholin-4-ylmethyl-benzoyl)-amino]-methyl}-pyrrolidin-3-ylmethyl)-N-isopropyl-4-methoxy-3-(3-methoxy-propoxy)-benzamide 1H-Indole-2-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide 1H-Indole-3-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide 2,3-Dihydro-benzo[1,4]dioxine-6-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide N-((3S*,4S*)-4-{[Cyclopropyl-(2-naphthalen-2-yl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-(2-phenoxy-acetyl)-amino]-methyl}-pyrrolidin-3-ylmethyl)-N-isopropyl-4-methoxy-3-(3-methoxy-propoxy)-benzamide N-((3S*,4S*)-4-{[Cyclopropyl-((S)-2-phenyl-propionyl)-amino]-methyl}-pyrrolidin-3-ylmethyl)-N-isopropyl-4-methoxy-3-(3-methoxy-propoxy)-benzamide N-((3S*,4S*)-4-([Cyclopropyl-((R)-2-phenyl-propionyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((S)-2-hydroxy-2-phenyl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((R)-2-hydroxy-2-phenyl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((R)-2-methoxy-2-phenyl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((S)-2-methoxy-2-phenyl-acetyl)-amino]-methyl}-pyrrolidin-3-ylmethyl)-N-isopropyl-4-methoxy-3-(3-methoxy-propoxy)-benzamide Tetrahydro-furan-3-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide Tetrahydro-furan-2-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide (S)-Tetrahydro-pyran-3-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide (R)-Tetrahydro-pyran-3-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide Tetrahydro-pyran-4-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide N-((3S,4S)-4-{[Cyclopropyl-(4-hydroxy-cyclohexanecarbonyl)-amino]-methyl}-pyrrolidin-3-ylmethyl)-N-isopropyl-4-methoxy-3-(3-methoxy-propoxy)-benzamide N-((3S,4S)-4-{[Cyclopropyl-(cis-4-methoxy-cyclohexanecarbonyl)-amino]-methyl}-pyrrolidin-3-ylmethyl)-N-isopropyl-4-methoxy-3-(3-methoxy-propoxy)-benzamide N-((3S,4S)-4-[Cyclopropyl-(trans-4-methoxy-cyclohexanecarbonyl)amino]-methyl}-pyrrolidin-3-ylmethyl)-N-isopropyl-4-methoxy-3-(3-methoxy-propoxy)-benzamide N-((3S,4S)-4-{[Cyclopropyl-((S)-2-tetrahydro-furan-2-yl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((R)-2-tetrahydro-furan-2-yl-acetyl)-amino]-methyl}-pyrrolidin-3-ylmethyl)-N-isopropyl-4-methoxy-3-(3-methoxy-propoxy)-benzamide N-((3S,4S)-4-{[Cyclopropyl-((S)-2-tetrahydro-pyran-2-yl-acetyl)-amino]-methyl}-pyrrolidin-3-ylmethyl)-N-isopropyl-4-methoxy-3-{3-methoxy-propoxy)-benzamide N-((3S,4S)-4-{[Cyclopropyl-((R)-2-tetrahydro-pyran-2-yl-acetyl)-amino]-methyl}-pyrrolidin-3-ylmethyl)-N-isopropyl-4-methoxy-3-(3-methoxy-propoxy)-benzamide (R)-1,2,3,4-Tetrahydro-naphthalene-2-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide (S)-1,2,3,4-Tetrahydro-naphthalene-2-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide N-((3S*,4S*)-4-{[Cyclopropyl-(2-tetrahydro-pyran-4-yl-acetyl)-amino]-methyl}-pyrrolidin-3-ylmethyl)-N-isopropyl-4-methoxy-3-(3-methoxy-propoxy)-benzamide Chroman-2-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide 2H-Chromene-3-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide (R)-2,3-Dihydro-benzo[1,4]dioxine-2-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide (S)-2,3-Dihydro-benzo[1,4]dioxine-2-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide 2-Oxo-1,2,3,4-tetrahydro-quinoline-4-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide 4,5,6,7-Tetrahydro-benzo[d]isoxazole-3-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide 3a,4,5,6,7,7a-Hexahydro-benzo[d]isoxazole-3-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide N-((3S,4S)-4-{[(2-Benzo[d]isoxazol-3-yl-acetyl)-cyclopropyl-amino]-methyl}-pyrrolidin-3-ylmethyl)-N-isopropyl-4-methoxy-3-(3-methoxy-propoxy)-benzamide 1,4,5,6-Tetrahydro-cyclopentapyrazole-3-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide Isoxazole-3-carboxylic acid cyclopropyl-[(3S*,4S*)-4-((isopropyl-[4-methoxy-3-(3-methoxy-propoxy)-benzoyl]-amino}-methyl)-pyrrolidin-3-ylmethyl]-amide 5-Methyl-isoxazole-3-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide 5-Cyclopropyl-isoxazole-3-carboxylic acid cyclopropyl-[(3S*,4S*)-4-({isopropyl-[4-methoxy-3-(3-methoxy-propoxy)-benzoyl]-amino}-methyl)-pyrrolidin-3-ylmethyl]-amide 5-Phenyl-isoxazole-3-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide 5-Methyl-pyrazine-2-carboxylic acid cyclopropyl-[(3S*,4S*)-4-({isopropyl-[4methoxy-3-(3-methoxy-propoxy)-benzoyl]-amino}-methyl)-pyrrolidin-3-ylmethyl]-amide Indan-2-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide 5-Oxo-1-phenyl-pyrrolidine-3-carboxylic acid cyclopropyl-[(3S*,4S*)-4-((isopropyl-[4-methoxy-3-(3-methoxy-propoxy)-benzoyl]-amino}-methyl)-pyrrolidin-3-ylmethyl]-amide N-Cyclopropyl-N-[(3S*,4S*)-4-({isopropyl-[4-methoxy-3-(3-methoxy-propoxy)-benzoyl]-amino}-methyl)-pyrrolidin-3-ylmethyl]-succinamide N-Cyclopropyl-N-[(3S*,4S*)-4-({isopropyl-[4-methoxy-3-(3-methoxy-propoxy)-benzoyl]-amino}-methyl)-pyrrolidin-3-ylmethyl]-N'-methyl-succinamide N-Cyclopropyl-N-[(3S*,4S*)-4-({isopropyl-[4-methoxy-3-(3-methoxy-propoxy)-benzoyl]-amino}-methyl)-pyrrolidin-3-ylmethyl]-succinamic acid methyl ester N-((3S,4S)-4-{[Cyclopropyl-(2-piperidin-4-yl-acetyl)-amino]-methyl}-pyrrolidin-3-ylmethyl)-N-isopropyl-4-methoxy-3-(3-methoxy-propoxy)-benzamide N-[(3S,4S)-4-({[2-(4-Amino-cyclohexyl)-acetyl]-cyclopropyl-amino}-methyl)-pyrrolidin-3-ylmethyl]-N-isopropyl-4-methoxy-3-(3-methoxy-propoxy)-benzamide
N-[(3S,4S)-4-({[2-(4-Amino-cyclohexyl)-acetyl]-cyclopropyl-amino}-methyl)-pyrrolidin-3-ylmethyl]-N-isopropyl-4-methoxy-3-(3-methoxy-propoxy)-benzamide
N-(3S,4S)-4-{[Cyclopropyl-(2-methyl-2-phenyl-propionyl)-amino]-methyl}-pyrrolidin-3-ylmethyl)-N-isopropyl-4-methoxy-3-(3-methoxy-propoxy)-benzamide
N-((3S,4S)-4-{[((S)-2-Hydroxy-2-phenyl-acetyl)-methyl-amino]-methyl}-pyrrolidin-3-ylmethyl)-N-isopropyl-4-methoxy-3-(3-methoxy-propoxy)-benzamide
N-((3S,4S)-4-{[((S)-2-Methoxy-2-phenyl-acetyl)-methyl-amino]-methyl}-pyrrolidin-3-ylmethyl)-N-isopropyl-4-methoxy-3-(3-methoxy-propoxy)-benzamide
N-((3S,4S)-4-{[((S)-2-Hydroxy-4-methyl-pentanoyl)-methyl-amino]-methyl}-pyrrolidin-3-ylmethyl)-N-isopropyl-4-methoxy-3-(3-methoxy-propoxy)-benzamide
N-((3S,4S)-4-{[((S)-2-Methoxy-2-cyclohexyl-acetyl)-methyl-amino]-methyl}-pyrrolidin-3-ylmethyl)-N-isopropyl-4-methoxy-3-(3-methoxy-propoxy)-benzamide
N-((3S,4S)-4-{[((S)-2-Hydroxy-3-methyl-butyryl)-methyl-amino]-methyl}-pyrrolidin-3-ylmethyl)-N-isopropyl-4-methoxy-3-(3-methoxy-propoxy)-benzamide
N-((3S,4S)-4-{[((S)-2-Hydroxy-3-phenyl-propionyl)-methyl-amino]-methyl}-pyrrolidin-3-ylmethyl)-N-isopropyl-4-methoxy-3-(3-methoxy-propoxy)-benzamide
N-((3S,4S)-4-([((S)-2-Cyclohexyl-2-hydroxy-acetyl)-methyl-amino]-methyl}-pyrrolidin-3-ylmethyl)-N-isopropyl-4-methoxy-3-(3-methoxy-propoxy)-benzamide
N-((3S ,4S)-4-{[((S)-3-Hydroxy-3-phenyl-propionyl)-methyl-amino]-methyl}-pyrrolidin-3-ylmethyl)-N-isopropyl-4-methoxy-3-(3-methoxy-propoxy)-benzamide
N-((3S,4S)-4-{[((R)-Hydroxy-3-phenyl-propionyl)-methyl-amino]-methyl}-pyrrolidin-3-ylmethyl)-N-isopropyl-4-methoxy-3-(3-methoxy-propoxy)-benzamide
N-((3S,4S)-4-{[(2-Furan-2-yl-acetyl)-methyl-amino]-methyl}-pyrrolidin-3-ylmethyl)-N-isopropyl-4-methoxy-3-(3-methoxy-propoxy)-benzamide
N-((3S,4S)-4-{[((S)-2-Methoxy-3-methyl-butyryl)-methyl-amino]-methyl}-pyrrolidin-3-ylmethyl)-N-isopropyl-4-methoxy-3-(3-methoxy-propoxy)-benzamide
N-((3S,4S)-4-{[((S)-2-Methoxy-4-methyl-pentanoyl)-methyl-amino]-methyl}-pyrrolidin-3-ylmethyl)-N-isopropyl-4-methoxy-3-(3-methoxy-propoxy)-benzamide
N-((3S*,4S*)-4-[(Benzoyl-methyl-amino)-methyl]-pyrrolidin-3-ylmethyl}-N-isopropyl-4-methoxy-3-(3-methoxy-propoxy)-benzamide
N-((3S,4)-4-{[(2-Cyclohexyl-acetyl)-methyl-amino]-methyl}-pyrrolidin-3-ylmethyl)-N-isopropyl-4-methoxy-3-(3methoxy-propoxy)-benzamide
N-Isopropyl-4-methoxy-N-[(3S*,4S*)-4-({[2-(3-methoxy-phenyl)-acetyl]-methyl-amino}-methyl)-pyrrolidin-3-ylmethyl]-3-(3-methoxy-propoxy)-benzamide
Indan-2-carboxylic acid [(3S,4S)-4-({isopropyl-[4-methoxy-3-(3-methoxy-propoxy)-benzoyl]-amino}-methyl)-pyrrolidin-3-ylmethyl]-methyl-amide
(R)-1,2,3,4-Tetrahydro-naphthalene-2-carboxylic acid [(3S,4S)-4-({isopropyl-[4-methoxy-3-(3-methoxy-propoxy)-benzoyl]-amino}-methyl)-pyrrolidin-3-ylmethyl]-methyl-amide
(S)-1,2,3,4-Tetrahydro-naphthalene-2-carboxylic acid [(3S,4S)-4-({isopropyl-[4-methoxy-3-(3-methoxy-propoxy)-benzoyl]-amino}-methyl)-pyrrolidin-3-ylmethyl]-methyl-amide
Tetrahydro-pyran-4-carboxylic acid [(3S*,4S*)-4-({isopropyl-[4-methoxy-3-(3-methoxy-propoxy)-benzoyl]-amino}-methyl)-pyrrolidin-3-ylmethyl]-methyl-amide
N-[(3S,4S)-4-({[2-(1-Hydroxy-cyclohexyl)-acetyl]-methyl-amino}-methyl)-pyrrolidin-3-ylmethyl]-N-isopropyl-4-methoxy-3-(3-methoxy-propoxy)-benzamide
N-Isopropyl-4-methoxy-N-[(3S,4S)-4-({[2-(4-methoxy-cyclohexyl)-acetyl]-methyl-amino}-methyl)-pyrrolidin-3-ylmethyl]-3-(3-methoxy-propoxy)-benzamide
N-Isopropyl-4-methoxy-N-[(3S,4S)-4-({[2-(4-methoxy-cyclohexyl)-acetyl]-methyl-amino}-methyl)-pyrrolidin-3-ylmethyl]-3-(3-methoxy-propoxy)-benzamide
3,4-Dihydro-2H-benzo[b][1,4]dioxepine-2-carboxylic acid [(3S,4S)-4-({isopropyl-[4-methoxy-3-(3-methoxy-propoxy)-benzoyl]-amino}-methyl)-pyrrolidin-3-ylmethyl]-methyl-amide
N-Isopropyl-4-methoxy-N-((3S,4S)-4-{[(cis-4-methoxy-cyclohexanecarbonyl)-methyl-amino]-methyl}-pyrrolidin-3-ylmethyl)-3-(3-methoxy-propoxy)-benzamide
N-Isopropyl-4-methoxy-N-((3S,4S)-4-{[(trans-4-methoxy-cyclohexanecarbonyl)-methyl-amino]-methyl}-pyrrolidin-3-ylmethyl)-3-(3-methoxy-propoxy)-benzamide
N-Isopropyl-4-methoxy-3-(3-methoxy-propoxy)-N-[(3S,4S)-4-(phenylacetylamino-methyl)-pyrrolidin-3-ylmethyl]-benzamide
Indan-2-carboxylic acid [(3S,4S)-4-({isopropyl-[4-methoxy-3-(3-methoxy-propoxy)-benzoyl]-amino}-methyl)-pyrrolidin-3-ylmethyl]-amide
N-{(3S,4S)-4-[((S)-2-Cyclohexyl-2-methoxy-acetylamino)-methyl]-pyrrolidin-3-ylmethyl}-N-isopropyl-4-methoxy-3-(3-methoxy-propoxy)-benzamide
N-Isopropyl-4-methoxy-N-{(3S,4S)-4-[((R)-2-methoxy-2-phenyl-acetylamino)-methyl]-pyrrolidin-3-ylmethyl}-3-(3-methoxy-propoxy)-benzamide
N-Isopropyl-4-methoxy-N-{(3S,4S)-4-[((S)-2-methoxy-2-phenyl-acetylamino)-methyl]-pyrrolidin-3-ylmethyl}-3-(3-methoxy-propoxy)-benzamide
N-{(3S,4S)-4-[((R)-2-Cyclohexyl-2-methoxy-acetylamino)-methyl]-pyrrolidin-3-yl methyl}-N-isopropyl-4-methoxy-3-(3-methoxy-propoxy)-benzamide
N-{(3S,4S)-4-[(Ethyl-phenylacetyl-amino)-methyl]-pyrrolidin-3-ylmethyl)-N-isopropyl-4-methoxy-3-(3-methoxy-propoxy)-benzamide
N-((3S,4S)-4-{[Ethyl-(2-tetrahydro-pyran-4-yl-acetyl)-amino]-methyl}-pyrrolidin-3-ylmethyl)-N-isopropyl-4-methoxy-3-(3-methoxy-propoxy)-benzamide
N-{(3S*,4S*)-4-[(Cyclobutyl-phenylacetyl-amino)-methyl]-pyrrolidin-3-ylmethyl)-N-isopropyl-4-methoxy-3-(3-methoxy-propoxy)-benzamide
N-((3S*,4S*)-4-[Cyclobutyl-(2-tetrahydro-pyran-4-yl-acetyl)-amino]-methyl}-pyrrolidin-3-ylmethyl)-N-isopropyl-4-methoxy-3-(3-methoxy-propoxy)-benzamide
N-Isopropyl-N-{(3S*,4S*)-4-[(isopropyl-phenylacetyl-amino)-methyl]-pyrrolidin-3-ylmethyl}-4-methoxy-3-(3-methoxy-propoxy)-benzamide
N-Isopropyl-N-((3S*,4S*)-4-{[isopropyl-(2-tetrahydro-pyran-4-yl-acetyl)-amino]-methyl}-pyrrolidin-3-ylmethyl)-4-methoxy-3-(3-methoxy-propoxy)-benzamide
N-{(3S*,4S*)-4-[(Cyclopropanecarbonyl-isobutyl-amino)-methyl]-pyrrolidin-3-ylmethyl}-N-isopropyl-4-methoxy-3-(3-methoxy-propoxy)-benzamide
N-((3S*,4S*)-4-[(Cyclobutanecarbonyl-isobutyl-amino)-methyl]-pyrrolidin-3-ylmethyl}-N-isopropyl-4-methoxy-3-(3-methoxy-propoxy)-benzamide N-((3S*,4S*)4-{[Isobutyl-(2-tetrahydro-pyran-4-yl-acetyl)-amino]-methyl}-pyrrolidin-3-ylmethyl)-N-isopropyl-4-methoxy-3-(3-methoxy-propoxy)-benzamide N-{(3S*,4S*)-4-[(Isobutyl-phenylacetyl-amino)-methyl]-pyrrolidin-3-ylmethyl}-N-isopropyl-4-methoxy-3-(3-methoxy-propoxy)-benzamide N-{(3S*,4S*)-4-[(Cyclopropylmethyl-phenylacetyl-amino)-methyl]-pyrrolidin-3-ylmethyl}-N-isopropyl-4-methoxy-3-(3-methoxy-propoxy)-benzamide N-((3S*,4S*)-4-{[Cyclopropylmethyl-(2-tetrahydro-pyran-4-yl-acetyl)-amino]-methyl}-pyrrolidin-3-ylmethyl)-N-isopropyl-4-methoxy-3-(3-methoxy-propoxy)-benzamide 1-(3-Methoxy-propyl)-3-methyl-1H-indole-6-carboxylic acid isopropyl-{(3S,4S)-4-[(methyl-phenylacetyl-amino)-methyl]-pyrrolidin-3-ylmethyl}-amide 1-(3-Methoxy-propyl)-3-methyl-1H-indole-6-carboxylic acid ((3S,4S)-4-{[(2-cyclohexyl-acetyl)-methyl-amino]-methyl}-pyrrolidin-3-ylmethyl)-isopropyl-amide N-{(3S,4S)-4-[(Cyclopropyl-phenylacetyl-amino)-methyl]-pyrrolidin-3-ylmethyl}-4-ethyl-N-isopropyl-3-(3-methoxy-propoxy)-benzamide N-((3S,4S)-4-{[(2-Cyclohexyl-acetyl)-methyl-amino]-methyl}-pyrrolidin-3-ylmethyl)-4-ethyl-N-isopropyl-3-(3-methoxy-propoxy)-benzamide 4-Ethyl-N-isopropyl-3-(3-methoxy-propoxy)-N-((3S,4S)-4-{[methyl-(2-tetrahydro-pyran-4-yl-acetyl)-amino]-methyl}-pyrrolidin-3-ylmethyl)-benzamide Tetrahydro-pyran-4-carboxylic acid [(3S,4S)-4-({[4-ethyl-3-(3-methoxy-propoxy)-benzoyl]-isopropyl-amino}-methyl)-pyrrolidin-3-ylmethyl]-methyl-amide N-((3S,4S)-4-{[Cyclopropyl-(2-tetrahydro-pyran-4-yl-acetyl)-amino]-methyl}-pyrrolidin-3-ylmethyl)-4-ethyl-N-isopropyl-3-(3-methoxy-propoxy)-benzamide Tetrahydro-pyran-4-carboxylic acid cyclopropyl-[(3S,4S)-4-({[4-ethyl-3-(3-methoxy-propoxy)-benzoyl]-isopropyl-amino}-methyl)-pyrrolidin-3-ylmethyl]-amide N-((3S,4S)-4-{[(3-Acetylamino-3-methyl-butyryl)-cyclopropyl-amino]-methyl}-pyrrolidin-3-ylmethyl)-4-ethyl-N-isopropyl-3-(3-methoxy-propoxy)-benzamide 4-Ethyl-N-((3S,4S)-4-{[((S)-2-hydroxy-2-phenyl-acetyl)-methyl-amino]-methyl}-pyrrolidin-3-ylmethyl)-N-isopropyl-3-(3-methoxy-propoxy)-benzamide N-[(3S,4S)-4-({[2-(1-Acetyl-piperidin-4-yl)-acetyl]-cyclopropyl-amino}-methyl)-pyrrolidin-3-ylmethyl]-4-ethyl-N-isopropyl-3-(3-methoxy-propoxy)-benzamide N-[(3S,4S)-4-({[2-(1-Acetyl-piperidin-4-yl)-acetyl]-methyl-amino}-methyl)-pyrrolidin-3-ylmethyl]-4-ethyl-N-isopropyl-3-(3-methoxy-propoxy)-benzamide 4-Ethyl-N-((3S,4S)-4-{[((S)-2-hydroxy-4-methyl-pentanoyl)-methyl-amino]-methyl}-pyrrolidin-3-ylmethyl)-N-isopropyl-3-(3-methoxy-propoxy)-benzamide 4-Ethyl-N-((3S,4S)-4-{[((S)-2-hydroxy-3-methyl-butyryl)-methyl-amino]-methyl}-pyrrolidin-3-ylmethyl)-N-isopropyl-3-(3-methoxy-propoxy)-benzamide Indan-2-carboxylic acid [(3S,4S)-4-({[4-ethyl-3-(3-methoxy-propoxy)-benzoyl]-isopropyl-amino}-methyl)-pyrrolidin-3-ylmethyl]-amide 4-Ethyl-N-isopropyl-3-(3-methoxy-propoxy)-N-{(3S,4S)-4-[(2-methyl-2-phenyl-propionylamino)-methyl]-pyrrolidin-3-ylmethyl}-benzamide 4-Ethyl-N-isopropyl-N-{(3S,4S)-4-[((R)-2-methoxy-2-phenyl-acetylamino)-methyl]-pyrrolidin-3-ylmethyl}-3-(3-methoxy-propoxy)-benzamide N-[(3S,4S)-4-({[2-(4-Amino-cyclohexyl)-acetyl]-methyl-amino}-methyl)-pyrrolidin-3-ylmethyl]-4-ethyl-N-isopropyl-3-(3-methoxy-propoxy)-benzamide N-[(3S,4S)-4-({[2-(4-Amino-cyclohexyl)-acetyl]-methyl-amino}-methyl)-pyrrolidin-3-ylmethyl]-4-ethyl-N-isopropyl-3-(3-methoxy-propoxy)-benzamide 5-Methyl-pyrazine-2-carboxylic acid [(3S,4S)-4-({[4-ethyl-3-(3-methoxy-propoxy)-benzoyl]-isopropyl-amino}-methyl)-pyrrolidin-3-ylmethyl]-methyl-amide (S)-2,3-Dihydro-benzo[1,4]dioxine-2-carboxylic acid [(3S,4S)-4-({[4-ethyl-3-(3-methoxy-propoxy)-benzoyl]-isopropyl-amino}-methyl)-pyrrolidin-3-ylmethyl]-methyl-amide (R)-2-Oxo-1,2,3,4-tetrahydro-quinoline-4-carboxylic acid [(3S,4S)-4-({[4-ethyl-3-(3-methoxy-propoxy)-benzoyl]-isopropyl-amino}-methyl)-pyrrolidin-3-ylmethyl]-methyl-amide (S)-2-Oxo-1,2,3,4-tetrahydro-quinoline-4-carboxylic acid [(3S,4S)-4-({[4-ethyl-3-(3-methoxy-propoxy)-benzoyl]-isopropyl-amino}-methyl)-pyrrolidin-3-ylmethyl]-methyl-amide N-Cyclopropyl-N-[(3S,4S)-4-({[4-ethyl-3-(3-methoxy-propoxy)-benzoyl]-isopropyl-amino}-methyl)-pyrrolidin-3-ylmethyl]-N'-methyl-succinamide 5-Methyl-pyrazine-2-carboxylic acid cyclopropyl-[(3S,4S)-4-({[4-ethyl-3-(3-methoxy-propoxy)-benzoyl]-isopropyl-amino}-methyl)-pyrrolidin-3-ylmethyl]-amide Isoxazole3-carboxylic acid cyclopropyl-[(3S,4S)-4-({[4-ethyl-3-(3-methoxy-propoxy)-benzoyl]-isopropyl-amino}-methyl)-pyrrolidin-3-ylmethyl]-amide N-[(3S,4S)-4-({[2-(4-Amino-cyclohexyl)-acetyl]-cyclopropyl-amino}-methyl)-pyrrolidin-3-ylmethyl]-4-ethyl-N-isopropyl-3-(3-methoxy-propoxy)-benzamide N-[(3S,4S)-4-({[2-(4-Amino-cyclohexyl)-acetyl]-cyclopropyl-amino}-methyl)-pyrrolidin-3-ylmethyl]-4-ethyl-N-isopropyl-3-(3-methoxy-propoxy)-benzamide (R)-Tetrahydro-furan-3-carboxylic acid cyclopropyl-[(3S,4S)-4-({[4-ethyl-3-(3-methoxy-proxy)-benzoyl]-isopropyl-amino}-methyl)-pyrrolidin-3-ylmethyl]-amide (S)-Tetrahydro-furan-3-carboxylic acid cyclopropyl-[(3S,4S)-4-({[4-ethyl-3-(3-methoxy-propoxy)-benzoyl]-1-isopropyl-amino}-methyl)-pyrrolidin-3-ylmethyl]-amide (R)-Tetrahydro-pyran-3-carboxylic acid cyclopropyl-[(3S,4S)-4-({[4-ethyl-3-(3-methoxy-proxy)-benzoyl]-isopropyl-amino}-methyl)-pyrrolidin-3-ylmethyl]-amide (S)-Tetrahydro-pyran-3-carboxylic acid cyclopropyl-[(3S,4S)-4-({[4-ethyl-3-(3-methoxy-propoxy)-benzoyl]-isopropyl-amino}-methyl)-pyrrolidin-3-ylmethyl]-amide N-((3S,4S)-4-{[Cyclopropyl-(cis-4-hydroxy-cyclohexanecarbonyl)-amino]-methyl}-pyrrolidin-3-ylmethyl)-4-ethyl-N-isopropyl-3-(3-methoxy-propoxy)-benzamide N-((3S,4S)-4-{[Cyclopropyl-(trans-4-hydroxy-cyclohexanecarbonyl)-amino]-methyl}-pyrrolidin-3-ylmethyl)-4-ethyl-N-isopropyl-3-(3-methoxy-propoxy)-benzamide (S)-Tetrahydro-pyran-3-carboxylic acid [(3S,4S)-4-({[4-ethyl-3-(3-methoxy-propoxy)-benzoyl]-isopropyl-amino}-methyl)-pyrrolidin-3-ylmethyl]-methyl-amide (R)-Tetrahydro-pyran-3-carboxylic acid [(3S,4S)-4-({[4-ethyl-3-(3-methoxy-propoxy)-benzoyl]-isopropyl-amino}-methyl)-pyrrolidin-3-ylmethyl]-methyl-amide N-Isopropyl-3-(3-methoxy-propoxy)-4-methyl-N-{(3S,4S)-4-[(methyl-phenylacetyl-amino)-methyl]-pyrrolidin-3-ylmethyl}-benzamide Tetrahydro-pyran-4-carboxylic acid [(3S,4S)-4-({isopropyl-[3-(3-methoxy-propoxy)-4-methyl-benzoyl]-amino}-methyl)-pyrrolidin-3-yl methyl]-methyl-amide N-Isopropyl-3-(3-methoxy-propoxy)-4-methyl-N-((3S,4S)-4-{[methyl-(2-tetrahydro-pyran-4-yl-acetyl)-amino]-methyl}-pyrrolidin-3-ylmethyl)-benzamide N-((3S,4S)-4-{[Cyclopropyl-((S)-2-methoxy-2-phenyl-acetyl)-amino]-methyl}-pyrrolidin-3-ylmethyl)-N-isopropyl-3-(3-methoxy-propoxy)-4-methyl-benzamide (S)-2,3-Dihydro-benzo[1,4]dioxine-2-carboxylic acid cyclopropyl-[(3S,4S)-4-({isopropyl-[3-(3-methoxy-propoxy)-4-methyl-benzoyl]-amino}-methyl)-pyrrolidin-3-ylmethyl]-amide N-((3S,4S)-4-{[((S)-2-Methoxy-2-phenyl-acetyl)-methyl-amino]-methyl}-pyrrolidin-3-ylmethyl)-N-isopropyl-3-(3-methoxy-propoxy)-4-methyl-benzamide (S)-2,3-Dihydro-benzo[1,4]dioxine-2-carboxylic acid [(3S,4S)-4-({isopropyl-[3-(3-methoxy-propoxy)-4-methyl-benzoyl]-amino}-methyl)-pyrrolidin-3-ylmethyl]-methyl-amide N-((3S,4S)-4-{[(3-Acetylamino-3-methyl-butyryl)-cyclopropyl-amino]-methyl}-pyrrolidin-3-ylmethyl)-N-isopropyl-3-(3-methoxy-propoxy)-4-methyl-benzamide N-((3S,4S)-4-{[((S)-2-Hydroxy-2-phenyl-acetyl)-methyl-amino]-methyl}-pyrrolidin-3-ylmethyl)-N-isopropyl-3-(3-methoxy-propoxy)-4-methyl-benzamide Tetrahydro-pyran-4-carboxylic acid cyclopropyl-[(3S,4S)-4-({isopropyl-[3-(3-methoxy-propoxy)-4-methyl-benzoyl]-amino}-methyl)-pyrrolidin-3-ylmethyl]-amide N-Isopropyl-3-(3-methoxy-propoxy)-4-methyl-N-[(3S,4S)-4-({methyl-[2-(3-oxo-3,4-dihydro-2H-benzo[1,4oxazin-6-yl)-acetyl]-aminomethyl)-pyrrolidin-3-yl methyl]-benzamide N-[(3S,4S)-4-({Cyclopropyl-[2-(3-oxo-3,4-dihydro-2H-benzo[1,4]oxazin-6-yl)-acetyl]-amino}-methyl)-pyrrolidin-3-ylmethyl]-N-isopropyl-3-(3-methoxy-propoxy)-4-methyl-benzamide N-((3S,4S)-4-{[Cyclopropyl-(2-tetrahydro-pyran-4-yl-acetyl)-amino]-methyl}-pyrrolidin-3-ylmethyl)-N-isopropyl-3-(3-methoxy-propoxy)-4-methyl-benzamide N-((3S,4S)-4-{[((S)-2-Cyclohexyl-2-methoxy-acetyl)-cyclopropyl-amino]-methyl}-pyrrolidin-3-ylmethyl)-N-isopropyl-3-(3-methoxy-propoxy)-4-methyl-benzamide N-((3S,4S)-4-{[((S)-2-Cyclohexy-2-methoxy-acetyl)-methyl-amino]-methyl}-pyrrolidin-3-ylmethyl)-N-isopropyl-3-(3-methoxy-propoxy)-4-methyl-benzamide N-((3S,4S)-4-{[((S)-2-Hydroxy-3-methyl-butyryl)-methyl-amino]-methyl}-pyrrolidin-3-ylmethyl)-N-isopropyl-3-(3-methoxy-propoxy)-4-methyl-benzamide N-[(3 S,4S)-4-({[2-(1-Acetyl-piperidin-4-yl)-acetyl]-cyclopropyl-amino}-methyl)-pyrrolidin-3-ylmethyl]-N-isopropyl-3-(3-methoxy-propoxy)-4-methyl-benzamide N-((3S,4S)-4-{[((S)-2-Hydroxy-4-methyl-pentanoyl)-methyl-amino]-methyl}-pyrrolidin-3-ylmethyl)-N-isopropyl-3-(3-methoxy-propoxy)-4-methyl-benzamide N-((3S,4S)-4-([(cis-4Hydroxy-cyclohexanecarbonyl)-methyl-amino]-methyl)-pyrrolidin-3-ylmethyl)-N-isopropyl-3-(3-methoxy-propoxy)-4-methyl-benzamide N-((3S,4S)-4-([((R)-3-Hydroxy-3-phenyl-propionyl)-methyl-amino]-methyl}-pyrrolidin-3-ylmethyl)-N-isopropyl-3-(3-methoxy-propoxy)-4-methyl-benzamide N-((3S,4S)-4-{[((S)-3-Hydroxy-3-phenyl-propionyl)-methyl-amino]-methyl}-pyrrolidin-3-ylmethyl)-N-isopropyl-3-(3-methoxy-propoxy)-4-methyl-benzamide N-[(3S,4S)-4-({[2-(1-Acetyl-piperidin-4-yl)-acetyl]-methyl-amino}-methyl)-pyrrolidin-3-ylmethyl]-N-isopropyl-3-(3-methoxy-propoxy)-4-methyl-benzamide N-((3S,4S)-4-{Cyclopropyl-(cis-4-hydroxy-cyclohexanecarbonyl)-amino]-methyl}-pyrrolidin-3-ylmethyl)-N-isopropyl-3-(3-methoxy-propoxy)-4-methyl-benzamide N-((3S,4S)-4-{[((S)-2-Hydroxy-3-phenyl-propionyl)-methyl-amino]-methyl}-pyrrolidin-3-ylmethyl)-N-isopropyl-3-(3-methoxy-propoxy)-4-methyl-benzamide N-((3S,4S)-4-{[((2-Furan-2-yl-acetyl)-methyl-amino]-methyl}-pyrrolidin-3-ylmethyl)-N-isopropyl-3-(3-methoxy-propoxy)-4-methyl-benzamide N-((3S,4S)-4-{[Cyclopropyl-((S)-2-hydroxy-4-methyl-pentanoyl)-amino]-methyl}-pyrrolidin-3-ylmethyl)-N-isopropyl-3-(3-methoxy-propoxy)-4-methyl-benzamide Indan-2-carboxylic acid [(3S,4S)-4-({isopropyl-[3-(3-methoxy-propoxy)-4-methyl-benzoyl]-amino}-methyl)-pyrrolidin-3-ylmethyl]-amide N-Isopropyl-3-(3-methoxy-propoxy)-4-methyl-N-{(3S,4S)-4-[(2-methyl-2-phenyl-propionylamino)-methyl]-pyrrolidin-3-ylmethyl}-benzamide N-Isopropyl-3-(3-methoxy-propoxy)-4-methyl-N-{(3S,4S)-4-[(2-tetrahydro-pyran-4-yl-acetylamino)-methyl]-pyrrolidin-3-ylmethyl}-benzamide (S)-2,3-Dihydro-benzo[1,4]dioxine-2-carboxylic acid [(3S,4S)-4-({isopropyl-[3-(3-methoxy-propoxy)-4-methyl-benzoyl]-amino}-methyl)-pyrrolidin-3-ylmethyl]-amide N-Isopropyl-3-(3-methoxy-propoxy)-4-methyl-N-((3S,4S)-4-{[methyl-((R)-2-tetrahydro-pyran-2-yl-acetyl)-amino]-methyl}-pyrrolidin-3-ylmethyl)-benzamide N-Isopropyl-3-(3-methoxy-propoxy)-4-methyl-N-((3S,4S)-4-{[methyl-((S)-2-tetrahydro-pyran-2-yl-acetyl)-amino]-methyl}-pyrrolidin-3-ylmethyl)-benzamide N-((3S,4S)-4-{[Cyclopropyl-((R)-2-tetrahydro-furan-2-yl-acetyl)-amino]-methyl}-pyrrolidin-3-ylmethyl)-N-isopropyl-3-(3-methoxy-propoxy)-4-methyl-benzamide N-((3S,4S)-4-{[Cyclopropyl-((S)-2-tetrahydro-furan-2-yl-acetyl)-amino]-methyl}-pyrrolidin-3-ylmethyl)-N-isopropyl-3-(3-methoxy-propoxy)-4-methyl-benzamide N-Isopropyl-N-((3S,4S)-4-{[(cis-4-methoxy-cyclohexanecarbornyl)-methyl-amino]-methyl}-pyrrolidin-3-ylmethyl)-3-(3-methoxy-propoxy)-4-methyl-benzamide N-Isopropyl-N-((3S,4S)-4-{[(trans-4-methoxy-cyclohexanecarbonyl)-methyl-amino]-methyl}-pyrrolidin-3-ylmethyl)-3-(3-methoxy-propoxy)-4-methyl-benzamide N-Isopropyl-N-((3S,4S)-4-{[(cis-4-methoxy-cyclohexanecarbonyl)-amino]-methyl}-pyrrolidin-3-ylmethyl)-3-(3-methoxy-propoxy)-4-methyl-benzamide N-Isopropyl-N-((3S,4S)-4-{[(trans-4-methoxy-cyclohexanecarbonyl)-amino]-methyl}-pyrrolidin-3-ylmethyl)-3-(3-methoxy-propoxy)-4-methyl-benzamide 1-(3-Methoxy-propyl)-1H-indole-6-carboxylic acid isopropyl-{(3S,4S)-4-[(methyl-phenylacetyl-amino) -methyl]-pyrrolidin-3-ylmethyl}-amide N-Cyclopropyl-N-{(3S,4S)-4-[(cyclopropyl-phenylacetyl-amino)-methyl]-pyrrolidin-3-ylmethyl}-4-methoxy-3-(3-methoxy-propoxy)-benzamide Cyclopropyl-[(3S,4S)-4-({cyclopropyl-[4-methoxy-3-(3-methoxy-propoxy)-benzoyl]-amino}-methyl)-pyrrolidin-3-ylmethyl]-carbamic acid benzyl ester Cyclopropyl-[(3S,4S)-4-({cyclopropyl-[4-methoxy-3-(3-methoxy-propoxy)-benzoyl]-amino}-methyl)-pyrrolidin-3-ylmethyl]-carbamic acid isobutyl ester Cyclopropyl-[(3S,4S)-4-({cyclopropyl-[4-methoxy-3-(3-methoxy-propoxy)-benzoyl]-amino}-methyl)-pyrrolidin-3-ylmethyl]-carbamic acid tetrahydro-pyran-4-yl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid benzyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid benzyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid isobutyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid pyridin-4-ylmethyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid 1-methyl-piperidin-4-ylmethyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid 2-methoxy-ethyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid tetrahydro-pyran-4-yl-methyl ester Cyclopropyl-[(3S*,4S*)-4-({isopropyl-[4-methoxy3(3-methoxy-propoxy)-benzoyl]-amino}-methyl)-pyrrolidin-3-ylmethyl]-carbamic acid 2,2-dimethyl-propyl ester Cyclopropyl-[(3S*,4S*)-4-({isopropyl-4-methoxy-3-(3-methoxy-propoxy)-benzoyl]-amino}-methyl)-pyrrolidin-3-ylmethyl]-carbamic acid 1-methyl-cyclopropyl-methyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid 2-acetylamino-2-methyl-propyl ester Cyclopropyl-[(3S*,4S*)-4-({isopropyl-[4-methoxy-3-(3-methoxy-propoxy)-benzoyl]-amino}- methyl)-pyrrolidin-3-ylmethyl]-carbamic acid phenyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid 2-methyl-2-methylcarbamoyl-propyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid 1-acetylamino-cyclopentylmethyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid 1-acetyl-piperidin-4-yl-methyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid 5-methyl-isoxazol-3-ylmethyl ester Cyclopropyl-[(3S*,4S*)-4-({isopropyl-[4-methoxy-3-(3-methoxy-propoxy)-benzoyl]-amino}-methyl)-pyrrolidin-3-ylmethyl]-carbamic acid naphthalen-1-yl ester Cyclopropyl-[(3S,4S)-4-({isopropyl-[4-methoxy-3-(3-methoxy-propoxy)-benzoyl]-amino}methyl)-pyrrolidin-3-ylmethyl]-carbamic acid cyclopropylmethyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid isobutyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid 4-methoxy phenyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid cyclohexyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid naphthalen-2-yl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid tetrahydro-pyran-4-yl ester Cyclopropyl-[(3S,4S)-4-({isopropyl-[4-methoxy-3-(3-methoxypropoxy)-benzoyl]-amino}-methyl)-pyrrolidin-3-ylmethyl]-carbamic acid 5methyl-[1,3]dioxan-5-ylmethyl ester Cyclopropyl-[(3S,4S)-4-({isopropyl-[4-methoxy-3-(3-methoxypropoxy)-benzoyl]-amino}-methyl)-pyrrolidin-3-ylmethyl]-carbamic acid 3(2-oxo-pyrrolidin-1-yl)-phenyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid 3-morpholin-4-yl-phenyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid (R)-1-(tetrahydro-furan-2-yl)methyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid (R)-1-phenyl-propyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid (R)-1-phenyl-ethyl ester Cyclopropyl-[(3S,4S)-4-(isopropyl-4-methoxy-3-(3-methoxy-propoxy)-benzoyl]-amino}-methyl)-pyrrolidin-3-ylmethyl]-carbamic acid phenyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid 2-methoxy phenyl ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid 3-methoxy-3-methyl-butyl ester Cyclopropyl-[(3S, 4S)-4-({isopropyl-[4-ethoxy-3-(3-methoxy-propoxy)-benzoyl]-amino}-methyl)-pyrrolidin-3-ylmethyl]-carbamic acid (R)-(tetrahydro-furan-3-yl)ester Cyclopropyl-[(3S,4S)-4-({isopropyl-[4-methoxy-3-(3-methoxy-propoxy)-benzoyl]-amino}-methyl)-pyrrolidin-3-ylmethyl]-carbamic acid (S)-(tetrahydro-furan-3-yl)ester

[(3S,4S)-4-({Isopropyl-[4-methoxy-3-(3-methoxy-propoxy)-benzoyl]-amino}-methyl)-pyrrolidin-3-ylmethyl]-methyl-carbamic acid 3-methoxy-3-methyl-butyl ester

[(3S,4S)-4-({Isopropyl-[4-methoxy-3-(3-methoxy-propoxy)-benzoyl]-amino}-methyl)-pyrrolidin-3-ylmethyl]-methyl-carbamic acid tetrahydro-pyran-4-yl ester Cyclopropyl-[(3S,4S)-4-({isopropyl-[3-(3-methoxy-propoxy)-4-methyl-benzoyl]-amino}-methyl)-pyrrolidin-3-ylmethyl]-carbamic acid tetrahydro-pyran-4-yl ester Cyclopropyl-[(3S,4S)-4-({isopropyl-[3-(3-methoxy-propoxy)-4-methyl-benzoyl]-amino}-methyl)-pyrrolidin-3-ylmethyl]-carbamic acid (S)-(tetrahydro-furan-3-yl) ester

[(3S,4S)-4-({Isopropyl-[3-(3-methoxy-propoxy)-4-methyl-benzoyl]-amino}-methyl)-pyrrolidin-3-ylmethyl]-methyl-carbamic acid tetrahydro-pyran-4-yl ester

[(3S,4S)-4-({Isopropyl-[3-(3-methoxy-propoxy)-4-methyl-benzoyl]-amino}-methyl)-pyrroidin-3- ylmethyl]-methyl-carbamic acid (S)-(tetrahydro-furan-3-yl)ester

[(3S,4S)-4-({Isopropyl-[3-(3-methoxy-propoxy)-4-methyl-benzoyl]-amino}-methyl)-pyrrolidin-3-ylmethyl]-methyl-carbamic acid 3-methoxy-3-methyl-butyl ester Cyclopropyl-[(3S,4S)-4-({isopropyl-[3-(3-methoxy-propoxy)-4-methyl-benzoyl]-amino}-methyl)-pyrrolidin-3-ylmethyl]-carbamic acid 3-methoxy-3-methyl-butyl ester

[(3S,4S)-4-({Isopropyl-[3-(3-methoxy-propoxy)-4-methyl-benzoyl]-amino}-methyl)-pyrrolidin-3-ylmethyl]-methyl-carbamic acid 4-methoxy phenyl ester

[(3S,4S)-4-({Isopropyl-[3-(3-methoxy-propoxy)-4-methyl-benzoyl]-amino}-methyl)-pyrrolidin-3-ylmethyl]-methyl-carbamic acid (R)-1-(tetrahydro-furan-2-yl)methyl ester Cyclopropyl-[(3S,4S)-4-({isopropyl-[3-(3-methoxy-propoxy)-4-methyl-benzoyl]-amino}-methyl)-pyrrolidin-3-ylmethyl]-carbamic acid 4-methoxy phenyl ester Cyclopropyl-[(3S,4S)-4-({isopropyl-[3-(3-methoxy-propoxy)-4-methyl-benzoyl]-amino}-methyl)-pyrrolidin-3-ylmethyl]-carbamic acid (R)-1-(tetrahydro-furan-2-yl)methyl ester

[(3S ,4S)-4-({Isopropyl-[3-(3-methoxy-propoxy)-4-methyl-benzoyl]-amino}-methyl)-pyrrolidin-3-ylmethyl]-methyl-carbamic acid 5-methyl-[1,3]dioxan-5-ylmethyl ester Cyclopropyl-[(3S,4S)-4-({isopropyl-[3-(3-methoxy-propoxy)-4-methyl-benzoyl[-amino}-methyl)-pyrrolidin-3-ylmethyl]-carbamic acid 5-methyl-isoxazol-3-ylmethyl ester

[(3S,4S)-4-({Isopropyl-[3-(3-methoxy-propoxy)-4-methyl-benzoyl]-amino}-methyl)-pyrrolidin-3-ylmethyl]-methyl-carbamic acid 5-methyl-isoxazol-3-ylmethyl ester Cyclopropyl-[(3S,4S)-4-({[4-ethyl-3-(3-methoxy-propoxy)-benzoyl]-isopropyl-amino}-methyl)-pyrrolidin-3-ylmethyl]-carbamic acid benzyl ester Cyclopropyl-[(3S,4S)-4-({[4-ethyl-3-(3-methoxy-propoxy)-benzoyl]-isopropyl-amino}-methyl)-pyrrolidin-3-ylmethyl]-carbamic acid tetrahydro-pyran-4-yl ester Cyclopropyl-[(3S,4S)-4-({[4-ethyl-3-(3-methoxy-propoxy)-benzoyl]-isopropyl-amino}-methyl)-pyrrolidin-3-ylmethyl]-carbamic acid 4methoxy phenyl ester

[(3S,4S)-4-({[4-Ethyl-3-(3-methoxy-propoxy)-benzoyl]-isopropyl-amino}-methyl)-pyrrolidin-3-ylmethyl]-methyl-carbamic acid tetrahydro-pyran-4-yl ester

[(3S,4S)-4-({[4-Ethyl-3-(3-methoxy-propoxy)-benzoyl]-isopropyl-amino}-methyl)-pyrrolidin-3-ylmethyl]-methyl-carbamic acid (R)-1-(tetrahydro-furan-2-yl)methyl ester

[(3S,4S)-4-({[4-Ethyl-3-(3-methoxy-propoxy)-benzoyl]-isopropyl-amino}-methyl)-pyrrolidin-3-ylmethyl]-methyl-carbamic acid (S)-(tetrahydro-furan-3-yl)ester

[(3S,4S)-4-({[4-Ethyl-3-(3-methoxy-propoxy)-benzoyl]-isopropyl-amino}-methyl)-pyrrolidin-3-ylmethyl]-methyl-carbamic acid 5-methyl-[1,3]dioxan-5-ylmethyl ester

[(3S,4S)-4-({[4-Ethyl-3-(3-methoxy-propoxy)benzoyl]-isopropyl-amino}-methyl)-pyrrolidin-3-ylmethyl]-methyl-carbamic acid 3-methoxy-3-methyl-butyl ester Cyclopropyl-[(3S,4S)-4-({isopropyl-[1-(3-methoxy-propyl)-3-methyl-1H-indole-6-carbonyl]-amino}-methyl)-pyrrolidin-3-ylmethyl]-carbamic acid benzyl ester Cyclopropyl-[(3S,4S)-4-({isopropyl-[1-(3-methoxy-propyl)-3-methyl-1H-indole-6-carbonyl]-amino}-methyl)-pyrrolidin-3-ylmethyl]-carbamic acid isobutyl ester Cyclopropyl-[(3S,4S)-4-({isopropyl-[1-(3-methoxy-propyl)-3-methyl-1H-indole-6-carbonyl]-amino}-methyl)-pyrrolidin-3-ylmethyl]-carbamic acid tetrahydro-pyran-4-yl ester Benzyl-methyl-carbamic acid (3S*,4S*)-4-({isopropyl-[4-methoxy-3-(3-methoxy-propoxy)-benzoyl]-amino}-methyl)-pyrrolidin-3-ylmethyl ester Diisobutyl-carbamic acid (3S,4S)-4-({isopropyl-[4-methoxy-3-(3-methoxy-propoxy)-benzoyl]-amino}-methyl)-pyrrolidin-3-ylmethyl ester Benzyl-cyclopropyl-carbamic acid (3S,4S)-4-({isopropyl-[4-methoxy-3-(3-methoxy-propoxy)-benzoyl]-amino}-methyl)-pyrrolidin-3-ylmethyl ester Isobutyl-methyl-carbamic acid (3S,4S)-4-({isopropyl-[4-methoxy-3-(3-methoxy-propoxy)-benzoyl]-amino}-methyl)-pyrrolidin-3-ylmethyl ester Cyclopropyl-(tetrahydro-pyran-4-ylmethyl)-carbamic acid (3S,4S)-4-({isopropyl-[4-methoxy-3-(3-methoxy-propoxy)-benzoyl]-amino}-methyl)-pyrrolidin-3-ylmethyl ester Cyclopropyl-(tetrahydro-pyran-4-yl)-carbamic acid (3S,4S)-4-({isopropyl-[4-methoxy-3-(3-methoxy-propoxy)-benzoyl]-amino}-methyl)-pyrrolidin-3-ylmethyl ester Cyclohexylmethyl-methyl-carbamic acid (3S,4S)-4-({[4-ethyl-3-(3-methoxy-propoxy)-benzoyl]-isopropyl-amino}-methyl)-pyrrolidin-3-ylmethyl ester Benzyl-cyclopropyl-carbamic acid (3S,4S)-4-({[4-ethyl-3-(3-methoxy-propoxy)-benzoyl]-isopropyl-amino}-methyl)-pyrrolidin-3-ylmethyl ester Cyclopropyl-(tetrahydro-pyran-4-ylmethyl)-carbamic acid (3S,4S)-4-({[4-ethyl-3-(3-methoxy-propoxy)-benzoyl]-isopropyl-amino}- methyl)-pyrrolidin-3-ylmethyl ester Cyclopropyl-(tetrahydro-pyran-3-ylmethyl)-carbamic acid (3S,4S)-4-({[4-ethyl-3-(3-methoxy-propoxy)-benzoyl]-isopropyl-amino}-methyl)-pyrrolidin-3-ylmethyl ester Cyclopropyl-(tetrahydro-pyran-4-yl)-carbamic acid (3S,4S)-4-({[4-ethyl-3-(3-methoxy-propoxy)-benzoyl]-isopropyl-amino}-methyl)-pyrrolidin-3-ylmethyl ester Cyclopropyl-(tetrahydro-pyran-2-ylmethyl)-carbamic acid (3S,4S)-4-({[4-ethyl-3-(3-methoxy-propoxy)-benzoyl]-isopropyl-amino}-methyl)-pyrrolidin-3-ylmethyl ester Cyclopropyl-(tetrahydro-pyran-4-yl)-carbamic acid (3S,4S)-4-({isopropyl-[1-(3-methoxy-propyl)-3-methyl-1H-indole-6-carbonyl]-amino}-methyl)-pyrrolidin-3-ylmethyl ester ((R)-1-Phenyl-propyl)-carbamic acid (3S,4S)-4-({isopropyl-[4-methoxy-3-(3-methoxy-propoxy)-benzoyl]-amino}-methyl)-pyrrolidin-3-ylmethyl ester
N-[(3S*,4S*)-4-(1-Cyclopropyl-3-furan-2-ylmethyl-ureidomethyl)-pyrrolidin-3-ylmethyl]-N-isopropyl-4-methoxy-3-(3-methoxy-propoxy)-benzamide
N-[(3S,4S)-4-(1-Cyclopropyl-3-furan-2-ylmethyl-ureidomethyl)-pyrrolidin-3-ylmethyl]-N-isopropyl-4-methoxy-3-(3-methoxy-propoxy)-benzamide
N-[(3S*,4S*)-4-(3-(4-Methoxy benzyl-1-cyclopropyl-ureidomethyl)-pyrrolidin-3-ylmethyl]-N-isopropyl-4-methoxy-3-(3-methoxy-propoxy)-benzamide
N-[(3S*,4S*)-4-(3-(4-Chloro benzyl-1-cyclopropyl-ureidomethyl)-pyrrolidin-3-ylmethyl]-N-isopropyl-4-methoxy-3-(3-methoxy-propoxy)-benzamide
N[(3S*,4S*)-4-(3-(4-Fluoro benzo-1-cyclopropyl-ureidomethyl)-pyrrolidin-3-ylmethyl]-N-isopropyl-4-methoxy-3-(3-methoxy-propoxy)-benzamide
N-[(3S*,4S*)-4-(3-Cyclohexylmethyl-1-cyclopropyl-ureidomethyl)-pyrrolidin-3-ylmethyl]-N-isopropyl-4-methoxy-3-(3-methoxy-propoxy)-benzamide
N-{(3S*,4S*)-4-[1-Cyclopropyl-3-(tetrahydro-pyran-4-ylmethyl)-ureidomethyl]-pyrolidin-3-ylmethyl}-N-isopropyl-4-methoxy-3-(3-methoxy-propoxy)-benzamide
N-[(3S*,4S*)-4-(1-Cyclopropyl-3-phenethyl-ureidomethyl)-pyrrolidin-3-ylmethyl]-N-isopropyl-4-methoxy-3-(3-methoxy-propoxy)-benzamide
N-[(3S*,4S*)-4-(1-Cyclopropyl-3,3-diphenyl-ureidomethyl)-pyrrolidin-3-ylmethyl]-N-isopropyl-4-methoxy-3-(3-methoxy-propoxy)-benzamide
N-[(3S*,4S*)-4-(1-Cyclopropyl-3,3-diisopropyl-ureidomethyl)-pyrrolidin-3-ylmethyl]-N-isopropyl-4-methoxy-3-(3-methoxy-propoxy)-benzamide
N-[(3S*,4S*)-4-(3-Benzyl-1-cyclopropyl-3-methyl-ureidomethyl)-pyrrolidin-3-ylmethyl]-N-isopropyl-4-methoxy-3-(3-methoxy-propoxy)-benzamide
N-[(3S*,4S*)-4-(3-Benzyl-1-cyclopropyl-3-ethyl-ureidomethyl)-pyrrolidin-3-ylmethyl]-N-isopropyl-4-methoxy-3-(3-methoxy-propoxy)-benzamide
N-[(3S,4S)-4-(3-Benzyl-1-cyclopropyl-3-ethyl-ureidomethyl)-pyrrolidin-3-ylmethyl]-N-isopropyl-4-methoxy-3-(3-methoxy-propoxy)-benzamide
N-[(3S*,4S*)-4-(3-Benzyl-1,3-dicyclopropyl-ureidomethyl)-pyrrolidin-3-ylmethyl]-N-isopropyl-4-methoxy-3-(3-methoxy-propoxy)-benzamide
N-[(3S*,4S*)-4-(1-Cyclopropyl-3-phenyl-ureidomethyl)-pyrrolidin-3-ylmethyl]-N-isopropyl-4-methoxy-3-(3-methoxy-propoxy)-benzamide
N-[(3S*,4S*)-4-3-Benzhydryl-1-cyclopropyl-ureidomethyl)-pyrrolidin-3-ylmethyl]-N-isopropyl-4-methoxy-3-(3-methoxy-propoxy)-benzamide
N-[(3S,4S)-4-(3-Benzyl-1-cyclopropyl-ureidomethyl)-pyrrolidin-3-ylmethyl]-N-isopropyl-4-methoxy-3-(3-methoxy-propoxy)-benzamide
N-[(3S,4S)-4-(1,3-Dicyclopropyl-3-phenyl-ureidomethyl)-pyrrolidin-3-ylmethyl]-N-isopropyl-4-methoxy-3-(3-methoxy-propoxy)-benzamide
N-[(3S,4S)-4(3-Cyclohexyl-1-cyclopropyl-ureidomethyl)-pyrrolidin-3-ylmethyl]-N-isopropyl-4-methoxy-3-(3-methoxy-propoxy)-benzamide
N-[(3S*,4S*)-4-(1-Cyclopropyl-3-naphthalen-1-yl-ureidomethyl)-pyrrolidin-3-ylmethyl]-N-isopropyl-4-methoxy-3-(3-methoxy-propoxy)-benzamide
N-[(3S,4S)-4-(1-Cyclopropyl-3-naphthalen-2-ylureidomethyl)-pyrrolidin-3-ylmethyl]-N-isopropyl-4-methoxy-3-(3-methoxy-propoxy)-benzamide
N-{(3S,4S)-4-[1-Cyclopropyl-3-((R)-1-phenyl-propyl)-ureidomethyl]-pyrrolidin-3-ylmethyl}-N-isopropyl-4-methoxy-3-(3-methoxy-propoxy)-benzamide
N-[(3S,4S)-4-(1-Cyclopropyl-3-isobutyl-3-methyl-ureidomethyl)-pyrrolidin-3-ylmethyl]-N-isopropyl-4-methoxy-3-(3-methoxy-propoxy)-benzamide
N-{(3S,4S)-4-[1-Cyclopropyl-3-((S)-1-phenyl-propyl)-ureidomethyl]-pyrrolidin-3-ylmethyl}-N-isopropyl-4-methoxy-3-(3-methoxy-propoxy)-benzamide
(R)-3-Phenyl-pyrrolidine-1-carboxylic acid cyclopropyl-[(3S,4S)-4-({isopropyl-[4-methoxy-3-(3-methoxy-propoxy)-benzoyl]-amino}-methyl)-pyrrolidin-3-ylmethyl]-amide
4-Ethyl-3-(3-hydroxy-propoxy)-N-isopropyl-N-{(3S,4S)-4-[(methyl-phenylacetyl-amino)-methyl]-pyrrolidin-3-ylmethyl}-benzamide
N-{(3S,4S)-4-[(Cyclopropyl-phenylacetyl-amino)-methyl]-pyrrolidin-3-ylmethyl}-3-(3-hydroxy-propoxy)-N-isopropyl[-4-methoxy-benzamide
N-{(3S*,4S*)-4-[(Cyclopropyl-phenylacetyl-amino)-methyl]-pyrrolidin-3-ylmethyl}-N-isopropyl-4-methoxy-3-(4-methoxy-butyl)-benzamide
N-{(3S*,4S*)-4-[(Cyclopropyl-phenylacetyl-amino)-methyl]-pyrrolidin-3-ylmethyl}-4-difluoromethyl-N-isopropyl-3-(3-methoxy-propoxy)-benzamide
8-(3-Methoxy-propoxy)-2,3-dihydro-benzo[1,4]dioxine-6-carboxylic acid {(3S*,4S*)-4-[(cyclopropyl-phenylacetyl-amino)-methyl]-pyrrolidin-3-ylmethyl}-isopropyl-amide
N-{(3S*,4S*)-4-[(Cyclopropyl-phenylacetyl-amino)-methyl]-pyrrolidin-3-ylmethyl}-N-isopropyl-4-methoxy-5-(3-methoxy-propoxy)-2-methyl-benzamide
2-Chloro-N-{(3S*,4S*)-4-[(cyclopropyl-phenylacetyl-amino)methyl]-pyrrolidin-3-ylmethyl}-N-isopropyl-4-methoxy-5-(3-methoxy-propoxy)-benzamide
3-Chloro-N-{(3S*,4S*)-4-[(cyclopropyl-phenylacetyl-amino)-methyl]-pyrrolidin-3-ylmethyl}-N-isopropyl-5-(3-methoxy-propoxy)-benzamide
4-Chloro-N-{(3S*4S*)-4-[(cyclopropyl-phenylacetyl-amino)-methyl]-pyrrolidin-3-ylmethyl}-N-isopropyl-3-(3-methoxy-propoxy)-benzamide
4-tert-Butyl-N-isopropyl-3-(3-methoxy-propoxy)-N-{(3S,4S)-4-[(methyl-phenylacetyl-amino)-methyl]-pyrrolidin-3-ylmethyl}-benzamide
N-Isopropyl-4-methoxy-3-(2-methoxy-ethoxymethyl)-N-{(3S,4S)-4-[(methyl-phenylacetyl-amino)-methyl]-pyrrolidin-3-ylmethyl}-benzamide
N-Isopropyl-3-(2-methoxy-ethoxymethyl)-N-{(3S,4S)-4-[(methyl-phenylacetyl-amino)-methyl]-pyrrolidin-3-ylmethyl}-4-trifluoromethoxy-benzamide
N-Isopropyl-4-methoxy-N-{(3S,4S)-4-[(methyl-phenylacetyl-amino)-methyl]-pyrrolidin-3-ylmethyl}-3-(3,3,3-trifluoro-propoxy)-benzamide
N-Isopropyl-4-methoxy-N-{(3S,4S)-4[(methyl-phenylacetyl-amino)-methyl]-pyrrolidin-3-ylmethyl}-3-(4,4,4-trifluoro-butoxy)-benzamide
N-{(3S,4S)-4-[(Cyclopropyl-phenylacetyl-amino)-methyl]-pyrrolidin-3-ylmethyl}-N-isopropyl-4-methoxy-3-(3-trifluoromethoxy-propoxy)-benzamide
N-{(3S,4S)-4-[(Cyclopropyl-phenylacetyl-amino)-methyl]-pyrrolidin-3-ylmethyl}-4-ethyl-N-isopropyl-3-(3-trifluoromethoxy-propoxy)-benzamide
N-Isopropyl-4-methoxy-3-(5-methyl-isoxazol-3-ylmethoxy)-N-{(3S,4S)-4-[(methyl-phenylacetyl-amino)-methyl]-pyrrolidin-3-ylmethyl}-benzamide N-{(3S,4S)-4-[(Cyclopropyl-phenylacetyl-amino)-methyl]-pyrrolidin-3-ylmethyl}-N-isopropyl-3-(2-methoxy-ethoxymethyl)-4-trifluoromethoxy-benzamide 3-(2-Ethoxy-ethoxy)-N-isopropyl-4-methoxy-N-{(3S,4S)-4-[(methyl-phenyl acetyl-amino)-methyl]-pyrrolidin-3-ylmethyl}-benzamide N-[(3S*,4S*)-4-({Cyclopropyl-[2-(4-methoxy-phenyl)-acetyl]-amino}-methyl)-pyrrolidin-3-ylmethyl]-N-isopropyl-4-methoxy-3-(3-methoxy-propoxy)-benzamide and N-[(3S*,4S*)-4-({Cyclopropyl-[4-methoxy-3-(3-methoxy-propoxy)-benzoyl]-amino}-methyl)-pyrrolidin-3-ylmethyl]-N-isopropyl-4-methoxy-3-(3-methoxy-propoxy)-benzamide or a pharmaceutically acceptable salt thereof.

5. The compound according to claim 1 with the formula

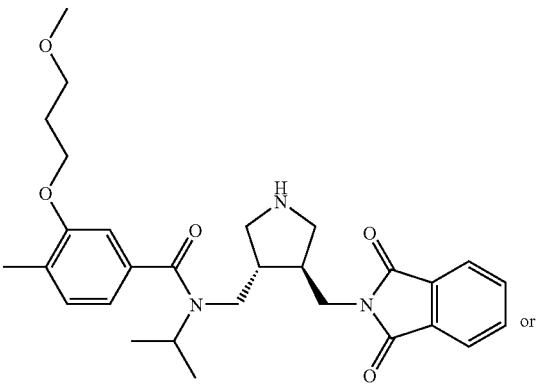

or

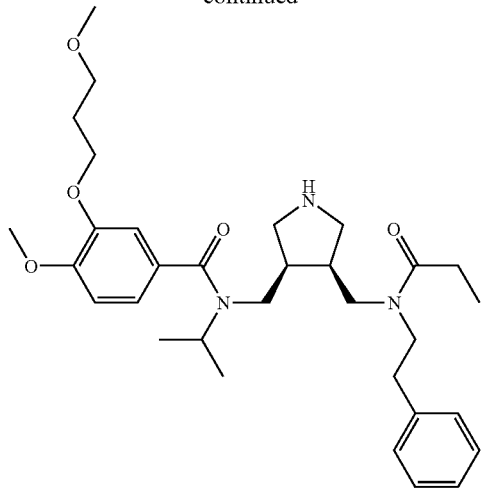

-continued or a pharmaceutically acceptable salt thereof.

6. A pharmaceutical composition, comprising:
a compound of the formula I according to claim 1, or a pharmaceutically acceptable salt thereof and
a pharmaceutically acceptable carrier material.

7. A method of treating hypertension, comprising:
administering to a warm-blooded animal in need of such treatment a pharmaceutically effective amount of a compound of the formula I according to claim 1, or a pharmaceutically acceptable salt thereof.

* * * * *